(12) United States Patent
Chen et al.

(10) Patent No.: US 11,691,989 B2
(45) Date of Patent: Jul. 4, 2023

(54) MACROCYCLIC INDOLES AS MCL-1 INHIBITORS

(71) Applicants: ASCENTAGE PHARMA (SUZHOU) CO., LTD., Suzhou (CN); THE REGENTS OF THE UNIVERSITY OF MICHIGAN, Ann Arbor, MI (US); ASCENTAGE PHARMA GROUP CORP LIMITED, Central Hong Kong (HK)

(72) Inventors: Hao Chen, Suzhou (CN); Wenming Chen, Suzhou (CN); Chao Li, Suzhou (CN); Dongbo Li, Suzhou (CN); Yu Jing, Suzhou (CN); Guozhi Tang, Suzhou (CN); Yunlong Zhou, Suzhou (CN); Shaomeng Wang, Superior Township, MI (US); Chao-Yie Yang, Ann Arbor, MI (US)

(73) Assignees: ASCENTAGE PHARMA (SUZHOU) CO., LTD., Suzhou (CN); THE REGENTS OF THE UNIVERSITY OF MICHIGAN, Ann Arbor, MI (US); ASCENTAGE PHARMA GROUP CORP LIMITED, Hong Kong (CN)

( * ) Notice: Subject to any disclaimer, the term of this patent is extended or adjusted under 35 U.S.C. 154(b) by 0 days.

(21) Appl. No.: 17/047,423

(22) PCT Filed: Nov. 20, 2019

(86) PCT No.: PCT/CN2019/119698
§ 371 (c)(1),
(2) Date: Oct. 14, 2020

(87) PCT Pub. No.: WO2020/103864
PCT Pub. Date: May 28, 2020

(65) Prior Publication Data
US 2022/0340595 A1    Oct. 27, 2022

(30) Foreign Application Priority Data

Nov. 22, 2018 (WO) ................ PCT/CN2018/116988

(51) Int. Cl.
*C07D 497/22* (2006.01)
*C07D 515/22* (2006.01)
*C07D 231/12* (2006.01)
*A61K 31/395* (2006.01)
*A61P 35/00* (2006.01)

(52) U.S. Cl.
CPC ............ *C07D 515/22* (2013.01); *A61P 35/00* (2018.01)

(58) Field of Classification Search
CPC .. C07D 497/22; C07D 515/22; C07D 231/12; A61K 31/395; A61P 35/00
See application file for complete search history.

(56) References Cited

U.S. PATENT DOCUMENTS

2017/0305926 A1    10/2017    Hird et al.

FOREIGN PATENT DOCUMENTS

| CN | 106456602 A | 2/2017 |
| WO | WO-2018/178226 A1 | 10/2018 |
| WO | WO-2018/178227 A1 | 10/2018 |
| WO | WO-2020/063792 A1 | 4/2020 |
| WO | WO-2020/254471 A1 | 12/2020 |

OTHER PUBLICATIONS

Adams et al., The Bcl-2 apoptotic switch in cancer development and therapy, Oncogene, 26(9):1324-37 (2007).
Amundson et al., An informatics approach identifying markers of chemosensitivity in human cancer cell lines, Cancer Res., 60(21):6101-10 (2000).
Beroukhim et al., The landscape of somatic copy-number alteration across human cancers, Nature, 463(7283):899-905 (2010).
Bingham et al., Over one hundred solvates of sulfathiazole, Chem. Commun., 603-4 (2001).
Caira et al., Preparation and crystal characterization of a polymorph, a monohydrate, and an ethyl acetate solvate of the antifungal fluconazole, J. Pharm. Sci., 93(3):601-11 (2004).
Danial et al., Cell death: critical control points, Cell, 116(2):205-19 (2004).
International Application No. PCT/CN2019/119698, International Search Report and Written Opinion, dated Feb. 27, 2020.
Kirkin et al., The role of Bcl-2 family members in tumorigenesis, Biochim. Biophys. Acta, 1644(2-3):229-49 (2004).
VanTonder et al., Preparation and physicochemical characterization of 5 niclosamide solvates and 1 hemisolvate, AAPS PharmSciTech., 5(1):E12 (2004).

(Continued)

*Primary Examiner* — Bruck Kifle
(74) *Attorney, Agent, or Firm* — Marshall, Gerstein & Borun LLP

(57) ABSTRACT

Disclosed is compound of formula I and the pharmaceutically acceptable salts and solvates thereof, wherein R, $R^{1a}$, $R^{1b}$, $R^{1h}$, $L^2$, $L^3$, #, #, # are as defined as set forth in the re) specification. Disclosed is compound of formula I for use to treat a condition or disorder responsive to Mcl-1 inhibition such as cancer.

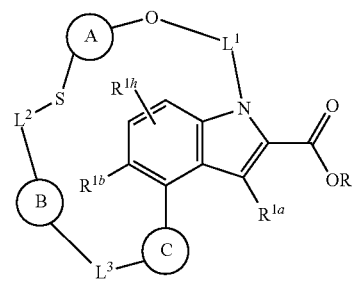

I

41 Claims, 12 Drawing Sheets

(56) References Cited

OTHER PUBLICATIONS

Wei et al., Inducing apoptosis and enhancing chemosensitivity to gemcitabine via RNA interference targeting Mcl-1 gene in pancreatic carcinoma cell, Cancer Chemother. Pharmacol., 62(6):1055-64 (2008).
Wertz et al., Sensitivity to antitubulin chemotherapeutics is regulated by MCL1 and FBW7, Nature, 471(7336):110-4 (2011).
Willis et al., Apoptosis initiated when BH3 ligands engage multiple Bcl-2 homologs, not Bax or Bak, Science, 315(5813):856-9 (2007).
European Patent Application No. 19887925.6, European Search Report, dated Apr. 30, 2021.

MACROCYCLIC INDOLES AS MCL-1 INHIBITORS

CROSS-REFERENCE TO RELATED APPLICATIONS

This is the U.S. national phase of International Application No. PCT/CN2019/119698, filed Nov. 20, 2019, which claims the benefit of International Application No. PCT/CN2018/116988, filed Nov. 22, 2018.

BACKGROUND OF THE INVENTION

Field of the Invention

The present disclosure provides Mcl-1 inhibitors, synthetic intermediates and methods to prepare Mcl-1 inhibitors, and therapeutic methods of treating conditions and diseases, e.g., cancer, wherein inhibition of Mcl-1 provides a benefit.

Background

Abnormal regulation of apoptosis pays an important role in cancer. The apoptosis pathway can be initiated by various extracellular and intracellular stresses, including growth factor deprivation, DNA damage, oncogene induction, and cytotoxic drugs (Danial and Korsmeyer, Cell 116:205-219 (2004)). The death signal leads to the oligomerization of the pro-apoptotic proteins Bax and Bak. Upon activation, they permeabilize the mitochondrial outer membrane and release apoptogenic factors into the cytoplasm. This process is tightly regulated by both pro-apoptotic (Bax, Bak, Bad, Bid, Bim, Bmf, NOXA, PUMA) and anti-apoptotic (Bcl-2, Bcl-xL, Bcl-w, Bcl2-A1, Mcl-1) members of the Bcl-2 family of proteins. The anti-apoptotic Bcl-2 proteins function to protect the cell from apoptotic insults, primarily by preventing disruption of mitochondrial outer membrane integrity by binding to the pro-apoptotic proteins. Adams and Cory Oncogene 26:1324-1337 (2007); Willis et al., Science 315: 856-859 (2007). Because tumor cells are under stress, alterations in their apoptotic signaling pathways are crucial for their survival.

Down-regulated apoptosis is implicated in the onset of cancer. Research has shown, for example, that anti-apoptotic proteins are over-expressed in many cancer cell types. Beroukhim et al., Nature 463:899-905 (2010); Kirkin et al., Biochimica et Biophysica Acta 1644:229-249 (2004); and Amundson et al., Cancer Research 60:6101-6110 (2000). This dysregulation results in the survival of cells that would otherwise have undergone apoptosis such as cancer cells. This suggests that neutralizing the function of anti-apoptotic Bcl-2 proteins may offer an effective strategy for the elimination of cancer cells. In addition, resistance to chemotherapy can be caused by the upregulation of anti-apoptotic Bcl-2 family proteins. Resistance to chemotherapy is a major cause of treatment failure and poor prognosis in many cancers.

An important anti-apoptotic member of the Bcl-2 family is myeloid cell leukemia-1 protein (Mcl-1) protein. Mcl-1 is one of the most frequently amplified anti-apoptotic genes in human cancers including prostate, lung, pancreatic, breast, ovarian, and cervical cancers, as well as melanoma, B-cell chronic lymphocytic leukemia (B-CLL), acute myeloid leukemia (AML) and acute lymphoblastic leukemia (ALL) Beroukhim et al., Nature 463:899-905 (2010). Moreover, its overexpression is implicated as a resistance factor for multiple therapies including widely prescribed microtubule-targeted agents for breast cancers, such as paclitaxel, vincristine, and gemcitabine. Wei et al., Cancer Chemother Pharmacol 62:1055-1064 (2008) and Wertz et al., Nature 471:110-114 (2011). These data suggest that Mcl-1 is an important target for a wide variety of cancers.

In many cancer cell types, the cancer cell's survival is attributed to the dysregulation of the apoptotic pathway caused by the over-expression of one or more anti-apoptotic Bcl-2 protein family members. Because of the important role for Bcl-2 family of proteins in regulating apoptosis in both cancerous and non-cancerous cells, and the inter-cell variability of Bcl-2 family protein expression, it could be advantageous to have a small molecule inhibitor that selectively targets and preferably binds to one type or a subset of anti-apoptotic Bcl-2 protein(s). A selective compound also may confer certain advantages in the clinical setting, by providing flexibility to select a dosing regimen to reduce on-target toxic effects in normal cells.

Because Mcl-1 protein is an important Bcl-2 family member associated with a number of diseases, there is a need for compounds which bind to and inhibit the activity of Mcl-1 protein.

BRIEF SUMMARY OF THE INVENTION

In one aspect, the present disclosure provides compounds represented by any one of Formulae I-III, III-A, III-B, IV, IV-A, IV-B, V, V-A, or V-B, below, and the pharmaceutically acceptable salts and solvates, e.g., hydrates, thereof, collectively referred to as "Compounds of the Disclosure." Compounds of the Disclosure are Mcl-1 inhibitors and/or synthetic intermediates used to prepare Mcl-1 inhibitors. Mcl-1 inhibitors are useful in treating or preventing diseases or conditions such as cancer wherein Mcl-1 inhibition provides a benefit.

In another aspect, the present disclosure provides compounds represented by any one of Formulae VI-XV or XVI, below, and the pharmaceutically acceptable salts and solvates, e.g., hydrates, thereof, collectively referred to as "Intermediates of the Disclosure." Intermediates of the Disclosure are synthetic intermediates that can be used to prepare Compounds of the Disclosure.

In another aspect, the present disclosure provides methods of treating or preventing a condition or disease by administering a therapeutically effective amount of a Compound of the Disclosure to a subject, e.g., a human patient, in need thereof. The disease or condition of interest treatable or preventable by inhibition of Mcl-1 is, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a Compound of the Disclosure to a subject at risk of developing a condition characterized by unwanted proliferating cells. In some embodiments, the Compounds of the Disclosure may reduce the proliferation of unwanted cells by inducing apoptosis in those cells.

In another aspect, the present disclosure provides a method of inhibiting Mcl-1 in a subject, comprising administering to the subject a therapeutically effective amount of at least one Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating or preventing diseases or conditions wherein inhibition of Mcl-1 provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in the treatment or prevention of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides methods of preparing Compounds of the Disclosure and Intermediates of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

I. Compounds of the Disclosure

Figure 1:
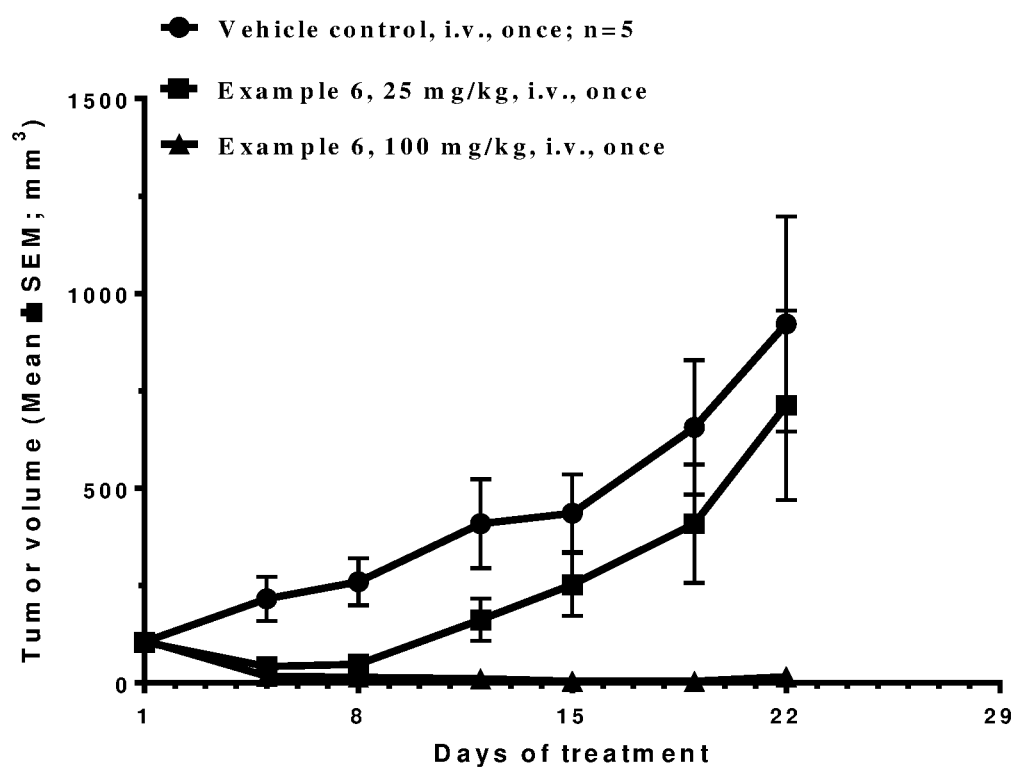
FIG. 1 is a line graph showing the in vivo efficacy by i.v. administration of Cpd. No. 6 (referred to as Example 6 in the figure) in the subcutaneous MV-4-11 tumor model.

Compounds of the Disclosure are Mcl-1 inhibitors and/or synthetic intermediates used to prepare Mcl-1 inhibitors. In one embodiment, Compounds of the Disclosure are compounds of Formula I:

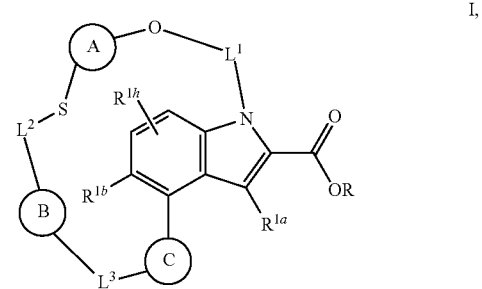

wherein:

R is selected from the group consisting of hydrogen and $C_1$-$C_6$ alkyl;

$R^{1a}$ is selected from the group consisting of hydrogen, halo, $C_1$-$C_4$ alkyl, $C_1$-$C_4$ haloalkyl, $C_2$-$C_4$ alkynyl, $C_3$-$C_6$ cycloalkyl, and —$(CH_2)_m N(R^{2a})(R^{2b})$;

$R^{2a}$ is selected from the group consisting of hydrogen and $C_1$-$C_4$ alkyl;

$R^{2b}$ is selected from the group consisting of hydrogen, $C_1$-$C_4$ alkyl, —C(=O)$R^{3a}$, and —S(=O)$_2 R^{3b}$; or $R^{2a}$ and $R^{2b}$ taken together with the nitrogen atom to which they are attached form a 3- to 6-membered optionally substituted heterocyclo;

m is 1, 2, or 3;

$R^{1a}$ is selected from the group consisting of $C_1$-$C_4$ alkyl, $C_1$-$C_4$ haloalkyl, $C_3$-$C_6$ cycloalkyl, optionally substituted 4- to 8-membered heterocyclo, optionally substituted $C_6$-$C_{10}$ aryl, and optionally substituted 5- to 10-membered heteroaryl;

$R^{3b}$ is selected from the group consisting of $C_1$-$C_4$ alkyl, $C_1$-$C_4$ haloalkyl, $C_3$-$C_6$ cycloalkyl, optionally substituted 4- to 8-membered heterocyclo, optionally substituted $C_6$-$C_{10}$ aryl, and optionally substituted 5- to 10-membered heteroaryl;

$R^{1b}$ is selected from the group consisting of hydrogen, halo, and $C_1$-$C_4$ alkyl;

$R^{1h}$ is selected from the group consisting of hydrogen, halo, and $C_1$-$C_4$ alkyl;

is selected from the group consisting of:

A-1

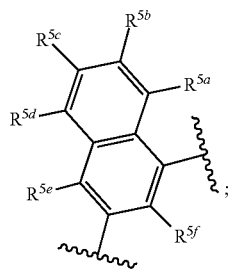

A-2

$R^{4a}$, $R^{4b}$, $R^{4c}$, and $R^{4d}$ are each independently selected from the group consisting of hydrogen, halo, cyano, amino, hydroxyl, $C_1$-$C_4$ alkyl, $C_1$-$C_4$ haloalkyl, and $C_1$-$C_4$ alkoxy;

$R^{5a}$, $R^{5b}$, $R^{5c}$, $R^{5d}$, $R^{5e}$, and $R^{5f}$ are each independently selected from the group consisting of hydrogen, halo, cyano, amino, hydroxyl, $C_1$-$C_4$ alkyl, $C_1$-$C_4$ haloalkyl, and $C_1$-$C_4$ alkoxy;

B is selected from the group consisting of arylenyl and heteroarylenyl;

C is selected from the group consisting of:

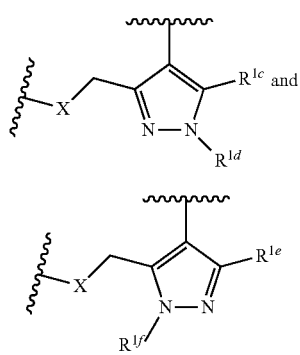

C-1

C-2 wherein —X— is attached to $L^3$;

$R^{1c}$ is selected from the group consisting of hydrogen, $C_1$-$C_4$ alkyl, halo, $C_1$-$C_4$ haloalkyl, and $C_3$-$C_6$ cycloalkyl;

$R^{1d}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl; or $R^{1c}$ and $R^{1d}$ taken together with the atoms to which they are attached form an optionally substituted 4- to 8-membered heterocyclo;

$R^{1e}$ is selected from the group consisting of hydrogen, halo, $C_1$-$C_4$ alkyl, $C_1$-$C_4$ haloalkyl, and $C_3$-$C_6$ cycloalkyl;

$R^{1f}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl;

X is selected from the group consisting of —O—, —S—, —S(=O)—, —S(=O)$_2$—, and —N($R^6$)—;

$R^6$ is selected from the group consisting of hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, —C(=O)$R^{7a}$, —S(=O)$_2R^{8a}$, (hydroxyl)$C_1$-$C_4$ alkyl, (5- to 10-membered heteroaryl)$C_1$-$C_4$ alkyl, ($C_1$-$C_4$ alkoxy)$C_1$-$C_4$ alkyl, (carboxamido)$C_1$-$C_4$ alkyl, —(CH$_2$)$_q$N($R^{13a}$)C(=O)$R^{7b}$, and —(CH$_2$)$_r$N($R^{13b}$)S(=O)$_2R^{8b}$;

$R^{7a}$ is selected from the group consisting of amino, $C_1$-$C_4$ alkyl, $C_1$-$C_4$ alkoxy, optionally substituted $C_3$-$C_6$ cycloalkyl, optionally substituted $C_6$-$C_{10}$ aryl, optionally substituted 5- to 10-membered heteroaryl, and ($C_6$-$C_{10}$ aryl)$C_1$-$C_4$ alkyl;

$R^{7bh}$ is selected from the group consisting of amino, $C_1$-$C_4$ alkyl, $C_1$-$C_4$ alkoxy, optionally substituted $C_3$-$C_6$ cycloalkyl, optionally substituted $C_6$-$C_{10}$ aryl, optionally substituted 5- to 10-membered heteroaryl, and ($C_6$-$C_{10}$ aryl)$C_1$-$C_4$ alkyl;

$R^{8a}$ is selected from the group consisting of amino, $C_1$-$C_4$ alkyl, optionally substituted $C_3$-$C_6$ cycloalkyl, optionally substituted $C_6$-$C_{10}$ aryl, optionally substituted 5- to 10-membered heteroaryl, and ($C_6$-$C_{10}$ aryl)$C_1$-$C_4$ alkyl;

$R^{8b}$ is selected from the group consisting of amino, $C_1$-$C_4$ alkyl, optionally substituted $C_3$-$C_6$ cycloalkyl, optionally substituted $C_6$-$C_{10}$ aryl, optionally substituted 5- to 10-membered heteroaryl, and ($C_6$-$C_{10}$ aryl)$C_1$-$C_4$ alkyl;

$R^{13a}$ is selected from the group consisting of hydrogen and $C_1$-$C_4$ alkyl;

$R^{13b}$ is selected from the group consisting of hydrogen and $C_1$-$C_4$ alkyl;

q is 1, 2, 3, or 4;

r is 1, 2, 3, or 4;

$L^1$ is —(CR$^{14a}$R$^{14b}$)$_s$—;

each $R^{14a}$ and $R^{14b}$ are independently selected from the group consisting of hydrogen and $C_1$-$C_4$ alkyl;

s is 2, 3, 4, 5, or 6;

$L^2$ is —(CR$^{14c}$R$^{14d}$)$_t$—;

each $R^{14c}$ and $R^{14d}$ are independently selected from the group consisting of hydrogen and $C_1$-$C_4$ alkyl;

t is 1, 2, 3, or 4;

$L^3$ is —(CR$^{14e}$R$^{14f}$)$_v$—;

each $R^{14e}$ and $R^{14f}$ are independently selected from the group consisting of hydrogen and $C_1$-$C_4$ alkyl; and v is 1, 2, 3, or 4, or a pharmaceutically acceptable salt or solvate thereof.

In another embodiment, Compounds of the Disclosure are compounds of Formula I, wherein $L^3$ is selected from the group consisting of —CH$_2$— and —CH(CH$_3$)—, or a pharmaceutically acceptable salt or solvate thereof.

In another embodiment, Compounds of the Disclosure are compounds of Formula I, wherein $L^2$ is selected from the group consisting of —CH$_2$— and —CH(CH$_3$)—, or a pharmaceutically acceptable salt or solvate thereof.

In another embodiment, Compounds of the Disclosure are compounds of Formula I, wherein $L^1$ is selected from the group consisting of —CH$_2$CH$_2$—, —CH-2CH$_2$CH$_2$—, and —CH$_2$CH$_2$CH$_2$CH$_2$—, or a pharmaceutically acceptable salt or solvate thereof.

In another embodiment, Compounds of the Disclosure are compounds of Formula II:

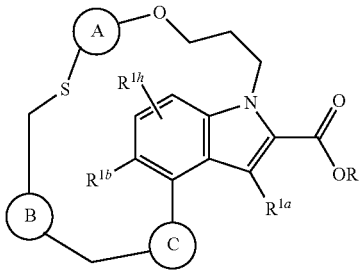

wherein R, $R^{1a}$, $R^{1b}$, $R^{1h}$,

Ⓐ, Ⓑ, and Ⓒ are as defined in connection with Formula I, or a pharmaceutically acceptable salt or solvate thereof.

In another embodiment, Compounds of the Disclosure are compounds of Formula III:

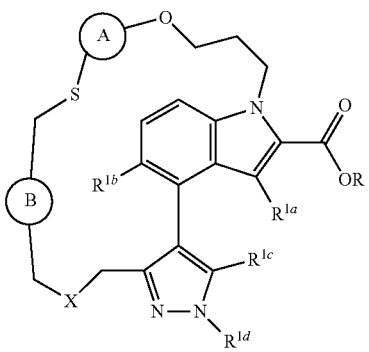

wherein R, $R^{1a}$, $R^{1b}$, $R^{1c}$, $R_{1d}$, X,

Ⓐ, and Ⓑ are as defined in connection with Formula I, or a pharmaceutically acceptable salt or solvate thereof. This particular embodiment is referred to as "Embodiment C1."

In another embodiment, Compounds of the Disclosure are compounds of Formula III-A:

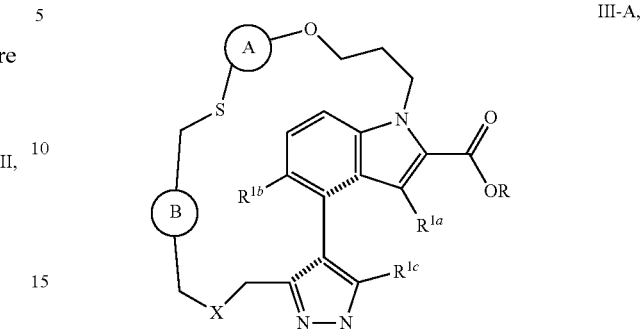

wherein R, $R_{1a}$, $R^{1b}$, $R^{1c}$, $R^{1d}$, X,

Ⓐ, and Ⓑ are as defined in connection with Formula III, or a pharmaceutically acceptable salt or solvate thereof. These compounds are atropisomers that can be separated by chiral HPLC and other resolution methods.

In another embodiment, Compounds of the Disclosure are compounds of Formula III-B:

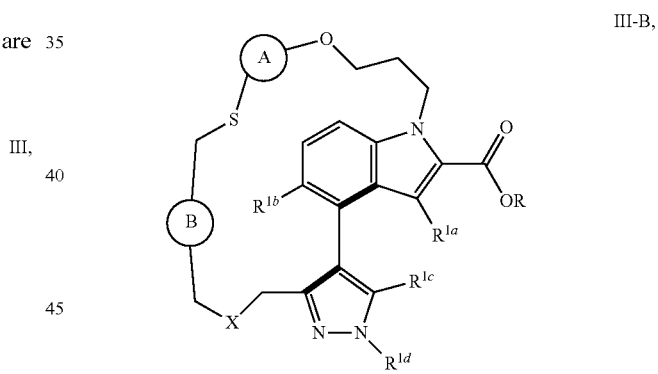

wherein R, $R^{1a}$, $R^{1b}$, $R^{1c}$, $R^{1d}$, X,

Ⓐ, and Ⓑ are as defined in connection with Formula III, or a pharmaceutically acceptable salt or solvate thereof. These compounds are atropisomers that can be separated by chiral HPLC and other resolution methods.

In another embodiment, Compounds of the Disclosure are compounds of any one of Formula I-III, III-A, or III-B, wherein:

$R^{1c}$ is selected from the group consisting of $C_1$-$C_4$ alkyl and $C_1$-$C_4$ haloalkyl; and $R^{1d}$ is selected from the group consisting of $C_1$-$C_4$ alkyl and (carboxamido)$C_1$-$C_4$ alkyl, or a pharmaceutically acceptable salt or solvate thereof.

In another embodiment, Compounds of the Disclosure are compounds of any one of Formula I-III, III-A, or III-B, wherein $R^{1c}$ and $R^{1d}$ are each methyl, or a pharmaceutically acceptable salt or solvate thereof.

In another embodiment, Compounds of the Disclosure are compounds of any one of Formula I-III, III-A, or III-B, wherein $R^{1c}$ and $R^{1d}$ taken together with the atoms to which they are attached form an optionally substituted 4- to 8-membered heterocyclo, or a pharmaceutically acceptable salt or solvate thereof. In another embodiment, $R^{1c}$ and $R^{1d}$ taken together with the atoms to which they are attached form an optionally substituted 5-membered heterocyclo. In another embodiment, $R^{1c}$ and $R^{1d}$ taken together with the atoms to which they are attached form an optionally substituted 6-membered heterocyclo.

In another embodiment, Compounds of the Disclosure are compounds of Formula IV:

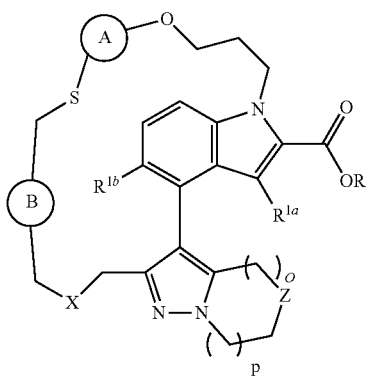

IV, wherein:

o is 0, 1, or 2;

p is 0 or 1;

with the proviso that when p is 0, Z is —$CR^{9a}R^{9b}$—;

Z is selected from the group consisting of —$CR^{9a}R^{9b}$—, —O—, —S—, S(=O)—, S(=O)$_2$—, and —N($R^{10}$)—;

$R^{9a}$ and $R^{9b}$ are independently selected from the group consisting of hydrogen and $C_1$-$C_4$ alkyl;

$R^{10}$ is selected from the group consisting of hydrogen, $C_1$-$C_4$ alkyl, —C(=O)$_2R^{11}$, and —S(=O)$_2R^{12}$;

$R^{11}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl;

$R^{12}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl; and R, $R^{1a}$, $R^{1b}$, X, (A), and (B)

are as defined in connection with Formula I, or a pharmaceutically acceptable salt or solvate thereof. This particular embodiment is referred to as "Embodiment C2."

In another embodiment, Compounds of the Disclosure are compounds of Formula IV-A:

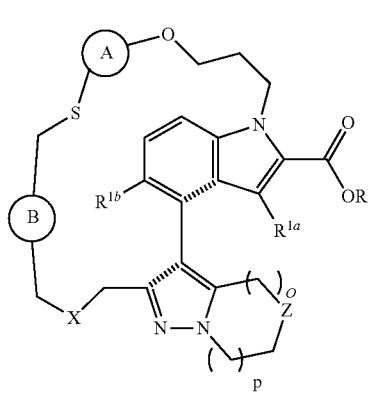

IV-A, wherein R, $R^{1a}$, $R^{1b}$, X, Z, o, p, (A), and (B)

are as defined in connection with Formula IV, or a pharmaceutically acceptable salt or solvate thereof. These compounds are atropisomers that can be separated by chiral HPLC and other resolution methods.

In another embodiment, Compounds of the Disclosure are compounds of Formula IV-B:

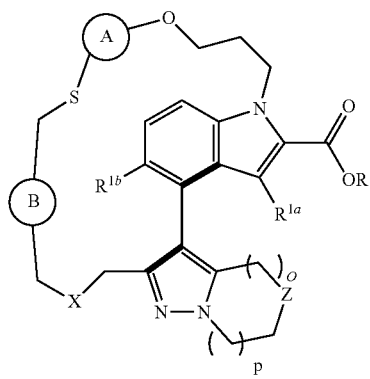

IV-B, wherein R, $R^{1a}$, $R^{1b}$, X, Z, o, p, (A), and (B)

are as defined in connection with Formula IV, or a pharmaceutically acceptable salt or solvate thereof. These compounds are atropisomers that can be separated by chiral HPLC and other resolution methods.

In another embodiment, Compounds of the Disclosure are compounds of any one of Formulae IV, IV-A, or IV-B, wherein Z is —O—, or a pharmaceutically acceptable salt or solvate thereof.

In another embodiment, Compounds of the Disclosure are compounds of any one of Formulae IV, IV-A, or IV-B, wherein Z is —CH$_2$—, or a pharmaceutically acceptable salt or solvate thereof.

In another embodiment, Compounds of the Disclosure are compounds of any one of Formulae IV, IV-A, or IV-B, wherein Z is —C(CH$_3$)$_2$—, or a pharmaceutically acceptable salt or solvate thereof.

In another embodiment, Compounds of the Disclosure are compounds of any one of Formulae IV, IV-A, or IV-B, wherein o is 1, or a pharmaceutically acceptable salt or solvate thereof.

In another embodiment, Compounds of the Disclosure are compounds of Formula V:

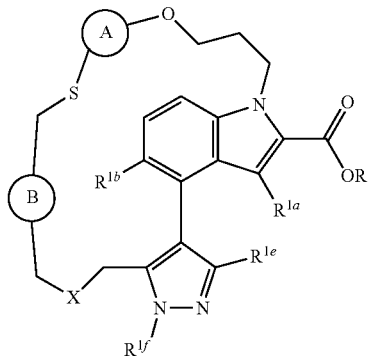

V, wherein R, R$^{1a}$, R$^{1b}$, R$^{1e}$, R$^{1f}$, X,

Ⓐ, and Ⓑ are as defined in connection with Formula I, or a pharmaceutically acceptable salt or solvate thereof. This particular embodiment is referred to as "Embodiment C3."

In another embodiment, Compounds of the Disclosure are compounds of Formula V-A:

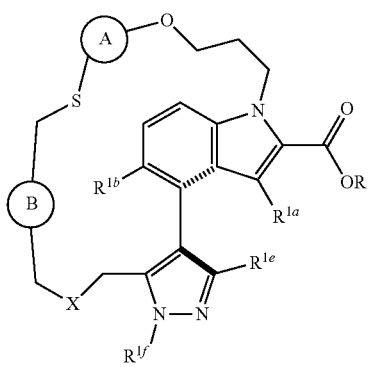

V-A, wherein R, R$^{1a}$, R$^{1b}$, R$^{1e}$, R$^{1f}$, X,

Ⓐ, and Ⓑ are as defined in connection with Formula V, or a pharmaceutically acceptable salt or solvate thereof.

In another embodiment, Compounds of the Disclosure are compounds of Formula V-B:

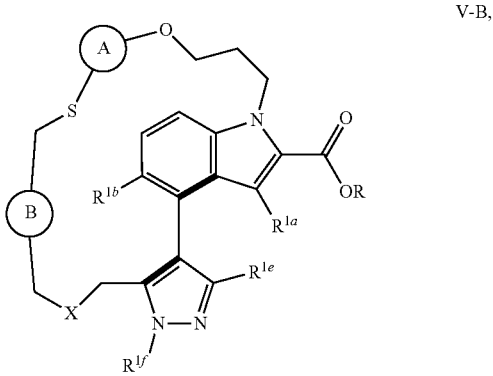

V-B, wherein R, R$^{1a}$, R$^{1b}$, R$^{1e}$, R$^{1f}$, X,

Ⓐ, and Ⓑ are as defined in connection with Formula V, or a pharmaceutically acceptable salt or solvate thereof.

In another embodiment, Compounds of the Disclosure are compounds of any one of Formulae V, V-A, or V-B, wherein:

R$^{1e}$ is selected from the group consisting of C$_1$-C$_4$ alkyl and C$_1$-C$_4$ haloalkyl; and R$^{1f}$ is selected from the group consisting of C$_1$-C$_4$ alkyl, (C$_1$-C$_4$ alkoxy)C$_1$-C$_4$ alkyl, and (carboxamido)C$_1$-C$_4$ alkyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein X is —O—, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein X is —S—, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein X is —S(=O)$_2$—, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein X is —N(R$^6$)—, or a pharmaceutically acceptable salt or solvate thereof. In another embodiment, R$^6$ is selected from the group consisting of hydrogen, C$_1$-C$_4$ alkyl, optionally substituted C$_6$-C$_{10}$ aryl, (C$_6$-C$_{10}$ aryl)C$_1$-C$_4$ alkyl, —S(=O)$_2$R$^{8a}$, (hydroxyl) C$_1$-C$_4$ alkyl, (5- to 10-membered heteroaryl)C$_1$-C$_4$ alkyl, (C$_1$-C$_4$ alkoxy)C$_1$-C$_4$ alkyl, (carboxamido)C$_1$-C$_4$ alkyl, and —(CH$_2$)$_n$N(H)S(=O)$_2$R$^{8b}$. In another embodiment, R$^{8a}$ is selected from the group consisting of C$_1$-C$_4$ alkyl, optionally substituted C$_3$-C$_6$ cycloalkyl, optionally substituted C$_6$-C$_{10}$ aryl, and (C$_6$-C$_{10}$ aryl)C$_1$-C$_4$ alkyl; and R$^{8b}$ is C$_1$-C$_4$ alkyl.

In another embodiment, Compounds of the Disclosure are compounds of any one of Formulae I-III, III-A, III-B, IV, IV-A, IV-B, V, V-A, or V-B, wherein (A)

is A-1, or a pharmaceutically acceptable salt or solvate thereof. In another embodiment, $R^{4a}$, $R^{4b}$, and $R^{4c}$ are each independently selected from the group consisting of hydrogen and halo; and $R^{4d}$ is hydrogen.

In another embodiment, Compounds of the Disclosure are compounds of any one of Formulae I-III, III-A, III-B, IV, IV-A, IV-B, V, V-A, or V-B, wherein (A)

is A-2, or a pharmaceutically acceptable salt or solvate thereof. In another embodiment, the 1-position of A-2 is attached to the oxygen atom and the 3-position of A-2 is attached to the sulfur atom. In another embodiment, $R^{5a}$, $R^{5b}$, $R^{5e}$, $R^{5d}$, and $R^{5e}$ are each independently selected from the group consisting of hydrogen and halo; and $R^{5f}$ is hydrogen.

In another embodiment, Compounds of the Disclosure are compounds of any one of Formulae I-III, III-A, III-B, IV, IV-A, IV-B, V, V-A, or V-B, wherein $R^{1a}$ is selected from the group consisting of hydrogen, halo, $C_1$-$C_4$ alkyl, $C_1$-$C_4$ haloalkyl, $C_2$-$C_4$ alkynyl, and —$CH_2N(H)(R^{2b})$; and $R^{2b}$ is selected from the group consisting of —$C(=O)R^{3a}$ and —$S(=O)_2R^{3b}$, or a pharmaceutically acceptable salt or solvate thereof. In another embodiment, $R^{1a}$ is selected from the group consisting of hydrogen, fluoro, chloro, methyl, ethyl, ethynyl, —$CH_2N(H)C(=O)CH_3$, and —$CH_2N(H)S(=O)_2CF_3$.

In another embodiment, Compounds of the Disclosure are compounds of any one of Formulae I-III, III-A, III-B, IV, IV-A, IV-B, V, V-A, or V-B, wherein $R^{1b}$ is halo, or a pharmaceutically acceptable salt or solvate thereof. In another embodiment, $R^{1b}$ is chloro.

In another embodiment, Compounds of the Disclosure are compounds of any one of Formulae I or II, wherein $R^{1h}$ is hydrogen, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein (B)

is arylenyl, or a pharmaceutically acceptable salt or solvate thereof. In another embodiment, In another embodiment, Compounds of the Disclosure are compounds of any one of Formulae I-III, III-A, III-B, IV, IV-A, IV-B, V, V-A, or V-B, wherein:

(B)

is selected from the group consisting of:

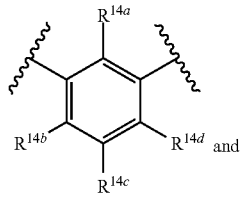

B-1

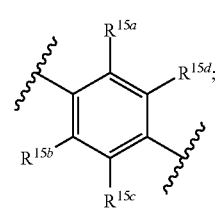

B-2

$R^{14a}$, $R^{14b}$, $R^{14c}$, and $R^{14d}$ are independently selected from the group consisting of hydrogen, halo, cyano, $C_1$-$C_4$ alkyl, $C_1$-$C_4$ haloalkyl, $C_1$-$C_4$ alkoxy, and $C_3$-$C_6$ cycloalkyl; and $R^{15a}$, $R^{15b}$, and $R^{15d}$ are independently selected from the group consisting of hydrogen, halo, cyano, $C_1$-$C_4$ alkyl, $C_1$-$C_4$ haloalkyl, $C_1$-$C_4$ alkoxy, and $C_3$-$C_6$ cycloalkyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein (B)

is B-1, or a pharmaceutically acceptable salt or solvate thereof. In another embodiment, $R^{14a}$, $R^{14b}$, $R^{14c}$, and $R^{14d}$ are each independently selected from the group consisting of hydrogen, halo, and $C_1$-$C_4$ alkyl.

In another embodiment, Compounds of the Disclosure are compounds of any one of Formulae I-III, III-A, III-B, IV, IV-A, IV-B, V, V-A, or V-B, wherein (B)

is B-2, or a pharmaceutically acceptable salt or solvate thereof. In another embodiment, $R^{15a}$, $R^{15b}$, $R^{15c}$, and $R^{15d}$ are each independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein (B)

is heteroarylenyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein:

B is selected from the group consisting of:

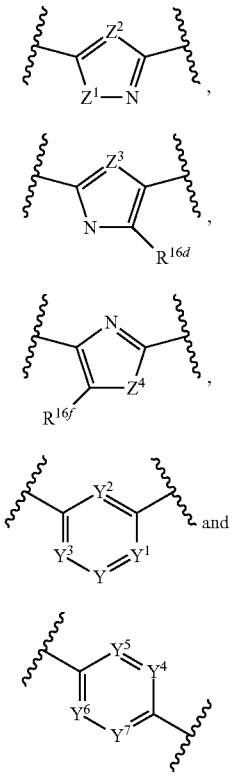

$Z^1$ is selected from the group consisting of —O—, —S—, and —N($R^{16a}$)—;
$R^{16a}$ is selected from the group consisting of hydrogen, $C_1$-$C_4$ alkyl, and $C_3$-$C_6$ cycloalkyl;
$Z^2$ is selected from the group consisting of —C($R^{16b}$)═ and —N═;
$R^{16b}$ is selected from the group consisting of hydrogen, halo, $C_1$-$C_4$ alkyl, and $C_3$-$C_6$ cycloalkyl;
$Z^3$ is selected from the group consisting of —O—, —S—, and —N($R^{16c}$)—;
$R^{16c}$ is selected from the group consisting of hydrogen, $C_1$-$C_4$ alkyl, and $C_3$-$C_6$ cycloalkyl;
$R^{16d}$ is selected from the group consisting of hydrogen, halo, $C_1$-$C_4$ alkyl, and $C_3$-$C_6$ cycloalkyl;
$Z^4$ is selected from the group consisting of —O—, —S—, and —N($R^{16e}$)—;
$R^{16e}$ is selected from the group consisting of hydrogen, $C_1$-$C_4$ alkyl, and $C_3$-$C_6$ cycloalkyl;
$R^{16f}$ is selected from the group consisting of hydrogen, halo, $C_1$-$C_4$ alkyl, and $C_3$-$C_6$ cycloalkyl;
Y is selected from the group consisting of —C($R^{17a}$)═ and —N═;
$Y^1$ is selected from the group consisting of —C($R^{17b}$)═ and —N═;
$Y^2$ is selected from the group consisting of —C($R^{17c}$)═ and —N═;
$Y^3$ is selected from the group consisting of —C($R^{17d}$)═ and —N═;
with proviso that at least one of Y, $Y^1$, $Y^2$, and $Y^3$ is —N═;
$R^{17a}$, $R^{17c}$, and $R^{17d}$ are independently selected from the group consisting of hydrogen, halo, cyano, $C_1$-$C_4$ alkyl, $C_1$-$C_4$ haloalkyl, and $C_1$-$C_4$ alkoxy;
$Y^4$ is selected from the group consisting of —C($R^{18a}$)═ and —N═;
$Y^5$ is selected from the group consisting of —C($R^{18b}$)═ and —N═;
$Y^6$ is selected from the group consisting of —C($R^{18c}$)═ and —N═;
$Y^7$ is selected from the group consisting of —C($R^{18d}$)═ and —N═;
with proviso that at least one of $Y^4$, $Y^5$, $Y^6$, and $Y^7$ is —N═;
$R^{18a}$, $R^{18b}$, $R^{18c}$, and $R^{18d}$ are independently selected from the group consisting of hydrogen, halo, cyano, $C_1$-$C_4$ alkyl, $C_1$-$C_4$ haloalkyl, and $C_1$-$C_4$ alkoxy, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein

B is B-3, or a pharmaceutically acceptable salt or solvate thereof. In another embodiment, $Z^1$ is selected from the group consisting of —O—, —S—, —N(H)—, and —N($CH_3$)—; and $Z^2$ is selected from the group consisting of —C(H)═, —C($CH_3$)═, and —N═.

In another embodiment, Compounds of the Disclosure are compounds of any one of Formulae I-III, III-A, III-B, IV, IV-A, IV-B, V, V-A, or V-B, wherein

B is B-4, or a pharmaceutically acceptable salt or solvate thereof. In another embodiment, $Z^3$ is selected from the group consisting of —O—, —S—, —N(H)—, and —N($CH_3$)—; and $R^{16d}$ is selected from the group consisting of hydrogen and methyl.

In another embodiment, Compounds of the Disclosure are compounds of any one of Formulae I-III, III-A, III-B, IV, IV-A, IV-B, V, V-A, or V-B, wherein

B is B-5, or a pharmaceutically acceptable salt or solvate thereof. In another embodiment, $Z^4$ is selected from the group consisting of —O—, —S—, —N(H)—, and —N($CH_3$)—; and $R^{16f}$ is selected from the group consisting of hydrogen and methyl.

In another embodiment, Compounds of the Disclosure are compounds of any one of Formulae I-III, III-A, III-B, IV, IV-A, IV-B, V, V-A, or V-B, wherein (B)

is B-6, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein (B)

is B-6;
Y is —N=;
$Y^1$ is selected from the group consisting of —C($R^{17b}$)= and —N=;
$Y^2$ is selected from the group consisting of —C($R^{17c}$)= and —N=;
$Y^3$ is selected from the group consisting of —C($R^{17d}$)= and —N=; and
$R^{17b}$, $R^{17c}$, and $R^{17d}$ are independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein (B)

is B-6;
Y is selected from the group consisting of —C($R^{17a}$)= and —N=;
$Y^1$ is —N=;
$Y^2$ is selected from the group consisting of —C($R^{17c}$)= and —N=;
$Y^3$ is selected from the group consisting of —C($R^{17d}$)= and —N=; and
$R^{17a}$, $R^{17c}$, and $R^{17d}$ are independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein (B)

is B-6;
Y is selected from the group consisting of —C($R^{17a}$)= and —N=;
$Y^1$ is selected from the group consisting of —C($R^{17b}$)= and —N=;
$Y^2$ is —N=;
$Y^3$ is selected from the group consisting of —C($R^{17d}$)= and —N=; and
$R^{17a}$, $R^{17b}$, and $R^{17d}$ are independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein (B)

is B-6;
Y is selected from the group consisting of —C($R^{17a}$)= and —N=;
$Y^1$ is selected from the group consisting of —C($R^{17b}$)= and —N=;
$Y^2$ is selected from the group consisting of —C($R^{17c}$)= and —N=;
$Y^3$ is —N=; and
$R^{17a}$, $R^{17b}$, and $R^{17c}$ are independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein (B)

is B-7, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein:

(B)

is B-7;
$Y^4$ is and —N=;
$Y^5$ is selected from the group consisting of —C($R^{18b}$)= and —N=;
$Y^6$ is selected from the group consisting of —C($R^{18c}$)= and —N=;
$Y^7$ is selected from the group consisting of —C($R^{18d}$)= and —N=; and
$R^{18b}$, $R^{18c}$, and $R^{18d}$ are independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein:

(B)

is B-7;
$Y^4$ is selected from the group consisting of —C($R^{18a}$)= and —N=;
$Y^5$ is —N=;
$Y^6$ is selected from the group consisting of —C($R^{18c}$)= and —N=;

$Y^7$ is selected from the group consisting of —C($R^{18d}$)═ and —N═; and $R^{18a}$, $R^{18c}$, and $R^{18d}$ are independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein:

(B)

is B-7;

$Y^4$ is selected from the group consisting of —C($R^{18a}$)═ and —N═;

$Y^5$ is selected from the group consisting of —C($R^{18b}$)═ and —N═;

$Y^6$ is —N═;

$Y^7$ is selected from the group consisting of —C($R^{18d}$)═ and —N═; and $R^{18a}$, $R^{18b}$, and $R^{18d}$ are independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein:

(B)

is B-7;

$Y^4$ is selected from the group consisting of —C($R^{18a}$)═ and —N═;

$Y^5$ is selected from the group consisting of —C($R^{18b}$)═ and —N═;

$Y^6$ is selected from the group consisting of —C($R^{18c}$)═ and —N═;

$Y^7$ is —N═; and $R^{18a}$, $R^{18b}$, and $R^{18c}$ are independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein (B)

is selected from the group consisting of:

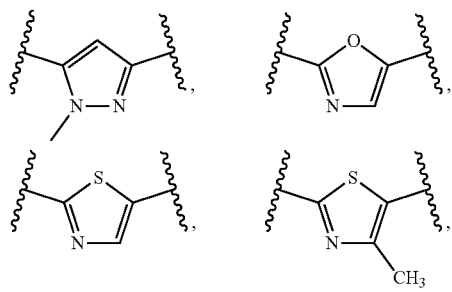

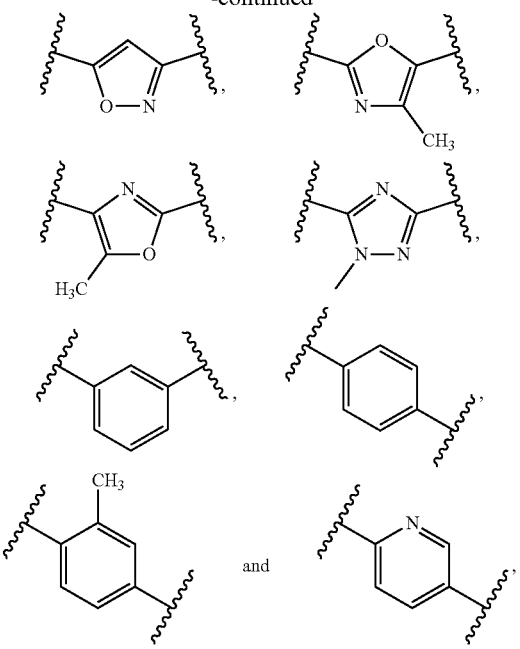

and or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein

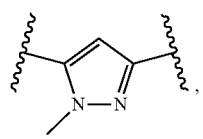 [SMILES: *c1cc(*)n(C)n1]

is:

or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein R is methyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein R is ethyl, or a pharmaceutically acceptable salt or solvate thereof.

In another embodiment, Compounds of the Disclosure are compounds of any one of Formulae I-III, III-A, III-B, IV, IV-A, IV-B, V, V-A, or V-B, wherein R is hydrogen, or a pharmaceutically acceptable salt or solvate thereof.

In another embodiment, Compounds of the Disclosure are compounds of Formulae I selected from group consisting of the compounds of Table 1, or a pharmaceutically acceptable salt or solvate thereof

TABLE 1

| Cpd No. | Structure | Name |
|---|---|---|
| 1 | 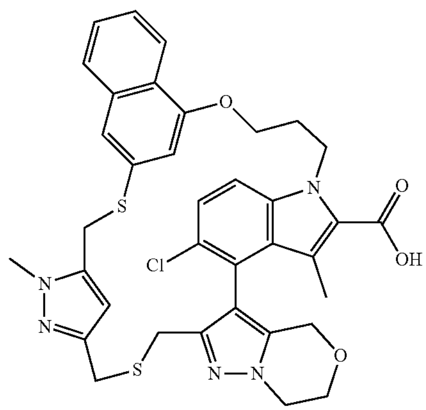 [SMILES: Cc1c(C(=O)O)n2c3ccc(Cl)c(c13)-c1c(nn3c1COCC3)CSCc1cc(n(C)n1)CSc1cc(c3ccccc3c1)OCCC2] | (Z)-1$^5$-chloro-1$^3$,6$^1$-dimethyl-2$^6$,2$^7$-dihydro-1$^1$H,2$^4$H,6$^1$H-10-oxa-4,8-dithia-2(3,2)-pyrazolo[5,1-c][1,4]oxazina-1(4,1)-indola-6(3,5)-pyrazola-9(3,1)-naphthalenacyclotridecaphane-1$^2$-carboxylic acid |
| 2 | 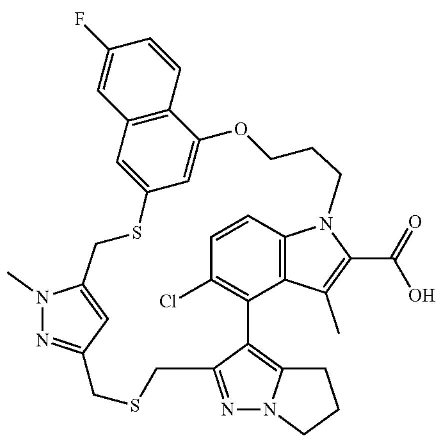 [SMILES: Cc1c(C(=O)O)n2c3ccc(Cl)c(c13)-c1c(nn3c1CCC3)CSCc1cc(n(C)n1)CSc1cc(c3ccc(F)cc3c1)OCCC2] | Z)-1$^5$-chloro-9$^6$-fluoro-1$^3$,6$^1$-dimethyl-2$^5$,2$^6$-dihydro-1$^1$H,2$^4$H,6$^1$H-10-oxa-4,8-dithia-1(4,1)-indola-2(3,2)-pyrrolo[1,2-b]pyrazola-6(3,5)-pyrazola-9(3,1)-naphthalenacyclotridecaphane-1$^2$-carboxylic acid |
| 3 | 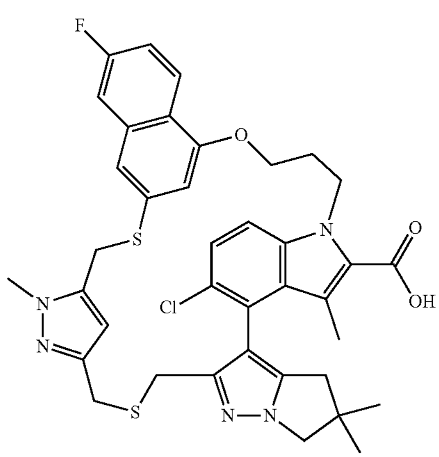 [SMILES: Cc1c(C(=O)O)n2c3ccc(Cl)c(c13)-c1c(nn3c1CC(C)(C)C3)CSCc1cc(n(C)n1)CSc1cc(c3ccc(F)cc3c1)OCCC2] | Z)-1$^5$-chloro-9$^6$-fluoro-1$^3$,2$^5$,2$^5$,6$^1$-tetramethyl-2$^5$,2$^6$-dihydro-1$^1$H,2$^4$H,6$^1$H-10-oxa-4,8-dithia-1(4,1)-indola-2(3,2)-pyrrolo[1,2-b]pyrazola-6(3,5)-pyrazola-9(3,1)-naphthalenacyclotridecaphane-1$^2$-carboxylic acid |

TABLE 1-continued

| Cpd No. | Structure | Name |
|---|---|---|
| 4 | 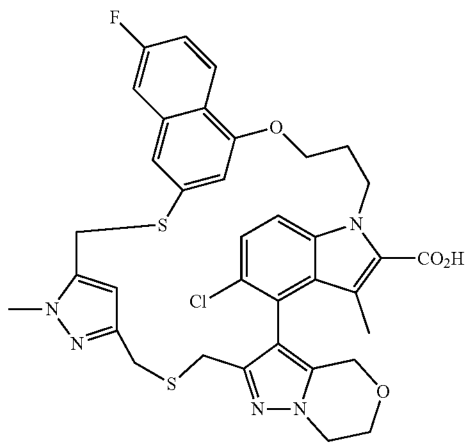 [SMILES: Cc1c(C(=O)O)n2c3ccc(Cl)c(c13)-c1c(nn3c1COCC3)CSCc1cc(n(C)n1)CSc1cc(c3ccc(F)cc3c1)OCCC2] | (Z)-1$^5$-chloro-9$^6$-fluoro-1$^3$,6$^1$-dimethyl-2$^6$,2$^7$-dihydro-1$^1$H,24H,6$^1$H-10-oxa-4,8-dithia-2(3,2)-pyrazolo[5,1-c][1,4]oxazina-1(4,1)-indola-6(3,5)-pyrazola-9(3,1)-naphthalenacyclotridecaphane-1$^2$-carboxylic acid |
| 5 | 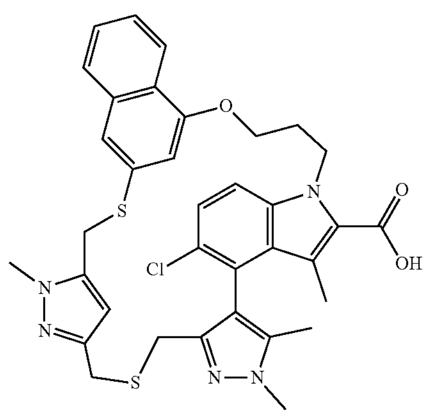 [SMILES: Cc1c(C(=O)O)n2c3ccc(Cl)c(c13)-c1c(nn(C)c1C)CSCc1cc(n(C)n1)CSc1cc(c3ccccc3c1)OCCC2] | (Z)-1$^5$-chloro-1$^3$,2$^1$,2$^5$,6$^1$-tetramethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid |
| 6 | 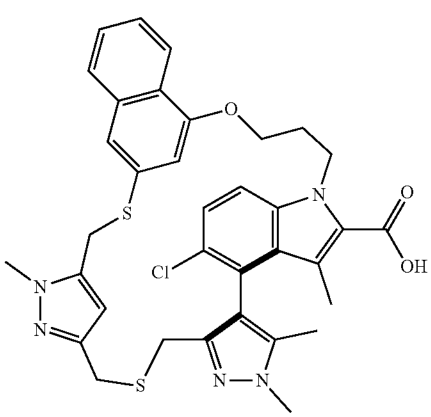 | (R)-(Z)-1$^5$-chloro-1$^3$,2$^1$,2$^5$,6$^1$-tetramethyl-1$^1$H,2$^1$H,6$^1$H-10-oxa-4,8-dithia-1(4,1)-indola-2(4,3),6(3,5)-dipyrazola-(3,1)-naphthalenacyclotridecaphane-1$^2$-carboxylic acid |

TABLE 1-continued

| Cpd No. | Structure | Name |
|---|---|---|
| 7 | 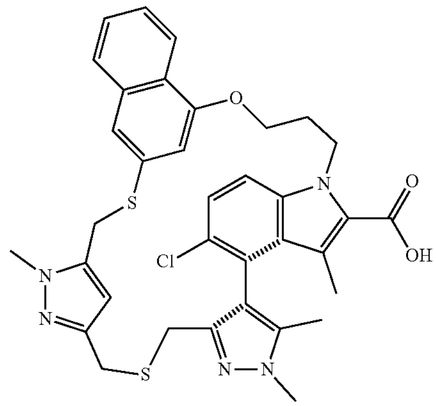 | (S)-(Z)-1⁵-chloro-1³,2¹,2⁵,6¹-tetramethyl-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid |
| 8 | 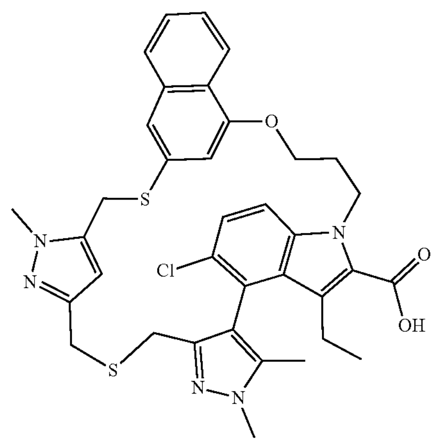 [SMILES: CCc1c(C(=O)O)n2c3ccc(Cl)c(c13)-c1c(nn(C)c1C)CSCc1cc(n(C)n1)CSc1cc(c3ccccc3c1)OCCC2] | (Z)-1⁵-chloro-1³-ethyl-2¹,2⁵,6¹-trimethyl-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid |
| 9 | 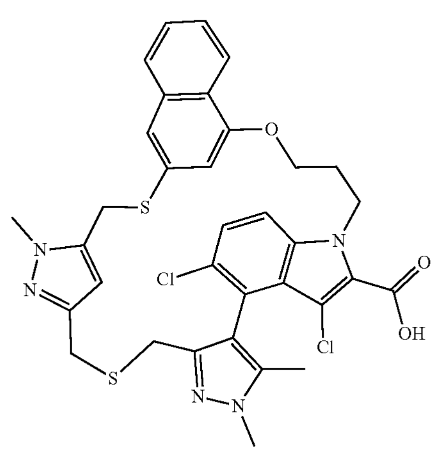 [SMILES: Cc1c2c(nn1C)CSCc1cc(n(C)n1)CSc1cc(c3ccccc3c1)OCCCn1c(C(=O)O)c(Cl)c3c-2c(Cl)ccc31] | (Z)-1³,1⁵-dichloro-2¹,2⁵,6¹-trimethyl-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid |

TABLE 1-continued

| Cpd No. | Structure | Name |
|---|---|---|
| 10 | 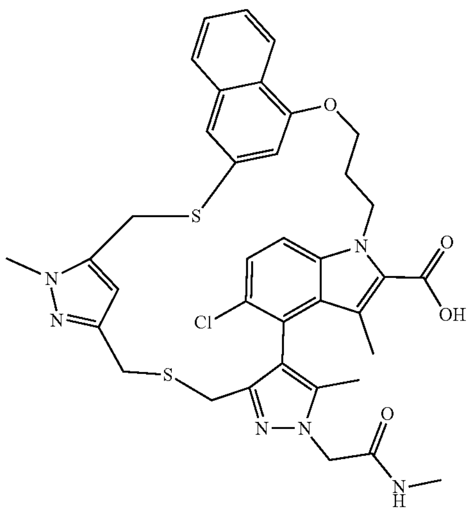 [SMILES: CNC(=O)Cn1nc2c(c1C)-c1c(Cl)ccc3c1c(C)c(C(=O)O)n3CCCOc1cc(cc3ccccc13)SCc1cc(nn1C)CSC2] | (Z)-1$^5$-chloro-1$^3$,2$^5$,6$^1$-trimethyl-2$^1$-(2-(methylamio)-2-oxoethyl)-1$^1$H,2$^1$H,6$^1$H-10-oxa-4,8-dithia-1(4,1)-indola-2(4,3),6(3,5)-dipyrazola-9(3,1)-naphthalenacycotridecaphane-1$^2$-carboxylic acid |
| 11 | 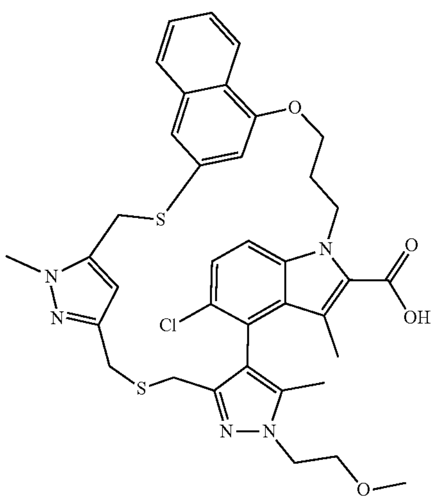 [SMILES: COCCn1nc2c(c1C)-c1c(Cl)ccc3c1c(C)c(C(=O)O)n3CCCOc1cc(cc3ccccc13)SCc1cc(nn1C)CSC2] | (Z)-1$^5$-chloro-2$^1$-(2-methoxyethyl)-1$^3$,2$^5$,6$^1$-trimethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid |
| 12 | 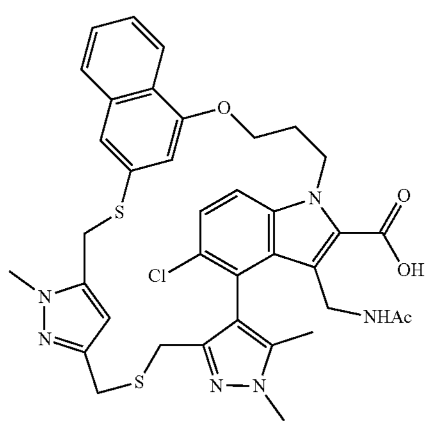 [SMILES: CC(=O)NCc1c(C(=O)O)n2c3ccc(Cl)c(c13)-c1c(nn(C)c1C)CSCc1cc(n(C)n1)CSc1cc(c3ccccc3c1)OCCC2] | (Z)-1$^3$-(acetamidomethyl)-1$^5$-chloro-2$^1$,2$^5$,6$^1$-trimethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid |

TABLE 1-continued

| Cpd No. | Structure | Name |
|---|---|---|
| 13 | 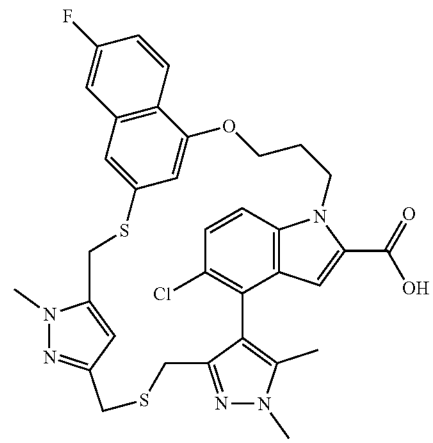 [SMILES: Cc1c2c(nn1C)CSCc1cc(n(C)n1)CSc1cc(c3ccc(F)cc3c1)OCCCn1c(C(=O)O)cc3c-2c(Cl)ccc31] | (Z)-1$^5$-chloro-9$^6$-fluoro-2$^1$,2$^5$,6$^1$-trimethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid |
| 14 | 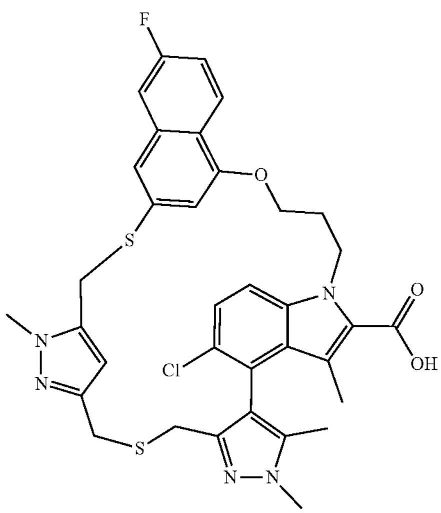 [SMILES: Cc1c(C(=O)O)n2c3ccc(Cl)c(c13)-c1c(nn(C)c1C)CSCc1cc(n(C)n1)CSc1cc(c3ccc(F)cc3c1)OCCC2] | (Z)-1$^5$-chloro-9$^6$-fluoro-1$^3$,2$^1$,2$^5$,6$^1$-tetramethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid |
| 15 | 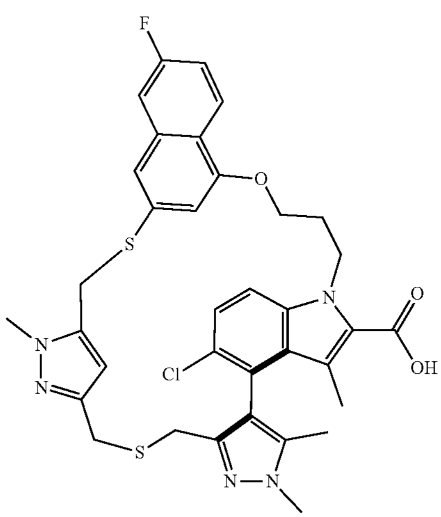 | (R)-(Z)-1$^5$-chloro-9$^6$-fluoro-1$^3$,2$^1$,2$^5$,6$^1$-tetramethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid |

TABLE 1-continued

| Cpd No. | Structure | Name |
|---|---|---|
| 16 | 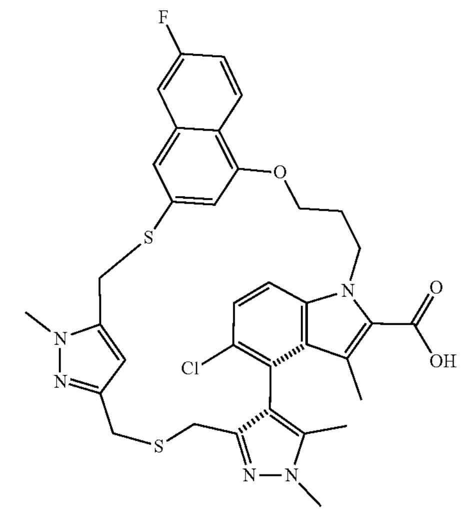 | (S)-(Z)-$1^5$-chloro-$9^6$-fluoro-$1^3,2^1,2^5,6^1$-tetramethyl-$1^1H,2^1H,6^1H$-10-oxa-4,8-dithia-1(4,1)-indola-2(4,3),6(3,5)-dipyrazola-9(3,1)-naphthalenacyclotridecaphane-$1^2$-carboxylic acid |
| 17 | 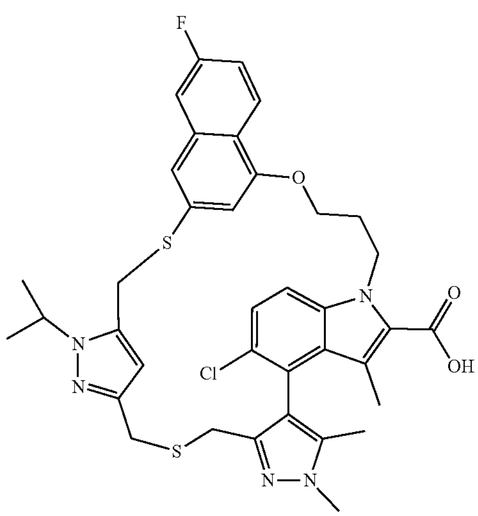 [SMILES: Cc1c(C(=O)O)n2c3ccc(Cl)c(c13)-c1c(nn(C)c1C)CSCc1cc(n(C(C)C)n1)CSc1cc(c3ccc(F)cc3c1)OCCC2] | (Z)-$1^5$-chloro-$9^6$-fluoro-$6^1$-isopropyl-$1^3,2^1,2^5$-trimethyl-$1^1H,2^1H,6^1H$-10-oxa-4,8-dithia-1(4,1)-indola-2(4,3),6(3,5)-dipyrazola-9(3,1)-naphthalenacyclotridecaphane-$1^2$-carboxylic acid |
| 18 | 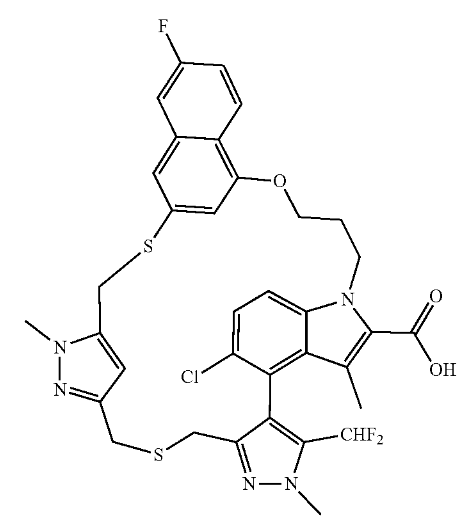 [SMILES: Cc1c(C(=O)O)n2c3ccc(Cl)c(c13)-c1c(nn(C)c1C(F)F)CSCc1cc(n(C)n1)CSc1cc(c3ccc(F)cc3c1)OCCC2] | (Z)-$1^5$-chloro-$2^5$-(difluoromethyl)-$9^6$-fluoro-$1^3,2^1,6^1$-trimethyl-$1^1H,2^1H,6^1H$-10-oxa-4,8-dithia-1(4,1)-indola-2(4,3),6(3,5)-dipyrazola-9(3,1)-naphthalenacyclotridecaphane-$1^2$-carboxylic acid |

TABLE 1-continued

| Cpd No. | Structure | Name |
|---|---|---|
| 19 | 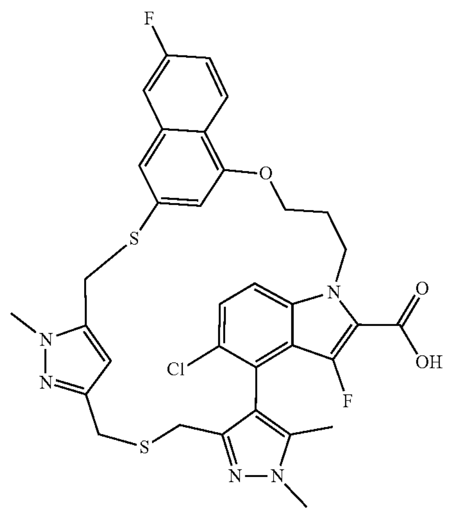 | (Z)-1$^5$-chloro-1$^3$,9$^6$-difluoro-2$^1$,2$^5$,6$^1$-trimethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid |
| 20 | 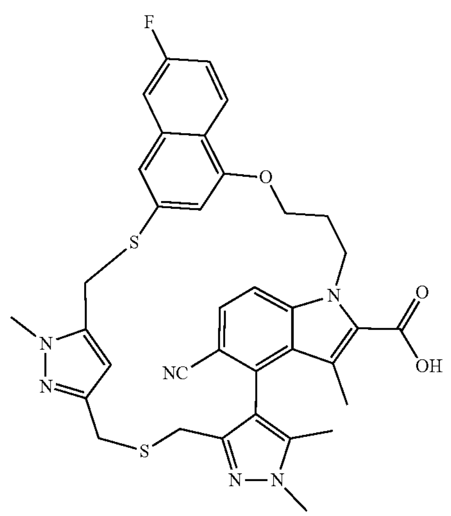 | (Z)-1$^5$-cyano-9$^6$-fluoro-1$^3$,2$^1$,2$^5$,6$^1$-tetramethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboyxlic acid |
| 21 | 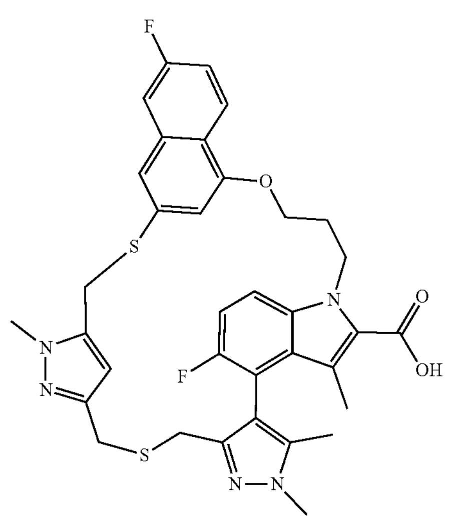 | (Z)-1$^5$,9$^6$-difluoro-1$^3$,2$^1$,2$^5$,6$^1$-tetramethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid |

TABLE 1-continued

| Cpd No. | Structure | Name |
|---|---|---|
| 22 | 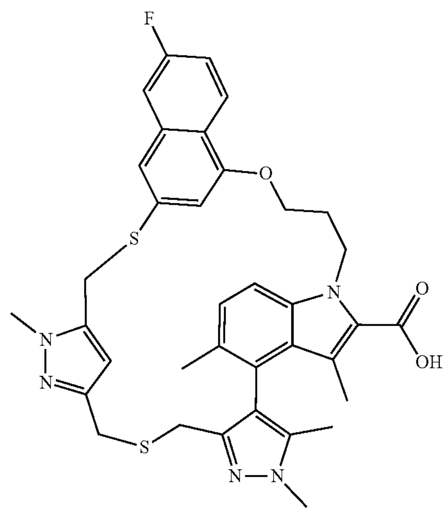 | (Z)-9⁶-fluoro-1³,1⁵,2¹,2⁵,6¹-pentamethyl-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid |
| 23 | 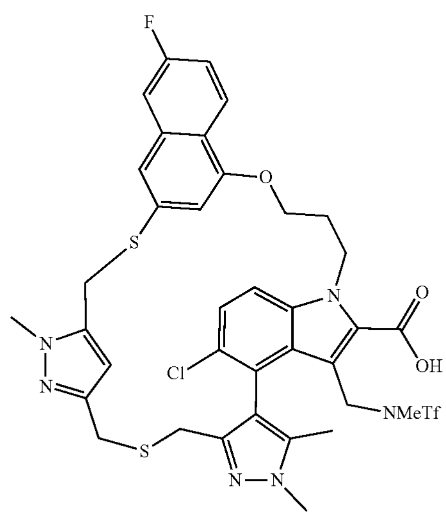 | (Z)-1⁵-chloro-9⁶-fluoro-2¹,2⁵,6¹-trimethyl-1³-(((1,1,1-trifluoro-N-methylmethyl)sulfonamido)methyl)-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid |
| 24 | 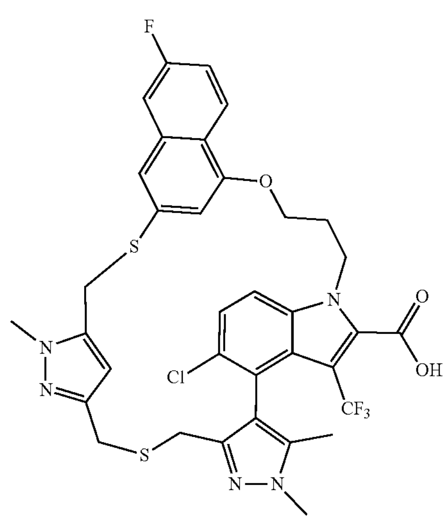 | (Z)-1⁵-chloro-9⁶-fluoro-2¹,2⁵,6¹-trimethyl-1³-(trifluoromethyl)-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid |

TABLE 1-continued

| Cpd No. | Structure | Name |
|---|---|---|
| 25 | 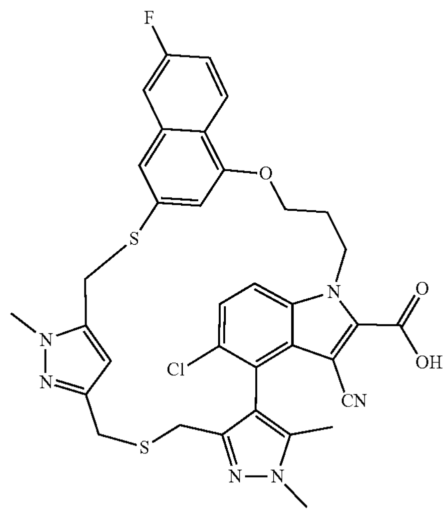 [SMILES: Cc1c2c(nn1C)CSCc1cc(n(C)n1)CSc1cc(c3ccc(F)cc3c1)OCCCn1c(C(=O)O)c(C#N)c3c-2c(Cl)ccc31] | (Z)-1$^5$-chloro-1$^3$-cyano-9$^6$-fluoro-2$^1$,2$^5$,6$^1$-trimethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid |
| 26 | 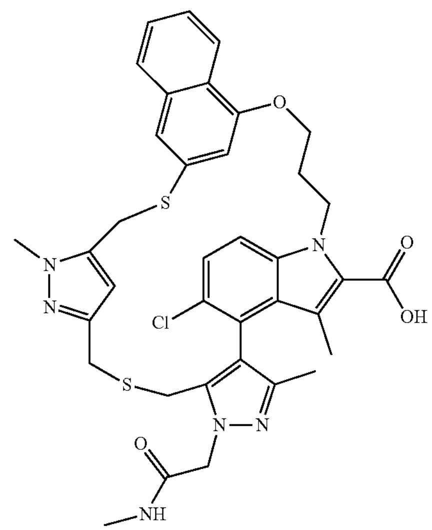 [SMILES: CNC(=O)Cn1nc(C)c2c1CSCc1cc(n(C)n1)CSc1cc(c3ccccc3c1)OCCCn1c(C(=O)O)c(C)c3c-2c(Cl)ccc31] | Z)-1$^5$-chloro-1$^3$,2$^3$,6$^1$-trimethyl-2$^1$-(2-(methylamino)-2-oxoethyl)-1$^1$H,2$^1$H,6$^1$H-10-oxa-4,8-dithia-1(4,1)-indola-2(4,5),6(3,5)-dipyrazola-9(3,1)-naphthalenacyclotridecaphane-1$^2$-carboxylic acid |
| 27 | 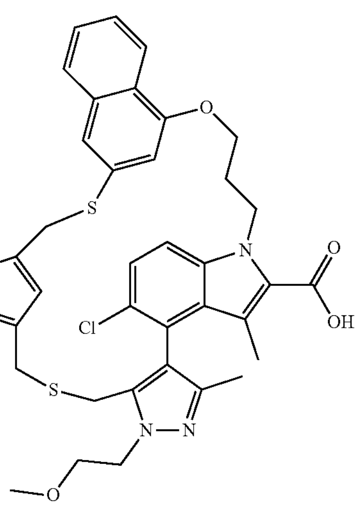 | (Z)-1$^5$-chloro-2$^1$-(2-methoxyethyl)-1$^3$,2$^3$,6$^1$-trimethyl-1$^1$H,2$^1$H,6$^1$H-10-oxa-4,8-dithia-1(4,1)-indola-2(4,5),6(3,5)-dipyrazola-9(3,1)-naphthalenacyclotridecaphane-1$^2$-carboxylic acid |

TABLE 1-continued

| Cpd No. | Structure | Name |
|---|---|---|
| 28 | 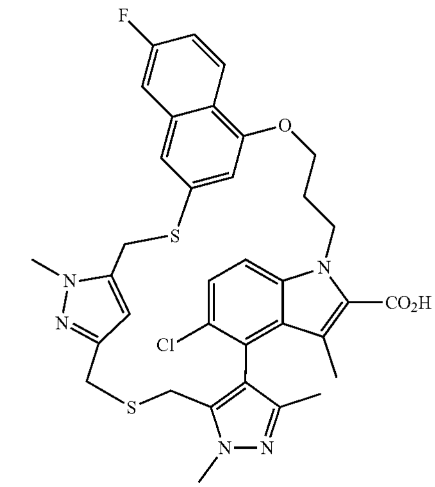 [SMILES: Cc1nn(C)c2c1-c1c(Cl)ccc3c1c(C)c(C(=O)O)n3CCCOc1cc(cc3cc(F)ccc13)SCc1cc(nn1C)CSC2] | (Z)-1$^5$-chloro-9$^6$-fluoro-1$^3$,2$^1$,2$^3$,6$^1$-tetramethyl-1$^1$H,2$^1$H,6$^1$H-10-oxa-4,8-dithia-1(4,1)-indola-2(4,5),6(3,5)-dipyrazola-9(3,1)-naphthalenacyclotridecaphane-1$^2$-carboxylic acid |
| 29 | 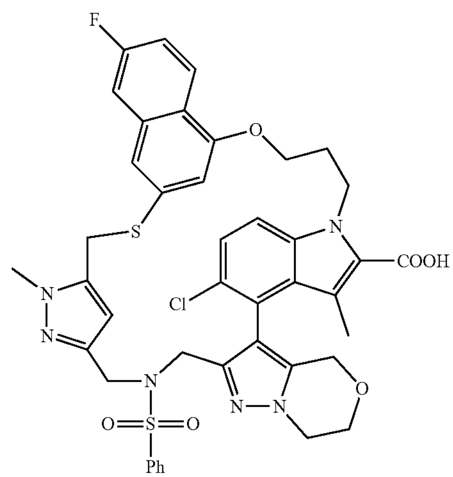 [SMILES: Cc1c(C(=O)O)n2c3ccc(Cl)c(c13)-c1c(nn3c1COCC3)CN(S(=O)(=O)c1ccccc1)Cc1cc(n(C)n1)CSc1cc(c3ccc(F)cc3c1)OCCC2] | (Z)-1$^5$-chloro-9$^6$-fluoro-1$^3$,6$^1$-dimethyl-4-(phenylsulfonyl)-26,27-dihydro-1$^1$H,2$^4$H,6$^1$H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1$^2$-carboxylic acid |
| 29A | 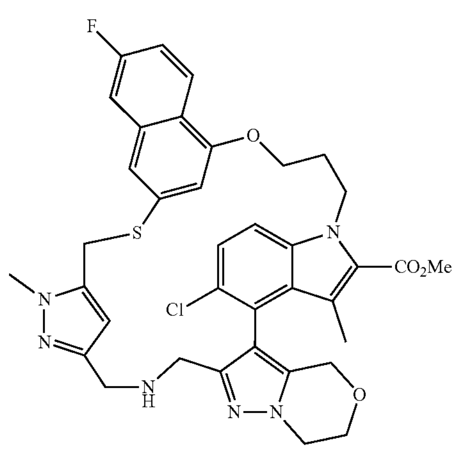 [SMILES: COC(=O)c1c(C)c2c3c(Cl)ccc2n1CCCOc1cc(cc2cc(F)ccc12)SCc1cc(nn1C)CNCc1nn2c(c1-3)COCC2] | Methyl (Z)-1$^5$-chloro-9$^6$-fluoro-1$^3$,6$^1$-dimethyl-2$^6$,2$^7$-dihydro-1$^1$H,2$^4$H,6$^1$H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1$^2$-carboxylate |

TABLE 1-continued

| Cpd No. | Structure | Name |
|---|---|---|
| 29B | 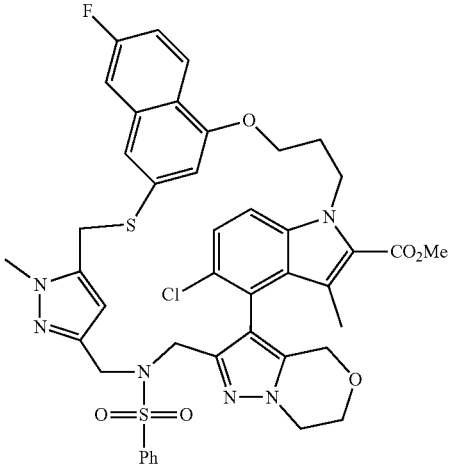 [SMILES: COC(=O)c1c(C)c2c3c(Cl)ccc2n1CCCOc1cc(cc2cc(F)ccc12)SCc1cc(nn1C)CN(S(=O)(=O)c1ccccc1)Cc1nn2c(c1-3)COCC2] | Methyl (Z)-$1^5$-chloro-$9^6$-fluoro-$1^3$,$6^1$-dimethyl-4-(phenylsulfonyl)-$2^6$,$2^7$-dihydro-$1^1$H,$2^4$H,$6^1$H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-$1^2$-carboxylate |
| 30 | 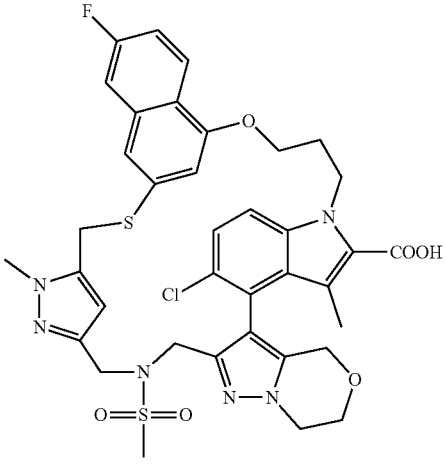 [SMILES: Cc1c(C(=O)O)n2c3ccc(Cl)c(c13)-c1c(nn3c1COCC3)CN(S(C)(=O)=O)Cc1cc(n(C)n1)CSc1cc(c3ccc(F)cc3c1)OCCC2] | (Z)-$1^5$-chloro-$9^6$-fluoro-$1^3$,$6^1$-dimethyl-4-(methylsulfonyl)-$2^6$,$2^7$-dihydro-$1^1$H,$2^4$H,$6^1$H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-$1^2$-carboxylic acid |
| 30A | 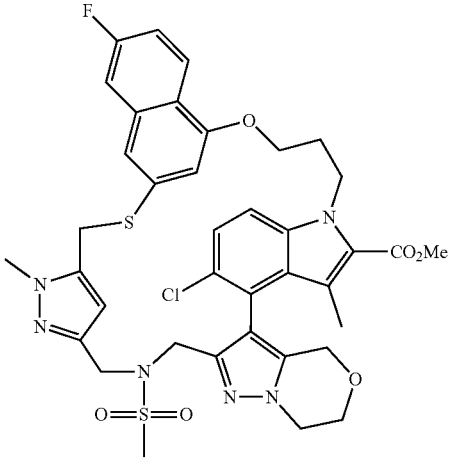 [SMILES: COC(=O)c1c(C)c2c3c(Cl)ccc2n1CCCOc1cc(cc2cc(F)ccc12)SCc1cc(nn1C)CN(S(C)(=O)=O)Cc1nn2c(c1-3)COCC2] | Methyl (Z)-$1^5$-chloro-$9^6$-fluoro-4-(isopropylsulfonyl)-$1^3$,$6^1$-dimethyl-$2^6$,$2^7$-dihydro-$1^1$H,$2^4$H,$6^1$H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-$1^2$-carboxylate |

TABLE 1-continued

| Cpd No. | Structure | Name |
|---|---|---|
| 31 | 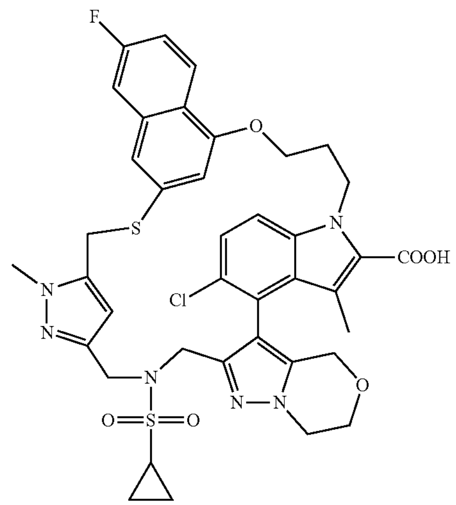 [SMILES: Cc1c(C(=O)O)n2c3ccc(Cl)c(c13)-c1c(nn3c1COCC3)CN(S(=O)(=O)C1CC1)Cc1cc(n(C)n1)CSc1cc(c3ccc(F)cc3c1)OCCC2] | (Z)-1⁵-chloro-4-(cyclopropylsulfonyl)-9⁶-fluoro-1³,6¹-dimethyl-2⁶,2⁷-dihydro-1¹H,2⁴H,6¹H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1²-carboxylic acid |
| 31A | 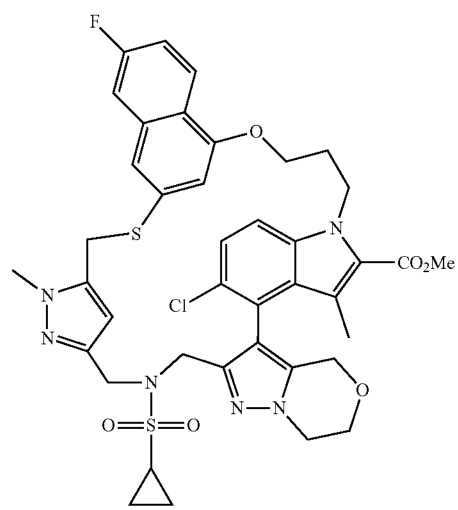 [SMILES: COC(=O)c1c(C)c2c3c(Cl)ccc2n1CCCOc1cc(cc2cc(F)ccc12)SCc1cc(nn1C)CN(S(=O)(=O)C1CC1)Cc1nn2c(c1-3)COCC2] | Methyl (Z)-1⁵-chloro-4-(cyclopropylsulfonyl)-9⁶-fluoro-1³,6¹-dimethyl-2⁶,2⁷-dihydro-1¹H,2⁴H,6¹H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1²-carboxylate |
| 32 | 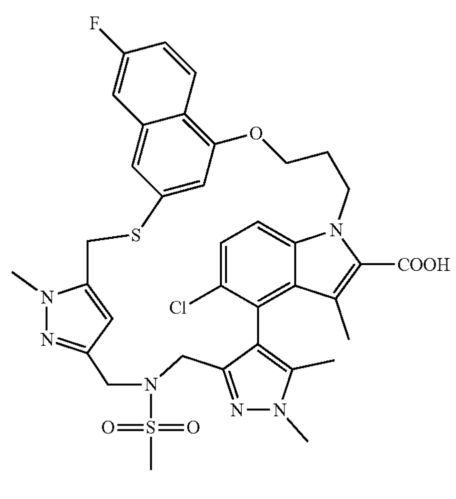 [SMILES: Cc1c(C(=O)O)n2c3ccc(Cl)c(c13)-c1c(nn(C)c1C)CN(S(C)(=O)=O)Cc1cc(n(C)n1)CSc1cc(c3ccc(F)cc3c1)OCCC2] | (Z)-1⁵-chloro-9⁶-fluoro-1³,2¹,2⁵,6¹-tetramethyl-4-(methylsulfonyl)-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |

TABLE 1-continued

| Cpd No. | Structure | Name |
|---|---|---|
| 32A | 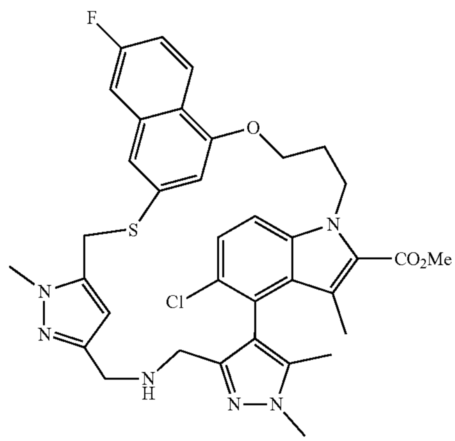 [SMILES: COC(=O)c1c(C)c2c3c(Cl)ccc2n1CCCOc1cc(cc2cc(F)ccc12)SCc1cc(nn1C)CNCc1nn(C)c(C)c1-3] | Methyl (Z)-1$^5$-chloro-9$^6$-fluoro-1$^3$,2$^1$,2$^5$,6$^1$-tetramethyl-1$^1$H,2$^1$H,6$^1$H-10-oxa-8-thia-4-aza-1(4,1)-indola-2(4,3),6(3,5)-dipyrazola-9(3,1)-naphthalenacyclotrideca-phane-1$^2$-carboxylate |
| 32B | 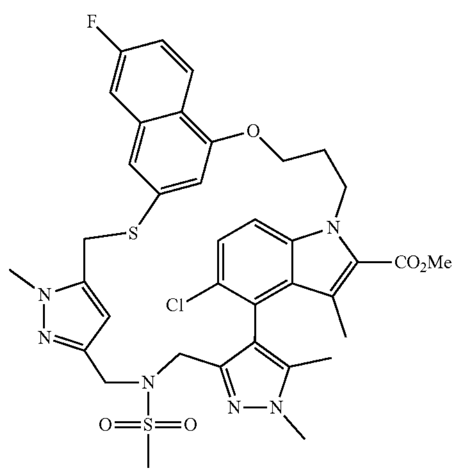 [SMILES: COC(=O)c1c(C)c2c3c(Cl)ccc2n1CCCOc1cc(cc2cc(F)ccc12)SCc1cc(nn1C)CN(S(C)(=O)=O)Cc1nn(C)c(C)c1-3] | methyl (Z)-1$^5$-chloro-9$^6$-fluoro-1$^3$,2$^1$,2$^5$,6$^1$-tetramethyl-4-(methylsulfonyl)-1$^1$H,2$^1$H,6$^1$H-10-oxa-8-thia-4-aza-1(4,1)-indola-2(4,3),6(3,5)-dipyrazola-9(3,1)-naphthalenacyclotridecaphane-1$^2$-carboxylate |
| 33 | 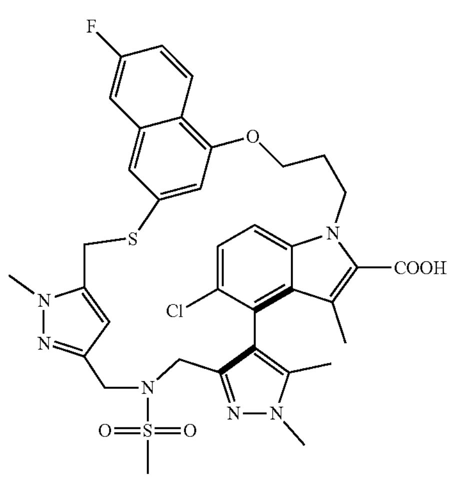 | (R)-(Z)-1$^5$-chloro-9$^6$-fluoro-1$^3$,2$^1$,2$^5$,6$^1$-tetramethyl-4-(methylsulfonyl)-1$^1$H,2$^1$H,6$^1$H-10-oxa-8-thia-4-aza-1(4,1)-indola-2(4,3),6(3,5)-dipyrazola-9(3,1)-naphthalenacyclotridecaphane-1$^2$-carboxylic acid |

TABLE 1-continued

| Cpd No. | Structure | Name |
|---|---|---|
| 34 | 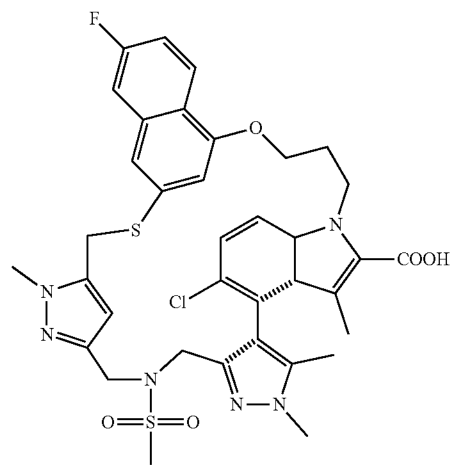 | (S)-(Z)-1$^5$-chloro-9$^6$-fluoro-1$^3$,2$^1$,2$^5$,6$^1$-tetramethyl-4-(methylsulfonyl)-1$^1$H,2$^1$H,6$^1$H-10-oxa-8-thia-4-aza-1(4,1)-indola-2(4,3),6(3,5)-dipyrazola-9(3,1)-naphthalenacyclotridecaphane-1$^2$-carboxylate |
| 35 | 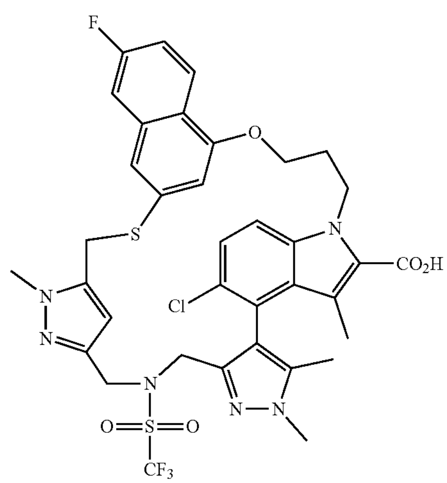 [SMILES: Cc1c(C(=O)O)n2c3ccc(Cl)c(c13)-c1c(nn(C)c1C)CN(S(=O)(=O)C(F)(F)F)Cc1cc(n(C)n1)CSc1cc(c3ccc(F)cc3c1)OCCC2] | (Z)-1$^5$-chloro-9$^6$-fluoro-1$^3$,2$^1$,2$^5$,6$^1$-tetramethyl-4-((trifluoromethyl)sulfonyl)-1$^1$H,2$^1$H,6$^1$H-10-oxa-8-thia-4-aza-1(4,1)-indola-2(4,3),6(3,5)-dipyrazola-9(3,1)-naphthalenacyclotridecaphane-1$^2$-carboxylic acid |
| 36 | 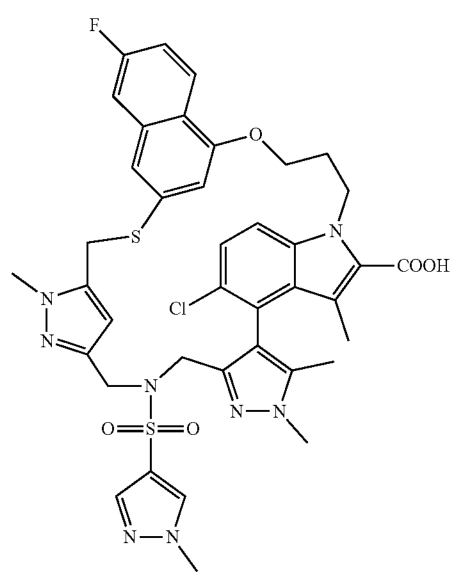 [SMILES: Cc1c(C(=O)O)n2c3ccc(Cl)c(c13)-c1c(nn(C)c1C)CN(S(=O)(=O)c1cnn(C)c1)Cc1cc(n(C)n1)CSc1cc(c3ccc(F)cc3c1)OCCC2] | (Z)-1$^5$-chloro-9$^6$-fluoro-1$^3$,2$^1$,2$^5$,6$^1$-tetramethyl-4-((1-methyl-1H-pyrazol-4-yl)sulfonyl)-1$^1$H,2$^1$H,6$^1$H-10-oxa-8-thia-4-aza-1(4,1)-indola-2(4,3),6(3,5)-dipyrazola-9(3,1)-naphthalenacyclotridecaphane-1$^2$-carboxylic acid |

TABLE 1-continued

| Cpd No. | Structure | Name |
|---|---|---|
| 37 | 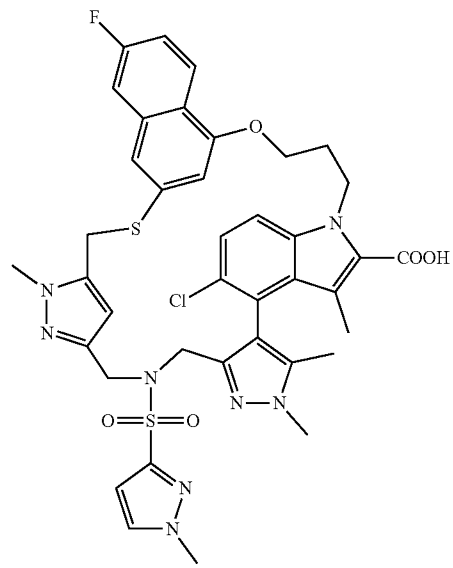 [SMILES: Cc1c(C(=O)O)n2c3ccc(Cl)c(c13)-c1c(nn(C)c1C)CN(S(=O)(=O)c1ccn(C)n1)Cc1cc(n(C)n1)CSc1cc(c3ccc(F)cc3c1)OCCC2] | (Z)-1⁵-chloro-9⁶-fluoro-1³,2¹,2⁵,6¹-tetramethyl-4-((1-methyl-1H-pyrazol-3-yl))sulfonyl)-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |
| 38 | 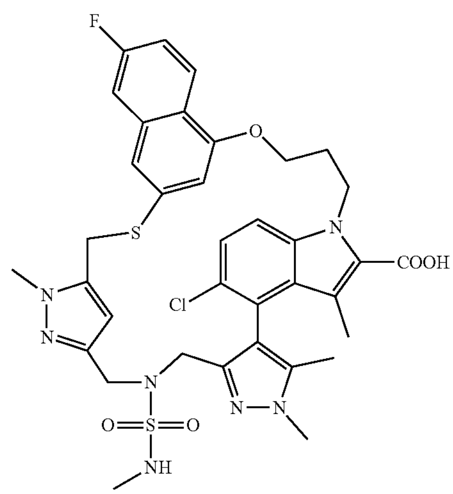 [SMILES: CNS(=O)(=O)N1Cc2cc(n(C)n2)CSc2cc(c3ccc(F)cc3c2)OCCCn2c(C(=O)O)c(C)c3c(c(Cl)ccc32)-c2c(nn(C)c2C)C1] | (Z)-1⁵-chloro-9⁶-fluoro-1³,2¹,2⁵,6¹-tetramethyl-4-(N-methylsulfamoyl)-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |
| 39 | 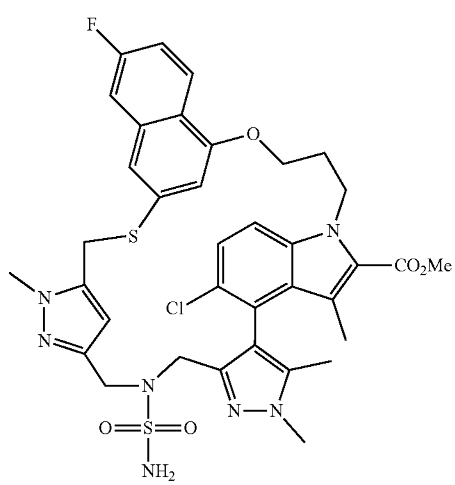 [SMILES: COC(=O)c1c(C)c2c3c(Cl)ccc2n1CCCOc1cc(cc2cc(F)ccc12)SCc1cc(nn1C)CN(S(N)(=O)=O)Cc1nn(C)c(C)c1-3] | (Z)-1⁵-chloro-9⁶-fluoro-1³,2¹,2⁵,6¹-tetramethyl-4-sulfamoyl-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |

TABLE 1-continued

| Cpd No. | Structure | Name |
|---|---|---|
| 40 | 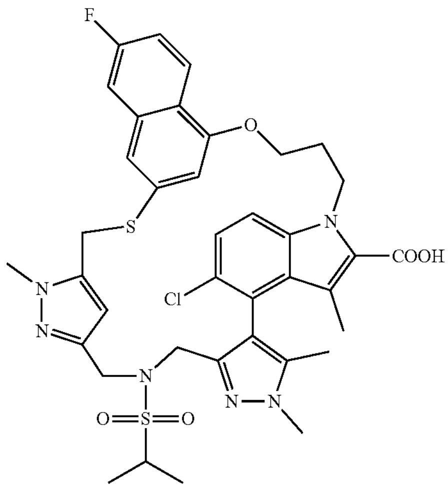 [SMILES: Cc1c(C(=O)O)n2c3ccc(Cl)c(c13)-c1c(nn(C)c1C)CN(S(=O)(=O)C(C)C)Cc1cc(n(C)n1)CSc1cc(c3ccc(F)cc3c1)OCCC2] | (Z)-1⁵-chloro-9⁶-fluoro-1³,2¹,2⁵,6¹-tetramethyl-4-(N,N-dimethylsulfamoyl)-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |
| 41 | 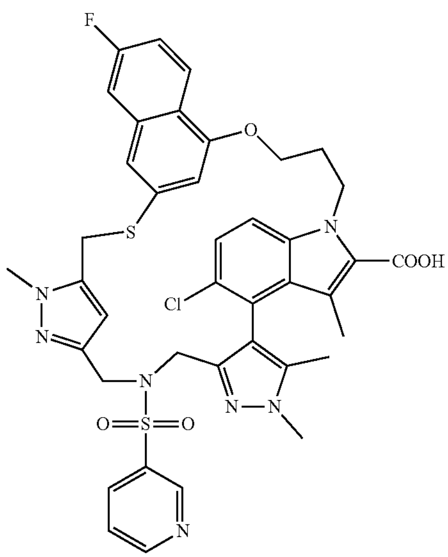 [SMILES: Cc1c(C(=O)O)n2c3ccc(Cl)c(c13)-c1c(nn(C)c1C)CN(S(=O)(=O)c1cccnc1)Cc1cc(n(C)n1)CSc1cc(c3ccc(F)cc3c1)OCCC2] | (Z)-1⁵-chloro-9⁶-fluoro-1³,2¹,2⁵,6¹-tetramethyl-4-(pyridin-3-ylsulfonyl)-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |
| 42 | 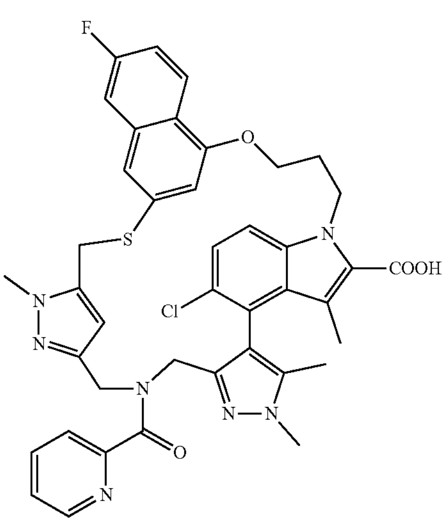 [SMILES: Cc1c(C(=O)O)n2c3ccc(Cl)c(c13)-c1c(nn(C)c1C)CN(C(=O)c1ccccn1)Cc1cc(n(C)n1)CSc1cc(c3ccc(F)cc3c1)OCCC2] | (Z)-1⁵-chloro-9⁶-fluoro-1³,2¹,2⁵,6¹-tetramethyl-4-picolinoyl-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |

TABLE 1-continued

| Cpd No. | Structure | Name |
|---|---|---|
| 43 | 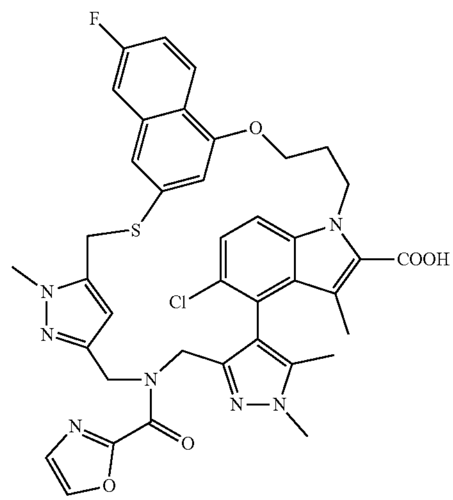 [SMILES: Cc1c(C(=O)O)n2c3ccc(Cl)c(c13)-c1c(nn(C)c1C)CN(C(=O)c1ncco1)Cc1cc(n(C)n1)CSc1cc(c3ccc(F)cc3c1)OCCC2] | (Z)-1⁵-chloro-9⁶-fluoro-1³,2¹,2⁵,6¹-tetramethyl-4-(oxazole-2-carbonyl)-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |
| 44 | 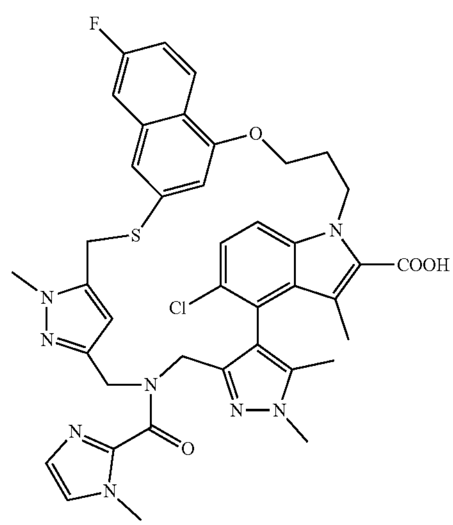 [SMILES: Cc1c(C(=O)O)n2c3ccc(Cl)c(c13)-c1c(nn(C)c1C)CN(C(=O)c1nccn1C)Cc1cc(n(C)n1)CSc1cc(c3ccc(F)cc3c1)OCCC2] | (Z)-1⁵-chloro-9⁶-fluoro-1³,2¹,2⁵,6¹-tetramethyl-4-(1-methyl-1H-imidazole-2-carbonyl)-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |
| 45 | 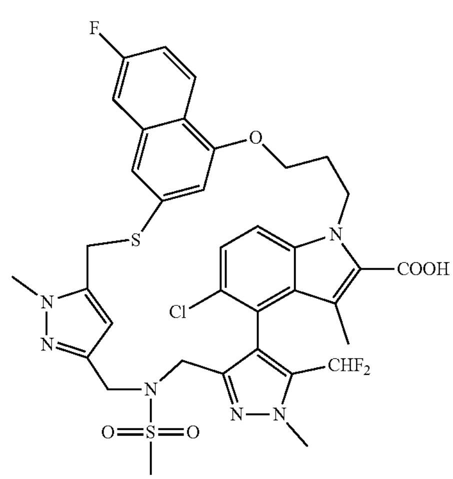 [SMILES: Cc1c(C(=O)O)n2c3ccc(Cl)c(c13)-c1c(nn(C)c1C(F)F)CN(S(C)(=O)=O)Cc1cc(n(C)n1)CSc1cc(c3ccc(F)cc3c1)OCCC2] | (Z)-1⁵-chloro-2⁵-(difluoromethyl)-9⁶-fluoro-1³,2¹,6¹-trimethyl-4-(methylsulfonyl)-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |

TABLE 1-continued

| Cpd No. | Structure | Name |
|---|---|---|
| 46 | 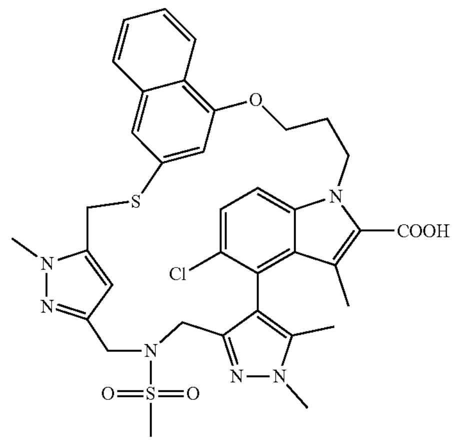 [SMILES: Cc1c(C(=O)O)n2c3ccc(Cl)c(c13)-c1c(nn(C)c1C)CN(S(C)(=O)=O)Cc1cc(n(C)n1)CSc1cc(c3ccccc3c1)OCCC2] | (Z)-1⁵-chloro-1³,2¹,2⁵,6¹-tetramethyl-4-(methylsulfonyl)-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |
| 47 | 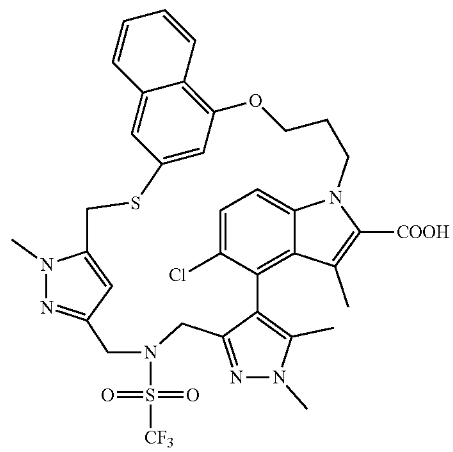 [SMILES: Cc1c(C(=O)O)n2c3ccc(Cl)c(c13)-c1c(nn(C)c1C)CN(S(=O)(=O)C(F)(F)F)Cc1cc(n(C)n1)CSc1cc(c3ccccc3c1)OCCC2] | (Z)-1⁵-chloro-1³,2¹,2⁵,6¹-tetramethyl-4-((trifluoromethyl)sulfonyl)-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |
| 48 | 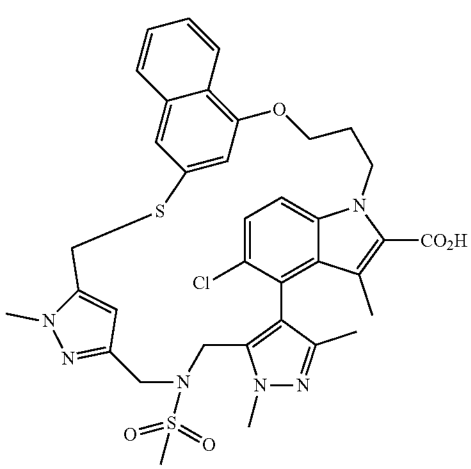 [SMILES: Cc1nn(C)c2c1-c1c(Cl)ccc3c1c(C)c(C(=O)O)n3CCCOc1cc(cc3ccccc13)SCc1cc(nn1C)CN(S(C)(=O)=O)C2] | (Z)-1⁵-chloro-1³,2¹,2³,6¹-tetramethyl-4-(methylsulfonyl)-1¹H,2¹H,6¹H-10-oxa-8-thia-4-aza-1(4,1)-indola-2(4,5),6(3,5)-dipyrazola-9(3,1)-naphthalenacyclotridecaphane-1²-carboxylic acid |

TABLE 1-continued

| Cpd No. | Structure | Name |
|---|---|---|
| 49 | 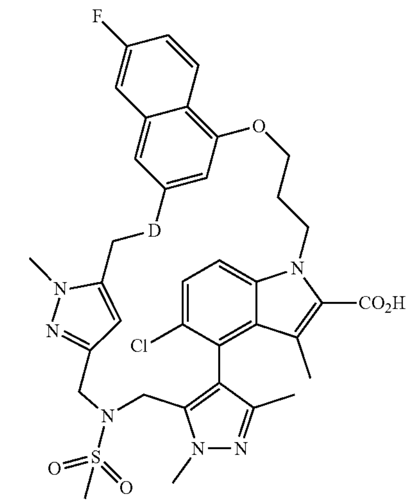 | (Z)-1⁵-chloro-9⁶-fluoro-1³,2¹,2³,6¹-tetramethyl-4-(methylsulfonyl)-1¹H,2¹H,6¹H-10-oxa-8-thia-4-aza-1(4,1)-indola-2(4,5),6(3,5)-dipyrazola-9(3,1)-naphthalenacyclotridecaphane-1²-carboxylic acid |
| 50 | 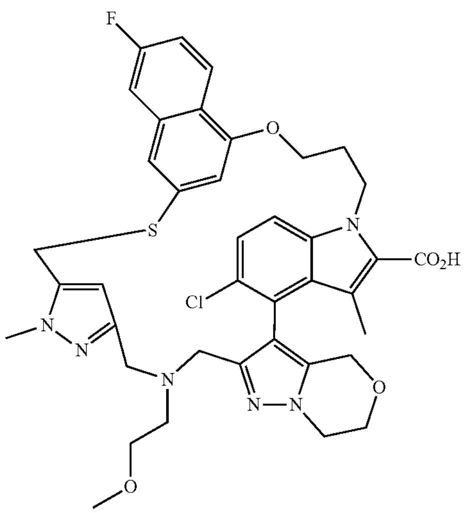 [SMILES: COCCN1Cc2cc(n(C)n2)CSc2cc(c3ccc(F)cc3c2)OCCCn2c(C(=O)O)c(C)c3c(c(Cl)ccc32)-c2c(nn3c2COCC3)C1] | (Z)-1⁵-chloro-9⁶-fluoro-4-(2-methoxyethyl)-1³,6¹-dimethyl-2⁶,2⁷-dihydro-1¹H,2⁴H,6¹H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1²-carboxylic acid |
| 51 | 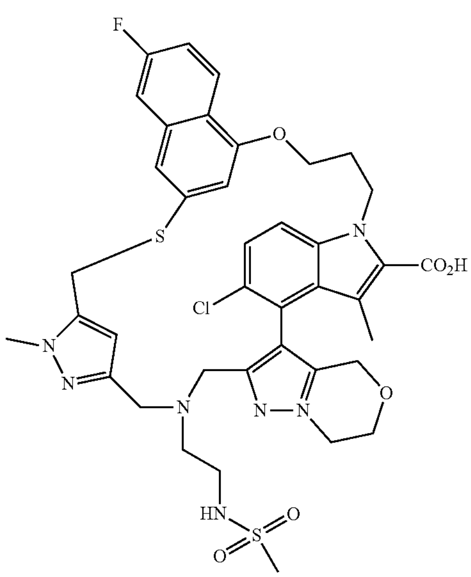 | (Z)-1⁵-chloro-9⁶-fluoro-1³,6¹-dimethyl-4-(2-(methylsulfonamido)ethyl)-26,27-dihydro-1¹H,2⁴H,6¹H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1²-carboxylic acid |

TABLE 1-continued

| Cpd No. | Structure | Name |
|---|---|---|
| 52 | 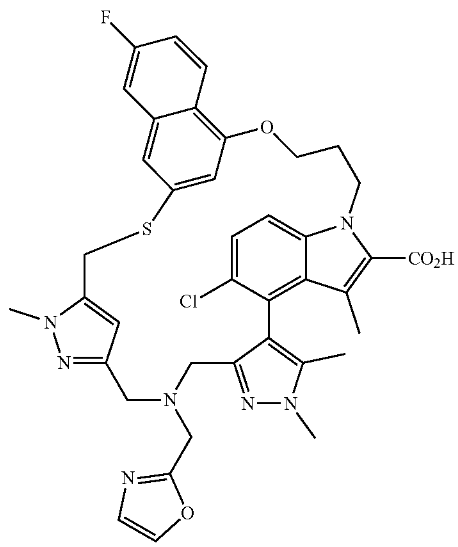 [SMILES: Cc1c(C(=O)O)n2c3ccc(Cl)c(c13)-c1c(nn(C)c1C)CN(Cc1ncco1)Cc1cc(n(C)n1)CSc1cc(c3ccc(F)cc3c1)OCCC2] | (Z)-1$^5$-chloro-9$^6$-fluoro-1$^3$,2$^1$,2$^5$,6$^1$-tetramethyl-4-(oxazol-2-ylmethyl)-1$^1$H,2$^1$H,6$^1$H-10-oxa-8-thia-4-aza-1(4,1)-indola-2(4,3),6(3,5)-dipyrazola-9(3,1)-naphthalenacyclotridecaphane-1$^2$-carboxylic acid |
| 53 | 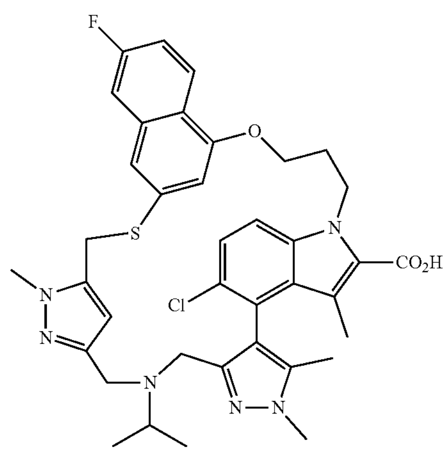 [SMILES: Cc1c(C(=O)O)n2c3ccc(Cl)c(c13)-c1c(nn(C)c1C)CN(C(C)C)Cc1cc(n(C)n1)CSc1cc(c3ccc(F)cc3c1)OCCC2] | (Z)-1$^5$-chloro-9$^6$-fluoro-4-isopropyl-1$^3$,2$^1$,2$^5$,6$^1$-tetramethyl-1$^1$H,2$^1$H,6$^1$H-10-oxa-8-thia-4-aza-1(4,1)-indola-2(4,3),6(3,5)-dipyrazola-9(3,1)-naphthalenacyclotridecaphane-1$^2$-carboxylic acid |
| 54 | 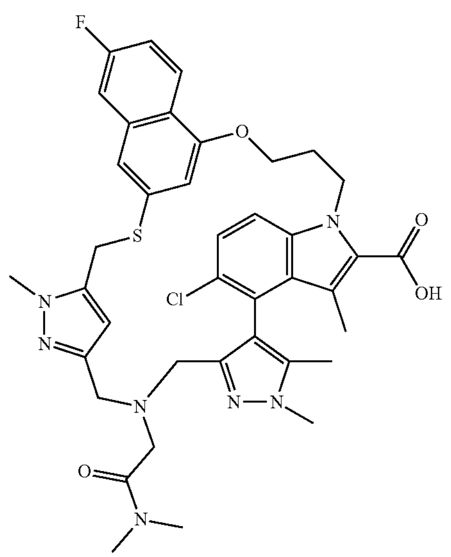 [SMILES: Cc1c(C(=O)O)n2c3ccc(Cl)c(c13)-c1c(nn(C)c1C)CN(CC(=O)N(C)C)Cc1cc(n(C)n1)CSc1cc(c3ccc(F)cc3c1)OCCC2] | (Z)-1$^5$-chloro-4-(2-(dimethylamino)-2-oxoethyl)-9$^6$-fluoro-1$^3$,2$^1$,2$^5$,6$^1$-tetramethyl-1$^1$H,2$^1$H,6$^1$H-10-oxa-8-thia-4-aza-1(4,1)-indola-2(4,3),6(3,5)-dipyrazola-9(3,1)-naphthalenacyclotridecaphane-1$^2$-carboxylic acid |

TABLE 1-continued

| Cpd No. | Structure | Name |
|---|---|---|
| 55 | 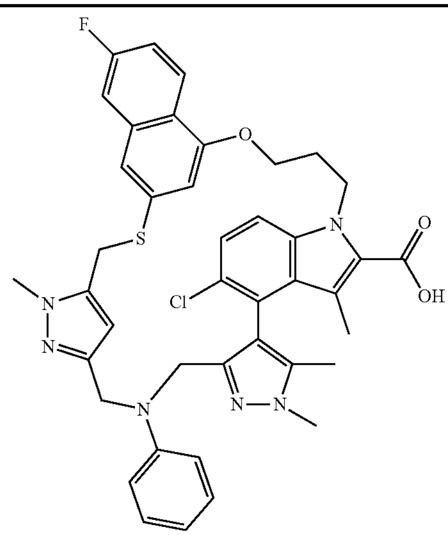 | Z)-1⁵-chloro-9⁶-fluoro-1³,2¹,2⁵,6¹-tetramethyl-4-phenyl-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid |

In another embodiment, the disclosure provides a pharmaceutical composition comprising a Compound of the Disclosure and a pharmaceutically acceptable carrier.

In another embodiment, Compounds of the Disclosure are enantiomerically enriched, e.g., the enantiomeric excess or "ee" of the compound is about 5% or more as measured by chiral HPLC. In another embodiment, the ee is about 10%. In another embodiment, the ee is about 20%. In another embodiment, the ee is about 30%. In another embodiment, the ee is about 40%. In another embodiment, the ee is about 50%. In another embodiment, the ee is about 60%. In another embodiment, the ee is about 70%. In another embodiment, the ee is about 80%. In another embodiment, the ee is about 85%. In another embodiment, the ee is about 90%. In another embodiment, the ee is about 91%. In another embodiment, the ee is about 92%. In another embodiment, the ee is about 93%. In another embodiment, the ee is about 94%. In another embodiment, the ee is about 95%. In another embodiment, the ee is about 96%. In another embodiment, the ee is about 97%. In another embodiment, the ee is about 98%. In another embodiment, the ee is about 99%.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with a suitable acid. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthyl enesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

II. Intermediates of the Disclosure

The disclosure also provides synthetic intermediates, collectively referred to as "Intermediates of the Disclosure," that can be used to prepare Compounds of the Disclosure.

In one embodiment, Intermediates of the Disclosure are compounds of Formula XXVI:

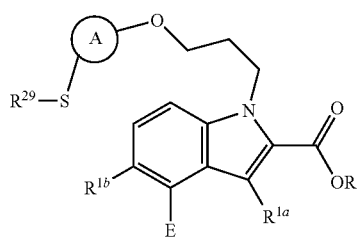

XXVI, wherein:

R is selected from the group consisting of hydrogen and $C_1$-$C_6$ alkyl;

$R^{1a}$ is selected from the group consisting of hydrogen, halo, $C_1$-$C_4$ alkyl, $C_1$-$C_4$ haloalkyl, $C_2$-$C_4$ alkynyl, $C_3$-$C_6$ cycloalkyl, —C(=O)H, and —(CH$_2$—)$_m$N(R$^{2a}$)(R$^{2b}$);

$R^{2a}$ is selected from the group consisting of hydrogen and $C_1$-$C_4$ alkyl;

$R^{2b}$ is selected from the group consisting of hydrogen, $C_1$-$C_4$ alkyl, —C(=O)R$^{3a}$, and —S(=O)$_2$R$^{3b}$; or $R^{2a}$ and $R^{2b}$ taken together with the nitrogen atom to which they are attached form a 3- to 6-membered optionally substituted heterocyclo;

m is 1, 2, or 3;

$R^{3a}$ is selected from the group consisting of $C_1$-$C_4$ alkyl, $C_1$-$C_4$ haloalkyl, $C_3$-$C_6$ cycloalkyl, optionally substituted 4- to 8-membered heterocyclo, optionally substituted $C_6$-$C_{10}$ aryl, and optionally substituted 5- to 10-membered heteroaryl;

$R^{3b}$ is selected from the group consisting of $C_1$-$C_4$ alkyl, $C_1$-$C_4$ haloalkyl, $C_3$-$C_6$ cycloalkyl, optionally substituted 4- to 8-membered heterocyclo, optionally substituted $C_6$-$C_{10}$ aryl, and optionally substituted 5- to 10-membered heteroaryl;

$R^{1b}$ is selected from the group consisting of hydrogen, halo, and $C_1$-$C_4$ alkyl;

is selected from the group consisting of:

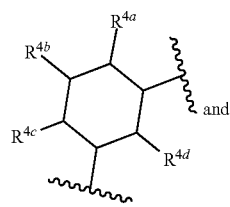

A-1

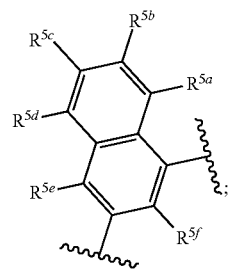

A-2

$R^{4a}$, $R^{4b}$, $R^{4c}$, and $R^{4d}$ are each independently selected from the group consisting of hydrogen, halo, cyano, amino, hydroxyl, $C_1$-$C_4$ alkyl, $C_1$-$C_4$ haloalkyl, and $C_1$-$C_4$ alkoxy;

$R^{5a}$, $R^{5b}$, $R^{5c}$, $R^{5d}$, $R^{5e}$, and $R^{5f}$ are each independently selected from the group consisting of hydrogen, halo, cyano, amino, hydroxyl, $C_1$-$C_4$ alkyl, $C_1$-$C_4$ haloalkyl, and $C_1$-$C_4$ alkoxy; and $R^{29}$ is selected from the group consisting of $R^{19}$ and

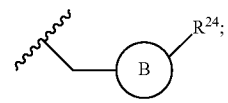

$R^{19}$ is selected from the group consisting of hydrogen and a protecting group;

E is selected from the group consisting of Br,

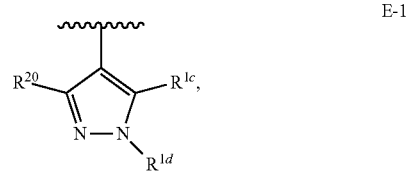

E-1

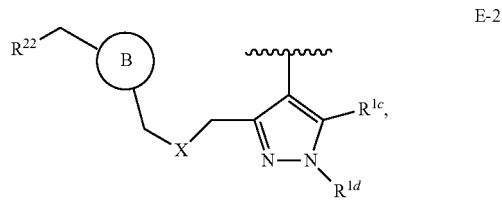

E-2

-continued

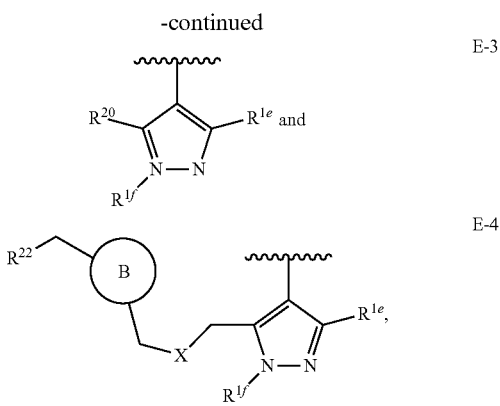

$R^{1c}$ is selected from the group consisting of hydrogen, $C_1$-$C_4$ alkyl, halo, $C_1$-$C_4$ haloalkyl, and $C_3$-$C_6$ cycloalkyl;

$R^{1d}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl; or $R^{1c}$ and $R^{1d}$ taken together with the atoms to which they are attached form an optionally substituted 4- to 8-membered heterocyclo;

$R^{1e}$ is selected from the group consisting of hydrogen, halo, $C_1$-$C_4$ alkyl, $C_1$-$C_4$ haloalkyl, and $C_3$-$C_6$ cycloalkyl;

$R^{1f}$ is selected from the group consisting of hydrogen, $C_1$-$C_4$ alkyl, $C_3$-$C_6$ cycloalkyl, (O—$C_4$ alkoxy)$C_1$-$C_4$ alkyl, and (carboxamido)$C_1$-$C_4$ alkyl;

$R^{20}$ is selected from the group consisting of —C(═O)H, —CH$_2$-LG, and —CH$_2$XR$^{21}$;

LG is a leaving group such as —Cl, Br, -OMs, and -OTs;

X is selected from the group consisting of —O—, —S—, and —N(H)—;

$R^{21}$ is selected from the group consisting of hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, (5- to 10-membered heteroaryl)$C_1$-$C_4$ alkyl, ($C_1$-$C_4$ alkoxy)$C_1$-$C_4$ alkyl, and a protecting group such as -THP, —Ac, and -Bz;

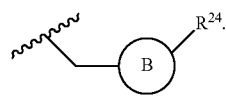

is selected from the group consisting of arylenyl and heteroarylenyl;

$R^{22}$ is selected from the group consisting of —OR$^{23}$ and a leaving group such Cl, Br, and OMs;

$R^{23}$ is selected from the group consisting of hydrogen and a protecting group such as -TBS, -THP, —Ac and -Bz; and $R^{24}$ is selected from the group consisting of —CH$_2$OR$^{25}$ and —C(═O)H; and $R^{25}$ is selected from the group consisting of hydrogen and a protecting group such as -TBS, -THP, —Ac and -Bz, or a pharmaceutically acceptable salt or solvate thereof.

In another embodiment, Intermediates of the Disclosure are compounds of Formula XXVI, wherein E is Br.

In another embodiment, Intermediates of the Disclosure are compounds of Formula XXVI, wherein E is E-1.

In another embodiment, Intermediates of the Disclosure are compounds of Formula XXVI, wherein E is E-2.

In another embodiment, Intermediates of the Disclosure are compounds of Formula XXVI, wherein E is E-3.

In another embodiment, Intermediates of the Disclosure are compounds of Formula XXVI, wherein E is E-4.

In another embodiment, Intermediates of the Disclosure are compounds of Formula XXVI, wherein $R^{29}$ is $R^{19}$.

In another embodiment, Intermediates of the Disclosure are compounds of Formula XXVI, wherein $R^{29}$ is

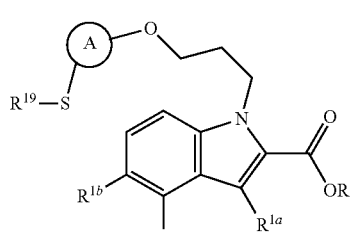

The following particular embodiments are directed to Intermediates of the Disclosure.

Embodiment I1. A compound of Formula XXVI of Formula VI:

VI, wherein:

R is $C_1$-$C_6$ alkyl;

$R^{1a}$ is selected from the group consisting of hydrogen, halo, $C_1$-$C_4$ alkyl, $C_1$-$C_4$ haloalkyl, $C_2$-$C_4$ alkynyl, $C_3$-$C_6$ cycloalkyl, —C(═O)H, and —(CH$_2$—)$_m$N(R$^{2a}$)(R$^{2b}$);

$R^{2a}$ is selected from the group consisting of hydrogen and $C_1$-$C_4$ alkyl;

$R^{2b}$ is selected from the group consisting of hydrogen, $C_1$-$C_4$ alkyl, —C(═O)R$^{3a}$, and —S(═O)$_2$R$^{3b}$; or $R^{2a}$ and $R^{2b}$ taken together with the nitrogen atom to which they are attached form a 3- to 6-membered optionally substituted heterocyclo;

m is 1, 2, or 3;

$R^{1a}$ is selected from the group consisting of $C_1$-$C_4$ alkyl, $C_1$-$C_4$ haloalkyl, $C_3$-$C_6$ cycloalkyl, optionally substituted 4- to 8-membered heterocyclo, optionally substituted $C_6$-$C_{10}$ aryl, and optionally substituted 5- to 10-membered heteroaryl;

$R^{ab}$ is selected from the group consisting of $C_1$-$C_4$ alkyl, $C_1$-$C_4$ haloalkyl, $C_3$-$C_6$ cycloalkyl, optionally substituted 4- to 8-membered heterocyclo, optionally substituted $C_6$-$C_{10}$ aryl, and optionally substituted 5- to 10-membered heteroaryl;

$R^{1b}$ is selected from the group consisting of hydrogen, halo, and $C_1$-$C_4$ alkyl;

is selected from the group consisting of:

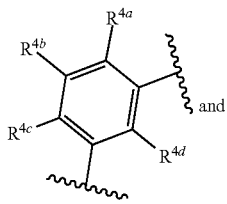

A-1

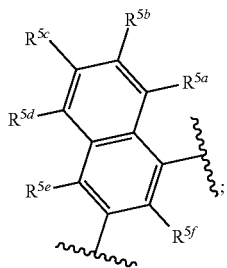

A-2

$R^{4a}$, $R^{4b}$, $R^{4c}$, and $R^{od}$ are each independently selected from the group consisting of hydrogen, halo, cyano, amino, hydroxyl, $C_1$-$C_4$ alkyl, $C_1$-$C_4$ haloalkyl, and $C_1$-$C_4$ alkoxy;

$R^{5a}$, $R^{5b}$, $R^{5c}$, $R^{5d}$, $R^{5e}$, and $R^{5f}$ are each independently selected from the group consisting of hydrogen, halo, cyano, amino, hydroxyl, $C_1$-$C_4$ alkyl, $C_1$-$C_4$ haloalkyl, and $C_1$-$C_4$ alkoxy; and $R^{19}$ is selected from the group consisting of hydrogen and a protecting group, or a pharmaceutically acceptable salt or solvate thereof.

Embodiment I2. A compound of Formula XXVI of Formula VII:

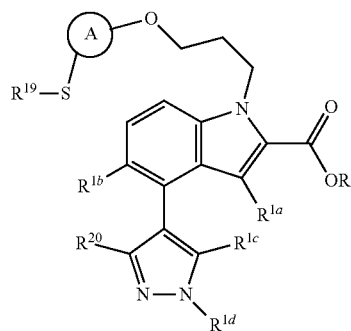

VII, wherein:

R, $R^{1a}$, $R^{1b}$, $R^{19}$, and

are as defined in connection with Formula VI of Embodiment I1;

$R^{1c}$ is selected from the group consisting of hydrogen, $C_1$-$C_4$ alkyl, halo, $C_1$-$C_4$ haloalkyl, and $C_3$-$C_6$ cycloalkyl;

$R^{1d}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl; or $R^{1c}$ and $R^{1d}$ taken together with the atoms to which they are attached form an optionally substituted 4- to 8-membered heterocyclo;

$R^{19}$ is selected from the group consisting of hydrogen and a protecting group;

$R^{20}$ is selected from the group consisting of —C(═O)H, —CH$_2$-LG, and —CH$_2$XR$^{21}$;

LG is a leaving group;

X is selected from the group consisting of —O—, —S—, and —N(H)—; and $R^{21}$ is selected from the group consisting of hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, (5- to 10-membered heteroaryl)$C_1$-$C_4$ alkyl, ($C_1$-$C_4$ alkoxy)$C_1$-$C_4$ alkyl, and a protecting group, or a pharmaceutically acceptable salt or solvate thereof.

Embodiment I3. A compound of Formula XXVI of Formula VIII:

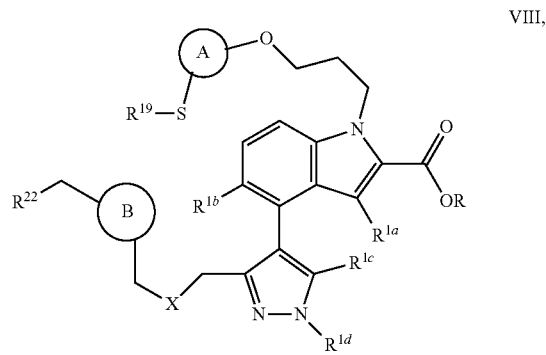

VIII, wherein:

R, $R^{1a}$, $R^{1b}$, $R^{1c}$, $R^{1a}R^{19}$, X, and

are as defined in connection with Formula VII of Embodiment I2;

is selected from the group consisting of arylenyl and heteroarylenyl;

$R^{22}$ is selected from the group consisting of —OR$^{23}$ and a leaving group; and $R^{23}$ is selected from the group consisting of hydrogen and a protecting group, or a pharmaceutically acceptable salt or solvate thereof.

Embodiment I4. A compound of Formula XXVI of Formula IX:

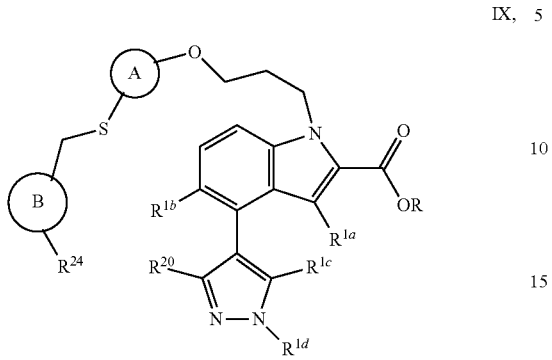

wherein:

R, $R^{1a}$, $R^{1b}$, $R^{1c}$, $R^{1d}$, $R^{20}$, and

A are as defined in connection with Formula VII of Embodiment I2;

B is selected from the group consisting of arylenyl and heteroarylenyl;

$R^{24}$ is selected from the group consisting of —$CH_2OR^{25}$ and —C(=O)H; and $R^{25}$ is selected from the group consisting of hydrogen and a protecting group, or a pharmaceutically acceptable salt or solvate thereof.

Embodiment I5. The compound of any one of Embodiments I2-14, wherein:

$R^{1c}$ is selected from the group consisting of hydrogen, $C_1$-$C_4$ alkyl, halo, $C_1$-$C_4$ haloalkyl, and $C_3$-$C_6$ cycloalkyl; and $R^{1d}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl.

Embodiment I6. The compound of Embodiment I5, wherein $R^{1c}$ and $R^{1d}$ are each methyl.

Embodiment I7. The compound of Embodiment I2 of Formula X:

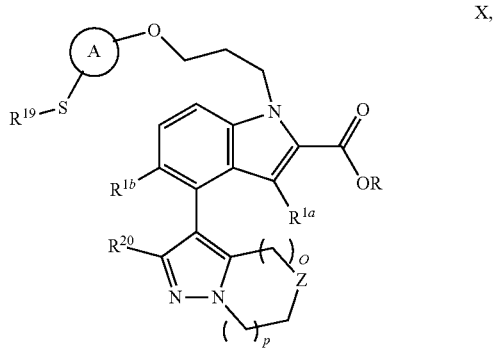

wherein:

o is 0, 1, or 2;

p is 0 or 1;

with the proviso that when p is 0, Z is —$CR^{9a}R^{9b}$—;

Z is selected from the group consisting of —$CR^{9a}R^{9b}$—, —O—, —S—, S(=O)—, S(=O)$_2$—, and —N($R^{10}$)—; and $R^{9a}$ and $R^{9b}$ are independently selected from the group consisting of hydrogen and $C_1$-$C_4$ alkyl.

Embodiment I8. The compound of Embodiment I3 of Formula XI:

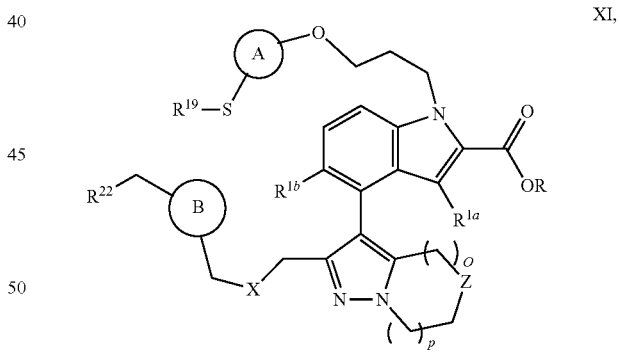

wherein:

o is 0, 1, or 2;

p is 0 or 1;

with the proviso that when p is 0, Z is —$CR^{9a}R^{9b}$—;

Z is selected from the group consisting of —$CR^{9a}R^{9b}$—, —O—, —S—, S(=O)—, S(=O)$_2$—, and —N($R^{10}$)—; and $R^{9a}$ and $R^{9b}$ are independently selected from the group consisting of hydrogen and $C_1$-$C_4$ alkyl.

Embodiment I9. The compound of Embodiment I4 of Formula XII:

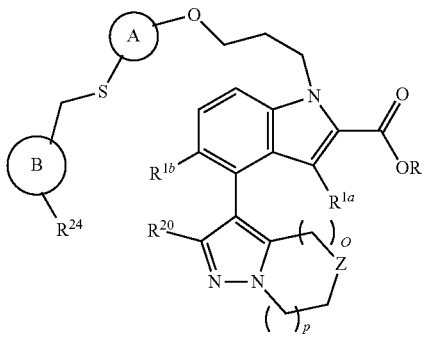

XII, wherein:
o is 0, 1, or 2;
p is 0 or 1;
with the proviso that when p is 0, Z is —CR$^{9a}$R$^{9b}$—;
Z is selected from the group consisting of —CR$^{9a}$R$^{9b}$—, —O—, —S—, S(=O)—, S(=O)$_2$—, and —N(R$^{10}$)—; and
R$^{9a}$ and R$^{9b}$ are independently selected from the group consisting of hydrogen and C$_1$-C$_4$ alkyl.

Embodiment I10. The compound of any one of any one of Embodiments I7-I9, wherein Z is —O—.

Embodiment I11. The compound of any one of any one of Embodiments I7-I9, wherein Z is —CH$_2$—.

Embodiment I12. The compound of any one of any one of Embodiments I7-I9, wherein Z is —C(CH$_3$)$_2$—.

Embodiment I13. The compound of any one of Embodiments I7-I12, wherein o is 1.

Embodiment I14. A compound of Formula XXVI of Formula XIII:

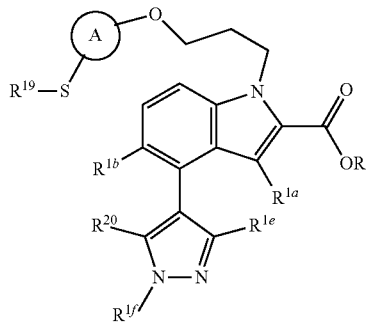

XIII, wherein:
R, R$^{1a}$, R$^{1b}$, R$^{19}$, and

Ⓐ are as defined in connection with Formula VI of Embodiment I1;
R$^{1e}$ is selected from the group consisting of hydrogen, halo, C$_1$-C$_4$ alkyl, C$_1$-C$_4$ haloalkyl, and C$_3$-C$_6$ cycloalkyl;
R$^{1f}$ is selected from the group consisting of hydrogen, C$_1$-C$_4$ alkyl, C$_3$-C$_6$ cycloalkyl, (C$_1$-C$_4$ alkoxy)C$_1$-C$_4$ alkyl, and (carboxamido)C$_1$-C$_4$ alkyl;

R$^{19}$ is selected from the group consisting of hydrogen and a protecting group;
R$^{20}$ is selected from the group consisting of —C(=O)H, —CH$_2$LG, and —CH$_2$XR$^{21}$;
LG is a leaving group;
X is selected from the group consisting of —O—, —S—, and —N(H)—; and
R$^{21}$ is selected from the group consisting of hydrogen and a protecting group,
or a pharmaceutically acceptable salt or solvate thereof.

Embodiment I15. A compound of Formula XXVI of Formula XIV:

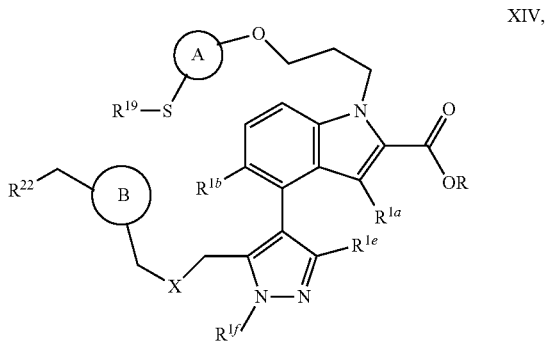

XIV, wherein:
R, R$^{1a}$, R$^{1b}$, R$^{1e}$, R$^{1f}$, R$^{19}$, X,

Ⓐ and are as defined in connection with Formula XIII of Embodiment I14;

Ⓑ is selected from the group consisting of arylenyl and heteroarylenyl;
R$^{22}$ is selected from the group consisting of —OR$^{23}$ and a leaving group; and
R$^{23}$ is selected from the group consisting of hydrogen and protecting group,
or a pharmaceutically acceptable salt or solvate thereof.

Embodiment I16. A compound of Formula XXVI of Formula XV:

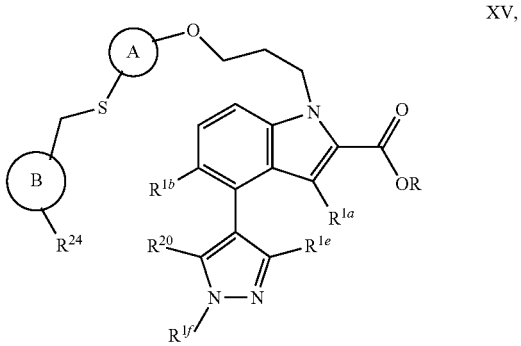

XV, wherein:

R, $R^{1a}$, $R^{1b}$, $R^{1e}$, $R^{1f}$, $R^{20}$, (A)

and are as defined in connection with Formula XIII of Embodiment I14;

(B)

is selected from the group consisting of arylenyl and heteroarylenyl;

$R^{24}$ is selected from the group consisting of —CH$_2$OR$^{25}$ and —C(=O)H;

$R^{25}$ is selected from the group consisting of hydrogen and a protecting group, or a pharmaceutically acceptable salt or solvate thereof.

Embodiment I17. The compound of any one of Embodiments I14-I16, wherein $R^{1e}$ is selected from the group consisting of C$_1$-C$_4$ alkyl and C$_1$-C$_4$ haloalkyl; and $R^{1f}$ is selected from the group consisting of C$_1$-C$_4$ alkyl, (C$_1$-C$_4$ alkoxy)C$_1$-C$_4$ alkyl, and (carboxamido)C$_1$-C$_4$ alkyl.

Embodiment I18. The compound of any one of Embodiments I1-I17, wherein (A)

is A-1.

Embodiment I19. The compound of Embodiment I18, wherein:

$R^{4a}$, $R^{4b}$, and $R^{4c}$ are each independently selected from the group consisting of hydrogen and halo; and $R^{4d}$ is hydrogen.

Embodiment I20. The compound of any one of Embodiments I1-I17, wherein (A)

is A-2.

Embodiment I21. The compound or process of Embodiment I20, wherein the 1-position of A-2 is attached to the oxygen atom and the 3-position of A-2 is attached to the sulfur atom.

Embodiment I22. The compound or process of Embodiments I20 or I21, wherein:

$R^{5a}$, $R^{5b}$, $R^{5c}$, $R^{5d}$, and $R^{5e}$ are each independently selected from the group consisting of hydrogen and halo; and $R^{5f}$ is hydrogen.

Embodiment I23. The compound of any one of Embodiments I1-I22, wherein:

$R^{1a}$ is selected from the group consisting of hydrogen, halo, C$_1$-C$_4$ alkyl, C$_1$-C$_4$ haloalkyl, C$_2$-C$_4$ alkynyl, and —CH$_2$N(H)(R$^{2b}$); and $R^{2b}$ is selected from the group consisting of —C(=O)R$^{3a}$ and —S(=O)$_2$R$^{3b}$.

Embodiment I24. The compound of Embodiment I23, wherein $R^{1a}$ is selected from the group consisting of hydrogen, fluoro, chloro, methyl, ethyl, ethynyl, —CH$_2$N(H)C(=O)CH$_3$, and —CH$_2$N(H)S(=O)$_2$CF$_3$.

Embodiment I25. The compound of any one of Embodiments I1-I24, wherein $R^{1b}$ is halo.

Embodiment I26. The compound of Embodiment I25, wherein $R^{1b}$ is chloro.

Embodiment I27. The compound of any one of Embodiments I3-16, I8-I13, or I15-I17, wherein (B)

is arylenyl.

Embodiment I28. The compound of Embodiment I27, wherein:

(B)

is selected from the group consisting of:

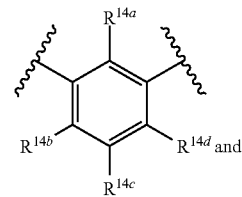
B-1

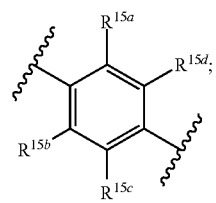
B-2

$R^{14a}$, $R^{14c}$, and $R^{14d}$ are each independently selected from the group consisting of hydrogen, halo, cyano, C$_1$-C$_4$ alkyl, C$_1$-C$_4$ haloalkyl, C$_1$-C$_4$ alkoxy, and C$_3$-C$_6$ cycloalkyl; and $R^{15a}$, $R^{15b}$, and $R^{15d}$ are each independently selected from the group consisting of hydrogen, halo, cyano, C$_1$-C$_4$ alkyl, C$_1$-C$_4$ haloalkyl, C$_1$-C$_4$ alkoxy, and C$_3$-C$_6$ cycloalkyl.

Embodiment I29. The compound of Embodiment I28, wherein (B)

is B-1, or a pharmaceutically acceptable salt or solvate thereof.

Embodiment I30. The compound of Embodiment I29, wherein $R^{14a}$, $R^{14b}$, $R^{14c}$, and $R^{14d}$ are each independently selected from the group consisting of hydrogen, halo, and C$_1$-C$_4$ alkyl.

Embodiment I31. The compound of Embodiment I28, wherein (B)

is B-2.

Embodiment I32. The compound of Embodiment I31, wherein $R^{15a}$, $R^{15b}$, $R^{15c}$, and $R^{15d}$ are each independently selected from the group consisting of hydrogen, halo, and $C_1$-$C_4$ alkyl.

Embodiment I33. The compound of any one of Embodiments I3-I6, I8-I13, or I15-I17, wherein (B)

is heteroarylenyl.

Embodiment I34. The compound of Embodiment I33, wherein:

(B)

is selected from the group consisting of:

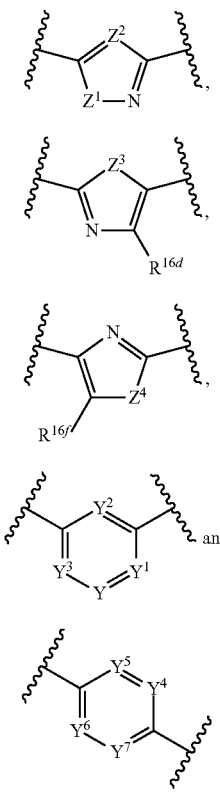

B-3

B-4

B-5

B-6

B-7

$Z^1$ is selected from the group consisting of —O—, —S—, and —N($R^{16a}$)—;

$R^{16a}$ is selected from the group consisting of hydrogen, $C_1$-$C_4$ alkyl, and $C_3$-$C_6$ cycloalkyl;

$Z^2$ is selected from the group consisting of —C($R^{16b}$)= and —N=;

$R^{16b}$ is selected from the group consisting of hydrogen, halo, $C_1$-$C_4$ alkyl, and $C_3$-$C_6$ cycloalkyl;

$Z^3$ is selected from the group consisting of —O—, —S—, and —N($R^{16c}$)—;

$R^{16c}$ is selected from the group consisting of hydrogen, $C_1$-$C_4$ alkyl, and $C_3$-$C_6$ cycloalkyl;

$R^{16d}$ is selected from the group consisting of hydrogen, halo, $C_1$-$C_4$ alkyl, and $C_3$-$C_6$ cycloalkyl;

$Z^4$ is selected from the group consisting of —O—, —S—, and —N($R^{16e}$)—;

$R^{16e}$ is selected from the group consisting of hydrogen, $C_1$-$C_4$ alkyl, and $C_3$-$C_6$ cycloalkyl;

$R^{16f}$ is selected from the group consisting of hydrogen, halo, $C_1$-$C_4$ alkyl, and $C_3$-$C_6$ cycloalkyl;

Y is selected from the group consisting of —C($R^{17a}$)= and —N=;

$Y^1$ is selected from the group consisting of —C($R^{17b}$)= and —N=;

$Y^2$ is selected from the group consisting of —C($R^{17c}$)= and —N=;

$Y^3$ is selected from the group consisting of —C($R^{17d}$)= and —N=;

with proviso that at least one of Y, Y', $Y^2$, and $Y^3$ is —N=;

$R^{17a}$, $R^{17b}$, $R^{17c}$, and $R^{17d}$ are each independently selected from the group consisting of hydrogen, halo, cyano, $C_1$-$C_4$ alkyl, $C_1$-$C_4$ haloalkyl, and $C_1$-$C_4$ alkoxy;

$Y^4$ is selected from the group consisting of —C($R^{18a}$)= and —N=;

$Y^5$ is selected from the group consisting of —C($R^{18b}$)= and —N=;

$Y^6$ is selected from the group consisting of —C($R^{18c}$)= and —N=;

$Y^7$ is selected from the group consisting of —C($R^{18d}$)= and —N=;

with proviso that at least one of $Y^4$, $Y^5$, $Y^6$, and $Y^7$ is —N=;

$R^{18a}$, $R^{18b}$$R^{18c}$, and $R^{18d}$ are each independently selected from the group consisting of hydrogen, halo, cyano, $C_1$-$C_4$ alkyl, $C_1$-$C_4$ haloalkyl, and $C_1$-$C_4$ alkoxy.

Embodiment I35. The compound of Embodiment I34, wherein (B)

is B-3, or a pharmaceutically acceptable salt or solvate thereof.

Embodiment I36. The compound of Embodiment I35, wherein:

$Z^1$ is selected from the group consisting of —O—, —S—, —N(H)—, and —N($CH_3$)—; and $Z^2$ is selected from the group consisting of —C(H)=, —C($CH_3$)=, and —N=.

Embodiment I37. The compound of Embodiment I34, wherein (B)

is B-4.

Embodiment I38. The compound of Embodiment I37, wherein:
$Z^3$ is selected from the group consisting of —O—, —S—, —N(H)—, and —N(CH$_3$)—;
$R^{16d}$ is selected from the group consisting of hydrogen and methyl.

Embodiment I39. The compound of Embodiment I34, wherein (B)

is B-5, or a pharmaceutically acceptable salt or solvate thereof.

Embodiment I40. The compound of Embodiment I39, wherein:
$Z^4$ is selected from the group consisting of —O—, —S—, —N(H)—, and —N(CH$_3$)—;
$R^{16f}$ is selected from the group consisting of hydrogen and methyl.

Embodiment I41. The compound of Embodiment I34, wherein (B)

is B-6.

Embodiment I42. The compound of Embodiment I41, wherein:
Y is —N═;
$Y^1$ is selected from the group consisting of —C(R$^{17b}$)═ and —N═;
$Y^2$ is selected from the group consisting of —C(R$^{17c}$)═ and —N═;
$Y^3$ is selected from the group consisting of —C(R$^{17d}$)═ and —N═; and
$R^{17b}$, $R^{17c}$, and $R^{17d}$ are each independently selected from the group consisting of hydrogen, halo, and C$_1$-C$_4$ alkyl.

Embodiment I43. The compound of Embodiment I41, wherein:
Y is selected from the group consisting of —C(R$^{17a}$)═ and —N═;
$Y^1$ is —N═;
$Y^2$ is selected from the group consisting of —C(R$^{17c}$)═ and —N═;
$Y^3$ is selected from the group consisting of —C(R$^{17d}$)═ and —N═; and
$R^{17a}$, $R^{17c}$, and $R^{17d}$ are each independently selected from the group consisting of hydrogen, halo, and C$_1$-C$_4$ alkyl.

Embodiment I44. The compound of Embodiment I41, wherein:
Y is selected from the group consisting of —C(R$^{17a}$)═ and —N═;
$Y^1$ is selected from the group consisting of —C(R$^{17b}$)═ and —N═;
$Y^2$ is —N═;
$Y^3$ is selected from the group consisting of —C(R$^{17d}$)═ and —N═; and
$R^{17a}$, $R^{17b}$, and $R^{17d}$ are each independently selected from the group consisting of hydrogen, halo, and C$_1$-C$_4$ alkyl.

Embodiment I45. The compound of Embodiment I41, wherein:
Y is selected from the group consisting of —C(R$^{17a}$)═ and —N═;
$Y^1$ is selected from the group consisting of —C(R$^{17b}$)═ and —N═;
$Y^2$ is selected from the group consisting of —C(R$^{17c}$)═ and —N═;
$Y^3$ is —N═; and
$R^{17a}$, $R^{17b}$, and $R^{17c}$ are each independently selected from the group consisting of hydrogen, halo, and C$_1$-C$_4$ alkyl.

Embodiment I46. The compound of Embodiment I34, wherein (B)

is B-7.

Embodiment I47. The compound of Embodiment I46, wherein:
$Y^4$ is and —N═;
$Y^5$ is selected from the group consisting of —C(R$^{18b}$)═ and —N═;
$Y^6$ is selected from the group consisting of —C(R$^{18c}$)═ and —N═;
$Y^7$ is selected from the group consisting of —C(R$^{18d}$)═ and —N═; and
$R^{18b}$, $R^{18c}$, and $R^{18d}$ are each independently selected from the group consisting of hydrogen, halo, and C$_1$-C$_4$ alkyl.

Embodiment I48. The compound of Embodiment I46, wherein:
$Y^4$ is selected from the group consisting of —C(R$^{18a}$)═ and —N═;
$Y^5$ is —N═;
$Y^6$ is selected from the group consisting of —C(R$^{18c}$)═ and —N═;
$Y^7$ is selected from the group consisting of —C(R$^{18d}$)═ and —N═; and
$R^{18a}$, $R^{18c}$, and $R^{18d}$ are each independently selected from the group consisting of hydrogen, halo, and C$_1$-C$_4$ alkyl.

Embodiment I49. The compound of Embodiment I46, wherein:
$Y^4$ is selected from the group consisting of —C(R$^{18a}$)═ and —N═;
$Y^5$ is selected from the group consisting of —C(R$^{18b}$)═ and —N═;
$Y^6$ is —N═;
$Y^7$ is selected from the group consisting of —C(R$^{18d}$)═ and —N═; and
$R^{18a}$, $R^{18b}$ and $R^{18d}$ are each independently selected from the group consisting of hydrogen, halo, and C$_1$-C$_4$ alkyl.

Embodiment I50. The compound of Embodiment I46, wherein:
$Y^4$ is selected from the group consisting of —C(R$^{18a}$)═ and —N═;
$Y^5$ is selected from the group consisting of —C(R$^{18b}$)═ and —N═;
$Y^6$ is selected from the group consisting of —C(R$^{18c}$)═ and —N═;
$Y^7$ is —N═; and
$R^{18a}$, $R^{18b}$ and $R^{18c}$ are each independently selected from the group consisting of hydrogen, halo, and C$_1$-C$_4$ alkyl.

Embodiment I51. The compound of any one of Embodiments I3-I6, I8-I13, or I15-I17, wherein (B)

is selected from the group consisting of:

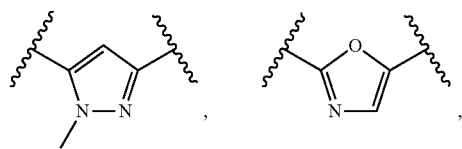

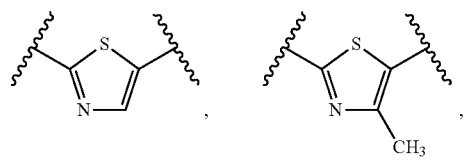

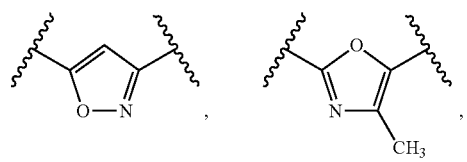

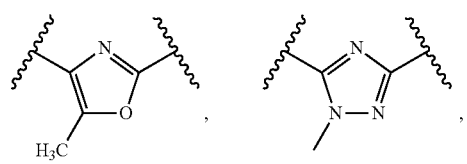

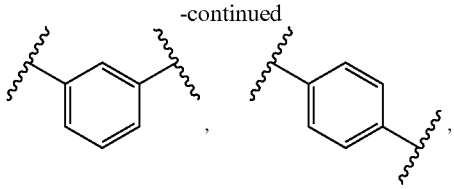

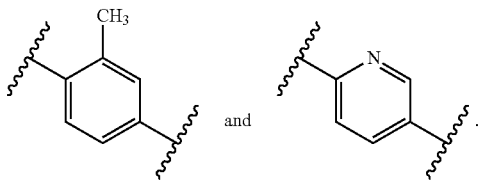

Embodiment I52. The compound of Embodiment I51, wherein

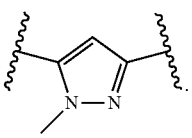

is:

[pyrazole structure]

Embodiment I53. The compound of any one of Embodiments I1-152, wherein R is selected from the group consisting of methyl and ethyl Embodiment I54. In another embodiment, Intermediates of the Disclosure are compounds of Formula XXVI selected from group consisting of the compounds of Table 2.

TABLE 2

| Int. No. | Structure | Name |
| --- | --- | --- |
| 1 | [structure] | Ethyl 4-(2-(bromomethyl)-6,7-dihydro-4H-pyrazolo[5,1-c][1,4]oxazin-3-yl)-5-chloro-1-(3-((3-((4-methoxybenzyl)thio)naphthalen-1-yl)oxy)propyl)-3-methyl-1H-indole-2-carboxylate |

TABLE 2-continued

| Int. No. | Structure | Name |
|---|---|---|
| 2 | 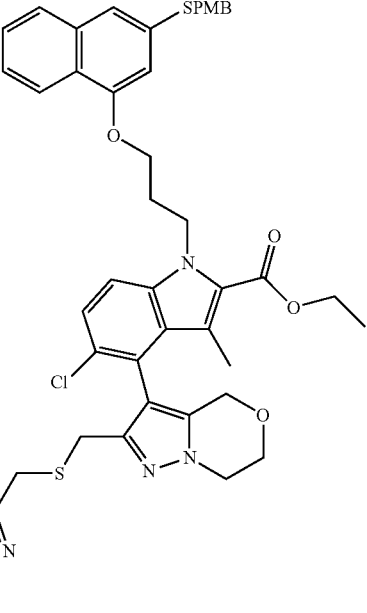 | Ethyl 4-(2-(((((5-(((tert-butyldimethylsilyl)oxy)methyl)-1-methyl-1H-pyrazol-3-yl)methyl)thio)methyl)-6,7-dihydro-4H-pyrazolo[5,1-c][1,4]oxazin-3-yl)-5-chloro-1-(3-((3-((4-methoxybenzyl)thio)naphthalen-1-yl)oxy)propyl)-3-methyl-1H-indole-2-carboxylate |
| 3 | 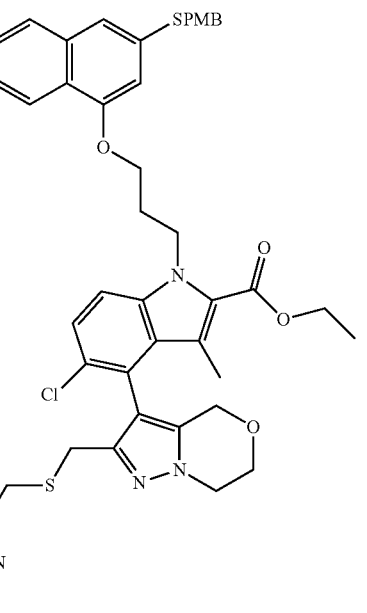 | Ethyl 5-chloro-4-(2-((((5-(hydroxymethyl)-1-methyl-1H-pyrazol-3-yl)methyl)thio)methyl)-6,7-dihydro-4H-pyrazolo[5,1-c][1,4]oxazin-3-yl)-1-(3-((3-((4-methoxybenzyl)thio)naphthalen-1-yl)oxy)propyl)-3-methyl-1H-indole-2-carboxylate |

TABLE 2-continued

| Int. No. | Structure | Name |
|---|---|---|
| 4 | 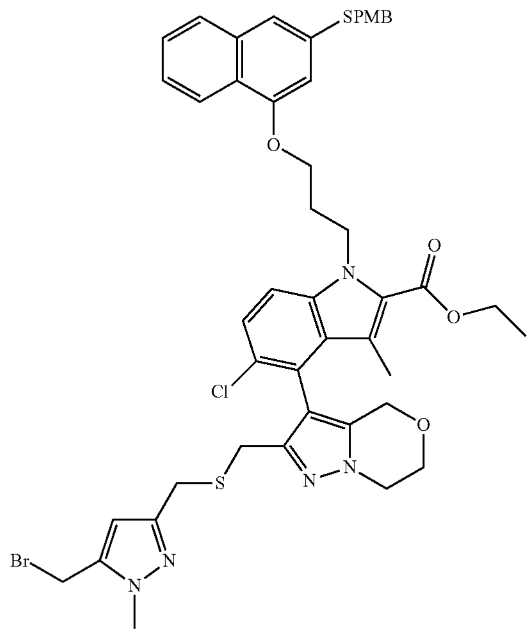 | Ethyl 4-(2-((((5-(bromomethyl)-1-methyl-1H-pyrazol-3-yl)methyl)thio)methyl)-6,7-dihydro-4H-pyrazolo[5,1-c][1,4]oxazin-3-yl)-5-chloro-1-(3-((3-((4-methoxybenzyl)thio)naphthalen-1-yl)oxy)propyl)-3-methyl-1H-indole-2-carboxylate |
| 5 | 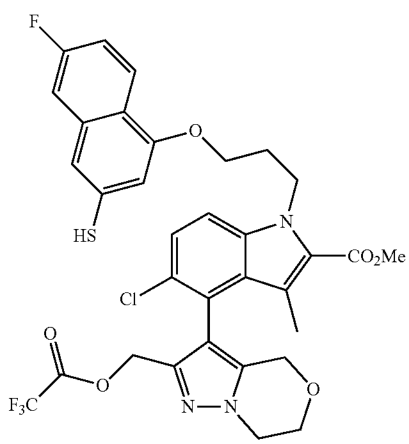 [SMILES: COC(=O)c1c(C)c2c(-c3c(COC(=O)C(F)(F)F)nn4c3COCC4)c(Cl)ccc2n1CCCOc1cc(S)cc2cc(F)ccc12] | Methyl 5-chloro-1-(3-((6-fluoro-3-mercaptonaphthalen-1-yl)oxy)propyl)-3-methyl-4-(2-((2,2,2-trifluoroacetoxy)methyl)-6,7-dihydro-4H-pyrazolo[5,1-c][1,4]oxazin-3-yl)-1H-indole-2-carboxylate |
| 6 | 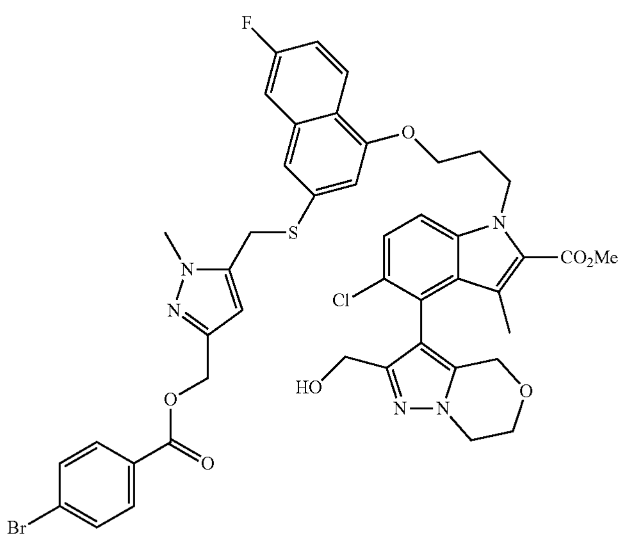 [SMILES: COC(=O)c1c(C)c2c(-c3c(CO)nn4c3COCC4)c(Cl)ccc2n1CCCOc1cc(SCc2cc(COC(=O)c3ccc(Br)cc3)nn2C)cc2cc(F)ccc12] | Methyl 1-(3-((3-(((3-(((4-bromobenzoyl)oxy)methyl)-1-methyl-1H-pyrazol-5-yl)methyl)thio)-6-fluoronaphthalen-1-yl)oxy)propyl)-5-chloro-4-(2-(hydroxymethyl)-6,7-dihydro-4H-pyrazolo[5,1-c][1,4]oxazin-3-yl)-3-methyl-1H-indole-2-carboxylate |

TABLE 2-continued

| Int. No. | Structure | Name |
|---|---|---|
| 7 | 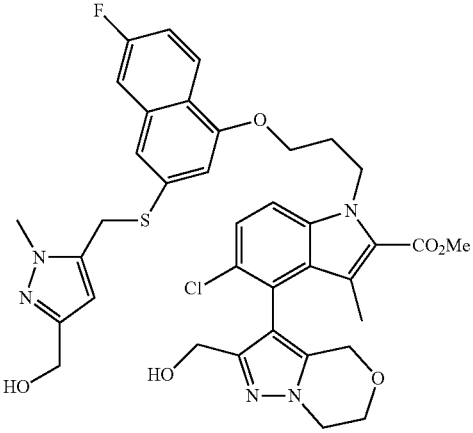 [SMILES: COC(=O)c1c(C)c2c(-c3c(CO)nn4c3COCC4)c(Cl)ccc2n1CCCOc1cc(SCc2cc(CO)nn2C)cc2cc(F)ccc12] | Methyl 5-chloro-1-(3-((6-fluoro-3-(((3-(hydroxymethyl)-1-methyl-1H-pyrazol-5-yl)methyl)thio)naphthalen-1-yl)oxy)propyl)-4-(2-(hydroxymethyl)-6,7-dihydro-4H-pyrazolo[5,1-c][1,4]oxazin-3-yl)-3-methyl-1H-indole-2-carboxylate |
| 8 | 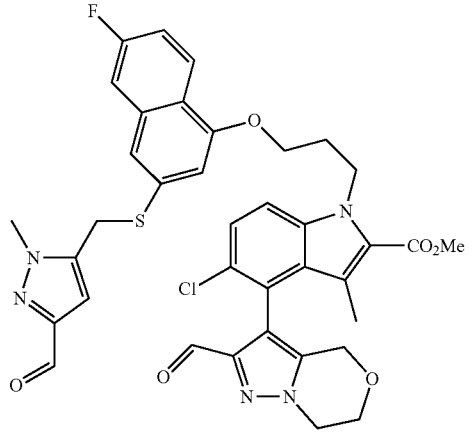 [SMILES: COC(=O)c1c(C)c2c(-c3c(C=O)nn4c3COCC4)c(Cl)ccc2n1CCCOc1cc(SCc2cc(C=O)nn2C)cc2cc(F)ccc12] | Methyl 5-chloro-1-(3-((6-fluoro-3-(((3-formyl-1-methyl-1H-pyrazol-5-yl)methyl)thio)naphthalen-1-yl)oxy)propyl)-4-(2-formyl-6,7-dihydro-4H-pyrazolo[5,1-c][1,4]oxazin-3-yl)-3-methyl-1H-indole-2-carboxylate |
| 9 | 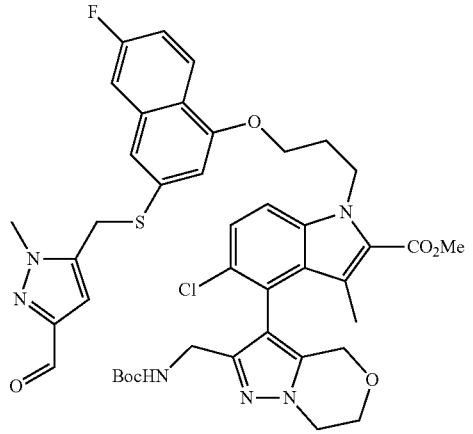 [SMILES: COC(=O)c1c(C)c2c(-c3c(CNC(=O)OC(C)(C)C)nn4c3COCC4)c(Cl)ccc2n1CCCOc1cc(SCc2cc(C=O)nn2C)cc2cc(F)ccc12] | Methyl 4-(2-(((tert-butoxycarbonyl)amino)methyl)-6,7-dihydro-4H-pyrazolo[5,1-c][1,4]oxazin-3-yl)-5-chloro-1-(3-((6-fluoro-3-(((3-formyl-1-methyl-1H-pyrazol-5-yl)methyl)thio)naphthalen-1-yl)oxy)propyl)-3-methyl-1H-indole-2-carboxylate |

TABLE 2-continued

| Int. No. | Structure | Name |
|---|---|---|
| 10 | 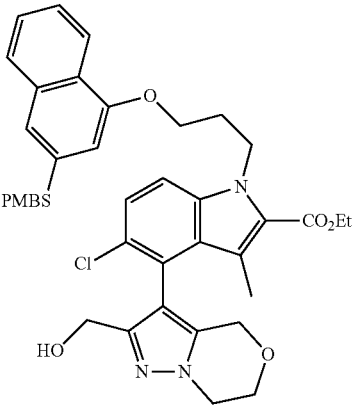 | Ethyl 5-chloro-4-(2-(hydroxymethyl)-6,7-dihydro-4H-pyrazolo[5,1-c][1,4]oxazin-3-yl)-1-(3-((3-((4-methoxybenzyl)thio)naphthalen-1-yl)oxy)propyl)-3-methyl-1H-indole-2-carboxylate |
| 11 | 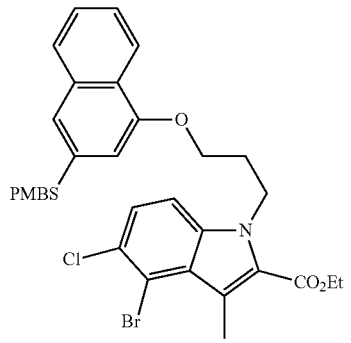 | Ethyl 4-bromo-5-chloro-1-(3-((3-((4-methoxybenzyl)thio)naphthalen-1-yl)oxy)propyl)-3-methyl-1H-indole-2-carboxylate |
| 12 | 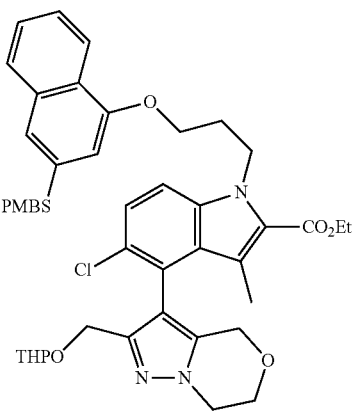 | Ethyl 5-chloro-1-(3-((3-((4-methoxybenzyl)thio)naphthalen-1-yl)oxy)propyl)-3-methyl-4-(2-(((tetrahydro-2H-pyran-2-yl)oxy)methyl)-6,7-dihydro-4H-pyrazolo[5,1-c][1,4]oxazin-3-yl)-1H-indole-2-carboxylate |

| Int. No. | Structure | Name |
|---|---|---|
| 14 | 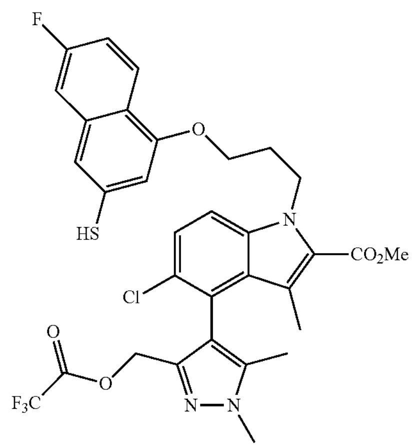 [SMILES: COC(=O)c1c(C)c2c(-c3c(COC(=O)C(F)(F)F)nn(C)c3C)c(Cl)ccc2n1CCCOc1cc(S)cc2cc(F)ccc12] | Methyl 5-chloro-4-(1,5-dimethyl-3-((2,2,2-trifluoroacetoxy)methyl)-1H-pyrazol-4-yl)-1-(3-((6-fluoro-3-mercaptonaphthalen-1-yl)oxy)propyl)-3-methyl-1H-indole-2-carboxylate |
| 15 | 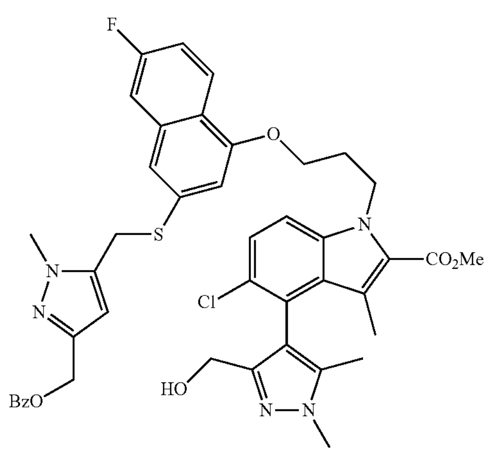 | Methyl 1-(3-((3-(((3-((benzoyloxy)methyl)-1-methyl-1H-pyrazol-5-yl)methyl)thio)-6-fluoronaphthalen-1-yl)oxy)propyl)-5-chloro-4-(3-(hydroxymethyl)-1,5-dimethyl-1H-pyrazol-4-yl)-3-methyl-1H-indole-2-carboxylate |
| 16 | 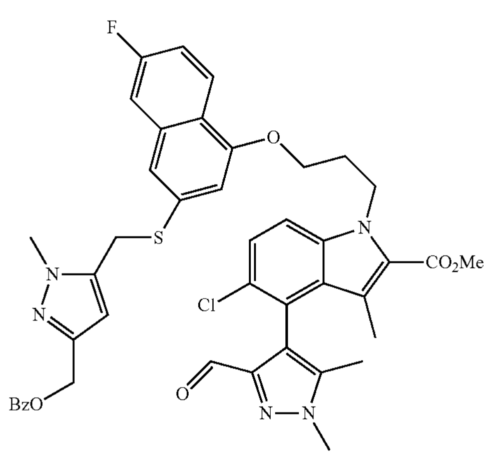 | Methyl 1-(3-((3-(((3-((benzoyloxy)methyl)-1-methyl-1H-pyrazol-5-yl)methyl)thio)-6-fluoronaphthalen-1-yl)oxy)propyl)-5-chloro-4-(3-formyl-1,5-dimethyl-1H-pyrazol-4-yl)-3-methyl-1H-indole-2-carboxylate |

TABLE 2-continued

| Int. No. | Structure | Name |
|---|---|---|
| 17 | 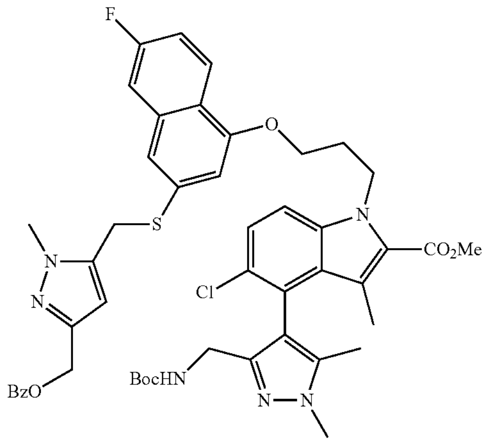 | Methyl 1-(3-((3-(((3-((benzoyloxy)-methyl)-1-methyl-1H-pyrazol-5-yl)methyl)thio)-6-fluoronaphtha-len-1-yl)oxy)propyl)-4-(3-(((tert-butoxycarbonyl)-amino)methyl)-1,5-dimethyl-1H-pyrazol-4-yl)-5-chloro-3-methyl-1H-indole-2-carboxylate |
| 18 | 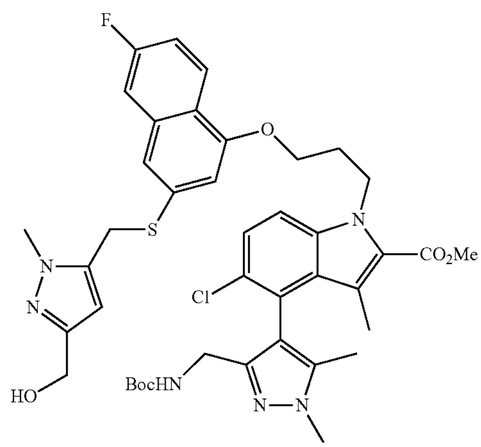 [SMILES: COC(=O)c1c(C)c2c(-c3c(CNC(=O)OC(C)(C)C)nn(C)c3C)c(Cl)ccc2n1CCCOc1cc(SCc2cc(CO)nn2C)cc2cc(F)ccc12] | Methyl 4-(3-(((tert-butoxycarbonyl)-amino)methyl)-1,5-dimethyl-1H-pyrazol-4-yl)-5-chloro-1-(3-((6-fluoro-3-(((3-(hydroxy-methyl)-1-methyl-1H-pyrazol-5-yl)methyl)thio)naph-thalen-1-yl)oxy)propyl)-3-methyl-1H-indole-2-carboxylate |
| 19 | 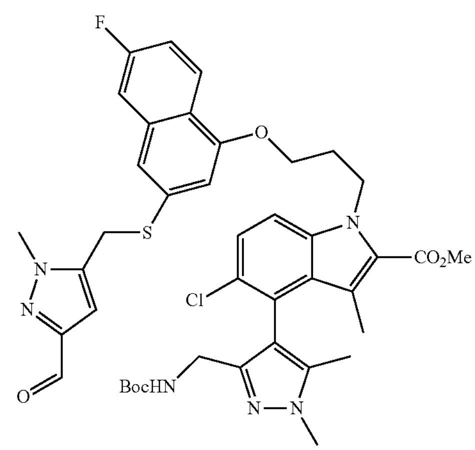 [SMILES: COC(=O)c1c(C)c2c(-c3c(CNC(=O)OC(C)(C)C)nn(C)c3C)c(Cl)ccc2n1CCCOc1cc(SCc2cc(C=O)nn2C)cc2cc(F)ccc12] | methyl 4-(3-(((tert-butoxycarbonyl)amino)methyl)-1,5-dimethyl-1H-pyrazol-4-yl)-5-chloro-1-(3-((6-fluoro-3-(((3-formyl-1-methyl-1H-pyrazol-5-yl)methyl)thio)-naphthalen-1-yl)oxy)propyl)-3-methyl-1H-indole-2-carboxylate |

TABLE 2-continued

| Int. No. | Structure | Name |
|---|---|---|
| 20 | 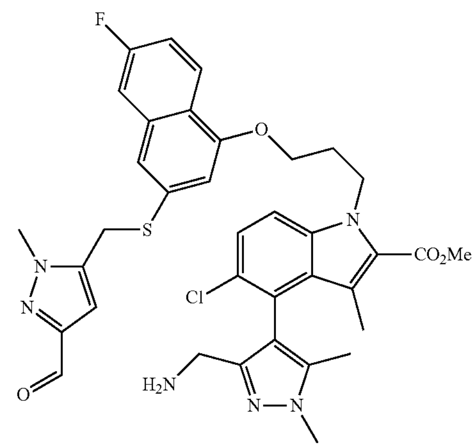 [SMILES: COC(=O)c1c(C)c2c(-c3c(CN)nn(C)c3C)c(Cl)ccc2n1CCCOc1cc(SCc2cc(C=O)nn2C)cc2cc(F)ccc12] | Methyl 4-(3-(aminomethyl)-1,5-dimethyl-1H-pyrazol-4-yl)-5-chloro-1-(3-((6-fluoro-3-(((3-formyl-1-methyl-1H-pyrazol-5-yl)methyl)thio)naphthalen-1-yl)oxy)propyl)-3-methyl-1H-indole-2-carboxylate |
| 21 | 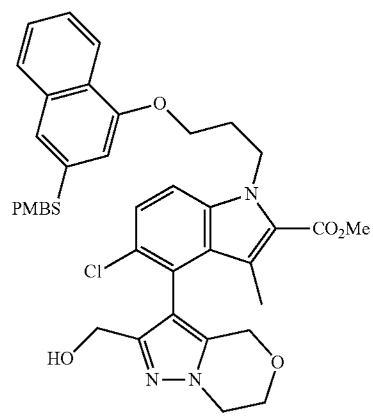 | Methyl 5-chloro-1-(3-((6-fluoro-3-((4-methoxybenzyl)thio)naphthalen-1-yl)oxy)propyl)-4-(2-(hydroxymethyl)-5,6-dihydro-4H-pyrrolo[1,2-b]pyrazol-3-yl)-3-methyl-1H-indole-2-carboxylate |
| 22 | 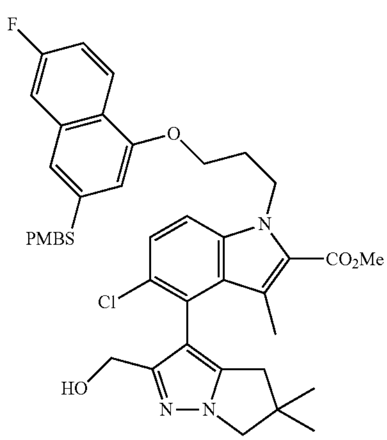 | Methyl 5-chloro-1-(3-((6-fluoro-3-((4-methoxybenzyl)thio)naphthalen-1-yl)oxy)propyl)-4-(2-(hydroxymethyl)-5,5-dimethyl-5,6-dihydro-4H-pyrrolo[1,2-b]pyrazol-3-yl)-3-methyl-1H-indole-2-carboxylate |

TABLE 2-continued

| Int. No. | Structure | Name |
|---|---|---|
| 23 | 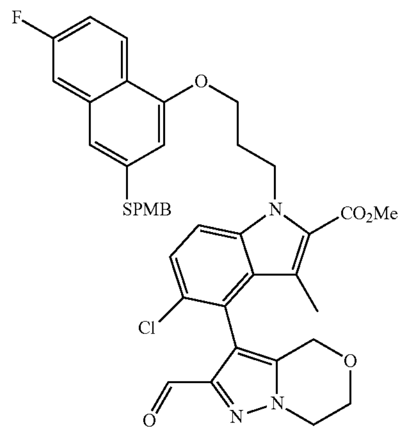 | Methyl 5-chloro-1-(3-((6-fluoro-3-((4-methoxybenzyl)thio)naphthalen-1-yl)oxy)propyl)-4-(2-formyl-6,7-dihydro-4H-pyrazolo[5,1-c][1,4]oxazin-3-yl)-3-methyl-1H-indole-2-carboxylate |
| 24 | 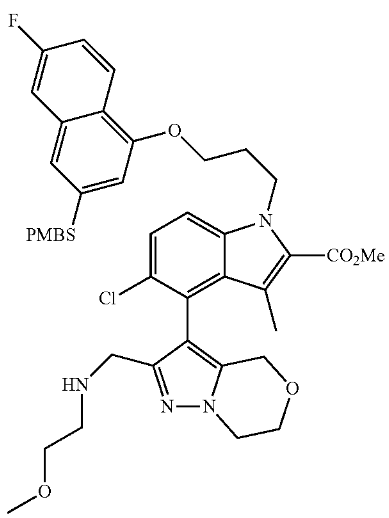 | Methyl 5-chloro-1-(3-((6-fluoro-3-((4-methoxybenzyl)thio)naphthalen-1-yl)oxy)propyl)-4-(2-(((2-methoxyethyl)amino)methyl)-6,7-dihydro-4H-pyrazolo[5,1-c][1,4]oxazin-3-yl)-3-methyl-1H-indole-2-carboxylate |
| 25 | 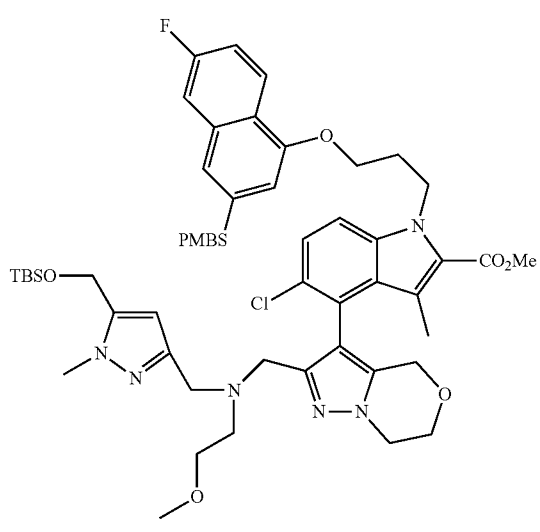 | Methyl 4-(2-(((((5-(((tert-butyldimethylsilyl)oxy)methyl)-1-methyl-1H-pyrazol-3-yl)methyl)(2-methoxyethyl)amino)methyl)-6,7-dihydro-4H-pyrazolo[5,1-c][1,4]oxazin-3-yl)-5-chloro-1-(3-((6-fluoro-3-((4-methoxybenzyl)thio)naphthalen-1-yl)oxy)propyl)-3-methyl-1H-indole-2-carboxylate |

TABLE 2-continued

| Int. No. | Structure | Name |
|---|---|---|
| 26 | 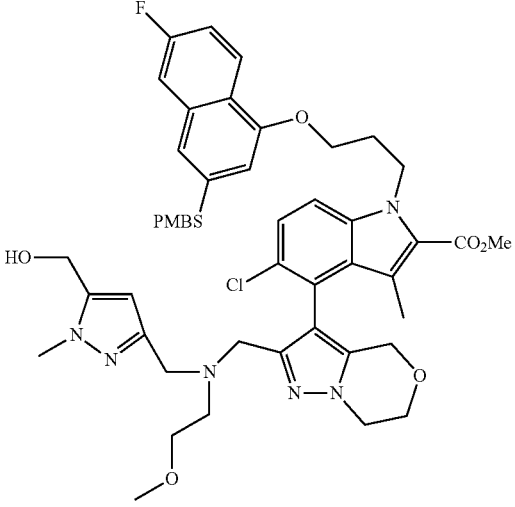 | Methyl 5-chloro-1-(3-((6-fluoro-3-((4-methoxybenzyl)thio)naphthalen-1-yl)oxy)propyl)-4-(2-((((5-(hydroxymethyl)-1-methyl-1H-pyrazol-3-yl)methyl)(2-methoxyethyl)amino)methyl)-6,7-dihydro-4H-pyrazolo[5,1-c][1,4]oxazin-3-yl)-3-methyl-1H-indole-2-carboxylate |
| 27 | 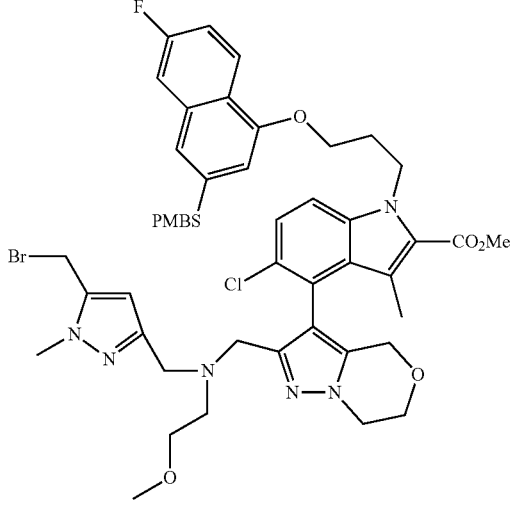 | Methyl 4-(2-((((5-(bromomethyl)-1-methyl-1H-pyrazol-3-yl)methyl)(2-methoxyethyl)amino)methyl)-6,7-dihydro-4H-pyrazolo[5,1-c][1,4]oxazin-3-yl)-5-chloro-1-(3-((6-fluoro-3-((4-methoxybenzyl)thio)naphthalen-1-yl)oxy)propyl)-3-methyl-1H-indole-2-carboxylate |
| 28 | 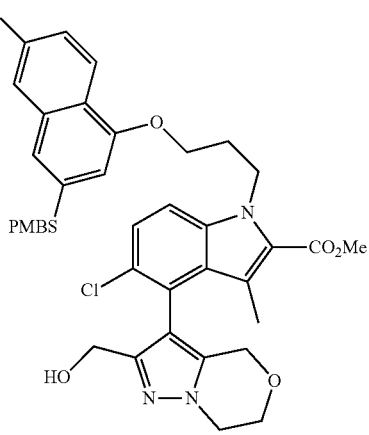 | Methyl 5-chloro-1-(3-((6-fluoro-3-((4-methoxybenzyl)thio)naphthalen-1-yl)oxy)propyl)-4-(2-(hydroxymethyl)-6,7-dihydro-4H-pyrazolo[5,1-c][1,4]oxazin-3-yl)-3-methyl-1H-indole-2-carboxylate |

TABLE 2-continued

| Int. No. | Structure | Name |
|---|---|---|
| 29 | 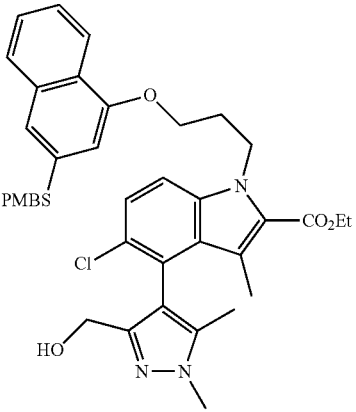 | Ethyl 5-chloro-4-(3-(hydroxymethyl)-1,5-dimethyl-1H-pyrazol-4-yl)-1-(3-((3-((4-methoxybenzyl)thio)naphthalen-1-yl)oxy)propyl)-3-methyl-1H-indole-2-carboxylate |
| 30 | 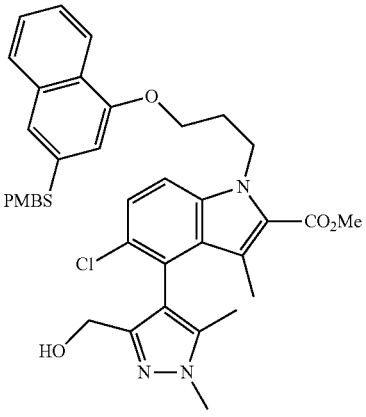 | Methyl 5-chloro-4-(3-(hydroxymethyl)-1,5-dimethyl-1H-pyrazol-4-yl)-1-(3-((3-((4-methoxybenzyl)thio)naphthalen-1-yl)oxy)propyl)-3-methyl-1H-indole-2-carboxylate |
| 31 | 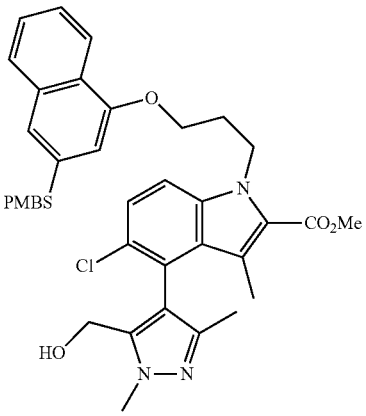 | Methyl 5-chloro-4-(5-(hydroxymethyl)-1,3-dimethyl-1H-pyrazol-4-yl)-1-(3-((3-((4-methoxybenzyl)thio)naphthalen-1-yl)oxy)propyl)-3-methyl-1H-indole-2-carboxylate |

| Int. No. | Structure | Name |
|---|---|---|
| 32 | 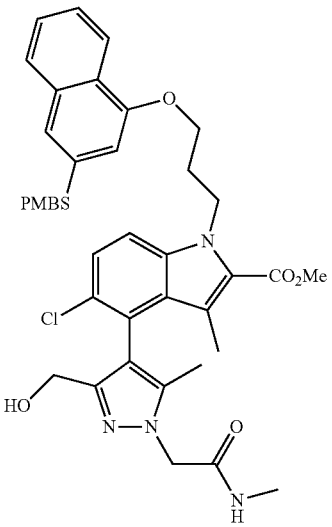 | Methyl 5-chloro-4-(3-(hydroxymethyl)-5-methyl-1-(2-(methylamino)-2-oxoethyl)-1H-pyrazol-4-yl)-1-(3-((3-((4-methoxybenzyl)thio)naphthalen-1-yl)oxy)propyl)-3-methyl-1H-indole-2-carboxylate |
| 33 | 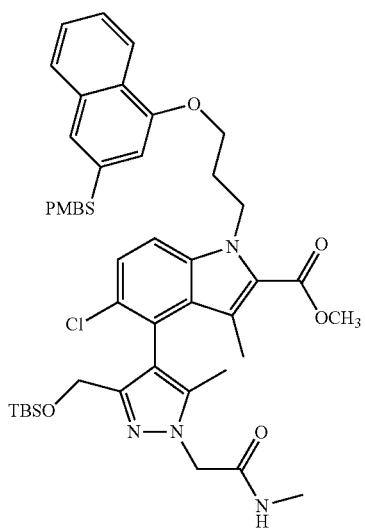 | Methyl 4-(3-(((tert-butyldimethylsilyl)oxy)methyl)-5-methyl-1-(2-(methylamino)-2-oxoethyl)-1H-pyrazol-4-yl)-5-chloro-1-(3-((3-((4-methoxybenzyl)thio)naphthalen-1-yl)oxy)propyl)-3-methyl-1H-indole-2-carboxylate |
| 34 | 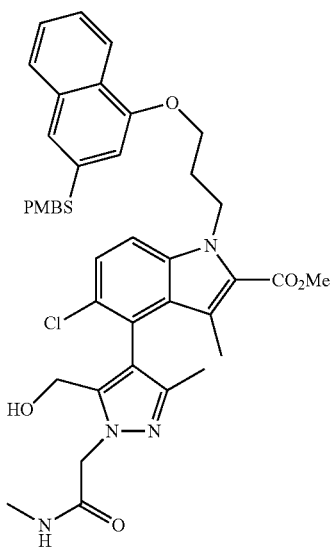 | Methyl 5-chloro-4-(5-(hydroxymethyl)-3-methyl-1-(2-(methylamino)-2-oxoethyl)-1H-pyrazol-4-yl)-1-(3-((3-((4-methoxybenzyl)thio)naphthalen-1-yl)oxy)propyl)-3-methyl-1H-indole-2-carboxylate |

TABLE 2-continued

| Int. No. | Structure | Name |
|---|---|---|
| 35 | 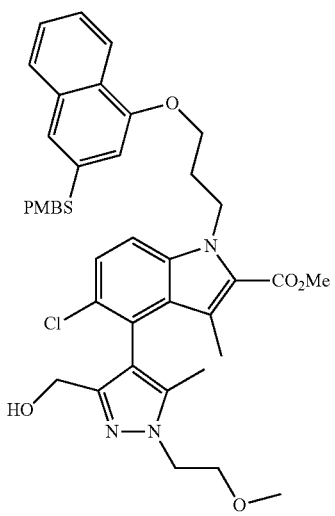 | Methyl 5-chloro-4-(3-(hydroxymethyl)-1-(2-methoxyethyl)-5-methyl-1H-pyrazol-4-yl)-1-(3-((3-((4-methoxybenzyl)thio)naphthalen-1-yl)oxy)propyl)-3-methyl-1H-indole-2-carboxylate |
| 36 | 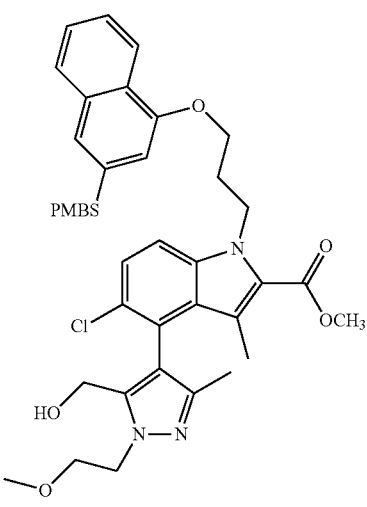 | methyl 5-chloro-4-(5-(hydroxymethyl)-1-(2-methoxyethyl)-3-methyl-1H-pyrazol-4-yl)-1-(3-((3-((4-methoxybenzyl)thio)naphthalen-1-yl)oxy)propyl)-3-methyl-1H-indole-2-carboxylate |
| 37 | 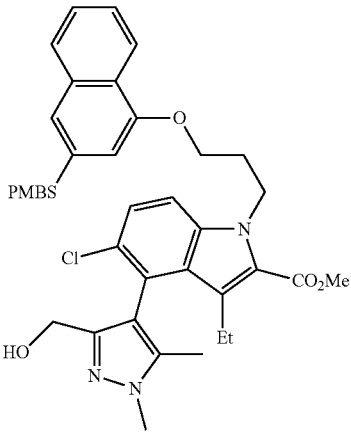 | Methyl 5-chloro-3-ethyl-4-(3-(hydroxymethyl)-1,5-dimethyl-1H-pyrazol-4-yl)-1-(3-((3-((4-methoxybenzyl)thio)naphthalen-1-yl)oxy)propyl)-1H-indole-2-carboxylate |

TABLE 2-continued

| Int. No. | Structure | Name |
|---|---|---|
| 38 | 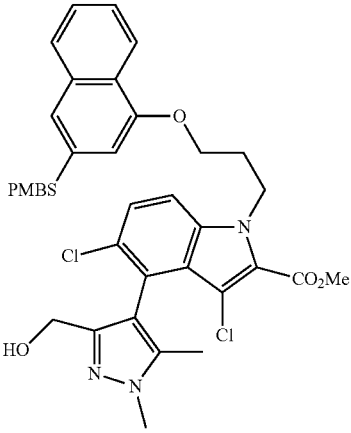 | Methyl 3,5-dichloro-4-(3-(hydroxymethyl)-1,5-dimethyl-1H-pyrazol-4-yl)-1-(3-((3-((4-methoxybenzyl)thio)naphthalen-1-yl)oxy)propyl)-1H-indole-2-carboxylate |
| 39 | 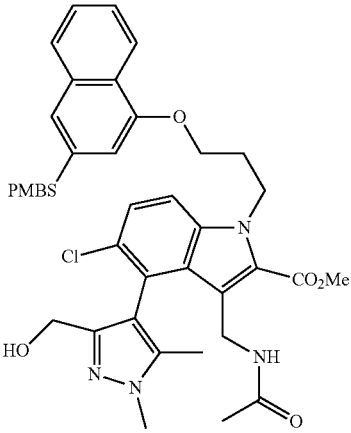 | Methyl 3-(acetamidomethyl)-5-chloro-4-(3-(hydroxymethyl)-1,5-dimethyl-1H-pyrazol-4-yl)-1-(3-((3-((4-methoxybenzyl)thio)naphthalen-1-yl)oxy)propyl)-1H-indole-2-carboxylate |
| 40 | 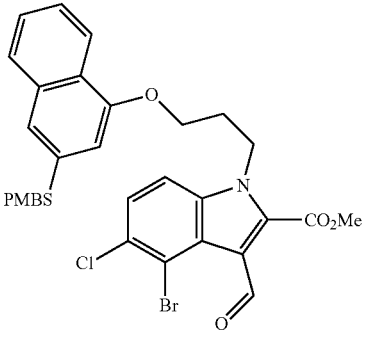 | Methyl 4-bromo-5-chloro-3-formyl-1-(3-((3-((4-methoxybenzyl)thio)naphthalen-1-yl)oxy)propyl)-1H-indole-2-carboxylate |
| 41 | 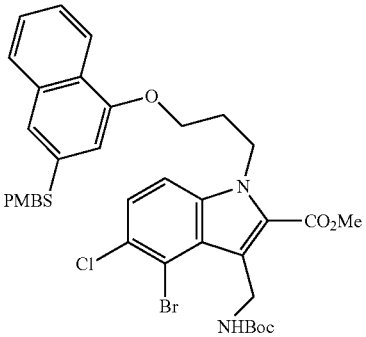 | Methyl 4-bromo-3-(((tert-butoxycarbonyl)amino)methyl)-5-chloro-1-(3-((3-((4-methoxybenzyl)thio)naphthalen-1-yl)oxy)propyl)-1H-indole-2-carboxylate |

TABLE 2-continued

| Int. No. | Structure | Name |
|---|---|---|
| 42 | 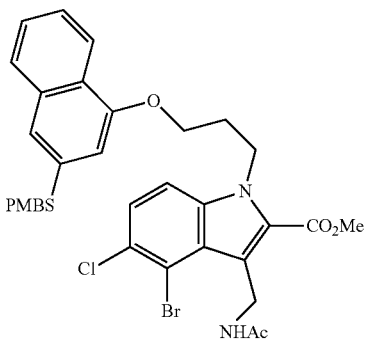 | Methyl 3-(acetamidomethyl)-4-bromo-5-chloro-1-(3-((3-((4-methoxybenzyl)thio)naphthalen-1-yl)oxy)propyl)-1H-indole-2-carboxylate |
| 43 | 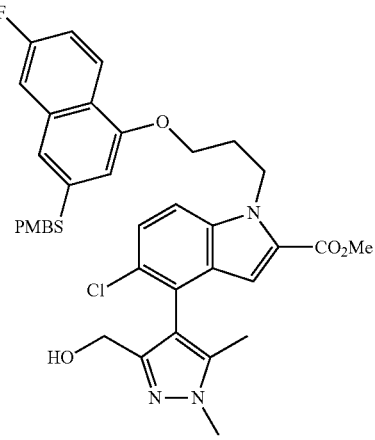 | Methyl 5-chloro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-1H-indole-2-carboxylate |
| 44 | 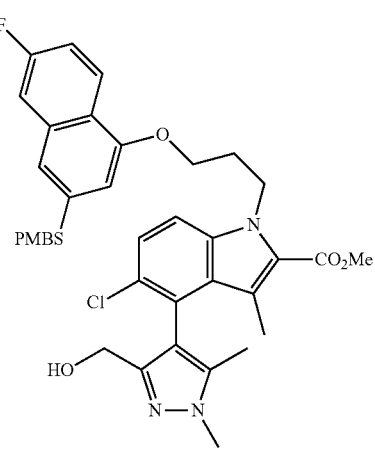 | Methyl 5-chloro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-3-methyl-1H-indole-2-carboxylate |

TABLE 2-continued

| Int. No. | Structure | Name |
|---|---|---|
| 45 | 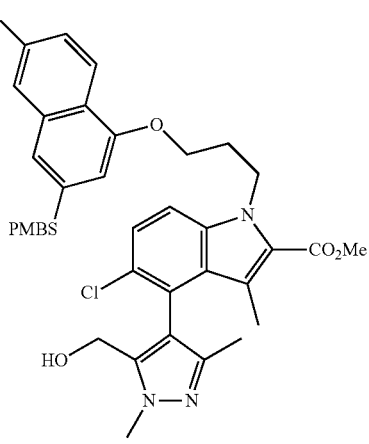 | Methyl 5-chloro-1-(3-((6-fluoro-3-((4-methoxybenzyl)thio)naphthalen-1-yl)oxy)propyl)-4-(5-(hydroxymethyl)-1,3-dimethyl-1H-pyrazol-4-yl)-3-methyl-1H-indole-2-carboxylate |
| 46 | 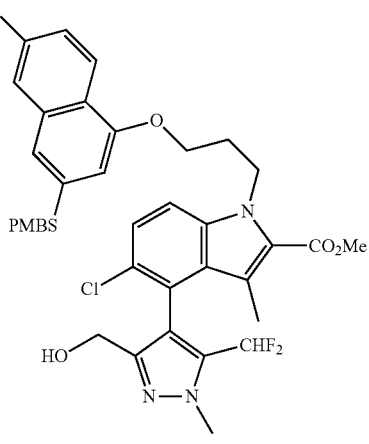 | Methyl 5-chloro-4-(5-(difluoromethyl)-3-(hydroxymethyl)-1-methyl-1H-pyrazol-4-yl)-1-(3-((6-fluoro-3-((4-methoxybenzyl)thio)naphthalen-1-yl)oxy)propyl)-3-methyl-1H-indole-2-carboxylate |
| 47 | 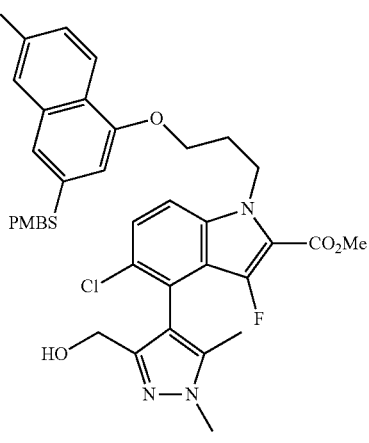 | Methyl 5-chloro-3-fluoro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-1H-indole-2-carboxylate |

TABLE 2-continued

| Int. No. | Structure | Name |
|---|---|---|
| 48 | 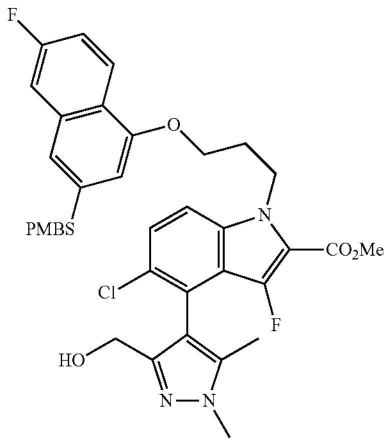 | Methyl 5-cyano-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-3-methyl-1H-indole-2-carboxylate |
| 49 | 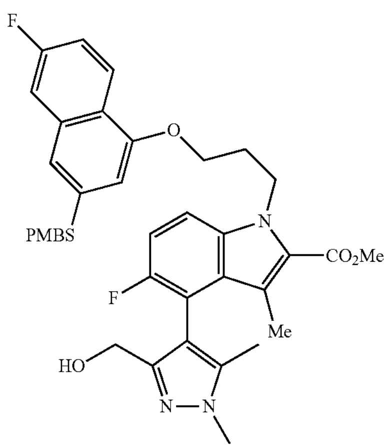 | Methyl 5-fluoro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-3-methyl-1H-indole-2-carboxylate |
| 50 | 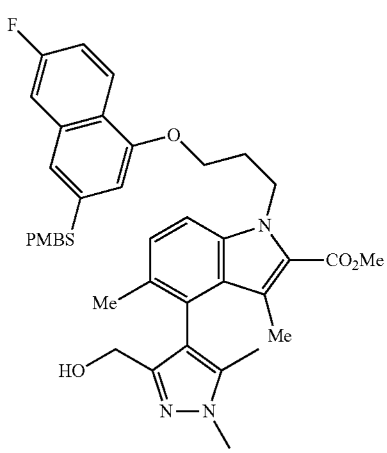 | Methyl 1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-3,5-dimethyl-1H-indole-2-carboxylate |

TABLE 2-continued

| Int. No. | Structure | Name |
|---|---|---|
| 51 | 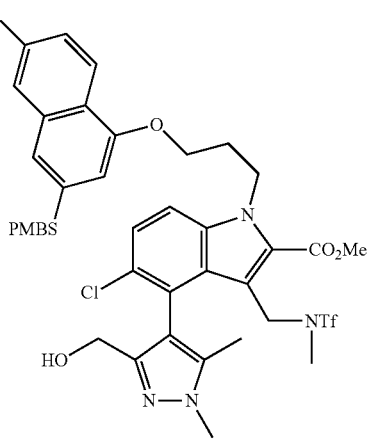 | Methyl 5-chloro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-3-(((1,1,1-trifluoro-N-methylmethyl)sulfonamido)methyl)-1H-indole-2-carboxylate |
| 52 | 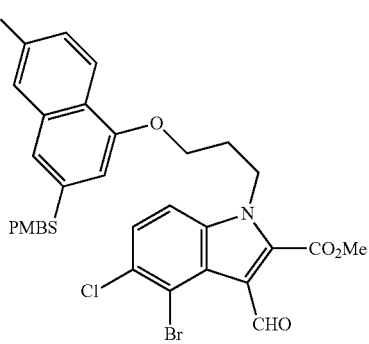 | Methyl 4-bromo-5-chloro-1-(3-((6-fluoro-3-((4-methoxybenzyl)thio)naphthalen-1-yl)oxy)propyl)-3-formyl-1H-indole-2-carboxylate |
| 53 | 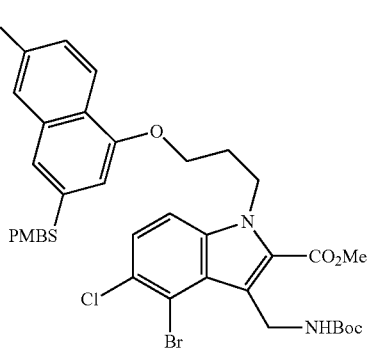 | Methyl 4-bromo-3-(((tert-butoxycarbonyl)amino)methyl)-5-chloro-1-(3-((6-fluoro-3-((4-methoxybenzyl)thio)naphthalen-1-yl)oxy)propyl)-1H-indole-2-carboxylate |
| 54 | 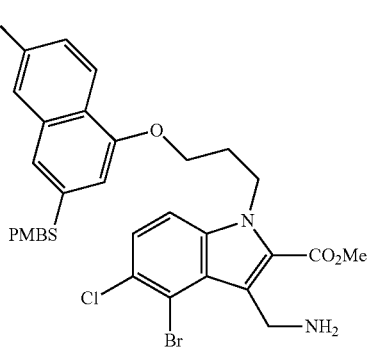 | Methyl 3-(aminomethyl)-4-bromo-5-chloro-1-(3-((6-fluoro-3-((4-methoxybenzyl)thio)naphthalen-1-yl)oxy)propyl)-1H-indole-2-carboxylate |

TABLE 2-continued

| Int. No. | Structure | Name |
|---|---|---|
| 55 | 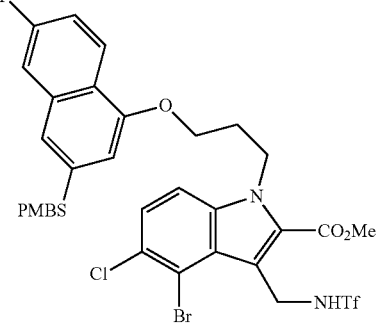 | Methyl 4-bromo-5-chloro-1-(3-((6-fluoro-3-((4-methoxybenzyl)thio)naphthalen-1-yl)oxy)propyl)-3-(((trifluoromethyl)sulfonamido)methyl)-1H-indole-2-carboxylate |
| 56 | 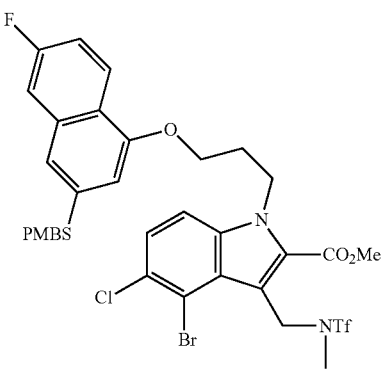 | Methyl 4-bromo-5-chloro-1-(3-((6-fluoro-3-((4-methoxybenzyl)thio)naphthalen-1-yl)oxy)propyl)-3-(((1,1,1-trifluoro-N-methylmethyl)sulfonamido)methyl)-1H-indole-2-carboxylate |
| 57 | 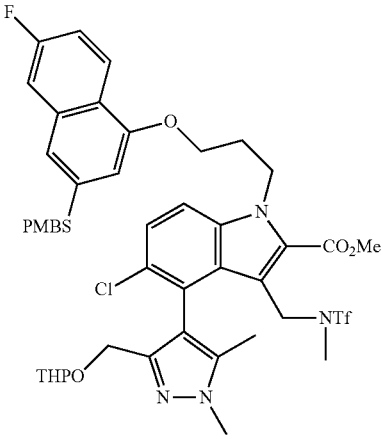 | Methyl 5-chloro-4-(1,5-dimethyl-3-(((tetrahydro-2H-pyran-2-yl)oxy)methyl)-1H-pyrazol-4-yl)-1-(3-((6-fluoro-3-((4-methoxybenzyl)thio)naphthalen-1-yl)oxy)propyl)-3-(((1,1,1-trifluoro-N-methylmethyl)sulfonamido)methyl)-1H-indole-2-carboxylate |
| 58 | 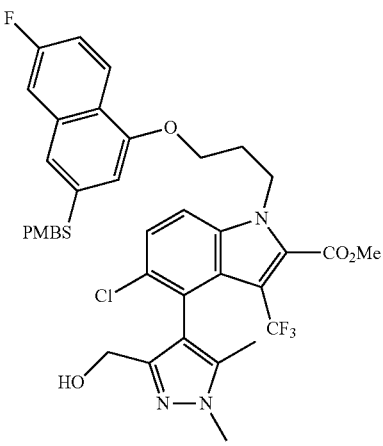 | Methyl 5-chloro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-3-(trifluoromethyl)-1H-indole-2-carboxylate |

TABLE 2-continued

| Int. No. | Structure | Name |
|---|---|---|
| 59 | 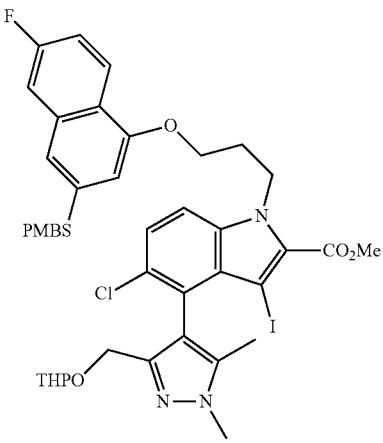 | Methyl 5-chloro-4-(1,5-dimethyl-3-(((tetrahydro-2H-pyran-2-yl)oxy)methyl)-1H-pyrazol-4-yl)-1-(3-((6-fluoro-3-((4-methoxybenzyl)thio)naphthalen-1-yl)oxy)propyl)-3-iodo-1H-indole-2-carboxylate |
| 60 | 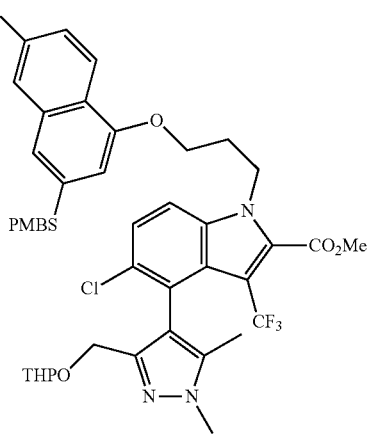 | Methyl 5-chloro-4-(1,5-dimethyl-3-(((tetrahydro-2H-pyran-2-yl)oxy)methyl)-1H-pyrazol-4-yl)-1-(3-((6-fluoro-3-((4-methoxybenzyl)thio)naphthalen-1-yl)oxy)propyl)-3-(trifluoromethyl)-1H-indole-2-carboxylate |
| 61 | 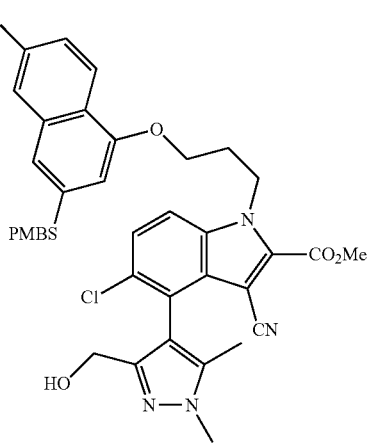 | Methyl 5-chloro-3-cyano-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-1H-indole-2-carboxylate |

| Int. No. | Structure | Name |
|---|---|---|
| 62 | 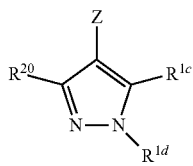 | Methyl 5-chloro-3-cyano-4-(1,5-dimethyl-3-(((tetrahydro-2H-pyran-2-yl)oxy)methyl)-1H-pyrazol-4-yl)-1-(3-((6-fluoro-3-((4-methoxybenzyl)thio)naphthalen-1-yl)oxy)propyl)-1H-indole-2-carboxylate |

III. Methods of Preparing Compounds and Intermediates of the Disclosure

The disclosure also provides methods of preparing Compounds of the Disclosure and/or Intermediates of the Disclosure.

In one embodiment, the disclosure provides a process for preparing a compound of Formula XXVI, see "II. Intermediates of the Disclosure" above, wherein E is E-1; $R^{29}$ is $R^{19}$; and $R^{19}$ is a protecting group, the process comprising reacting a compound of Formula XXVI, wherein E is —Br; $R^{29}$ is $R^{19}$; and $R^{19}$ is a protecting group, with a compound of Formula XX:

XX,

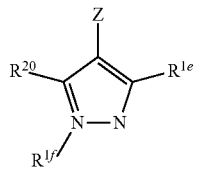

wherein:
Z is —$BR^{26a}R^{26b}$;
$R^{26a}$ and $R^{26b}$ are selected from the group consisting of hydroxy and alkoxy; or
$R^{26a}$ and $R^{26b}$ taken together form a linkage —$O(CR^{27a}R^{27b})_uO$—;
$R^{27a}$ and $R^{27b}$ are each independently selected from the group consisting of hydrogen and $C_{1-4}$ alkyl;
u is 2, 3, or 4;
$R^{1c}$ is selected from the group consisting of hydrogen, $C_1$-$C_4$ alkyl, halo, $C_1$-$C_4$ haloalkyl, and $C_3$-$C_6$ cycloalkyl;
$R^{1d}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl; or
$R^{1c}$ and $R^{1d}$ taken together with the atoms to which they are attached form an optionally substituted 4- to 8-membered heterocyclo;
$R^{20}$ is —$CH_2XR^{21}$;
X is selected from the group consisting of —O—, —S—, and —N(H)—; and
$R^{21}$ is a protecting group,
in presence of a palladium catalyst in a solvent.

In another embodiment, the disclosure provides a process for preparing a compound of Formula XXVI, wherein E is E-3; $R^{29}$ is $R^{19}$; and $R^{19}$ is a protecting group, the process comprising reacting a compound of Formula XXVI, wherein E is —Br; $R^{29}$ is $R^{19}$; and $R^{19}$ is a protecting group, with a compound of Formula XXIV:

XXIV, wherein:
Z is —$BR^{26a}R^{26b}$;
$R^{26a}$ and $R^{26b}$ are selected from the group consisting of hydroxy and alkoxy; or
$R^{26a}$ and $R^{26b}$ taken together form a linkage —$O(CR^{27a}R^{27b})_uO$—;
$R^{27a}$ and $R^{27b}$ are each independently selected from the group consisting of hydrogen and $C_{1-4}$ alkyl;
u is 2, 3, or 4;
$R^{1e}$ is selected from the group consisting of hydrogen, halo, $C_1$-$C_4$ alkyl, $C_1$-$C_4$ haloalkyl, and $C_3$-$C_6$ cycloalkyl;
$R^{1f}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl;
$R^{20}$ is —$CH_2XR^{21}$;
X is selected from the group consisting of —O—, —S—, and —N(H)—; and
$R^{21}$ is a protecting group,
in presence of a palladium catalyst in a solvent.

In another embodiment, the disclosure provides a process for preparing a compound of Formula XXVI, wherein E is E-2; $R^{29}$ is $R^{19}$; and $R^{19}$ is a protecting group, the process comprising reacting a compound of Formula XXVI, wherein E is E-1, $R^{29}$ is $R^{19}$; $R^{19}$ is a protecting group, and $R^{20}$ is —$CH_2$-LG, with a compound of Formula XXI:

 XXI, wherein;

is selected from the group consisting of arylenyl and heteroarylenyl;

$R^{22}$ is —$OR^{23}$;

$R^{23}$ is a protecting group;

$R^{28}$ is —$C(=O)R^{28a}$; and $R^{28a}$ is $C_1$-$C_6$ alkyl, in a solvent and, optionally, in the presence of a base.

In another embodiment, the disclosure provides process for preparing a compound of Formula XXVI, wherein E is E-4; $R^{29}$ is $R^{19}$; and $R^{19}$ is a protecting group, the process comprising reacting a compound of Formula XXVI, wherein E is E-3, $R^{29}$ is $R^{19}$; $R^{19}$ is a protecting group, and $R^{20}$ is —$CH_2$-LG, with a compound of Formula XXI:

 XXI, wherein;

is selected from the group consisting of arylenyl and heteroarylenyl;

$R^{22}$ is —$OR^{23}$;

$R^{23}$ is a protecting group;

$R^{28}$ is —$C(=O)R^{28a}$; and $R^{28a}$ is $C_1$-$C_6$ alkyl, in a solvent and, optionally, in the presence of a base.

In another embodiment, the disclosure provides a process for preparing a compound of Formula XXVI, wherein $R^{29}$ is E is

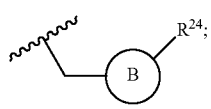

E-3; $R^{20}$ is —$CH_2XR^{21}$; is —O—; $R^{21}$ is a protecting group; $R^{24}$ is —CH and $R^{25}$ is a protecting group, the process comprising reacting a compound of Formula XXVI, wherein E is E-3; $R^{20}$ is —$CH_2XR^{21}$; X is —O—; $R^{21}$ is a protecting group; $R^{29}$ is $R^{19}$; and $R^{19}$ is hydrogen, with a compound of Formula XXV:

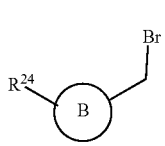 XXV, wherein;

is selected from the group consisting of arylenyl and heteroarylenyl;

$R^{24}$ is —$CH_2OR^{25}$; and $R^{25}$ is a protecting group, in a solvent and, optionally, in the presence of a base.

In another embodiment, the disclosure provides a process for preparing a compound of Formula XXVI, wherein $R^{29}$ is E is

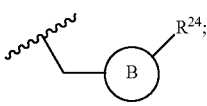

E-1; $R^{20}$ is —$CH_2XR^{21}$; is —O—; $R^{21}$ is a protecting group; $R^{24}$ is —$CH_2OR^{25}$; and $R^{25}$ is a protecting group, the process comprising reacting a compound of Formula XXVI, wherein E is E-1; $R^{20}$ is —$CH_2XR^{21}$; is —O—; $R^{21}$ is a protecting group; $R^{29}$ is $R^{19}$; and $R^{19}$ is hydrogen, with a compound of Formula XXV:

 XXV, wherein;

is selected from the group consisting of arylenyl and heteroarylenyl;

$R^{24}$ is —$CH_2OR^{25}$; and $R^{25}$ is a protecting group, in a solvent and, optionally, in the presence of a base.

In another embodiment, the disclosure provides a process of preparing a compound of Formula III, see "I. Compounds of the Disclosure" above, wherein R is hydrogen, the process comprising hydrolyzing a compound of Formula III, wherein R is $C_1$-$C_6$ alkyl, in the presence of a base, e.g., NaOH or KOH, in a solvent.

In another embodiment, the disclosure provides a process of preparing a compound of Formula IV, see "I. Compounds of the Disclosure" above, wherein R is hydrogen, the process comprising hydrolyzing a compound of Formula IV, wherein R is $C_1$-$C_6$ alkyl, in the presence of a base in a solvent.

In another embodiment, the disclosure provides a process of preparing a compound of Formula III, see "I. Compounds of the Disclosure" above, wherein R is hydrogen, the process comprising hydrolyzing a compound of Formula V, wherein R is $C_1$-$C_6$ alkyl, in the presence of a base in a solvent.

In another embodiment, the disclosure provides a process of preparing a compound of Formula III-A in 95% ee or more, or a compound of Formula III-B in 95% ee or more, the process comprising separating a compound of Formula III by chiral HPLC.

In another embodiment, the disclosure provides a process of preparing a compound of Formula IV-A in 95% ee or more, or a compound of Formula IV-B in 95% ee or more, the process comprising separating a compound of Formula IV by chiral HPLC.

In another embodiment, the disclosure provides a process of preparing a compound of Formula V-A in 95% ee or more, or a compound of Formula V-B in 95% ee or more, the process comprising separating a compound of Formula V by chiral HPLC.

The following particular embodiments directed to methods of preparing Compounds of the Disclosure and Intermediates of the Disclosure.

Scheme P1

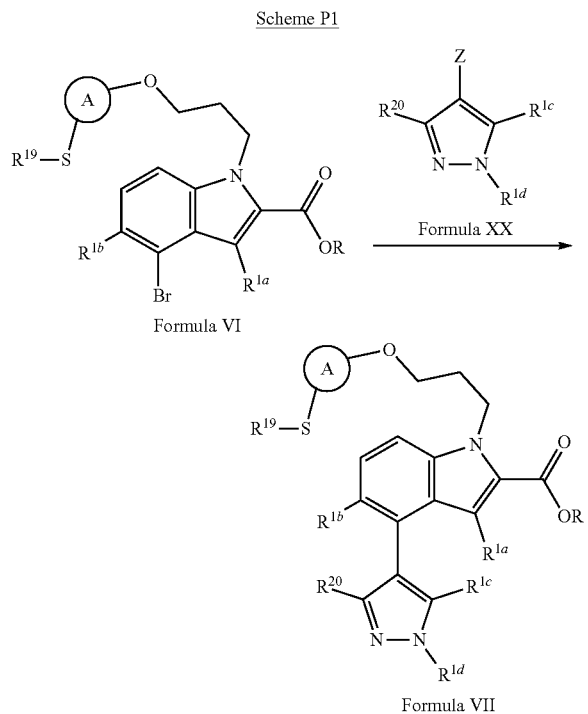

Formula VI

Formula VII

Embodiment P1. A process of preparing a compound of Embodiment I2 of Formula VII, wherein:

$R^{19}$ is a protecting group;

$R^{20}$ is —$CH_2XR^{21}$;

X is selected from the group consisting of —O—, —S—, and —N(H)—; and $R^{21}$ is a protecting group the process comprising reacting a compound of Embodiment I1 of Formula VI, wherein $R^{19}$ is a protecting group, with compound of Formula XX:

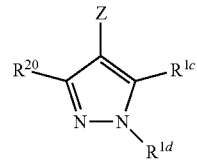

XX, wherein:

Z is —$BR^{26a}R^{26b}$;

$R^{26a}$ and $R^{26b}$ are selected from the group consisting of hydroxy and alkoxy; or $R^{26a}$ and $R^{26b}$ taken together form a linkage —O($CR^{27a}R^{27}$)$_u$O—;

$R^{27a}$ and $R^{27b}$ are each independently selected from the group consisting of hydrogen and $C_{1-4}$ alkyl;

u is 2, 3, or 4;

$R^{1c}$ is selected from the group consisting of hydrogen, $C_1$-$C_4$ alkyl, halo, $C_1$-$C_4$ haloalkyl, and $C_3$-$C_6$ cycloalkyl;

$R^{1d}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl; or $R^{1c}$ and $R^{1d}$ taken together with the atoms to which they are attached form an optionally substituted 4- to 8-membered heterocyclo;

$R^{20}$ is —$CH_2XR^{21}$;

X is selected from the group consisting of —O—, —S—, and —N(H)—; and $R^{21}$ is a protecting group, in presence of a palladium catalyst in a solvent.

Scheme P2

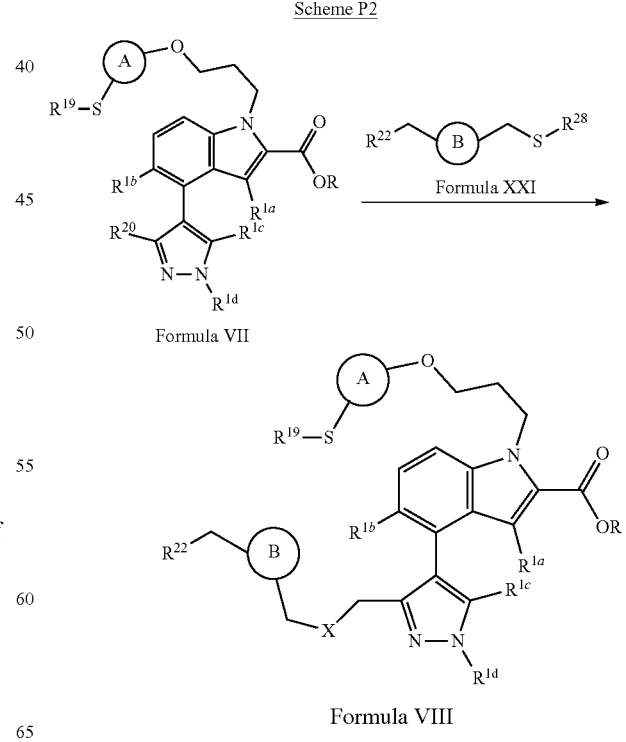

Formula VII

Formula VIII

Embodiment P2. A process of preparing a compound of Embodiment I3 of Formula VIII, wherein:
$R^{19}$ is a protecting group;
X is —S—;
$R^{22}$ is —$OR^{23}$; and
$R^{23}$ is a protecting group,
the process comprising reacting a compound of Embodiment I2 of Formula VII, wherein:
$R^{19}$ is a protecting group;
$R^{20}$ is —$CH_2$-LG; and
LG is Br,
with a compound of Formula XXI:

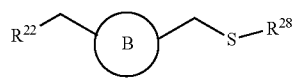

XXI, wherein;

is selected from the group consisting of arylenyl and heteroarylenyl;
$R^{22}$ is —$OR^{23}$;
$R^{23}$ is a protecting group;
$R^{28}$ is —C(=O)$R^{28a}$; and
$R^{28a}$ is $C_1$-$C_6$ alkyl,
in a solvent and, optionally, in the presence of a base.

Embodiment P3. A process of preparing a compound of Embodiment I3 of Formula VIII, wherein:
$R^{19}$ is a protecting group;
X is —N(H)—;
$R^{22}$ is —$OR^{23}$; and
$R^{23}$ is a protecting group,
the process comprising reacting a compound of Embodiment I2 of Formula VII, wherein:
$R^{19}$ is a protecting group;
$R^{20}$ is —$CH_2XR^{21}$;
X is —N(H)—; and
$R^{21}$ is hydrogen,
with a compound of Formula XXII:

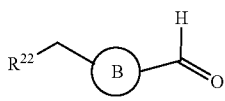

XXII, wherein;

is selected from the group consisting of arylenyl and heteroarylenyl;
$R^{22}$ is —$OR^{23}$; and
$R^{23}$ is a protecting group,
in a solvent in a presence of a reducing agent, e.g., $NaBH(OAc)_3$.

Scheme P3

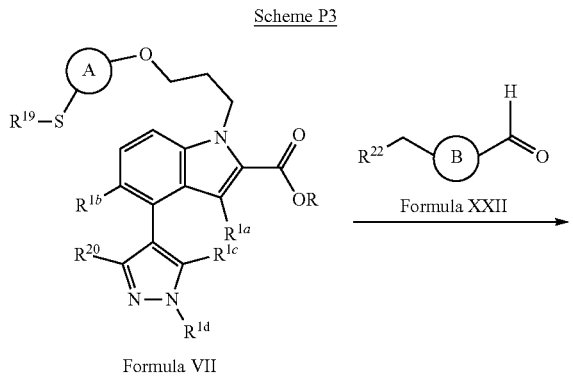

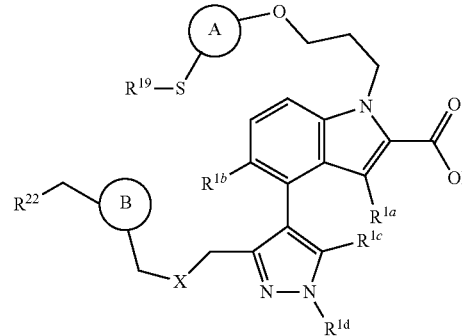

Scheme P4

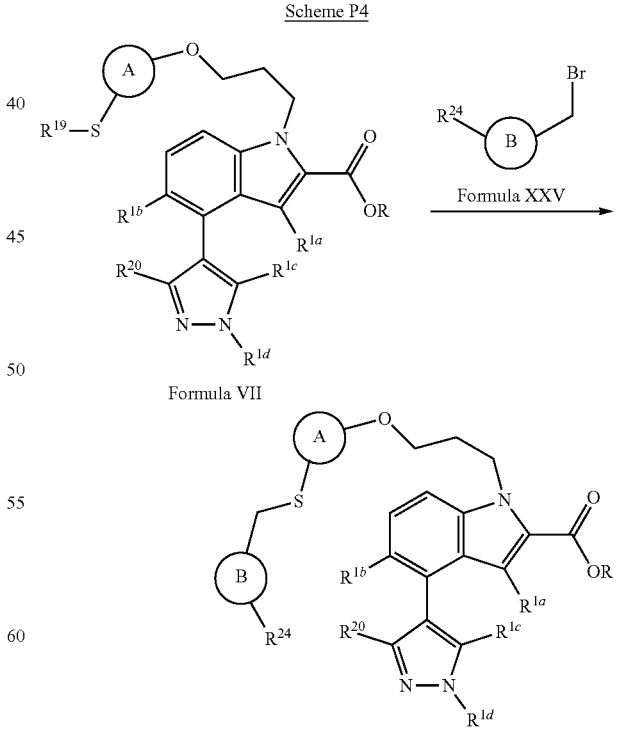

Embodiment P4. A process of preparing a compound of Embodiment I4 of Formula IX, wherein:
$R^{20}$ is —$CH_2XR^{21}$;
X is —O—;
$R^{21}$ is a protecting group;
$R^{24}$ is —$CH_2OR^{25}$; and
$R^{25}$ is a protecting group
the process comprising reacting a compound of Embodiment I2 of Formula VII, wherein:
$R^{19}$ is hydrogen;
$R^{20}$ is —$CH_2OR^{21}$; and
$R^{21}$ is a protecting group,
with a compound of Formula XXV:

XXV, wherein;

is selected from the group consisting of arylenyl and heteroarylenyl;
$R^{24}$ is —$CH_2OR^{25}$; and
$R^{25}$ is a protecting group,
in a solvent and, optionally, in the presence of a base.

Scheme P5

Embodiment P5. A process of preparing a compound of Embodiment I7 of Formula X, wherein:
$R^{19}$ is a protecting group;
$R^{20}$ is —$CH_2XR^{21}$;
X is selected from the group consisting of —O—, —S—, and —N(H)—; and
$R^{21}$ is a protecting group
the process comprising reacting a compound of Embodiment I1 of Formula VI, wherein $R^{19}$ is a protecting group,
with compound of Formula XXIII:

XXIII, wherein:
Z is —$BR^{26a}R^{26b}$;
$R^{26a}$ and $R^{26b}$ are selected from the group consisting of hydroxy and alkoxy; or
$R^{26a}$ and $R^{26b}$ taken together form a linkage —$O(CR^{27a}R^{27})_uO$—;
$R^{27a}$ and $R^{27b}$ are each independently selected from the group consisting of hydrogen and $C_{1-4}$ alkyl;
u is 2, 3, or 4;
o is 0, 1, or 2;
p is 0 or 1;
with the proviso that when p is 0, Z is —$CR^{9a}R^{9b}$—;
Z is selected from the group consisting of —$CR^{9a}R^{9b}$—, —O—, —S—, S(=O)—, S(=O)$_2$—, and —N($R^{10}$)—; and
$R^{9a}$ and $R^{9b}$ are independently selected from the group consisting of hydrogen and
$C_1$-$C_4$ alkyl,
$R^{20}$ is —$CH_2XR^{21}$;
X is selected from the group consisting of —O—, —S—, and —N(H)—; and
$R^{21}$ is a protecting group,
in presence of a palladium catalyst in a solvent.

Scheme P5

Formula XI

Embodiment P6. A process of preparing a compound of Embodiment I8 of Formula XI, wherein:
$R^{19}$ is a protecting group;
X is —S—;
$R^{22}$ is —$OR^{23}$; and
$R^{23}$ is a protecting group,
the process comprising reacting a compound of Embodiment I7 of Formula X:
wherein:
$R^{19}$ is a protecting group; and
$R^{20}$ is —$CH_2$-LG, e.g., LG is Br;
with a compound of Formula XXI:

XXI, wherein;

B is selected from the group consisting of arylenyl and heteroarylenyl;
$R^{22}$ is —$OR^{23}$;
$R^{23}$ is a protecting group;
$R^{28}$ is —C(=O)$R^{28a}$; and
$R^{28a}$ is $C_1$-$C_6$ alkyl,
in a solvent and, optionally, in the presence of a base.

Scheme P7

Formula X

Formula XI

Embodiment P7. A process of preparing a compound of Embodiment I8 of Formula XI, wherein:
$R^{19}$ is a protecting group;
X is —N(H)—;
$R^{22}$ is —$OR^{23}$; and
$R^{23}$ is a protecting group,
the process comprising reacting a compound of Embodiment I7 of Formula X, wherein:
$R^{19}$ is a protecting group; and
$R^{20}$ is —$CH_2XR^{21}$;
X is —N(H)—; and
$R^{21}$ is hydrogen,
with a compound of Formula XXII:

XXII, wherein;

B is selected from the group consisting of arylenyl and heteroarylenyl;
$R^{22}$ is —$OR^{23}$; and
$R^{23}$ is a protecting group,
in a solvent in the presence of a reducing agent, e.g., NaBH(OAc)$_3$.

Scheme P8

Formula X

-continued

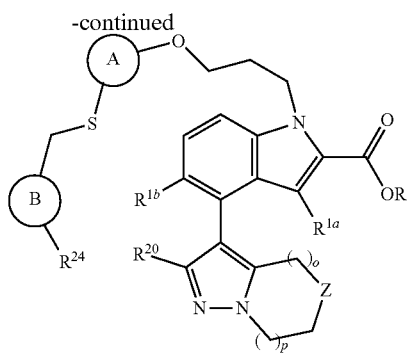

Formula XII

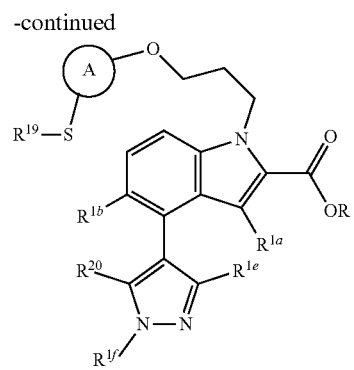

Formula XIII

Embodiment P8. A process of preparing a compound of Embodiment I9 of Formula XII, wherein:
$R^{20}$ is —$CH_2XR^{21}$;
X is —O—;
$R^{21}$ is a protecting group,
$R^{24}$ is —$CH_2OR^{25}$; and
$R^{25}$ is a protecting group
the process comprising reacting a compound of Embodiment I7 of Formula X, wherein:
$R^{19}$ is hydrogen; and
$R^{20}$ is —$CH_2OR^{21}$; and
$R^{21}$ is a protecting group,
with a compound of Formula XXV:

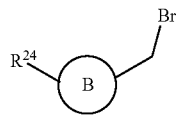

wherein;

is selected from the group consisting of arylenyl and heteroarylenyl;
$R^{24}$ is —$CH_2OR^{25}$; and
$R^{25}$ is a protecting group,
in a solvent and, optionally, in the presence of a base.

Scheme P9

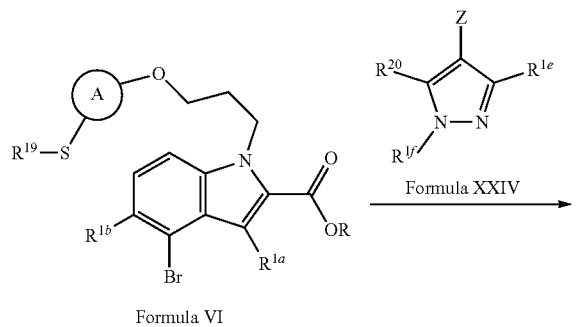

Embodiment P9. A process of preparing a compound of Embodiment I14 of Formula XIII, wherein:
$R^{19}$ is a protecting group;
$R^{20}$ is —$CH_2XR^{21}$; and
X is selected from the group consisting of —O—, —S—, and —N(H)—; and
$R^{21}$ is a protecting group
the process comprising reacting a compound of Embodiment I1 of Formula VI, wherein $R^{19}$ is a protecting group, with compound of Formula XXIV:

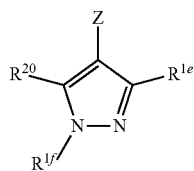

wherein:
Z is —$BR^{26a}R^{26b}$;
$R^{26a}$ and $R^{26b}$ are selected from the group consisting of hydroxy and alkoxy; or
$R^{26a}$ and $R^{26b}$ taken together form a linkage —$O(CR^{27a}R^{27})_uO$—;
$R^{27a}$ and $R^{27b}$ are each independently selected from the group consisting of hydrogen and $C_{1-4}$ alkyl;
u is 2, 3, or 4;
$R^{1e}$ is selected from the group consisting of hydrogen, halo, $C_1$-$C_4$ alkyl, $C_1$-$C_4$ haloalkyl, and $C_3$-$C_6$ cycloalkyl;
$R^{1f}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl;
$R^{20}$ is —$CH_2XR^{21}$;
X is selected from the group consisting of —O—, —S—, and —N(H)—; and
$R^{21}$ is a protecting group,
in presence of a palladium catalyst in a solvent.

Scheme P10

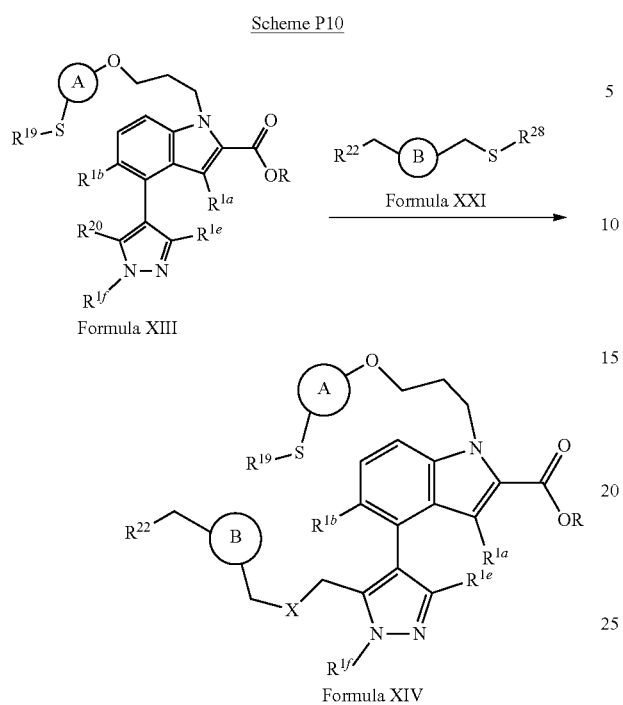

Formula XIII

Formula XIV

Embodiment P10. A process of preparing a compound of Embodiment I15 of Formula XIV, wherein:

$R^{19}$ is a protecting group;

X is —S—;

$R^{22}$ is —$OR^{23}$; and $R^{23}$ is a protecting group, the process comprising reacting a compound of Embodiment I14 of Formula XIII, wherein:

$R^{19}$ is a protecting group; and $R^{20}$ is —$CH_2$-LG, e.g., LG is Br, with a compound of Formula XXI:

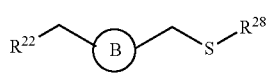

wherein;

is selected from the group consisting of arylenyl and heteroarylenyl;

$R^{22}$ is —$OR^{23}$;

$R^{23}$ is a protecting group;

$R^{28}$ is —C(=O)$R^{28a}$; and $R^{28a}$ is $C_1$-$C_6$ alkyl, in a solvent in the presence of a base.

Scheme P11

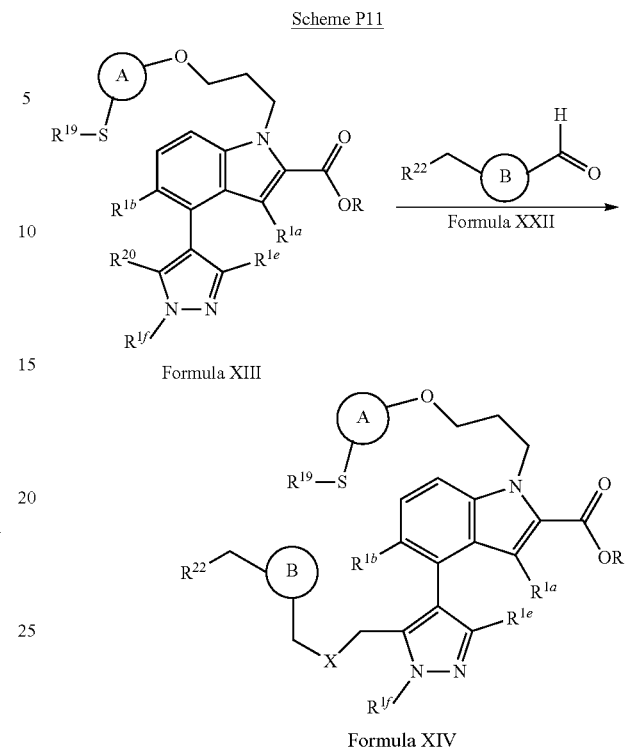

Formula XIII

Formula XIV

Embodiment P11. A process of preparing a compound of Embodiment I15 of Formula XIV, wherein:

$R^{19}$ is a protecting group;

X is —N(H)—;

$R^{22}$ is —$OR^{23}$; and $R^{23}$ is a protecting group, the process comprising reacting a compound of Embodiment I14 of Formula XIII, wherein:

$R^{19}$ is a protecting group; and $R^{20}$ is —$CH_2XR^{21}$;

X is —N(H)—; and $R^{21}$ is hydrogen, with a compound of Formula XXII:

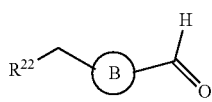

wherein;

is selected from the group consisting of arylenyl and heteroarylenyl;

$R^{22}$ is —$OR^{23}$; and $R^{23}$ is a protecting group, in a solvent in the presence of a reducing agent, e.g., NaBH(OAc)$_3$.

Scheme P12

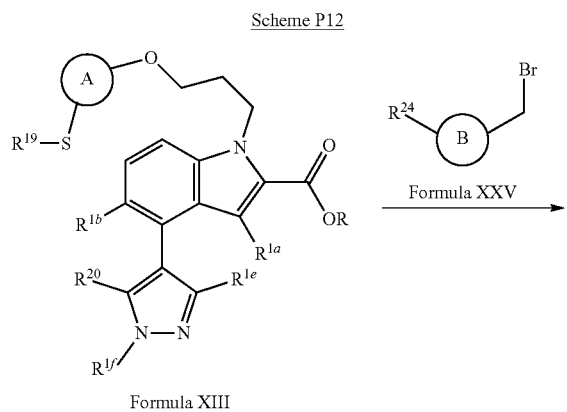

Formula XIII

Formula XV

Scheme P13

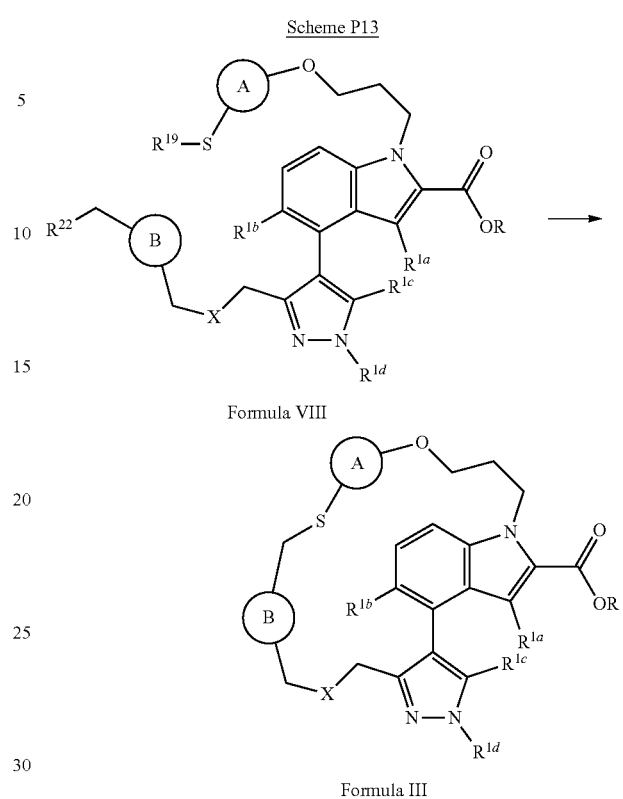

Formula VIII

Formula III

Embodiment P12. A process of preparing a compound of Embodiment I16 of Formula XV, wherein:
$R^{20}$ is —$CH_2XR^{21}$;
X is —O—;
$R^{21}$ is a protecting group,
$R^{24}$ is —$CH_2OR^{25}$; and
$R^{25}$ is a protecting group
the process comprising reacting a compound of Embodiment I14 of Formula XIII, wherein:
$R^{19}$ is hydrogen; and
$R^{20}$ is —$CH_2OR^{21}$; and
$R^{21}$ is a protecting group,
with a compound of Formula XXV:

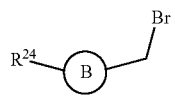 XXV, wherein;

is selected from the group consisting of arylenyl and heteroarylenyl;
$R^{24}$ is —$CH_2OR^{25}$; and
$R^{25}$ is a protecting group,
in a solvent and, optionally, in the presence of a base.

Embodiment P13. A process of preparing a compound of Embodiment C1 of Formula III, wherein:
R is $C_1$-$C_6$ alkyl; and
X is selected from the group consisting of —S— and —N(H)—;
the process comprising allowing a compound of Formula VIII of Embodiment I3, wherein:
$R^{19}$ is hydrogen;
X is selected from the group consisting of —S— and —N(H)—;
$R^{22}$ is a leaving group; and
to cyclize, optionally in the presence of a base, e.g., $K_2CO_3$, in a solvent.

Scheme P14

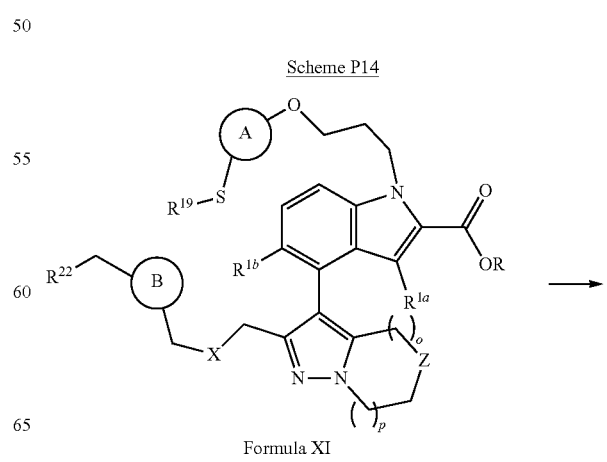

Formula XI

-continued

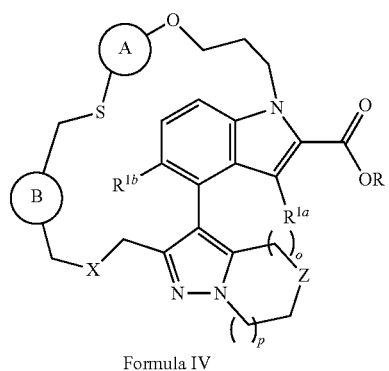
Formula IV

Embodiment P14. A process of preparing a compound of Embodiment C2 of Formula IV, wherein:

R is $C_1$-$C_6$ alkyl; and

X is selected from the group consisting of —S— and —N(H)—, the process comprising allowing of Embodiment I8 of Formula XI, wherein:

$R^{19}$ is hydrogen;

X is selected from the group consisting of —S— and —N(H)—; and $R^{22}$ is a leaving group, to cyclize in a solvent, optionally in the presence of a base.

Scheme P15

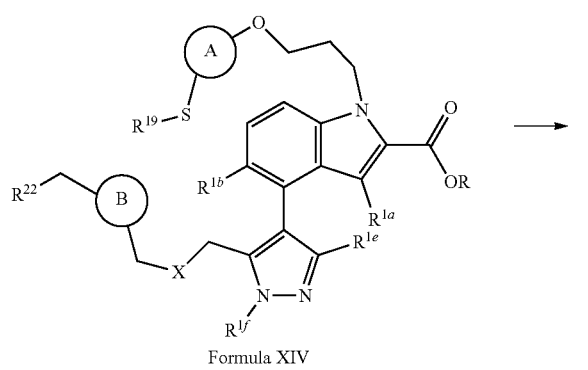
Formula XIV

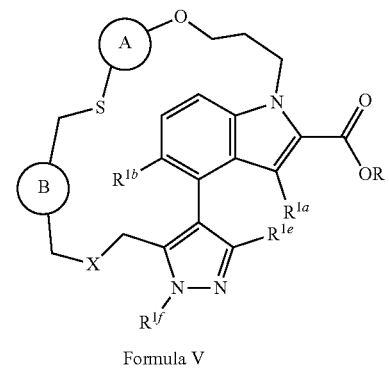
Formula V

Embodiment P15. A process of preparing a compound of Embodiment C3 of Formula V, wherein:

R is $C_1$-$C_6$ alkyl; and

X is selected from the group consisting of —S— and —N(H)—, the process comprising allowing a compound of Formula XIV of Embodiment 115, wherein:

$R^{19}$ is hydrogen;

X is selected from the group consisting of —S— and —N(H)—; and $R^{22}$ is a leaving group, to cyclize in a solvent, optionally in the presence of a base.

Scheme P16

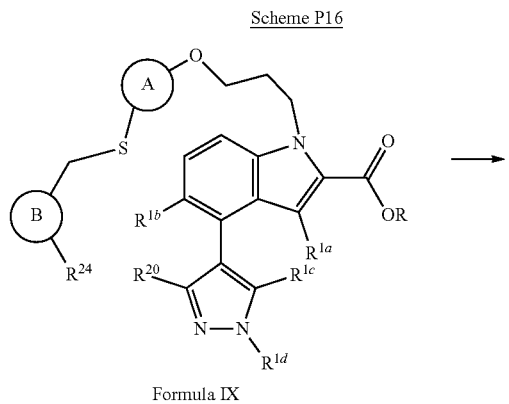
Formula IX

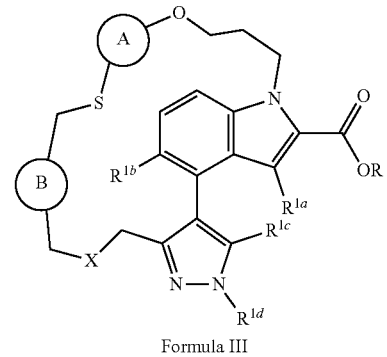
Formula III

Embodiment P16. A process of preparing the compound of Embodiment Clof Formula III, wherein:

R is $C_1$-$C_6$ alkyl; and

X is —N(H)—, the process comprising allowing a compound of Formula IX of Embodiment I4, wherein:

$R^{20}$ is —$CH_2XR^{21}$;

X is —N(H)—;

$R^{21}$ is hydrogen; and $R^{24}$ is —C(=O)H, to cyclize in a solvent in the presence of a reducing agent, e.g., $NaBH(OAc)_3$.

Scheme P17

[Structure: Formula XII]

[Structure: Formula IV]

Embodiment P17. A process of preparing a compound of Embodiment C2 of Formula IV, wherein:

R is $C_1$-$C_6$ alkyl; and

X is —N(H)—, the process comprising allowing a compound of Formula XII of Embodiment I9, wherein:

$R^{20}$ is —$CH_2XR^{21}$;

X is —N(H)—;

$R^{21}$ is hydrogen; and $R^{24}$ is —C(=O)H, to cyclize in a solvent in the presence of a reducing agent.

Scheme P18

[Structure: Formula XV]

[Structure: Formula V]

Embodiment P18. A process of preparing a compound of Embodiment C3 of Formula V, wherein:

R is $C_1$-$C_6$ alkyl; and

X is —N(H)—, the process comprising allowing a compound of Formula XV of Embodiment I16, wherein $R^{20}$ is —$CH_2XR^{21}$;

X is —N(H)—;

$R^{21}$ is hydrogen; and $R^{24}$ is —C(=O)H, to cyclize in a solvent in the presence of a reducing agent, e.g., $NaBH(OAc)_3$, in a solvent.

Scheme P19

[Structure: Formula IX]

[Structure: Formula III]

Embodiment P19. A process of preparing a compound of Embodiment C1 of Formula III, wherein:

R is $C_1$-$C_6$ alkyl;

X is —N($R^6$)—; and $R^6$ is selected from the group consisting of hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, and (5- to 10-membered heteroaryl)$C_1$-$C_4$ alkyl, ($C_1$-$C_4$ alkoxy)$C_1$-$C_4$ alkyl, the process comprising reacting a compound of Formula IX of Embodiment I4, wherein:

$R^{20}$ is —C(=O)H; and
$R^{24}$ is —C(=O)H, with $R^6NH_2$ is the presence of a reducing agent, e.g., NaBH(OAc)$_3$, in a solvent, wherein:

$R^6$ is selected from the group consisting of hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, and (5- to 10-membered heteroaryl)$C_1$-$C_4$ alkyl, ($C_1$-$C_4$ alkoxy)$C_1$-$C_4$ alkyl.

Scheme P20

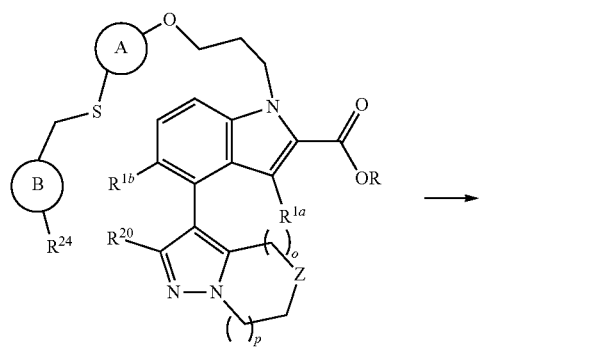

Formula XII

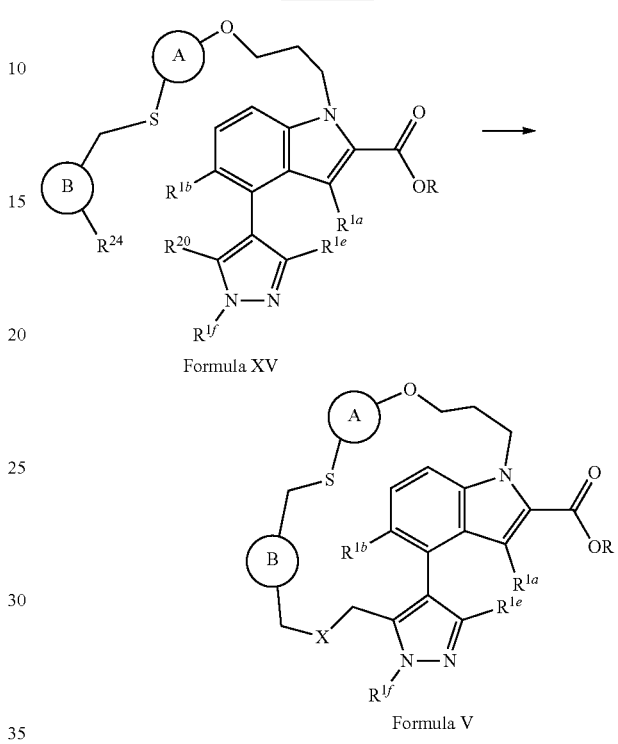

Formula IV

Embodiment P20. A process of preparing a compound of Embodiment C3 of Formula IV, wherein:

R is $C_1$-$C_6$ alkyl;
X is —N($R^6$)—; and
$R^6$ is selected from the group consisting of hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, and (5- to 10-membered heteroaryl)$C_1$-$C_4$ alkyl, ($C_1$-$C_4$ alkoxy)$C_1$-$C_4$ alkyl, the process comprising reacting a compound of Formula XII of Embodiment I9, wherein:

$R^{20}$ is —C(=O)H; and
$R^{24}$ is —C(=O)H, with $R^6NH_2$ is the presence of a reducing agent, e.g., NaBH(OAc)$_3$, in a solvent, wherein:

$R^6$ is selected from the group consisting of hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, and (5- to 10-membered heteroaryl)$C_1$-$C_4$ alkyl, ($C_1$-$C_4$ alkoxy)$C_1$-$C_4$ alkyl.

Scheme P21

Formula XV

Formula V

Embodiment P21. A process of preparing a compound of Embodiment C3 of Formula V, wherein:

R is $C_1$-$C_6$ alkyl;
X is —N($R^6$)—; and
$R^6$ is selected from the group consisting of hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, and (5- to 10-membered heteroaryl)$C_1$-$C_4$ alkyl, ($C_1$-$C_4$ alkoxy)$C_1$-$C_4$ alkyl, the process comprising reacting a compound of Formula XV of Embodiment I16, wherein:

$R^{20}$ is —C(=O)H; and
$R^{24}$ is —C(=O)H, with $R^6NH_2$ is the presence of a reducing agent, e.g., NaBH(OAc)$_3$, in a solvent, wherein:

$R^6$ is selected from the group consisting of hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, and (5- to 10-membered heteroaryl)$C_1$-$C_4$ alkyl, ($C_1$-$C_4$ alkoxy)$C_1$-$C_4$ alkyl.

Embodiment P22. The process of any one of Embodiments P1-P21, wherein (A)

is A-1.

Embodiment P23. The process of Embodiment P22, wherein $R^{4a}$, $R^{4b}$, and $R^{oo}$ are each independently selected from the group consisting of hydrogen and halo.

Embodiment P24. The process of Embodiment P23, wherein $R^{od}$ is hydrogen.

Embodiment P25. The process of any one of Embodiments P1-P24, wherein (A)

is A-2.

Embodiment P26. The process or process of Embodiment P25, wherein the 1-position of A-2 is attached to the oxygen atom and the 3-position of A-2 is attached to the sulfur atom.

Embodiment P27. The process or process of Embodiments P25 or P26, wherein $R^{5a}$, $R^{5b}$, $R^{5c}$, $R^{5d}$, and $R^{5e}$ are each independently selected from the group consisting of hydrogen and halo; and $R^{5f}$ is hydrogen.

Embodiment P28. The process of any one of Embodiments P1-P27, wherein:

$R^{1a}$ is selected from the group consisting of hydrogen, halo, $C_1$-$C_4$ alkyl, $C_1$-$C_4$ haloalkyl, $C_2$-$C_4$ alkynyl, and —$CH_2N(H)(R^{2b})$; and $R^{2b}$ is selected from the group consisting of —$C(=O)R^{3a}$ and —$S(=O)_2R^{3b}$.

Embodiment P29. The process of Embodiment P28, wherein $R^{1a}$ is selected from the group consisting of hydrogen, fluoro, chloro, methyl, ethyl, ethynyl, —$CH_2N(H)C(=O)CH_3$, and —$CH_2N(H)S(=O)_2CF_3$.

Embodiment P30. The process of any one of Embodiments P1-P29, wherein $R^{1b}$ is halo.

Embodiment P31. The process of Embodiment P30, wherein $R^{1b}$ is chloro.

Embodiment P32. The process of any one of Embodiments P2-P4, P5-P8, or P10-P31, wherein (B)

is aryl enyl.

Embodiment P33. The process of Embodiment P32, wherein:

(B)

is selected from the group consisting of:

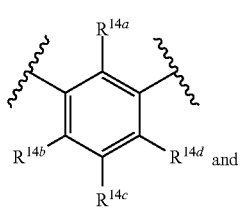

B-1

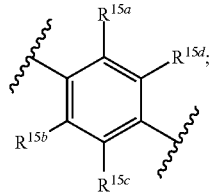

B-2

$R^{14a}$, $R^{14c}$, and $R^{14d}$ are each independently selected from the group consisting of hydrogen, halo, cyano, $C_1$-$C_4$ alkyl, $C_1$-$C_4$ haloalkyl, $C_1$-$C_4$ alkoxy, and $C_3$-$C_6$ cycloalkyl; and $R^{15a}$, $R^{15b}$, and $R^{15d}$ are each independently selected from the group consisting of hydrogen, halo, cyano, $C_1$-$C_4$ alkyl, $C_1$-$C_4$ haloalkyl, $C_1$-$C_4$ alkoxy, and $C_3$-$C_6$ cycloalkyl.

Embodiment P34. The process of Embodiment P33, wherein (B)

is B-1, or a pharmaceutically acceptable salt or solvate thereof.

Embodiment P35. The process of Embodiment P34, wherein $R^{14a}$, $R^{14b}$, $R^{14c}$, and $R^{14d}$ are each independently selected from the group consisting of hydrogen, halo, and $C_1$-$C_4$ alkyl.

Embodiment P36. The process of Embodiment P33, wherein (B)

is B-2.

Embodiment P37. The process of Embodiment P36, wherein $R^{15a}$, $R^{15b}$, $R^{15c}$, and $R^{15d}$ are each independently selected from the group consisting of hydrogen, halo, and $C_1$-$C_4$ alkyl.

Embodiment P38. The process of any one of Embodiments P2-P4, P5-P8, or P10-P31, wherein (B)

is heteroarylenyl.

Embodiment P39. The process of Embodiment P38, wherein:

(B)

is selected from the group consisting of:

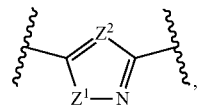

B-3

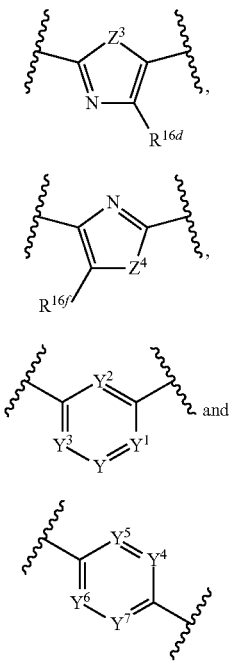

B-4

B-5

B-6

B-7

$Z^1$ is selected from the group consisting of —O—, —S—, and —N($R^{16a}$)—;
$R^{16a}$ is selected from the group consisting of hydrogen, $C_1$-$C_4$ alkyl, and $C_3$-$C_6$ cycloalkyl;
$Z^2$ is selected from the group consisting of —C($R^{16b}$)═ and —N═;
$R^{16b}$ is selected from the group consisting of hydrogen, halo, $C_1$-$C_4$ alkyl, and $C_3$-$C_6$ cycloalkyl;
$Z^3$ is selected from the group consisting of —O—, —S—, and —N($R^{16c}$)—;
$R^{16c}$ is selected from the group consisting of hydrogen, $C_1$-$C_4$ alkyl, and $C_3$-$C_6$ cycloalkyl;
$R^{16d}$ is selected from the group consisting of hydrogen, halo, $C_1$-$C_4$ alkyl, and $C_3$-$C_6$ cycloalkyl;
$Z^4$ is selected from the group consisting of —O—, —S—, and —N($R^{16e}$)—;
$R^{16e}$ is selected from the group consisting of hydrogen, $C_1$-$C_4$ alkyl, and $C_3$-$C_6$ cycloalkyl;
$R^{16f}$ is selected from the group consisting of hydrogen, halo, $C_1$-$C_4$ alkyl, and $C_3$-$C_6$ cycloalkyl;
Y is selected from the group consisting of —C($R^{17a}$)═ and —N═;
$Y^1$ is selected from the group consisting of —C($R^{17b}$)═ and —N═;
$Y^2$ is selected from the group consisting of —C($R^{17c}$)═ and —N═;
$Y^3$ is selected from the group consisting of —C($R^{17d}$)═ and —N═;
with proviso that at least one of Y, $Y^1$, $Y^2$, and $Y^3$ is —N═;
$R^{17a}$, $R^{17b}$, $R^{17c}$, and $R^{17d}$ are each independently selected from the group consisting of hydrogen, halo, cyano, $C_1$-$C_4$ alkyl, $C_1$-$C_4$ haloalkyl, and $C_1$-$C_4$ alkoxy;
$Y^4$ is selected from the group consisting of —C($R^{18a}$)═ and —N═;
$Y^5$ is selected from the group consisting of —C($R^{18b}$)═ and —N═;
$Y^6$ is selected from the group consisting of —C($R^{18c}$)═ and —N═;
$Y^7$ is selected from the group consisting of —C($R^{18d}$)═ and —N═;
with proviso that at least one of $Y^4$, $Y^5$, $Y^6$, and $Y^7$ is —N═;
$R^{18a}$, $R^{18b}$, $R^{18c}$, and $R^{18d}$ are each independently selected from the group consisting of hydrogen, halo, cyano, $C_1$-$C_4$ alkyl, $C_1$-$C_4$ haloalkyl, and $C_1$-$C_4$ alkoxy.

Embodiment P40. The process of Embodiment P39, wherein (B)

is B-3, or a pharmaceutically acceptable salt or solvate thereof.

Embodiment P41. The process of Embodiment P40, wherein:
$Z^1$ is selected from the group consisting of —O—, —S—, —N(H)—, and —N(CH$_3$)—; and
$Z^2$ is selected from the group consisting of —C(H)═, —C(CH$_3$)═, and —N═.

Embodiment P42. The process of Embodiment P39, wherein (B)

is B-4.

Embodiment P43. The process of Embodiment P42, wherein:
$Z^3$ is selected from the group consisting of —O—, —S—, —N(H)—, and —N(CH$_3$)—;
$R^{16d}$ is selected from the group consisting of hydrogen and methyl.

Embodiment P44. The process of Embodiment P39, wherein (B)

is B-5, or a pharmaceutically acceptable salt or solvate thereof.

Embodiment P45. The process of Embodiment P44, wherein:
$Z^4$ is selected from the group consisting of —O—, —S—, —N(H)—, and —N(CH$_3$)—;
$R^{16f}$ is selected from the group consisting of hydrogen and methyl.

Embodiment P45. The process of Embodiment P39, wherein (B)

is B-6.

Embodiment P46. The process of Embodiment P45, wherein:
Y is —N═;
$Y^1$ is selected from the group consisting of —C($R^{17b}$)═ and —N═;

$Y^2$ is selected from the group consisting of —C(R$^{17c}$)═ and —N═;
$Y^3$ is selected from the group consisting of —C(R$^{17d}$)═ and —N═; and
R$^{ub}$, R$^{uc}$, and R$^{17d}$ are each independently selected from the group consisting of hydrogen, halo, and C$_1$-C$_4$ alkyl.

Embodiment P47. The process of Embodiment P45, wherein:
Y is selected from the group consisting of —C(R$^{17a}$)═ and —N═;
$Y^1$ is —N═;
$Y^2$ is selected from the group consisting of —C(R$^{17c}$)═ and —N═;
$Y^3$ is selected from the group consisting of —C(R$^{17d}$)═ and —N═; and
R$^{17a}$, R$^{17c}$, and R$^{17d}$ are each independently selected from the group consisting of hydrogen, halo, and C$_1$-C$_4$ alkyl.

Embodiment P48. The process of Embodiment P45, wherein:
Y is selected from the group consisting of —C(R$^{17a}$)═ and —N═;
$Y^1$ is selected from the group consisting of —C(R$^{17b}$)═ and —N═;
$Y^2$ is —N═;
$Y^3$ is selected from the group consisting of —C(R$^{17d}$)═ and —N═; and
R$^{17a}$, R$^{17b}$, and R$^{17d}$ are each independently selected from the group consisting of hydrogen, halo, and C$_1$-C$_4$ alkyl.

Embodiment P48. The process of Embodiment P45, wherein:
Y is selected from the group consisting of —C(R$^{17a}$)═ and —N═;
$Y^1$ is selected from the group consisting of —C(R$^{17b}$)═ and —N═;
$Y^2$ is selected from the group consisting of —C(R$^{17c}$)═ and —N═;
$Y^3$ is —N═; and
R$^{17a}$, R$^{17b}$, and R$^{17c}$ are each independently selected from the group consisting of hydrogen, halo, and C$_1$-C$_4$ alkyl.

Embodiment P50. The process of Embodiment P39, wherein $$\text{B}$$

is B-7.

Embodiment P51. The process of Embodiment P50, wherein:
$Y^4$ is and —N═;
$Y^5$ is selected from the group consisting of —C(R$^{18b}$)═ and —N═;
$Y^6$ is selected from the group consisting of —C(R$^{18c}$)═ and —N═;
$Y^7$ is selected from the group consisting of —C(R$^{18d}$)═ and —N═; and
R$^{18b}$, R$^{18c}$, and R$^{18a}$ are each independently selected from the group consisting of hydrogen, halo, and C$_1$-C$_4$ alkyl.

Embodiment P52. The process of Embodiment P50, wherein:
$Y^4$ is selected from the group consisting of —C(R$^{18a}$)═ and —N═;
$Y^5$ is —N═;
$Y^6$ is selected from the group consisting of —C(R$^{18c}$)═ and —N═;
$Y^7$ is selected from the group consisting of —C(R$^{18d}$)═ and —N═; and
R$^{18a}$, R$^{18c}$, and R$^{18d}$ are each independently selected from the group consisting of hydrogen, halo, and C$_1$-C$_4$ alkyl.

Embodiment P53. The process of Embodiment P50, wherein:
$Y^4$ is selected from the group consisting of —C(R$^{18a}$)═ and —N═;
$Y^5$ is selected from the group consisting of —C(R$^{18b}$)═ and —N═;
$Y^6$ is —N═;
$Y^7$ is selected from the group consisting of —C(R$^{18d}$)═ and —N═; and
R$^{18a}$, R$^{18b}$, and R$^{18d}$ are each independently selected from the group consisting of hydrogen, halo, and C$_1$-C$_4$ alkyl.

Embodiment P54. The process of Embodiment P50, wherein:
$Y^4$ is selected from the group consisting of —C(R$^{18a}$)═ and —N═;
$Y^5$ is selected from the group consisting of —C(R$^{18b}$)═ and —N═;
$Y^6$ is selected from the group consisting of —C(R$^{18c}$)═ and —N═;
$Y^7$ is —N═; and
R$^{18a}$, R$^{18b}$, and R$^{18c}$ are each independently selected from the group consisting of hydrogen, halo, and C$_1$-C$_4$ alkyl.

Embodiment P55. The process of any one of Embodiments P2-P4, P5-P8, or P10-P31, wherein $$\text{B}$$

is selected from the group consisting of:

-continued

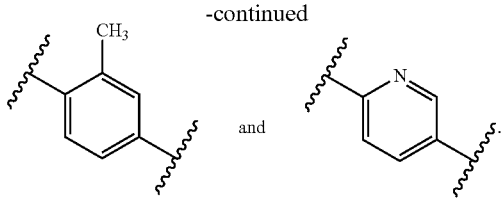
and

Embodiment P56. The process of Embodiment P55, wherein

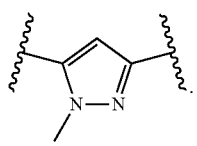 [SMILES: *c1cc(*)n(C)n1]

is:

Embodiment P57. The process of any one of Embodiments P1-P56, wherein R is methyl or ethyl.

IV. Methods of Treating Disease with Compounds of the Disclosure

Compounds of the Disclosure inhibit Mcl-1 and are useful in the treatment or prevention of a variety of diseases and conditions. In particular, Compounds of the Disclosure are useful in methods of treating or preventing a disease or condition wherein inhibition of Mcl-1 provides a benefit, for example, cancers and proliferative diseases. In one embodiment, such a cancer is referred to as a "Mcl-1 mediated cancer." Cancers responsive to Mcl-1 inhibition are known in the art. The therapeutic methods of this disclosure comprise administering a therapeutically effective amount of a Compound of the Disclosure to a subject in need thereof. The present methods also encompass administering a second therapeutic agent to the subject in addition to the Compound of the Disclosure. The second therapeutic agent is selected from drugs known as useful in treating the disease or condition afflicting the subject in need thereof, e.g., a chemotherapeutic agent and/or radiation known as useful in treating a particular cancer.

The present disclosure provides Compounds of the Disclosure as Mcl-1 inhibitors for the treatment of diseases and conditions wherein inhibition of Mcl-1 has a beneficial effect. Compounds of the Disclosure typically have a half maximal inhibitory concentration ($IC_{50}$) for inhibiting Mcl-1 of less than 100 µM, e.g., less than 50 µM, less than 25 µM, and less than 5 µM, less than about 1 less than about 0.5 less than about 0.1 less than about 0.05 or less than about 0.01 µM. In one embodiment, the present disclosure relates to a method of treating an individual suffering from a disease or condition wherein inhibition of Mcl-1 provides a benefit comprising administering a therapeutically effective amount of a Compound of the Disclosure to an individual in need thereof.

Since Compounds of the Disclosure are inhibitors of Mcl-1 protein, a number of diseases and conditions mediated by Mcl-1 can be treated by employing these compounds. The present disclosure is thus directed generally to a method for treating a condition or disorder responsive to Mcl-1 inhibition in an animal, e.g., a human, suffering from, or at risk of suffering from, the condition or disorder, the method comprising administering to the animal an effective amount of one or more Compounds of the Disclosure.

The present disclosure is further directed to a method of inhibiting Mcl-1 in a subject in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent, packaged separately or together, and an insert having instructions for using these active agents.

In one embodiment, a Compound of the Disclosure is administered in conjunction with a second therapeutic agent useful in the treatment of a disease or condition wherein inhibition of Mcl-1 provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human patient is treated with a Compound of the Disclosure, or a pharmaceutical composition comprising a Compound of the Disclosure, wherein the compound is administered in an amount sufficient to inhibit Mcl-1 activity in the patient.

In another aspect, the present disclosure provides a method of treating cancer in a subject comprising administering a therapeutically effective amount of a Compound of the Disclosure. While not being limited to a specific mechanism, in some embodiments, Compounds of the Disclosure treat cancer by inhibiting Mcl-1. Examples of treatable cancers include, but are not limited to, any one or more of the cancers of Table 3.

TABLE 3

| | | | |
|---|---|---|---|
| adrenal cancer | acinic cell carcinoma | acoustic neuroma | acral lentigious melanoma |
| acrospiroma | acute eosinophilic leukemia | acute erythroid leukemia | acute lymphoblastic leukemia |
| acute megakaryoblastic leukemia | acute monocytic leukemia | acute promyelocytic leukemia | adenocarcinoma |
| adenoid cystic carcinoma | adenoma | adenomatoid odontogenic tumor | adenosquamous carcinoma |
| adipose tissue neoplasm | adrenocortical carcinoma | adult T-cell leukemia/lymphoma | aggressive NK-cell leukemia |
| AIDS-related lymphoma | alveolar rhabdomyosarcoma | alveolar soft part sarcoma | ameloblastic fibroma |
| anaplastic large cell lymphoma | anaplastic thyroid cancer | angioimmunoblastic T-cell lymphoma | angiomyolipoma |
| angiosarcoma | astrocytoma | atypical teratoid rhabdoid tumor | B-cell chronic lymphocytic leukemia |
| B-cell prolymphocytic leukemia | B-cell lymphoma | basal cell carcinoma | biliary tract cancer |
| bladder cancer | blastoma | bone cancer | Brenner tumor |
| Brown tumor | Burkitt's lymphoma | breast cancer | brain cancer |
| carcinoma | carcinoma in situ | carcinosarcoma | cartilage tumor |
| cementoma | myeloid sarcoma | chondroma | chordoma |
| choriocarcinoma | choroid plexus papilloma | clear-cell sarcoma of the kidney | craniopharyngioma |
| cutaneous T-cell lymphoma | cervical cancer | colorectal cancer | Degos disease |
| desmoplastic small round cell tumor | diffuse large B-cell lymphoma | dysembryoplastic neuroepithelial tumor | dysgerminoma |
| embryonal carcinoma | endocrine gland neoplasm | endodermal sinus tumor | enteropathy-associated T-cell lymphoma |
| esophageal cancer | fetus in fetu | fibroma | fibrosarcoma |
| follicular lymphoma | follicular thyroid cancer | ganglioneuroma | gastrointestinal cancer |
| germ cell tumor | gestational choriocarcinoma | giant cell fibroblastoma | giant cell tumor of the bone |
| glial tumor | glioblastoma multiforme | glioma | gliomatosis cerebri |
| glucagonoma | gonadoblastoma | granulosa cell tumor | gynandroblastoma |
| gallbladder cancer | gastric cancer | hairy cell leukemia | hemangioblastoma |
| head and neck cancer | hemangiopericytoma | hematological cancer | hepatoblastoma |
| hepatosplenic T-cell lymphoma | Hodgkin's lymphoma | non-Hodgkin's lymphoma | invasive lobular carcinoma |
| intestinal cancer | kidney cancer | laryngeal cancer | lentigo maligna |
| lethal midline carcinoma | leukemia | leydig cell tumor | liposarcoma |
| lung cancer | lymphangioma | lymphangiosarcoma | lymphoepithelioma |
| lymphoma | acute lymphocytic leukemia | acute myelogeous leukemia | chronic lymphocytic leukemia |
| liver cancer | small cell lung | non-small cell lung cancer | MALT lymphoma cancer |
| malignant fibrous histiocytoma | malignant peripheral nerve sheath tumor | malignant triton tumor | mantle cell lymphoma |
| marginal zone B-cell lymphoma | mast cell leukemia | mediastina germ cell tumor | medullary carcinoma of the breast |
| medullary thyroid cancer | medulloblastoma | melanoma | meningioma |
| merkel cell cancer | mesothelioma | metastatic urothelial carcinoma | mixed Mullerian tumor |
| mucinous tumor | multiple myeloma | muscle tissue neoplasm | mycosis fungoides |
| myxoid liposarcoma | myxoma | myxosarcoma | nasopharyngeal carcinoma |
| neurinoma | neuroblastoma | neurofibroma | neuroma |
| nodular melanoma | ocular cancer | oligoastrocytoma | oligodendroglioma |
| oncocytoma | optic nerve sheath meningioma | optic nerve tumor | oral cancer |
| osteosarcoma | ovarian cancer | Pancoast tumor | papillary thyroid cancer |

TABLE 3-continued

| | | | |
|---|---|---|---|
| paraganglioma | pinealoblastoma | pineocytoma | pituicytoma |
| pituitary adenoma | pituitary tumor | plasmacytoma | polyembryoma |
| precursor T-lymphoblastic lymphoma | primary central nervous system lymphoma | primary effusion lymphoma | preimary peritoneal cancer |
| prostate cancer | pancreatic cancer | pharyngeal cancer | pseudomyxoma periotonei |
| renal cell carcinoma | renal medullary carcinoma | retinoblastoma | rhabdomyoma |
| rhabdomyosarcoma | Richter's transformation | rectal cancer | sarcoma |
| Schwannomatosis | seminoma | Sertoli cell tumor | sex cord-gonadal stromal tumor |
| signet ring cell carcinoma | skin cancer | small blue round cell tumors | small cell carcinoma |
| soft tissue sarcoma | somatostatinoma | soot wart | spinal tumor |
| splenic marginal zone lymphoma | squamous cell carcinoma | synovial sarcoma | Sezary's disease |
| small intestine cancer | squamous carcinoma | stomach cancer | T-cell lymphoma |
| testicular cancer | thecoma | thyroid cancer | transitional cell carcinoma |
| throat cancer | urachal cancer | urogenital cancer | urothelial carcinoma |
| uveal melanoma | uterine cancer | verrucous carcinoma | visual pathway glioma |
| vulvar cancer | vaginal cancer | Waldenstrom's macroglobulinemia | Warthin's tumor |
| Wilms' tumor | | | |

In another embodiment, the cancer is a solid tumor. In another embodiment, the cancer a hematological cancer. Exemplary hematological cancers include, but are not limited to, the cancers listed in Table 4. In another embodiment, the hematological cancer is acute lymphocytic leukemia, chronic lymphocytic leukemia (including B-cell chronic lymphocytic leukemia), or acute myeloid leukemia.

TABLE 4

| | |
|---|---|
| acute lymphocytic leukemia (ALL) | acute eosinophilic leukemia |
| acute myeloid leukemia (AML) | acute erythroid leukemia |
| chronic lymphocytic leukemia (CLL) | acute lymphoblastic leukemia |
| small lymphocytic lymphoma (SLL) | acute megakaryoblastic leukemia |
| multiple myeloma (MM) | acute monocytic leukemia |
| Hodgkins lymphoma (HL) | acute promyelocytic leukemia |
| non-Hodgkin's lymphoma (NHL) | acute myelogeous leukemia |
| mantle cell lymphoma (MCL) | B-cell prolymphocytic leukemia |
| marginal zone B-cell lymphoma | B-cell lymphoma |
| splenic marginal zone lymphoma | MALT lymphoma |
| follicular lymphoma (FL) | precursor T-lymphoblastic lymphoma |
| Waldenstrom's macroglobulinemia (WM) | T-cell lymphoma |
| diffuse large B-cell lymphoma (DLBCL) | mast cell leukemia |
| marginal zone lymphoma (MZL) | adult T cell leukemia/lymphoma |
| hairy cell leukemia (HCL) | aggressive NK-cell leukemia |
| Burkitt's lymphoma (BL) | angioimmunoblastic T-cell lymphoma |
| Richter's transformation | |

In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome. Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the Mcl-1 inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, about 0.05, about 0.5, about 5, about 10, about 20, about 30, about 40, about 50, about 100, about 150, about 200, about 250, about 300, about 350, about 400, about 450, or about 500 milligrams, including all doses between 0.005 and 500 milligrams.

The dosage of a composition containing a Compound of the Disclosure, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 5504 kg, about 5754 kg, about 6004 kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketoconazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; *vinca* alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DM1, cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransylcytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU101, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, C1-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDCl25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a Compound of the Disclosure, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a Compound of the Disclosure also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

The disclosure provides the following particular embodiments in connection with treating a disease in a subject Embodiment I. A method of treating a subject, the method comprising administering to the subject a therapeutically effective amount of a Compound of the Disclosure, wherein the subject has cancer, a chronic autoimmune disorder, an inflammatory condition, a proliferative disorder, sepsis, or a viral infection.

Embodiment II. The method Embodiment I, wherein the subject has cancer.

Embodiment III. The method of Embodiment II, wherein the cancer is any one or more of the cancers of Table 3.

Embodiment IV. The method of Embodiment II, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment V. The method of Embodiment II, wherein the cancer is any one or more of the cancers of Table 4.

Embodiment VI. The method of any one of Embodiments I-V further comprising administering a therapeutically effective amount of a second therapeutic agent useful in the treatment of the disease or condition.

Embodiment VII. A pharmaceutical composition comprising a Compound of the Disclosure and a pharmaceutically acceptable excipient for use in treating cancer, a chronic autoimmune disorder, an inflammatory condition, a proliferative disorder, sepsis, or a viral infection.

Embodiment VIII. The pharmaceutical composition of Embodiment VII for use in treating cancer.

Embodiment IX. The pharmaceutical composition of Embodiment VIII, wherein the cancer is any one or more of the cancers of Table 3.

Embodiment X. The pharmaceutical composition of Embodiment IX, wherein the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XI. The pharmaceutical composition of Embodiment VIII, wherein the cancer is any one or more of the cancers of Table 4.

Embodiment XII. A Compound of the Disclosure for use in treatment of cancer, a chronic autoimmune disorder, an inflammatory condition, a proliferative disorder, sepsis, or a viral infection.

Embodiment XIII The compound of Embodiment XII for use in treating cancer.

Embodiment XIV. The compound of Embodiment XIII, wherein the cancer is any one or more of the cancers of Table 3.

Embodiment XV. The compound of Embodiment XIII, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XVI. The compound of Embodiment XIII, wherein the cancer is any one or more of the cancers of Table 4.

Embodiment XVII. Use of a Compound of the Disclosure for the manufacture of a medicament for treatment of cancer, a chronic autoimmune disorder, an inflammatory condition, a proliferative disorder, sepsis, or a viral infection.

Embodiment XVIII. The use of Embodiment XVII for the treatment of cancer.

Embodiment XIX. The use of Embodiment XVIII, wherein the cancer is any one or more of the cancers of Table 3.

Embodiment XX. The use of Embodiment XVIII, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XXI. The use of Embodiment XVIII, wherein the cancer is any one or more of the cancers of Table 4.

V. Kits of the Disclosure

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure, e.g., the method of any one of Embodiments I-VI. In one embodiment, the compound or composition is packaged in a unit dosage form. The kit further can include a device suitable for administering the composition according to the intended route of administration.

VI. Definitions

The term "a disease or condition wherein inhibition of Mcl-1 provides a benefit" pertains to a disease or condition in which Mcl-1, is important or necessary, e.g., for the onset, progress, expression of that disease or condition, or a disease or a condition which is known to be treated by an Mcl-1 inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by a Mcl-1 inhibitor for any particular cell type, for example, by assays which conveniently can be used to assess the activity of particular compounds.

The terms "Mcl-1" or "Myeloid Cell Leukemia Sequence 1" refer to a protein in humans encoded by the MCL1 gene. The term Mcl-1 includes isoforms and mutants of Mcl-1.

Mcl-1 belongs to the Bcl-2 family. Alternative splicing occurs at this locus and two transcript variants encoding distinct isoforms have been identified. The longer gene product (isoform 1) enhances cell survival by inhibiting apoptosis while the alternatively spliced shorter gene product (isoform 2) promotes apoptosis and is death-inducing.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, Compounds of the Disclosure are inhibitors of Mcl-1 and can be used in treating or preventing diseases and conditions wherein inhibition of Mcl-1 provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to a subject in need thereof. In the case of a cancer or other proliferation disorder, the therapeutically effective amount of the agent may reduce (i.e., retard to some extent or stop) unwanted cellular proliferation; reduce the number of cancer cells; reduce the tumor size; inhibit (i.e., retard to some extent or stop) cancer cell infiltration into peripheral organs; inhibit (i.e., retard to some extent or stop) tumor metastasis; inhibit, to some extent, tumor growth; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to a subject in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to a subject in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

In the present disclosure, the term "protecting group" as used herein refers to group that blocks, i.e., protects, an amine or hydroxy functionality while reactions are carried out on other functional groups or parts of the molecule.

Those skilled in the art will be familiar with the selection, attachment, and cleavage of protecting groups, and will appreciate that different protective groups are known in the art, the suitability of one protective group or another being dependent on the particular the synthetic scheme planned. Treatises on the subject are available for consultation, such as Wuts, "Greene's Protective Groups in Organic Synthesis", 5th Ed., J. Wiley & Sons, Inc., NY, 2014. Suitable amine protecting groups include, but are not limited to, carbobenzyloxy (Cbz), tert-butyloxycarbonyl (BOC), 9-fluorenylmethyloxycarbonyl (FMOC), and benzyl (Bn) groups. Suitable hydroxy protecting groups include, but are not limited to, tetrahydropyran (THP), —C(=O)CH$_3$ (Ac), and —C(=O)Ph (Bz), and silyl-based protecting groups such as -TMS and -TBS.

In the present disclosure, the term "leaving group" refers to an atom or group of atoms that becomes detached from an atom or group of atoms in what is considered to be the residual or main part of the molecule in a specified reaction. Non-limiting exemplary leaving groups include —Cl, —I, —Br, -OTf, -OMs, and -OTs.

In the present disclosure, the term "halo" as used by itself or as part of another group refers to —Cl, —F, —Br, or —I.

In the present disclosure, the term "nitro" as used by itself or as part of another group refers to —NO$_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing from one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl is a $C_{1-10}$ alkyl. In another embodiment, the alkyl is a $C_{1-6}$ alkyl. In another embodiment, the alkyl is a $C_{1-4}$ alkyl. In another embodiment, the alkyl is a straight chain $C_{1-10}$ alkyl. In another embodiment, the alkyl is a branched chain $C_{3-10}$ alkyl. In another embodiment, the alkyl is a straight chain $C_{1-6}$ alkyl. In another embodiment, the alkyl is a branched chain $C_{3-6}$ alkyl. In another embodiment, the alkyl is a straight chain $C_{1-4}$ alkyl. In another embodiment, the alkyl is a branched chain $C_{3-4}$ alkyl. In another embodiment, the alkyl is a straight or branched chain $C_{3-4}$ alkyl. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl.

In the present disclosure, the term "optionally substituted alkyl" as used by itself or as part of another group means that the alkyl as defined above is either unsubstituted or substituted with one, two, or three substituents independently selected from the group consisting of nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, and cycloalkyl. In one embodiment, the optionally substituted alkyl is substituted with two substituents. In another embodiment, the optionally substituted alkyl is substituted with one substituent. Non-limiting exemplary optionally substituted alkyl groups include —CH$_2$CH$_2$NO$_2$, —CH$_2$SO$_2$CH$_3$CH$_2$CH$_2$CO$_2$H, —CH$_2$CH$_2$SO$_2$CH$_3$, —CH$_2$CH$_2$COPh, and —CH$_2$C$_6$H$_{11}$.

In the present disclosure, the term "cycloalkyl" as used by itself or as part of another group refers to saturated and partially unsaturated (containing one or two double bonds) cyclic aliphatic hydrocarbons containing one, two, or three rings having from three to twelve carbon atoms, i.e., $C_{3-12}$ cycloalkyl, or the number of carbons designated. In one embodiment, the cycloalkyl group has two rings. In one embodiment, the cycloalkyl group has one ring. In another embodiment, the cycloalkyl group is a $C_{3-8}$ cycloalkyl group. In another embodiment, the cycloalkyl group is a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, and cyclohexenyl.

In the present disclosure, the term "optionally substituted cycloalkyl" as used by itself or as part of another group means that the cycloalkyl as defined above is either unsubstituted or substituted with one, two, or three substituents independently selected from the group consisting of from halo, nitro, cyano, hydroxy, amino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted cycloalkyl is substituted with two substituents. In another embodiment, the optionally substituted cycloalkyl is substituted with one substituent. In another embodiment, the optionally substituted cycloalkyl is substituted with one amino or (amino)alkyl substituent. Non-limiting exemplary optionally substituted cycloalkyl groups include:

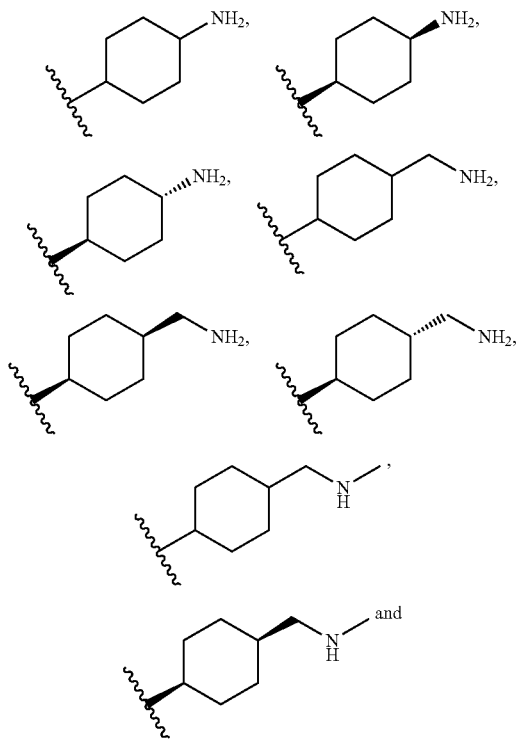

-continued

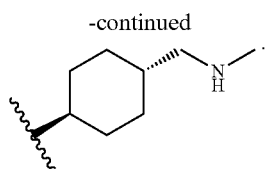

In the present disclosure, the term "alkenyl" as used by itself or as part of another group refers to an alkyl group as defined above containing one, two, or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group means the alkenyl as defined above is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, optionally substituted aryl, optionally substituted heteroaryl, and optionally substituted heterocyclo.

In the present disclosure, the term "alkynyl" as used by itself or as part of another group refers to an alkyl group as defined above containing one, two, or three carbon-to-carbon triple bonds. In one embodiment, the alkynyl has one carbon-to-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

In the present disclosure, the term "optionally substituted alkynyl" as used herein by itself or as part of another group means the alkynyl as defined above is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, optionally substituted aryl, optionally substituted heteroaryl, and optionally substituted heterocyclo.

In the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "hydroxyalkyl" as used by itself or as part of another group refers to an alkyl group substituted with one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups. In another embodiment, the hydroxyalkyl group is a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

In the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom.

In one embodiment, the alkoxy group is a $C_{1-4}$ alkoxy group. In another embodiment, the alkoxy group is a $C_{1-4}$ alkyl attached to a terminal oxygen atom, e.g., methoxy, ethoxy, and tert-butoxy.

In the present disclosure, the term "alkylthio" as used by itself or as part of another group refers to a sulfur atom substituted by an optionally substituted alkyl group. In one embodiment, the alkylthio group is a $C_{1-4}$ alkylthio group. Non-limiting exemplary alkylthio groups include —$SCH_3$ and —$SCH_2CH_3$.

In the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

In the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryl" as used by itself or as part of another group refers to a monocyclic or bicyclic aromatic ring system having from six to fourteen carbon atoms, i.e., $C_6$-$C_{14}$ aryl, or the number of carbon atoms designated. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl. In another embodiment, the aryl group is phenyl.

In the present disclosure, the term "optionally substituted aryl" as used herein by itself or as part of another group means that the aryl as defined above is either unsubstituted or substituted with one to five substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. 113:6521 In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Non-limiting examples include:

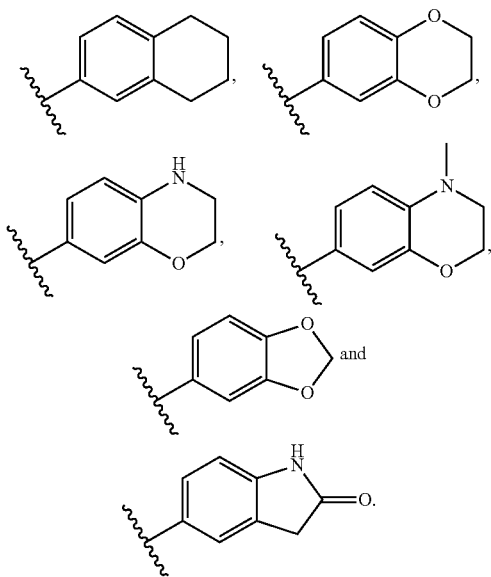

In the present disclosure, the term "arylenyl" as used by itself or part of another group refers to a divalent form of an optionally substituted aryl group. In one embodiment, the arylenyl is a divalent form of an optionally substituted phenyl. In one embodiment, the arylenyl is a divalent form of phenyl. Non-limiting exemplary alkylenyl groups include:

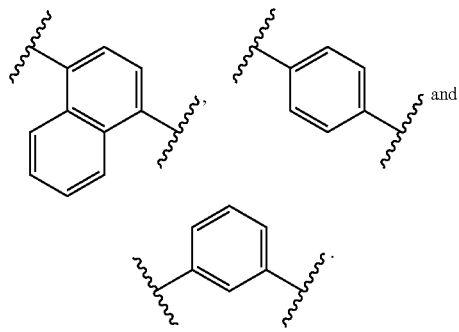

In the present disclosure, the term "aryloxy" as used by itself or as part of another group refers to an optionally substituted aryl attached to a terminal oxygen atom. A non-limiting exemplary aryloxy group is PhO—.

In the present disclosure, the term "aralkyloxy" as used by itself or as part of another group refers to an aralkyl group attached to a terminal oxygen atom. A non-limiting exemplary aralkyloxy group is PhCH$_2$O—.

In the present disclosure, the term "heteroaryl" or "heteroaromatic" refers to monocyclic and bicyclic aromatic ring systems having 5 to 14 ring atoms, i.e., a 5- to 14-membered heteroaryl, wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), or indazolyl (e.g., 1H-indazol-3-yl). The term "heteroaryl" is also meant to include possible N-oxides. A non-limiting exemplary N-oxide is pyridyl N-oxide. The heteroaryl can be attached to the remained of the molecule through any available carbon or nitrogen atom.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In the present disclosure, the term "optionally substituted heteroaryl" as used by itself or as part of another group means that the heteroaryl as defined above is either unsubstituted or substituted with one to four substituents, e.g., one or two substituents, independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted heteroaryl has one substituent. Any available carbon or nitrogen atom can be substituted.

The term optionally substituted heteroaryl is also meant to include groups having fused optionally substituted cycloalkyl and fused optionally substituted heterocyclo rings. Non-limiting examples include:

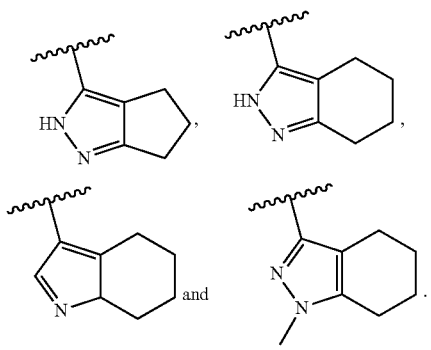

In another embodiment, the heteroaryl is an optionally substituted 9- to 14-membered bicyclic aromatic ring system, wherein at least one carbon atom of one of the rings is replaced with a heteroatom independently selected from the group consisting of oxygen, nitrogen, and sulfur. In another embodiment, the heteroaryl is an optionally substituted 9-membered bicyclic aromatic ring system, wherein one or two carbon atoms of one of the rings is replaced with a heteroatom independently selected from the group consisting of oxygen, nitrogen, and sulfur. Non-limiting exemplary 9- to 14-membered bicyclic aromatic ring systems include:

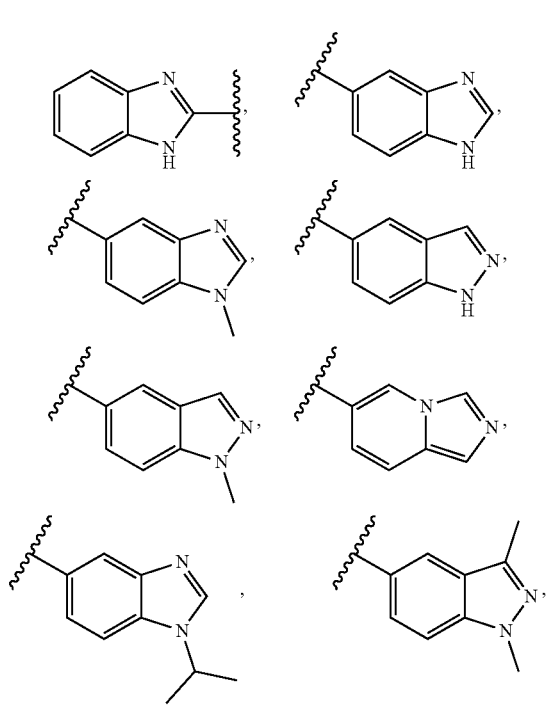

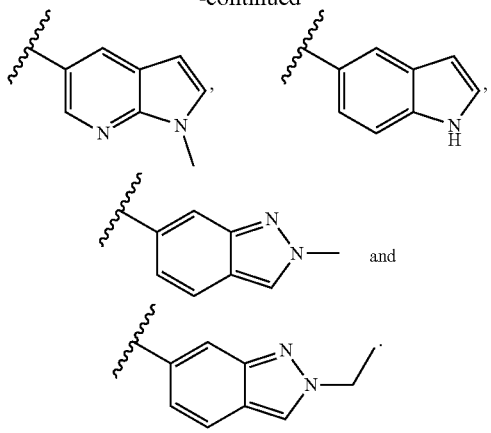

In the present disclosure, the term "heteroarylenyl" as used herein by itself or part of another group refers to a divalent form of an optionally substituted heteroaryl group. In one embodiment, the heteroarylenyl is a 5-membered heteroarylenyl. Non-limiting examples of a 5-membered heteroarylenyl include:

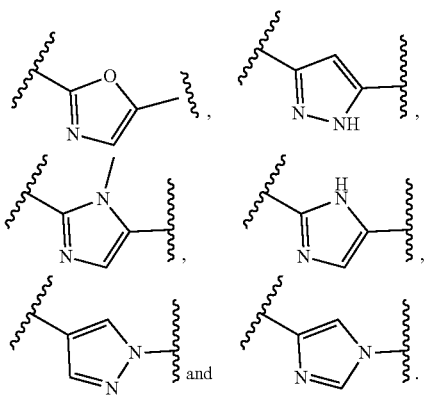

In one embodiment, the heteroarylenyl is a 6-membered heteroarylenyl. Non-limiting examples of a 6-membered heteroarylenyl include:

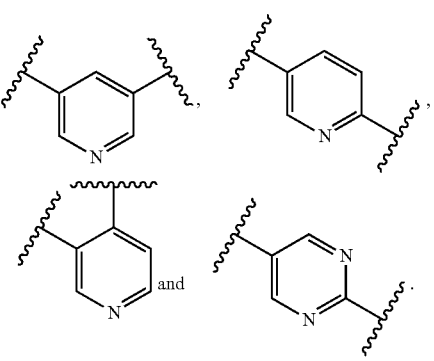

In the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members, i.e., a 3- to 14-membered heterocyclo, wherein at least one carbon atom of one of the rings is replaced with a heteroatom. In one embodiment, the heterocyclo is a 4- to 8-membered heterocyclo. Each heteroatom is independently selected from the group consisting of oxygen, sulfur, including sulfoxide and sulfone, and/or nitrogen atoms, which can be oxidized or quaternized. The term "heterocyclo" is meant to include groups wherein a ring —CH$_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" is also meant to include groups having fused optionally substituted aryl groups, e.g., indolinyl, chroman-4-yl. In one embodiment, the heterocyclo group is a 5- or 6-membered cyclic group containing one ring and one or two oxygen and/or nitrogen atoms. The heterocyclo can be optionally linked to the rest of the molecule through any available carbon or nitrogen atom. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

In the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, alkoxycarbonyl, CF$_3$C(=O)—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. Substitution may occur on any available carbon or nitrogen atom, or both. Non-limiting exemplary optionally substituted heterocyclo groups include:

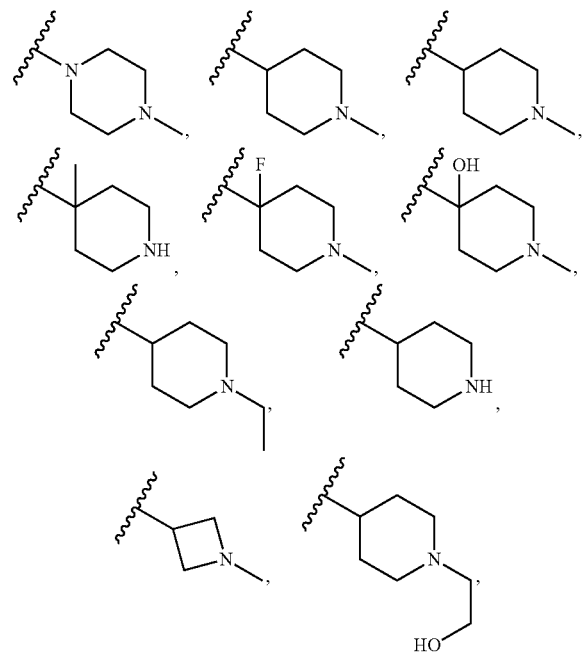

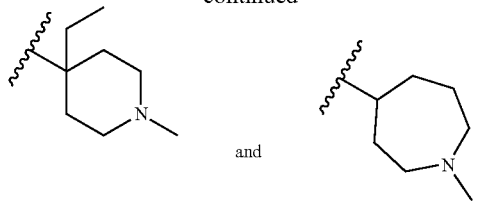

and

In the present disclosure, the term "amino" as used by itself or as part of another group refers to a radical of the formula —NR$^{30a}$R$^{30b}$ wherein R$^{30a}$ and R$^{30b}$ are independently hydrogen, alkyl, hydroxyalkyl, optionally substituted cycloalkyl, optionally substituted aryl, optionally substituted heterocyclo, or optionally substituted heteroaryl, or R$^{30a}$ and R$^{30b}$ are taken together to form a 3- to 8-membered optionally substituted heterocyclo. In one embodiment, R$^{30a}$ and R$^{30b}$ are independently hydrogen or C$_{1-4}$ alkyl. Non-limiting exemplary amino groups include —NH$_2$ and —N(H)(CH$_3$).

In the present disclosure, the term "(amino)alkyl" as used by itself or as part of another group refers to an alkyl group substituted with an amino group. In one embodiment, the (amino)alkyl is a C$_{1-6}$ alkyl substituted with an amino group, i.e., an (amino)C$_{1-6}$ alkyl. In another embodiment, the (amino)alkyl is an (amino)C$_{1-4}$ alkyl. Non-limiting exemplary (amino)alkyl groups include —CH$_2$NH$_2$, —CH$_2$CH$_2$NH$_2$, —CH$_2$CH$_2$N(H)CH-3, —CH$_2$CH$_2$N(CH$_3$)$_2$, and —CH$_2$N(H)cyclopropyl.

In the present disclosure, the term "carboxamido" as used by itself or as part of another group refers to a radical of formula —C(=O)NR$^{31a}$R$^{31b}$, wherein R$^{31a}$ and R$^{31b}$ are each independently hydrogen, optionally substituted alkyl, hydroxyalkyl, optionally substituted cycloalkyl, optionally substituted aryl, optionally substituted heterocyclo, or optionally substituted heteroaryl, or R$^{31a}$ and R$^{31b}$ taken together with the nitrogen to which they are attached form a 3- to 8-membered optionally substituted heterocyclo group. In one embodiment, R$^{31a}$ and R$^{31b}$ are each independently hydrogen or optionally substituted alkyl. In one embodiment, R$^{31a}$ and R$^{31b}$ are taken together to taken together with the nitrogen to which they are attached form a 3- to 8-membered optionally substituted heterocyclo group. Non-limiting exemplary carboxamido groups include —CONH$_2$, —CON(H)CH$_3$, —CON(CH$_3$)$_2$, and —CON(H)Ph.

In the present disclosure, the term "amido" as used by itself or as part of another group refers to a radical of formula —N(R$^{32a}$)C(=O)R$^{32b}$, wherein R$^{32a}$ is hydrogen or C$_{1-4}$ alkyl; and R$^{32b}$ is C$_{1-6}$ alkyl, optionally substituted cycloalkyl, optionally substituted aryl, C$_{1-4}$ alkoxy, or amino. In one embodiment, R$^{32a}$ is hydrogen. In another embodiment, R$^{32b}$ is C$_{1-4}$ alkyl, C$_{1-4}$ alkoxy, or amino. Non-limiting exemplary amido groups include —N(H)C(=O)CH$_3$, —N(H)C(=O)OCH$_3$, and —N(H)C(=O)N(H)CH$_3$.

In the present disclosure, the term "sulfonamido" as used by itself or as part of another group refers to a radical of the formula —SO$_2$NR$^{8a}$R$^{8b}$, wherein R$^{8a}$ and R$^{8b}$ are each independently hydrogen, optionally substituted alkyl, or optionally substituted aryl, or R$^{8a}$ and R$^{8b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

In the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

In the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

In the present disclosure, the term "alkoxycarbonyl" as used by itself or as part of another group refers to a carbonyl group, i.e., —C(=O)—, substituted by an alkoxy group. Non-limiting exemplary alkoxycarbonyl groups include —C(=O)OMe, —C(=O)OEt, and —C(=O)OtBu.

In the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

In the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

In the present disclosure, the term "mercaptoalkyl" as used by itself or as part of another group refers to any of the above-mentioned alkyl groups substituted by a —SH group.

In the present disclosure, the term "carboxy" as used by itself or as part of another group refers to a radical of the formula —COOH.

In the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

In the present disclosure, the terms "aralkyl" or "arylalkyl" as used by themselves or as part of another group refers to an alkyl group substituted with one, two, or three optionally substituted aryl groups. In one embodiment, the optionally substituted aralkyl group is a C$_{1-4}$ alkyl substituted with one optionally substituted aryl group. In one embodiment, the optionally substituted aralkyl group is a C$_1$ or C$_2$ alkyl substituted with one optionally substituted aryl group. In one embodiment, the optionally substituted aralkyl group is a C$_1$ or C$_2$ alkyl substituted with one optionally substituted phenyl group. Non-limiting exemplary optionally substituted aralkyl groups include benzyl, phenethyl, —CHPh$_2$, —CH$_2$(4-F-Ph), —CH$_2$(4-Me-Ph), —CH$_2$(4-CF$_3$-Ph), and —CH(4-F-Ph)$_2$.

In the present disclosure, the terms "(heterocyclo)alkyl" as used by itself or part of another group refers to an alkyl group substituted with one or two optionally substituted heterocyclo groups. In one embodiment, the (heterocyclo)alkyl is a C$_{1-4}$ alkyl substituted with one optionally substituted heterocyclo group, i.e., a (heterocyclo)C$_{1-4}$ alkyl. In another embodiment, the (heterocyclo)alkyl is a C$_{1-4}$ alkyl substituted with one optionally substituted 4- to 8-membered heterocyclo group, i.e., a (4- to 8-membered heterocyclo)C$_{1-4}$ alkyl. In another embodiment, the (heterocyclo)alkyl is a C$_1$ alkyl substituted with one optionally substituted 4- to 8-membered heterocyclo group, i.e., (4- to 8-membered heterocyclo)-CH$_2$—. Non-limiting exemplary (heterocyclo)alkyl groups include:

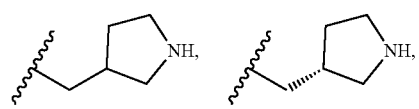

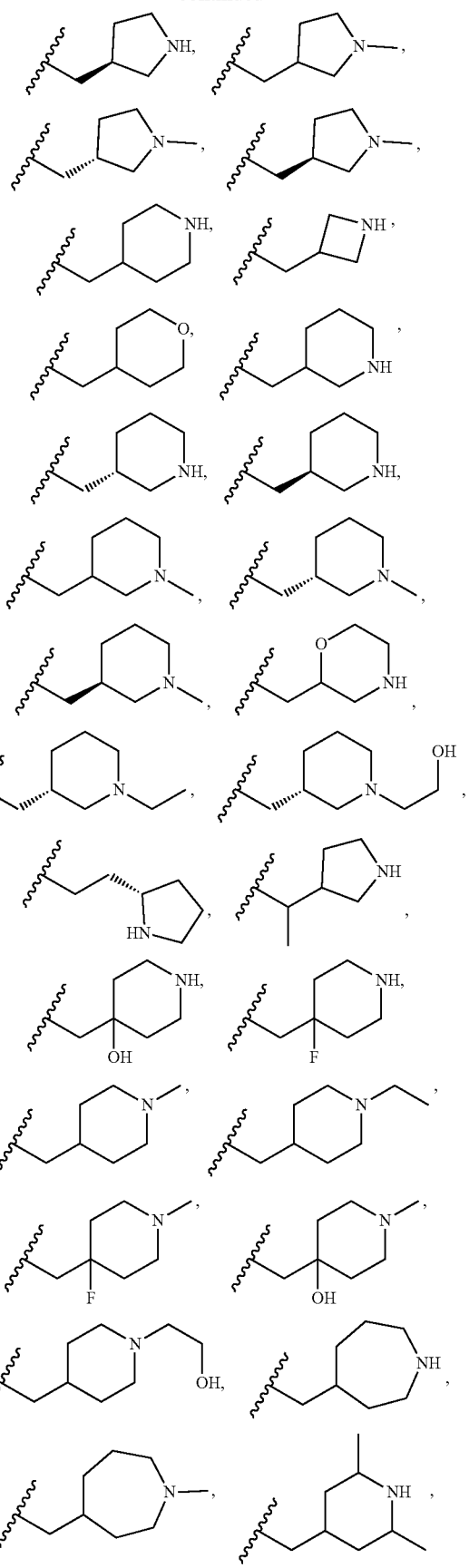

-continued

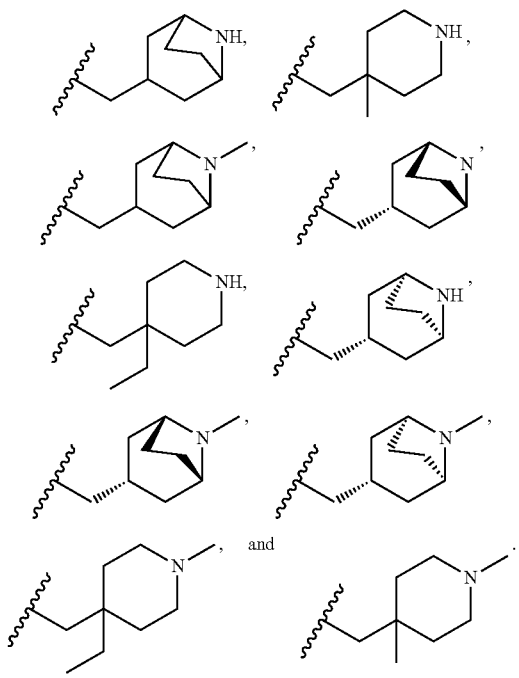

In the present disclosure, the terms "(cycloalkyl)alkyl" as used by itself or part of another group refers to an alkyl group substituted with one or two optionally substituted cycloalky groups. In one embodiment, the (cycloalkyl)alkyl is a $C_{1-4}$ alkyl substituted with one optionally substituted cycloalkyl group, i.e., a (cycloalkyl)$C_{1-4}$ alkyl. In another embodiment, the (cycloalkyl)alkyl is a $C_{1-4}$ alkyl substituted with one amino- or (alkyl)amino-substituted cycloalkyl. Non-limiting exemplary (cycloalkyl)alkyl groups include:

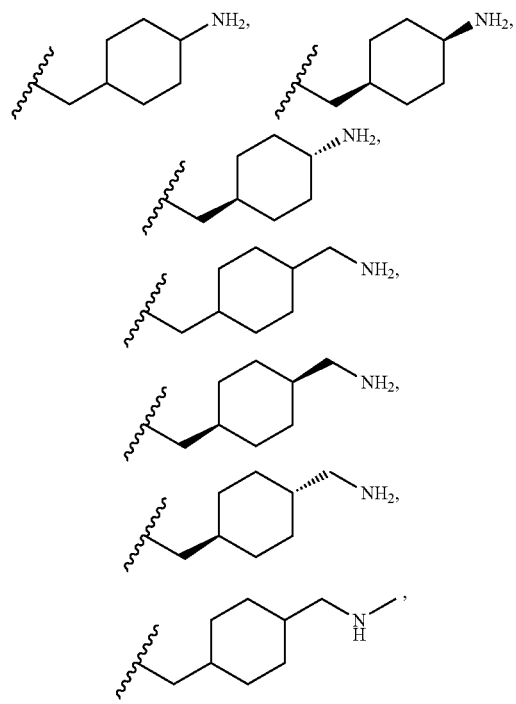

-continued

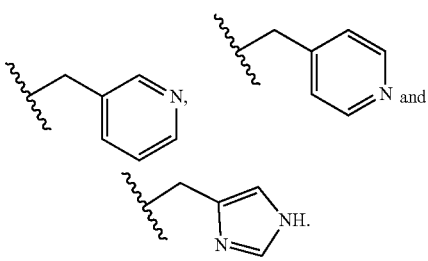

In the present disclosure, the terms "(heteroaryl)alkyl" as used by itself or part of another group refers to an alkyl group substituted with one or two optionally substituted heteroaryl groups. In one embodiment, the (heteroaryl)alkyl is a $C_{1-4}$ alkyl substituted with one optionally substituted heteroaryl group, i.e., a (heteroaryl)$C_{1-4}$ alkyl. In another embodiment, the (heteroaryl)alkyl is a $C_{1-4}$ alkyl substituted with one optionally substituted 5- or 6-membered heteroaryl group, i.e., a (5- or 6-membered heteroaryl)$C_{1-4}$ alkyl. Non-limiting exemplary (heteroaryl)alkyl groups include:

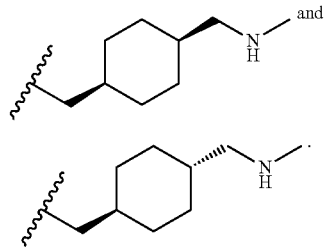

Compounds of the Disclosure and certain Intermediates of the Disclosure exist as stereoisomers, i.e., isomers that differ only in the spatial arrangement of atoms, including optical isomers and conformational isomers (or conformers) and tautomers. The disclosure includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

As used herein, the term "stereoisomers" is a general term for all isomers of individual molecules that differ only in the orientation of their atoms in space. It includes enantiomers, atropisomers, and isomers of compounds with more than one chiral center that are not mirror images of one another (diastereomers).

The term "chiral center" or "asymmetric carbon atom" refers to a carbon atom to which four different groups are attached.

The term "atropisomer" refers to a stereoisomer arising because of hindered rotation about a single bond. Atropisomers display axial chirality.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction. Enantiomers may be separated by chiral chromatography using methods well known in the art.

The term "racemic" or "racemate" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as ($[α]_{obs}/[α]_{max}$)*100, where $[α]_{obs}$ is the optical rotation of the mixture of enantiomers and $[α]_{max}$ is the optical rotation of the pure enantiomer. Determination of enantiomeric excess is possible using a variety of analytical techniques, including NMR spectroscopy, chiral column chromatography, or optical polarimetry. Compounds of the Disclosure or Intermediates of the Disclosure that are racemic can be separated by chiral HPLC, e.g., using a CHIRALPAK IE column. In one embodiment, Compounds of the Disclosure or Intermediates of the Disclosure have an ee of about 70% or more, e.g., about 80% or more, about 90% or more, about 91% or more, about 92% or more, about 93% or more, about 94% or more, about 95% or more, about 96% or more, about 97% or more, about 98% or more, or about 99% or more.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure. Certain compounds of the Disclosure are enantioenriched.

The term "about," as used herein, includes the recited number±10%. Thus, "about 10" means 9 to 11.

EXAMPLES

General Schemes

Compounds of the Disclosure and Intermediates of the Disclosure can be prepared according to the following General Schemes.

General Scheme 1 describes exemplary reaction steps and conditions for the preparation of compounds of Formulae X, XI, and IV, wherein (A)

is A-2 and X is —S—.

In step 1, a compound of Formula X, wherein R is $C_1$-$C_6$ alkyl, (A)

is A-2, $R^{19}$ is a protecting group, i.e., PMB, and $R^{20}$ is —$CH_2XR^{21}$ is —O— and $R^{21}$ is hydrogen, i.e., $R^{20}$ is —$CH_2OH$, is reacted with $CBr_4$ to give a compound of Formula X, wherein $R^{20}$ is —$CH_2$-LG, and the leaving group is —Br, i.e., $R^{20}$ is —$CH_2Br$.

Other methods to convert an alcohol to an alkyl halide are known in the art.

In step 2, the alkyl bromide of Formula X is reacted with a compound of Formula XXI, wherein $R^{22}$ is —$OR^{23}$ and $R^{23}$ is a protecting group, i.e., $R^{22}$ is -OTBS, $R^{28}$ is —C(=O)$R^{28a}$, and $R^{28a}$ is $C_1$-$C_6$ alkyl, i.e., $R^{28}$ is —C(=O)$CH_3$, to give a compound of Formula XI, wherein X is —S— and $R^{22}$ is —$OR^{23}$ and $R^{23}$ is a protecting group, i.e., $R^{22}$ is -OTBS.

In step 3, the compound of Formula XI, wherein $R^{22}$ is -OTBS is converted to a compound of Formula XI, wherein $R^{22}$ is a leaving group, i.e., $R^{22}$ is —Br.

In step 4, the protecting group, i.e., PMB, is removed and the resulting compound, i.e., a compound of Formula XI, wherein $R^{19}$ is hydrogen, is cyclized to give a compound of Formula IV, wherein R is $C_1$-$C_6$ alkyl.

In step 5, the ester is hydrolyzed to give a compound of Formula IV, wherein R is hydrogen.

General Scheme 1

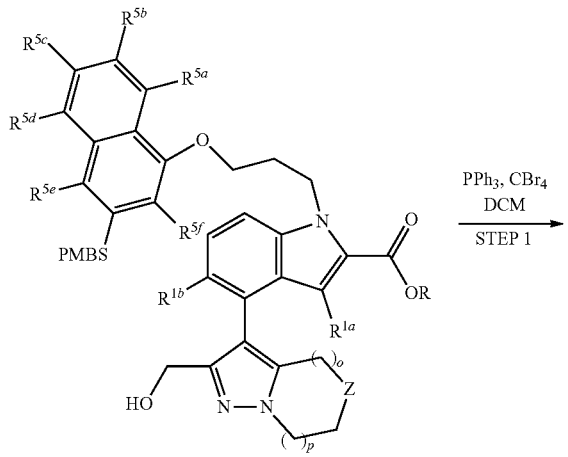

R = $C_1$-$C_6$ alkyl
Formula X
(wherein $R^{20}$ is ——$CH_2OH$)

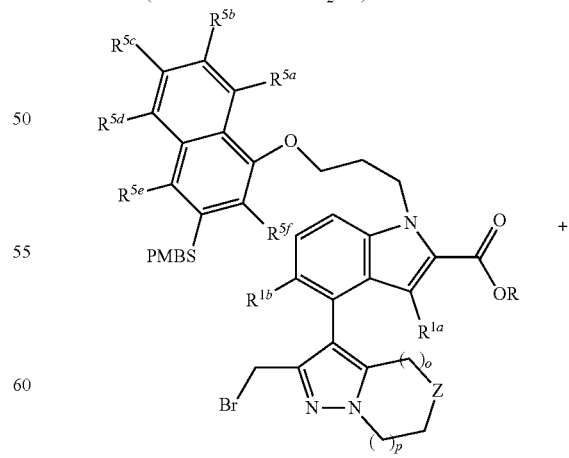

R = $C_1$-$C_6$ alkyl
Formula X
(wherein $R^{20}$ is ——$CH_2Br$)

-continued

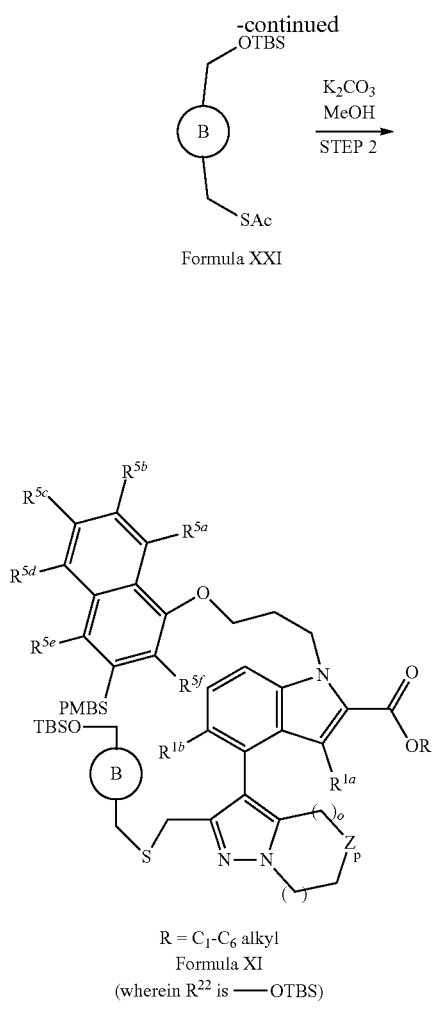

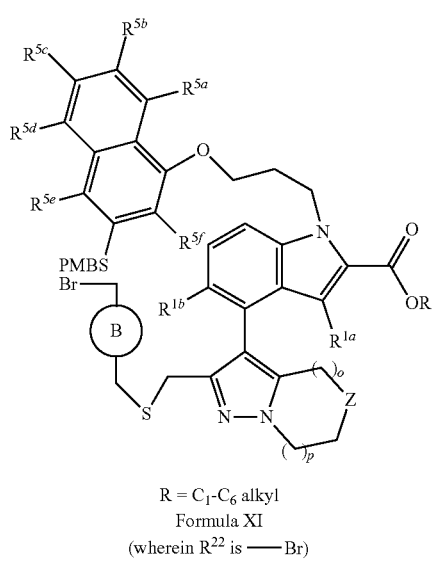

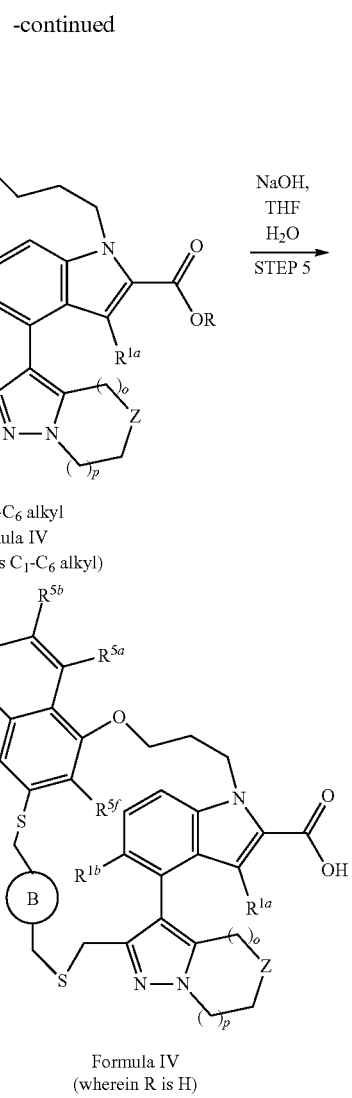

General Scheme 2 describes exemplary reaction steps and conditions for the preparation of compounds of Formulae III, VII, and VIII, wherein

is A-2. In step 1, a compound of Formula VII, wherein R is $C_1$-$C_6$ alkyl,

is A-2, $R^{19}$ is a protecting group, i.e., PMB, and $R^{20}$ is —$CH_2XR^{21}$, is —O—, and $R^{21}$ is hydrogen, i.e., $R^{20}$ is —$CH_2OH$, is reacted with $CBr_4$ to give a compound of Formula VII, wherein $R^{20}$ is —$CH_2$-LG, and the leaving group is —Br, i.e., $R^{20}$ is —$CH_2Br$. Other methods to convert an alcohol to an alkyl halide are known in the art. In step 2, the alkyl bromide of Formula VII is reacted with a compound of Formula XXI, wherein $R^{22}$ is —$OR^{23}$ and $R^{23}$ is a protecting group, i.e., $R^{22}$ is -OTBS, $R^{28}$ is —C(=O)$R^{28a}$, and $R^{28a}$ is $C_1$-$C_6$ alkyl, i.e., $R^{28}$ is —C(=O)CH$_3$, to give a compound of Formula VIII, wherein X is —S— and $R^{22}$ is —OR$^{23}$, $R^{23}$ is a protecting group, i.e., $R^{22}$ is -OTBS. In step 3, the compound of Formula VIII, wherein $R^{22}$ is -OTBS is converted to a compound of Formula VIII, wherein $R^{22}$ is a leaving group, i.e., $R^{22}$ is —Br. In step 4, the protecting group, i.e., PMB, is removed and the resulting compound, i.e., a compound of Formula VIII, wherein $R^{19}$ is hydrogen, is cyclized to give a compound of Formula III, wherein R is $C_1$-$C_6$ alkyl. In step 5, the ester is hydrolyzed to give a compound of Formula III, wherein R is hydrogen.

General Scheme 2

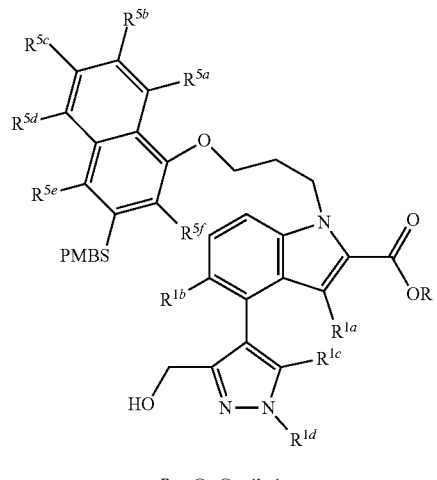

R = C$_1$-C$_6$ alkyl
Formula VII
(wherein R$^{20}$ is —CH$_2$OH)

PPh$_3$, CBr$_4$
DCM
STEP 1

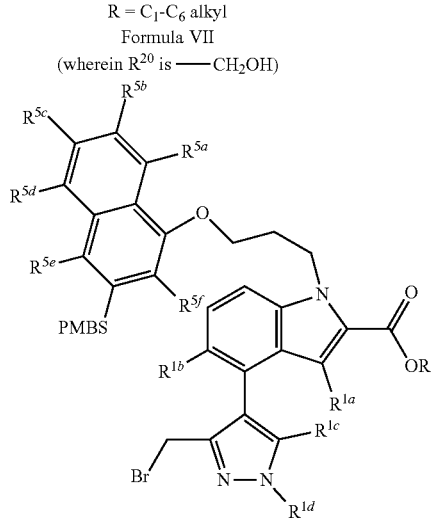

R = C$_1$-C$_6$ alkyl
Formula VII
(wherein R$^{20}$ is —CH$_2$Br)

+

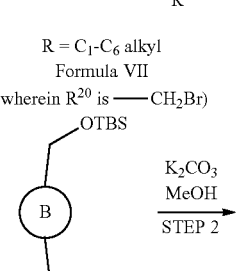

Formula XXI

K$_2$CO$_3$
MeOH
STEP 2

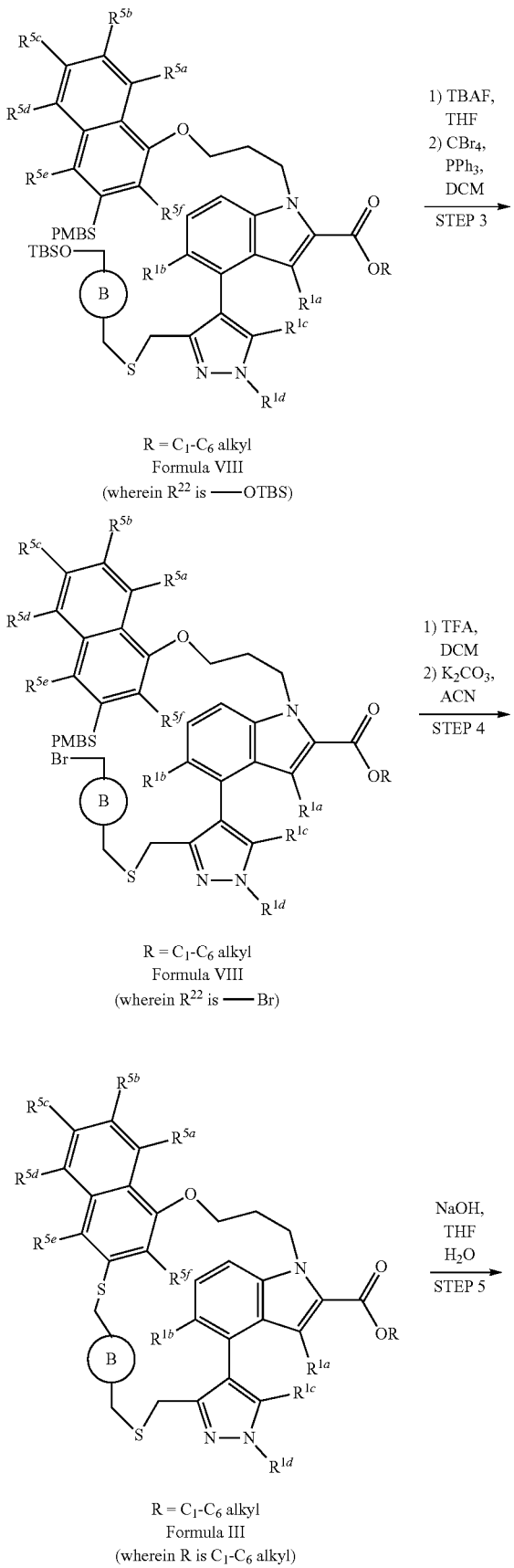

R = C$_1$-C$_6$ alkyl
Formula VIII
(wherein R$^{22}$ is —OTBS)

1) TBAF, THF
2) CBr$_4$, PPh$_3$, DCM
STEP 3

R = C$_1$-C$_6$ alkyl
Formula VIII
(wherein R$^{22}$ is —Br)

1) TFA, DCM
2) K$_2$CO$_3$, ACN
STEP 4

NaOH, THF, H$_2$O
STEP 5

R = C$_1$-C$_6$ alkyl
Formula III
(wherein R is C$_1$-C$_6$ alkyl)

-continued

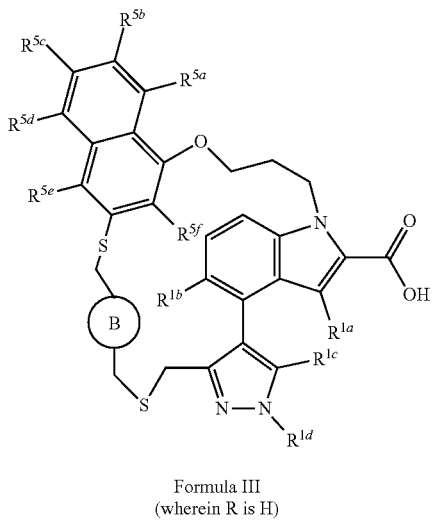

Formula III
(wherein R is H)

General Scheme 3

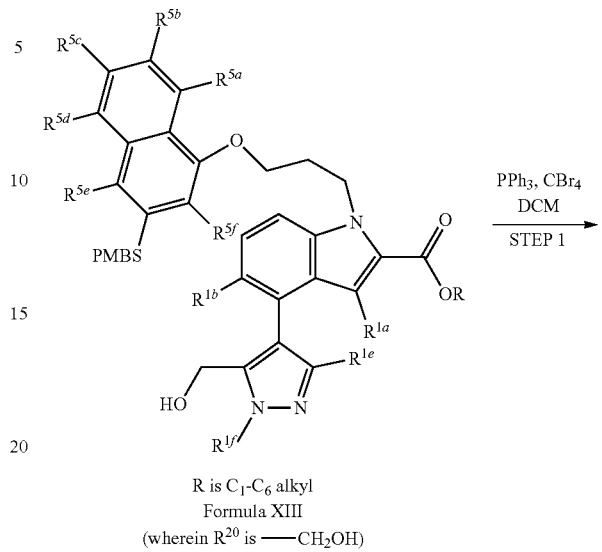

R is $C_1$-$C_6$ alkyl
Formula XIII
(wherein $R^{20}$ is —CH$_2$OH)

General Scheme 3 describes exemplary reaction steps and conditions for the preparation of compounds of Formulae XIII, XIV, and V, wherein (A)

is A-2. In step 1, a compound of Formula XIII, wherein R is $C_1$-$C_6$ alkyl, (A)

is A-2, $R^{19}$ is a protecting group, i.e., PMB, and $R^{20}$ is —CH$_2$X$R^{21}$, X is —O—, and $R^{21}$ is hydrogen, i.e., $R^{20}$ is —CH$_2$OH, is reacted with CBr$_4$ to give a compound of Formula X, wherein $R^{20}$ is —CH$_2$-LG, and the leaving group is —Br, i.e., $R^{20}$ is —CH$_2$Br. Other methods to convert an alcohol to an alkyl halide are known in the art. In step 2, the alkyl bromide of Formula XIII is reacted with a compound of Formula XXI, wherein $R^{22}$ is —O$R^{23}$ and $R^{23}$ is a protecting group, i.e., $R^{22}$ is -OTBS, $R^{28}$ is —C(=O)$R^{28a}$, and $R^{28a}$ is $C_1$-$C_6$ alkyl, i.e., $R^{28}$ is —C(=O)CH$_3$, to give a compound of Formula XIV, wherein X is —S— and $R^{22}$ is —O$R^{23}$, $R^{23}$ is a protecting group, i.e., $R^{22}$ is -OTBS. In step 3, the compound of Formula XIV, wherein $R^{22}$ is -OTBS is converted to a compound of Formula XIV, wherein $R^{22}$ is a leaving group, i.e., $R^{22}$ is —Br. In step 4, the protecting group, i.e., PMB, is removed and the resulting compound, i.e., a compound of Formula XIV, wherein $R^{19}$ is hydrogen, is cyclized to give a compound of Formula V, wherein R is $C_1$-$C_6$ alkyl. In step 5, the ester is hydrolyzed to give a compound of Formula V, wherein R is hydrogen.

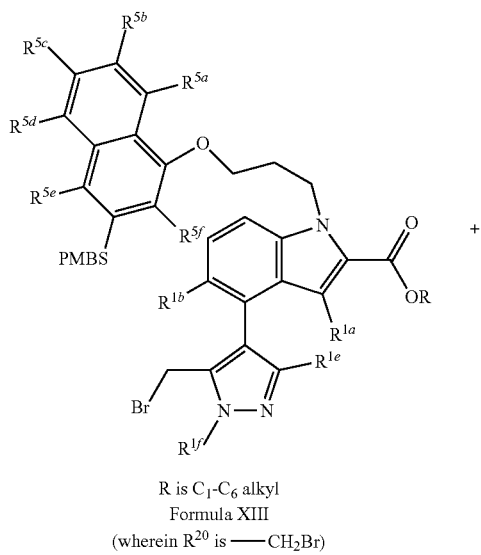

R is $C_1$-$C_6$ alkyl
Formula XIII
(wherein $R^{20}$ is —CH$_2$Br)

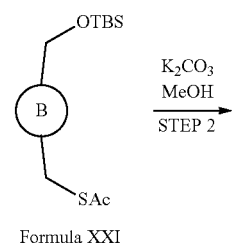

Formula XXI

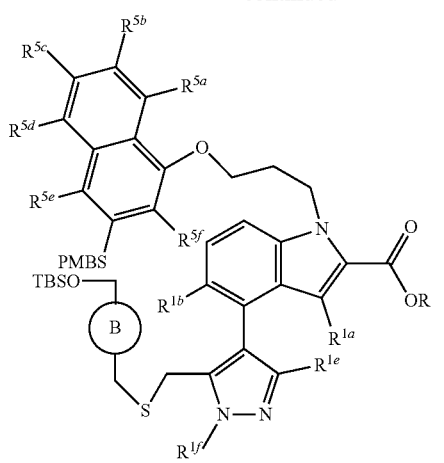

R is C$_1$-C$_6$ alkyl
Formula XIV
(wherein R$^{22}$ is —OTBS)

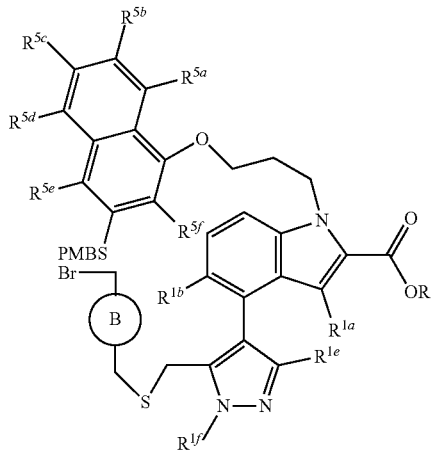

R is C$_1$-C$_6$ alkyl
Formula XIV
(wherein R$^{22}$ is —Br)

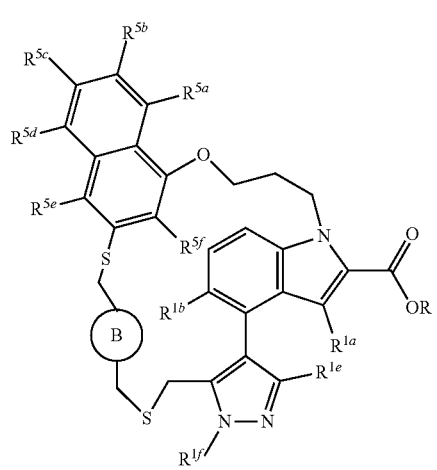

R is C$_1$-C$_6$ alkyl
Formula V
(wherein R is C$_1$-C$_6$ alkyl)

1) TBAF, THF
2) CBr$_4$, PPh$_3$, DCM
STEP 3

1) TFA, DCM
2) K$_2$CO$_3$, ACN
STEP 4

NaOH, THF H$_2$O
STEP 5

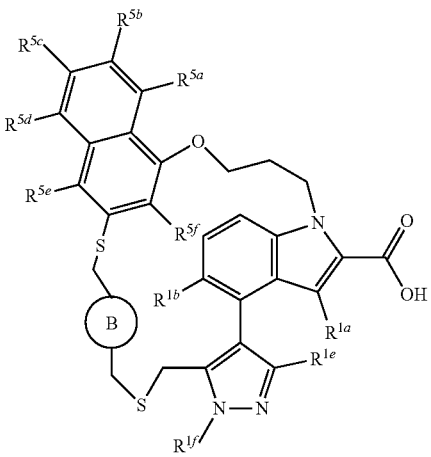

Formula V
(wherein R is H)

General Scheme 4 describes exemplary reaction steps and conditions for the preparation of compounds of Formulae X, XII, and IV, wherein

Ⓐ is A-2. In step 1, a compound of Formula X wherein R$^{20}$ is —CH$_2$OTHP is converted to a compound of Formula X, wherein R$^{20}$ is —CH$_2$OC(=O)CF$_3$. This compound is reacted with a compound of Formula XXIIA. The resulting compound is deprotected to give a compound of Formula XII, wherein R$^{20}$ and R$^{24}$ are each —CH$_2$OH. This compound is oxidized to give a compound of Formula XII, wherein R$^{20}$ and R$^{24}$ are each —C(=O)H. In step 4, this compound is reacted with BocNH$_2$ to give a compound of Formula IV, wherein R$^6$ is H after removal of the Boc group. A compound of Formula IV, wherein R$^6$ is H is further functionalized at R$^6$, and the ester is hydrolyzed to give a compound of Formula IV, wherein R is H.

General Scheme 4
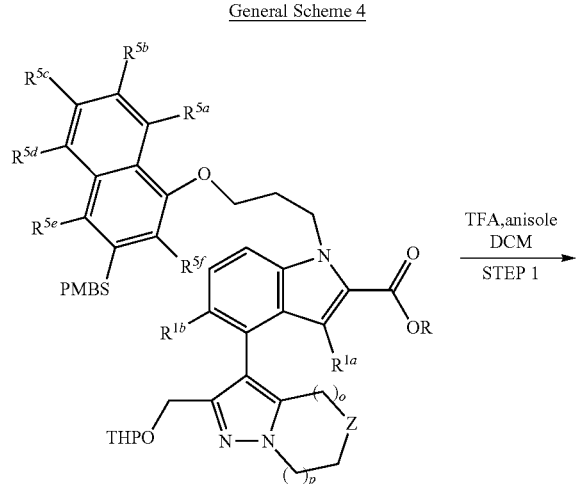
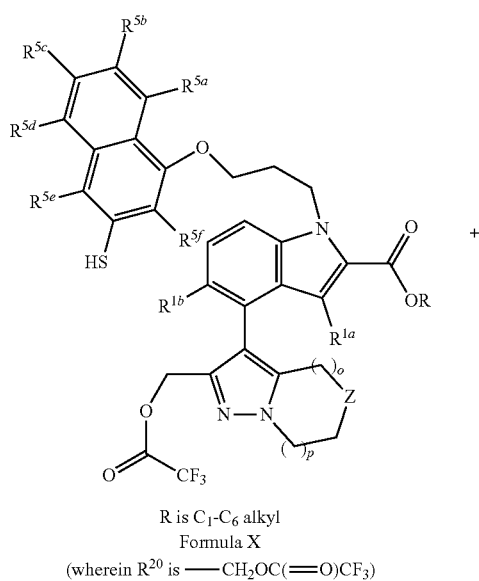
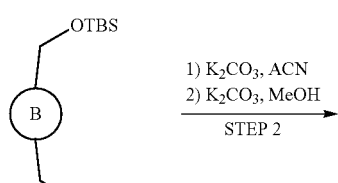
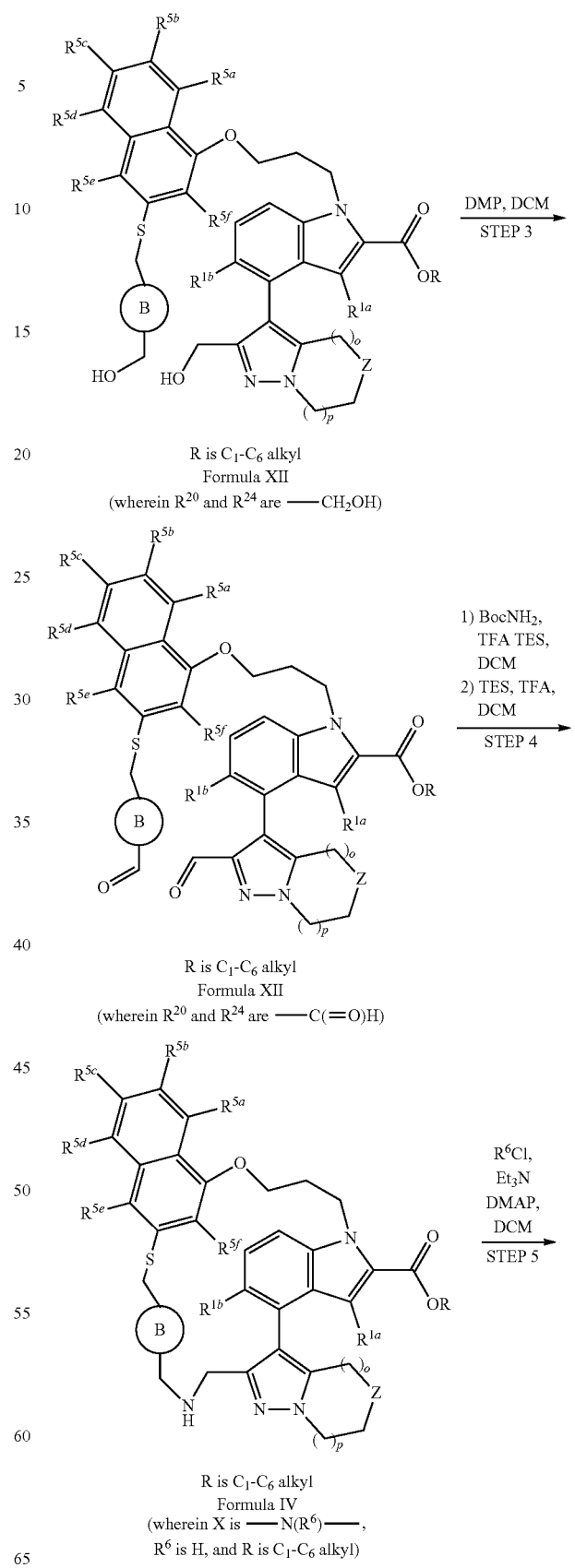

-continued

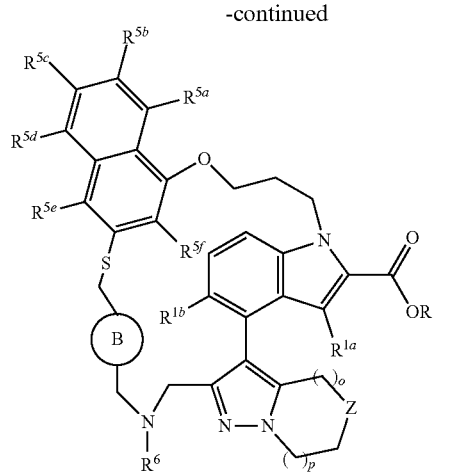

R is $C_1$-$C_6$ alkyl
Formula IV
(wherein X is —N($R^6$)—
and R is $C_1$-$C_6$ alkyl)

NaOH, THF, $H_2O$ MeOH →

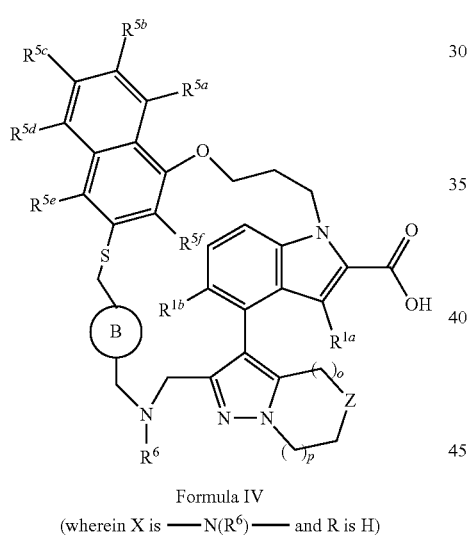

Formula IV
(wherein X is —N($R^6$)— and R is H)

General Scheme 5 describes exemplary reaction steps and conditions for the preparation of compounds of Formulae VII, IX, and III, wherein (A)

is A-2. In step 1, a compound of Formula VII, wherein $R^{20}$ is —$CH_2OH$ is converted to a compound of Formula X, wherein $R^{20}$ is —$CH_2OC(=O)CF_3$. This compound is reacted with a compound of Formula XXIIA, and the —$C(=O)CF_3$ group is removed to give a compound of Formula IX, wherein $R^{20}$—$CH_2OH$ and $R^{24}$ are each —$CH_2OBz$. The compound is oxidized to give a compound of Formula IX, $R^{20}$ is —$C(=O)H$, and this compound is reacted with $BocNH_2$ to give a compound of Formula IX, wherein $R^{20}$ is —CHN(H)Boc. In step 5, the Bz group is removed and the resulting compound is oxidized then deprotected in step 6 to give a compound of Formula IX, wherein $R^{20}$ is —$CHNH_2$ and $R^{24}$ is —C(=O)H. This compound is treated with a reducing agent, e.g., NaB(H)$OAc_3$ to give a compound of Formula III, wherein $R^6$ is hydrogen. This compound is further functionalized at $R^6$, and the ester is be hydrolyzed to give a compound of Formula III, wherein R is H.

General Scheme 5

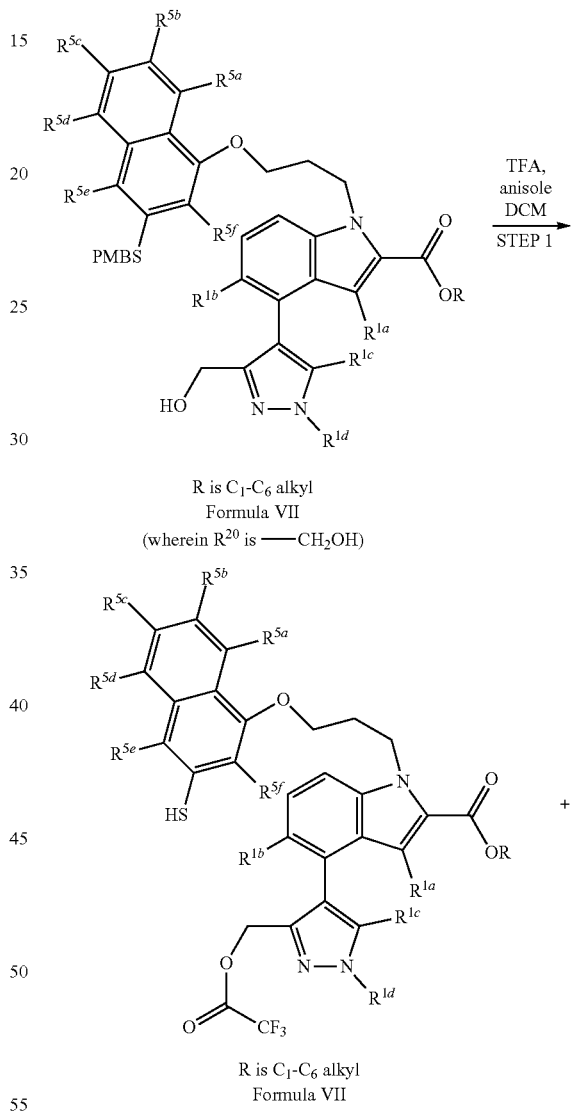

R is $C_1$-$C_6$ alkyl
Formula VII
(wherein $R^{20}$ is —$CH_2OH$)

R is $C_1$-$C_6$ alkyl
Formula VII
(wherein $R^{20}$ is —$CH_2OC(=O)CF_3$)

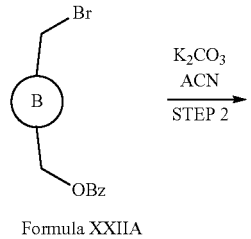

Formula XXIIA

195
-continued

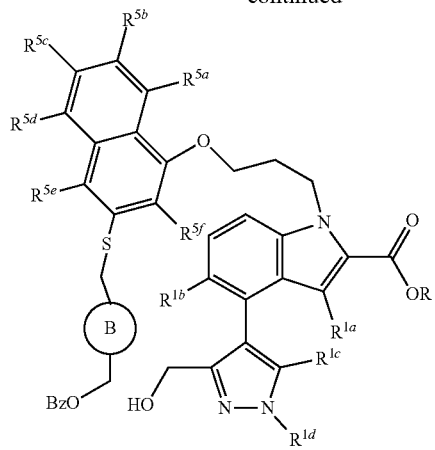

R is C$_1$-C$_6$ alkyl
Formula IX
(wherein R$^{20}$ is —CH$_2$OH and
R$^{24}$ is —CH$_2$OBz)

DMP, DCM
STEP 3 →

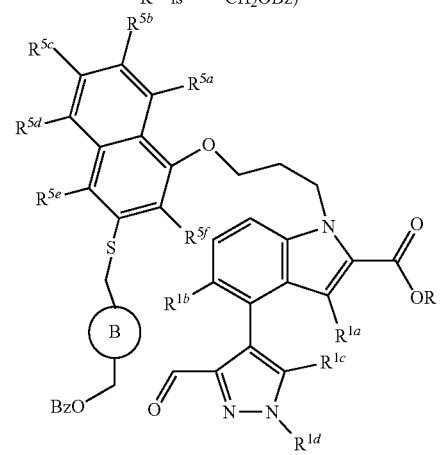

R is C$_1$-C$_6$ alkyl
Formula IX
(wherein R$^{20}$ is —C(=O)H and
R$^{24}$ is —CH$_2$OBz)

BocNH$_2$,
TFA TES,
DCM
STEP 4 →

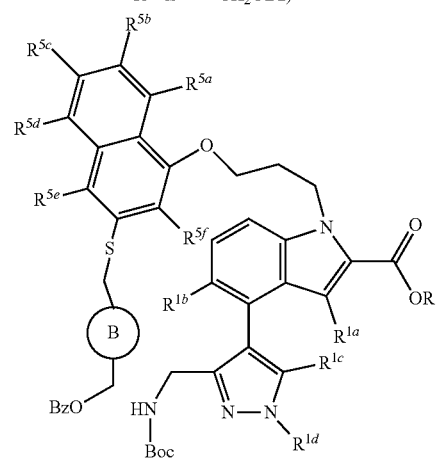

R is C$_1$-C$_6$ alkyl
Formula IX
(wherein R$^{20}$ is —CH$_2$N(H)Boc and
R$^{24}$ is —CH$_2$OBz)

K$_2$CO$_3$
MeOH
STEP 5 →

196
-continued

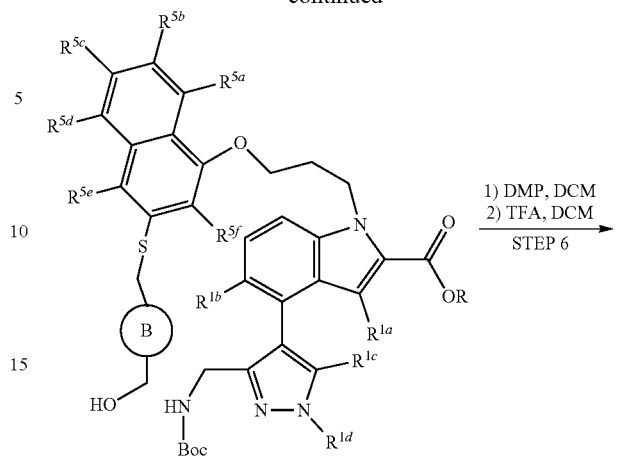

R is C$_1$-C$_6$ alkyl
Formula IX
(wherein R$^{20}$ is —CH$_2$N(H)Boc and
R$^{24}$ is —CH$_2$OH)

1) DMP, DCM
2) TFA, DCM
STEP 6 →

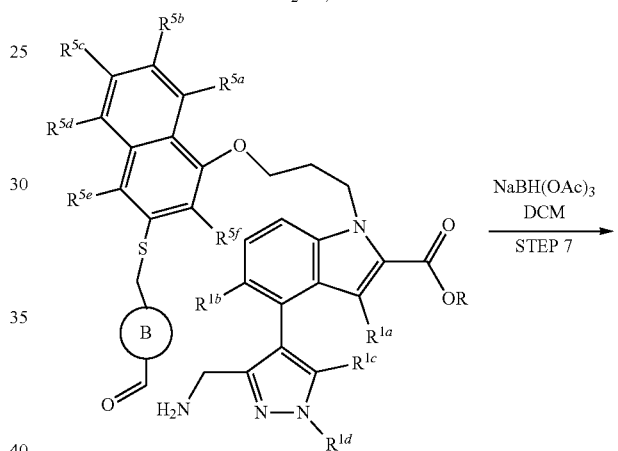

R is C$_1$-C$_6$ alkyl
Formula IX
(wherein R$^{20}$ is —CH$_2$NH$_2$ and
R$^{24}$ is —C(=O)H)

NaBH(OAc)$_3$
DCM
STEP 7 →

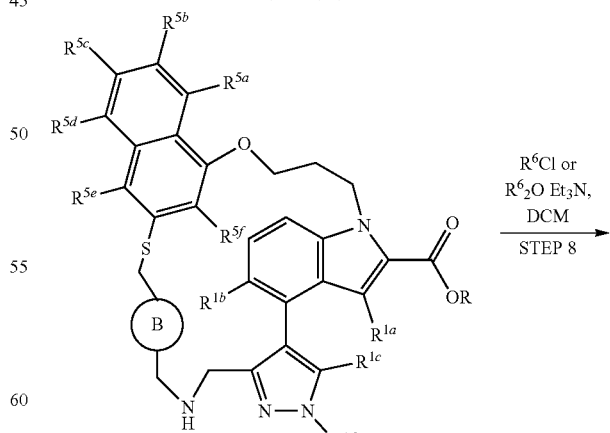

R is C$_1$-C$_6$ alkyl
Formula III
(wherein X is —N(R$^6$)—, R$^6$ is H, and
R is C$_1$-C$_6$ alkyl)

R$^6$Cl or
R$^6$$_2$O Et$_3$N,
DCM
STEP 8 →

-continued

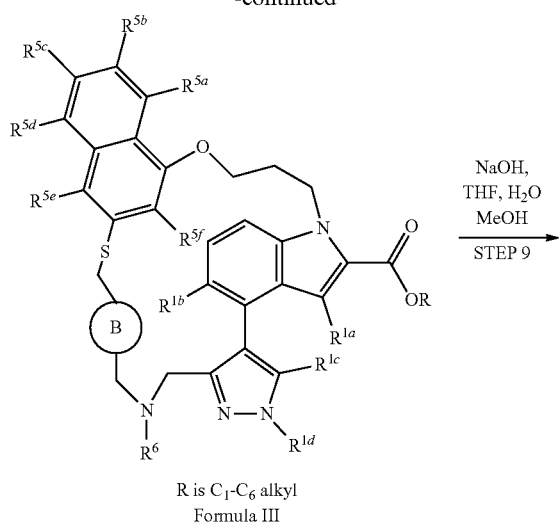

R is C$_1$-C$_6$ alkyl
Formula III
(wherein X is —N(R$^6$)— and R is C$_1$-C$_6$ alkyl)

Formula III
(wherein X is —N(R$^6$)— and R is H)

General Scheme 6

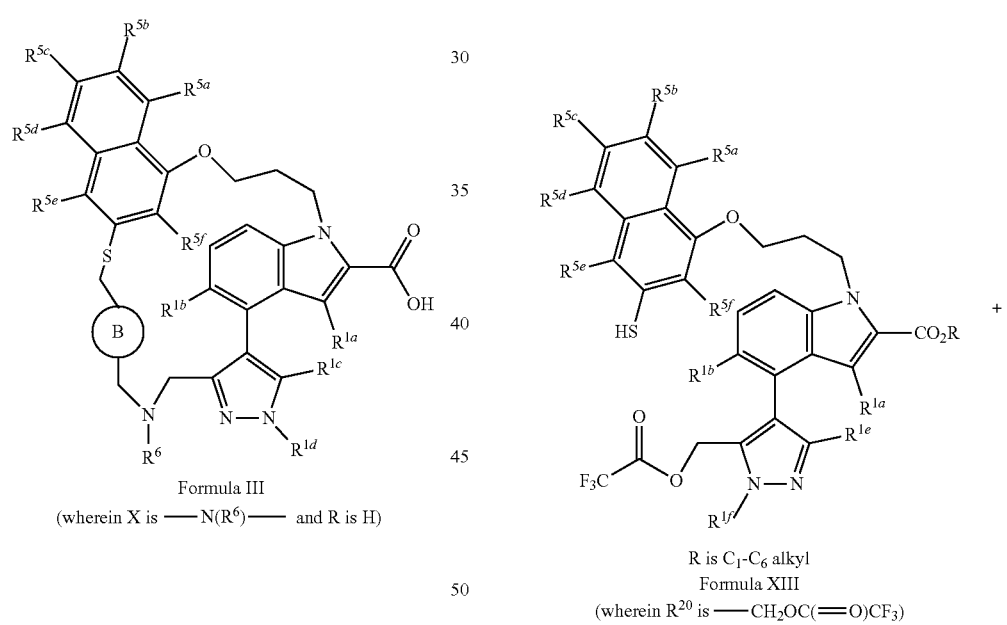

R is C$_1$-C$_6$ alkyl
Formula XIII
(wherein R$^{20}$ is —CH$_2$OH)

R is C$_1$-C$_6$ alkyl
Formula XIII
(wherein R$^{20}$ is —CH$_2$OC(=O)CF$_3$)

General Scheme 6 describes exemplary reaction steps and conditions for the preparation of compounds of Formulae XIII, XV, and V wherein (A)

is A-2 as described in General Scheme 5 for compounds of Formulae VII, IX, and III.

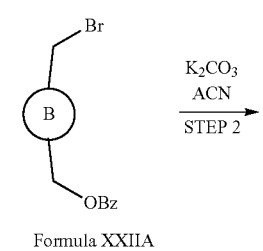

Formula XXIIA

199

-continued

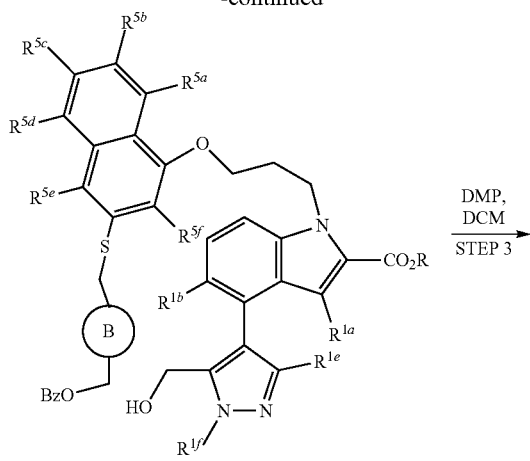

R is $C_1$-$C_6$ alkyl
Formula XV
(wherein $R^{20}$ is —$CH_2OH$ and
$R^{24}$ is —$CH_2OBz$)

DMP,
DCM
STEP 3

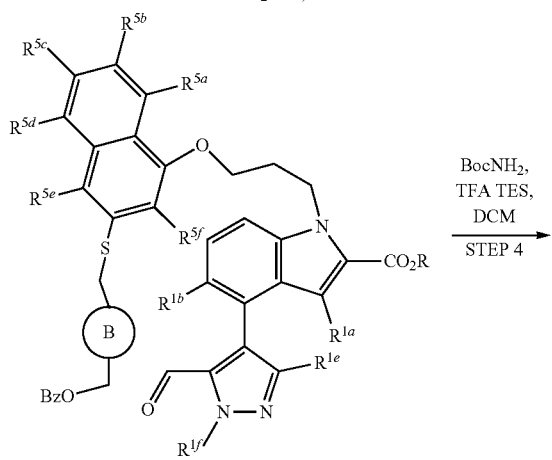

R is $C_1$-$C_6$ alkyl
Formula XV
(wherein $R^{20}$ is —C(=O)H and
$R^{24}$ is —$CH_2OBz$)

BocNH$_2$,
TFA TES,
DCM
STEP 4

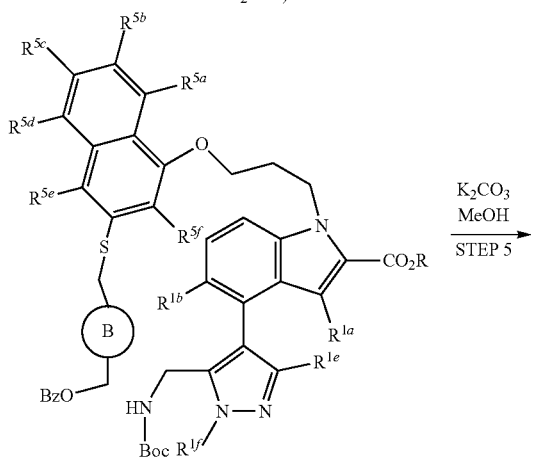

R is $C_1$-$C_6$ alkyl
Formula XV
(wherein $R^{20}$ is —$CH_2N(H)Boc$ and
$R^{24}$ is —$CH_2OBz$)

K$_2$CO$_3$
MeOH
STEP 5

200

-continued

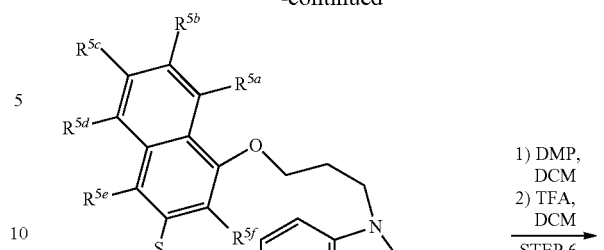

1) DMP,
DCM
2) TFA,
DCM
STEP 6

R is $C_1$-$C_6$ alkyl
Formula XV
(wherein $R^{20}$ is —$CH_2N(H)Boc$ and
$R^{24}$ is —$CH_2OH$)

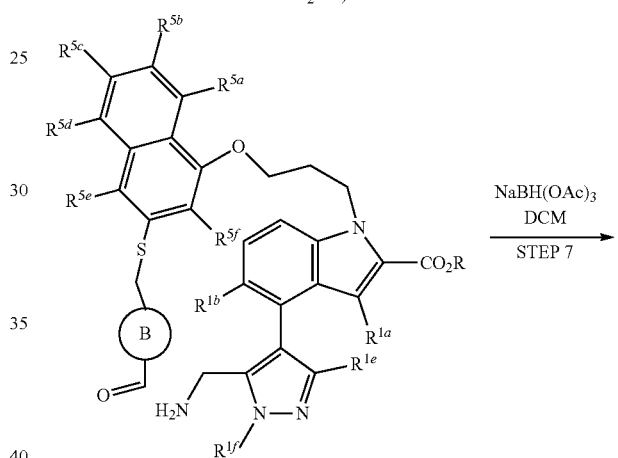

R is $C_1$-$C_6$ alkyl
Formula XV
(wherein $R^{20}$ is —$CH_2NH_2$ and
$R^{24}$ is —C(=O)H)

NaBH(OAc)$_3$
DCM
STEP 7

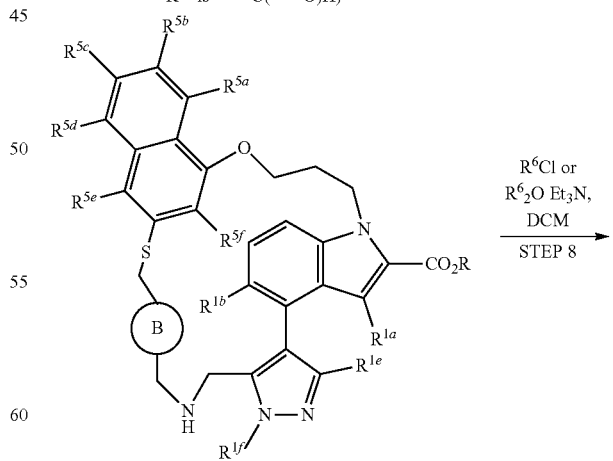

R is $C_1$-$C_6$ alkyl
Formula V
(wherein X is —N($R^6$)—, $R^6$ is H, and
R is $C_1$-$C_6$ alkyl)

$R^6$Cl or
$R^6_2$O Et$_3$N,
DCM
STEP 8

-continued

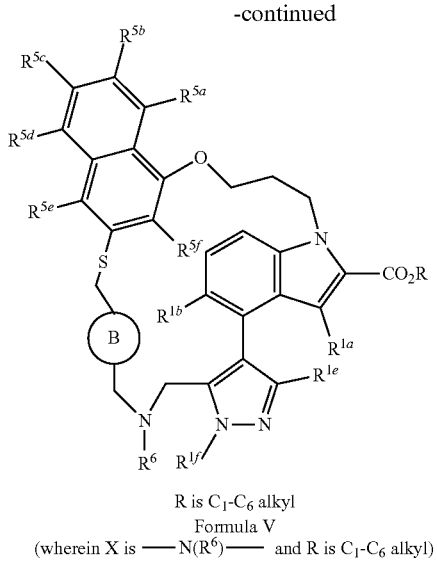

R is $C_1$-$C_6$ alkyl
Formula V
(wherein X is —N($R^6$)— and R is $C_1$-$C_6$ alkyl)

NaOH,
THF, $H_2O$
MeOH
STEP 9

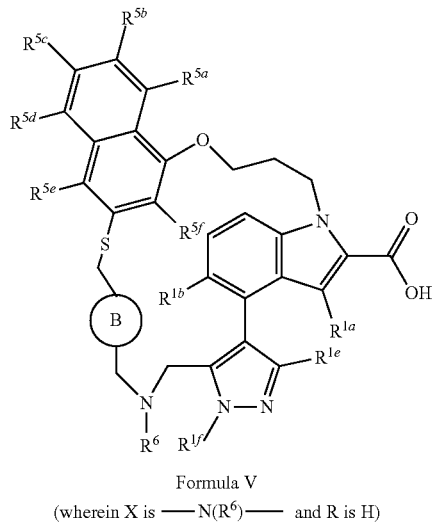

Formula V
(wherein X is —N($R^6$)— and R is H)

General Scheme 7 describes exemplary reaction steps and conditions for the preparation of compounds of Formulae X, XI, and IV, wherein (A)

is A-2. In step 1, a compound of Formula X, wherein R is $C_1$-$C_6$ alkyl, (A)

is A-2, $R^{19}$ is a protecting group, i.e., $R^{19}$ is PMB, and $R^{20}$ is —$CH_2XR^{21}$, is —O—, and $R^{21}$ is hydrogen, i.e., $R^{20}$ is —$CH_2OH$, is oxidized to give a compound of Formula X, wherein $R^{20}$ is —C(=O)H. In step 2, reductive amination of a compound of Formula X, wherein $R^{20}$ is —C(=O)H with $R^{21}$—$NH_2$, wherein $R^{21}$ is hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, (5- to 10-membered heteroaryl)$C_1$-$C_4$ alkyl, or ($C_1$-$C_4$ alkoxy)$C_1$-$C_4$ alkyl, gives a compound of Formula X, wherein $R^{21}$ is hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, (5- to 10-membered heteroaryl)$C_1$-$C_4$ alkyl, or ($C_1$-$C_4$ alkoxy)$C_1$-$C_4$ alkyl. In step 3, a second reductive amination with a compound of Formula XXII, wherein $R^{22}$ is —$OR^{23}$, $R^{23}$ is a protecting group, and the protecting group is TBS, i.e., $R^{22}$ is -OTBS, gives a compound of Formula XI. In step 4, the compound of Formula XI, wherein $R^{22}$ is -OTBS is deprotected and converted to a compound of Formula XI, wherein $R^{22}$ is a leaving group, i.e., $R^{22}$ is —Br. In step 5, the compound of Formula XI is cyclized to give a compound of Formula IV. In this example, $R^{21}$ of Formula XI corresponds to $R^6$ of Formula IV. In step 6, a compound of Formula IV, wherein R is $C_1$-$C_6$ alkyl is hydrolyzed to give a compound of Formula IV, wherein R is hydrogen.

General Scheme 7

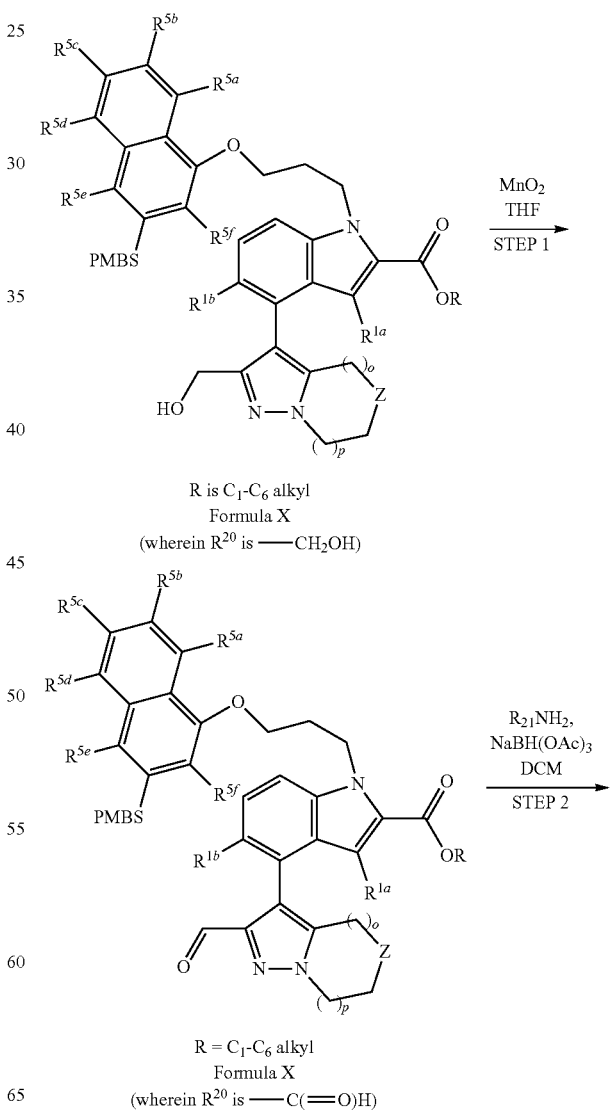

-continued
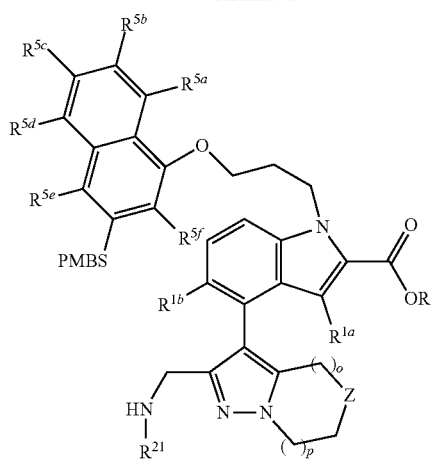
Formula X
(wherein R²¹ is hydrogen, C₁-C₄ alkyl, etc,)
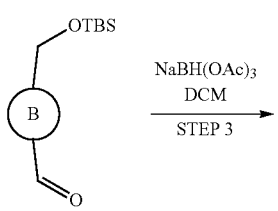
Formula XXI
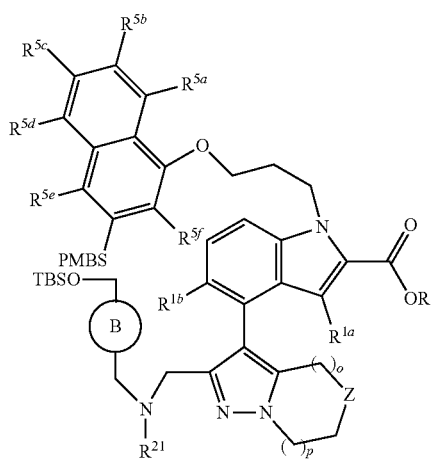
Formula XI
(wherein R²² is —OTBS)
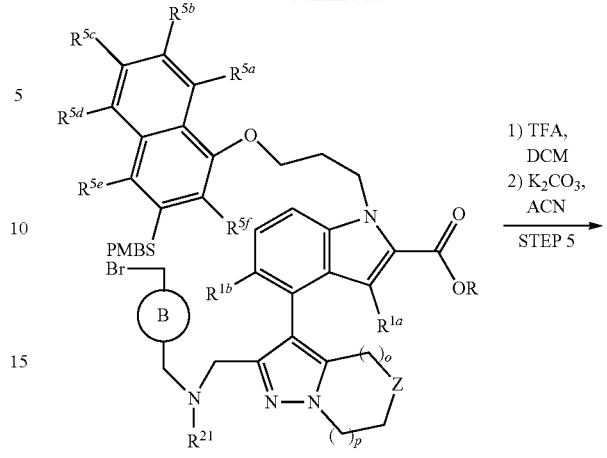
Formula XI
(wherein R²² is —Br)
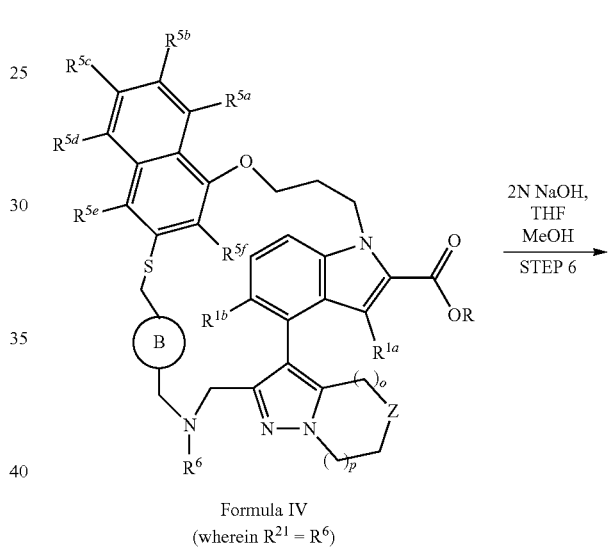
Formula IV
(wherein R²¹ = R⁶)
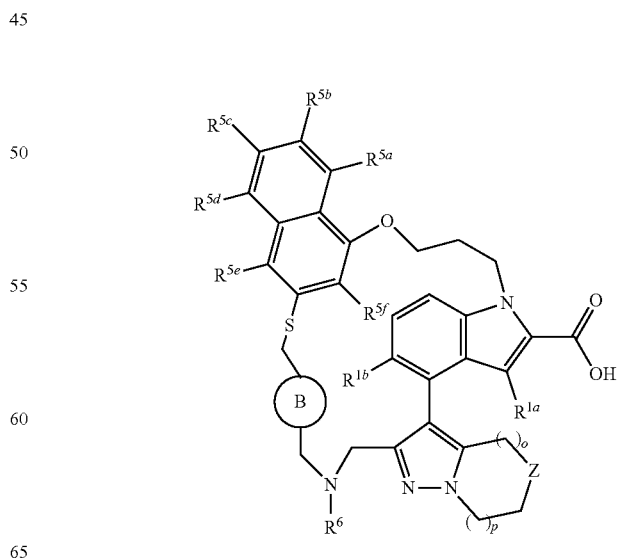
Formula IV General Scheme 8 describes exemplary reaction steps and conditions for the preparation of compounds of Formulae XII, XIII, and III, wherein

is A-2. In step 1, a compound of Formula VII, wherein R is $C_1$-$C_6$ alkyl,

is A-2, $R^{19}$ is a protecting group, i.e., $R^{19}$ is PMB, $R^{20}$ is —$CH_2XR^{21}$, is —O—, and $R^{21}$ is hydrogen, i.e., $R^{20}$ is —$CH_2OH$, is oxidized to give a compound of Formula VII, wherein $R^{20}$ is —C(=O)H. In step 2, reductive amination of a compound of Formula VII, wherein $R^{20}$ is —C(=O)H, with $R^{21}$—$NH_2$, wherein $R^{21}$ is hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-m emb ered heteroaryl, (5- to 10-membered heteroaryl)$C_1$-$C_4$ alkyl, or ($C_1$-$C_4$ alkoxy)$C_1$-$C_4$ alkyl, gives a compound of Formula VII, wherein $R^{21}$ is hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, (5- to 10-membered heteroaryl)$C_1$-$C_4$ alkyl, or ($C_1$-$C_4$ alkoxy)$C_1$-$C_4$ alkyl. In step 3, a second reductive amination with a compound of Formula XXII, wherein $R^{22}$ is —$OR^{23}$ and $R^{23}$ is a protecting group, and the protecting group is TBS, i.e., $R^{22}$ is -OTBS, gives a compound of Formula VIII. In step 4, the compound of Formula VIII, wherein $R^{22}$ is -OTBS is deprotected and converted to a compound of Formula VIII, wherein $R^{22}$ is a leaving group, i.e., $R^{22}$ is —Br. In step 5, the compound of Formula VIII is cyclized to give a compound of Formula III. In this example, $R^{21}$ of Formula VIII corresponds to $R^6$ of Formula III. In step 6, a compound of Formula III, wherein R is $C_1$-$C_6$ alkyl is hydrolyzed to give a compound of Formula III, wherein R is hydrogen.

Scheme 8

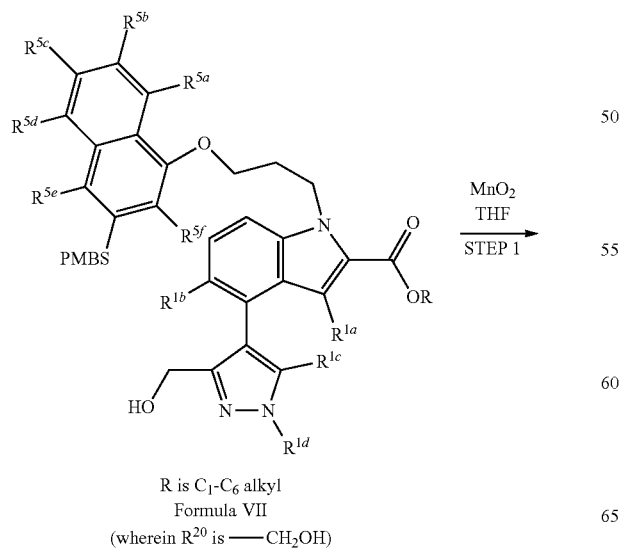

R is $C_1$-$C_6$ alkyl
Formula VII
(wherein $R^{20}$ is —$CH_2OH$)

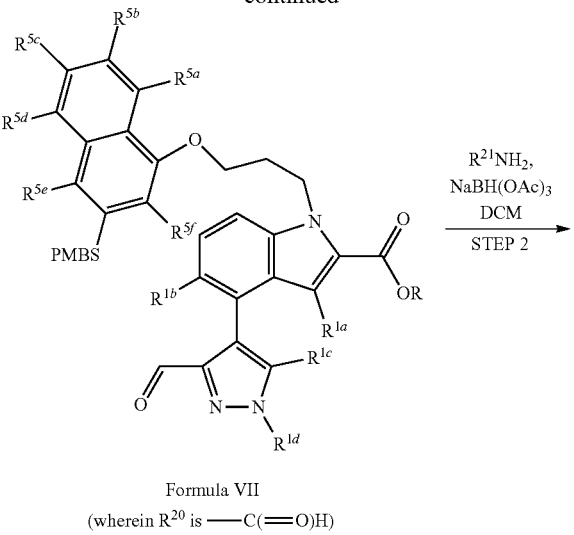

Formula VII
(wherein $R^{20}$ is —C(=O)H)

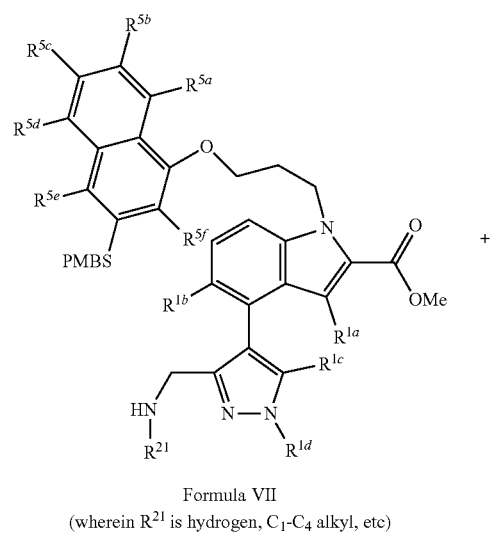

Formula VII
(wherein $R^{21}$ is hydrogen, $C_1$-$C_4$ alkyl, etc)

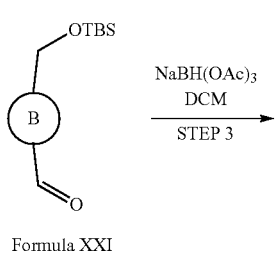

Formula XXI

207
-continued
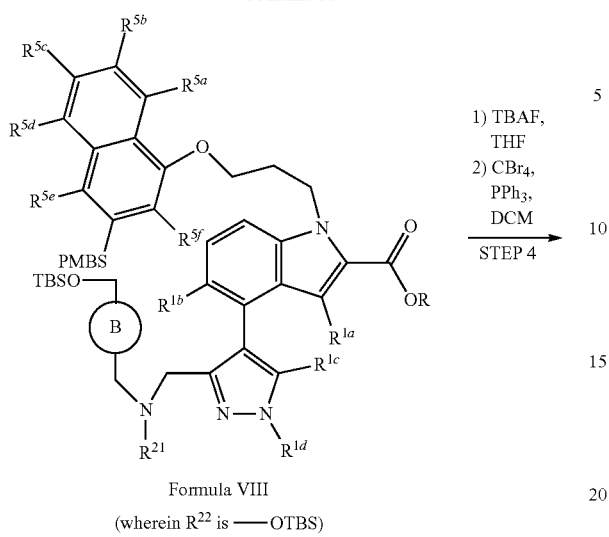
Formula VIII
(wherein R²² is —OTBS)
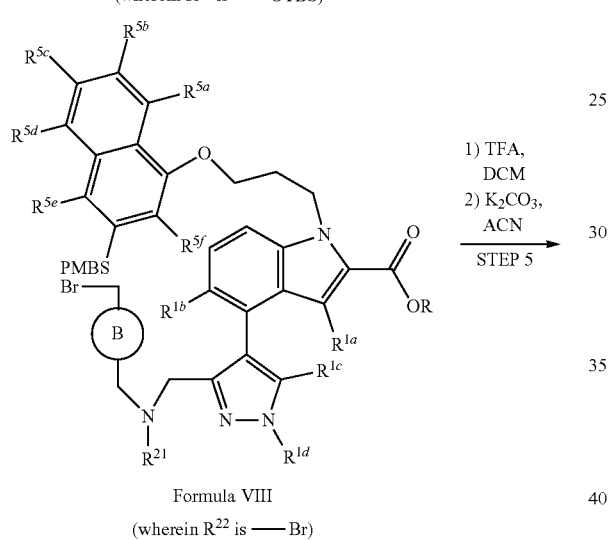
Formula VIII
(wherein R²² is —Br)
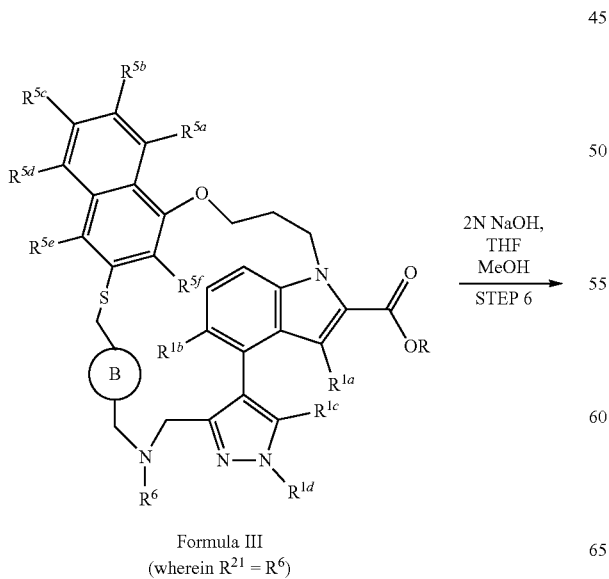
Formula III
(wherein R²¹ = R⁶)
208
-continued
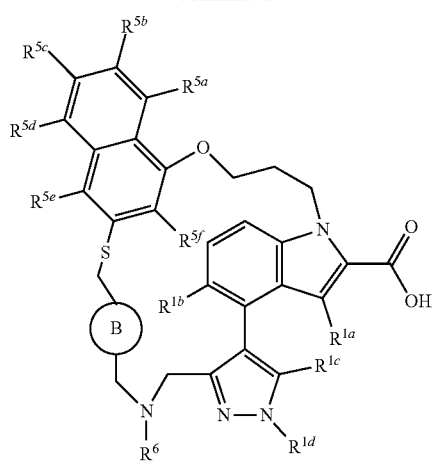
Formula III
Example 1
Synthesis of (Z)-1⁵-chloro-1³,6¹-dimethyl-2⁶,2⁷-dihydro-1¹H,2⁴H,6¹H-10-oxa-4,8-dithia-2(3,2)-pyrazolo[5,1-c][1,4]oxazina-1(4,1)-indola-6(3,5)-pyrazola-9(3,1)-naphthalenacyclotridecaphane-1²-carboxylic acid (Cpd. No. 1)
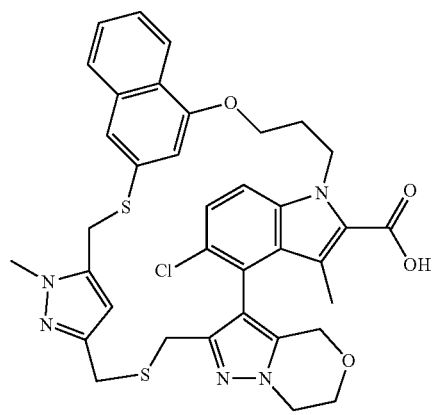 [SMILES: Cc1c(C(=O)O)n2c3ccc(Cl)c(c13)-c1c(nn3c1COCC3)CSCc1cc(n(C)n1)CSc1cc(c3ccccc3c1)OCCC2]

209

Step A: Ethyl 4-(2-(bromomethyl)-6,7-dihydro-4H-pyrazolo[5,1-c][1,4]oxazin-3-yl)-5-chloro-1-(3-((3-((4-methoxybenzyl)thio)naphthalen-1-yl)oxy)propyl)-3-methyl-1H-indole-2-carboxylate (Intermediate No. 1)

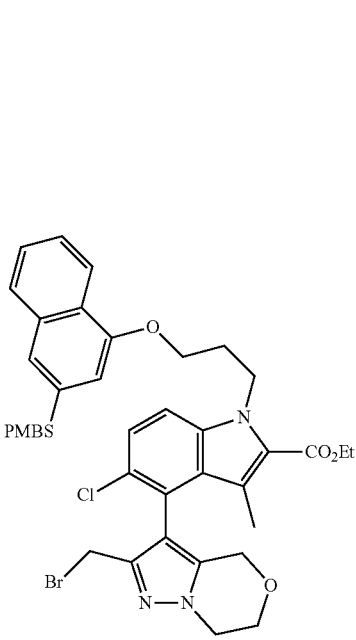

Under Ar, to a solution of ethyl 5-chloro-4-(2-(hydroxymethyl)-6,7-dihydro-4H-pyrazolo[5,1-c][1,4]oxazin-3-yl)-1-(3-((3-((4-methoxybenzyl)thio)naphthalen-1-yl)oxy)propyl)-3-methyl-1H-indole-2-carboxylate (Intermediate No. 10, 320 mg, 0.44 mmol) and $CBr_4$ (219 mg, 0.661 mmol) in dry dichloromethane (DCM) (8 mL) was added $Ph_3P$ (173 mg, 0.661 mmol), the reaction mixture was stirred at room temperature for 3 h. After removal of volatiles under reduced pressure, the residue was purified by silica gel column (hexane:ethyl acetate (EA), 1:2) to afford the title compound (250 mg, 72%) as a white solid. MS: 788.4 (M+H$^+$).

210

Step B: Ethyl 4-(2-((((5-(((tert-butyldimethylsilyl)oxy)methyl)-1-methyl-1H-pyrazol-3-yl)methyl)thio)methyl)-6,7-dihydro-4H-pyrazolo[5,1-c][1,4]oxazin-3-yl)-5-chloro-1-(3-((3-((4-methoxybenzyl)thio)naphthalen-1-yl)oxy)propyl)-3-methyl-1H-indole-2-carboxylate (Intermediate No. 2)

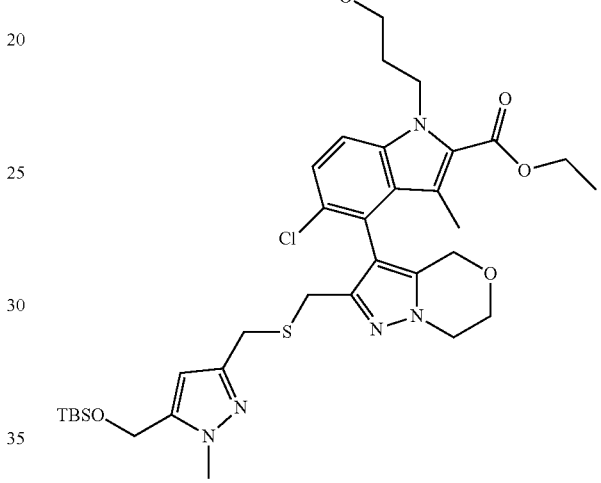

Under Ar, to a solution of ethyl 4-(2-(bromomethyl)-6,7-dihydro-4H-pyrazolo[5,1-c][1,4]oxazin-3-yl)-5-chloro-1-(3-((3-((4-methoxybenzyl)thio)naphthalen-1-yl)oxy)propyl)-3-methyl-1H-indole-2-carboxylate (Step A, 250 mg, 0.32 mmol) and 5-((5-(((tert-butyldimethylsilyl)oxy)methyl)-1-methyl-1H-pyrazol-3-yl)methyl) ethanethioate (Intermediate D1, 299 mg, 0.95 mmol) in dry tetrahydrofuran (THF) (5 mL) and dry MeOH (10 mL) was added $K_2CO_3$ (219 mg, 1.584 mmol) at room temperature, then the reaction mixture was stirred at 40° C. for 2 h. The resulting mixture was acidified by AcOH, and concentrated under reduced pressure to give a yellow oil, which was re-taken into DCM. The resulting mixture was filtered off, and the filtrate was concentrated under reduced pressure to give the crude title compound as a yellow oil, which was directly used without purification. MS: 980.5 (M+H$^+$).

211

Step C: Ethyl 5-chloro-4-(2-(((((5-(hydroxymethyl)-1-methyl-1H-pyrazol-3-yl)methyl)thio)methyl)-6,7-dihydro-4H-pyrazolo[5,1-c][1,4]oxazin-3-yl)-1-(3-((3-((4-methoxybenzyl)thio)naphthalen-1-yl)oxy)propyl)-3-methyl-1H-indole-2-carboxylate (Intermediate No. 3)

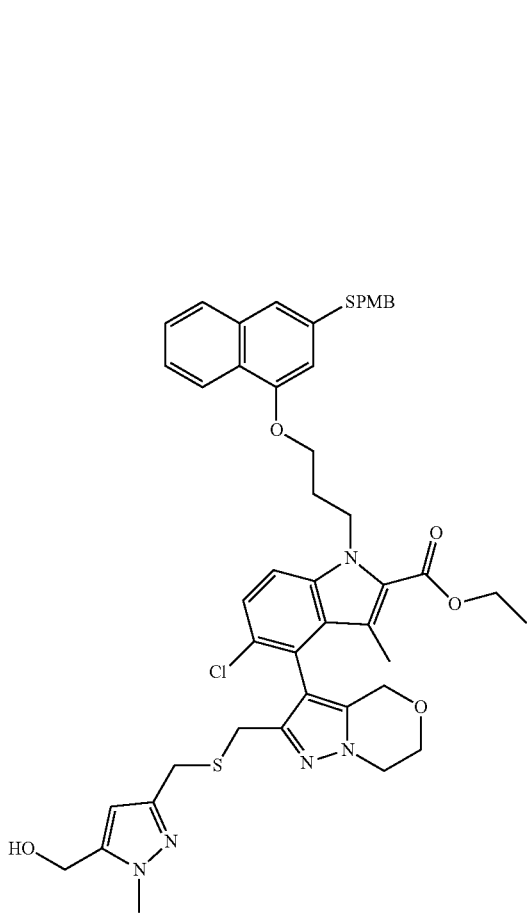

Under Ar, to a solution of the crude ethyl 4-(2-(((((5-(((tert-butyldimethylsilyl)oxy)methyl)-1-methyl-1H-pyrazol-3-yl)methyl)thio)methyl)-6,7-dihydro-4H-pyrazolo[5,1-c][1,4]oxazin-3-yl)-5-chloro-1-(3-((3-((4-methoxybenzyl)thio)naphthalen-1-yl)oxy)propyl)-3-methyl-1H-indole-2-carboxylate (Step B) in dry THF (10 mL) was added TBAF·H₂O (248 mg, 0.95 mmol) at room temperature, then the reaction mixture was stirred at room temperature for 5 h. After removal of volatiles under reduced pressure, the residue was purified by silica gel column (DCM:MeOH, 15:1) to afford the crude title compound as a yellow oil. The yellow oil was used for the next step without further purification. MS: 866.6 (M+H$^+$).

212

Step D: Ethyl 4-(2-(((((5-(bromomethyl)-1-methyl-1H-pyrazol-3-yl)methyl)thio)methyl)-6,7-dihydro-4H-pyrazolo[5,1-c][1,4]oxazin-3-yl)-5-chloro-1-(3-((3-((4-methoxybenzyl)thio)naphthalen-1-yl)oxy)propyl)-3-methyl-1H-indole-2-carboxylate (Intermediate No. 4)

Under Ar, to a solution of the crude ethyl 5-chloro-4-(2-(((((5-(hydroxymethyl)-1-methyl-1H-pyrazol-3-yl)methyl)thio)methyl)-6,7-dihydro-4H-pyrazolo[5,1-c][1,4]oxazin-3-yl)-1-(3-((3-((4-methoxybenzyl)thio)naphthalen-1-yl)oxy)propyl)-3-methyl-1H-indole-2-carboxylate (Step C, 344 mg) and CBr₄ (197 mg, 0.60 mmol) in dry DCM (10 mL) was added Ph₃P (156 mg, 0.60 mmol) at room temperature, then the mixture was stirred at room temperature for 3 h. After removal of volatiles under reduced pressure, the residue was purified by silica gel column (DCM:MeOH, 30:1) to afford the title compound (200 mg, 54% over 3 steps). MS: 928.4 (M+H$^+$).

Step E: (Z)-1$^5$-chloro-1$^3$,6$^1$-dimethyl-2$^6$,2$^7$-dihydro-1$^1$H,2$^4$H,6$^1$H-10-oxa-4,8-dithia-2(3,2)-pyrazolo[5,1-c][1,4]oxazina-1 (4,1)-indola-6(3,5)-pyrazola-9(3,1)-naphthalenacyclotridecaphane-1$^2$-carboxylic acid (Cpd. No. 1)

Under Ar, to a solution of ethyl 4-(2-(((((5-(bromomethyl)-1-methyl-1H-pyrazol-3-yl)methyl)thio)methyl)-6,7-dihydro-4H-pyrazolo[5,1-c][1,4]oxazin-3-yl)-5-chloro-1-(3-((3-((4-methoxybenzyl)thio)naphthalen-1-yl)oxy)propyl)-3-methyl-1H-indole-2-carboxylate (Step D, 200 mg, 0.22 mmol) in DCM (1 mL) were added TES (1 mL) and TFA (3 mL) at room temperature, and then the mixture was stirred at 35° C. for overnight. After removal of volatiles under reduced pressure, the resulting yellow oil was directly used without purification. MS: 808.3 (M+H$^+$).

Under Ar, to a solution of the above yellow oil in dry acetonitrile (10 mL) was added K₂CO₃ (171 mg, 1.236 mmol) at room temperature, and then the reaction mixture was stirred at room temperature for 2 h. The mixture was filtered off and the filtrate was concentrated under reduced pressure to give a yellow oil, which was directly used without purification. MS: 728.4 (M+H$^+$).

To a solution of the above yellow oil in THF (8 ml) and water (1 mL) was added NaOH (60 mg, 1.5 mmol), then the mixture was stirred at 70° C. for 2 h. After cooling down to room temperature, the mixture was acidified by AcOH, and partitioned with EA (10 mL) and water (2 mL). The organic layer was separated, and the aqueous layer was extracted with EA twice, the combined organic layer was concentrated under reduced pressure to give a yellow oil, which was purified by C18 pre-HPLC column to afford the title compound (28 mg, 13% over 3 steps) as a white solid. $^1$H NMR (500 MHz, DMSO-d$_6$) δ 8.17 (d, J=8.2 Hz, 1H), 7.74 (dd, J=16.5, 8.5 Hz, 2H), 7.52 (t, J=8.2 Hz, 2H), 7.41 (s, 1H), 7.23 (d, J=9.0 Hz, 1H), 6.65 (s, 1H), 5.15-5.01 (m, 1H), 4.86 (s, 1H), 4.62 (m, 1H), 4.40 (m, 2H), 4.29 (d, J=15.5 Hz, 1H), 4.21 (d, J=15.2 Hz, 1H), 4.16 (d, J=5.3 Hz, 2H), 4.09 (d, J=5.4 Hz, 2H), 3.97 (d, J=8.6 Hz, 1H), 3.86 (brs, 1H), 3.71 (s, 3H), 3.43-3.30 (m, 1H), 3.22 (d, J=13.3 Hz, 1H), 3.13 (d, J=14.2 Hz, 1H), 2.95 (d, J=14.2 Hz, 1H), 2.46-2.30 (m, 2H), 2.07 (s, 3H). MS: 700.4 (M+H$^+$).

Example 2

Synthesis of (Z)-1$^5$-chloro-9$^6$-fluoro-1$^3$,6$^1$-dimethyl-2$^5$,2$^6$-dihydro-1$^1$H,2$^4$H,6$^1$H-10-oxa-4,8-dithia-1(4,1)-indola-2(3,2)-pyrrolo[1,2-b]pyrazola-6(3,5)-pyrazola-9(3,1)-naphthalenacyclotridecaphane-1$^2$-carboxylic acid (Cpd. No. 2)

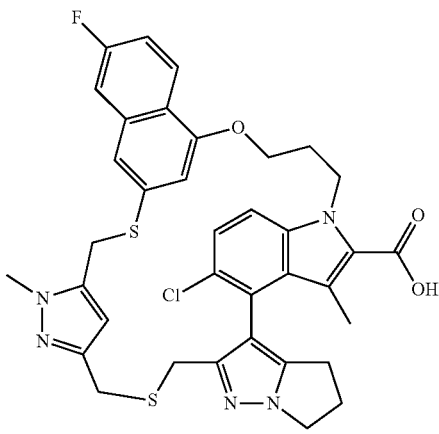 [SMILES: Cc1c(C(=O)O)n2c3ccc(Cl)c(c13)-c1c(nn3c1CCC3)CSCc1cc(n(C)n1)CSc1cc(c3ccc(F)cc3c1)OCCC2]

Essentially the same protocol of the preparation of Cpd. No. 1 of EXAMPLE 1 was used to afford Cpd. No. 2 (19 mg) as a white solid. $^1$H NMR (500 MHz, DMSO-d$_6$) δ 8.22 (dd, J=9.1, 5.8 Hz, 1H), 7.70 (d, J=9.1 Hz, 1H), 7.55 (dd, J=10.3, 2.3 Hz, 1H), 7.43-7.33 (m, 2H), 7.25 (d, J=9.0 Hz, 1H), 6.66 (s, 1H), 5.09-5.04 (m, 1H), 4.90 (s, 1H), 4.65-4.55 (m, 1H), 4.28 (dd, J=38.1, 15.6 Hz, 2H), 4.17-4.11 (m, 2H), 4.05-3.95 (m, 1H), 3.90-3.86 (m, 1H), 3.70 (s, 3H), 3.35 (d, J=13.0 Hz, 1H), 3.26 (d, J=13.5 Hz, 1H), 3.14 (d, J=14.0 Hz, 1H), 2.98 (d, J=14.0 Hz, 1H), 2.62-2.57 (m, 4H), 2.45-2.35 (m, 2H), 2.07 (s, 3H). MS: 702.5 (M+H$^+$).

Example 3

Synthesis of (Z)-1$^5$-chloro-9$^6$-fluoro-1$^3$,2$^5$,2$^5$,6$^1$-tetramethyl-2$^5$,2$^6$-dihydro-1$^1$H,2$^4$H,6$^1$H-10-oxa-4,8-dithia-1(4,1)-indola-2(3,2)-pyrrolo[1,2-b]pyrazola-6(3,5)-pyrazola-9(3,1)-naphthalenacyclotridecaphane-1$^2$-carboxylic acid (Cpd. No. 3)

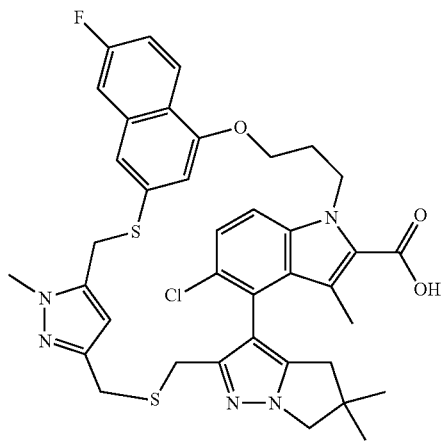 [SMILES: Cc1c(C(=O)O)n2c3ccc(Cl)c(c13)-c1c(nn3c1CC(C)(C)C3)CSCc1cc(n(C)n1)CSc1cc(c3ccc(F)cc3c1)OCCC2]

Essentially the same protocol of the preparation of Cpd. No. 1 of EXAMPLE 1 was used to afford Cpd. No. 3 (35 mg) as a white solid. $^1$H NMR (500 MHz, DMSO-d$_6$) δ 8.23 (dd, J=9.2, 5.8 Hz, 1H), 7.69 (d, J=9.1 Hz, 1H), 7.55 (dd, J=10.3, 2.6 Hz, 1H), 7.41-7.35 (m, 2H), 7.23 (d, J=8.9 Hz, 1H), 6.65 (s, 1H), 5.12-5.01 (m, 1H), 4.90 (s, 1H), 4.64-4.57 (m, 1H), 4.27 (dd, J=44.7, 15.6 Hz, 2H), 3.98-3.93 (m, 2H), 3.91 (s, 2H), 3.90-3.87 (m, 2H), 3.72 (s, 3H), 3.32 (d, J=13.0 Hz, 1H), 3.24 (d, J=13.0 Hz, 1H), 3.12 (d, J=14.0 Hz, 1H), 2.98 (d, J=14.0 Hz, 1H), 2.43 (d, J=4.6 Hz, 2H), 2.11 (s, 3H), 1.24 (s, 3H), 1.23 (s, 3H). MS: 730.5 (M+H$^+$).

Example 4

Synthesis of (Z)-1$^5$-chloro-9$^6$-fluoro-1$^3$,6$^1$-dimethyl-2$^6$,2$^7$-dihydro-1$^1$H,24H,6$^1$H-10-oxa-4,8-dithia-2(3,2)-pyrazolo[5,1-c][1,4]oxazina-1(4,1)-indola-6(3,5)-pyrazola-9(3,1)-naphthalenacyclotridecaphane-1$^2$-carboxylic acid (Cpd. No. 4)

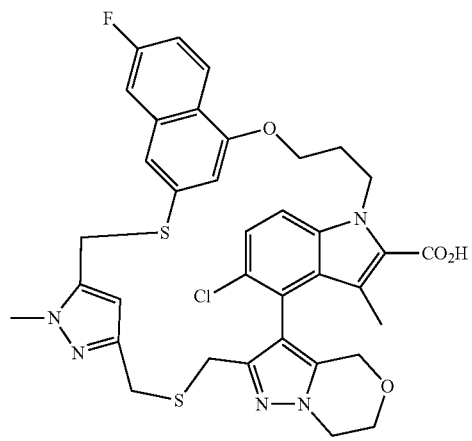 [SMILES: Cc1c(C(=O)O)n2c3ccc(Cl)c(c13)-c1c(nn3c1COCC3)CSCc1cc(n(C)n1)CSc1cc(c3ccc(F)cc3c1)OCCC2]

Essentially the same protocol of the preparation Cpd. No. 1 of EXAMPLE 1 was used to afford Cpd. No. 4 (4 mg) as a white solid. $^1$H NMR (500 MHz, DMSO-d$_6$) δ 8.19 (dd, J=9.2, 6.0 Hz, 1H), 7.70 (d, J=9.0 Hz, 1H), 7.52 (dd, J=10.1, 2.0 Hz, 1H), 7.38-7.30 (m, 2H), 7.23 (d, J=9.0 Hz, 1H), 6.61 (s, 1H), 5.07-4.98 (m, 1H), 4.84 (s, 1H), 4.67-4.51 (m, 1H), 4.37 (s, 2H), 4.28 (d, J=15.6 Hz, 1H), 4.20 (d, J=15.5 Hz, 1H), 4.13 (d, J=4.8 Hz, 2H), 4.06 (d, J=4.8 Hz, 2H), 3.99-3.90 (m, 1H), 3.86-3.78 (m, 1H), 3.68 (s, 3H), 3.31 (m, 2H), 3.20 (d, J=13.3 Hz, 1H), 3.11 (d, J=14.1 Hz, 1H), 2.96 (d, J=14.1 Hz, 1H), 2.40-2.33 (m, 1H), 2.03 (s, 3H). MS: 719.7 (M+H$^+$).

Example 5

Synthesis of (Z)-1$^5$-chloro-1$^3$,2$^1$,2$^5$,6$^1$-tetramethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid (Cpd. No. 5)

Essentially the same protocol used to prepare Cpd. No. 1 of EXAMPLE 1 was used to afford Cpd. No. 5 (130 mg) as a white solid. $^1$H NMR (500 MHz, DMSO-d$_6$) δ 8.16 (d, J=7.9 Hz, 1H), 7.75 (t, J=9.2 Hz, 2H), 7.58-7.46 (m, 2H), 7.41 (s, 1H), 7.25 (d, J=9.0 Hz, 1H), 6.67 (s, 1H), 5.06 (dd, J=14.2, 4.6 Hz, 1H), 4.84 (s, 1H), 4.62 (dd, J=14.0, 9.4 Hz, 1H), 4.38-4.17 (m, 2H), 3.99 (q, J=8.0 Hz, 1H), 3.86 (dd, J=8.3, 4.5 Hz, 1H), 3.77 (s, 3H), 3.72 (s, 3H), 3.30 (d, J=13.0 Hz, 1H), 3.19-3.09 (m, 2H), 2.94 (d, J=14.2 Hz, 1H), 2.46-2.30 (m, 2H), 2.02 (s, 3H), 1.93 (s, 3H). MS: 672.4 (M+H$^+$).

Example 6

Synthesis of (R)-(Z)-1$^5$-chloro-1$^3$,2$^1$,2$^5$,6$^1$-tetramethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid (Cpd. No. 6)

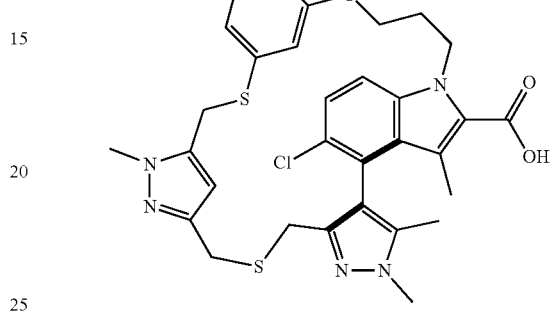

Cpd. No. 5 (113 mg) was subjected to chiral SFC resolution with a CHIRALPAK IE column to provide Cpd. No. 6 (40 mg, 98% e e) as a white solid. MS: 672.4 (M+H$^+$).

Example 7

Synthesis of (S)-(Z)-1$^5$-chloro-1$^3$,2$^1$,2$^5$,6$^1$-tetramethyl-1$^1$H,2$^1$H,6$^1$11-10-oxa-4,8-dithia-1(4,1)-indola-2(4,3),6(3,5)-dipyrazola-9(3,1)-naphthalenacyclotridecaphane-1$^2$-carboxylic acid (Cpd. No. 7)

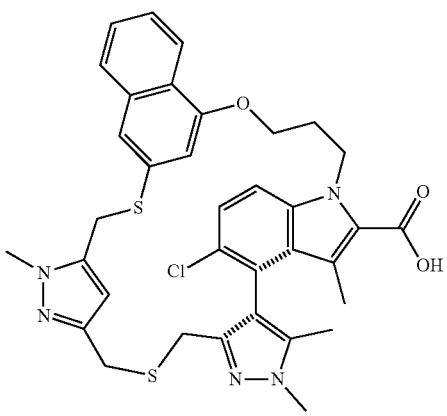

Cpd. No. 5 (113 mg) was subjected to chiral SFC resolution with a CHIRALPAK IE column to provide Cpd. No. 7 (42 mg, 99% ee) as a white solid. MS: 672.3 (M+H$^+$).

Example 8

Synthesis of (Z)-1⁵-chloro-1³-ethyl-2¹,2⁵,6¹-trimethyl-1¹H,2¹H,6¹11-10-oxa-4,8-dithia-1(4,1)-indola-2(4,3),6(3,5)-dipyrazola-9(3,1)-naphthalenacyclotridecaphane-1²-carboxylic acid (Cpd. No. 8)

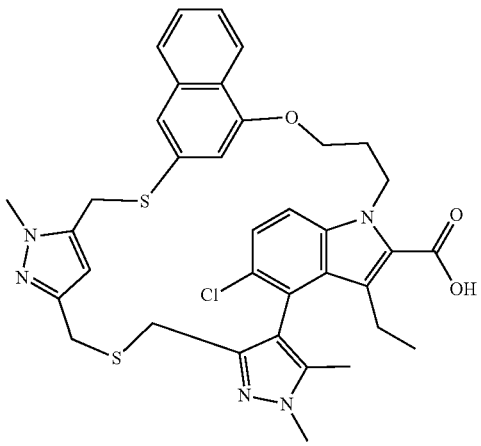 [SMILES: CCc1c(C(=O)O)n2c3ccc(Cl)c(c13)-c1c(nn(C)c1C)CSCc1cc(n(C)n1)CSc1cc(c3ccccc3c1)OCCC2]

Essentially the same protocol used to prepare Cpd. No. 1 of EXAMPLE 1 was used to afford Cpd. No. 8 (3.5 mg) as a white solid. $^1$H NMR (500 MHz, DMSO-d$_6$) δ 8.20 (d, J=7.6 Hz, 1H), 7.77 (d, J=8.2 Hz, 1H), 7.66 (d, J=9.1 Hz, 1H), 7.53 (s, 1H), 7.58-7.48 (m, 1H), 7.40 (s, 1H), 7.15 (d, J=9.0 Hz, 1H), 6.66 (s, 1H), 5.09-5.02 (m, 1H), 4.91 (s, 1H), 4.30 (d, J=15.5 Hz, 1H), 4.16 (d, J=15.5 Hz, 1H), 3.97 (d, J=6.3 Hz, 1H), 3.91 (d, J=8.2 Hz, 1H), 3.77 (s, 3H), 3.71 (s, 3H), 3.16 (brs, 2H), 3.03 (d, J=13.8 Hz, 2H), 2.93 (d, J=13.8 Hz, 1H), 2.54 (brs, 2H), 2.42 (brs, 2H), 1.99 (s, 3H), 0.79 (t, J=7.3 Hz, 3H). MS: 687.4 (M+H⁺).

Example 9

Synthesis of (Z)-1³,1⁵-dichloro-2¹,2⁵,6¹-trimethyl-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid (Cpd. No. 9)

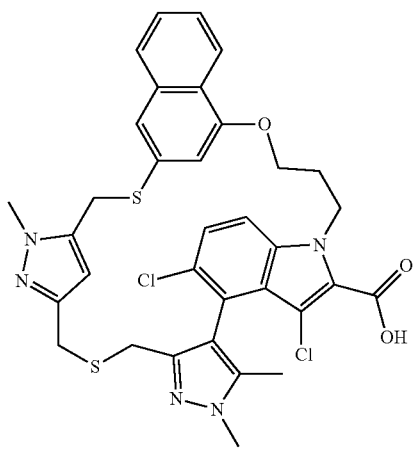 [SMILES: Cc1c2c(nn1C)CSCc1cc(n(C)n1)CSc1cc(c3ccccc3c1)OCCCn1c(C(=O)O)c(Cl)c3c-2c(Cl)ccc31]

Essentially the same protocol used to prepare Cpd. No. 1 of EXAMPLE 1 was used to afford Cpd. No. 9 (10.9 mg) as a white solid. $^1$H NMR (500 MHz, DMSO-d$_6$) δ 8.16 (d, J=8.1 Hz, 1H), 7.87 (d, J=9.2 Hz, 1H), 7.75 (d, J=7.8 Hz, 1H), 7.56-7.46 (m, 2H), 7.39 (s, 1H), 7.37 (d, J=9.1 Hz, 1H), 6.73 (s, 1H), 5.07 (dd, J=14.6, 4.9 Hz, 1H), 5.01 (s, 1H), 4.72 (dd, J=13.7, 8.6 Hz, 1H), 4.34-4.23 (m, 2H), 4.00 (q, J=8.1 Hz, 1H), 3.95-3.87 (m, 1H), 3.77 (s, 3H), 3.71 (s, 3H), 3.32 (d, J=13.2 Hz, 1H), 3.22 (d, J=13.2 Hz, 1H), 3.16 (d, J=13.8 Hz, 1H), 3.01 (d, J=13.8 Hz, 1H), 2.43 (brs, 2H), 1.95 (s, 3H). MS: 693.3 (M+H⁺).

Example 10

Synthesis of (Z)-1⁵-chloro-1³,2⁵,6¹-trimethyl-2¹-(2-(methylamino)-2-oxoethyl)-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid (Cpd. No. 10)

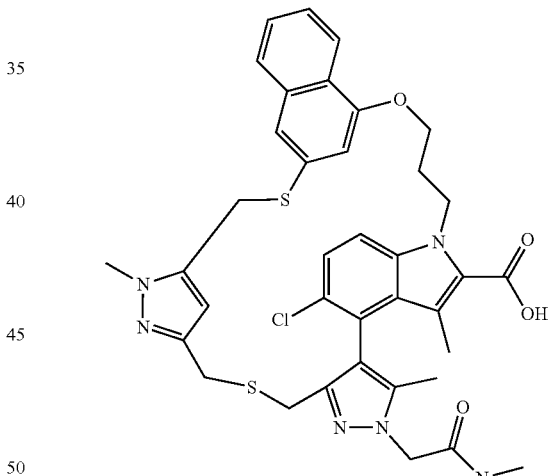

Essentially the same protocol used to prepare Cpd. No. 1 of EXAMPLE 1 was used to afford Cpd. No. 10 (3.7 mg) as a white solid. $^1$H NMR (500 MHz, DMSO-d$_6$) δ 8.16 (d, J=7.7 Hz, 1H), 8.12-8.07 (m, 1H), 7.78-7.70 (m, 2H), 7.56-7.47 (m, 2H), 7.41 (d, J=1.2 Hz, 1H), 7.28-7.20 (m, 1H), 6.67 (s, 1H), 5.10-5.03 (m, 1H), 4.88 (s, 1H), 4.81-4.69 (m, 3H), 4.63 (d, J=10.2 Hz, 1H), 4.30 (d, J=15.6 Hz, 1H), 4.23 (d, J=15.5 Hz, 1H), 4.02-3.94 (m, 1H), 3.88-3.84 (m, 1H), 3.72 (s, 3H), 3.58-3.11 (m, 2H), 2.95 (d, J=14.1 Hz, 1H), 2.66 (d, J=4.6 Hz, 3H), 2.45-2.35 (m, 2H), 2.06 (s, 3H), 1.90 (s, 3H). MS: 729.2 (M+H⁺).

Example 11

Synthesis of (Z)-1⁵-chloro-2¹-(2-methoxyethyl)-1³,2⁵,6¹-trimethyl-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid (Cpd. No. 11)

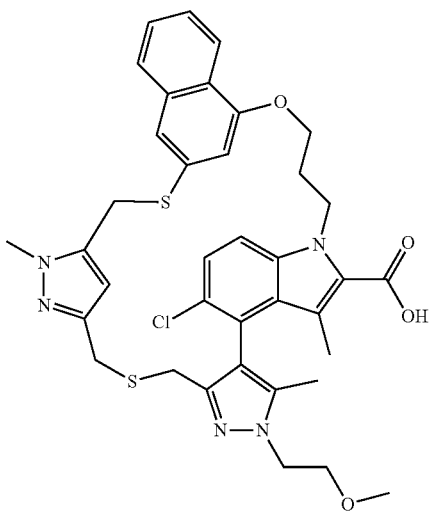 [SMILES: COCCn1nc2c(c1C)-c1c(Cl)ccc3c1c(C)c(C(=O)O)n3CCCOc1cc(cc3ccccc13)SCc1cc(nn1C)CSC2]

Essentially the same protocol used to prepare Cpd. No. 1 of EXAMPLE 1 was used to afford Cpd. No. 11 (10.5 mg) as a white solid. ¹H NMR (500 MHz, DMSO-$d_6$) δ 8.17 (d, J=7.6 Hz, 1H), 7.72 (d, J=7.1 Hz, 1H), 7.65-7.58 (m, 1H), 7.56-7.46 (m, 1H), 7.51 (s, 1H), 7.28 (s, 1H), 7.10-7.05 (m, 1H), 6.65 (s, 1H), 5.09-5.04 (m, 1H), 4.65-4.62 (m, 2H), 4.33-4.20 (m, 2H), 4.08-3.92 (m, 2H), 3.72-3.60 (m, 5H), 3.50-3.22 (m, 5H), 3.27 (s, 3H), 3.20-3.10 (m, 2H), 3.03 (d, J=14.3 Hz, 1H), 1.92 (s, 3H), 1.83 (s, 3H). MS: 716.2 (M+H⁺).

Example 12

Synthesis of (Z)-1³-(acetamidomethyl)-1⁵-chloro-2¹,2⁵,6¹-trimethyl-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid (Cpd. No. 12)

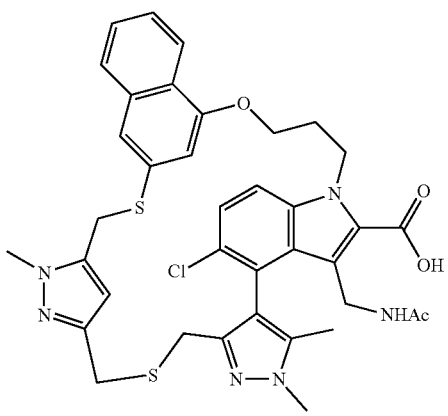 [SMILES: CC(=O)NCc1c(C(=O)O)n2c3ccc(Cl)c(c13)-c1c(nn(C)c1C)CSCc1cc(n(C)n1)CSc1cc(c3ccccc3c1)OCCC2]

Essentially the same protocol used to prepare Cpd. No. 1 of EXAMPLE 1 was used to afford Cpd. No. 12 (5 mg) as a white solid. ¹H NMR (500 MHz, DMSO-$d_6$) δ 8.17 (d, J=7.8 Hz, 1H), 7.77 (t, J=9.1 Hz, 2H), 7.58-7.46 (m, 2H), 7.42 (s, 1H), 7.34 (t, J=4.1 Hz, 1H), 7.28 (d, J=8.9 Hz, 1H), 6.66 (s, 1H), 5.14 (dd, J=14.8, 5.1 Hz, 1H), 4.94 (s, 1H), 4.68 (dd, J=13.9, 8.8 Hz, 1H), 4.29 (d, J=15.5 Hz, 1H), 4.21 (d, J=14.7 Hz, 2H), 3.98-3.92 (m, 3H), 3.71 (s, 3H), 3.68 (s, 3H), 3.23 (d, J=13.3 Hz, 1H), 3.08 (dd, J=13.8, 2.5 Hz, 2H), 2.93 (d, J=13.7 Hz, 1H), 2.43 (brs, 2H), 1.93 (s, 3H), 1.71 (s, 3H). MS: 729.3 (M+H⁺).

Example 13

Synthesis of (Z)-1⁵-chloro-9⁶-fluoro-2¹,2⁵,6¹-trimethyl-1¹H,2¹H,6¹E-10-oxa-4,8-dithia-1(4,1)-indola-2(4,3),6(3,5)-dipyrazola-9(3,1)-naphthalenacyclotridecaphane-1²-carboxylic acid (Cpd. No. 13)

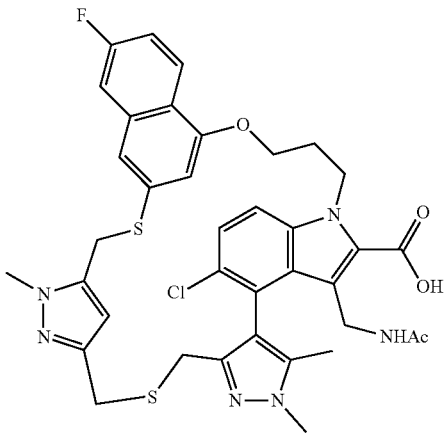 [SMILES: CC(=O)NCc1c(C(=O)O)n2c3ccc(Cl)c(c13)-c1c(nn(C)c1C)CSCc1cc(n(C)n1)CSc1cc(c3ccc(F)cc3c1)OCCC2]

Essentially the same protocol used to prepare Cpd. No. 1 of EXAMPLE 1 was used to afford Cpd. No. 13 (15 mg) as a white solid. ¹H NMR (500 MHz, DMSO-$d_6$) δ 8.27 (dd, J=9.4, 5.7 Hz, 1H), 7.73 (d, J=9.0 Hz, 1H), 7.57 (dd, J=10.2, 2.7 Hz, 1H), 7.45-7.36 (m, 2H), 7.27 (d, J=8.9 Hz, 1H), 6.82 (s, 1H), 6.63 (s, 1H), 5.19 (dd, J=14.4, 4.7 Hz, 1H), 4.95 (s, 1H), 4.66 (dd, J=14.0, 9.3 Hz, 1H), 4.36-4.19 (m, 2H), 3.96 (q, J=7.9 Hz, 1H), 3.86 (dd, J=9.1, 4.5 Hz, 1H), 3.80 (s, 3H), 3.70 (s, 3H), 3.42 (q, J=13.1 Hz, 2H), 3.07 (d, J=13.9 Hz, 1H), 2.85 (d, J=13.9 Hz, 1H), 2.50-2.37 (m, 2H), 2.00 (s, 3H). MS: 676.4 (M+H⁺).

Example 14

Synthesis of (Z)-1⁵-chloro-9⁶-fluoro-1³,2¹,2⁵,6¹-tetramethyl-1¹H,2¹H,6¹E-10-oxa-4,8-dithia-1(4,1)-indola-2(4,3),6(3,5)-dipyrazola-9(3,1)-naphthalenacyclotridecaphane-1²-carboxylic acid (Cpd. No. 14)

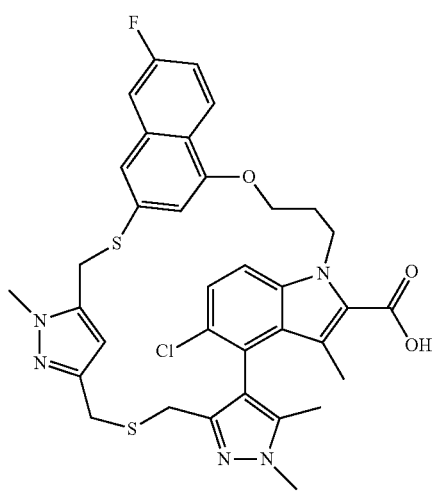 [SMILES: Cc1c(C(=O)O)n2c3ccc(Cl)c(c13)-c1c(nn(C)c1C)CSCc1cc(n(C)n1)CSc1cc(c3ccc(F)cc3c1)OCCC2]

Essentially the same protocol used to prepare Cpd. No. 1 of EXAMPLE 1 was used to afford Cpd. No. 14 (393 mg) as a white solid. $^1$H NMR (500 MHz, DMSO-d$_6$) δ 8.19 (dd, J=9.2, 5.9 Hz, 1H), 7.69 (d, J=9.1 Hz, 1H), 7.52 (dd, J=10.3, 2.4 Hz, 1H), 7.43-7.30 (m, 2H), 7.24 (d, J=9.0 Hz, 1H), 6.62 (s, 1H), 5.03 (dd, J=9.9, 4.8 Hz, 1H), 4.85 (s, 1H), 4.59 (t, J=10.0 Hz, 1H), 4.28 (d, J=15.6 Hz, 1H), 4.21 (d, J=15.5 Hz, 1H), 3.98-3.93 (m, 2H), 3.74 (s, 3H), 3.69 (s, 3H), 3.28 (d, J=13.1 Hz, 1H), 3.13 (dd, J=15.3, 13.6 Hz, 2H), 2.94 (d, J=14.1 Hz, 1H), 2.42-2.30 (m, 2H), 1.99 (s, 3H), 1.90 (s, 3H). MS: 690.4 (M+H⁺); 712.3 (M+Na⁺).

Example 15

Synthesis of (R)-(Z)-1⁵-chloro-9⁶-fluoro-1³,2¹,2⁵,6¹-tetramethyl-1¹H,2¹H,6¹E-10-oxa-4,8-dithia-1(4,1)-indola-2(4,3),6(3,5)-dipyrazola-9(3,1)-naphthalenacyclotridecaphane-1²-carboxylic acid (Cpd. No. 15)

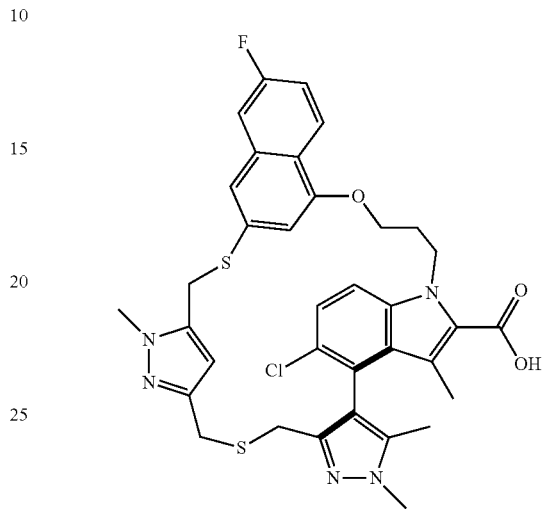

Cpd. No. 14 (390 mg) was subjected to chiral SFC resolution with a CHIRALPAK IE column to provide Cpd. No. 15 (129 mg, >99% aee) as a white solid. MS: 690.2 (M+H⁺); 712.2 (M+Na⁺).

Example 16

Synthesis of (S)-(Z)-1⁵-chloro-9⁶-fluoro-1³,2¹,2⁵,6¹-tetramethyl-1¹11,2¹H,6¹H-10-oxa-4,8-dithia-1(4,1)-indola-2(4,3),6(3,5)-dipyrazola-9(3,1)-naphthalenacyclotridecaphane-1²-carboxylic acid (Cpd. No. 16)

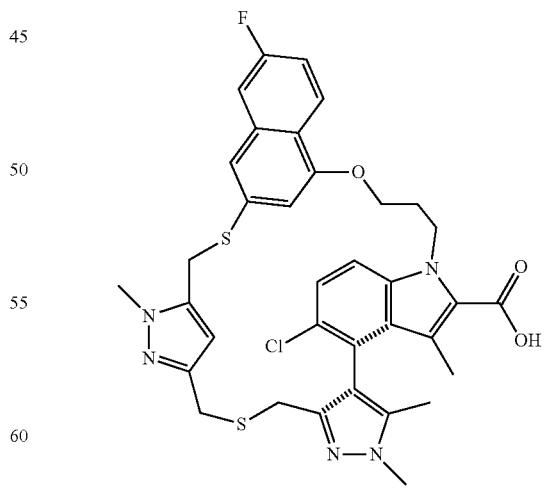

Cpd. No. 14 (390 mg) was subjected to chiral SFC resolution with a CHIRALPAK IE column to provide Cpd. No. 16 (124 mg, 98% ee) as a white solid. MS: 690.2 (M+H⁺); 712.1 (M+Na⁺).

Example 17

Synthesis of (Z)-1⁵-chloro-9⁶-fluoro-6¹-isopropyl-1³,2¹,2⁵-trimethyl-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid (Cpd. No. 17)

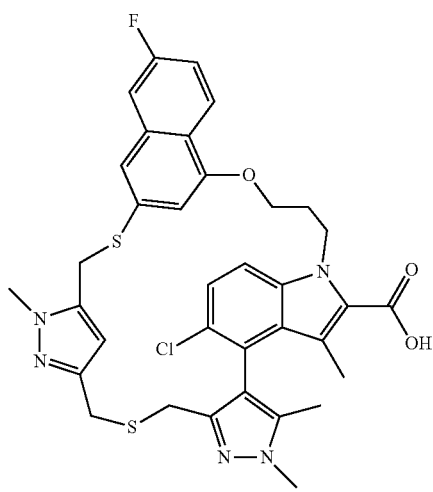 [SMILES: Cc1c(C(=O)O)n2c3ccc(Cl)c(c13)-c1c(nn(C)c1C)CSCc1cc(n(C)n1)CSc1cc(c3ccc(F)cc3c1)OCCC2]

Essentially the same protocol used to prepare Cpd. No. 1 of EXAMPLE 1 was used to afford Cpd. No. 17 (13 mg) as a white solid. $^1$H NMR (500 MHz, DMSO-$d_6$) δ 8.19 (dd, J=8.9, 5.9 Hz, 1H), 7.76 (d, J=9.0 Hz, 1H), 7.54 (d, J=8.4 Hz, 1H), 7.43-7.33 (m, 2H), 7.28 (d, J=8.9 Hz, 1H), 6.70 (s, 1H), 5.10-5.03 (m, 1H), 4.86 (s, 1H), 4.66-4.57 (m, 2H), 4.33 (d, J=15.5 Hz, 1H), 4.25 (d, J=15.6 Hz, 1H), 4.01 (d, J=7.9 Hz, 1H), 3.89 (d, J=5.5 Hz, 1H), 3.77 (s, 3H), 3.32 (d, J=13.0 Hz, 1H), 3.18 (dd, J=16.6, 13.8 Hz, 2H), 3.03 (d, J=14.0 Hz, 1H), 2.47-2.34 (m, 2H), 2.01 (s, 3H), 1.93 (s, 3H), 1.35 (d, J=6.4 Hz, 3H), 1.32 (d, J=6.4 Hz, 3H). MS: 718.7 (M+H⁺).

Example 18

Synthesis of (Z)-1⁵-chloro-2⁵-(difluoromethyl)-9⁶-fluoro-1³,2¹,6¹-trimethyl-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid (Cpd. No. 18)

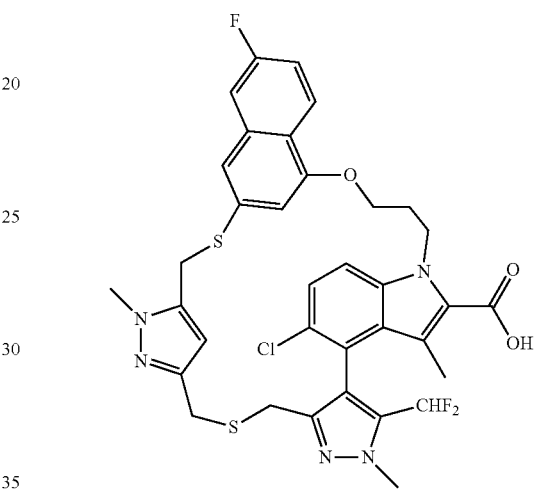

Essentially the same protocol used to prepare Cpd. No. 1 of EXAMPLE 1 was used to afford Cpd. No. 18 (32.7 mg) as a white solid. $^1$H NMR (500 MHz, DMSO-$d_6$) δ 8.22 (dd, J=9.1, 5.9 Hz, 1H), 7.78 (d, J=9.1 Hz, 1H), 7.55 (dd, J=10.2, 2.2 Hz, 1H), 7.41-7.34 (m, 2H), 7.29 (d, J=9.0 Hz, 1H), 6.88 (t, J=52.2 Hz, 1H), 6.62 (s, 1H), 5.06 (dd, J=13.8, 4.3 Hz, 1H), 4.91 (s, 1H), 4.68-4.60 (m, 1H), 4.26 (dd, J=35.0, 15.5 Hz, 2H), 4.01-3.93 (m, 4H), 3.89 (dd, J=14.6, 7.5 Hz, 1H), 3.70 (s, 3H), 3.15 (dd, J=13.6, 10.1 Hz, 2H), 3.02-2.90 (m, 2H), 2.39 (d, J=5.0 Hz, 2H), 2.01 (s, 3H). MS: 726.4 (M+H⁺).

Example 19

Synthesis of (Z)-1$^5$-chloro-1$^3$,9$^6$-difluoro-2$^1$,2$^5$,6$^1$-trimethyl-1$^1$H,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid (Cpd. No. 19)

Example 20

Synthesis of (Z)-1$^5$-cyano-9$^6$-fluoro-1$^3$,2$^1$,2$^5$,6$^1$-tetramethyl-1$^1$H-1,2$^1$H,6$^1$H-10-oxa-4,8-dithia-1(4,1)-indola-2(4,3),6(3,5)-dipyrazola-9(3,1)-naphthalenacyclotridecaphane-1$^2$-carboxylic acid (Cpd No. 20)

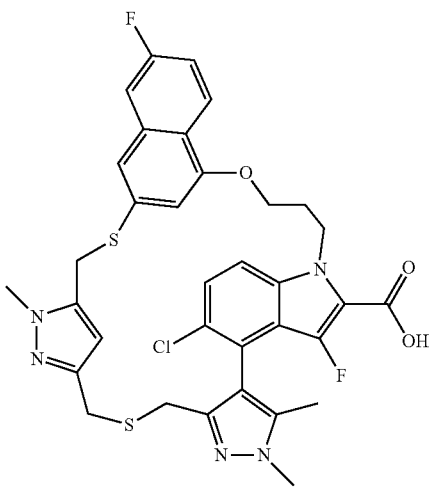 [SMILES: Cc1c2c(nn1C)CSCc1cc(n(C)n1)CSc1cc(c3ccc(F)cc3c1)OCCCn1c(C(=O)O)c(F)c3c-2c(Cl)ccc31]

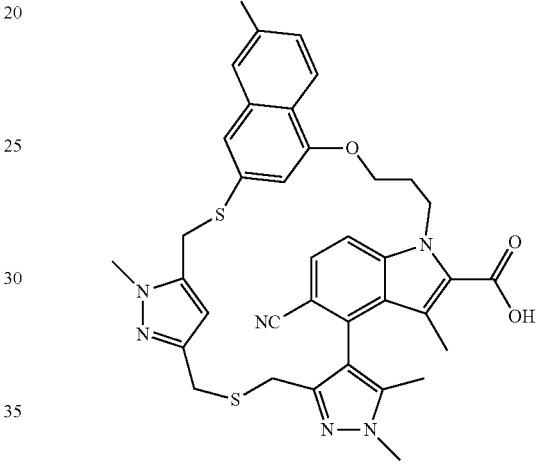

Essentially the same protocol used to prepare Cpd. No. 1 of EXAMPLE 1 was used to afford Cpd. No. 19 (23.6 mg) as a white solid. $^1$H NMR (500 MHz, DMSO-d$_6$) δ 8.24 (dd, J=9.3, 5.7 Hz, 1H), 7.81 (d, J=9.0 Hz, 1H), 7.55 (dd, J=10.3, 2.7 Hz, 1H), 7.38 (d, J=6.5 Hz, 2H), 7.35 (d, J=9.0 Hz, 1H), 6.70 (s, 1H), 5.12-5.06 (m, 1H), 5.02 (s, 1H), 4.70-4.62 (m, 1H), 4.31 (d, J=2.9 Hz, 2H), 4.01 (q, J=8.0 Hz, 1H), 3.88 (dd, J=9.1, 5.5 Hz, 1H), 3.77 (s, 3H), 3.71 (s, 3H), 3.36 (d, J=13.0 Hz, 2H), 3.15 (d, J=13.9 Hz, 1H), 2.97 (d, J=13.9 Hz, 1H), 2.47-2.36 (m, 2H), 2.00 (s, 3H). MS: 694.8 (M+H$^+$).

Essentially the same protocol used to prepare Cpd. No. 1 of EXAMPLE 1 was used to afford Cpd. No. 20 (4 mg) as a white solid. $^1$H NMR (500 MHz, DMSO-d$_6$) δ 8.20-8.13 (m, 1H), 7.87 (d, J=8.8 Hz, 1H), 7.51 (s, 1H), 7.51 (d, J=16.9 Hz, 1H), 7.34 (s, 2H), 6.62 (s, 1H), 5.06 (dd, J=15.3, 5.1 Hz, 1H), 4.82 (s, 1H), 4.66 (dd, J=13.6, 5.9 Hz, 1H), 4.25 (d, J=15.7 Hz, 1H), 4.00 (q, J=8.1 Hz, 1H), 3.82 (d, J=7.6 Hz, 2H), 3.76 (s, 3H), 3.67 (s, 3H), 3.23 (d, J=13.2 Hz, 1H), 3.11 (d, J=13.2 Hz, 1H), 3.02 (d, J=13.8 Hz, 1H), 2.86 (d, J=13.8 Hz, 1H), 2.39 (brs, 2H), 2.04 (s, 3H), 1.96 (s, 3H). MS: 681.8 (M+H$^+$).

Example 21

Synthesis of (Z)-1⁵,9⁶-difluoro-1³,2¹,2⁵,6¹-tetramethyl-1¹H,2¹H,6¹H-10-oxa-4,8-dithia-1(4,1)-indola-2(4,3), 6(3,5)-dipyrazola-9(3,1)-naphthalenacyclotridecaphane-1²-carboxylic acid (Cpd. No. 21)

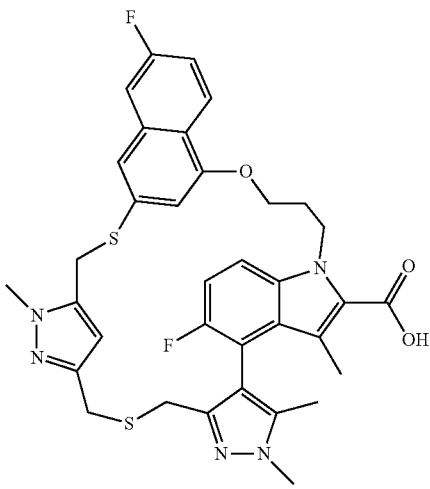 [SMILES: Cc1c(C(=O)O)n2c3ccc(F)c(c13)-c1c(nn(C)c1C)CSCc1cc(n(C)n1)CSc1cc(c3ccc(F)cc3c1)OCCC2]

Essentially the same protocol used to prepare Cpd. No. 1 of EXAMPLE 1 was used to afford Cpd. No. 21 (8 mg) as a white solid. ¹H NMR (500 MHz, DMSO-d₆) δ 8.18 (dd, J=9.3, 5.8 Hz, 1H), 7.74-7.62 (m, 1H), 7.51 (d, J=9.9 Hz, 1H), 7.35-7.32 (m, 2H), 7.03 (t, J=9.2 Hz, 1H), 6.65 (s, 1H), 5.05 (d, J=14.6 Hz, 1H), 4.87 (s, 1H), 4.58 (dd, J=13.9, 9.2 Hz, 1H), 4.28 (d, J=15.8 Hz, 1H), 4.22 (d, J=15.6 Hz, 1H), 3.99 (d, J=8.4 Hz, 1H), 3.83 (q, J=7.8 Hz, 1H), 3.74 (s, 3H), 3.69 (s, 3H), 3.24 (d, J=13.4 Hz, 1H), 3.19 (d, J=13.4 Hz, 1H), 3.10 (d, J=14.2 Hz, 1H), 2.95 (d, J=14.2 Hz, 1H), 2.38 (brs, 2H), 2.05 (s, 3H), 1.95 (s, 3H). MS: 674.8 (M+H⁺).

Example 22

Synthesis of (Z)-9⁶-fluoro-1³, 1⁵,2¹,2⁵,6¹-pentamethyl-1¹H,2¹H,6¹H-10-oxa-4,8-dithia-1(4,1)-indola-2(4,3), 6(3,5)-dipyrazola-9(3,1)-naphthalenacyclotridecaphane-1²-carboxylic acid (Cpd. No. 22)

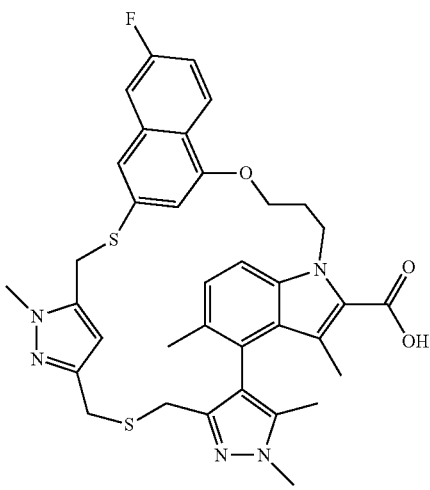 [SMILES: Cc1ccc2c3c(C)c(C(=O)O)n2CCCOc2cc(cc4cc(F)ccc24)SCc2cc(nn2C)CSCc2nn(C)c(C)c2-c13]

Essentially the same protocol used to prepare Cpd. No. 1 of EXAMPLE 1 was used to afford Cpd. No. 22 (7.6 mg) as a white solid. ¹H NMR (500 MHz, DMSO-d₆) δ 8.31-8.13 (m, 1H), 7.53 (d, J=10.2 Hz, 1H), 7.47 (d, J=8.6 Hz, 1H), 7.41-7.32 (m, 2H), 7.04 (d, J=8.5 Hz, 1H), 6.53 (s, 1H), 5.04-4.97 (m, 1H), 4.87 (s, 1H), 4.55 (t, J=11.6 Hz, 1H), 4.28 (d, J=15.7 Hz, 1H), 4.13 (d, J=15.5 Hz, 1H), 3.83 (d, J=7.7 Hz, 2H), 3.74 (s, 3H), 3.68 (s, 3H), 3.27 (d, J=13.4 Hz, 1H), 3.09 (d, J=13.4 Hz, 1H), 3.00 (d, J=13.8 Hz, 1H), 2.86 (d, J=13.8 Hz, 1H), 2.35 (brs, 2H), 1.98 (s, 3H), 1.92 (s, 3H), 1.87 (s, 3H). MS: 670.8 (M+H⁺).

Example 23

Synthesis of (Z)-1⁵-chloro-9⁶-fluoro-2¹,2⁵,6¹-trimethyl-1³-(((1,1,1-trifluoro-N-methylmethyl)sulfonamido)methyl)-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid (Cpd. No. 23)

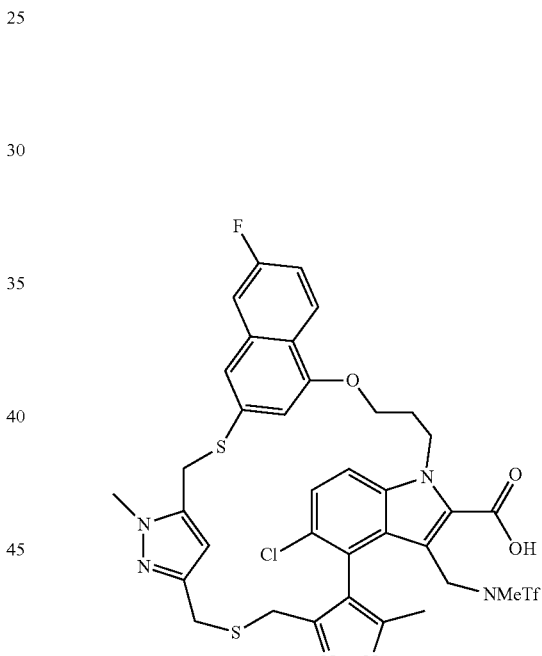

Essentially the same protocol used to prepare Cpd. No. 1 of EXAMPLE 1 was used to afford Cpd. No. 23 (10 mg) as a white solid. ¹H NMR (500 MHz, DMSO-d₆) δ 8.24 (dd, J=9.3, 5.7 Hz, 1H), 7.84 (d, J=9.0 Hz, 1H), 7.57 (d, J=10.6 Hz, 1H), 7.45-7.30 (m, 3H), 6.61 (s, 1H), 5.11 (dd, J=13.7, 6.8 Hz, 1H), 5.01 (s, 1H), 4.89 (d, J=12.2 Hz, 1H), 4.75 (dd, J=13.4, 6.0 Hz, 1H), 4.38 (s, 1H), 4.30 (d, J=15.5 Hz, 1H), 4.20 (d, J=15.5 Hz, 1H), 4.00 (t, J=7.8 Hz, 1H), 3.93 (t, J=8.1 Hz, 1H), 3.72 (s, 3H), 3.70 (s, 3H), 3.23 (d, J=13.4 Hz, 1H), 3.08 (d, J=13.6 Hz, 1H), 3.00 (q, J=13.6 Hz, 2H), 2.48 (s, 3H), 2.47-2.42 (m, 2H) 1.98 (s, 3H). MS: 851.5 (M+H⁺).

Example 24

Synthesis of (Z)-1⁵-chloro-9⁶-fluoro-2¹,2⁵,6¹-trimethyl-1³-(trifluoromethyl)-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid (Cpd. No. 24)

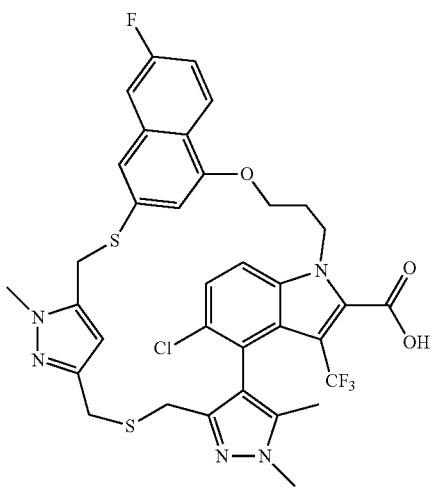

Essentially the same protocol used to prepare Cpd. No. 1 of EXAMPLE 1 was used to afford Cpd. No. 24 (3.1 mg) as a white solid. ¹H NMR (500 MHz, DMSO-d₆) δ 8.24 (dd, J=9.3, 5.7 Hz, 1H), 7.81 (d, J=9.0 Hz, 1H), 7.55 (dd, J=10.3, 2.7 Hz, 1H), 7.38 (d, J=6.5 Hz, 2H), 7.35 (d, J=9.0 Hz, 1H), 6.70 (s, 1H), 5.12-5.06 (m, 1H), 5.02 (s, 1H), 4.66 (dd, J=13.7, 8.9 Hz, 1H), 4.31 (d, J=2.9 Hz, 2H), 4.01 (q, J=8.0 Hz, 1H), 3.88 (dd, J=9.1, 5.5 Hz, 1H), 3.77 (s, 3H), 3.71 (s, 3H), 3.36 (d, J=13.0 Hz, 2H), 3.15 (d, J=13.9 Hz, 1H), 2.97 (d, J=13.9 Hz, 1H), 2.48-2.32 (m, 2H), 2.00 (s, 3H). MS: 744.7 (M+H⁺).

Example 25

Synthesis of (Z)-1⁵-chloro-1³-cyano-9⁶-fluoro-2¹,2⁵,6¹-trimethyl-1¹H,2¹H,6¹H-10-oxa-4,8-dithia-1(4,1)-indola-2(4,3),6(3,5)-dipyrazola-9(3,1)-naphthalenacyclotridecaphane-1²-carboxylic acid (Cpd. No. 25)

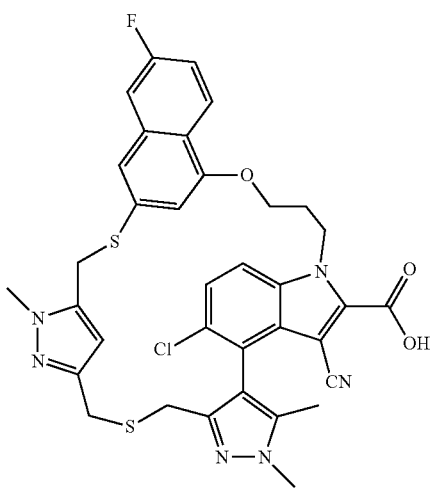 [SMILES: Cc1c2c(nn1C)CSCc1cc(n(C)n1)CSc1cc(c3ccc(F)cc3c1)OCCCn1c(C(=O)O)c(C#N)c3c-2c(Cl)ccc31]

Essentially the same protocol used to prepare Cpd. No. 1 of EXAMPLE 1 was used to afford Cpd. No. 25 (2.5 mg) as a white solid. ¹H NMR (500 MHz, DMSO-d₆) δ 8.17 (dd, J=9.3, 5.7 Hz, 1H), 7.98 (d, J=8.7 Hz, 1H), 7.51 (t, J=10.2 Hz, 2H), 7.35 (d, J=9.9 Hz, 2H), 6.74 (s, 1H), 5.28-5.19 (m, 1H), 5.07 (s, 1H), 4.78-4.72 (m, 1H), 4.33-4.27 (m, 1H), 4.03-3.95 (m, 1H), 3.74 (s, 3H), 3.72 (s, 3H), 3.25-3.05 (m, 4H), 2.61-2.44 (m, 2H), 2.07-2.00 (m, 2H), 1.98 (s, 3H). MS: 701.7 (M+H⁺).

Example 26

Synthesis of (Z)-1⁵-chloro-1³,2³,6¹-trimethyl-2¹-(2-(methylamino)-2-oxoethyl)-1¹H,2¹H,6¹H-10-oxa-4,8-dithia-1(4,1)-indola-2(4,5),6(3,5)-dipyrazola-9(3,1)-naphthalenacyclotridecaphane-1²-carboxylic acid (Cpd. No. 26)

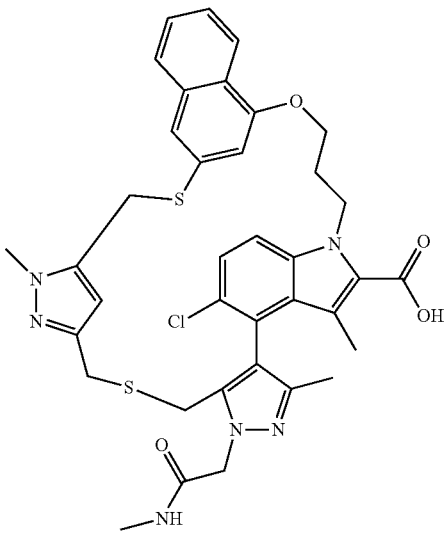 [SMILES: CNC(=O)Cn1nc(C)c2c1CSCc1cc(n(C)n1)CSc1cc(c3ccccc3c1)OCCCn1c(C(=O)O)c(C)c3c-2c(Cl)ccc31]

Essentially the same protocol used to prepare Cpd. No. 1 of EXAMPLE 1 was used to afford Cpd. No. 26 (7.7 mg) as a white solid. ¹H NMR (500 MHz, DMSO-d₆) δ 8.22-8.16 (m, 1H), 8.02-7.99 (m, 1H), 7.76-7.70 (m, 1H), 7.60 (d, J=9.0 Hz, 1H), 7.55-7.47 (m, 2H), 7.31 (s, 1H), 7.03 (d, J=8.9 Hz, 1H), 6.68 (s, 1H), 5.12-5.09 (m, 1H), 4.84-4.69 (m, 2H), 4.72 (d, J=16.0 Hz, 1H), 4.30 (d, J=15.5 Hz, 1H), 4.08 (d, J=15.4 Hz, 1H), 4.02-3.85 (m, 2H), 3.69 (s, 3H), 3.22-3.10 (m, 3H), 3.04 (d, J=14.3 Hz, 1H), 2.66 (d, J=4.7 Hz, 3H), 2.59-2.53 (m, 1H), 2.44-2.40 (m, 2H), 1.97 (s, 3H), 1.83 (s, 3H). MS: 729.2 (M+H⁺).

Example 27

Synthesis of (Z)-1⁵-chloro-2¹-(2-methoxyethyl)-1³,2³,6¹-trimethyl-1¹H,2¹H,6¹H-10-oxa-4,8-dithia-1(4,1)-indola-2(4,5),6(3,5)-dipyrazola-9(3,1)-naphthalenacyclotridecaphane-1²-carboxylic acid (Cpd. No. 27)

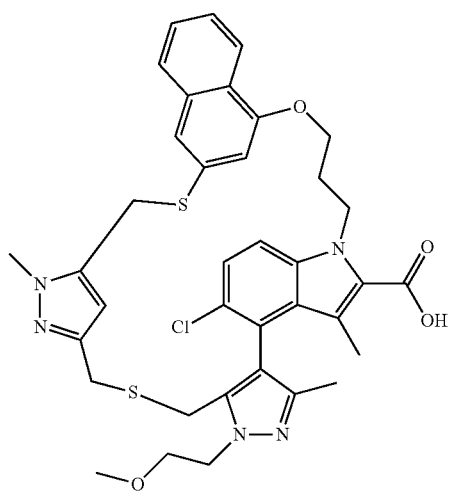 [SMILES: COCCn1nc(C)c2c1CSCc1cc(n(C)n1)CSc1cc(c3ccccc3c1)OCCCn1c(C(=O)O)c(C)c3c-2c(Cl)ccc31]

Essentially the same protocol used to prepare Cpd. No. 1 of EXAMPLE 1 was used to afford Cpd. No. 27 (5.0 mg) as a white solid. $^1$H NMR (500 MHz, DMSO-d$_6$) δ 8.16 (d, J=8.0 Hz, 1H), 7.76 (d, J=7.6 Hz, 1H), 7.73 (d, J=9.0 Hz, 1H), 7.57-7.46 (m, 2H), 7.41 (s, 1H), 7.29-7.19 (m, 1H), 6.66 (s, 1H), 5.10-5.03 (m, 1H), 4.89 (s, 1H), 4.70-4.60 (m, 1H), 4.34-4.15 (m, 3H), 4.01-3.92 (m, 1H), 3.90-3.85 (m, 1H), 3.72 (s, 3H), 3.68-3.63 (m, 3H), 3.42-3.36 (m, 3H), 3.23 (s, 3H), 3.21-3.10 (m, 2H), 2.94 (d, J=14.1 Hz, 1H), 2.01 (s, 3H), 1.93 (s, 3H). MS: 716.2 (M+H⁺).

Example 28

Synthesis of (Z)-1⁵-chloro-9⁶-fluoro-1³,2¹,2³,6¹-tetramethyl-1¹H,2¹H,6¹11-10-oxa-4,8-dithia-1(4,1)-indola-2(4,5),6(3,5)-dipyrazola-9(3,1)-naphthalenacyclotridecaphane-1²-carboxylic acid (Cpd. No. 28)

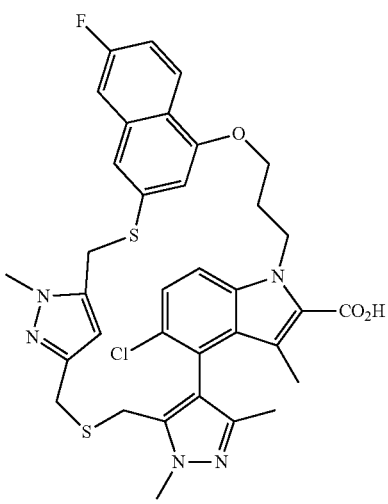 [SMILES: Cc1nn(C)c2c1-c1c(Cl)ccc3c1c(C)c(C(=O)O)n3CCCOc1cc(cc3cc(F)ccc13)SCc1cc(nn1C)CSC2]

Essentially the same protocol used to prepare Cpd. No. 1 of EXAMPLE 1 was used to afford Cpd. No. 28 (10 mg) as a white solid. $^1$H NMR (500 MHz, DMSO-d$_6$) δ 8.26 (s, 1H), 7.58 (d, J=8.9 Hz, 1H), 7.54 (d, J=10.1 Hz, 1H), 7.36 (s, 2H), 7.09 (d, J=8.7 Hz, 1H), 6.54 (s, 1H), 5.02 (d, J=15.1 Hz, 1H), 4.78 (s, 1H), 4.67-4.58 (m, 1H), 4.26 (d, J=15.6 Hz, 1H), 4.11 (d, J=15.6 Hz, 1H), 3.87-3.78 (m, 2H), 3.75 (s, 3H), 3.64 (s, 3H), 3.31-3.22 (m, 2H), 3.13 (d, J=14.1 Hz, 1H), 2.97 (d, J=14.2 Hz, 1H), 2.42-2.29 (m, 2H), 1.96 (s, 3H), 1.80 (s, 3H). MS: 690.5 (M+H⁺).

Example 29

Synthesis of (Z)-1⁵-chloro-9⁶-fluoro-1³, 6¹-dimethyl-4-(phenylsulfonyl)-26,27-dihydro-1¹H,2⁴H,6¹H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1²-carboxylic acid (Cpd. No. 29)

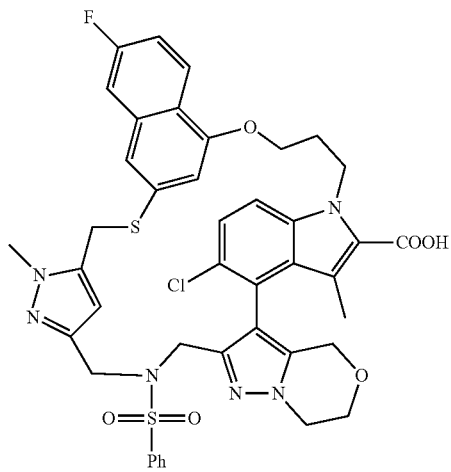 [SMILES: Cc1c(C(=O)O)n2c3ccc(Cl)c(c13)-c1c(nn3c1COCC3)CN(S(=O)(=O)c1ccccc1)Cc1cc(n(C)n1)CSc1cc(c3ccc(F)cc3c1)OCCC2]

Step A: Methyl 5-chloro-1-(3-((6-fluoro-3-mercaptonaphthalen-1-yl)oxy)propyl)-3-methyl-4-(2-((2,2,2-trifluoroacetoxy)methyl)-6,7-dihydro-4H-pyrazolo[5,1-c][1,4]oxazin-3-yl)-1H-indole-2-carboxylate (Intermediate No. 5)

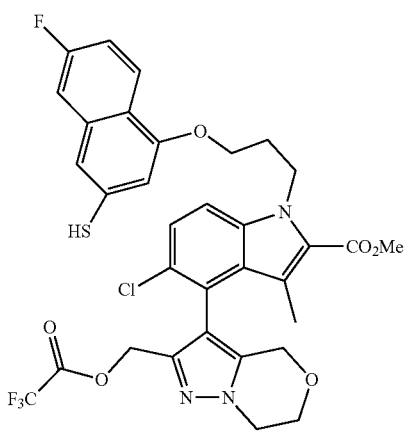 [SMILES: COC(=O)c1c(C)c2c(-c3c(COC(=O)C(F)(F)F)nn4c3COCC4)c(Cl)ccc2n1CCCOc1cc(S)cc2cc(F)ccc12]

In an argon flushed 100 mL round-bottomed flask, methyl 5-chloro-1-(3-((6-fluoro-3-((4-methoxybenzyl)thio)naphthalen-1-yl)oxy)propyl)-3-methyl-4-(2-(((tetrahydro-2H-pyran-2-yl)oxy)methyl)-6,7-dihydro-4H-pyrazolo[5,1-c][1,4]oxazin-3-yl)-1H-indole-2-carboxylate (prepared by the same procedure of Step C of Intermediate D1, 0.51 g, 0.626 mmol) and triethylsilane (0.728 g, 6.26 mmol) were dissolved into CH$_2$Cl$_2$ (1.7 mL) and TFA (5.0 mL) under argon to give a yellow solution. The reaction mixture was stirred at 36° C. for 18 h and then at 50° C. for 3 h. After cooling down to room temperature and removal of volatiles under reduced pressure, the crude title compound was used directly in the next step without purification. MS: 706.6 (M+H$^+$).

Step B: Methyl 1-(3-((3-(((3-(((4-bromobenzoyl)oxy)methyl)-1-methyl-1H-pyrazol-5-yl)methyl)thio)-6-fluoronaphthalen-1-yl)oxy)propyl)-5-chloro-4-(2-(hydroxymethyl)-6,7-dihydro-4H-pyrazolo[5,1-c][1,4]oxazin-3-yl)-3-methyl-1H-indole-2-carboxylate (Intermediate No. 6)

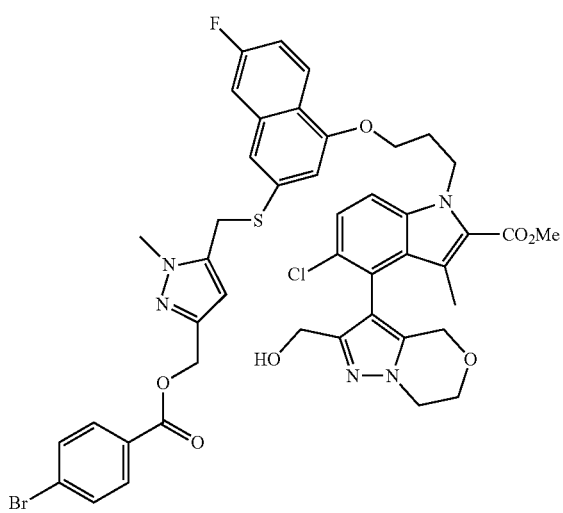 [SMILES: COC(=O)c1c(C)c2c(-c3c(CO)nn4c3COCC4)c(Cl)ccc2n1CCCOc1cc(SCc2cc(COC(=O)c3ccc(Br)cc3)nn2C)cc2cc(F)ccc12]

In an argon flushed 100 mL round-bottomed flask, the crude methyl 5-chloro-1-(3-((6-fluoro-3-mercaptonaphthalen-1-yl)oxy)propyl)-3-methyl-4-(2-((2,2,2-trifluoroacetoxy)methyl)-6,7-dihydro-4H-pyrazolo[5,1-c][1,4]oxazin-3-yl)-1H-indole-2-carboxylate (Step A, 0.442 g), (5-(bromomethyl)-1-methyl-1H-pyrazol-3-yl)methyl 4-bromobenzoate (0.24 g, 0.63 mmol), and K$_2$CO$_3$ (0.433 g, 3.13 mmol) were dissolved in dry acetonitrile (15 mL) under argon to give a yellow suspension. The reaction was stirred at room temperature for 18 h. After removal of volatiles under reduced pressure, the residue was loaded to silica gel column and eluted with MeOH:DCM (1:20) to afford the title compound (400 mg, 70% over 2 steps) as a yellow solid. MS: 918.6 (M+H$^+$).

Step C: Methyl 5-chloro-1-(3-((6-fluoro-3-(((3-(hydroxymethyl)-1-methyl-1H-pyrazol-5-yl)methyl)thio)naphthalen-1-yl)oxy)propyl)-4-(2-(hydroxymethyl)-6,7-dihydro-4H-pyrazolo[5,1-c][1,4]oxazin-3-yl)-3-methyl-1H-indole-2-carboxylate (Intermediate No. 7)

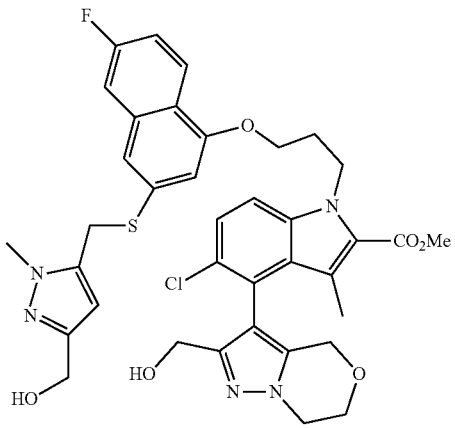 [SMILES: COC(=O)c1c(C)c2c(-c3c(CO)nn4c3COCC4)c(Cl)ccc2n1CCCOc1cc(SCc2cc(CO)nn2C)cc2cc(F)ccc12]

In an argon flushed 100 mL round-bottomed flask, methyl 1-(3-((3-(((3-(((4-bromobenzoyl)oxy)methyl)-1-methyl-1H-pyrazol-5-yl)methyl)thio)-6-fluoronaphth-alen-1-yl)oxy)propyl)-5-chloro-4-(2-(hydroxymethyl)-6,7-dihydro-4H-pyrazolo[5,1-c][1,4]oxazin-3-yl)-3-methyl-1H-indole-2-carboxylate (Step B, 400 mg, 0.44 mmol) and K$_2$CO$_3$ (301 mg, 2.18 mmol) were dissolved in dry MeOH (10 mL) under argon to give a yellow solution. The reaction was stirred at 25° C. for 3 h. H$_2$O (20 mL) was added to the reaction mixture followed by extraction with dichloromethane 3 times. The combined organic layer was dried over Na$_2$SO$_4$, and concentrated under reduced pressure to give the crude product, which was loaded to silica gel column and eluted with MeOH:DCM (1:20) to afford the title compound (250 mg, 78%) as a white solid. MS: 734.5 (M+H$^+$).

Step D: Methyl 5-chloro-1-(3-((6-fluoro-3-(((3-formyl-1-methyl-1H-pyrazol-5-yl)methyl)thio)naphthalen-1-yl)oxy)propyl)-4-(2-formyl-6,7-dihydro-4H-pyrazolo[5,1-c][1,4]oxazin-3-yl)-3-methyl-1H-indole-2-carboxylate (Intermediate No. 8)

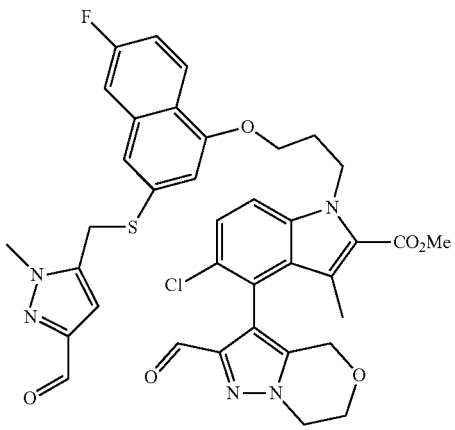 [SMILES: COC(=O)c1c(C)c2c(-c3c(C=O)nn4c3COCC4)c(Cl)ccc2n1CCCOc1cc(SCc2cc(C=O)nn2C)cc2cc(F)ccc12]

In an argon flushed 100 mL round-bottomed flask, methyl 5-chloro-1-(3-((6-fluoro-3-(((3-(hydroxymethyl)-1-methyl-1H-pyrazol-5-yl)methyl)thio)naphthalen-1-yl)oxy)propyl)-4-(2-(hydroxymethyl)-6,7-dihydro-4H-pyrazolo[5,1-c][1,4]oxazin-3-yl)-3-methyl-1H-indole-2-carboxylate (Step C, 230 mg, 0.313 mmol) and DMP (332 mg, 0.783 mmol) were dissolved in dry $CH_2Cl_2$ (10 mL) under argon at 0° C. to give a white suspension. The reaction mixture was stirred at 0° C. for 0.5 h and then at room temperature for 1 h. Sat. $NaHCO_3$ (10 mL) was added to the reaction mixture followed by extraction with DCM 3 times. The combined organic layer was dried over $Na_2SO_4$, and concentrated under reduced pressure to give the crude product, which was added to a silica gel column and was eluted with MeOH:DCM (1:30) to afford the title compound (208 mg, 91%) as a white solid. MS: 730.4 $(M+H^+)$.

Step E: Methyl 4-(2-(((tert-butoxycarbonyl)amino)methyl)-6,7-dihydro-4H-pyrazolo[5,1-c][1,4]oxazin-3-yl)-5-chloro-1-(3-((6-fluoro-3-(((3-formyl-1-methyl-1H-pyrazol-5-yl)methyl)thio)naphthalen-1-yl)oxy)propyl)-3-methyl-1H-indole-2-carboxylate (Intermediate No. 9)

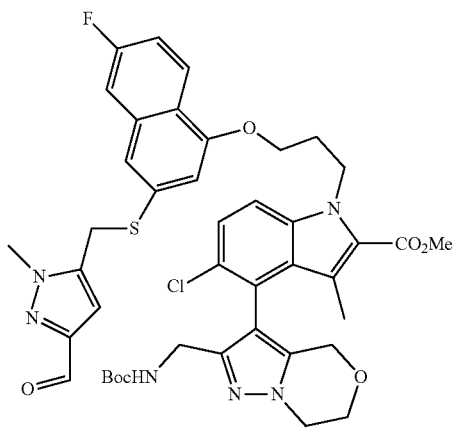 [SMILES: COC(=O)c1c(C)c2c(-c3c(CNC(=O)OC(C)(C)C)nn4c3COCC4)c(Cl)ccc2n1CCCOc1cc(SCc2cc(C=O)nn2C)cc2cc(F)ccc12]

In an argon flushed 25 mL round-bottomed flask, methyl 5-chloro-1-(3-((6-fluoro-3-(((3-formyl-1-methyl-1H-pyrazol-5-yl)methyl)thio)-naphthalen-1-yl)oxy)propyl)-4-(2-formyl-6,7-dihydro-4H-pyrazolo[5,1-c][1,4]oxazin-3-yl)-3-methyl-1H-indole-2-carboxylate (Step D, 300 mg, 0.411 mmol), tert-butyl carbamate (48.1 mg, 0.411 mmol) and TFA (937 mg, 8.22 mmol) were dissolved in dry $CH_2Cl_2$ (20 mL) under argon at 0° C. to give a light yellow solution; the reaction was stirred at room temperature for 0.5 h and triethylsilane (478 mg, 4.11 mmol) was added dropwise at 0° C. The reaction was stirred for 16 h at room temperature. After removal of volatiles under reduced pressure, the crude title compound was used directly in the next step without purification. MS: 831.5 $(M+H^+)$.

Step F: Methyl (Z)-1⁵-chloro-9⁶-fluoro-1³,6¹-dimethyl-2⁶,2⁷-dihydro-1¹H,2⁴H, 6¹H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1²-carboxylate (Cpd. No. 29A)

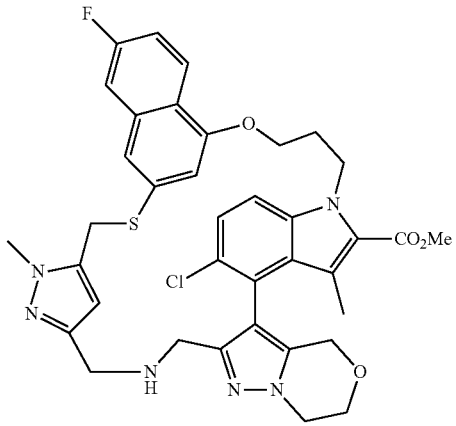 [SMILES: COC(=O)c1c(C)c2c3c(Cl)ccc2n1CCCOc1cc(cc2cc(F)ccc12)SCc1cc(nn1C)CNCc1nn2c(c1-3)COCC2]

In an argon flushed 50 mL round-bottomed flask, the crude methyl (Z)-1⁵-chloro-9⁶-fluoro-1³,6¹-dimethyl-2⁶,2⁷-dihydro-1¹H,2⁴H,6¹H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1²-carboxylate (Step E, 200 g, 0.241 mmol), triethylsilane (0.559 g, 4.81 mmol), and TFA (1.23 g, 10.77 mmol) were dissolved in dry $CH_2Cl_2$ (5 mL) under argon to give a yellow solution. The reaction was stirred at room temperature for 2 h. After removal of volatiles under reduced pressure, the residue was loaded to silica gel column and eluted with MeOH:DCM (1:40→1:10) to afford the title compound (88 mg, 51% over 2 steps) as a yellow solid. MS: 715.3 $(M+H^+)$.

Step G: Methyl (Z)-1⁵-chloro-9⁶-fluoro-1³, 6¹-dimethyl-4-(phenylsulfonyl)-2⁶,2⁷-dihydro-1¹H,2⁴H, 6¹H-10-oxa-8-thia-4-aza-2(3,2)-pyrazolo[5,1-c][1,4]oxazina-1(4,1)-indola-6(3,5)-pyrazola-9(3,1)-naphthalen-acyclotridecaphane-1²-carboxylate (Cpd. No. 29B)

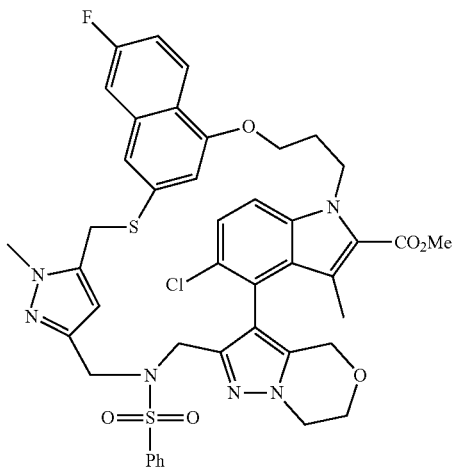 [SMILES: COC(=O)c1c(C)c2c3c(Cl)ccc2n1CCCOc1cc(cc2cc(F)ccc12)SCc1cc(nn1C)CN(S(=O)(=O)c1ccccc1)Cc1nn2c(c1-3)COCC2]

In an argon flushed 25 mL round-bottomed flask, methyl (Z)-1⁵-chloro-9⁶-fluoro-1³,6¹-dimethyl-2⁶,2⁷-dihydro-1¹H,2⁴H,6¹H-10-oxa-8-thia-4-aza-2(3,2)-pyrazolo[5,1-c][1,4]oxazina-1(4,1)-indola-6(3,5)-pyrazola-9(3,1)-naphthalena-cyclotridecaphane-1²-carboxylate (Step F, 20 mg, 0.028 mmol), DMAP (1.025 mg, 8.39 μmol), DIPEA (18.07 mg, 0.140 mmol) and benzenesulfonyl chloride (24.69 mg, 0.140 mmol) were dissolved in dry CH$_2$Cl$_2$ (2 mL) under argon to give a yellow solution. The reaction was stirred at room temperature for 3 h. After removal of volatiles under reduced pressure, the residue was loaded to silica gel column and eluted with MeOH:DCM (1:50→1:25) to afford the title compound (12 mg, 50%) as a yellow solid. MS: 855.7 (M+H⁺).

Step H: (Z)-1⁵-chloro-9⁶-fluoro-1³, 6¹-di methyl-4-(phenylsulfonyl)-2⁶,2⁷-dihydro-1¹H,2⁴H,6¹H-10-oxa-8-thia-4-aza-2(3,2)-pyrazolo[5,1-c][1,4]oxazina-1(4,1)-indola-6(3,5)-pyrazola-9(3,1)-naphthalen-acyclotridecaphane-1²-carboxylic acid (Cpd. No. 29)

In an argon flushed 25 mL round-bottomed flask, methyl (Z)-1⁵-chloro-9⁶-fluoro-1³,6¹-dimethyl-4-(phenylsulfonyl)-2⁶,2⁷-dihydro-1¹H,2⁴H,6¹H-10-oxa-8-thia-4-aza-2(3,2)-pyrazolo[5,1-c][1,4]oxazina-1(4,1)-indola-6(3,5)-pyrazola-9(3,1)-naphthalen-acyclotridecaphane-12-carboxylate (Step G, 12 mg, 0.014 mmol) was dissolved in THF (1 mL), MeOH (1 mL) and H$_2$O (1 mL). NaOH (11.2 mg, 0.280 mmol) was added to the reaction and stirred at room temperature for 3 h. TFA (0.2 mL) was added to the reaction and the resulting mixture was concentrated under reduced pressure. The residue was purified by C18 prep-HPLC column to afford the title compound (4 mg, 34%) as a white solid. ¹H NMR (500 MHz, DMSO-d$_6$) δ 8.24 (d, J=5.6 Hz, 1H), 7.66 (d, J=7.5 Hz, 2H), 7.54 (d, J=9.0 Hz, 1H), 7.48 (t, J=8.4 Hz, 2H), 7.40-7.32 (m, 4H), 6.95 (d, J=8.9 Hz, 1H), 6.44 (s, 1H), 4.95 (d, J=14.2 Hz, 1H), 4.59 (s, 2H), 4.28 (t, J=12.8 Hz, 2H), 4.22-4.15 (m, 2H), 4.10-4.13 (m, 2H), 4.08-3.98 (m, 4H), 3.89 (d, J=15.0 Hz, 1H), 3.70 (s, 2H), 3.60 (s, 3H), 3.44 (d, J=15.4 Hz, 1H), 2.42-2.30 (m, 2H), 1.67 (s, 3H). MS: 841.7 (M+H⁺).

Example 30

Synthesis of (Z)-1⁵-chloro-9⁶-fluoro-1³, 6¹-di methyl-4-(methylsulfonyl)-2⁶,2⁷-dihydro-1¹H,2⁴H, 6¹H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1²-carboxylic acid (Cpd. No. 30)

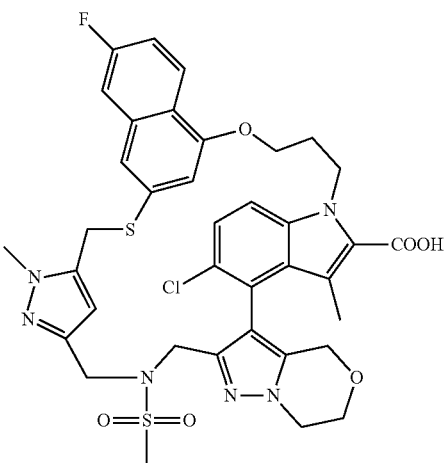 [SMILES: Cc1c(C(=O)O)n2c3ccc(Cl)c(c13)-c1c(nn3c1COCC3)CN(S(C)(=O)=O)Cc1cc(n(C)n1)CSc1cc(c3ccc(F)cc3c1)OCCC2]

Step A: Methyl (Z)-1⁵-chloro-9⁶-fluoro-4-(isopropylsulfonyl)-1³, 6¹-dim ethyl-2⁶,2⁷-dihydro-1¹H,2⁴H, 6¹H-10-oxa-8-thia-4-aza-2(3,2)-pyrazolo[5,1-c][1,4]oxazina-1 (4,1)-indola-6(3,5)-pyrazola-9(3,1)-naphthalenacyclotridecaphane-1²-carboxylate (Cpd. No. 3 OA)

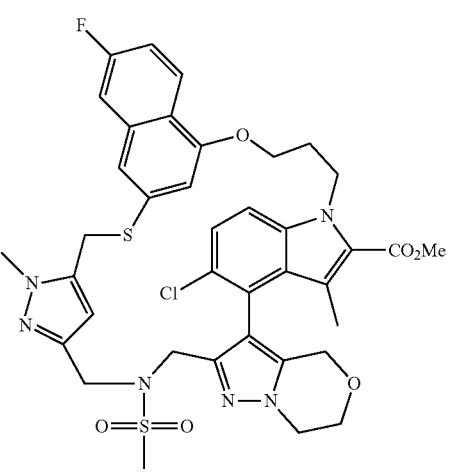 [SMILES: COC(=O)c1c(C)c2c3c(Cl)ccc2n1CCCOc1cc(cc2cc(F)ccc12)SCc1cc(nn1C)CN(S(C)(=O)=O)Cc1nn2c(c1-3)COCC2]

In an argon flushed 25 mL round-bottomed flask, methyl (Z)-1⁵-chloro-9⁶-fluoro-1³,6¹-dimethyl-2⁶,2⁷-dihydro-1¹H, 2⁴H, 6¹H-10-oxa-8-thia-4-aza-2 (3,2)-pyrazolo[5,1-c][1,4]oxazina-1(4,1)-indola-6(3,5)-pyrazola-9(3,1)-naphthalena-cyclotridecaphane-1²-carboxylate (Cpd. No. 29A, 22 mg, 0.031 mmol), MSCl (10.6 mg, 0.092 mmol), DIPEA (19.9 mg, 0.154 mmol) and DMAP (1.13 mg, 9.23 μmol) were dissolved in dry CH$_2$Cl$_2$ (2 mL) under argon to give a yellow solution. The reaction was stirred at 25° C. for 2 h. After removal of volatiles under reduced pressure, the residue was loaded to silica gel column and eluted with MeOH:DCM (1:30) to afford the title compound (15 mg, 59%) as a yellow solid. MS: 793.6 (M+H$^+$).

Step B: (Z)-1$^5$-chloro-9$^6$-fluoro-4-(isopropylsulfo-nyl)-1$^3$, 6$^1$-di methyl-2$^6$,2$^7$-dihydro-1$^1$H,2$^4$H,6$^1$H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1$^2$-carboxylic acid (Cpd. No. 30)

In an argon flushed 25 mL round-bottomed flask, methyl (Z)-1$^5$-chloro-9$^6$-fluoro-4-(isopropylsulfonyl)-1$^3$,6$^1$-dimethyl-2$^6$,2$^7$-dihydro-1$^1$H,2$^4$H,6$^1$H-10-oxa-8-thia-4-aza-2(3, 2)-pyrazolo[5,1-c][1,4]oxazina-1(4,1)-indola-6(3,5)-pyrazola-9(3,1)-naphthalen-acyclotridecaphane-1$^2$-carboxylate (Step A, 11 mg, 0.014 mmol) and sodium hydroxide (11.09 mg, 0.277 mmol) were dissolved in MeOH (3 mL), THF (1 mL) and H$_2$O (1 mL) under argon to give a yellow solution. The reaction was stirred at room temperature for 16 h. The reaction was acidified by TFA and the resulting mixture was concentrated under reduced pressure. The residue was purified by C18 prep-HPLC column to afford the title compound (1.5 mg, 14%) as a white solid. $^1$H NMR (500 MHz, DMSO-d$_6$) δ 8.20 (dd, J=9.1, 6.0 Hz, 1H), 7.58 (d, J=9.2 Hz, 1H), 7.48 (dd, J=10.1, 2.2 Hz, 1H), 7.33 (td, J=9.0, 2.4 Hz, 1H), 7.29 (s, 1H), 7.00 (d, J=9.1 Hz, 1H), 6.49 (s, 1H), 4.99 (d, J=14.6 Hz, 1H), 4.75 (s, 1H), 4.70-4.60 (m, 1H), 4.36 (d, J=3.5 Hz, 2H), 4.27 (d, J=15.5 Hz, 1H), 4.18 (s, 2H), 4.10 (d, J=15.6 Hz, 1H), 4.07-4.03 (m, 2H), 3.89-3.82 (m, 1H), 3.82-3.75 (m, 3H), 3.75-3.70 (m, 1H), 3.67 (s, 3H), 3.61 (d, J=15.6 Hz, 1H), 3.53 (d, J=16.1 Hz, 1H), 2.75 (s, 3H), 2.41-2.31 (m, 2H), 1.95 (s, 3H). MS: 779.5 (M+H$^+$).

Example 31

Synthesis of (Z)-1$^5$-chloro-4-(cyclopropylsulfonyl)-9$^6$-fluoro-1$^3$, 6$^1$-di methyl-2$^6$,2$^7$-dihydro-1$^1$H,2$^4$H, 6$^1$H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1$^2$-carboxylic acid (Cpd. No. 31)

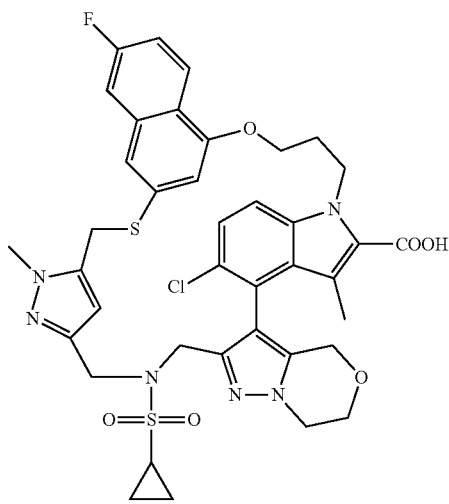 [SMILES: Cc1c(C(=O)O)n2c3ccc(Cl)c(c13)-c1c(nn3c1COCC3)CN(S(=O)(=O)C1CC1)Cc1cc(n(C)n1)CSc1cc(c3ccc(F)cc3c1)OCCC2]

Step A: Methyl (Z)-1$^5$-chloro-4-(cyclopropylsulfo-nyl)-9$^6$-fluoro-1$^3$, 6$^1$-di methyl-2$^6$,2$^7$-dihydro-1$^1$H, 2$^4$H,6$^1$H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1$^2$-carboxylate (Cpd. No. 31A)

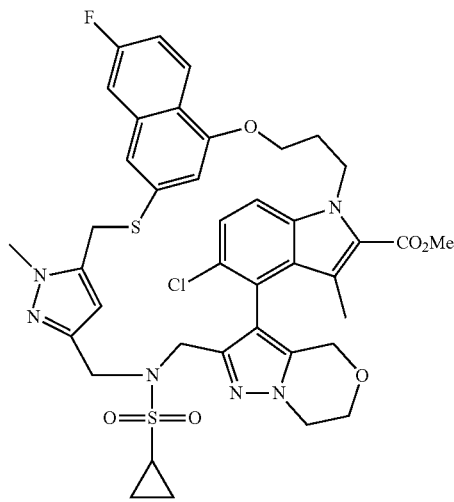 [SMILES: COC(=O)c1c(C)c2c3c(Cl)ccc2n1CCCOc1cc(cc2cc(F)ccc12)SCc1cc(nn1C)CN(S(=O)(=O)C1CC1)Cc1nn2c(c1-3)COCC2]

In an argon flushed 25 mL round-bottomed flask, methyl (Z)-1$^5$-chloro-9$^6$-fluoro-1$^3$,6$^1$-dimethyl-2$^6$,2$^7$-dihydro-1$^1$H, 2$^4$H, 6$^1$H-10-oxa-8-thia-4-aza-2 (3,2)-pyrazolo[5,1-c][1,4]oxazina-1(4,1)-indola-6(3,5)-pyrazola-9(3,1)-naphthalena-cyclotridecaphane-1$^2$-carboxylate (Cpd. No. 29A, 22 mg, 0.031 mmol), DIPEA (19.9 mg, 0.154 mmol), and DMAP (1.13 mg, 9.23 μmol) were dissolved in dry CH$_2$Cl$_2$ (2 mL) under argon to give a yellow solution. Cyclopropanesulfonyl chloride (12.97 mg, 0.092 mmol) was added and the reaction mixture was stirred for 3 h. After removal of volatiles under reduced pressure, the residue was directly used in the next step without purification. MS: 819.5 (M+H$^+$).

Step B: (Z)-1$^5$-chloro-4-(cyclopropylsulfonyl)-9$^6$-fluoro-1$^3$,6$^1$-dimethyl-2$^6$,2$^7$-dihydro-1$^1$H,2$^4$H,6$^1$H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1$^2$-carboxylic acid (Cpd. No. 31)

In a argon flushed 25 mL round-bottomed flask, the crude methyl (Z)-1$^5$-chloro-4-(cyclopropyl sulfonyl)-9$^6$-fluoro-1$^3$, 6$^1$-dimethyl-2$^6$,2$^7$-dihydro-1$^1$H,2$^4$H, 6$^1$H-10-oxa-8-thia-4-aza-2(3,2)-pyrazolo[5,1-c][1,4]oxazina-1(4,1)-indola-6(3, 5)-pyrazola-9(3,1)-naphthalenacyclotridecaphane-1$^2$-carboxylate (Step A, 12 mg) and NaOH (11.72 mg, 0.293 mmol) were dissolved in MeOH (3 mL), THF (1 mL) and H$_2$O (1 mL) under argon to give a yellow solution. The reaction was stirred at room temperature for 16 h. The mixture was acidified by TFA and purified by C18 prep-HPLC column to afford the title compound (1.5 mg, 13%) as a white solid. $^1$H NMR (500 MHz, DMSO-d$_6$) δ 8.27-8.14 (m, 1H), 7.62 (d, J=9.1 Hz, 1H), 7.50 (d, J=8.3 Hz, 1H), 7.34 (d, J=12.3 Hz, 2H), 7.06 (d, J=9.0 Hz, 1H), 6.50 (s, 1H), 5.00 (d, J=14.8 Hz, 1H), 4.78 (s, 1H), 4.63 (t, J=13.4 Hz, 1H), 4.37 (s, 2H), 4.28 (d, J=15.7 Hz, 1H), 4.22-4.15 (m, 3H), 4.10-4.04 (m, 2H), 3.92-3.81 (m, 4H), −3.75-3.69 (m, 1H), 3.66 (s, 3H), 3.58 (d, J=15.5 Hz, 1H), 2.40-2.28 (m, 2H), 2.46-2.41 (m, 1H), 2.00 (s, 3H), 0.77 (d, J=4.1 Hz, 2H), 0.58 (dd, J=24.4, 8.0 Hz, 2H). MS: 805.4 (M+H$^+$).

Example 32

Synthesis of (Z)-1$^5$-chloro-9$^6$-fluoro-1$^3$,2$^1$,2$^5$,6$^1$-tetramethyl-4-(methyl sulfonyl)-1$^1$-H,2$^1$H, 6'H-10-oxa-8-thia-4-aza-1(4,1)-indola-2(4,3),6(3,5)-dipyrazola-9(3,1)-naphthalenacyclotridecaphane-1$^2$-carboxylic acid (Cpd. No. 32)

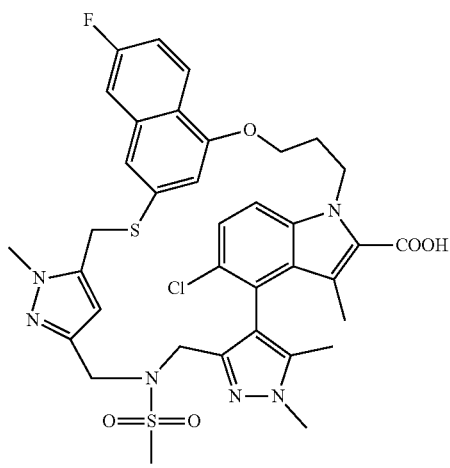 [SMILES: Cc1c(C(=O)O)n2c3ccc(Cl)c(c13)-c1c(nn(C)c1C)CN(S(C)(=O)=O)Cc1cc(n(C)n1)CSc1cc(c3ccc(F)cc3c1)OCCC2]

Step A: Methyl 5-chloro-4-(1,5-dimethyl-3-((2,2,2-trifluoroacetoxy)methyl)-1H-pyrazol-4-yl)-1-(3-((6-fluoro-3-mercaptonaphthalen-1-yl)oxy)propyl)-3-methyl-1H-indole-2-carboxylate (Intermediate No. 14)

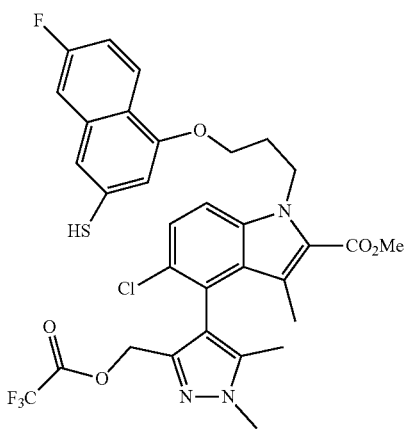 [SMILES: COC(=O)c1c(C)c2c(-c3c(COC(=O)C(F)(F)F)nn(C)c3C)c(Cl)ccc2n1CCCOc1cc(S)cc2cc(F)ccc12]

In an argon flushed 250 mL round-bottomed flask, methyl 5-chloro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-3-methyl-1H-indole-2-carboxylate (Intermediate No. 44, 5.8 g, 8.26 mmol) and anisole (8.93 g, 83 mmol) were dissolved in dry CH$_2$Cl$_2$ (5.0 mL) and TFA (50 mL) under argon to give a yellow solution. The reaction mixture was heated to 50° C. with an oil bath and stirred for 3 h. After cooling down to room temperature and removal of volatiles under reduced pressure, the crude title compound was used directly in the next step without purification. MS: 678.5 (M+H$^+$).

Step B: Methyl 1-(3-((3-(((3-((benzoyloxy)methyl)-1-methyl-1H-pyrazol-5-yl)methyl)thio)-6-fluoronaphthalen-1-yl)oxy)propyl)-5-chloro-4-(3-(hydroxymethyl)-1,5-dimethyl-1H-pyrazol-4-yl)-3-methyl-1H-indole-2-carboxylate (Intermediate No. 15)

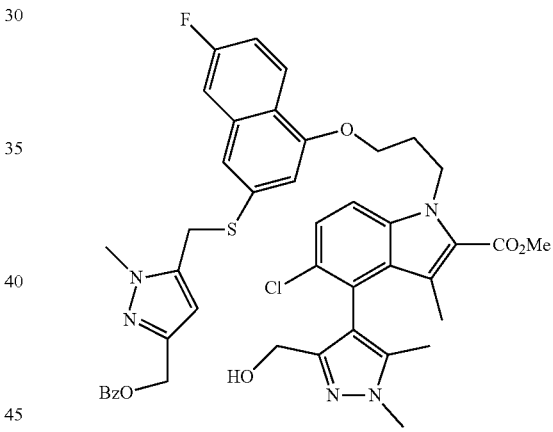

In an argon flushed 250 mL round-bottomed flask, the crude methyl 5-chloro-4-(1,5-dimethyl-34(2,2,2-trifluoroacetoxy)methyl)-1H-pyrazol-4-yl)-1-(3-((6-fluoro-3-mercaptonaphthalen-1-yl)oxy)propyl)-3-methyl-1H-indole-2-carboxylate (Step A, 5.6 g), (5-(bromomethyl)-1-methyl-1H-pyrazol-3-yl)methyl benzoate (2.81 g, 9.08 mmol), and K$_2$CO$_3$ (5.71 g, 41.3 mmol) were dissolved in dry acetonitrile (50 mL) under argon to give a yellow solution. The reaction was stirred at room temperature for overnight. H$_2$O (100 mL) was added to the reaction mixture followed by extraction with ethyl acetate twice. The combined organic layer was dried over Na$_2$SO$_4$, and concentrated under reduced pressure to give the crude product, which was loaded to a silica gel column and eluted with MeOH:DCM (1:25) to afford the title compound (5.5 g, 82% over 2 steps) as a white solid. MS: 811.9 (M+H$^+$).

Step C: Methyl 1-(3-((3-(((3-((benzoyloxy)methyl)-1-methyl-1H-pyrazol-5-yl)methyl)thio)-6-fluoronaphthalen-1-yl)oxy)propyl)-5-chloro-4-(3-formyl-1,5-dimethyl-1H-pyrazol-4-yl)-3-methyl-1H-indole-2-carboxylate (Intermediate No. 16)

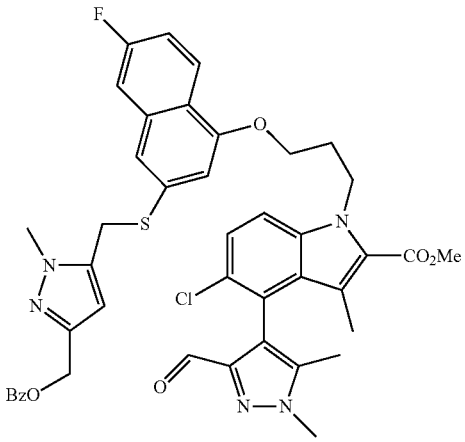

In an argon flushed 50 mL round-bottomed flask, methyl 1-(3-((3-(((3-((benzoyloxy)methyl)-1-methyl-1H-pyrazol-5-yl)methyl)thio)-6-fluoronaphthalen-1-yl)oxy)propyl)-5-chloro-4-(3-(hydroxymethyl)-1,5-dimethyl-1H-pyrazol-4-yl)-3-methyl-1H-indole-2-carboxylate (Step B, 4.0 g, 4.94 mmol) and DMP (2.51 g, 5.92 mmol) were dissolved in dry $CH_2Cl_2$ (50 mL) under argon at 0° C. to give a yellow solution. The reaction was stirred at 0° C. for 1 h. Sat. $NaHCO_3$ (20 mL) was added to the reaction mixture followed by extraction with DCM twice. The combined organic layer was dried over $Na_2SO_4$, and concentrated under reduced pressure to give the crude product, which was loaded to silica gel column and eluted with MeOH:DCM (1:50) to afford the title compound (3.8 g, 95%) as a white solid. MS: 808.8 (M+H$^+$).

Step D: Methyl 1-(3-((3-(((3-((benzoyloxy)-methyl)-1-methyl-1H-pyrazol-5-yl)methyl)thio)-6-fluoronaphtha-len-1-yl)oxy)propyl)-4-(3-(((tert-butoxycarbonyl)-amino)methyl)-1,5-dimethyl-1H-pyrazol-4-yl)-5-chloro-3-methyl-1H-indole-2-carboxylate (Intermediate No. 17)

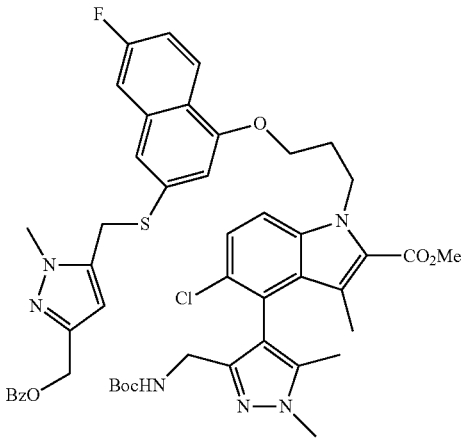

In an argon flushed 250 mL round-bottomed flask, methyl 1-(3-((3-(((3-((benzoyloxy)methyl)-1-methyl-1H-pyrazol-5-yl)methyl)thio)-6-fluoronaphthalen-1-yl)oxy)propyl)-5-chloro-4-(3-formyl-1,5-dimethyl-1H-pyrazol-4-yl)-3-methyl-1H-indole-2-carboxylate (Step C, 3.8 g, 4.70 mmol), tert-butyl carbamate (1.65 g, 14.1 mmol), TFA (2.68 g, 23.51 mmol) and triethylsilane (3.28 g, 28.2 mmol) were dissolved in dry $CH_2Cl_2$ (80 mL) under argon to give a yellow solution at 0° C. The reaction was gradually warmed to room temperature, and stirred at room temperature for 16 h. The resulting mixture was neutralized with sat. $NaHCO_3$ (50 mL) and extracted with dichloromethane three times. The combined organic layer was combined, dried over $Na_2SO_4$, and concentrated under reduced pressure to give the crude product, which was loaded to silica gel column and eluted with EA:DCM, 1:3) to afford the title compound (4.2 g, 98%) as a white solid. MS: 910.6 (M+H$^+$).

Step E: Methyl 4-(3-(((tert-butoxycarbonyl)-amino)methyl)-1,5-dimethyl-1H-pyrazol-4-yl)-5-chloro-1-(3-((6-fluoro-3-(((3-(hydroxy-methyl)-1-methyl-1H-pyrazol-5-yl)methyl)thio)naph-thalen-1-yl)oxy)propyl)-3-methyl-1H-indole-2-carboxylate (Intermediate No. 18)

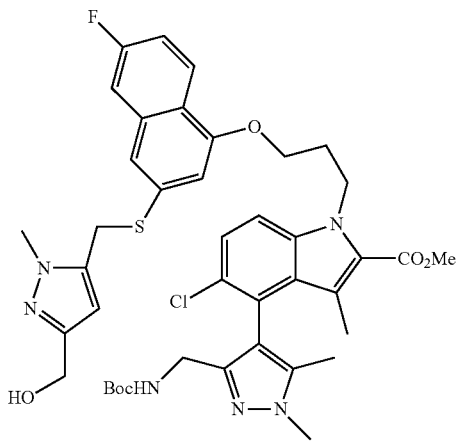 [SMILES: COC(=O)c1c(C)c2c(-c3c(CNC(=O)OC(C)(C)C)nn(C)c3C)c(Cl)ccc2n1CCCOc1cc(SCc2cc(CO)nn2C)cc2cc(F)ccc12]

In an argon flushed 250 mL round-bottomed flask, methyl 1-(3-((3-(((3-((benzoyloxy)-methyl)-1-methyl-1H-pyrazol-5-yl)methyl)thio)-6-fluoronaphtha-len-1-yl)oxy)propyl)-4-(3-(((tert-butoxycarbonyl)amino)methyl)-1,5-dim ethyl-1H-pyrazol-4-yl)-5-chloro-3-methyl-1H-indole-2-carboxylate (Step D, 4.2 g, 4.62 mmol) and $K_2CO_3$ (3.19 g, 23.09 mmol) were dissolved in MeOH (40 mL) under argon to give a yellow solution. The reaction was stirred at room temperature for overnight. Sat. $NaHCO_3$ (100 mL) was added to the reaction mixture followed by extraction with dichloromethane three times.

The combined organic layer was dried $Na_2SO_4$, and concentrated under reduced pressure to give the crude product, which was loaded to silica gel column and eluted with MeOH:DCM (1:50→1:20) to afford the title compound (3.4 g, 91%) as a white solid. MS: 805.7 (M+H$^+$).

Step F: methyl 4-(3-(((tert-butoxycarbonyl)amino)
methyl)-1,5-dim ethyl-1H-pyrazol-4-yl)-5-chloro-1-
(3-((6-fluoro-3-(((3-formyl-1-methyl-1H-pyrazol-5-
yl)methyl)thio)-naphthalen-1-yl)oxy)propyl)-3-
methyl-1H-indole-2-carboxylate (Intermediate No. 19)

Step G: Methyl 4-(3-(aminomethyl)-1,5-dimethyl-
1H-pyrazol-4-yl)-5-chloro-1-(3-((6-fluoro-3-(((3-
formyl-1-methyl-1H-pyrazol-5-yl)methyl)thio)naph-
thalen-1-yl)oxy)-propyl)-3-methyl-1H-indole-2-
carboxylate (Intermediate No. 20)

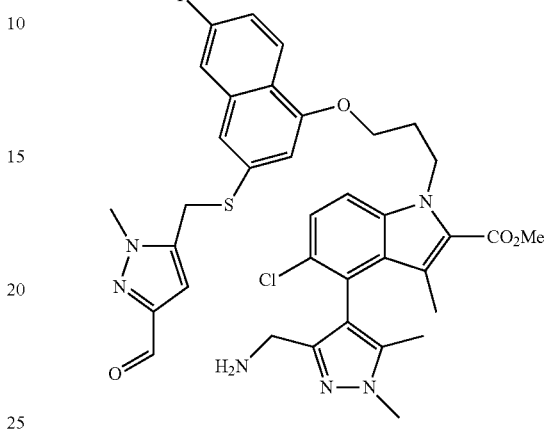

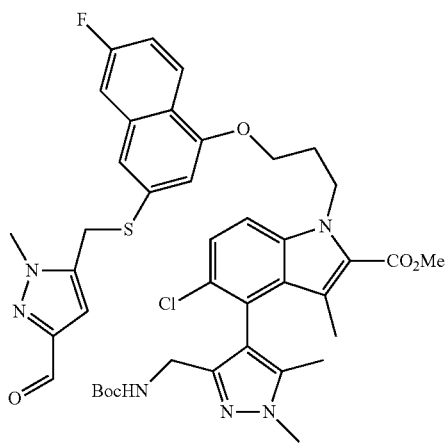 [SMILES: COC(=O)c1c(C)c2c(-c3c(CNC(=O)OC(C)(C)C)nn(C)c3C)c(Cl)ccc2n1CCCOc1cc(SCc2cc(C=O)nn2C)cc2cc(F)ccc12]

In an argon flushed 100 mL round-bottomed flask, methyl 4-(3-(((tert-butoxycarbonyl)amino)methyl)-1,5-dimethyl-1H-pyrazol-4-yl)-5-chloro-1-(3-((6-fluoro-3-(((3-formyl-1-methyl-1H-pyrazol-5-yl)methyl)thio)naphthalen-1-yl)oxy) propyl)-3-methyl-1H-indole-2-carboxylate (Step F, 1.7 g, 1.270 mmol) was dissolved in $CH_2Cl_2$ (8.0 mL) and TFA (2.0 mL) under argon to give a yellow solution. The reaction was stirred at room temperature for 3 h. After removal of volatiles under reduced pressure, the crude title compound was used directly in the next step without purification. MS: 703.4 (M+H$^+$).

Step H: Methyl (Z)-1$^5$-chloro-9$^6$-fluoro-1$^3$,2$^1$,2$^5$,6$^1$-
tetramethyl-1$^1$H,2$^1$H,6$^1$H-10-oxa-8-thia-4-aza-1(4,
1)-indola-2(4,3),6(3,5)-dipyrazola-9(3,1)-naphtha-
lenacyclotrideca-phane-1$^2$-carboxylate (Cpd. No. 32A)

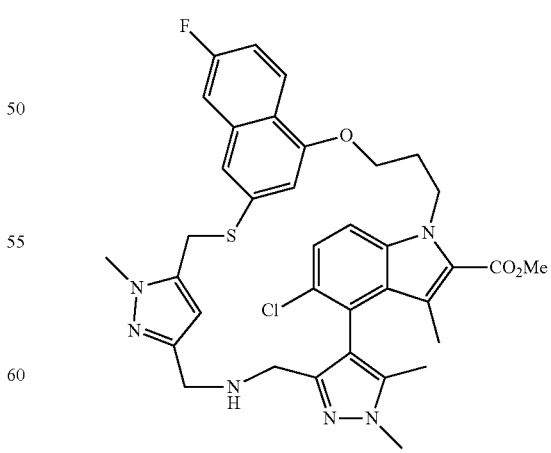

In an argon flushed 50 mL round-bottomed flask, methyl 4-(3-(((tert-butoxycarbonyl)-amino)methyl)-1,5-dimethyl-1H-pyrazol-4-yl)-5-chloro-1(3-((6-fluoro-3(((3-hydroxy-mehtly)-1-methyl-1H-pyrazol-5-yl)methyl)thio)naph-thalen-1-yl)oxy)-prpyl)-3-methyl-1H-indole-2-carboxylate (Step E, 3.4 g, 4.22 mmol) and DMP (1.93 g, 4.56 mmol) were dissolved in dry $CH_2Cl_2$ (50 mL) under argon at 0° C. to give a yellow solution. The reaction was stirred at 0° C. for 1 h. Sat. NaHCO$_3$ (20 mL) was added to the reaction mixture followed by extraction with dichloromethane twice. The combined organic layer was over dried Na$_2$SO$_4$, and concentrated under reduced pressure to give the crude product, which was loaded to silica gel column and eluted with MeOH:DCM (1:50→1:30) to afford the title compound (3.0 g, 88%) as a white solid. MS: 803.9 (M+H$^+$).

In an argon flushed 50 mL round-bottomed flask, the crude methyl 4-(3-(aminomethyl)-1,5-dimethyl-1H-pyrazol-4-yl)-5-chloro-1-(3-((6-fluoro-3-(((3-formyl-1-methyl- 1H-pyrazol-5-yl)methyl)thio)naphthalen-1-yl)oxy)-propyl)-3-methyl-1H-indole-2-carboxylate (Step G, 1.1 g), sodium acetate (0.154 g, 1.877 mmol) and acetic acid (0.113 g, 1.877 mmol) were dissolved in dry $CH_2Cl_2$ (100 mL) under argon to give a yellow solution. The reaction was stirred at room temperature for 0.5 h, $NaBH(OAc)_3$ (400 mg, 1.88 mmol) was added with one portion at 0° C. The reaction was gradually warmed up to room temperature and stirred for 3 h. Sat. $NaHCO_3$ (20 mL) was added to the reaction mixture followed by extraction with dichloromethane 3 times. The combined organic layer was dried over $Na_2SO_4$, and concentrated under reduced pressure to give the crude product, which was loaded to silica gel column, and eluted with MeOH:DCM (1:25) to afford the title compound (320 mg, 74% over 2 steps) as a white solid. MS: 687.6 (M+H$^+$).

Step I: methyl (Z)-1$^5$-chloro-9$^6$-fluoro-1$^3$,2$^1$,2$^5$,6$^1$-tetramethyl-4-(methylsulfonyl)-1$^1$H,2$^1$H,6$^1$H-10-oxa-8-thia-4-aza-1(4,1)-indola-2(4,3),6(3,5)-dipyrazola-9(3,1)- naphthalenacyclotridecaphane-1$^2$-carboxylate (Cpd. No. 32B)

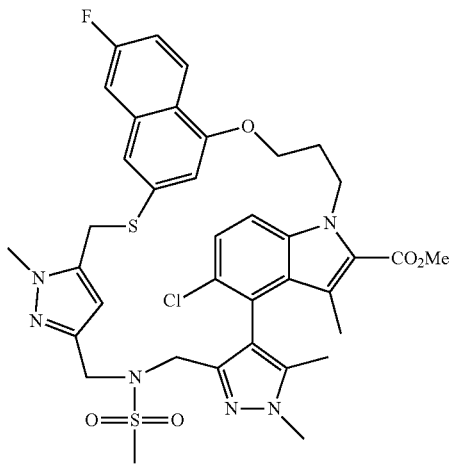 [SMILES: COC(=O)c1c(C)c2c3c(Cl)ccc2n1CCCOc1cc(cc2cc(F)ccc12)SCc1cc(nn1C)CN(S(C)(=O)=O)Cc1nn(C)c(C)c1-3]

In an argon flushed 50 mL round-bottomed flask, (Z)-1$^5$-chloro-9$^6$-fluoro-1$^3$,2$^1$,2$^5$,6$^1$-tetramethyl-1$^1$H,2$^1$H,6$^1$H-10-oxa-8-thia-4-aza-1(4,1)-indola-2(4,3),6(3,5)-dipyrazola-9(3,1)-naphthalenacyclo-trideca-phane-1$^2$-carboxylate (Step H, 320 mg, 0.47 mmol), DIEPA (182 mg, 1.410 mmol), DMAP (17 mg, 0.141 mmol) and MSCl (108 mg, 0.940 mmol) were dissolved in dry $CH_2Cl_2$ (2 mL) under argon to give a yellow solution. The reaction was stirred at room temperature for 2 h. After removal of volatiles under reduced pressure, the crude title compound was used in the next step without purification. MS: 765.7 (M+H$^+$).

Step J: (Z)-1$^5$-chloro-9$^6$-fluoro-1$^3$,2$^1$,2$^5$,6$^1$-tetramethyl-4-(methyl sulfonyl)-1$^1$H,2$^1$H, 6$^1$H-10-oxa-8-thia-4-aza-1(4,1)-indola-2(4,3),6(3,5)-dipyrazola-9(3,1)-naphthalenacyclotridecaphane-1$^2$-carboxylic acid (Cpd. No. 32)

In an argon flushed 50 mL round-bottomed flask, the crude methyl (Z)-1$^5$-chloro-9$^6$-fluoro-1$^3$,2$^1$,2$^5$,6$^1$-tetramethyl-4-(methylsulfonyl)-1$^1$H,2$^1$H,6$^1$H-10-oxa-8-thia-4-aza-1(4,1)-indola-2(4,3),6(3,5)-dipyrazola-9(3,1)-naphthalenacyclotridecaphane-1$^2$-carboxylate (Step I, 360 mg) and sodium hydroxide (188 mg, 4.70 mmol) was dissolved into THF (1 mL), MeOH (3 mL) and $H_2O$ (1 mL). The reaction was stirred at room temperature for 18 h. The mixture was adjusted to pH=3 with 1N HCl followed by extraction with dichloromethane 3 times. The combined organic layer was dried over $Na_2SO_4$, and concentrated under reduced pressure to give the crude product, which was purified by C18 prep-HPLC column to afford the title compound (180 mg, 51% over 2 steps) as a white solid. $^1$H NMR (500 MHz, DMSO-d$_6$) δ 8.21 (dd, J=9.2, 5.8 Hz, 1H), 7.57 (d, J=9.1 Hz, 1H), 7.49 (dd, J=10.2, 2.4 Hz, 1H), 7.34 (td, J=8.9, 2.5 Hz, 1H), 7.31 (s, 1H), 6.99 (d, J=9.0 Hz, 1H), 6.49 (s, 1H), 4.99 (d, J=14.6 Hz, 1H), 4.75 (s, 1H), 4.65 (t, J=10.9 Hz, 1H), 4.27 (d, J=15.6 Hz, 1H), 4.10 (d, J=15.6 Hz, 1H), 3.90-3.84 (m, 1H), 3.79 (s, 3H), 3.78-3.68 (m, 3H), 3.67 (s, 3H), 3.55 (t, J=16.4 Hz, 2H), 2.75 (s, 3H), 2.29-2.44 (m, 2H), 1.92 (s, 3H), 1.90 (s, 3H). MS: 751.6 (M+H$^+$).

Example 33

Synthesis of (R)-(Z)-1$^5$-chloro-9$^6$-fluoro-1$^3$,2$^1$,2$^5$, 6$^1$-tetramethyl-4-(methylsulfonyl)-1$^1$H,2$^1$H, 6'H-10-oxa-8-thia-4-aza-1(4,1)-indola-2(4,3),6(3,5)-dipyrazola-9(3,1)- naphthalenacyclotridecaphane-1$^2$-carboxylic acid (Cpd. No. 33)

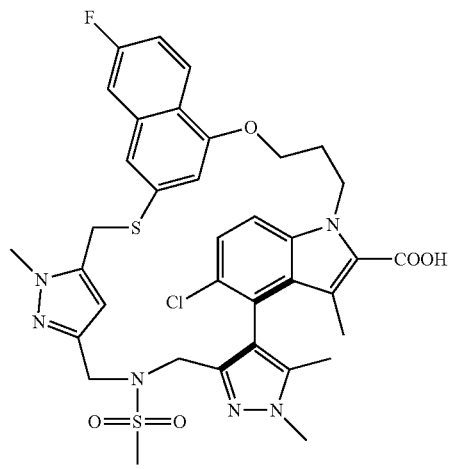

Cpd. No. 32 (169 mg) was subjected to chiral SFC resolution with a (R,R)-WHELK column to provide Cpd. No. 33 (78 mg, 98% ee) as a white solid. MS: 751.2 (M+H$^+$).

Example 34

Synthesis of (S)-(Z)-1⁵-chloro-9⁶-fluoro-1³,2¹,2⁵,6¹-tetramethyl-4-(methylsulfonyl)-1¹H,2¹H, 6¹H-10-oxa-8-thia-4-aza-1(4,1)-indola-2(4,3),6(3,5)-dipyrazola-9(3,1)- naphthalenacyclotridecaphane-1²-carboxylate (Cpd. No. 34)

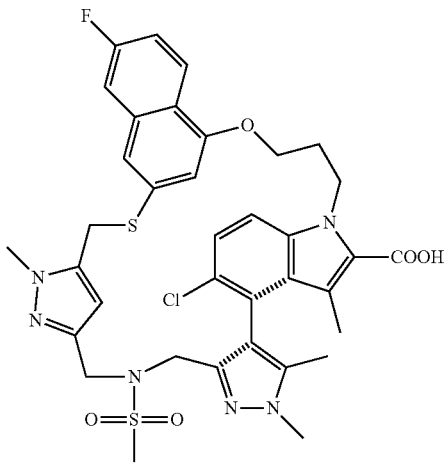

Cpd. No. 32 (169 mg) was subjected to chiral SFC resolution with (R,R)-WHELK column to provide Cpd. No. 34 (74 mg, 99% ee) as a white solid. MS: 751.2 (M+H⁺).

Example 35

Synthesis of (Z)-1⁵-chloro-9⁶-fluoro-1³,2¹,2⁵,6¹-tetramethyl-4-((trifluoromethyl)sulfonyl)-1¹H,2¹H, 6¹H-10-oxa-8-thia-4-aza-1(4,1)-indola-2(4,3),6(3,5)-dipyrazola-9(3,1)- naphthalenacyclotridecaphane-1²-carboxylic acid (Cpd. No. 35)

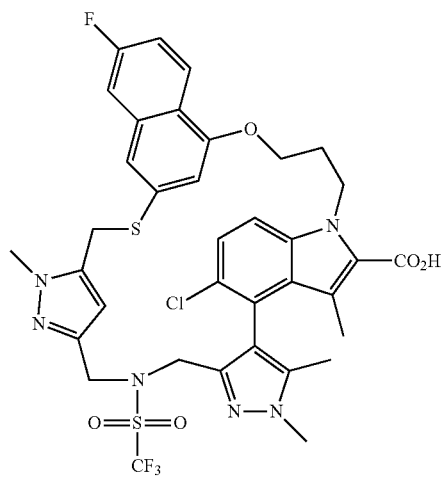 [SMILES: Cc1c(C(=O)O)n2c3ccc(Cl)c(c13)-c1c(nn(C)c1C)CN(S(=O)(=O)C(F)(F)F)Cc1cc(n(C)n1)CSc1cc(c3ccc(F)cc3c1)OCCC2]

Essentially the same protocol used to prepare Cpd. No. 32 of EXAMPLE 32 (Steps I and J) was used to afford Cpd. No. 35 (6 mg) as a white solid. ¹H NMR (500 MHz, DMSO-d₆) δ 8.18 (dd, J=9.0, 5.9 Hz, 1H), 7.62 (d, J=8.9 Hz, 1H), 7.48 (d, J=10.1 Hz, 1H), 7.36 (s, 1H), 7.38-7.28 (m, 1H), 7.07 (d, J=8.9 Hz, 1H), 6.45 (s, 1H), 5.05-4.95 (m, 1H), 4.68-4.59 (m, 1H), 4.29 (d, J=15.5 Hz, 1H), 4.22-4.15 (m, 1H), 4.00 (d, J=15.5 Hz, 1H), 3.91 (d, J=15.3 Hz, 1H), 3.82-3.72 (m, 4H), 3.63 (s, 3H), 3.53-3.33 (m, 4H), 2.36 (s, 2H), 1.94 (s, 3H), 1.91 (s, 3H). MS: 805.6 (M+H⁺).

Example 36

Synthesis of (Z)-1⁵-chloro-9⁶-fluoro-1³,2¹,2⁵,6¹-tetramethyl-4#1-methyl-1H-pyrazol-4-yl)sulfonyl)-1¹H,2¹H,6¹H-10-oxa-8-thia-4-aza-1(4,1)-indola-2(4,3),6(3,5)-dipyrazola-9(3,1)- naphthalenacyclotridecaphane-1²-carboxylic acid (Cpd. No. 36)

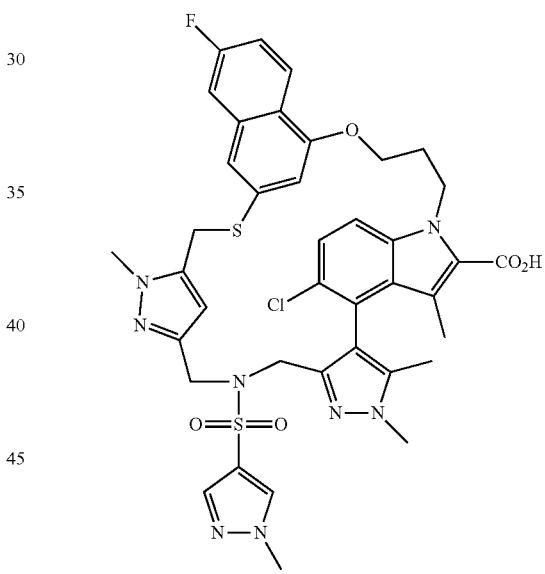

Essentially the same protocol used to prepare Cpd. No. 32 of EXAMPLE 32 (Steps I and J) was used to afford Cpd. No. 36 as a white solid. ¹H NMR (500 MHz, DMSO-d₆) δ 8.26-8.17 (m, 1H), 7.95 (s, 1H), 7.50 (d, J=9.9 Hz, 1H), 7.47 (s, 1H), 7.43 (d, J=8.6 Hz, 1H), 7.38-7.28 (m, 2H), 6.86 (d, J=6.8 Hz, 1H), 6.51 (s, 1H), 5.04 (d, J=12.1 Hz, 1H), 4.53 (s, 1H), 4.49-4.40 (m, 2H), 4.28 (d, J=15.2 Hz, 1H), 4.16 (d, J=15.6 Hz, 1H), 4.06 (d, J=15.4 Hz, 1H), 3.88 (d, J=15.1 Hz, 1H), 3.85-3.78 (m, 2H), 3.80 (s, 3H), 3.77 (s, 3H), 3.73-3.62 (m, 1H), 3.67 (s, 3H), 2.40-2.30 (m, 2H), 1.82 (s, 3H), 1.60 (s, 3H). MS: 817.7 (M+H⁺).

Example 37

Synthesis of (Z)-1⁵-chloro-9⁶-fluoro-1³,2¹,2⁵,6¹-tetramethyl-4#1-methyl-1H-pyrazol-3-yl))sulfonyl)-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid (Cpd. No. 37)

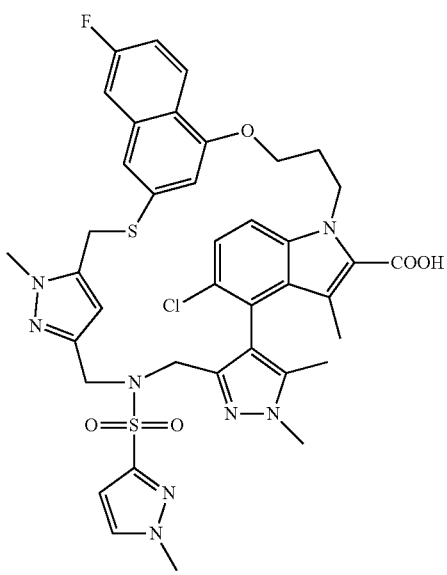 [SMILES: Cc1c(C(=O)O)n2c3ccc(Cl)c(c13)-c1c(nn(C)c1C)CN(S(=O)(=O)c1ccn(C)n1)Cc1cc(n(C)n1)CSc1cc(c3ccc(F)cc3c1)OCCC2]

Essentially the same protocol used to prepare Cpd. No. 32 of EXAMPLE 32 (Steps I and J) was used to afford Cpd. No. 37 (3.5 mg) as a white solid. ¹H NMR (500 MHz, DMSO-d₆) δ 8.29 (dd, J=8.5, 5.9 Hz, 1H), 7.62 (s, 1H), 7.54 (d, J=10.3 Hz, 1H), 7.45 (s, 1H), 7.40 (s, 1H), 7.37 (t, J=8.0 Hz, 1H), 6.88 (d, J=9.2 Hz, 1H), 6.39 (s, 1H), 6.32 (s, 1H), 4.98 (d, J=13.9 Hz, 1H), 4.73 (s, 1H), 4.60 (t, J=13.3 Hz, 1H), 4.24 (d, J=15.9 Hz, 1H), 4.08 (d, J=15.7 Hz, 1H), 4.01 (d, J=15.7 Hz, 1H), 3.94 (d, J=15.2 Hz, 1H), 3.87 (d, J=15.1 Hz, 1H), 3.77 (s, 3H), 3.74 (s, 3H), 3.60-3.53 (m, 4H), 3.49 (d, J=15.3 Hz, 2H), 2.40-2.30 (m, 2H), 1.85 (s, 3H), 1.76 (s, 3H). MS: 817.8 (M+H⁺).

Example 38

Synthesis of (Z)-1⁵-chloro-9⁶-fluoro-1³,2¹,2⁵,6¹-tetramethyl-4-(N-methylsulfamoyl)-1¹H,2¹H,6¹H-10-oxa-8-thia-4-aza-1 (4,1)-indola-2(4,3),6(3,5)-dipyrazola-9(3,1)- naphthalenacyclotridecaphane-1²-carboxylic acid (Cpd. No. 38)

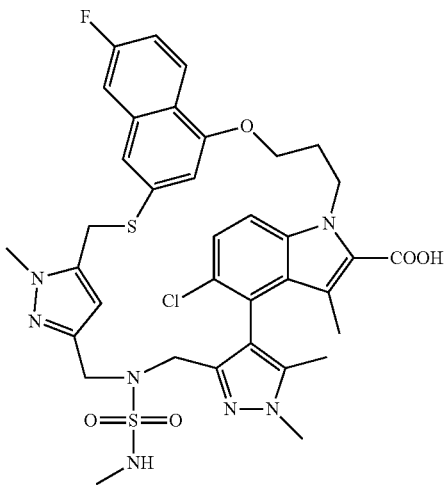 [SMILES: CNS(=O)(=O)N1Cc2cc(n(C)n2)CSc2cc(c3ccc(F)cc3c2)OCCCn2c(C(=O)O)c(C)c3c(c(Cl)ccc32)-c2c(nn(C)c2C)C1]

Essentially the same protocol used to prepare Cpd. No. 32 of EXAMPLE 32 (Steps I and J) was used to afford Cpd. No. 38 (5.8 mg) as a white solid. ¹H NMR (500 MHz, DMSO-d₆) δ 8.21 (dd, J=9.0, 5.8 Hz, 1H), 7.57 (d, J=9.1 Hz, 1H), 7.49 (dd, J=10.1, 2.3 Hz, 1H), 7.37-7.30 (m, 2H), 7.02 (d, J=9.0 Hz, 1H), 6.54 (d, J=4.5 Hz, 1H), 6.46 (s, 1H), 5.05-4.96 (m, 1H), 4.92 (s, 1H), 4.64 (t, J=10.4 Hz, 1H), 4.29 (d, J=15.7 Hz, 1H), 4.13 (d, J=15.7 Hz, 1H), 3.79 (s, 3H), 3.82-3.77 (m, 2H), 3.74 (d, J=15.7 Hz, 1H), 3.69-3.65 (m, 1H), 3.63 (s, 3H), 3.63-3.58 (m, 2H), 2.41-2.25 (m, 2H), 2.15 (d, J=3.7 Hz, 3H), 1.94 (s, 3H), 1.91 (s, 3H). MS: 766.5 (M+H⁺).

Example 39

Synthesis of (Z)-1⁵-chloro-9⁶-fluoro-1³,2¹,2⁵,6¹-tetramethyl-4-sulfamoyl-1¹H,2¹H,6¹H-10-oxa-8-thia-4-aza-1 (4,1)-indola-2(4,3),6(3,5)-dipyrazola-9(3,1)-naphthalenacyclotridecaphane-1²-carboxylic acid (Cpd. No. 39)

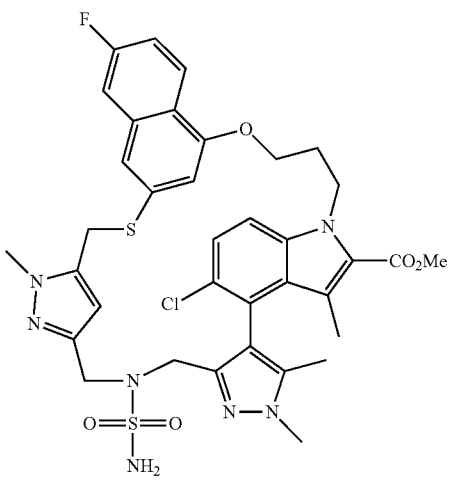 [SMILES: COC(=O)c1c(C)c2c3c(Cl)ccc2n1CCCOc1cc(cc2cc(F)ccc12)SCc1cc(nn1C)CN(S(N)(=O)=O)Cc1nn(C)c(C)c1-3]

Essentially the same protocol used to prepare Cpd. No. 32 of EXAMPLE 32 (Steps I and J) was used to afford Cpd. No. 39 (5.8 mg) as a white solid. $^1$H NMR (500 MHz, DMSO-d$_6$) δ 8.23 (dd, J=8.3, 6.1 Hz, 1H), 7.62 (d, J=9.3 Hz, 1H), 7.48 (d, J=9.9 Hz, 1H), 7.35 (t, J=8.3 Hz, 1H), 7.29 (s, 1H), 6.99 (d, J=8.9 Hz, 1H), 6.54 (s, 1H), 6.48 (s, 2H), 5.02 (d, J=14.9 Hz, 1H), 4.84 (s, 1H), 4.69 (t, J=13.4 Hz, 1H), 4.31 (d, J=15.8 Hz, 1H), 4.12 (d, J=15.5 Hz, 1H), 3.99-3.88 (m, 1H), 3.82 (s, 3H), 3.79-3.72 (m, 1H), 3.71 (s, 3H), 3.68-3.61 (m, 4H), 2.45-2.32 (m, 2H), 1.95 (s, 3H), 1.93 (s, 3H). MS: 752.6 (M+H⁺).

Example 40

Synthesis of (Z)-1⁵-chloro-9⁶-fluoro-1³,2¹,2⁵,6¹-tetramethyl-4-(N, N-dimethylsulfamoyl)-1¹H,2¹H,6¹H-10-oxa-8-thia-4-aza-1 (4,1)-indola-2(4,3),6(3,5)-dipyrazola-9(3,1)- naphthalenacyclotridecaphane-1²-carboxylic acid (Cpd. No. 40)

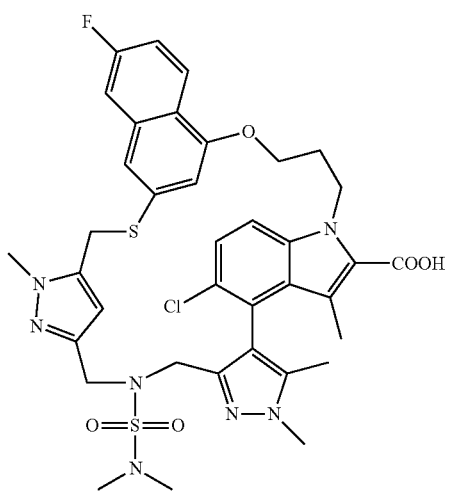 [SMILES: Cc1c(C(=O)O)n2c3ccc(Cl)c(c13)-c1c(nn(C)c1C)CN(S(=O)(=O)N(C)C)Cc1cc(n(C)n1)CSc1cc(c3ccc(F)cc3c1)OCCC2]

Essentially the same protocol used to prepare Cpd. No. 32 of EXAMPLE 32 (Steps I and J) was used to afford Cpd. No. 40 (10 mg) as a white solid. $^1$H NMR (500 MHz, DMSO-d$_6$) δ 8.18 (dd, J=9.0, 5.9 Hz, 1H), 7.60 (d, J=9.1 Hz, 1H), 7.49 (dd, J=10.1, 2.3 Hz, 1H), 7.34 (s, 1H), 7.32 (dd, J=9.0, 2.3 Hz, 1H), 7.08 (d, J=9.0 Hz, 1H), 6.45 (s, 1H), 5.02 (d, J=14.6 Hz, 1H), 4.96 (s, 1H), 4.64 (t, J=9.8 Hz, 1H), 4.28 (d, J=15.6 Hz, 1H), 4.13 (d, J=15.6 Hz, 1H), 3.88-3.74 (m, 3H), 3.78 (s, 3H), 3.65 (s, 3H), 3.62 (s, 3H), 3.58 (d, J=15.4 Hz, 1H), 2.38 (s, 6H), 2.40-2.30 (m, 2H), 1.92 (s, 3H), 1.92 (s, 3H). MS: 780.6 (M+H⁺).

Example 41

Synthesis of (Z)-1⁵-chloro-9⁶-fluoro-1³,2¹,2⁵,6¹-tetramethyl-4-(pyridin-3-ylsulfonyl)-1¹H,2¹H,6¹H-10-oxa-8-thia-4-aza-1 (4,1)-indola-2(4,3),6(3,5)-dipyrazola-9(3,1)- naphthalenacyclotridecaphane-1²-carboxylic acid (Cpd. No. 41)

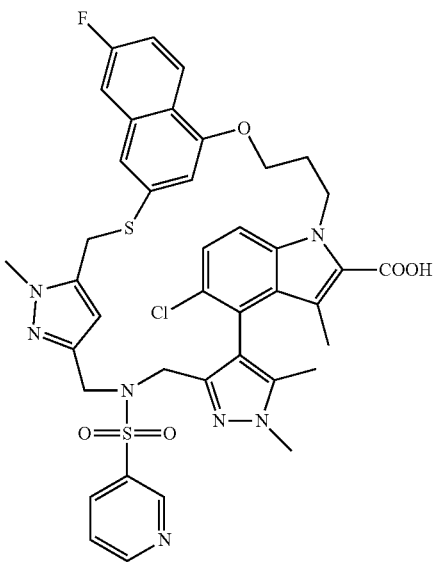 [SMILES: Cc1c(C(=O)O)n2c3ccc(Cl)c(c13)-c1c(nn(C)c1C)CN(S(=O)(=O)c1cccnc1)Cc1cc(n(C)n1)CSc1cc(c3ccc(F)cc3c1)OCCC2]

Essentially the same protocol used to prepare Cpd. No. 32 of EXAMPLE 32 (Steps I and J) was used to afford Cpd. No. 41 (18 mg) as a white solid. $^1$H NMR (500 MHz, DMSO-d$_6$) δ 8.81 (d, J=1.8 Hz, 1H), 8.65 (d, J=4.5 Hz, 1H), 8.25 (dd, J=9.1, 5.9 Hz, 1H), 8.04 (d, J=8.1 Hz, 1H), 7.53 (d, J=9.1 Hz, 1H), 7.50 (dd, J=10.4, 2.3 Hz, 1H), 7.43 (dd, J=7.9, 4.8 Hz, 1H), 7.39-7.32 (m, 2H), 6.94 (d, J=9.0 Hz, 1H), 6.48 (s, 1H), 4.94 (d, J=14.6 Hz, 1H), 4.62 (d, J=14.0 Hz, 1H), 4.58 (s, 1H), 4.21 (d, J=15.8 Hz, 1H), 4.09 (d, J=15.7 Hz, 1H), 4.01 (d, J=4.1 Hz, 2H), 3.96 (d, J=15.4 Hz, 1H), 3.79-3.72 (m, 2H), 3.73 (s, 3H), 3.61 (s, 3H), 3.52-3.41 (m, 1H), 2.43-2.26 (m, 2H), 1.80 (s, 3H), 1.63 (s, 3H). MS: 814.8 (M+H⁺).

Example 42

Synthesis of (Z)-1$^5$-chloro-9$^6$-fluoro-1$^3$,2$^1$,2$^5$,6$^1$-tetramethyl-4-picolinoyl-1$^1$H,2$^1$H,6$^1$H-10-oxa-8-thia-4-aza-1 (4,1)-indola-2(4,3),6(3,5)-dipyrazola-9(3,1)-naphthalenacyclotridecaphane-1$^2$-carboxylic acid (Cpd. No. 42)

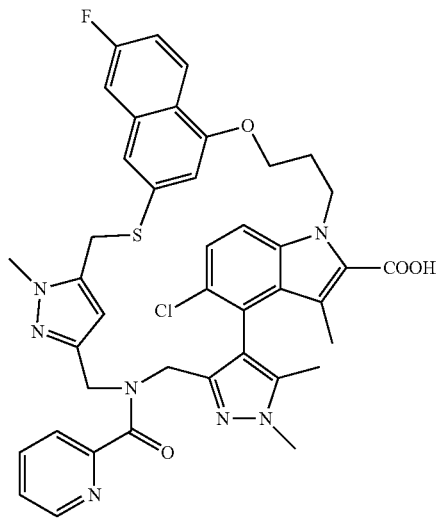 [SMILES: Cc1c(C(=O)O)n2c3ccc(Cl)c(c13)-c1c(nn(C)c1C)CN(C(=O)c1ccccn1)Cc1cc(n(C)n1)CSc1cc(c3ccc(F)cc3c1)OCCC2]

Essentially the same protocol used to prepare Cpd. No. 32 of EXAMPLE 32 (Steps I and J) was used to afford Cpd. No. 42 (14 mg) as a white solid. $^1$H NMR (500 MHz, DMSO-$d_6$, two sets of hydrogens in NMR, the molar ratio is 1:1.) δ 8.53 (d, J=3.5 Hz, 1H), 8.45 (d, J=3.9 Hz, 1H), 8.36-8.30 (m, 1H), 8.29-8.21 (m, 1H), 7.89 (t, J=7.5 Hz, 1H), 7.80 (t, J=7.6 Hz, 1H), 7.57 (dd, J=7.4, 5.1 Hz, 2H), 7.52 (d, J=9.5 Hz, 2H), 7.46 (dd, J=13.5, 8.1 Hz, 2H), 7.39 (s, 2H), 7.35 (dd, J=12.6, 9.3 Hz, 3H), 7.29 (s, 1H), 6.95 (d, J=8.9 Hz, 1H), 6.85 (d, J=8.9 Hz, 1H), 6.48 (s, 2H), 5.19 (s, 1H), 4.99 (d, J=14.2 Hz, 2H), 4.78 (s, 1H), 4.69 (dd, J=22.4, 12.9 Hz, 2H), 4.36 (d, J=15.8 Hz, 1H), 4.26 (d, J=16.2 Hz, 1H), 4.19-4.09 (m, 3H), 4.07 (d, J=12.6 Hz, 2H), 4.00-3.87 (m, 5H), 3.86-3.82 (m, 2H), 3.79 (s, 3H), 3.70-3.61 (m, 8H), 3.55 (s, 3H), 2.45-2.36 (m, 2H), 2.35-2.25 (m, 2H), 2.01 (s, 3H), 1.93 (s, 3H), 1.89 (s, 3H), 1.81 (s, 3H). MS: 778.5 (M+H$^+$).

Example 43

Synthesis of (Z)-1$^5$-chloro-9$^6$-fluoro-1$^3$,2$^1$,2$^5$,6$^1$-tetramethyl-4-(oxazole-2-carbonyl)-1$^1$H,2$^1$H,6$^1$H-10-oxa-8-thia-4-aza-1(4,1)-indola-2(4,3),6(3,5)-dipyrazola-9(3,1)- naphthalenacyclotridecaphane-1$^2$-carboxylic acid (Cpd. No. 43)

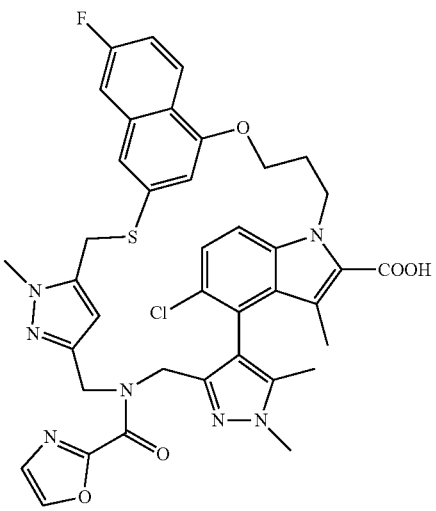 [SMILES: Cc1c(C(=O)O)n2c3ccc(Cl)c(c13)-c1c(nn(C)c1C)CN(C(=O)c1ncco1)Cc1cc(n(C)n1)CSc1cc(c3ccc(F)cc3c1)OCCC2]

Essentially the same protocol used to prepare Cpd. No. 32 of EXAMPLE 32 (Steps I and J) was used to afford Cpd. No. 43 (12 mg) as a white solid. $^1$H NMR (500 MHz, DMSO-$d_6$, two sets of hydrogens in NMR, the molar ratio is 1:1) δ 8.34-8.27 (m, 2H), 8.26 (s, 1H), 8.20 (s, 1H), 7.58 (s, 1H), 7.56 (s, 1H), 7.47 (s, 1H), 7.45 (s, 1H), 7.40 (s, 1H), 7.37-7.33 (m, 2H), 7.32 (s, 2H), 7.30 (s, 1H), 6.96 (d, J=9.0 Hz, 1H), 6.90 (d, J=9.0 Hz, 1H), 6.52 (d, J=8.2 Hz, 2H), 5.03 (s, 1H), 4.99 (d, J=12.7 Hz, 2H), 4.89 (s, 1H), 4.76-4.62 (m, 3H), 4.44 (d, J=16.9 Hz, 1H), 4.34 (d, J=15.7 Hz, 1H), 4.29 (d, J=15.9 Hz, 2H), 4.21 (d, J=13.6 Hz, 1H), 4.12 (s, 1H), 4.09 (s, 1H), 4.05-3.85 (m, 5H), 3.77 (s, 3H), 3.68 (s, 3H), 3.65 (s, 3H), 3.57 (s, 3H), 3.51-3.40 (m, 3H), 2.45-2.38 (m, 2H), 2.37-2.29 (m, 2H), 1.96 (s, 3H), 1.92 (s, 3H), 1.89 (s, 6H). MS: 768.5 (M+H$^+$).

Example 44

Synthesis of (Z)-1⁵-chloro-9⁶-fluoro-1³,2¹,2⁵,6¹-tetramethyl-4-(1-methyl-1H-imidazole-2-carbonyl)-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid (Cpd. No. 44)

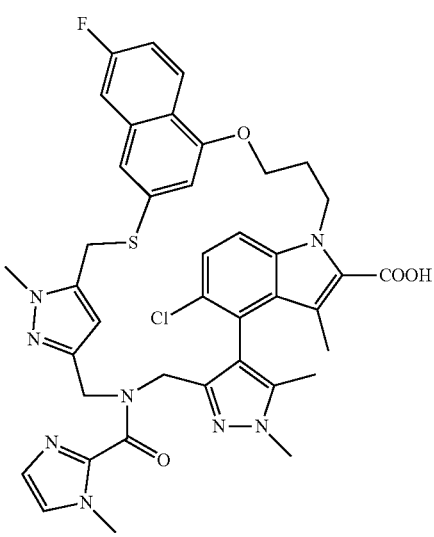 [SMILES: Cc1c(C(=O)O)n2c3ccc(Cl)c(c13)-c1c(nn(C)c1C)CN(C(=O)c1nccn1C)Cc1cc(n(C)n1)CSc1cc(c3ccc(F)cc3c1)OCCC2]

Essentially the same protocol used to prepare Cpd. No. 32 of EXAMPLE 32 (Steps I and J) was used to afford Cpd. No. 44 (13 mg) as a white solid. $^1$H NMR (500 MHz, DMSO-d$_6$, two sets of hydrogens in NMR, the molar ratio is 1:1.) δ 8.39 (dd, J=8.9, 5.8 Hz, 1H), 8.20 (dd, J=9.1, 5.8 Hz, 1H), 7.61 (d, J=9.0 Hz, 1H), 7.56-7.52 (m, 2H), 7.49 (s, 1H), 7.44-7.35 (m, 4H), 7.33 (t, J=8.8 Hz, 1H), 7.30-7.15 (m, 3H), 7.00 (d, J=9.1 Hz, 1H), 6.83 (d, J=8.9 Hz, 1H), 6.55 (d, J=8.3 Hz, 2H), 5.09 (s, 1H), 4.99 (d, J=10.5 Hz, 2H), 4.76-4.67 (dd, J=26.1, 14.2 Hz, 2H), 4.66 (s, 1H), 4.39 (d, J=15.8 Hz, 1H), 4.26 (d, J=15.9 Hz, 1H), 4.18-4.06 (m, 2H), 4.05-3.85 (m, 8H), 3.79 (s, 3H), 3.73 (s, 3H), 3.72 (s, 3H), 3.69 (s, 3H), 3.64 (s, 3H), 3.62 (s, 3H), 3.55-3.35 (m, 4H), 2.45-2.30 (m, 4H), 1.98 (s, 3H), 1.93 (s, 3H), 1.91 (s, 3H), 1.86 (s, 3H). MS: 781.6 (M+H⁺).

Example 45

Synthesis of (Z)-1⁵-chloro-2⁵-(difluoromethyl)-9⁶-fluoro-1³,2¹,6¹-trimethyl-4-(methylsulfonyl)-1¹H, 2¹H,6¹H-10-oxa-8-thia-4-aza-1(4,1)-indola-2(4,3),6(3,5)-dipyrazola-9(3,1)-naphthalenacyclotridecaphane-1²-carboxylic acid (Cpd. No. 45)

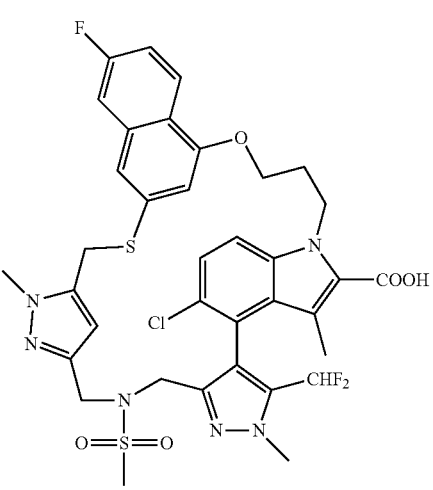 [SMILES: Cc1c(C(=O)O)n2c3ccc(Cl)c(c13)-c1c(nn(C)c1C(F)F)CN(S(C)(=O)=O)Cc1cc(n(C)n1)CSc1cc(c3ccc(F)cc3c1)OCCC2]

Essentially the same protocol used to prepare Cpd. No. 32 of EXAMPLE 32 (Steps I and J) was used to afford Cpd. No. 45 (4.6 mg) as a white solid. $^1$H NMR (500 MHz, DMSO-d$_6$) δ 13.48 (s, 1H), 8.22 (dd, J=9.2, 5.8 Hz, 1H), 7.66 (d, J=9.2 Hz, 1H), 7.52 (dd, J=10.3, 2.2 Hz, 1H), 7.40-7.32 (m, 2H), 7.05 (d, J=9.0 Hz, 1H), 6.86 (t, J=52.1 Hz, 1H), 6.49 (s, 1H), 5.02 (d, J=14.6 Hz, 1H), 4.85 (s, 1H), 4.71 (t, J=11.8 Hz, 1H), 4.29 (d, J=15.4 Hz, 1H), 4.11 (d, J=15.5 Hz, 1H), 4.03 (s, 3H), 3.96-3.91 (m, 1H), 3.83-3.56 (m, 8H), 2.79 (s, 3H), 2.39 (brs, 2H), 1.92 (s, 3H). MS: 787.6 (M+H⁺).

Example 46

Synthesis of (Z)-1$^5$-chloro-1$^3$,2$^1$,2$^5$,6$^1$-tetramethyl-4-(methyl sulfonyl)-1$^1$1-1,2$^1$H,6$^1$H-10-oxa-8-thia-4-aza-1(4,1)-indola-2(4,3),6(3,5)-dipyrazola-9(3,1)-naphthalenacyclotridecaphane-1$^2$-carboxylic acid (Cpd. No. 46)

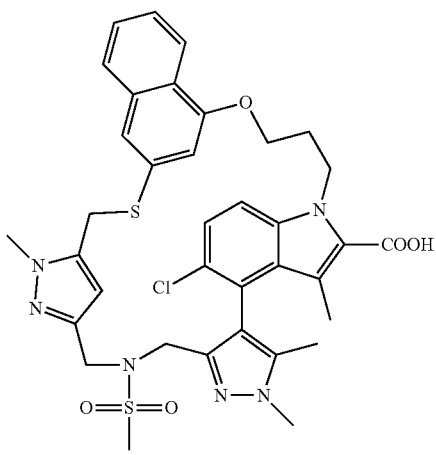 [SMILES: Cc1c(C(=O)O)n2c3ccc(Cl)c(c13)-c1c(nn(C)c1C)CN(S(C)(=O)=O)Cc1cc(n(C)n1)CSc1cc(c3ccccc3c1)OCCC2]

Essentially the same protocol used to prepare Cpd. No. 32 of EXAMPLE 32 (Steps I and J) was used to afford Cpd. No. 46 (25 mg) as a white solid. $^1$H NMR (500 MHz, DMSO-d$_6$) δ 8.15 (d, J=8.5 Hz, 1H), 7.70 (d, J=8.0 Hz, 1H), 7.56 (d, J=9.0 Hz, 1H), 7.52-7.46 (m, 2H), 7.30 (s, 1H), 6.95 (d, J=8.5 Hz, 1H), 6.50 (s, 1H), 5.03-4.98 (m, 1H), 4.69 (s, 1H), 4.66-4.62 (m, 1H), 4.23 (d, J=15.5 Hz, 1H), 4.05 (d, J=15.5 Hz, 1H), 3.90-3.86 (m, 1H), 3.78 (s, 3H), 3.72 (d, J=20.0 Hz, 2H), 3.66 (s, 3H), 3.55 (d, J=15.0 Hz, 1H), 3.45 (d, J=15.5 Hz, 2H), 2.71 (s, 3H), 2.38 (brs, 2H), 1.91 (s, 3H), 1.89 (s, 3H). MS: 733.5, 735.6 (M+H$^+$).

Example 47

Synthesis of (Z)-1$^5$-chloro-1$^3$,2$^1$,2$^5$,6$^1$-tetramethyl-4-((trifluoromethyl)sulfonyl)-1$^1$H,2$^1$H,6$^1$H-10-oxa-8-thia-4-aza-1(4,1)-indola-2(4,3),6(3,5)-dipyrazola-9(3,1)- naphthalenacyclotridecaphane-1$^2$-carboxylic acid (Cpd. No. 47)

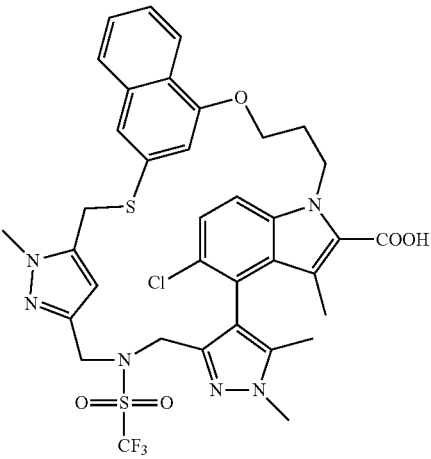 [SMILES: Cc1c(C(=O)O)n2c3ccc(Cl)c(c13)-c1c(nn(C)c1C)CN(S(=O)(=O)C(F)(F)F)Cc1cc(n(C)n1)CSc1cc(c3ccccc3c1)OCCC2]

Essentially the same protocol used to prepare Cpd. No. 32 of EXAMPLE 32 (Steps I and J) was used to afford Cpd. No. 47 (22 mg) as a white solid. $^1$H NMR (500 MHz, DMSO-d$_6$) δ 8.13 (d, J=7.5 Hz, 1H), 7.70 (d, J=8.5 Hz, 1H), 7.61 (d, J=9.0 Hz, 1H), 7.51-7.45 (m, 2H), 7.37 (s, 1H), 7.03 (d, J=9.0 Hz, 1H), 6.45 (s, 1H), 5.03-4.98 (m, 1H), 4.89 (s, 1H), 4.65-4.61 (m, 1H), 4.26-4.17 (m, 2H), 3.99-3.90 (m, 3H), 3.79 (s, 3H), 3.75-3.66 (m, 3H), 3.61 (s, 3H), 2.42-2.31 (m, 2H), 1.94 (s, 3H), 1.91 (s, 3H). MS: 787.5, 789.4 (M+H$^+$).

Example 48

Synthesis of (Z)-1$^5$-chloro-1$^3$,2$^1$,2$^3$,6$^1$-tetramethyl-4-(methylsulfonyl)-1$^1$H,2$^1$H,6$^1$H-10-oxa-8-thia-4-aza-1(4,1)-indola-2(4,5),6(3,5)-dipyrazola-9(3,1)-naphthalenacyclotridecaphane-1$^2$-carboxylic acid (Cpd. No. 48)

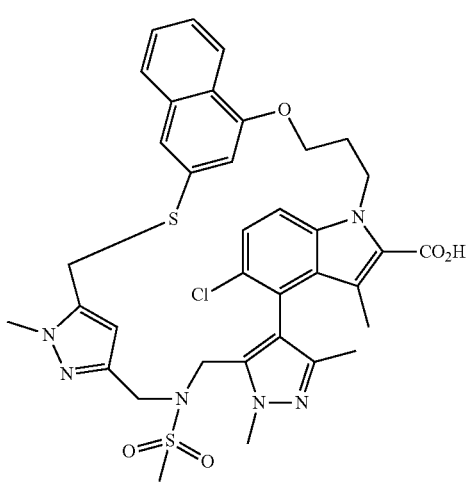 [SMILES: Cc1nn(C)c2c1-c1c(Cl)ccc3c1c(C)c(C(=O)O)n3CCCOc1cc(cc3ccccc13)SCc1cc(nn1C)CN(S(C)(=O)=O)C2]

Essentially the same protocol used to prepare Cpd. No. 32 of EXAMPLE 32 was used to afford Cpd. No. 48 (3.5 mg) as a white solid. $^1$H NMR (500 MHz, DMSO-$d_6$) δ 8.20 (d, J=8.1 Hz, 1H), 7.75 (d, J=8.1 Hz, 1H), 7.64-7.48 (m, 3H), 7.33 (s, 1H), 6.93 (d, J=9.0 Hz, 1H), 6.60 (s, 1H), 5.04-5.01 (m, 1H), 4.70 (brs, 1H), 4.51 (s, 1H), 4.24 (d, J=15.3 Hz, 1H), 4.07 (d, J=15.3 Hz, 1H), 4.03-3.96 (m, 1H), 3.92-3.87 (m, 6H), 3.74 (s, 3H), 3.65 (d, J=16.0 Hz, 1H), 3.53 (d, J=16.0 Hz, 1H), 2.48 (s, 3H), 2.45-2.38 (m, 2H), 1.91 (s, 3H), 1.78 (s, 3H). MS: 734.5 (M+H$^+$).

Example 49

Synthesis of (Z)-1$^5$-chloro-9$^6$-fluoro-1$^3$,2$^1$,2$^3$,6$^1$-tetramehtyl-4-(methylsulfonyl)-1$^1$H,2$^1$H,6$^1$H-10-oxa-8-thia-4-aza-1(4,1)-indola-2(4,5),6(3,5)-dipyrazola-9(3,1)- naphthalenacyclotridecaphane-1$^2$-carboxylic acid (Cpd. No. 49)

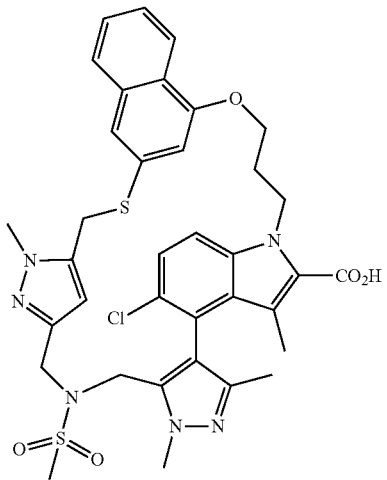 [SMILES: Cc1nn(C)c2c1-c1c(Cl)ccc3c1c(C)c(C(=O)O)n3CCCOc1cc(cc3ccccc13)SCc1cc(nn1C)CN(S(C)(=O)=O)C2]

Essentially the same protocol used to prepare Cpd. No. 32 of EXAMPLE 32 was used to afford Cpd. No. 49 (16 mg) as a white solid. $^1$H NMR (500 MHz, DMSO-$d_6$) δ 13.18 (br, 1H), 8.23 (dd, J=8.9, 5.8 Hz, 1H), 7.57-7.47 (m, 2H), 7.37 (t, J=7.7 Hz, 1H), 7.31 (s, 1H), 6.93 (d, J=9.0 Hz, 1H), 6.56 (s, 1H), 4.99 (d, J=14.5 Hz, 1H), 4.69-4.58 (m, 1H), 4.53 (s, 1H), 4.24 (d, J=15.6 Hz, 1H), 4.08 (d, J=15.4 Hz, 1H), 3.98-3.90 (m, 2H), 3.88-3.77 (m, 5H), 3.71 (s, 3H), 3.62 (dd, J=15.4, 5.6 Hz, 2H), 2.47 (s, 3H), 2.42-2.33 (m, 2H), 1.90 (s, 3H), 1.76 (s, 3H). MS: 751.6 (M+H$^+$).

Example 50

Synthesis of (Z)-1$^5$-chloro-9$^6$-fluoro-4-(2-methoxyethyl)-1$^3$, 6$^1$-dim ethyl-2$^6$,2$^7$-dihydro-1$^1$H,2$^4$H,6$^1$H-10-oxa-8-thia-4-aza-2(3,2)-pyrazolo[5,1-c][1,4] oxazina-1 (4,1)-indola-6(3,5)-pyrazola-9(3,1)-naphthalenacyclotridecaphane-1$^2$-carboxylic acid (Cpd. No. 50)

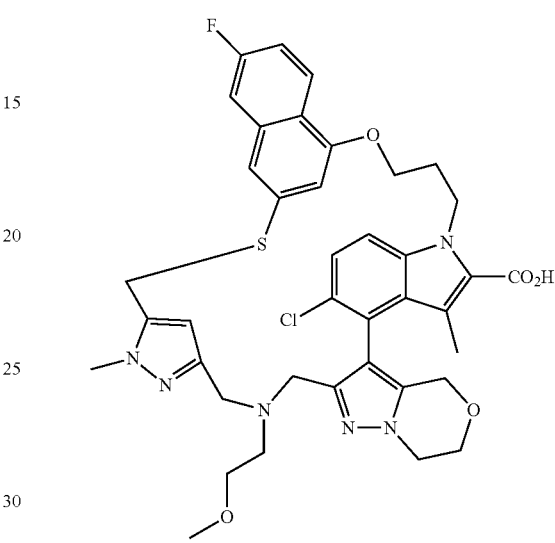

Step A: Methyl 5-chloro-1-(3-((6-fluoro-3-((4-methoxybenzyl)thio)naphthalen-1-yl)oxy)propyl)-4-(2-formyl-6,7-dihydro-4H-pyrazolo[5,1-c][1,4] oxazin-3-yl)-3-methyl-1H-indole-2-carboxylate (Intermediate No. 23)

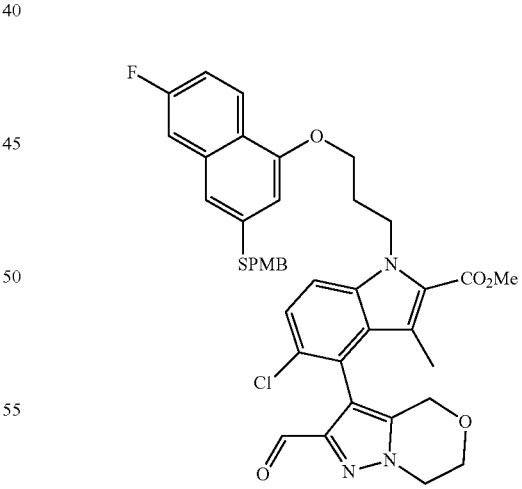

Under Ar, the reaction mixture of methyl 5-chloro-1-(3-((6-fluoro-3-((4-methoxybenzyl)thio)naphthalen-1-yl)oxy) propyl)-4-(2-(hydroxymethyl)-6,7-dihydro-4H-pyrazolo[5,1-c][1,4]oxazin-3-yl)-3-methyl-1H-indole-2-carboxylate (Intermediate No. 28, 630 mg, 0.86 mmol) and manganese (IV) oxide (2.25 g, 25.9 mmol) in dry THF (15 mL) was refluxed for 2 h. After cooling down to room temperature, the resulting mixture was filtered off, and the filtrate was concentrated to give a brown oil, which was purified by silica gel column (DCM:EA, 1:0→2:3) to afford the title compound (340 mg, 54%) as a light yellow oil. MS: 728.8 (M+H⁺); 750.4, 752.1(M+Na⁺).

Step B: Methyl 5-chloro-1-(3-((6-fluoro-3-((4-methoxybenzyl)thio)naphthalen-1-yl)oxy)propyl)-4-(2-(((2-methoxyethyl)amino)methyl)-6,7-dihydro-4H-pyrazolo[5,1-c][1,4]oxazin-3-yl)-3-methyl-1H-indole-2-carboxylate (Intermediate No. 24)

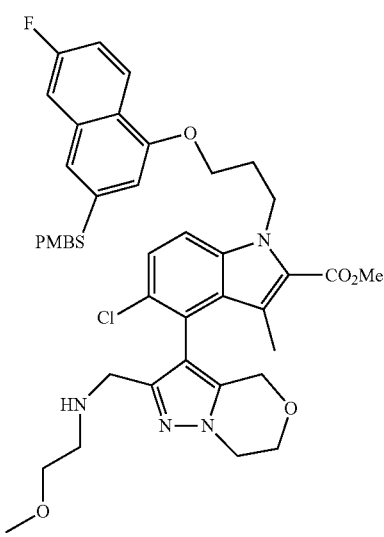

Under Ar, to a solution of 2-methoxyethan-1-amine (93 mg, 1.236 mmol, 3) and methyl 5-chloro-1-(3-((6-fluoro-3-((4-methoxybenzyl)thio)naphthalen-1-yl)oxy)propyl)-4-(2-formyl-6,7-dihydro-4H-pyrazolo[5,1-c][1,4]oxazin-3-yl)-3-methyl-1H-indole-2-carboxylate (Step A, 300 mg, 0.41 mmol) in dry DCM (20 mL) was added sodium triacetoxyborohydride (262 mg, 1.236 mmol) at 0° C., the reaction mixture was stirred at room temperature for 16 h. The resulting mixture was quenched with aq. NaHCO₃, and extracted with DCM twice. The combined organic layer was washed with brine, dried over Na₂SO₄ and concentrated under reduced pressure to give a yellow oil, which was purified by silica gel column (DCM:MeOH, 10:1) to afford the title compound (320 mg, 99%) as a yellow oil. MS: 788.9 (M+H⁺).

Step C: Methyl 4-(2-(((((5-(((tert-butyldimethylsilyl)oxy)methyl)-1-methyl-1H-pyrazol-3-yl)methyl)(2-methoxyethyl)amino)methyl)-6,7-dihydro-4H-pyrazolo[5,1-c][1,4]oxazin-3-yl)-5-chloro-1-(3-((6-fluoro-3-((4-methoxybenzyl)thio)naphthalen-1-yl)oxy)propyl)-3-methyl-1H-indole-2-carboxylate (Intermediate No. 25)

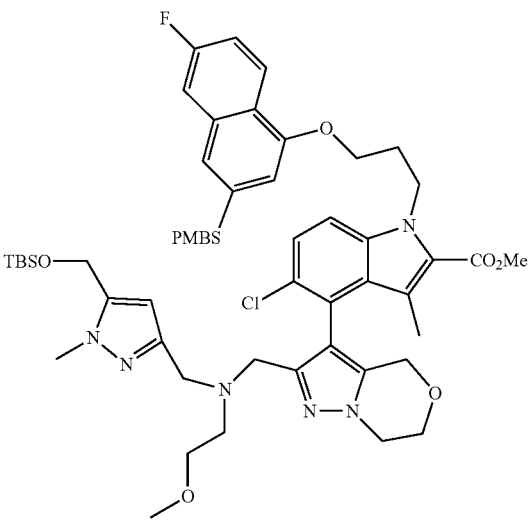

Under Ar, to a solution of methyl 5-chloro-1-(3-((6-fluoro-3-((4-methoxybenzyl)thio)naphthalen-1-yl)oxy)propyl)-4-(24(2-methoxyethyl)amino)methyl)-6,7-dihydro-4H-pyrazolo[5,1-c][1,4]oxazin-3-yl)-3-methyl-1H-indole-2-carboxylate (Step B, 320 mg, 0.41 mmol) and 5-(((tert-butyldimethylsilyl)oxy)methyl)-1-methyl-1H-pyrazole-3-carbaldehyde (Intermediate D3, 103 mg, 0.41 mmol) in dry DCM (20 mL) was added sodium triacetoxyborohydride (258 mg, 1.22 mmol) at 0° C., the reaction mixture was stirred at room temperature for 16 h. The resulting mixture was quenched with aq. NaHCO₃, and extracted with DCM twice. The combined organic layer was washed with brine, dried over Na₂SO₄ and concentrated under reduced pressure to give a yellow oil, which was purified by silica gel column (DCM:MeOH, 10:1) to afford the title compound (400 mg, 96%) as a yellow oil. MS: 1027.3 (M+H⁺).

Step D: Methyl 5-chloro-1-(3-((6-fluoro-3-((4-methoxybenzyl)thio)naphthalen-1-yl)oxy)propyl)-4-(2-((((5-(hydroxymethyl)-1-methyl-1H-pyrazol-3-yl)methyl)(2-methoxyethyl)amino)methyl)-6,7-dihydro-4H-pyrazolo[5,1-c][1,4]oxazin-3-yl)-3-methyl-1H-indole-2-carboxylate (Intermediate No. 26)

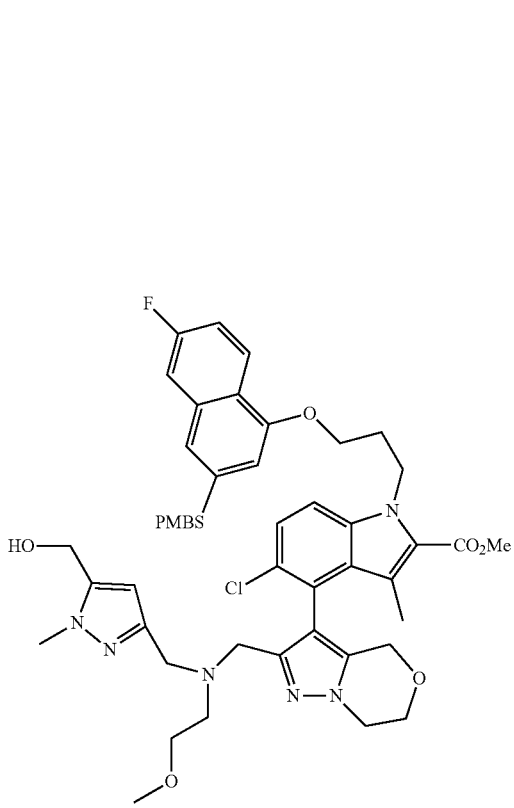

Under Ar, to a solution of methyl 4-(2-((((5-(((tert-butyldimethylsilyl)oxy)methyl)-1-methyl-1H-pyrazol-3-yl)methyl)(2-methoxyethyl)amino)methyl)-6,7-dihydro-4H-pyrazolo[5,1-c][1,4]oxazin-3-yl)-5-chloro-1-(3-((6-fluoro-3-((4-methoxybenzyl)thio)naphthalen-1-yl)oxy)propyl)-3-methyl-1H-indole-2-carboxylate (Step C, 400 mg, 0.39 mmol) in dry THF (5 mL) was added TBAF (3 mL, 3 mmol, 1.0 M in THF), the reaction mixture was stirred at room temperature for 2 h. The resulting mixture was diluted with water (50 mL), and extracted with EA twice. The combined organic layer was washed with brine, dried over $Na_2SO_4$ and concentrated under reduced pressure to give a yellow oil, which was purified by silica gel column (DCM:MeOH, 10:1) to afford the title compound (280 mg, 79%) as a yellow oil. MS: 912.8 (M+H$^+$).

Step D: Methyl 4-(2-((((5-(bromomethyl)-1-methyl-1H-pyrazol-3-yl)methyl)(2-methoxyethyl)amino)methyl)-6,7-dihydro-4H-pyrazolo[5,1-c][1,4]oxazin-3-yl)-5-chloro-1-(3-((6-fluoro-3-((4-methoxybenzyl)thio)naphthalen-1-yl)oxy)propyl)-3-methyl-1H-indole-2-carboxylate (Intermediate No. 27)

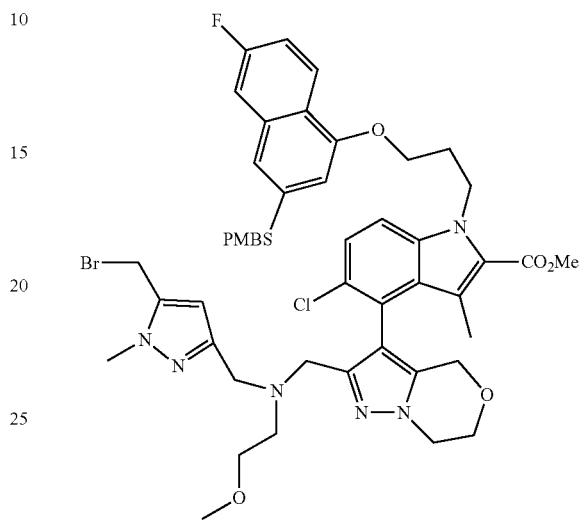

Under Ar, to a solution of methyl 5-chloro-1-(3-((6-fluoro-3-((4-methoxybenzyl)thio)naphthalen-1-yl)oxy)propyl)-4-(2-((((5-(hydroxymethyl)-1-methyl-1H-pyrazol-3-yl)methyl)(2-methoxyethyl)amino)methyl)-6,7-dihydro-4H-pyrazolo[5,1-c][1,4]oxazin-3-yl)-3-methyl-1H-indole-2-carboxylate (Step C, 280 mg, 0.31 mmol) and $Ph_3P$ (242 mg, 0.92 mmol) in dry DCM (20 mL) was added $CBr_4$ (306 mg, 0.92 mmol), then the reaction mixture was stirred at room temperature for 2 h. After removal of volatiles under reduced pressure, the residue was purified by silica gel column (DCM:MeOH, 10:1) to afford the crude title compound (299 mg) as a yellow oil, which was used for the next step without further purification. MS: 975.9 (M+H$^+$).

Step E: (Z)-1$^5$-chloro-9$^6$-fluoro-4-(2-methoxyethyl)-1$^3$,6$^1$-dimethyl-2$^6$,2$^7$-dihydro-1$^1$H,2$^4$H,6$^1$H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1$^2$-carboxylic acid (Cpd. No. 50)

Under Ar, to a solution of the crude methyl 4-(2-((((5-(bromomethyl)-1-methyl-1H-pyrazol-3-yl)methyl)(2-methoxyethyl)amino)methyl)-6,7-dihydro-4H-pyrazolo[5,1-c][1,4]oxazin-3-yl)-5-chloro-1-(3-((6-fluoro-3-((4-methoxybenzyl)thio)naphthalen-1-yl)oxy)propyl)-3-methyl-1H-indole-2-carboxylate (Step D, 299 mg) in DCM (2 mL) was added triethylsilane (2 mL) and TFA (6 mL), the reaction mixture was stirred at room temperature for 16 h. After removal of volatiles under reduced pressure, the resulting yellow oil was directly used without purification. Under Ar the residue was re-dissolved into dry acetonitrile (30 mL), and $K_2CO_3$ (420 mg, 3.02 mmol) was added; the reaction mixture was stirred at room temperature for 2 h. The resulting mixture was filtered off, and the filtrate was concentrated under reduced pressure to give a yellow oil, which was directly used without purification MS: 774.4 (M+H$^+$).

Under Ar, to a solution of the above yellow oil in THF (3 mL) and MeOH (3 mL) was added 2N NaOH (3 mL), the reaction mixture was stirred at room temperature for 16 h. After removal of volatiles under reduced pressure, the residue was diluted with water (20 mL), and adjusted to pH=2-3 with 1N HCl. The resulting mixture was extracted with EA three times, washed with brine, dried over $Na_2SO_4$ and concentrated under reduced pressure to give a yellow oil, which was purified by C18 prep-HPLC column to afford the title compound (40 mg, 17% for 3 steps) as a white solid. $^1$H NMR (500 MHz, DMSO-$d_6$) δ 7.84-7.69 (m, 1H), 7.67-7.12 (m, 6H), 6.67-6.47 (m, 1H), 5.17-4.90 (m, 1H), 4.73-4.58 (m, 1H), 4.58-4.39 (m, 2H), 4.39-4.00 (m, 6H), 3.99-3.61 (m, 6H), 3.34-3.05 (m, 10H), 2.46-2.22 (m, 2H), 2.11-1.82 (m, 3H). MS: 760.9 (M+H$^+$).

Example 51

Synthesis of (Z)-1$^5$-chloro-9$^6$-fluoro-1$^3$, 6$^1$-di methyl-4-(2-(methyl sulfonamido)ethyl)-26,27-di-hydro-1$^1$H,2$^4$H,6$^1$H-10-oxa-8-thia-4-aza-2(3,2)-pyrazolo[5,1-c][1,4]oxazina-1(4,1)-indola-6(3,5)-pyrazola-9(3,1)-naphthalenacyclotridecaphane-1$^2$-carb oxylic acid (Cpd. No. 51)

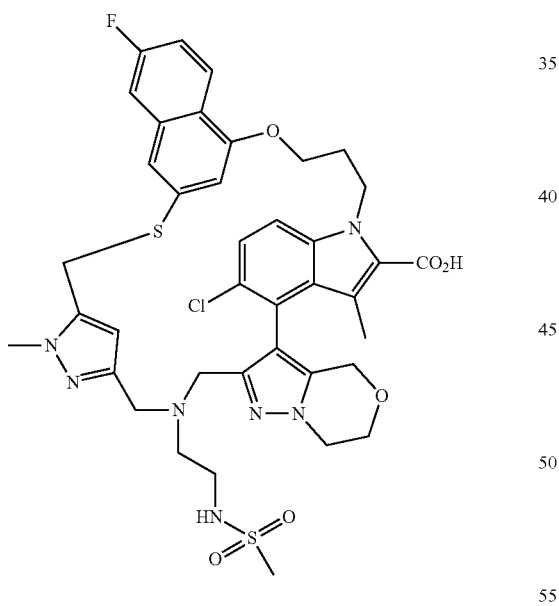

Example 52

Synthesis of (Z)-1$^5$-chloro-9$^6$-fluoro-1$^3$,2$^1$,2$^5$,6$^1$-tetramethyl-4-(oxazol-2-ylmethyl)-1$^1$H,2$^1$H,6$^1$H-10-oxa-8-thia-4-aza-1(4,1)-indola-2(4,3),6(3,5)-dipyrazola-9(3,1)- naphthalenacyclotridecaphane-1$^2$-carboxylic acid (Cpd. No. 52)

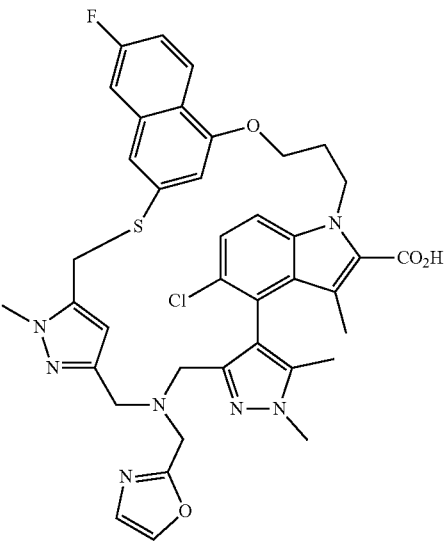 [SMILES: Cc1c(C(=O)O)n2c3ccc(Cl)c(c13)-c1c(nn(C)c1C)CN(Cc1ncco1)Cc1cc(n(C)n1)CSc1cc(c3ccc(F)cc3c1)OCCC2]

Essentially the same protocol used to prepare Cpd. No. 50 of EXAMPLE 50 was used to afford Cpd. No. 51 (6.9 mg) as a white solid. $^1$H NMR (500 MHz, DMSO-$d_6$) δ 8.26-7.42 (m, 3H), 7.41-7.16 (m, 3H), 6.59 (s, 1H), 5.10-4.99 (m, 1H), 4.69-4.35 (m, 2H), 4.36-4.00 (m, 5H), 4.00-3.79 (m, 1H), 3.74 (s, 3H), 3.62-3.42 (m, 4H), 3.31-3.06 (m, 6H), 2.90 (s, 3H), 2.67-2.51 (m, 2H), 2.45-2.25 (m, 2H), 1.98 (s, 3H). MS: 823.6 (M+H$^+$).

Essentially the same protocol used to prepare Cpd. No. 50 of EXAMPLE 50 was used to afford Cpd. No. 52 (35.2 mg) as a white solid. $^1$H NMR (500 MHz, DMSO-$d_6$) δ 8.13-8.02 (m, 1H), 7.86 (s, 1H), 7.82 (t, J=8.6 Hz, 1H), 7.50-7.42 (m, 1H), 7.34 (dd, J=9.2, 4.1 Hz, 2H), 7.30-7.23 (m, 1H), 7.09 (s, 1H), 6.73 (s, 1H), 5.12 (d, J=4.4 Hz, 2H), 4.60 (d, J=9.4 Hz, 1H), 4.35 (t, J=9.1 Hz, 2H), 4.04 (d, J=6.6 Hz, 1H), 3.93-3.84 (m, 2H), 3.82 (s, 3H), 3.77 (s, 3H), 3.46-3.39 (m, 5H), 2.50-2.36 (m, 2H), 1.97 (s, 3H), 1.95 (s, 3H). MS: 755.5 (M+H$^+$); 776.44 (M+Na$^+$).

Example 53

Synthesis of (Z)-1⁵-chloro-9⁶-fluoro-4-isopropyl-1³,2¹,2⁵,6¹-tetramethyl-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid (Cpd. No. 53)

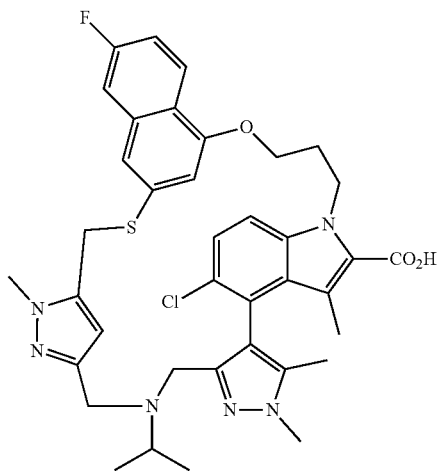 [SMILES: Cc1c(C(=O)O)n2c3ccc(Cl)c(c13)-c1c(nn(C)c1C)CN(C(C)C)Cc1cc(n(C)n1)CSc1cc(c3ccc(F)cc3c1)OCCC2]

Essentially the same protocol used to prepare Cpd. No. 50 of EXAMPLE 50 was used to afford Cpd. No. 53 (4.6 mg) as a white solid. $^1$H NMR (500 MHz, DMSO-d$_6$, sodium carboxylate) δ 7.98 (s, 1H), 7.76 (d, J=8.6 Hz, 1H), 7.46 (t, J=9.4 Hz, 2H), 7.27 (s, 2H), 6.76 (s, 1H), 5.28-4.97 (m, 2H), 4.65 (d, J=15.1 Hz, 1H), 4.40 (d, J=15.0 Hz, 1H), 4.30 (d, J=15.4 Hz, 1H), 4.09 (s, 1H), 3.78 (s, 3H), 3.76 (s, 3H), 3.43-3.40 (m, 2H), 3.15 (d, J=12.9 Hz, 1H), 2.99 (d, J=14.5 Hz, 1H), 2.80 (d, J=12.3 Hz, 1H), 2.42-2.14 (m, 2H), 2.00 (s, 3H), 1.92 (s, 3H), 1.72-1.63 (m, 1H), 0.12 (d, J=5.3 Hz, 3H), −0.35 (s, 3H). MS: 716.6 (M+H⁺).

Example 54

Synthesis of (Z)-1⁵-chloro-4-(2-(dimethylamino)-2-oxoethyl)-9⁶-fluoro-1³,2¹,2⁵,6¹-tetramethyl-1¹H,2¹H,6¹H-10-oxa-8-thia-4-aza-1(4,1)-indola-2(4,3),6(3,5)-dipyrazola-9(3,1)-naphthalenacyclotridecaphane-1²-carboxylic acid (Cpd. No. 54)

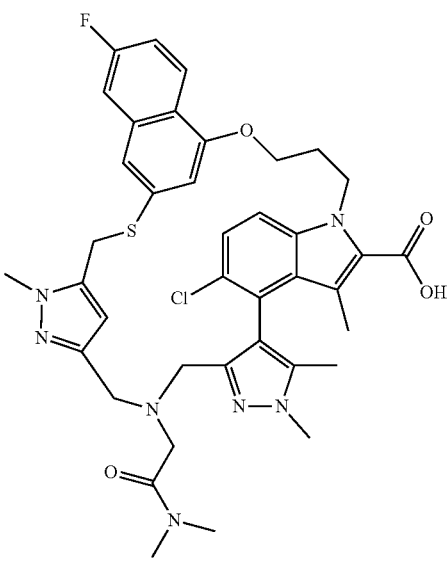 [SMILES: Cc1c(C(=O)O)n2c3ccc(Cl)c(c13)-c1c(nn(C)c1C)CN(CC(=O)N(C)C)Cc1cc(n(C)n1)CSc1cc(c3ccc(F)cc3c1)OCCC2]

Essentially the same protocol used to prepare Cpd. No. 50 of EXAMPLE 50 was used to afford Cpd. No. 54 (25 mg) as a white solid. $^1$H NMR (500 MHz, DMSO-d$_6$) δ 8.15 (s, 1H), 7.84-7.72 (m, 1H), 7.57-7.16 (m, 5H), 6.56 (s, 1H), 5.08 (d, J=14.3 Hz, 1H), 4.69-4.61 (m, 1H), 4.28 (t, J=20.6 Hz, 2H), 3.93-3.78 (m, 8H), 3.70 (s, 3H), 2.81-2.63 (m, 6H), 2.42-2.28 (m, 3H), 2.01-1.94 (m, 8H). MS: 758.5 (M+H⁺).

Example 55

Synthesis of (Z)-1⁵-chloro-9⁶-fluoro-1³,2¹,2⁵,6¹-tetramethyl-4-phenyl-1¹H,2¹H,6¹E-10-oxa-8-thia-4-aza-1(4,1)-indola-2(4,3),6(3,5)-dipyrazola-9(3,1)-naphthalenacyclotridecaphane-1²-carboxylic acid (Cpd. No. 55)

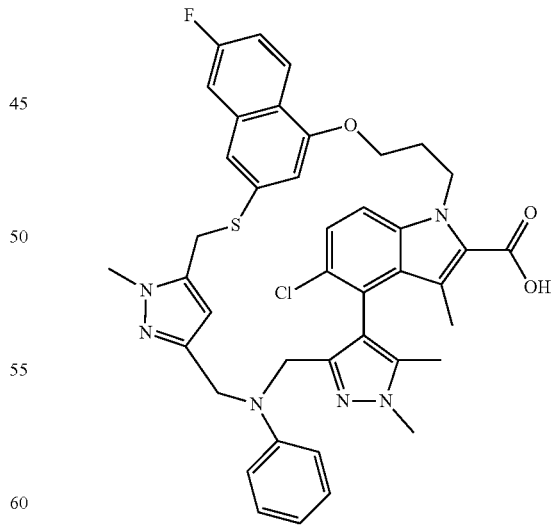

Essentially the same protocol used to prepare Cpd. No. 50 of EXAMPLE 50 was used to afford Cpd. No. 55 (7.5 mg) as a white solid. $^1$H NMR (500 MHz, DMSO-d$_6$) δ 13.38 (s, 1H), 8.34 (dd, J=9.2, 5.7 Hz, 1H), 7.59 (d, J=9.0 Hz, 1H), 7.48 (dd, J=10.2, 2.5 Hz, 1H), 7.39 (dd, J=8.8, 2.2 Hz, 1H), 7.32 (s, 1H), 7.02 (d, J=9.0 Hz, 1H), 6.86 (t, J=7.9 Hz, 2H), 6.68 (d, J=8.2 Hz, 2H), 6.46 (s, 1H), 6.37 (t, J=7.1 Hz, 1H), 5.11 (s, 1H), 5.01 (d, J=14.7 Hz, 1H), 4.75 (t, J=11.1 Hz, 1H), 4.36 (d, J=15.8 Hz, 1H), 4.09 (d, J=15.8 Hz, 1H), 3.99 (d, J=15.5 Hz, 1H), 3.92-3.81 (m, 3H), 3.77 (s, 3H), 3.68 (s, 3H), 3.61 (d, J=8.0 Hz, 2H), 2.41-2.27 (m, 2H), 1.97 (s, 3H), 1.89 (s, 3H). MS: 750.3 (M+H⁺).

Example 56

Synthesis of 3-((4-Methoxybenzyl)thio)naphthalen-1-ol (Intermediate A1)

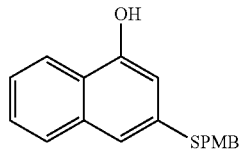

Step A:
4-((tert-Butyldimethylsilyl)oxy)naphthalen-2-ol

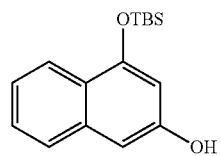 [SMILES: CC(C)(C)[Si](C)(C)Oc1cc(O)cc2ccccc12]

Under Ar, to a solution of naphthalene-1,3-diol (40 g, 250 mmol) in dry DCM (200 mL) was added imidazole (25.5 g, 375 mmol) at 0° C., followed by TBSCl (35.8 g, 237 mmol). The reaction mixture was allowed to warm up to room temperature and stirred for 3 h. Water was added to quench the reaction, and the resulting mixture was extracted with DCM twice. The combined DCM layer was washed with brine, dried over Na₂SO₄, and concentrated under reduced pressure to give a yellow oil, which was purified by silica gel column (hexane:EA, 1:0→10:1) to afford the title compound (37 g, 54%) as a yellow oil. ¹H NMR (500 MHz, DMSO-d₆) δ 9.63 (s, 1H), 7.91 (d, J=8.3 Hz, 1H), 7.61 (d, J=8.2 Hz, 1H), 7.36 (t, J=7.5 Hz, 1H), 7.23 (t, J=7.5 Hz, 1H), 6.75 (d, J=1.7 Hz, 1H), 6.55 (d, J=2.1 Hz, 1H), 1.04 (s, 9H), 0.26 (s, 6H).

Step B:
4-((tert-Butyldimethylsilyl)oxy)naphthalen-2-yl trifluoromethanesulfonate

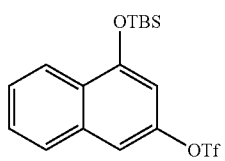 [SMILES: CC(C)(C)[Si](C)(C)Oc1cc(OS(=O)(=O)C(F)(F)F)cc2ccccc12]

Under Ar, to a solution of 4-((tert-butyldimethylsilyl)oxy) naphthalen-2-ol (Step A, 37.1 g, 135 mmol) in dry DCM (200 mL) was added DIEPA (26.2 g, 203 mmol) at 0° C., followed by Tf₂O (49.6 g, 176 mmol), the reaction mixture was stirred at 0° C. for 1 h. Water was added to quench the reaction, and the resulting mixture was extracted with DCM twice. The combined DCM layer was dried over Na₂SO₄, and concentrated under reduced pressure to give a brown oil, which was purified by silica gel column (hexane:DCM, 10:1) to afford the title compound (47.4 g, 86%) as a colorless oil. ¹H NMR (500 MHz, DMSO-d₆) δ 8.13 (m, 1H), 8.04 (m, 1H), 7.75 (d, J=2.5 Hz, 1H), 7.67-7.63 (m, 2H), 6.94 (d, J=2.5 Hz, 1H), 1.04 (s, 9H), 0.31 (s, 6H). MS: 407.1 (M+H⁺).

Step C: tert-Butyl((3-((4-methoxybenzyl)thio)naphthalen-1-yl)oxy)dimethylsilane

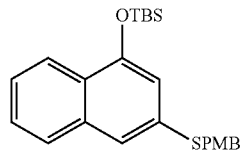

Under Ar, to a solution of 4-((tert-butyldimethylsilyl)oxy) naphthalen-2-yl trifluoromethanesulfonate (Step B, 47.4 g, 117 mmol) and (4-methoxyphenyl)methanethiol (23.38 g, 152 mmol) in dry dioxane (150 mL) was added Pd₂(dba)₃ (5.34 g, 5.83 mmol), Xantphos (6.75 g, 11.66 mmol) and DIEPA (45.2 g, 350 mmol), the reaction mixture was heated to reflux for overnight. After removal of volatiles under reduced pressure, the residue was purified by silica gel column (hexane:EA, 10:1) to afford the title compound (42.3 g, 88%) as a white solid. ¹H NMR (500 MHz, DMSO-d₆) δ 7.99 (d, J=8.5 Hz, 1H), 7.78 (d, J=8.0 Hz, 1H), 7.51-7.44 (m, 3H), 7.30 (d, J=8.5 Hz, 2H), 6.85 (d, J=8.0 Hz, 2H), 6.75 (s, 1H), 4.26 (s, 2H), 3.71 (s, 3H), 1.03 (s, 9H), 0.23 (s, 6H). MS: 411.5 (M+H⁺).

Step D: 3-((4-Methoxybenzyl)thio)naphthalen-1-ol (Intermediate A1)

Under Ar, to a solution of tert-butyl ((3-((4-methoxybenzyl)thio)naphthalen-1-yl)oxy)dimethyl silane (Step C, 64.9 g, 158 mmol) in dry THF (200 mL) was added TBAF3.H₂O (20.7 g, 79 mmol), the reaction mixture was stirred at room temperature for 1 h. The formed precipitate was collected by filtration to afford the title compound (45 g, 96%) as a white solid. ¹H NMR (500 MHz, DMSO-d₆) δ 10.25 (s, 1H), 8.03 (d, J=8.3 Hz, 1H), 7.70 (d, J=8.2 Hz, 1H), 7.45 (t, J=7.5 Hz, 1H), 7.36 (t, J=7.6 Hz, 1H), 7.33-7.27 (m, 3H), 6.86 (d, J=8.4 Hz, 2H), 6.79 (s, 1H), 4.24 (s, 2H), 3.71 (s, 3H). MS: 297.2 (M+H⁺).

Example 57

Synthesis of 6-Fluoro-3-((4-methoxybenzyl)thio) naphthalen-1-ol (Intermediate A2)

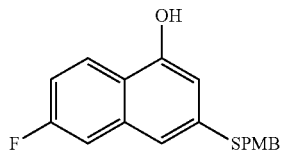

Step A: 2-(3-Fluorophenyl)acetyl chloride

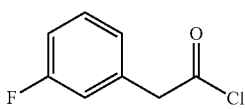

To a solution of 2-(3-fluorophenyl)acetic acid (150 g, 973 mmol) in DCM was added sulfurous dichloride (579 g, 4866 mmol) slowly, the reaction mixture was heated to 50° C. for 4 h. After cooling down to room temperature and removal of volatiles under reduced pressure, the residue was directly used without purification.

Step B: Ethyl 4-(3-fluorophenyl)-3-oxobutanoate

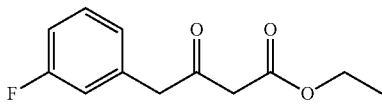 [SMILES: CCOC(=O)CC(=O)Cc1cccc(F)c1]

To a solution of 2,2-dimethyl-1,3-dioxane-4,6-dione (140 g, 973 mmol) in DCM was added DIEPA (151 g, 1168 mmol), then a solution of 2-(3-fluorophenyl)acetyl chloride (Step A, 168 g, 973 mmol) in DCM was added dropwise to the mixture at 0° C. After addition, the reaction mixture was allowed to warm up to room temperature and stirred for overnight. The reaction was quenched with water and the resulting mixture was partitioned with DCM and water, the aqueous layer was extracted with DCM twice, the organic layer was combined, washed with 1N HCl and brine, dried over Na$_2$SO$_4$, and concentrated under reduced pressure to afford a yellow solid, which was re-taken into EtOH. The resulting mixture was then heated to 90° C. for overnight. After removal of volatiles under reduced pressure, the mixture was purified by silica gel column (hexane:EA, 19:1→9:1) to afford the title compound (190 g, 90% over 2 steps) as a white solid. MS: 225.2 (M+H$^+$).

Step C: 6-Fluoronaphthalene-1,3-diol

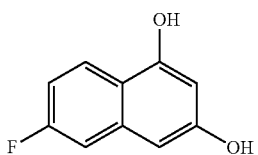 [SMILES: Oc1cc(O)c2ccc(F)cc2c1]

Ethyl 4-(3-fluorophenyl)-3-oxobutanoate (Step B, 34 g, 152 mmol) was added into concentrated sulfuric acid (112 g, 1137 mmol) with small portions at 0° C. After addition, the mixture was stirred for overnight at room temperature. The mixture was poured onto ice, and the resulting mixture was extracted with DCM twice, the organic layer was combined, washed with brine, dried over Na$_2$SO$_4$, and concentrated under reduce pressure to afford a yellow oil, which was purified by silica gel column (hexane:EA, 1:1→1:4) to afford the title compound (15 g, 56%) as an white solid. MS: 179.0 (M+H$^+$).

Step D: 4-((tert-Butyl dimethyl silyl)oxy)-7-fluoronaphthalen-2-ol

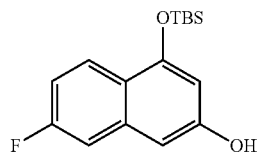 [SMILES: CC(C)(C)[Si](C)(C)Oc1cc(O)cc2cc(F)ccc12]

Under Ar, to a solution of 6-fluoronaphthalene-1,3-diol (Step C, 58 g, 326 mmol), imidazole (26.6 g, 391 mmol) in dry DCM (150 mL) was slowly added TBSCl (46.6 g, 309 mmol) at −5° C., then the reaction mixture was stirred 2 h at −5° C., and quenched with water. The mixture was extracted with DCM 3 times, the organic layer was combined, washed with brine, dried over Na$_2$SO$_4$, and concentrated under reduce pressure to afford a yellow oil, which was purified by silica gel column (DCM:MeOH, 19:1) to afford the title compound (69.5 g, 73%) as a yellow solid. MS: 293.2 (M+H$^+$).

Step E: 4-((tert-Butyl dimethyl silyl)oxy)-7-fluoronaphthalen-2-yl trifluoromethanesulfonate

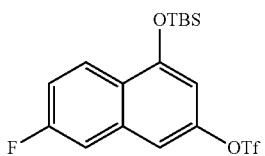

Under Ar, to a solution of 4-((tert-butyldimethylsilyl)oxy)-7-fluoronaphthalen-2-ol (Step D, 40.3 g, 138 mmol) in dry DCM (200 mL) was added DIEPA (21.4 g, 165 mmol) and Tf$_2$O (42.7 g, 151 mmol) slowly at 0° C., then the reaction mixture was stirred for 30 min. Water was added to quench the reaction and the resulting mixture was extracted with DCM twice, the organic layer was combined, washed with brine, dried over Na$_2$SO$_4$, and concentrated under reduce pressure to afford a yellow oil, which was purified by silica gel column (hexane:EA, 10:1) to afford the title compound (40.5 g, 69%) as a yellow oil. MS: 370.2 (M-TBS+H$^+$).

Step F: tert-Butyl((6-fluoro-3-((4-methoxybenzyl)thio)naphthalen-1-yl)oxy)dimethylsilane

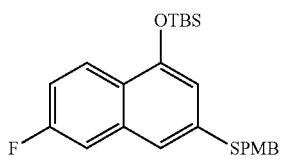

Under Ar, to a mixture of 4-((tert-butyldimethylsilyl)oxy)-7-fluoronaphthalen-2-yl trifluoromethane sulfonate (Step E, 40.5 g, 96 mmol), Xantphos (5.53 g, 9.55 mmol), and Pd$_2$(dba)$_3$ (4.37 g, 4.78 mmol) was added dry dioxane and DIEPA (37.0 g, 287 mmol), (4-methoxyphenyl)methanethiol (19.2 g, 124 mmol) were followed, then the reaction mixture was degased for 10 min, and heated to 110° C. for overnight. After cooling down to room temperature, the mixture was filtrated off and the filtrate was concentrated to give a dark oil, which was purified by silica gel column (hexane:EA, 50:1) to afford the title compound (41.0 g, quantitatively) as a light yellow solid. MS: 429.3 (M+H$^+$).

Step G: 6-Fluoro-3-((4-methoxybenzyl)thio)naphthalen-1-ol (Intermediate A2)

Under Ar, to a solution of tert-butyl((6-fluoro-3-((4-methoxybenzyl)thio)naphthalen-1-yl)oxy)dimethylsilane (Step F, 41.0 g, 96 mmol) in dry THF (150 mL) was added TBAF3.H$_2$O (10.0 g, 38.3 mmol) with small portions, then the reaction mixture was stirred for 3 h at room temperature. Water was added to quench the reaction and the resulting mixture was extracted with EA twice, the organic layer was combined, washed with brine, dried over Na$_2$SO$_4$, and concentrated under reduced pressure to afford a yellow oil, which was purified by silica gel column (hexane:DCM, 1:4) to afford the title compound (25.0 g, 83%) as a white solid. $^1$H NMR (500 MHz, DMSO-d$_6$) δ 10.43 (s, 1H), 8.06 (dd, J=9.2, 6.0 Hz, 1H), 7.48 (dd, J=10.5, 2.5 Hz, 1H), 7.33 (d, J=8.6 Hz, 2H), 7.28 (s, 1H), 7.23 (dd, J=8.9, 2.5 Hz, 1H), 6.86 (d, J=8.6 Hz, 2H), 6.74 (d, J=1.4 Hz, 1H), 4.24 (s, 2H), 3.71 (s, 3H); MS: 315.1 (M+H$^+$).

Example 58

Synthesis of Ethyl 4-bromo-5-chloro-3-methyl-1H-indole-2-carboxylate (Intermediate B1)

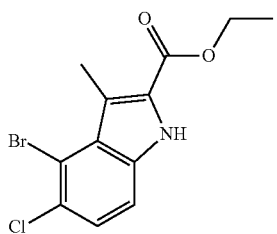 [SMILES: CCOC(=O)c1[nH]c2ccc(Cl)c(Br)c2c1C]

Step A: Ethyl (E)-2-(2-(3-bromo-4-chlorophenyl)hydrazineylidene)butanoate

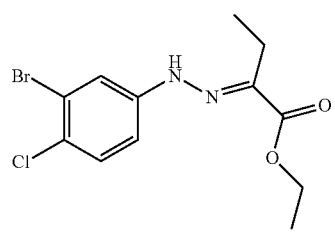 [SMILES: CCOC(=O)/C(CC)=N/Nc1ccc(Cl)c(Br)c1]

To a suspension of 3-bromo-4-chloroaniline (10 g, 48.4 mmol) in the mixed solvent of conc. HCl (20 mL), water (100 mL) and AcOH (30 mL) was added a solution of sodium nitrite (4.01 g, 58.1 mmol) in water (100 mL) at 0° C. for 30 min. After addition, the mixture was stirred at 0° C. for 40 min. Ethyl 2-ethyl-3-oxobutanoate (9.96 g, 63.0 mmol) was added into the reaction mixture, and KOH (8.15 g, 145 mmol) and EtOH (250 mL) were subsequently followed at 0° C. After addition, the reaction mixture was adjusted to pH=7 by KOH, stirred at room temperature for 2 h, and then stirred at 80° C. for 3 h. After removal of volatiles under reduced pressure, the residue was extracted with EA (200 mL) twice, the combined organic layer was concentrated under reduced pressure to give a yellow solid, which was purified by silica gel column (hexane:EA, 5:1) to afford the title compound (14 g, 87%) as a yellow solid. MS: 333.1 (M+H$^+$).

Step B: Ethyl 4-bromo-5-chloro-3-methyl-1H-indole-2-carboxylate (Intermediate B1)

To a solution of ethyl (E)-2-(2-(3-bromo-4-chlorophenyl)hydrazineylidene)butanoate (Step A, 14 g, 43.8 mmol) in EtOH (120 mL) was added conc. H$_2$SO$_4$ (12.89 g, 131 mmol) at 0° C., and then the mixture was heated to reflux for 4 h. After cooling down to room temperature, the resulting mixture was poured into ice-water slowly and the formed precipitate was collected by filtration, the collected solid was purified by silica gel column (hexane:EA, 4:1) and pre-HPLC to afford the title compound (1.1 g, 8%) as a white solid $^1$H NMR (500 MHz, DMSO-d$_6$) δ 12.02 (s, 1H), 7.48 (d, J=8.7 Hz, 1H), 7.44 (d, J=8.8 Hz, 1H), 4.39 (q, J=7.0 Hz, 2H), 2.85 (s, 3H), 1.39 (t, J=7.1 Hz, 3H). MS: 314.0 (M−H$^−$).

Example 59

Synthesis of Methyl 4-bromo-5-chloro-1H-indole-2-carboxylate (Intermediate B2)

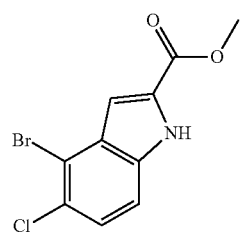

Step A: methyl (Z)-2-azido-3-(2-bromo-3-chlorophenyl)acrylate

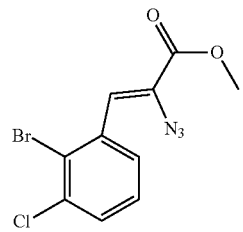 [SMILES: COC(=O)/C(=C/c1cccc(Cl)c1Br)N=[N+]=[N-]]

Under N$_2$, in a 2000 mL three-necked round-bottomed flask sodium methanolate (74 g, 1.37 mol) was dissolved in MeOH (800 mL) to give a white suspension, 2-bromo-3-chlorobenzaldehyde (100 g, 0.46 mol) was added to the reaction mixture at −20° C. Methyl 2-azidoacetate (157.33 g, 1.37 mol) was added to the mixture dropwise over 20 min. Then the reaction mixture was stirred at room temperature for 20 h. H₂O (1000 mL) was added to the reaction mixture followed by extraction with dichloromethane (500 mL×3). The combined organic layer was washed brine and dried over Na₂SO₄, and concentrated under reduced pressure to give a dark yellow solid, which was purified by silica gel column (hexane:EA, 5:1) to afford the title compound (73 g, 51%) as a yellow solid. $^1$H NMR (400 MHz, CDCl₃) δ 7.93 (d, J=7.8 Hz, 1H), 7.45-7.41 (m, 1H), 7.32-7.28 (m, 1H), 7.24 (s, 1H), 3.96 (s, 3H). MS: 317.0 (M+H$^+$).

Step B: Methyl 4-bromo-5-chloro-1H-indole-2-carboxylate (Intermediate B2)

Under N₂, in a 1000 mL round-bottomed flask equipped with an efficient condenser methyl (Z)-2-azido-3-(2-bromo-3-chlorophenyl)acrylate (Step A, 73 g, 0.23 mol) was dissolved into toluene (460 mL) to give a yellow suspension. Then the reaction mixture was heated to reflux for 4 h. After cooling down to room temperature, the reaction mixture was stirred for 1 h at 0° C. with ice-water bath. The formed precipitate was collected by filtration and rinsed with cold toluene (50 mL) to afford the title compound (41 g, 61%) as a white solid. $^1$H NMR (400 MHz, CDCl₃) δ 9.05 (brs, 1H), 7.41-7.31 (m, 2H), 7.26 (dd, J=2.4, 0.9 Hz, 1H), 3.98 (s, 3H). MS: 289.0 (M+H$^+$).

Example 60

Synthesis of Methyl 4-bromo-5-chloro-3-methyl-1H-indole-2-carboxylate (Intermediate B3)

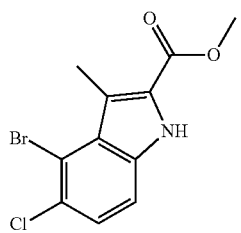 [SMILES: COC(=O)c1[nH]c2ccc(Cl)c(Br)c2c1C]

Step A: Methyl 4-bromo-5-chloro-3-formyl-1H-indole-2-carboxylate

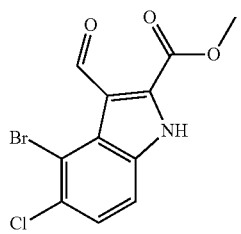

Under Ar, to a mixture of methyl 4-bromo-5-chloro-1H-indole-2-carboxylate (Intermediate B2, 11 g, 38.1 mmol) and N,N-dimethylformamide (6.97 g, 95 mmol) in DCE (120 mL) was added POCl₃ (14.61 g, 95 mmol) dropwise at 0° C. After the addition, the reaction mixture was stirred at 95° C. for overnight. After cooling down to room temperature, the collected precipitate was rinsed with water, dried under reduced pressure to afford the title compound (16 g, quantitatively) as a light brown solid. MS: 315.9 (M+H$^+$).

Step B: Methyl 4-bromo-5-chloro-3-methyl-1H-indole-2-carboxylate (Intermediate B3)

Under Ar, to a solution of methyl 4-bromo-5-chloro-3-formyl-1H-indole-2-carboxylate (8.52 g, 26.9 mmol) in TFA (60 mL) was added triethylsilane (12.52 g, 108 mmol) at 0° C., and then the reaction mixture was stirred at room temperature for 5 h. Sat. NaHCO₃ was added to quench the reaction and the resulting mixture was extracted with EA twice, the organic layer was combined, washed with brine, dried over Na₂SO₄, and concentrated under reduce pressure to afford a yellow solid, which was purified by silica gel column (hexane:EA, 5:1) to afford the title compound (3.8 g, 47%) as a white solid. $^1$H NMR (500 MHz, DMSO-d₆) δ 12.05 (s, 1H), 7.45 (d, J=8.7 Hz, 1H), 7.41 (d, J=8.7 Hz, 1H), 3.90 (s, 3H), 2.83 (s, 3H). MS: 299.9 (M−H).

Example 61

Synthesis of 4-bromo-5-chloro-3-ethyl-1H-indole-2-carboxylate (Intermediate B4)

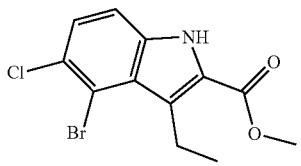 [SMILES: CCc1c(C(=O)OC)[nH]c2ccc(Cl)c(Br)c12]

Step A: Methyl 3-acetyl-4-bromo-5-chloro-1H-indole-2-carboxylate

In a nitrogen flushed 100 mL two-necked round-bottomed flask aluminum trichloride (4.62 g, 34.7 mmol) was dissolved in DCE (10 mL) under nitrogen to give a white suspension in ice/water bath. Acetic anhydride (3.54 g, 34.7 mmol) was dropped to the reaction mixture. After 5 min, methyl 4-bromo-5-chloro-1H-indole-2-carboxylate (Intermediate B2, 2 g, 6.93 mmol) in DCE (20 ml) was dropped to the reaction mixture. Then the mixture was refluxed for 24 h. After cooling to room temperature, H₂O (50 mL) was added to the reaction mixture followed by extraction with ethyl acetate (30 mL×3). The combined organic layer was washed brine and dried Na₂SO₄, and concentrated under reduced pressure to give the crude product, which was loaded to silica gel column and then eluted with ethyl acetate/hexane (1:1) to afford the title compound (1.77 g, 77%) as a yellow solid. ¹H NMR (400 MHz, DMSO-d₆) δ 12.70 (s, 1H), 7.51 (d, J=1.8 Hz, 2H), 3.89 (s, 3H), 2.61 (s, 3H). MS: 331.0 (M+H⁺).

Step B: methyl 4-bromo-5-chloro-3-ethyl-1H-indole-2-carboxylate (Intermediate B4)

In a nitrogen flushed 250 mL round-bottomed flask methyl 3-acetyl-4-bromo-5-chloro-1H-indole-2-carboxylate (Step A, 1.02 g, 3.09 mmol) was dissolved in TFA (10 mL) under nitrogen to give a yellow solution. Triethylsilane (1.794 g, 15.43 mmol) was added to the mixture in one portion. Then the reaction mixture was stirred for overnight at room temperature. Sat. Na₂CO₃ was added to quench the reaction, and the resulting mixture was extracted with EA (20 mL×3). The combined organic layer was washed with brine, dried over Na₂SO₄, and concentrated under reduced pressure to give the crude product, which was loaded to silica gel column and then eluted with ethyl acetate/hexane (1:2) to afford the title compound (776 mg, 79%) as a white solid. ¹H NMR (400 MHz, DMSO-d6) δ 12.10 (s, 1H), 7.46 (d, J=8.7 Hz, 1H), 7.42 (d, J=8.7 Hz, 1H), 3.91 (s, 3H), 3.40-3.28 (m, 2H), 1.21 (t, J=7.3 Hz, 3H). MS: 317.0 (M+H⁺).

Example 62

Synthesis of Methyl 4-bromo-3,5-di chloro-1H-indole-2-carboxylate (Intermediate B5)

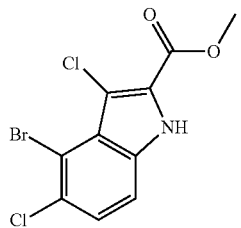 [SMILES: COC(=O)c1[nH]c2ccc(Cl)c(Br)c2c1Cl]

In a nitrogen flushed 50 mL two-necked round-bottomed flask methyl 4-bromo-5-chloro-1H-indole-2-carboxylate (Intermediate B2, 660 mg, 2.287 mmol) was dissolved in dry THF (10 mL) under nitrogen to give a colorless solution at 0° C. 1-chloropyrrolidine-2,5-dione (336 mg, 2.52 mmol) was added to the reaction mixture in one portion. Then the reaction mixture was stirred for overnight at room temperature. H₂O (10 mL) was added to the reaction mixture followed by extraction with ethyl acetate (20 mL×3). The combined organic layer was washed with brine, dried over Na₂SO₄, and concentrated under reduced pressure to give the crude product, which was loaded to silica gel column and then eluted with ethyl acetate/hexane (1:2) to give the title compound (739 mg, quantitatively) as a white solid. ¹H NMR (400 MHz, DMSO-d₆) δ 12.71 (s, 1H), 7.51 (s, 2H), 3.93 (s, 3H). MS: 323.1 (M+H⁺).

Example 63

Synthesis of Methyl 4-bromo-5-chloro-3-fluoro-1H-indole-2-carboxylate (Intermediate B6)

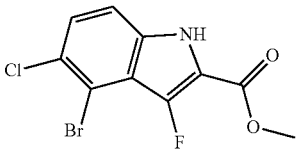 [SMILES: COC(=O)c1[nH]c2ccc(Cl)c(Br)c2c1F]

Under Ar, to a solution of methyl 4-bromo-5-chloro-1H-indole-2-carboxylate (Intermediate B2, 1 g, 3.47 mmol) in 1,2-Dichloroethane (20 mL) was added 1-fluoro-2,4,6-trimethylpyridin-1-ium trifluoromethanesulfonate (3.01 g, 10.40 mmol), the reaction mixture was heated to 80° C. for 28 h. After cooling down to room temperature, sat. NaHCO₃ was added to quench the reaction, and the resulting mixture was extracted with DCM twice. The combined DCM layer was washed with brine, dried over Na₂SO₄, and concentrated under reduced pressure to give a light yellow oil, which was purified by silica gel column (hexane:EA, 1:0→4:1) to afford the title compound (250 mg, 24%) as a white solid. ¹H NMR (500 MHz, CDCl₃) δ 8.57 (s, 1H), 7.43 (d, J=8.8 Hz, 1H), 7.29 (dd, J=8.7, 2.0 Hz, 1H), 4.04 (s, 3H).

Example 64

Synthesis of Methyl 4-bromo-5-cyano-3-methyl-1H-indole-2-carboxylate (Intermediate B7)

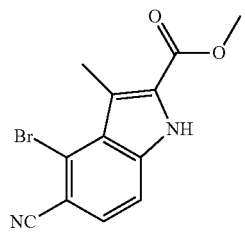 [SMILES: COC(=O)c1[nH]c2ccc(C#N)c(Br)c2c1C]

Step A: (2-Bromo-3-iodophenyl)methanol

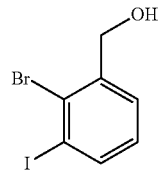

Under Ar, to a solution of 2-bromo-3-iodobenzoic acid (1.7 g, 5.20 mmol) in THF (10 mL) was added borane in THF (7.80 mL, 7.8 mmol, 1.0 M) at 0° C. Then the reaction mixture was stirred for 2 h at 70° C. After cooling down to room temperature, the mixture was poured onto ice. The resulting mixture was extracted with ethyl acetate (10 mL×3). The combined organic layer was washed with brine, dried with Na₂SO₄ and concentrated under reduced pressure to give a yellow oil, which was purified by silica gel column (hexane:EA, 1:0→3:1) to afford the title compound (1.32 g, 81%) as a white solid. MS: 313.9 (M+H$^+$).

Step B: 2-Bromo-3-iodobenzaldehyde

Under Ar, to a solution of (2-bromo-3-iodophenyl)methanol (Step A, 9.24 g, 29.5 mmol) in DCM (50 mL) was added manganese (IV) oxide (20.54 g, 236 mmol) at room temperature. Then the reaction mixture was stirred for overnight at room temperature. The reaction mixture was filtered off through a Buchner funnel and the filtrate was concentrated under reduced pressure to give a yellow oil, which was purified by silica gel column (hexane:EA, 1:0→5:1) to afford the title compound (8.40 g, 91%) as a white solid. MS: 311.9 (M+H$^+$).

Step C: Methyl (Z)-2-azido-3-(2-bromo-3-iodophenyl)acrylate

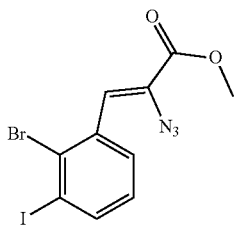 [SMILES: COC(=O)/C(=C/c1cccc(I)c1Br)N=[N+]=[N-]]

Under Ar, to a solution of NaOMe (1.10 g, 20.36 mmol) in MeOH (20 mL) was added 2-bromo-3-iodobenzaldehyde (Step B, 2.11 g, 6.79 mmol) at −20° C., methyl 2-azidoacetate (2.34 g, 20.36 mmol) was added to the reaction mixture dropwise over 5 min. After addition, the reaction mixture was allowed to warm up to room temperature and stirred for overnight. The reaction was quenched with water and the resulting mixture was partitioned with DCM and water, the aqueous layer was extracted with DCM twice, the organic layer was combined, washed with brine, dried over Na$_2$SO$_4$, and concentrated under reduced pressure to afford a yellow solid. which was purified by silica gel column (hexane:EA, 1:0→5:1) to afford the title compound (1.2 g, 43%) as a white solid. $^1$H NMR (400 MHz, CHCl$_3$) δ 7.96 (dd, J=7.9, 1.4 Hz, 1H), 7.86 (dd, J=7.9, 1.6 Hz, 1H), 7.25 (s, 1H), 7.13-7.04 (m, 1H), 3.97 (s, 3H). MS: 408.9 (M+H$^+$).

Step D: Methyl 4-bromo-5-iodo-1H-indole-2-carboxylate

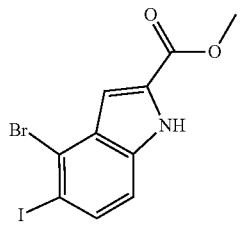

Under Ar, a solution of methyl (Z)-2-azido-3-(2-bromo-3-iodophenyl)acrylate (Step C, 1.2 g, 2.94 mmol) in dry PhMe (10 mL) was refluxed 3 h. After cooling down to 0° C., the formed precipitate was collected by filtration to afford the title compound (0.57 g, 51%) as a white solid. $^1$H NMR (400 MHz, DMSO-d$_6$) δ 12.49 (s, 1H), 7.71 (d, J=8.6 Hz, 1H), 7.29 (dd, J=8.6, 1.0 Hz, 1H), 7.05-6.99 (m, 1H), 3.90 (s, 3H). MS: 380.9 (M+H$^+$).

Step E: Methyl 4-bromo-3-formyl-5-iodo-1H-indole-2-carboxylate

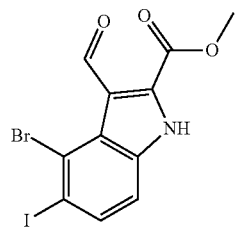 [SMILES: COC(=O)c1[nH]c2ccc(I)c(Br)c2c1C=O]

Under Ar, to a solution of methyl 4-bromo-5-iodo-1H-indole-2-carboxylate (Step D, 1.8 g, 4.57 mmol) and N,N-dimethylformamide (0.835 g, 11.42 mmol) in DCE (15 mL) was added POCl$_3$ (1.751 g, 11.42 mmol) dropwise over 5 min at 0° C.; then the reaction mixture was refluxed for 4 h. After cooling down to room temperature, sat. NaHCO$_3$ (10 mL) was added to the reaction mixture followed by extraction with ethyl acetate (50 mL×3). The combined organic layer was dried Na$_2$SO$_4$, and concentrated under reduced pressure to afford a yellow solid, which was purified by silica gel column (hexane:EA, 1:0→3:1) to afford the title compound (1.5 g, 78%) as a yellow solid. MS: 423.0 (M+H$^+$)

Step F: Methyl 4-bromo-5-iodo-3-methyl-1H-indole-2-carboxylate

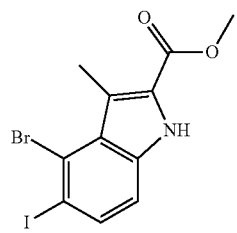 [SMILES: COC(=O)c1[nH]c2ccc(I)c(Br)c2c1C]

Under Ar, to a solution of methyl 4-bromo-3-formyl-5-iodo-1H-indole-2-carboxylate (Step E, 1.5 g, 3.55 mmol) in TFA (10 mL) was added triethylsilane (1.653 g, 14.22 mmol); then the reaction was stirred for 4 h at room temperature. The mixture was poured onto ice, and the aqueous layer was adjusted to pH=8 with sat. NaHCO$_3$, and extracted with ethyl acetate (10 mL×3). The combined organic layer was washed brine, dried Na$_2$SO$_4$, and concentrated under reduced pressure to afford a yellow solid, which was purified by silica gel column (hexane:EA, 1:0→5:1) to afford the title compound (1.25 g, 86%) as a yellow solid. MS: 409.0 (M+H$^+$).

Step G: Methyl 4-bromo-5-cyano-3-methyl-1H-indole-2-carboxylate (Intermediate B7)

Under Ar, to a solution of methyl 4-bromo-5-iodo-3-methyl-1H-indole-2-carboxylate (Step F, 800 mg, 2.03 mmol) and dicyanozinc (119 mg, 1.015 mmol) in dry DMF (10 mL) was added Pd(PPh$_3$)$_4$ (117 mg, 0.102 mmol); then the reaction mixture was stirred for 0.5 h at 120° C. with microwave assistance. H$_2$O (20 mL) was added to the reaction mixture followed by extraction with ethyl acetate (20 mL×3). The combined organic layer was dried over Na$_2$SO$_4$, concentrated under reduced pressure to afford a yellow solid, which was purified by silica gel column (hexane:EA, 1:0→3:1) to afford the title compound (0.56 g, 94%) as a white solid. $^1$H NMR (400 MHz, DMSO-d$_6$) δ 12.37 (s, 1H), 7.62-7.49 (m, 2H), 3.91 (s, 3H), 2.80 (s, 3H). MS: 294.1 (M+H$^+$).

Example 65

Synthesis of Methyl 4-bromo-5-fluoro-3-methyl-1H-indole-2-carboxylate (Intermediate B8)

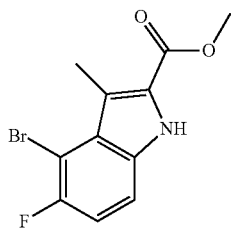

Essentially the same protocol used to prepare Intermediate B3 was used to afford Intermediate B8 (1.86 g) as a yellow solid. $^1$H NMR (400 MHz, DMSO-d$_6$) δ 11.95 (s, 1H), 7.42 (dd, J=8.9, 4.4 Hz, 1H), 7.25 (t, J=9.1 Hz, 1H), 3.89 (s, 3H), 2.80 (s, 3H). MS: 287.1 (M+H$^+$).

Example 66

Synthesis of Methyl 4-bromo-3,5-dimethyl-1H-indole-2-carboxylate (Intermediate B9)

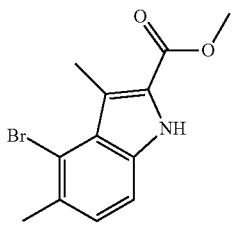

Essentially the same protocol used to prepare Intermediate B3 was used to afford Intermediate B9 (1.07 g) as a yellow solid. MS: 283.1 (M+H$^+$).

Example 67

Synthesis of 2-(((Tetrahydro-2H-pyran-2-yl)oxy)methyl)-3-(4,4,5,5-tetramethyl-1,3,2-dioxaborolan-2-yl)-5,6-dihydro-4H-pyrrolo[1,2-b]pyrazole (Intermediate C1)

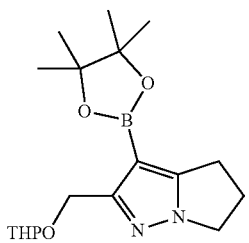

Step A: Nitrosoproline

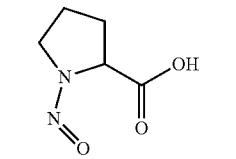

To a solution of L-proline (50 g, 434 mmol) in water (50 mL) was added conc. HCl (40 mL), a solution of sodium nitrite (47.9 g, 695 mmol) in water (50 mL) was slowly added at 0° C. The reaction mixture was stirred for 1 h and extracted with DCM 10 times, the organic layer was combined, dried over Na$_2$SO$_4$, and concentrated under reduced pressure to give the crude title compound as a white solid (57.7 g, 92%), which was directly use without purification. MS: 144.9 (M+H$^+$).

Step B: 3-Oxo-5,6-dihydro-3H-pyrrolo[1,2-c][1,2,3]
oxadiazol-7(4H)-ium-3a-ide

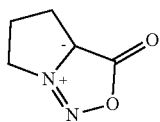

To a solution of nitroso-L-proline (Step A, 57.7 g, 401 mmol) in DCM was added TFAA (84 g, 401 mmol) slowly at 5° C., and the reaction mixture was stirred for 0.5 h. After removal of volatiles under reduced pressure, the crude title compound as a brown solid was collected and directly used without purification (50.5 g, quantitatively). $^1$H NMR (500 MHz, CDCl$_3$) δ 4.47 (t, J=7.7 Hz, 2H), 2.99-2.92 (m, 2H), 2.85-2.76 (m, 2H). MS: 127.0 (M+H$^+$).

Step C: Methyl 5,6-dihydro-4H-pyrrolo[1,2-b]pyrazole-2-carboxylate

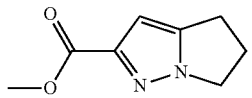

3-oxo-5,6-dihydro-3H-pyrrolo[1,2-c][1,2,3]oxadiazol-7(4H)-ium-3a-ide (Step B, 21 g, 167 mmol) was added into 1,2-diethoxyethylene, and methyl propiolate (42.0 g, 500 mmol) was followed. The reaction mixture was heated to 130° C. for overnight. After cooling down to room temperature and removal of volatiles under reduced pressure, the residue was purified by silica gel column (hexane:EA, 5:1) to afford the title compound (6.6 g, 24%) as a white solid. $^1$H NMR (500 MHz, DMSO-d$_6$) δ 6.48 (s, 1H), 4.12 (t, J=7.3 Hz, 2H), 3.76 (s, 3H), 2.85 (t, J=7.4 Hz, 2H), 2.18-2.09 (m, 2H). MS: 166.9 (M+H$^+$).

Step D: (5,6-Dihydro-4H-pyrrolo[1,2-b]pyrazol-2-yl)methanol

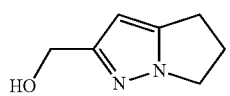

Under Ar, to a mixture of methyl 5,6-dihydro-4H-pyrrolo[1,2-b]pyrazole-2-carboxylate (Step C, 4.5 g, 27.1 mmol) in dry THF (100 mL) was added LiAlH$_4$ (1.23 g, 32.5 mmol) with small portions at 0° C. The reaction mixture was stirred at 0° C. for 2 h and quenched with cold water (4.5 mL), followed by aq. NaOH (15%, 4.5 mL) and water (13.5 mL). The resulting mixture was further stirred for 40 min at room temperature. After filtration through celite, the filtrate was concentrated under reduced pressure to afford the crude title compound as a colorless oil, which was directly used for without purification. MS: 139.0 (M+H$^+$).

Step E: (3-Iodo-5,6-dihydro-4H-pyrrolo[1,2-b]pyrazol-2-yl)methanol

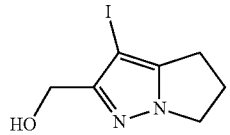

Under Ar, to a mixture of (5,6-dihydro-4H-pyrrolo[1,2-b]pyrazol-2-yl)methanol (Step D, 3.0 g, 21.71 mmol) in dry acetonitrile (80 mL) was added NIS (5.37 g, 23.88 mmol) slowly at 0° C., then the reaction mixture was stirred for 1 h at room temperature. Water was added into the mixture, and the resulting mixture was extracted with EA 3 times, the organic layer was combined, washed with brine, dried over Na$_2$SO$_4$, concentrated under reduced pressure to afford the crude title compound (4.1 g, 63% over 2 steps) as a white solid, which was directly used without purification. $^1$H NMR (500 MHz, DMSO-d$_6$) δ 4.84 (t, J=5.4 Hz, 1H), 4.21 (d, J=5.5 Hz, 2H), 4.04 (t, J=7.2 Hz, 2H), 2.67 (t, J=7.3 Hz, 2H), 2.49-2.40 (m, 2H). MS: 265.1 (M+H$^+$).

Step F: 3-Iodo-2-(((tetrahydro-2H-pyran-2-yl)oxy)methyl)-5,6-dihydro-4H-pyrrolo[1,2-b]pyrazole

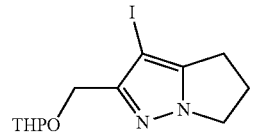

Under Ar, to a solution of (3-iodo-5,6-dihydro-4H-pyrrolo[1,2-b]pyrazol-2-yl)methanol (Step E, 4.1 g, 15.5 mmol) in dry THF (20 mL) was added DHP (1.96 g, 23.29 mmol) and TsOH.H$_2$O (0.30 g, 1.55 mmol), and the reaction mixture was stirred at 40° C. for 4 h. After concentrated under reduced pressure, the residue was purified by silica gel column (hexane:EA, 2:1→1:2) to afford the title compound (4.3 g, 80%) as a colorless oil. MS: 349.1 (M+H$^+$).

Step G: 24(Tetrahydro-2H-pyran-2-yl)oxy)methyl)-3-(4,4,5,5-tetramethyl-1,3,2-dioxaborolan-2-yl)-5,6-dihydro-4H-pyrrolo[1,2-b]pyrazole (Intermediate C1)

Under Ar, to a mixture of 3-iodo-2-(((tetrahydro-2H-pyran-2-yl)oxy)methyl)-5,6-dihydro-4H-pyrrolo[1,2-b]pyrazole (Step F, 2.0 g, 5.74 mmol) in dry THF (20 mL) was added i-PrMgBr (1.69 g, 11.47 mmol) at 0° C., then the reaction mixture was stirred at 0° C. for 30 min, 2-isopropoxy-4,4,5,5-tetramethyl-1,3,2-dioxaborolane (3.21 g, 17.23 mmol) was followed, and the reaction mixture was further stirred for 2 h at room temperature. The reaction was quenched with aqueous NH$_4$Cl, extracted with EA 3 times. The organic layer was combined, washed with brine, dried over Na$_2$SO$_4$, and concentrated under reduced pressure to give a yellow oil, which was purified by silica gel column (hexane:EA, 4:1→1:2) to afford the title compound (2.3 g, 98%) as a colorless oil. MS: 349.4 (M+H$^+$).

Example 68

Synthesis of 5,5-dimethyl-2-(((tetrahydro-2H-pyran-2-yl)oxy)methyl)-3-(4,4,5,5-tetramethyl-1,3,2-dioxaborolan-2-yl)-5,6-dihydro-4H-pyrrolo[1,2-b]pyrazole (Intermediate C2)

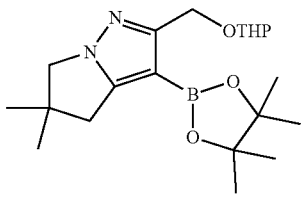

Step A: 1-(tert-butyl) 2-methyl 4,4-dimethyl-5-oxopyrrolidine-1,2-dicarboxylate

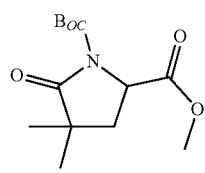 [SMILES: COC(=O)C1CC(C)(C)C(=O)N1C(=O)OC(C)(C)C]

Under Ar, to a solution of 1-(tert-butyl) 2-methyl 5-oxopyrrolidine-1,2-dicarboxylate (25 g, 103 mmol) in dry THF (375 mL) was added LiHMDS (206 mL, 1 M in THF) at −78° C. The mixture was stirred at −78° C. for 15 min and MeI (29.2 g, 206 mmol) was added. The reaction mixture was stirred at −78° C. for 15 min and then 2 h at room temperature. The reaction mixture was quenched with aq. NH$_4$Cl and water (100 mL) was followed, the resulting mixture was extracted with EA 3 times. The combined organic layer was washed with brine, dried over Na$_2$SO$_4$ and concentrated under reduced pressure to give a light yellow oil, which was purified by silica gel column (hexane:EA, 10:1→6:1) to afford the title compound (10.9 g, 39%) as a white solid.

Step B: 1-(tert-butyl) 2-methyl 4,4-dimethylpyrrolidine-1,2-dicarboxylate

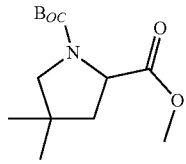 [SMILES: COC(=O)C1CC(C)(C)CN1C(=O)OC(C)(C)C]

Under Ar, to a solution of 1-(tert-butyl) 2-methyl 5-oxopyrrolidine-1,2-dicarboxylate (Step A, 14.5 g, 53.4 mmol) in dry THF (145 mL) was added Et$_3$BHNa (64 mL, 1.0 M in THF) at −78° C. The reaction mixture was stirred at −78° C. for 1 h, and then quenched with sat. NaHCO$_3$ at 0° C. and H$_2$O$_2$ (10 mL) was followed. The resulting mixture was diluted with water and extracted with DCM 3 times; the combined DCM layer was washed with brine, dried over Na$_2$SO$_4$, and concentrated under reduced pressure to give a colourless oil, which was directly used without purification.

Under Ar, to a solution of the above oil in dry DCM was added TES (12.4 g, 107 mmol) and BF$_3$·Et$_2$O (15.2 g, 107 mmol) was followed at −78° C. The reaction mixture was stirred at −78° C. for 2 h, and quenched with sat. NaHCO$_3$ solution. The resulting mixture was extracted with DCM twice; the combined organic layer was dried over Na$_2$SO$_4$ and concentrated under reduced pressure to give a light yellow oil, which was purified by silica gel column (hexane:EA, 20:1→10:1) to afford the title compound (10.0 g, 73% over two steps) as a colourless oil. $^1$H NMR (500 MHz, CDCl$_3$) δ 4.37-4.28 (m, 1H), 3.78-3.72 (m, 3H), 3.40-3.23 (m, 2H), 2.08-2.04 (m, 1H), 1.81-1.68 (m, 1H), 1.51-1.43 (m, 9H), 1.18-1.06 (m, 6H).

Step C: 1-(tert-butoxycarbonyl)-4,4-dimethylpyrrolidine-2-carboxylic acid

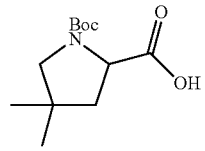

Under Ar, a mixture of 1-(tert-butyl) 2-methyl 4,4-dimethylpyrrolidine-1,2-dicarboxylate (Step B, 10.0 g, 38.9 mmol) and LiOH.H$_2$O (4.65 g, 194 mmol) in MeOH/THF/water (v/v, 40 mL/40 mL/20 mL) was stirred at 50° C. for 2 h. After removal of volatiles under reduced pressure, the residue was diluted with water and extracted with EA at once. The aqueous layer was adjusted to pH=5-6 with AcOH, then was extracted with EA 3 times, the organic layer was combined, washed with brine, dried over Na$_2$SO$_4$, and concentrated under reduced pressure to afford the title compound (9.0 g, 95%) as a colourless oil.

Step D: 4,4-dimethylpyrrolidine-2-carboxylic acid

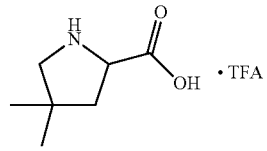

A solution of 1-(tert-butoxycarbonyl)-4,4-dimethylpyrrolidine-2-carboxylic acid (Step C, 9.0 g, 37 mmol) in DCM/TFA (v/v, 50 mL/25 mL) was stirred at room temperature for 1 h. After removal of volatiles under reduced pressure, the product was directly used without purification.

Step E: 5,5-dimethyl-5,6-dihydro-4H-pyrrolo[1,2-c][1,2,3]oxadiazol-7-ium-3-olate

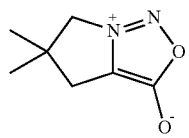

Under Ar, to a solution of the crude 4,4-dimethylpyrrolidine-2-carboxylic acid (Step D) with 2,2,2-trifluoroacetaldehyde (37 mmol) in water (40 mL) was added NaNO₂ (4.0 g, 58 mmol). The reaction mixture was stirred at 0° C. for 1 h and then extracted with DCM 8 times, the organic layer was combined, dried over Na₂SO₄, and concentrated under reduced pressure to give an off-white solid, which was directly used without purification.

Under Ar, to a solution of the above solid in dry DCM (50 mL) was added TFAA (23 g, 110 mmol) at 0° C. The reaction mixture was stirred at 0° C. for 1 h. After removal of volatiles under reduced pressure, the residue was purified by silica gel column (hexane:EA, 2:1→1:1) to afford the title compound (3.0 g, 53% over 3 steps) as a brown oil. MS: 155.1 (M+H⁺).

Step F: Ethyl 5,5-dimethyl-5,6-dihydro-4H-pyrrolo[1,2-b]pyrazole-2-carboxylate

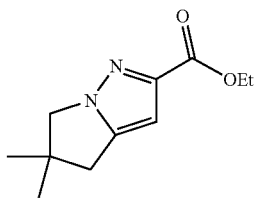

Under Ar, a mixture of 5,5-dimethyl-5,6-dihydro-4H-pyrrolo[1,2-c][1,2,3]oxadiazol-7-ium-3-olate (Step E, 3.0 g, 19.5 mmol) and ethyl propiolate (5.73 g, 58.4 mmol) in 1,2-diethoxyethane (45 mL) was stirred at 120° C. for 16 h. After cooling down to room temperature and removal of volatiles under reduced pressure, the residue was purified by silica gel column (hexane:EA, 10:1→2:1) to afford the title compound (2.9 g, 72%) as a yellow oil.

Step G: (5,5-dimethyl-5,6-dihydro-4H-pyrrolo[1,2-b]pyrazol-2-yl)methanol

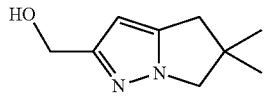

Under Ar, to a solution of ethyl 5,5-dimethyl-5,6-dihydro-4H-pyrrolo[1,2-b]pyrazole-2-carboxylate (Step F, 2.9 g, 13.9 mmol) in dry THF (30 mL) was added LiAlH₄ (783 mg, 20.9 mmol) in portions at 0° C., the reaction mixture was stirred at 0° C. for 1 h and subsequently quenched with water, 15% NaOH, and water (v/v, 0.8 mL/2.4 mL/0.8 mL). The resulting mixture was stirred at room temperature for another 1 h. After filtration, the filtrate was concentrated to give the crude title compound as a light yellow oil, which was directly used without purification. MS:167.1 (M+H⁺).

Step H: 5,5-dimethyl-2-(((tetrahydro-2H-pyran-2-yl)oxy)methyl)-5,6-dihydro-4H-pyrrolo[1,2-b]pyrazole

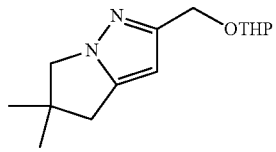

Under Ar, to a solution of (5,5-dimethyl-5,6-dihydro-4H-pyrrolo[1,2-b]pyrazol-2-yl)methanol (Step G, 3.1 g, 13.9 mmol) in dry THF (50 mL) was added TsOH.H₂O (265 mg, 1.39 mmol) and DHP (5.85 g, 69.6 mmol), and the reaction mixture was stirred at room temperature for overnight. After removal of volatiles under reduced pressure, the residue was purified by silica gel column (hexane:EA, 1:1) to afford the title compound (2.5 g, 71% over 2 steps) as a colourless oil. MS: 251.3 (M+H⁺).

Step I: 3-iodo-5,5-dimethyl-2-(((tetrahydro-2H-pyran-2-yl)oxy)methyl)-5,6-dihydro-4H-pyrrolo[1,2-b]pyrazole

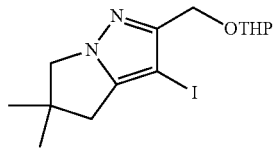

Under Ar, to a solution of 5,5-dimethyl-2-(((tetrahydro-2H-pyran-2-yl)oxy)methyl)-5,6-dihydro-4H-pyrrolo[1,2-b]pyrazole (Step H, 1.25 g, 4.99 mmol) in dry acetonitrile (20 mL) was added NIS (1.12 g, 4.99 mmol). The reaction mixture was stirred at room temperature for 6 h. Water was added, and the resulting mixture was extracted with EA twice. The combined EA layer was dried over Na₂SO₄ and concentrated under reduced pressure to give a light yellow oil, which was purified by silica gel column (hexane:EA, 3:1) to afford the title compound (1.0 g, 53%) as a colourless oil. MS 377.2 (M+H⁺).

Step J: 5,5-dimethyl-2-(((tetrahydro-2H-pyran-2-yl)oxy)methyl)-3-(4,4,5,5-tetramethyl-1,3,2-dioxaborolan-2-yl)-5,6-dihydro-4H-pyrrolo[1,2-b]pyrazole (Intermediate C2)

Under Ar, to a solution of 3-iodo-5,5-dimethyl-2-(((tetrahydro-2H-pyran-2-yl)oxy)methyl)-5,6-dihydro-4H-pyrrolo[1,2-b]pyrazole (Step I, 1.0 g, 2.66 mmol) in dry THF (20 mL) was added i-PrMgBr (5.32 mL, 1.0 M in THF) at 0° C. and stirred for 20 min, 2-isopropoxy-4,4,5,5-tetramethyl-1,3,2-dioxaborolane (990 mg, 5.32 mmol) was added; the reaction mixture was stirred at room temperature for 1 h, and then quenched with sat. NH₄Cl. The resulting mixture was extracted with EA 3 times, washed with brine, dried over Na₂SO₄, and concentrated under reduced pressure to give a yellow oil, which was purified by silica gel column (hexane:EA, 10:1→5:1) to afford the title compound (640 mg, 64%) as a colourless oil. MS: 377.4 (M+H⁺).

Example 69

2-(((Tetrahydro-2H-pyran-2-yl)oxy)methyl)-3-(4,4,5,5-tetramethyl-1,3,2-dioxaborolan-2-yl)-6,7-dihydro-4H-pyrazolo[5,1-c][1,4]oxazine (Intermediate C3)

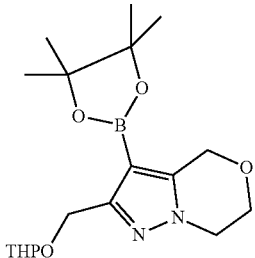

Step A: 4-Nitrosomorpholine-3-carboxylic acid

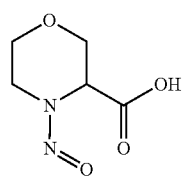 [SMILES: O=NN1CCOCC1C(=O)O]

To a solution of morpholine-3-carboxylic acid (62.6 g, 477 mmol) in H$_2$O (50 mL) was added conc. HCl (70 mL), and a solution of sodium nitrite (52.7 g, 764 mmol) in H$_2$O (80 mL) was followed slowly at 0° C. The reaction mixture was stirred for 1 h, and then extracted with DCM 10 times. The organic layer was combined, dried over Na$_2$SO$_4$, and concentrated under reduced pressure to give the title compound (73.6 g, 96%) as a white solid, which was directly used without purification. MS: 161.1 (M+H$^+$).

Step B: 3-Oxo-6,7-dihydro-3H-[1,2,3]oxadiazolo[4,3-c][1,4]oxazin-8(4H)-ium-3a-ide

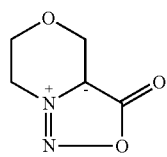

To a solution of 4-nitrosomorpholine-3-carboxylic acid (Step A, 73.6 g, 460 mmol) in DCM was added TFAA (97 g, 460 mmol) slowly at 5° C., and the reaction mixture was stirred for 30 min. After removal of volatiles under reduced pressure, the brown residue was passed through a short silica gel column to afford the title compound (55.0 g, 84%) as a white solid. MS: 163.0 (M+H$^+$)

Step C: Methyl 6,7-dihydro-4H-pyrazolo[5,1-c][1,4]oxazine-2-carboxylate

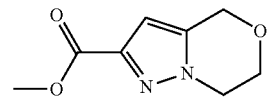

To a solution of 3-oxo-6,7-dihydro-3H-[1,2,3]oxadiazolo[4,3-c][1,4]oxazin-8(4H)-ium-3a-ide (Step B, 16.0 g, 113 mmol) in xylene (200 mL) was added methyl propiolate (25.1 g, 298 mmol), the reaction mixture was heated to 125° C. for 3 h. After cooling down to room temperature, the second portion of methyl propiolate (13 mL)) was added and the reaction was heated to 125° C. for another 7 h. After cooling down to room temperature and removal of volatiles under reduced pressure, the residue was recrystallized from hexane and ethyl actetate (v/v, 10/1) to afford the title compound (20 g, 98%) as a white solid. MS: 183.0 (M+H$^+$).

Step D: (6,7-Dihydro-4H-pyrazolo[5,1-c][1,4]oxazin-2-yl)methanol

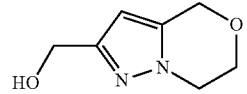

Under Ar, to a mixture of methyl 6,7-dihydro-4H-pyrazolo[5,1-c][1,4]oxazine-2-carboxylate (Step C, 20.5 g, 113 mmol) in dry THF (100 mL) was added LiAlH$_4$ (4.27 g, 113 mmol) at 0° C., then the reaction mixture was stirred at 0° C. for 2 h. Water (4.3 mL) was dropwise added to quench the reaction at 0° C., 15% NaOH (4.3 mL) was followed, and water (13 mL) was added finally. The resulting mixture was stirred for 40 min at room temperature. After filtration through celite, the filtrate was concentrated under reduced pressure to give the crude title compound as a colourless oil, which was directly used without purification. MS: 155.1 (M+H$^+$).

Step E: (3-Iodo-6,7-dihydro-4H-pyrazolo[5,1-c][1,4]oxazin-2-yl)methanol

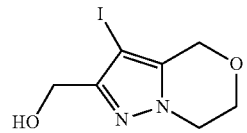

Under Ar, to a mixture of the crude (6,7-dihydro-4H-pyrazolo[5,1-c][1,4]oxazin-2-yl)methanol (Step D, 17.7 g, 115 mmol) in dry acetonitrile (150 mL) was added NIS (38.8 g, 172 mmol) slowly at 0° C., then the reaction mixture was stirred at room temperature for 3 h. Water was added to the reaction, and the resulting mixture was extracted with EA 3 times, the organic layer was combined, washed with brine, dried over Na$_2$SO$_4$, and concentrated under reduced pressure to give the crude title compound as a brown solid, which was directly used without purification. MS: 281.3 (M+H$^+$).

Step F: 3-Iodo-2-(((tetrahydro-2H-pyran-2-yl)oxy)
methyl)-6,7-dihydro-4H-pyrazolo[5,1-c][1,4]oxazine

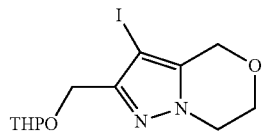

Under Ar, to a solution of the crude (3-iodo-6,7-dihydro-4H-pyrazolo[5,1-c][1,4]oxazin-2-yl)methanol (Step E, 25.0 g) in dry THF (200 mL) was added DHP (7.51 g, 89 mmol) and TsOH.H$_2$O (0.424 g, 2.232 mmol), and the reaction mixture was heated to 40° C. for 4 h. After cooling down to room temperature and removal of volatiles under reduced pressure, the residue was purified by silica gel column (hexane:EA, 1:4) to afford the title compound (25.0 g, 77% over 3 steps) as a colourless oil. MS: 281.3 (M−THP+H$^+$).

Step G: 24(Tetrahydro-2H-pyran-2-yl)oxy)methyl)-3-(4,4,5,5-tetramethyl-1,3,2-dioxaborolan-2-yl)-6,7-dihydro-4H-pyrazolo[5,1-c][1,4]oxazine (Intermediate C3)

Under Ar, to a solution of 3-iodo-2-(((tetrahydro-2H-pyran-2-yl)oxy)methyl)-6,7-dihydro-4H-pyrazolo[5,1-c][1,4]oxazine (Step G, 5.0 g, 13.73 mmol) in dry THF (10 mL) was added i-PrMgBr (4.0 g, 27.4 mmol) at 0° C., then the mixture was stirred at 0° C. for 30 min. 2-isopropoxy-4,4,5,5-tetramethyl-1,3,2-dioxaborolane (5.11 g, 27.5 mmol) was followed, the reaction mixture was stirred at room temperature for another 2 h, and quenched with aq. NH$_4$Cl. The resulting mixture was extracted with EA 3 times, the organic layer was combined, washed with brine, dried over Na$_2$SO$_4$, and concentrated under reduced pressure to give a light yellow oil, which was purified by silica gel column (hexane:EA, 3:1) to afford the title compound (3.36 g, 67%) as a colourless oil. MS: 365.2 (M+H$^+$).

Example 70

Synthesis of 1,3-dimethyl-5-(((tetrahydro-2H-pyran-2-yl)oxy)methyl)-4-(4,4,5,5-tetramethyl-1,3,2-dioxaborolan-2-yl)-1H-pyrazole (Intermediate C4)

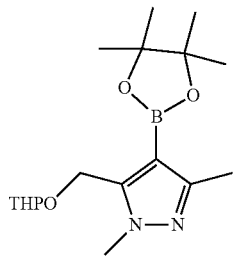

Step A: 4-Iodo-1,3-dimethyl-5-(((tetrahydro-2H-pyran-2-yl)oxy)methyl)-1H-pyrazole

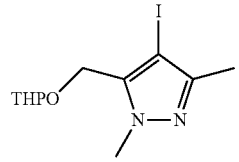

Under Ar, a solution of 4-iodo-1,3-dimethyl-1H-pyrazol-5-yl)methanol (500 mg, 1.984 mmol) in dry THF (10 mL) was added TsOH.H$_2$O (75 mg, 0.397 mmol) and DHP (417 mg, 4.96 mmol), and the reaction mixture was stirred at room temperature for overnight. Sat. NaHCO$_3$ was added and the mixture was extracted with EA twice. The combined EA layer was washed with brine, dried over Na$_2$SO$_4$ and concentrated under reduced pressure to give a crude title compound (567 mg) as a yellow oil. MS: 337.6 (M+H$^+$).

Step B: 1,3-dimethyl-5-(((tetrahydro-2H-pyran-2-yl)oxy)methyl)-4-(4,4,5,5-tetramethyl-1,3,2-dioxaborolan-2-yl)-1H-pyrazole (Intermediate C4)

Under Ar, to a solution of the crude 4-iodo-1,3-dimethyl-5-(((tetrahydro-2H-pyran-2-yl)oxy)methyl)-1H-pyrazole (Step A, 567 mg) in dry THF (10 mL) was added i-PrMgBr (745.3 mg, 5.06 mmol) at 0° C., then the mixture was stirred at 0° C. for 1 h, 2-isopropoxy-4,4,5,5-tetramethyl-1,3,2-dioxaborolane (941 mg, 5.06 mmol) was added; the reaction mixture was stirred at room temperature for 2 h and then quenched with sat. NH$_4$Cl. The resulting mixture was extracted with EA twice, the combined EA layer was washed with brine, dried over Na$_2$SO$_4$, concentrated under reduced pressure to dryness. The residue was purified by silica gel column (hexane:EA, 3:1) to afford the title compound (497 mg, 88% over 2 steps) as a colorless oil. MS: 337.7 (M+H$^+$).

Example 71

Synthesis of 1,5-dimethyl-3-(((tetrahydro-2H-pyran-2-yl)oxy)methyl)-4-(4,4,5,5-tetramethyl-1,3,2-dioxaborolan-2-yl)-1H-pyrazole (Intermediate C5)

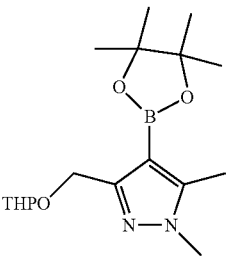

Essentially the same protocol used to prepare Intermediate C4 was used to afford Intermediate C5 (12 g) as a colorless oil. MS: 337.8 (M+H$^+$).

Example 72

Synthesis of 2-(3-(((tert-butyldimethylsilyl)oxy)methyl)-5-methyl-4-(4,4,5,5-tetramethyl-1,3,2-dioxaborolan-2-yl)-1H-pyrazol-1-yl)-N-methylacetamide (Intermediate C6)

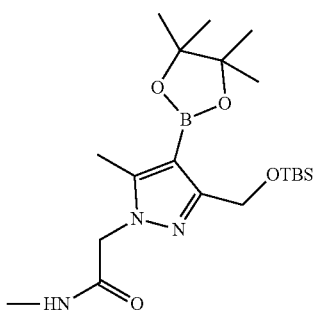 [SMILES: CNC(=O)Cn1nc(CO[Si](C)(C)C(C)(C)C)c(B2OC(C)(C)C(C)(C)O2)c1C]

Step A: Ethyl 2-(3-(((tert-butyldimethylsilyl)oxy)methyl)-4-iodo-5-methyl-1H-pyrazol-1-yl)acetate In a dried 100 mL round flask, 3-(((tert-butyldimethylsilyl)oxy)methyl)-4-iodo-5-methyl-1H-pyrazole (2.0 g, 5.68 mmol) was dissolved in dry DMF (60 mL), ethyl 2-chloroacetate (0.765 g, 6.24 mmol) and $Cs_2CO_3$ (3.70 g, 11.35 mmol) were added to the reaction mixture. The reaction was stirred for 2 h at room temperature and then diluted with $H_2O$ (100 mL), the resulting mixture was extracted with EA 3 times, the combined EA layer was washed with saturated NaCl, dried over $Na_2SO_4$, and concentrated under reduced pressure to give the crude product, which was purified with silica gel column (hexane:EA, 3:2) to afford the title compound (0.8 g, 32%) as a colorless oil. $^1$H NMR (400 MHz, $CDCl_3$) δ 4.88 (s, 2H), 4.64 (s, 2H), 4.25 (q, J=7.1 Hz, 2H), 2.28 (s, 3H), 1.30 (t, J=7.1 Hz, 3H), 0.94 (s, 9H), 0.13 (s, 6H). MS: 439.1 (M+H$^+$).

Step B: 2-(3-(((tert-butyldimethylsilyl)oxy)methyl)-4-iodo-5-methyl-1H-pyrazol-1-yl)-N-methylacetamide

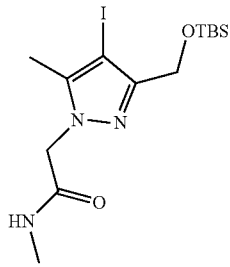 [SMILES: CNC(=O)Cn1nc(CO[Si](C)(C)C(C)(C)C)c(I)c1C]

In a dried 100 ml round flask, ethyl 2-(3-(((tert-butyldimethylsilyl)oxy)methyl)-4-iodo-5-methyl-1H-pyrazol-1-yl)acetate (Step A, 400 mg, 0.91 mmol) was dissolved in MeOH (10 mL). A Solution of $MeNH_2$ in MeOH (5.0 eq) was added to the reaction mixture, and the reaction mixture was stirred for 1 h. After removal of volatiles under reduced pressure, the residue was purified with silica gel column (EA:heptane=10%-100%) to afford the title compound (250 mg, 65%) as a colorless oil. $^1$H NMR (400 MHz, $CDCl_3$) δ 6.05 (s, 1H), 4.77 (s, 2H), 4.66 (s, 2H), 2.80 (d, J=4.9 Hz, 3H), 2.31 (s, 3H), 0.95 (s, 9H), 0.16 (s, 6H). MS: 424.1 (M+H$^+$).

Step C: 2-(3-(((tert-butyldimethylsilyl)oxy)methyl)-5-methyl-4-(4,4,5,5-tetramethyl-1,3,2-dioxaborolan-2-yl)-1H-pyrazol-1-yl)-N-methylacetamide (Intermediate C6)

In a dried 50 mL two-necked round-bottomed flask, 2-(3-(((tert-butyldimethylsilyl)oxy)methyl)-4-iodo-5-methyl-1H-pyrazol-1-yl)-N-methyl acetamide (Step B, 545 mg, 1.287 mmol) was dissolved in dry THF (10 mL) under nitrogen. The mixture was cooled down to 0° C. i-PrMgBr (990 mg, 6.72 mmol) was added and the mixture was stirred for 1 h at 0° C., 2-isopropoxy-4,4,5,5-tetramethyl-1,3,2-dioxaborolane (719 mg, 3.86 mmol) was added and the reaction mixture was allowed to warm up to room temperature, and stirred for 2 h. After removal of volatiles under reduced pressure, the residue was purified with silica gel column (EA:hep=10%-70%) to afford the title compound (340 mg, 62%) as a colorless oil. $^1$H NMR (400 MHz, $CDCl_3$) δ 5.95 (s, 1H), 4.89 (s, 2H), 4.85 (s, 2H), 2.77 (d, J=4.9 Hz, 3H), 2.40 (s, 3H), 1.30 (d, J=24.4 Hz, 12H), 0.90 (s, 9H), 0.08 (s, 6H). MS: 423.3 (M+H$^+$).

Example 73

Synthesis of 2-(5-(((tert-butyldimethylsilyl)oxy)methyl)-3-methyl-4-(4,4,5,5-tetramethyl-1,3,2-dioxaborolan-2-yl)-1H-pyrazol-1-yl)-N-methyl acetamide (Intermediate C7)

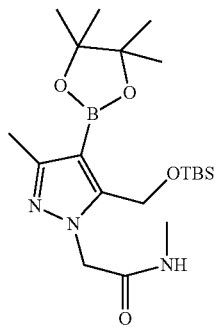 [SMILES: CNC(=O)Cn1nc(C)c(B2OC(C)(C)C(C)(C)O2)c1CO[Si](C)(C)C(C)(C)C]

Essentially the same protocol used to prepare Intermediate C6 was used to afford Intermediate C7 (160 mg) as a colorless oil. $^1$H NMR (400 MHz, CDCl$_3$) δ 6.21 (s, 1H), 4.83 (s, 2H), 4.72 (s, 2H), 2.78 (d, J=4.9 Hz, 3H), 2.42 (s, 3H), 1.32 (s, 12H), 0.94 (s, 9H), 0.13 (s, 6H). MS: 423.3 (M+H$^+$).

Example 74

Synthesis of 3-(((tert-butyldimethylsilyl)oxy)methyl)-1-(2-methoxyethyl)-5-methyl-4-(4,4,5,5-tetramethyl-1,3,2-dioxaborolan-2-yl)-1H-pyrazole (Intermediate C8)

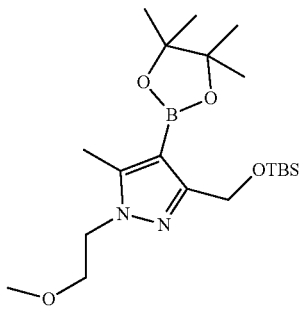 [SMILES: COCCn1nc(CO[Si](C)(C)C(C)(C)C)c(B2OC(C)(C)C(C)(C)O2)c1C]

Step A: 3-(((tert-butyldimethylsilyl)oxy)methyl)-4-iodo-1-(2-methoxyethyl)-5-methyl-1H-pyrazole

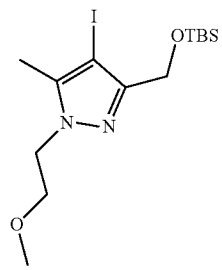 [SMILES: COCCn1nc(CO[Si](C)(C)C(C)(C)C)c(I)c1C]

In a dried 100 mL round flask, 3-(((tert-butyldimethylsilyl)oxy)methyl)-4-iodo-5-methyl-1H-pyrazole (1.3 g, 3.69 mmol) was dissolved in dry DMF (20 mL) under nitrogen, 1-bromo-2-methoxyethane (0.56 g, 4.06 mmol) and Cs$_2$CO$_3$ (2.40 g, 7.38 mmol) were added to the mixture, the reaction was stirred for 2 h at room temperature and then diluted with H$_2$O (100 mL). The resulting mixture was extracted with EA 3 times, the combined EA layer was washed with sat. NaCl, dried over Na$_2$SO$_4$, and concentrated under reduced pressure to give the crude product, which was purified by silica gel column (hexane:EA, 1:1) to afford the title compound (520 mg, 34%) as a colourless oil. $^1$H NMR (400 MHz, CDCl$_3$) δ 4.72 (s, 2H), 4.38 (t, J=5.8 Hz, 2H), 3.74 (t, J=5.8 Hz, 2H), 3.33 (s, 3H), 2.25 (s, 3H), 0.92 (s, 9H), 0.12 (s, 6H). MS: 411.1 (M+H$^+$).

Step B: 3-(((tert-butyldimethylsilyl)oxy)methyl)-1-(2-methoxyethyl)-5-methyl-4-(4,4,5,5-tetramethyl-1,3,2-dioxaborolan-2-yl)-1H-pyrazole (Intermediate C8)

In a 50 mL two-necked round-bottomed flask, 3-(((tert-butyldimethylsilyl)oxy) methyl)-4-iodo-1-(2-methoxyethyl)-5-methyl-1H-pyrazole (Step A, 500 mg, 1.22 mmol) was dissolved in dry THF (10 mL) under nitrogen. The mixture was cooled to 0° C. i-MgBr (890 mg, 6.04 mmol) was added and the mixture was stirred for 1 h at 0° C., then 2-isopropoxy-4,4,5,5-tetramethyl-1,3,2-dioxaborolane (680 mg, 3.66 mmol) was added to the mixture. The reaction mixture was allowed to warm up to room temperature, and stirred for 2 h. The reaction mixture was quenched with water and diluted with dichloromethane. The organic layer was separated, washed with sat. NaCl, dried over Na$_2$SO$_4$, and concentrated under reduced pressure to give the crude product, which was loaded to silica gel column and then eluted with ethyl acetate/hexane from 10% to 50% to afford the title compound (480 mg, 96%) as a colourless oil. $^1$H NMR (400 MHz, CDCl$_3$) δ 4.94 (s, 2H), 4.35 (t, J=6.1 Hz, 2H), 3.77 (t, J=6.1 Hz, 2H), 3.34 (s, 3H), 2.37 (s, 3H), 1.31 (s, 12H), 0.91 (s, 9H), 0.08 (s, 6H). MS: 411.3 (M+H$^+$).

Example 75

Synthesis of 5-(((tert-butyldimethylsilyl)oxy)methyl)-1-(2-methoxyethyl)-3-methyl-4-(4,4,5,5-tetramethyl-1,3,2-dioxaborolan-2-yl)-1H-pyrazole (Intermediate C9)

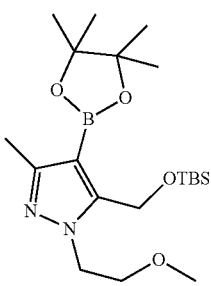

Essentially the same protocol used to prepare Intermediate C8 was used to afford Intermediate C9 (230 mg) as a colorless oil. $^1$H NMR (400 MHz, CDCl$_3$) δ 4.79 (s, 2H), 4.19 (t, J=5.7 Hz, 2H), 3.74 (t, J=5.7 Hz, 2H), 3.31 (s, 3H), 2.44 (s, 3H), 1.31 (s, 12H), 0.93 (s, 9H), 0.12 (s, 6H).

Example 76

Synthesis of 5-(Difluoromethyl)-1-methyl-3-(((tetrahydro-2H-pyran-2-yl)oxy)methyl)-4-(4,4,5,5-tetramethyl-1,3,2-dioxaborolan-2-yl)-1H-pyrazole (Intermediate C10)

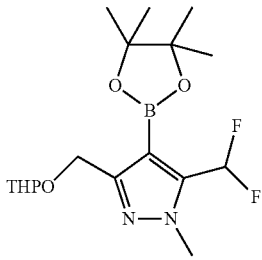

Step A: (5-(((tert-butyl dimethyl silyl)oxy)methyl)-1-methyl-1H-pyrazol-3-yl)methyl benzoate

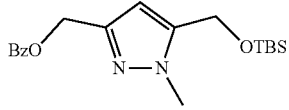

Under Ar, to a solution of (5-(((tert-butyldimethylsilyl)oxy)methyl)-1-methyl-1H-pyrazol-3-yl)methanol (2.50 g, 9.75 mmol) in dry DCM (25 mL) was added DMAP (0.20 g, 0.98 mmol) and benzoic anhydride (2.43 g, 10.72 mmol), and the reaction mixture was stirred at room temperature for overnight. After removal of volatiles under reduced pressure, the residue was purified by silica gel column (hexane:EA, 10:1→4:1) to afford the title compound (2.40 g, 68%) as colourless oil. MS: 362.2 (M+H⁺).

Step B: (5-(Hydroxymethyl)-1-methyl-1H-pyrazol-3-yl)methyl benzoate

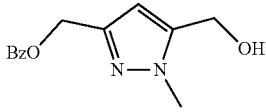

Under Ar, to a solution of (5-(((tert-butyldimethyl silyl)oxy)methyl)-1-methyl-1H-pyrazol-3-yl)methyl benzoate (Step A, 2.40 g, 6.66 mmol), AcOH (0.80 g, 13.31 mmol) in dry THF (20 mL) was added 1N TBAF in THF (20 mL, 20 mmol), then the reaction mixture was stirred at room temperature for 3 h. Water was added to quench the reaction and the resulting mixture was extracted with EA 3 times. The combined EA layer was washed with aq. NaHCO₃, brine, dried over Na₂SO₄, and concentrated under reduced pressure to give a yellow oil, which was purified by silica gel column (hexane:EA, 3:1→1:2) to afford the title compound (1.15 g, 70%) as a white solid. MS: 247.4 (M+H⁺).

Step C: (5-Formyl-1-methyl-1H-pyrazol-3-yl)methyl benzoate

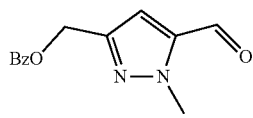

Under Ar, to a solution of (5-(hydroxymethyl)-1-methyl-1H-pyrazol-3-yl)methyl benzoate (Step B, 1.15 g, 4.67 mmol) in dry DCM (20 mL) was added DMP (3.96 g, 9.34 mmol), then the reaction was stirred at room temperature for 1 h and then diluted with EtOAc. After filtration, the filtrate was concentrated under reduced pressure to give a light yellow oil, which was purified by silica gel column (DCM: MeOH, 100:1) to afford the title compound (1.05 g, 92%) as a white solid. MS: 245.2 (M+H⁺).

Step D: (5-(Difluoromethyl)-1-methyl-1H-pyrazol-3-yl)methyl benzoate

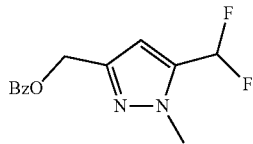

Under Ar, to a solution of (5-formyl-1-methyl-1H-pyrazol-3-yl)methyl benzoate (Step C, 1.05 g, 4.30 mmol) in dry DCM (20 mL) was added DAST (2.85 g, 12.90 mmol) at 0° C., the reaction solution was stirred at room temperature for overnight and quenched with sat NaHCO₃. The resulting mixture was extracted with DCM twice, the combined organic layer was washed with brine, dried over Na₂SO₄, and concentrated under reduced pressure to give a yellow oil, which was purified by silica gel column (hexane:EA, 10:1→5:1) to afford the title compound (0.90 g, 79%) as a colourless oil. MS: 267.2 (M+H⁺).

Step E: (5-(Difluoromethyl)-4-iodo-1-methyl-1H-pyrazol-3-yl)methyl benzoate

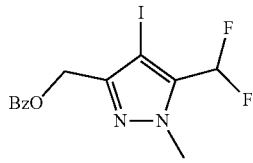

Under Ar, to a solution of (5-(difluoromethyl)-1-methyl-1H-pyrazol-3-yl)methyl benzoate (Step D, 900 mg, 3.38 mmol) in AcOH (6 mL) was added a solution of NIS (913 mg, 4.06 mmol) in TFA (6 mL). The reaction solution was stirred at 80° C. for 1 h. After cooling down to room temperature and removal of volatiles under reduced pressure, the residue was diluted with EA, the organic layer was washed with aq. Na₂S₂O₃ and sat. NaHCO₃, dried over Na₂SO₄, and concentrated under reduced pressure to give a yellow oil, which was purified by silica gel column (hexane: EA, 10:1) to afford the title compound (1.25 g, 94%) as white solid. MS: 392.0 (M+H$^+$).

Step F: (5-(Difluoromethyl)-4-iodo-1-methyl-1H-pyrazol-3-yl)methanol

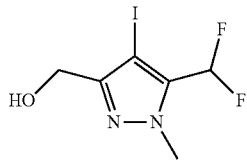

To a solution of (5-(difluoromethyl)-4-iodo-1-methyl-1H-pyrazol-3-yl)methyl benzoate (Step E, 1.25 g, 3.19 mmol) in MeOH (25 mL) was added K$_2$CO$_3$ (2.20 g, 15.94 mmol), and the reaction mixture was stirred at room temperature for 1 h. Water was added, and the resulting mixture was extracted with EA 3 times. The combined organic layer was washed with brine, dried over Na$_2$SO$_4$, and concentrated under reduced pressure to give the crude title compound (918 mg) as a yellow oil, which was directly used for next step without further purification.

Step G: 5-(difluoromethyl)-4-iodo-1-methyl-3-(((tetrahydro-2H-pyran-2-yl)oxy)methyl)-1H-pyrazole

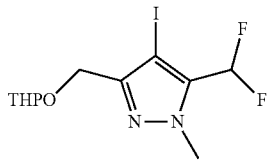

Under Ar, to a solution of the crude (5-(difluoromethyl)-4-iodo-1-methyl-1H-pyrazol-3-yl)methanol (Step F, 918 mg) in dry THF (15 mL) was added DHP (670 mg, 7.97 mmol) and TsOH.H$_2$O (60.6 mg, 0.319 mmol), and the reaction mixture was stirred at room temperature for overnight. After removal of volatiles under reduced pressure, the residue was purified by silica gel column (hexane:EA, 10:1) afford the title compound (1.08 g, 91% for two steps) as a colourless oil. MS: 271.2 (M-OTHP+H$^+$).

Step H: 5-(difluoromethyl)-1-methyl-3-(((tetrahydro-2H-pyran-2-yl)oxy)methyl)-4-(4,4,5,5-tetramethyl-1,3,2-dioxaborolan-2-yl)-1H-pyrazole (Intermediate C10)

Under Ar, to a solution of 5-(difluoromethyl)-4-iodo-1-methyl-3-(((tetrahydro-2H-pyran-2-yl)oxy)methyl)-1H-pyrazole (Step G, 750 mg, 2.02 mmol) in dry THF (12 mL) was added 2.8N i-PrMgBr in THF (2.06 mL, 5.77 mmol) at 0° C. and the mixture was stirred for 20 min. 2-Isopropoxy-4,4,5,5-tetramethyl-1,3,2-dioxaborolane (1125 mg, 6.05 mmol) was added and the reaction mixture was stirred at room temperature for 1 h. The reaction was quenched with sat. aq. NH$_4$Cl and extracted with EA twice. The combined EA layers were dried over anhydrous Na$_2$SO$_4$ and concentrated under reduced pressure to give a yellow oil, which was purified by silica gel column chromatography (hexane:EA, 10:1) to afford the title compound (530 mg, 71%) as a colourless oil. MS: 289.2 (M-THP+H$^+$).

Example 77

Synthesis of S-((5-(((tert-butyldimethylsilyl)oxy)methyl)-1-methyl-1H-pyrazol-3-yl)methyl) ethanethioate (Intermediate D1)

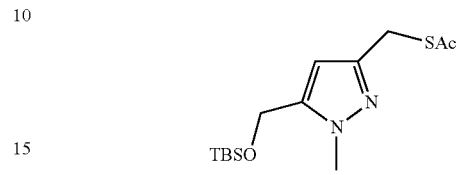

Step A: 3-(Bromomethyl)-5-(((tert-butyl dimethyl silyl)oxy)methyl)-1-methyl-1H-pyrazole

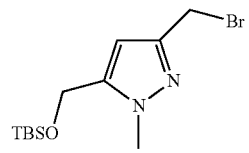 [SMILES: Cn1nc(CBr)cc1CO[Si](C)(C)C(C)(C)C]

Under Ar, PPh$_3$ (511 mg, 1.95 mmol) and CBr$_4$ (647 mg, 1.95 mmol) were added subsequently to a solution of (5-(((tert-butyldimethyl silyl)oxy)methyl)-1-methyl-1H-pyrazol-3-yl)methanol (250 mg, 0.98 mmol) in dry DCM (10 mL). The reaction mixture was stirred for 3 h. After removal of volatiles under reduced pressure, the residue was purified by silica gel column (hexane:DCM, 1:4) to afford the title compound (300 mg, 96%) as a yellow oil. MS: 320.6 (M+H$^+$).

Step B: S-((5-(((tert-butyldimethylsilyl)oxy)methyl)-1-methyl-1H-pyrazol-3-yl)methyl) ethanethioate (Intermediate D1)

Under Ar, to a solution of 3-(bromomethyl)-5-(((tert-butyldimethylsilyl)oxy)methyl)-1-methyl-1H-pyrazole (Step A, 380 mg, 1.19 mmol) in dry THF (15 mL) was added KSAc (272 mg, 2.38 mmol), then the reaction mixture was heated to reflux for 1 h. After cooling down to room temperature and removal of volatiles under reduced pressure, the residue was purified by silica gel column (hexane: EA, 3:2) to afford the title compound (110 mg, 29%) as a yellow oil. MS: 316.1 (M+H$^+$); 337.2 (M+Na$^+$).

Example 78

Synthesis of S-((5-(((tert-butyldimethylsilyl)oxy)methyl)-1-isopropyl-1H-pyrazol-3-yl)methyl) ethanethioate (Intermediate D2)

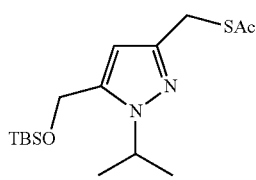

Essentially the same protocol used to prepare Intermediate D1 was used to afford Intermediate D2 (210 mg) as a yellow oil. MS: 344.3 (M+H⁺).

Example 79

Synthesis of 5-(((tert-Butyldimethylsilyl)oxy)methyl)-1-methyl-1H-pyrazole-3-carbaldehyde (Intermediate D3)

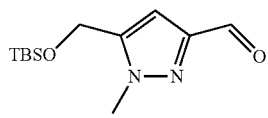 [SMILES: Cn1nc(C=O)cc1CO[Si](C)(C)C(C)(C)C]

Under Ar, to a solution of (5-(((tert-butyldimethylsilyl)oxy)methyl)-1-methyl-1H-pyrazol-3-yl)methanol (2.00 g, 7.80 mmol) in dry DCM (20 mL) was added DMP (6.62 g, 15.60 mmol) at 0° C. The reaction mixture was stirred at room temperature for 2 h. A mixed solvent of EA and hexane (v/v, 1:1) was added, and the formed precipitate was filtered off. The filtrate was concentrated under reduced pressure to give a yellow oil, which was purified by silica gel column (hexane:EA, 10:1→5:1) to afford the title compound (1.70 g, 86%) as a white foam. MS: 255.7 (M+H⁺).

Example 80

Synthesis of Ethyl 5-chloro-4-(2-(hydroxymethyl)-6,7-dihydro-4H-pyrazolo[5,1-c][1,4]oxazin-3-yl)-1-(3-((3-((4-methoxybenzyl)thio)naphthalen-1-yl)oxy)propyl)-3-methyl-1H-indole-2-carboxylate (Intermediate No. 10)

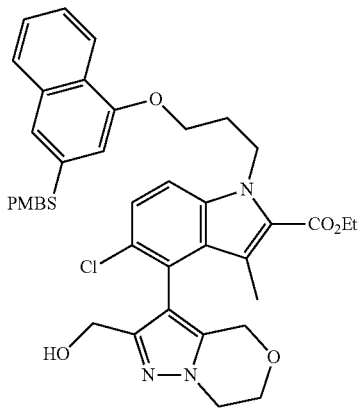

Step A: (3-(3-Bromopropoxy)naphthalen-1-yl)(4-methoxybenzyl)sulfane

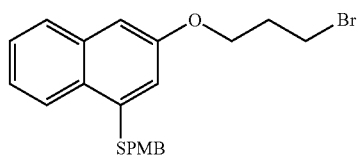

Under Ar, to a solution of 3-((4-methoxybenzyl)thio)naphthalen-1-ol (Intermediate A1, 12 g, 40.5 mmol) in dry acetonitrile (160 mL) was added 1,3-dibromopropane (82 g, 405 mmol) and K₂CO₃ (28.0 g, 202 mmol), then the reaction mixture was stirred at 70° C. for 5 h. After cooling down to room temperature and filtration, the filtrate was concentrated under reduced pressure to give a light yellow oil, which was purified by silica gel column (hexane:EA, 5:1 and then DCM) to afford the title compound (11.1 g, 66%) as a white solid. ¹H NMR (500 MHz, DMSO-d₆) δ 8.12 (d, J=8.2 Hz, 1H), 7.79 (d, J=8.2 Hz, 1H), 7.53 (t, J=7.5 Hz, 1H), 7.46 (d, J=7.8 Hz, 2H), 7.40-7.33 (m, 2H), 6.96-6.86 (m, 3H), 4.34 (s, 2H), 4.28 (t, J=5.8 Hz, 2H), 3.81 (t, J=6.5 Hz, 2H), 3.73 (s, 3H), 2.40 (m, 2H).

Step B: Ethyl 4-bromo-5-chloro-1-(3-((3-((4-methoxybenzyl)thio)naphthalen-1-yl)oxy)propyl)-3-methyl-1H-indole-2-carboxylate (Intermediate No. 11)

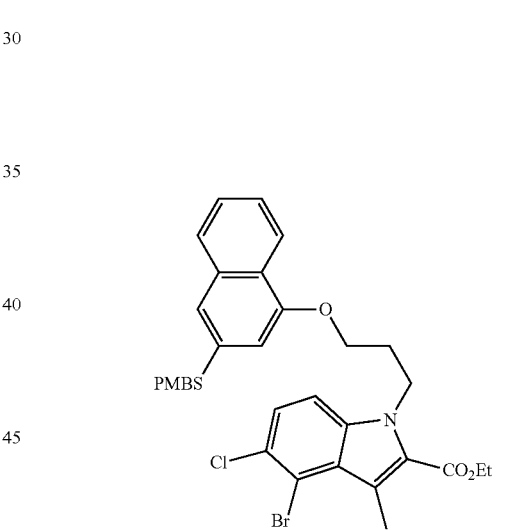

Under Ar, to a solution of ethyl 4-bromo-5-chloro-3-methyl-1H-indole-2-carboxylate (Intermediate B1, 650 mg, 2.05 mmol)) in dry DMF (15 mL) was added Cs₂CO₃ (1.34 g, 4.11 mmol and (4-(3-bromopropoxy)naphthalen-2-yl)(4-methoxybenzyl)sulfane (Step A, 1.03 g, 2.46 mmol) at room temperature, and then the reaction mixture was stirred at 80° C. for 2 h. After cooling down to room temperature, the mixture was partitioned with EA (30 mL) and water (30 mL), the aqueous layer was extracted with EA twice. The combined organic layer was washed with brine, dried over Na₂SO₄, and concentrated under reduced pressure to give a yellow oil, which was purified by silica gel column (hexane:EA, 2:1) to afford the title compound (1.2 g, 89%) as a white solid. MS: 652.2 (M+H⁺).

Step C: Ethyl 5-chloro-1-(3-((3-((4-methoxybenzyl)thio)naphthalen-1-yl)oxy)propyl)-3-methyl-4-(2-(((tetrahydro-2H-pyran-2-yl)oxy)methyl)-6,7-dihydro-4H-pyrazolo[5,1-c][1,4]oxazin-3-yl)-1H-indole-2-carboxylate (Intermediate No. 12)

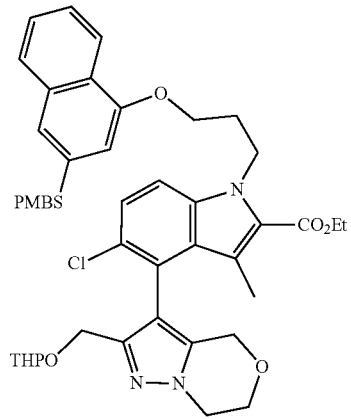

Under Ar, the mixture of ethyl 4-bromo-5-chloro-1-(3-((3-((4-methoxybenzyl)thio)naphthalen-1-yl)oxy)propyl)-3-methyl-1H-indole-2-carboxylate (Step B, 300 mg, 0.459 mmol), 2-(((tetrahydro-2H-pyran-2-yl)oxy)methyl)-3-(4,4,5,5-tetramethyl-1,3,2-dioxaborolan-2-yl)-6,7-dihydro-4H-pyrazolo[5,1-c][1,4]oxazine (Intermediate C3, 301 mg, 0.827 mmol), $K_2CO_3$ (381 mg, 2.76 mmol) and $Pd(Ph_3P)_4$ (159 mg, 0.138 mmol) in the mixed solvent of dioxane (10 mL) and water (2 mL) was stirred at 120° C. with microwave assistance for 1.5 h. After cooling down to room temperature and removal of volatiles under reduced pressure, the residue was partitioned with EA and water, the organic layer was separated, and the aqueous layer was extracted with EA twice. The combined organic layer was dried over $Na_2SO_4$, and concentrated under reduced pressure to give a yellow oil, which was purified by silica gel column (hexane:EA, 1:1) to afford the title compound (350 mg, 94%) as a white solid. MS: 810.4 (M+H$^+$).

Step D: Ethyl 5-chloro-4-(2-(hydroxymethyl)-6,7-dihydro-4H-pyrazolo[5,1-c][1,4]oxazin-3-yl)-1-(3-((3-((4-methoxybenzyl)thio)naphthalen-1-yl)oxy)propyl)-3-methyl-1H-indole-2-carboxylate (Intermediate No. 10)

Under Ar, to a solution of ethyl 5-chloro-1-(3-((3-((4-methoxybenzyl)thio)naphthalen-1-yl)oxy)propyl)-3-methyl-4-(2-(((tetrahydro-2H-pyran-2-yl)oxy)methyl)-6,7-dihydro-4H-pyrazolo[5,1-c][1,4]oxazin-3-yl)-1H-indole-2-carboxylate (Step B, 350 mg, 0.432 mmol) in dry MeOH (10 mL) and THF (4 mL) was added TsOH.H$_2$O (24.6 mg, 0.130 mmol)), then the reaction mixture was stirred at room temperature for overnight. After removal of volatiles under reduced pressure, the residue was purified by silica gel column (DCM:MeOH, 20:1) to afford the title compound (270 mg, 87%) as a light yellow foam. MS: 726.4 (M+H$^+$).

Example 81

Synthesis of Methyl 5-chloro-1-(3-((6-fluoro-3-((4-methoxybenzyl)thio)naphthalen-1-yl)oxy)propyl)-4-(2-(hydroxymethyl)-5,6-dihydro-4H-pyrrolo[1,2-b]pyrazol-3-yl)-3-methyl-1H-indole-2-carboxylate (Intermediate No. 21)

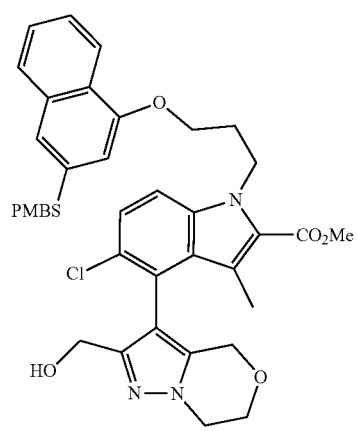

Essentially the same protocol used to prepare Intermediate No. 10 was used to afford Intermediate No. 21 (230 mg) as a white solid. MS: 714.7 (M+H$^+$).

Example 82

Synthesis of Methyl 5-chloro-1-(3-((6-fluoro-3-((4-methoxybenzyl)thio)naphthalen-1-yl)oxy)propyl)-4-(2-(hydroxymethyl)-5,5-dimethyl-5,6-dihydro-4H-pyrrolo[1,2-b]pyrazol-3-yl)-3-methyl-1H-indole-2-carboxylate (Intermediate No. 22)

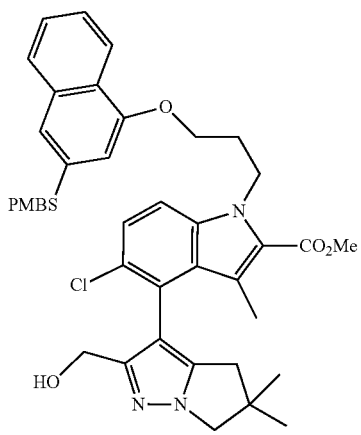

Essentially the same protocol used to prepare Intermediate No. 10 was used to afford Intermediate No. 22 (290 mg) as a white foam. MS: 742.6 (M+H$^+$).

Example 83

Synthesis of Methyl 5-chloro-1-(3-((6-fluoro-3-((4-methoxybenzyl)thio)naphthalen-1-yl)oxy)propyl)-4-(2-(hydroxymethyl)-6,7-dihydro-4H-pyrazolo[5,1-c][1,4]oxazin-3-yl)-3-methyl-1H-indole-2-carboxylate (Intermediate No. 28)

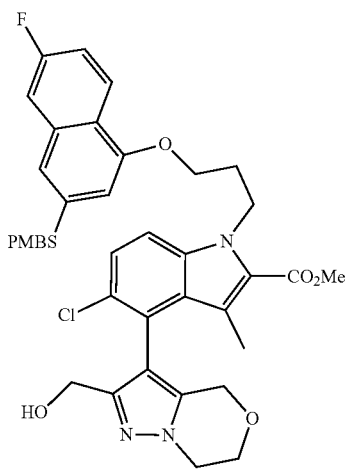

Essentially the same protocol used to prepare Intermediate No. 10 was used to afford Intermediate No. 28 (350 mg) as a white foam. MS: 730.3 (M+H$^+$).

Example 84

Synthesis of Ethyl 5-chloro-4-(3-(hydroxymethyl)-1,5-dimethyl-1H-pyrazol-4-yl)-1-(3-((3-((4-methoxybenzyl)thio)naphthalen-1-yl)oxy)propyl)-3-methyl-1H-indole-2-carboxylate (Intermediate No. 29)

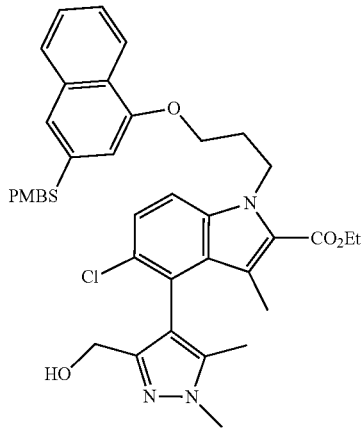

Essentially the same protocol used to prepare Intermediate No. 10 was used to afford Intermediate No. 29 (950 mg) as a white solid. MS: 698.3 (M+H$^+$).

Example 85

Synthesis of Methyl 5-chloro-4-(3-(hydroxymethyl)-1,5-dimethyl-1H-pyrazol-4-yl)-1-(3-((3-((4-methoxybenzyl)thio)naphthalen-1-yl)oxy)propyl)-3-methyl-1H-indole-2-carboxylate (Intermediate No. 30)

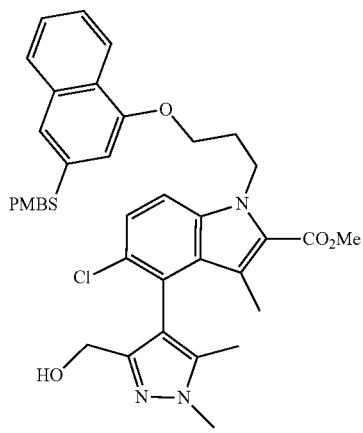

Essentially the same protocol used to prepare Intermediate No. 10 was used to afford Intermediate No. 30 (6.7 g) as a white solid. MS: 684.2 (M+H$^+$).

Example 86

Synthesis of Methyl 5-chloro-4-(5-(hydroxymethyl)-1,3-dimethyl-1H-pyrazol-4-yl)-1-(3-((3-((4-methoxybenzyl)thio)naphthalen-1-yl)oxy)propyl)-3-methyl-1H-indole-2-carboxylate (Intermediate No. 31)

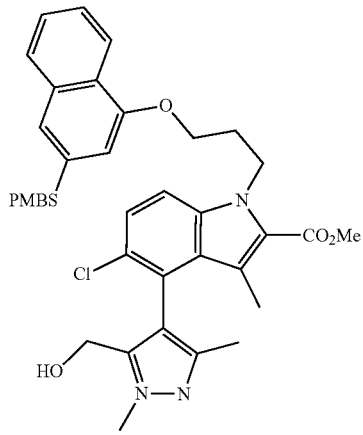

Essentially the same protocol used to prepare Intermediate No. 10 was used to afford Intermediate No. 31 (130 g) as a white foam. MS: 684.3 (M+H$^+$).

Example 87

Synthesis of Methyl 5-chloro-4-(3-(hydroxymethyl)-5-methyl-1-(2-(methylamino)-2-oxoethyl)-1H-pyrazol-4-yl)-1-(3-((3-((4-methoxybenzyl)thio)naphthalen-1-yl)oxy)propyl)-3-methyl-1H-indole-2-carboxylate (Intermediate No. 32)

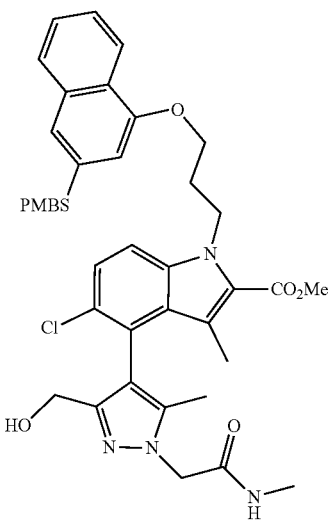

Step A: Methyl 4-(3-(((tert-butyldimethylsilyl)oxy)methyl)-5-methyl-1-(2-(methyl amino)-2-oxoethyl)-1H-pyrazol-4-yl)-5-chloro-1-(3-((3-((4-methoxybenzyl)thio)naphthalen-1-yl)oxy)propyl)-3-methyl-1H-indole-2-carboxylate (Intermediate No. 33)

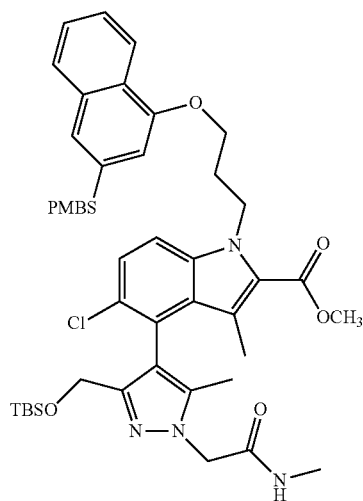

Methyl 4-bromo-5-chloro-1-(3-((3-((4-methoxybenzyl)thio)naphthalen-1-yl)oxy) propyl)-3-methyl-1H-indole-2-carboxylate (257 mg, 0.402 mmol), 2-(3-(((tert-butyldimethylsilyl)oxy)methyl)-5-methyl-4-(4,4,5,5-tetramethyl-1,3,2-dioxaborolan-2-yl)-1H-pyrazol-1-yl)-N-methylacetamide (Intermediate C7, 341 mg, 0.804 mmol), and $K_2CO_3$ (334 mg, 2.413 mmol) and $Pd(PPh_3)_4$ were dissolved into dioxane (12 mL) and $H_2O$ (2 mL) under nitrogen. The reaction mixture was stirred for 2.5 h at 110° C. with microwave assistance. After removal of volatiles under reduced pressure, the residue was loaded to silica gel column and then eluted with ethyl acetate/hexane from 10% to 100% to afford the title compound (280 mg, 81%) as a colorless oil. MS: 855.3 (M+H$^+$).

Step B: Methyl 5-chloro-4-(3-(hydroxymethyl)-5-methyl-1-(2-(methylamino)-2-oxoethyl)-1H-pyrazol-4-yl)-1-(3-((3-((4-methoxybenzyl)thio)naphthalen-1-yl)oxy)propyl)-3-methyl-1H-indole-2-carboxylate (Intermediate No. 32)

Methyl 4-(3-(((tert-butyl dimethyl silyl)oxy)methyl)-5-methyl-1-(2-(methylamino)-2-oxoethyl)-1H-pyrazol-4-yl)-5-chloro-1-(3-((3-((4-methoxybenzyl)thio)naphthalen-1-yl)oxy)propyl)-3-methyl-1H-indole-2-carboxylate (Step A, 240 mg, 0.28 mmol) was dissolved in dry THF (10 mL) under $N_2$, TBAF.3H$_2$O (147 mg, 0.56 mmol) was added and the reaction mixture was stirred for 3 h at room temperature. After removal of volatiles under reduced pressure, the crude product was loaded to silica gel column and then eluted with ethyl acetate/MeOH from 100% to 90% to afford the title compound (128 mg, 62%) as a colorless oil. MS: 741.3 (M+H$^+$).

Example 88

Synthesis of Methyl 5-chloro-4-(5-(hydroxymethyl)-3-methyl-1-(2-(methylamino)-2-oxoethyl)-1H-pyrazol-4-yl)-1-(3-((3-((4-methoxybenzyl)thio)naphthalen-1-yl)oxy)propyl)-3-methyl-1H-indole-2-carboxylate (Intermediate No. 34)

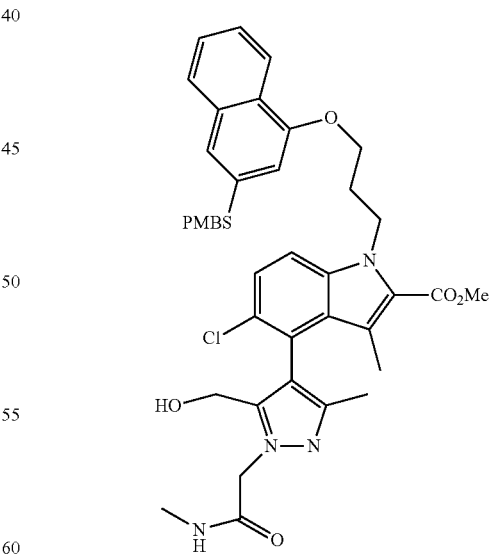

Essentially the same protocol used to prepare Intermediate No. 32 was used to afford Intermediate No. 34 (256 mg) as a colorless oil. MS: 741.4 (M+H$^+$).

Example 89

Synthesis of Methyl 5-chloro-4-(3-(hydroxymethyl)-1-(2-methoxyethyl)-5-methyl-1H-pyrazol-4-yl)-1-(3-((3-((4-methoxybenzyl)thio)naphthalen-1-yl)oxy)propyl)-3-methyl-1H-indole-2-carboxylate (Intermediate No. 35)

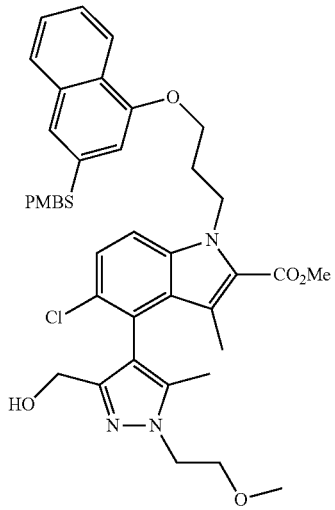

Essentially the same protocol used to prepare Intermediate No. 32 was used to afford Intermediate No. 35 (128 mg) as a colorless oil. MS: 728.4 (M+H$^+$).

Example 90

Synthesis of methyl 5-chloro-4-(5-(hydroxymethyl)-1-(2-methoxyethyl)-3-methyl-1H-pyrazol-4-yl)-1-(3-((3-((4-methoxybenzyl)thio)naphthalen-1-yl)oxy)propyl)-3-methyl-1H-indole-2-carboxylate (Intermediate No. 36)

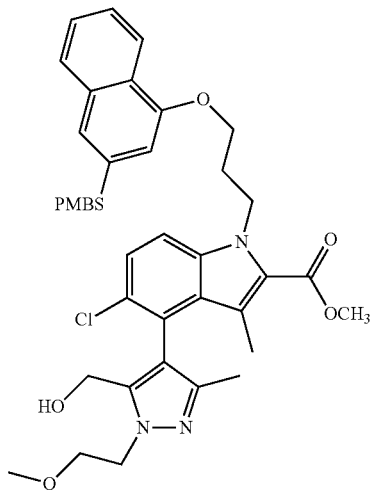

Essentially the same protocol used to prepare Intermediate No. 32 was used to afford Intermediate No. 36 (120 mg) as a colorless oil. MS: 728.4 (M+H$^+$).

Example 91

Synthesis of Methyl 5-chloro-3-ethyl-4-(3-(hydroxymethyl)-1,5-dimethyl-1H-pyrazol-4-yl)-1-(3-((3-((4-methoxybenzyl)thio)naphthalen-1-yl)oxy)propyl)-1H-indole-2-carboxylate (Intermediate No. 37)

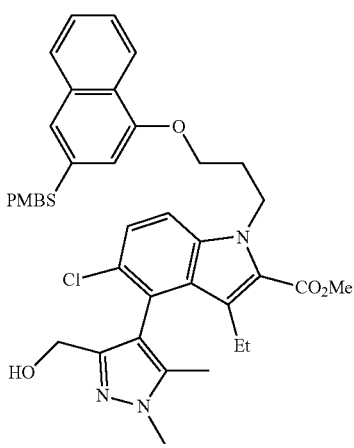

Essentially the same protocol used to prepare Intermediate No. 10 was used to afford Intermediate No. 37 (290 mg) as a white solid. MS: 699.3 (M+H$^+$).

Example 92

Synthesis of Methyl 3,5-dichloro-4-(3-(hydroxymethyl)-1,5-dimethyl-1H-pyrazol-4-yl)-1-(3-((3-((4-methoxybenzyl)thio)naphthalen-1-yl)oxy)propyl)-1H-indole-2-carboxylate (Intermediate No. 38)

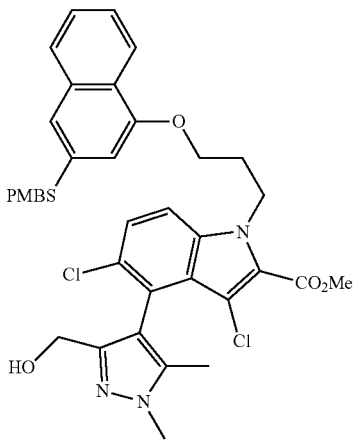

Essentially the same protocol used to prepare Intermediate No. 10 was used to afford Intermediate No. 38 (220 mg) as a white solid. MS: 705.3 (M+H$^+$).

Example 93

Synthesis of Methyl 3-(acetamidomethyl)-5-chloro-4-(3-(hydroxymethyl)-1,5-dimethyl-1H-pyrazol-4-yl)-1-(3-((3-((4-methoxybenzyl)thio)naphthalen-1-yl)oxy)propyl)-1H-indole-2-carboxylate (Intermediate No. 39)

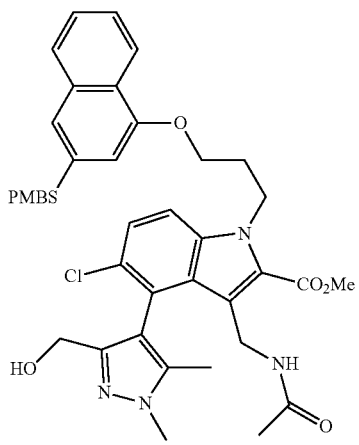

Step A: Methyl 4-bromo-5-chloro-3-formyl-1-(3-((3-((4-methoxybenzyl)thio)naphthalen-1-yl)oxy)propyl)-1H-indole-2-carboxylate (Intermediate No. 40)

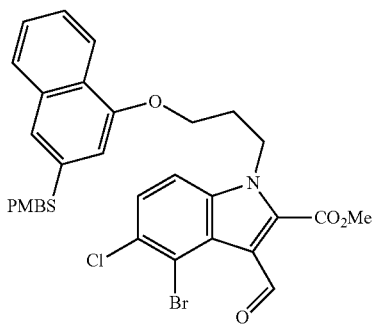

Under Ar, to a solution of methyl 4-bromo-5-chloro-3-formyl-1H-indole-2-carboxylate (Step A of Intermediate B3, 1.3 g, 4.11 mmol) in dry DMF (15 mL) was added Cs$_2$CO$_3$ (2.68 g, 8.21 mmol) and (4-(3-bromopropoxy)naphthalen-2-yl)(4-methoxybenzyl)sulfane (Step A of Intermediate No. 10, 2.06 g, 4.93 mmol), then the reaction mixture was stirred at 90° C. for 3 h. After cooling down to room temperature, the mixture was partitioned with EA (20 mL) and water (30 mL). The organic layer was separated, and the aqueous layer was extracted with EA twice. The combined organic layer was dried over Na$_2$SO$_4$, and concentrated under reduced pressure to give a yellow oil, which was purified by silica gel column (hexane:EA, 4:1) to afford the title compound (700 mg, 26%) as a white solid. MS: 652.1 (M+H$^+$).

Step B: Methyl 4-bromo-3-(((tert-butoxycarbonyl)amino)methyl)-5-chloro-1-(3-((3-((4-methoxybenzyl)thio)naphthalen-1-yl)oxy)propyl)-1H-indole-2-carboxylate (Intermediate No. 41)

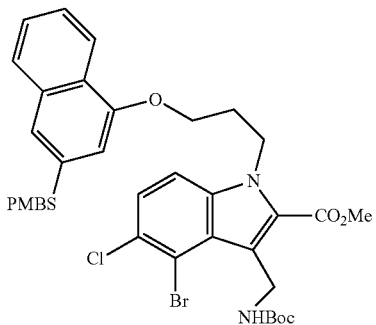

Under Ar, to a solution of methyl 4-bromo-5-chloro-3-formyl-1-(3-((3-((4-methoxybenzyl)thio)naphthalen-1-yl)oxy)propyl)-1H-indole-2-carboxylate (Step A, 1.5 g, 2.297 mmol) and tert-butyl carbamate (1.35 g, 11.49 mmol) in dry DCM (20 mL) was added TFA (1.31 g, 11.49 mmol) and triethylsilane (1.34 g, 11.49 mmol) at room temperature, then the reaction mixture was stirred at room temperature for overnight. After removal of volatiles under reduced pressure, the residue was purified by silica gel column (hexane:EA, 5:1) to afford the title compound (1.5 g, 87%) as a white solid. MS: 753.3 (M+H$^+$).

Step C: Methyl 3-(acetamidomethyl)-4-bromo-5-chloro-1-(3-((3-((4-methoxybenzyl)thio)naphthalen-1-yl)oxy)propyl)-1H-indole-2-carboxylate (Intermediate No. 42)

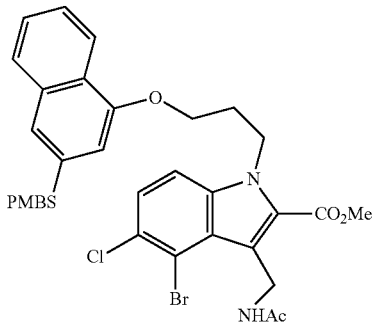

Methyl 4-bromo-3-(((tert-butoxycarbonyl)amino)methyl)-5-chloro-1-(3-((3-((4-methoxybenzyl)thio)naphthalen-1-yl)oxy)propyl)-1H-indole-2-carboxylate (Step B, 1 g, 1.326 mmol) was treated with the HCl solution in MeOH (10 mL, 1.6 M) at room temperature for overnight. After removal of volatiles under reduced pressure, the resulting white solid was directly used for the next step without purification. MS: 653.1 (M+H$^+$).

Under Ar, to a solution of the above white solid (400 mg) in dry DCM (10 mL) were added Et$_3$N (234 mg, 2.317 mmol) and AcCl (91 mg, 1.159 mmol) at 0° C., then the reaction mixture was stirred for 2 h. The resulting mixture was partitioned with DCM (10 mL) and 1N HCl (6 mL), the organic layer was separated, the aqueous layer was extracted with DCM twice. The combined organic layer was washed with sat. NaHCO$_3$ and brine, dried over Na$_2$SO$_4$, and concentrated under reduced pressure to afford the title compound (280 mg, 69% over 2 steps) as a white solid. MS: 695.1 (M+H$^+$).

Step D: Methyl 3-(acetamidomethyl)-5-chloro-4-(3-(hydroxymethyl)-1,5-dimethyl-1H-pyrazol-4-yl)-1-(3-((3-((4-methoxybenzyl)thio)naphthalen-1-yl)oxy)propyl)-1H-indole-2-carboxylate (Intermediate No. 39)

Under Ar, to a mixture of methyl 3-(acetamidomethyl)-4-bromo-5-chloro-1-(3-((3-((4-methoxybenzyl)thio)naphthalen-1-yl)oxy)propyl)-1H-indole-2-carboxylate (Step C, 270 mg, 0.388 mmol), Cs$_2$CO$_3$ (758 mg, 2.327 mmol), 1,5-dimethyl-3-(((tetrahydro-2H-pyran-2-yl)oxy)methyl)-4-(4,4,5,5-tetramethyl-1,3,2-dioxaborolan-2-yl)-1H-pyrazole (Intermediate C5, 326 mg, 0.970 mmol) and Pd(Ph$_3$P)$_4$ (159 mg, 0.138 mmol) was added dioxane (10 mL) and water (2 mL), then the reaction mixture was stirred with microwave assistance at 100° C. for 1.5 h. After cooling down to room temperature, the resulting mixture was partitioned with EA (20 mL) and water (8 mL), the organic layer was separated, and the aqueous layer was extracted with EA twice. The combined organic layer was dried over Na$_2$SO$_4$, and concentrated under reduced pressure to give a yellow oil, which was purified by silica gel column (DCM:MeOH, 10:1) to afford a yellow oil (140 mg). Under Ar the resulting yellow oil was dissolved into MeOH (3 mL), and TsOH.H$_2$O (10 mg, 0.06 mmol) was added. The reaction mixture was stirred at room temperature for overnight. After removal of volatiles under reduced pressure, the residue was purified by silica gel column (DCM:MeOH, 15:1) to afford the title compound (100 mg, 35% over 2 steps) as a white solid. MS: 741.4 (M+H$^+$).

Example 94

Synthesis of Methyl 5-chloro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-1H-indole-2-carboxylate (Intermediate No. 43)

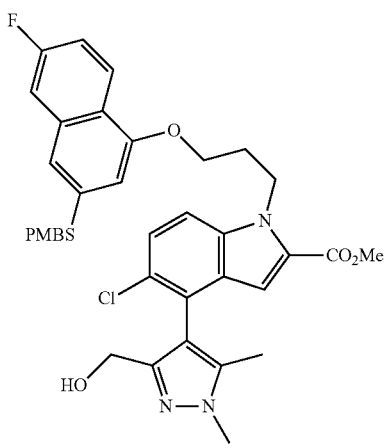

Essentially the same protocol used to prepare Intermediate No. 10 was used to afford Intermediate No. 43 (250 mg) as a white solid. MS: 688.4 (M+H$^+$).

Example 95

Synthesis of Methyl 5-chloro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-3-methyl-1H-indole-2-carboxylate (Intermediate No. 44)

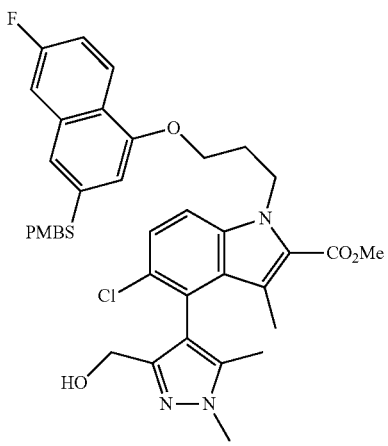

Essentially the same protocol used to prepare Intermediate No. 10 was used to afford Intermediate No. 44 (15 g) as a white solid. MS: 702.6 (M+H$^+$).

Example 96

Synthesis of Methyl 5-chloro-1-(3-((6-fluoro-3-((4-methoxybenzyl)thio)naphthalen-1-yl)oxy)propyl)-4-(5-(hydroxymethyl)-1,3-dimethyl-1H-pyrazol-4-yl)-3-methyl-1H-indole-2-carboxylate (Intermediate No. 45)

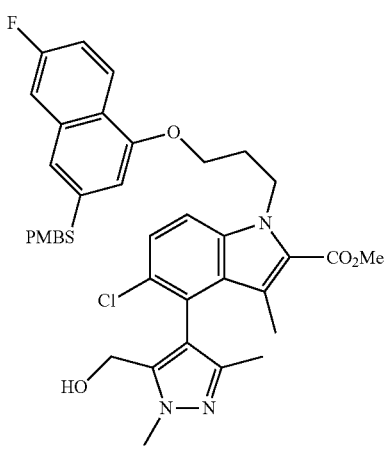

Essentially the same protocol used to prepare Intermediate No. 10 was used to afford Intermediate No. 45 (500 mg) as a light yellow solid. MS: 702.7 (M+H$^+$).

Example 97

Synthesis of Methyl 5-chloro-4-(5-(difluoromethyl)-3-(hydroxymethyl)-1-methyl-1H-pyrazol-4-yl)-1-(3-((6-fluoro-3-((4-methoxybenzyl)thio)naphthalen-1-yl)oxy)propyl)-3-methyl-1H-indole-2-carboxylate (Intermediate No. 46)

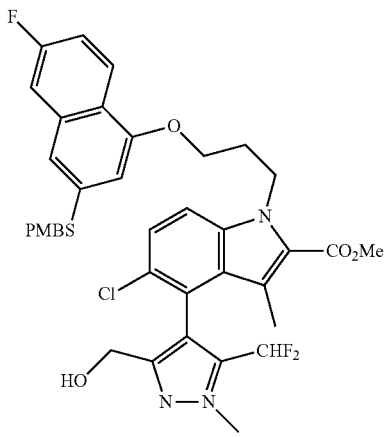

Essentially the same protocol used to prepare Intermediate No. 10 was used to afford Intermediate No. 46 (380 mg) as a white solid. MS: 760.6 (M+Na$^+$).

Example 98

Synthesis of Methyl 5-chloro-3-fluoro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-1H-indole-2-carboxylate (Intermediate No. 47)

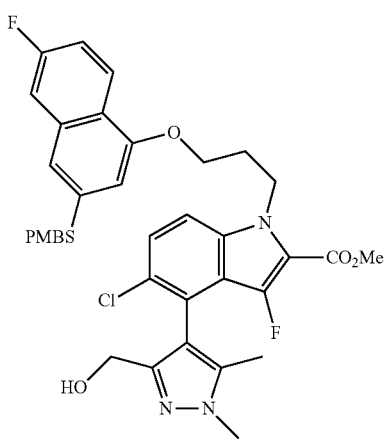

Essentially the same protocol used to prepare Intermediate No. 10 was used to afford Intermediate No. 47 (300 mg) as a white foam. MS: 706.7 (M+H$^+$).

Example 99

Synthesis of Methyl 5-cyano-1-(3-((6-fluoro-3-((4-methoxybenzyl)thio)naphthalen-1-yl)oxy)propyl)-4-(3-(hydroxymethyl)-1,5-dim ethyl-1H-pyrazol-4-yl)-3-methyl-1H-indole-2-carboxylate (Intermediate No. 48)

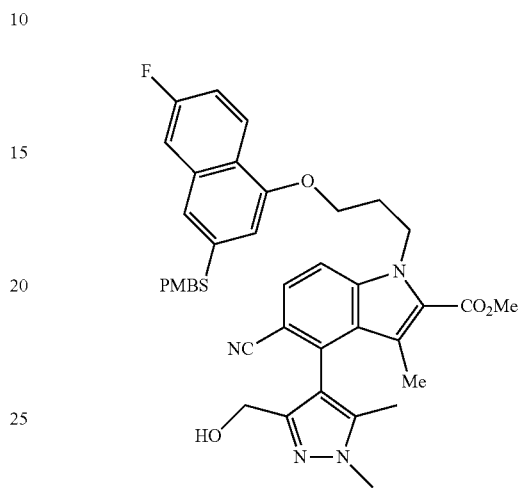

Essentially the same protocol used to prepare Intermediate No. 10 was used to afford Intermediate No. 48 (170 mg) as a white solid. MS: 693.3 (M+H$^+$).

Example 100

Synthesis of Methyl 5-fluoro-1-(3-((6-fluoro-3-((4-methoxybenzyl)thio)naphthalen-1-yl)oxy)propyl)-4-(3-(hydroxymethyl)-1,5-dim ethyl-1H-pyrazol-4-yl)-3-methyl-1H-indole-2-carboxylate (Intermediate No. 49)

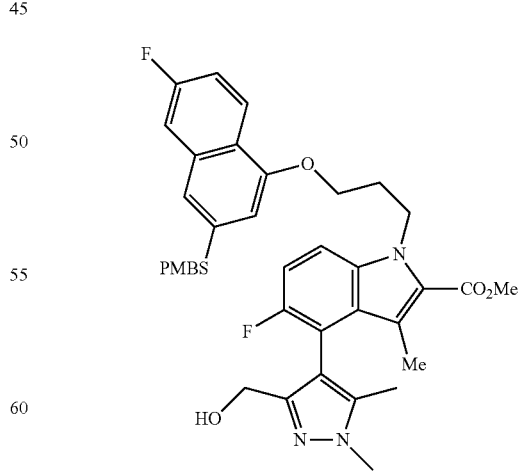

Essentially the same protocol used to prepare Intermediate No. 10 was used to afford Intermediate No. 49 (145 mg) as a white foam. MS: 686.4 (M+H$^+$).

Example 101

Synthesis of Methyl 1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-3,5-dimethyl-1H-indole-2-carboxylate (Intermediate No. 50)

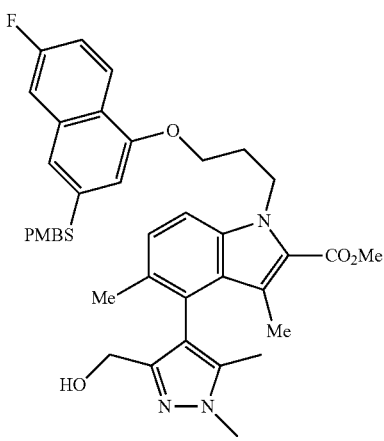

Essentially the same protocol used to prepare Intermediate No. 10 was used to afford Intermediate No. 50 (180 mg) as a white foam. MS: 682.3 (M+H$^+$).

Example 102

Synthesis of Methyl 5-chloro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-3-(((1,1,1-trifluoro-N-methylmethyl)sulfonamido)methyl)-1H-indole-2-carboxylate (Intermediate No. 51)

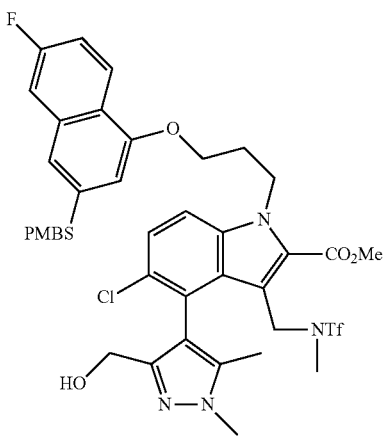

Step A: (4-(3-bromopropoxy)-7-fluoronaphthalen-2-yl)(4-methoxybenzyl)sulfane

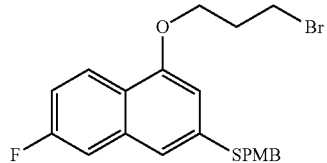

Under Ar, to a solution of 6-fluoro-3-((4-methoxybenzyl)thio)naphthalen-1-ol (Intermediate A2, 12 g, 38.2 mmol) in dry acetonitrile (200 mL) was added 1,3-dibromopropane (77 g, 382 mmol) and K$_2$CO$_3$ (26.4 g, 191 mmol), and the reaction mixture was stirred at 50° C. for overnight. After filtration and removal of volatiles under reduced pressure, the filtrate was concentrated under reduced pressure to give a yellow oil, which was purified by silica gel column (hexane:DCM, 1:1) to afford the title compound (15.5 g, 93%) as a white solid. $^1$H NMR (500 MHz, CDCl$_3$) δ 8.12 (dd, J=9.1, 5.8 Hz, 1H), 7.26 (t, J=9.2 Hz, 4H), 7.15 (dd, J=8.8, 2.3 Hz, 1H), 6.84 (d, J=8.5 Hz, 2H), 6.65 (s, 1H), 4.29-4.07 (m, 4H), 3.79 (s, 3H), 3.67 (t, J=6.4 Hz, 2H), 2.44 (dd, J=12.2, 6.1 Hz, 2H). MS: 435.1, 437.0 (M+H$^+$).

Step B: Methyl 4-bromo-5-chloro-1-(3-((6-fluoro-3-((4-methoxybenzyl)thio)naphthalen-1-yl)oxy)propyl)-3-formyl-1H-indole-2-carboxylate (Intermediate No. 52)

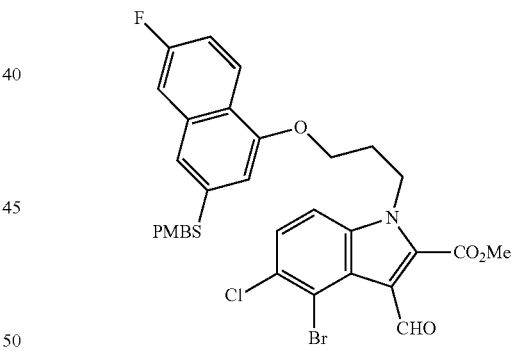

Under Ar, to a solution of (4-(3-bromopropoxy)-7-fluoronaphthalen-2-yl)(4-methoxybenzyl)sulfane (Step B, 2.48 g, 5.69 mmol) in dry DMF was added methyl 4-bromo-5-chloro-3-formyl-1H-indole-2-carboxylate (Step A of Intermediate B3, 1.0 g, 3.16 mmol) and Cs$_2$CO$_3$ (3.09 g, 9.48 mmol), and the reaction mixture was stirred at 70° C. for 5 h. After cooling down to room temperature, water was added to the reaction mixture and the resulting mixture was extracted with EA twice, the combined organic layer was washed with brine, dried over Na$_2$SO$_4$, and concentrated under reduced pressure to give a yellow oil, which was purified by silica gel column (hexane:EA, 3:1) to afford the title compound (890 mg, 42%) as a white solid. MS: 692.1 (M+Na$^+$).

Step C: Methyl 4-bromo-3-(((tert-butoxycarbonyl)amino)methyl)-5-chloro-1-(3-((6-fluoro-3-((4-methoxybenzyl)thio)naphthalen-1-yl)oxy)propyl)-1H-indole-2-carboxylate (Intermediate No. 53)

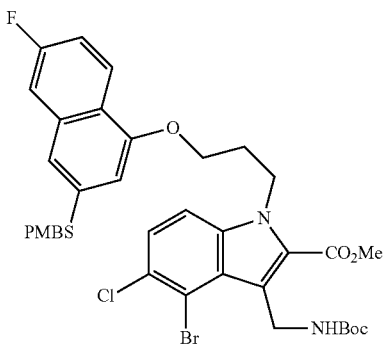

Under Ar, to a solution of methyl 4-bromo-5-chloro-1-(3-((6-fluoro-3-((4-methoxybenzyl)thio)naphthalen-1-yl)oxy)propyl)-3-formyl-1H-indole-2-carboxylate (Step B, 0.89 g, 1.33 mmol) in dry DCM (10 mL) was added tert-butyl carbamate (0.78 g, 6.63 mmol), TFA (0.756 g, 6.63 mmol), and triethylsilane (0.771 g, 6.63 mmol) at 0° C., and then the reaction mixture was stirred at room temperature for 16 h. Sat. NaHCO$_3$ was added to quench the reaction, and the resulting reaction mixture was extracted with DCM three times. The combined organic layer was washed with brine, dried over Na$_2$SO$_4$, concentrated to give a light yellow oil, which was purified by silica gel column (DCM:EA, 3:1) to afford the title compound (800 mg, 78%) as a white solid. MS: 692.1 (M-Boc+Na$^+$).

Step D: Methyl 3-(aminomethyl)-4-bromo-5-chloro-1-(3-((6-fluoro-3-((4-methoxybenzyl)thio)naphthalen-1-yl)oxy)propyl)-1H-indole-2-carboxylate (Intermediate No. 54)

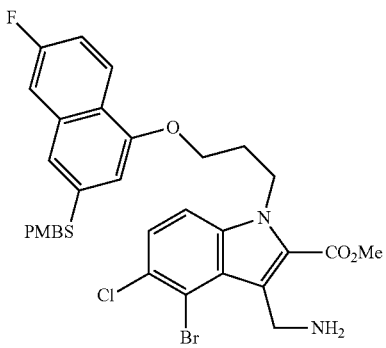

A solution of methyl 4-bromo-3-(((tert-butoxycarbonyl)amino)methyl)-5-chloro-1-(3-((6-fluoro-3-((4-methoxybenzyl)thio)naphthalen-1-yl)oxy)propyl)-1H-indole-2-carboxylate (100 mg, 0.13 mmol) in 2N HCl solution in MeOH (10 mL) was stirred room temperature for 1 h. After removal of volatiles under reduced pressure, the residue was purified by silica gel column (DCM:MeOH, 10:1) to afford the title compound (87 mg) as a white solid. MS: 671.1 (M+H$^+$)

Step E: Methyl 4-bromo-5-chloro-1-(3-((6-fluoro-3-((4-methoxybenzyl)thio)naphthalen-1-yl)oxy)propyl)-3-(((trifluoromethyl)sulfonamido)methyl)-1H-indole-2-carboxylate (Intermediate No. 55)

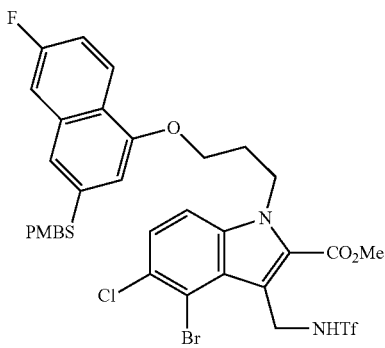

Under Ar, to a solution of methyl 3-(aminomethyl)-4-bromo-5-chloro-1-(3-((6-fluoro-3-((4-methoxybenzyl)thio)naphthalen-1-yl)oxy)propyl)-1H-indole-2-carboxylate (Step D, 380 mg, 0.565 mmol) in dry DCM (30 mL) was added Et$_3$N (172 mg, 1.70 mmol) and the Tf$_2$O (0.24 g, 0.85 mmol) solution in DCM (2 mL) slowly at −45° C., and then the reaction mixture was stirred at room temperature for 30 min. Water was added to quench the reaction, and the resulting mixture was extracted with DCM twice, the organic layer was combined, washed with brine, dried over Na$_2$SO$_4$, and concentrated under reduce pressure to give a light yellow oil, which was purified by silica gel column (hexane:EA, 3:1) to afford the title compound (350 mg, 77%) as a white solid. MS:824.9 (M+Na$^+$).

Step F: Methyl 4-bromo-5-chloro-1-(3-((6-fluoro-3-(4-methoxybenzyl)thio)naphthalen-1-yl)oxy)propyl)-3-(((1,1,1-trifluoro-N-methylmethyl)sulfonamido)methyl)-1H-indole-2-carboxylate (Intermediate No. 56)

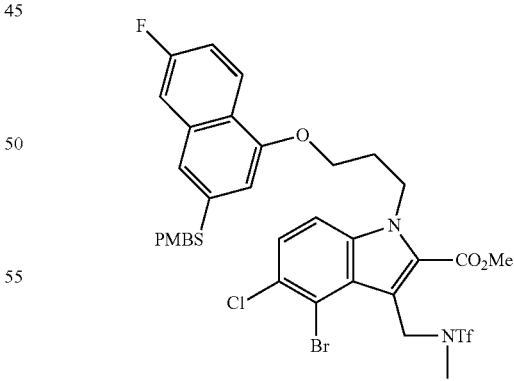

Under Ar, to a solution of methyl 4-bromo-5-chloro-1-(3-((6-fluoro-3-((4-methoxybenzyl)thio)naphthalen-1-yl)oxy)propyl)-3-((((trifluoromethyl)sulfonamido)methyl)-1H-indole-2-carboxylate (Step E, 220 mg, 0.27 mmol) in dry DMF (8 mL) was added NaH (19.7 mg, 0.82 mmol) at 0° C., and MeI (78 mg, 0.55 mmol), and the reaction mixture was stirred at room temperature for 1 h. Water was added to quench the reaction, and the resulting mixture was extracted with EA twice, the organic layer was combined, washed with brine, dried over Na$_2$SO$_4$, and concentrated under reduce pressure to give a light yellow oil, which was purified by silica gel column (hexane:EA, 3:1) to afford the title compound (220 mg, 98%) as a white solid. MS:819.1 (M+H$^+$).

Step G: Methyl 5-chloro-4-(1,5-dimethyl-3-(((tetrahydro-2H-pyran-2-yl)oxy)methyl)-1H-pyrazol-4-yl)-1-(3-((6-fluoro-3-((4-methoxybenzyl)thio)naphthalen-1-yl)oxy)propyl)-3-(((1,1,1-trifluoro-N-methylmethyl)sulfonamido)methyl)-1H-indole-2-carboxylate (Intermediate No. 57)

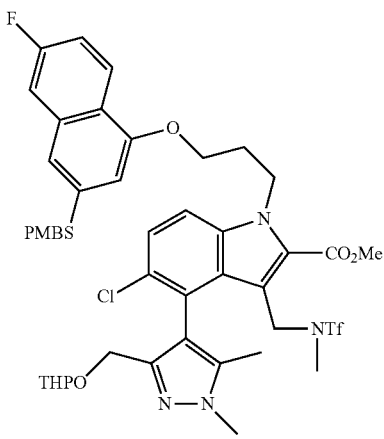

Under Ar, a mixture of methyl 4-bromo-5-chloro-1-(3-((6-fluoro-3-((4-methoxybenzyl)thio)naphthalen-1-yl)oxy)propyl)-3-(((1,1,1-trifluoro-N-methylmethyl)sulfonamido)methyl)-1H-indole-2-carboxylate (200 mg, 0.244 mmol), Cs$_2$CO$_3$ (0.16 g, 0.49 mmol), Pd(Ph$_3$P)$_4$ (0.028 g, 0.024 mmol), and 1,5-dimethyl-3-(((tetrahydro-2H-pyran-2-yl)oxy)methyl)-4-(4,4,5,5-tetramethyl-1,3,2-dioxaborolan-2-yl)-1H-pyrazole (Intermediate D1, 99 mg, 0.29 mmol) in dioxane (0.8 mL) and water (0.20 mL) was stirred at 110° C. for 1 hour with microwave assistance. After cooling down to room temperature, water was added to the reaction mixture and the resulting mixture was extracted with EA twice, the organic layer was combined, washed with brine, dried over Na$_2$SO$_4$, and concentrated under reduce pressure to give a yellow oil, which was purified by silica gel column (DCM:MeOH, 40:1) to afford the title compound (112 mg, 48%) as a white solid. MS: 948.9 (M+H$^+$).

Step H: Methyl 5-chloro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-3-(((1,1,1-trifluoro-N-methylmethyl)sulfonamido)methyl)-1H-indole-2-carboxylate (Intermediate No. 51)

Under Ar, to a solution of methyl 5-chloro-1-(3-((6-fluoro-3-((4-methoxybenzyl)thio)naphthalen-1-yl)oxy)propyl)-4-(3-(hydroxymethyl)-1,5-di methyl-1H-pyrazol-4-yl)-3-(((1,1,1-trifluoro-N-methylmethyl)sulfonamido)methyl)-1H-indole-2-carboxylate (140 mg, 0.15 mmol) in a mixed solvent of dry MeOH (10 mL) and THF (3 mL) was added TsOH.H$_2$O (5.62 mg, 0.03 mmol), then the reaction mixture was stirred at 50° C. for 1 h. After removal of volatiles under reduced pressure, the residue was purified by silica gel column (DCM:MeOH, 40:1) to afford the title compound (96 mg, 75%) as white foam solid. MS: 864.9 (M+H$^+$).

Example 103

Synthesis of Methyl 5-chloro-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-3-(trifluoromethyl)-1H-indole-2-carboxylate (Intermediate No. 58)

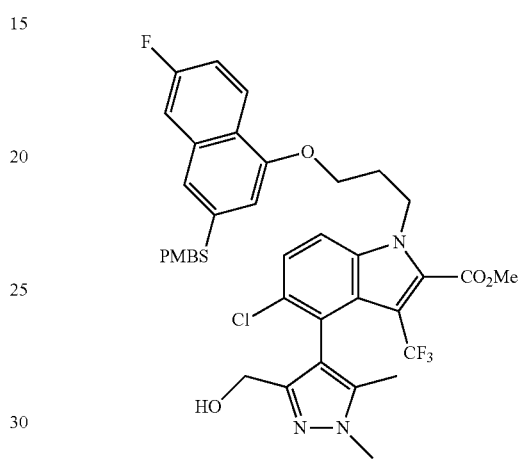

Step A: Methyl 5-chloro-4-(1,5-dimethyl-3-(((tetrahydro-2H-pyran-2-yl)oxy)methyl)-1H-pyrazol-4-yl)-1H-indole-2-carboxylate

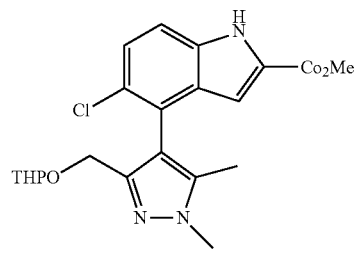

Under Ar, a mixture of methyl 4-bromo-5-chloro-1H-indole-2-carboxylate (Intermediate B2, 2 g, 6.93 mmol), 1,5-dimethyl-3-(((tetrahydro-2H-pyran-2-yl)oxy)methyl)-4-(4,4,5,5-tetramethyl-1,3,2-dioxaborolan-2-yl)-1H-pyrazol e (Intermediate C1, 4.66 g, 13.86 mmol), Pd(Ph$_3$P)$_4$ (1.60 g, 1.39 mmol) and K$_2$CO$_3$ (5.75 g, 41.6 mmol) in dioxane (50 mL) and water (5 mL) was stirred at 110° C. for 20 h. After cooling down to room temperature, water was added to the reaction mixture and the resulting mixture was extracted with EA twice, the organic layer was combined, washed with brine, dried over Na$_2$SO$_4$, and concentrated under reduce pressure to give a brown oil, which was purified by silica gel column (DCM:MeOH, 10:1) to afford the crude title compound (5.8 g) as a yellow oil. The yellow oil was used for the next step without further purification. MS: 419.5 (M+H$^+$).

Step B: Methyl 5-chloro-4-(1,5-dimethyl-3-(((tetrahydro-2H-pyran-2-yl)oxy)methyl)-1H-pyrazol-4-yl)-3-iodo-1H-indole-2-carboxylate

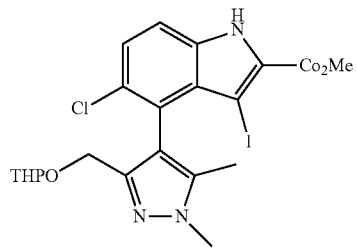

Under Ar, to a solution of methyl 5-chloro-4-(1,5-dimethyl-3-(((tetrahydro-2H-pyran-2-yl)oxy)methyl)-1H-pyrazol-4-yl)-1H-indole-2-carboxylate (Step A, 5.6 g, 13.4 mmol) in acetone (50 mL) was added NIS (3.01 g, 13.40 mmol) at 0° C., and then the mixture was stirred at room temperature for overnight. The solvent was removed under reduced pressure to give a brown oil, which was re-dissolved into EA. The organic layer was washed with sat. $Na_2S_2O_3$, brine, dried over $Na_2SO_4$, and concentrated under reduce pressure to give a brown oil, which was purified by silica gel column (DCM:MeOH, 10:1) to afford the crude title compound (6.1 g) as a brown oil. The brown oil was used for the next step without further purification. MS: 544.6 (M+H$^+$).

Step C: Methyl 5-chloro-4-(1,5-dimethyl-3-(((tetrahydro-2H-pyran-2-yl)oxy)methyl)-1H-pyrazol-4-yl)-1-(3-((6-fluoro-3-((4-methoxybenzyl)thio)naphthalen-1-yl)oxy)propyl)-3-iodo-1H-indole-2-carboxylate (Intermediate No. 59)

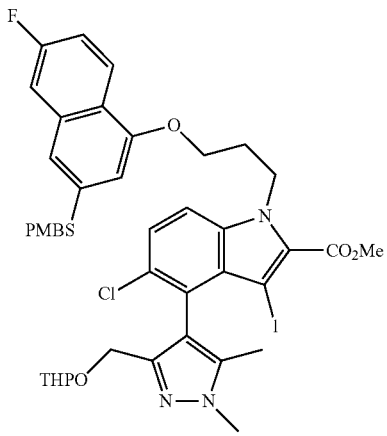

Under Ar, to a solution of methyl 5-chloro-4-(1,5-dimethyl-3-(((tetrahydro-2H-pyran-2-yl)oxy)methyl)-1H-pyrazol-4-yl)-3-iodo-1H-indole-2-carboxylate (Step B, 6.6 g, 7.28 mmol), and (4-(3-bromopropoxy)-7-fluoronaphthalen-2-yl)(4-methoxybenzyl)sulfane (Step A of EXAMPLE 23, 3.80 g, 8.74 mmol) in dry DMF (60 mL) was added $Cs_2CO_3$ (4.75 g, 14.56 mmol), and the reaction mixture was stirred at 70° C. for 3 h. After cooling down to room temperature, water was added and the resulting mixture was extracted with EA twice, the organic layer was combined, washed with brine, dried over $Na_2SO_4$, and concentrated under reduce pressure to give a yellow oil, which was purified by silica gel column (Hex:EA, 1:1) to afford the title compound (3.62 g, 55% over 3 steps) as a yellow foam. MS: 899.8 (M+H$^+$).

Step D: Methyl 5-chloro-4-(1,5-dimethyl-3-(((tetrahydro-2H-pyran-2-yl)oxy)methyl)-1H-pyrazol-4-yl)-1-(3-((6-fluoro-3-((4-methoxybenzyl)thio)naphthalen-1-yl)oxy)propyl)-3-(trifluoromethyl)-1H-indole-2-carboxylate (Intermediate No. 60)

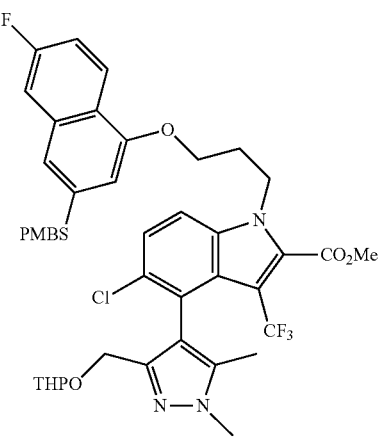

Under Ar, a mixture of methyl 5-chloro-4-(1,5-dimethyl-3-(((tetrahydro-2H-pyran-2-yl)oxy)methyl)-1H-pyrazol-4-yl)-1-(3-((6-fluoro-3-((4-methoxybenzyl)thio)naphthalen-1-yl)oxy)propyl)-3-iodo-1H-indole-2-carboxylate (Step C, 300 mg, 0.33 mmol), methyl 2,2-difluoro-2-(fluorosulfonyl)acetate (513 mg, 2.67 mmol), copper(I) iodide (509 mg, 2.67 mmol), and Pd(Ph$_3$P)$_4$ (19.30 mg, 0.017 mmol) in dry DMF (5 mL) was stirred at 100° C. for 1 h. After cooling to room temperature, water was added to the reaction mixture and the resulting mixture was extracted with EA twice. The organic layer was combined, washed with brine, dried over $Na_2SO_4$, and concentrated under reduce pressure to give a yellow oil, which was purified by silica gel column (DCM:MeOH, 40:1) to afford the title compound (150 mg, 54%) as white solid. MS: 840.5 (M+H$^+$).

Step E: Methyl 5-chloro-1-(3-((6-fluoro-3-((4-methoxybenzyl)thio)naphthalen-1-yl)oxy)propyl)-4-(3-(hydroxymethyl)-1,5-di methyl-1H-pyrazol-4-yl)-3-(trifluoromethyl)-1H-indole-2-carboxylate (Intermediate No. 58)

Under Ar, to a solution of methyl 5-chloro-4-(1,5-dimethyl-3-(((tetrahydro-2H-pyran-2-yl)oxy)methyl)-1H-pyrazol-4-yl)-1-(3-((6-fluoro-3-((4-methoxybenzyl)thio)naphthalen-1-yl)oxy)propyl)-3-(trifluoromethyl)-1H-indole-2-carboxylate (150 mg, 0.18 mmol) in a mixed solvent of dry MeOH (8 mL) and DCM (2 mL) was added TsOH.H$_2$O (10.2 mg, 0.054 mmol), and the reaction mixture was stirred at room temperature for overnight. NaHCO$_3$ (11 mg) was added to quench the reaction and the resulting mixture was concentrated under reduced pressure to give a yellow oil, which was purified by silica gel column (DCM:MeOH, 20:1) to afford the title compound (130 mg, 96%) as a white solid. MS: 756.5 (M+H$^+$).

Example 104

Synthesis of Methyl 5-chloro-3-cyano-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-1H-indole-2-carboxylate (Intermediate No. 61)

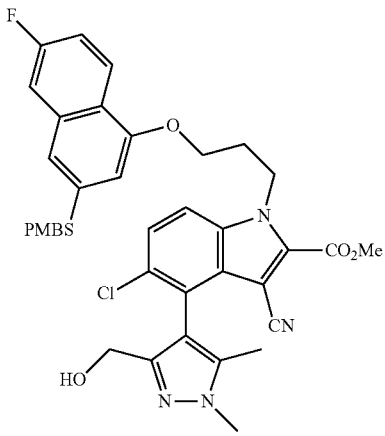

Step A: Methyl 5-chloro-3-cyano-4-(1,5-dimethyl-3-(((tetrahydro-2H-pyran-2-yl)oxy)methyl)-1H-pyrazol-4-yl)-1-(3-((6-fluoro-3-((4-methoxybenzyl)thio)naphthalen-1-yl)oxy)propyl)-1H-indole-2-carboxylate (Intermediate No. 62)

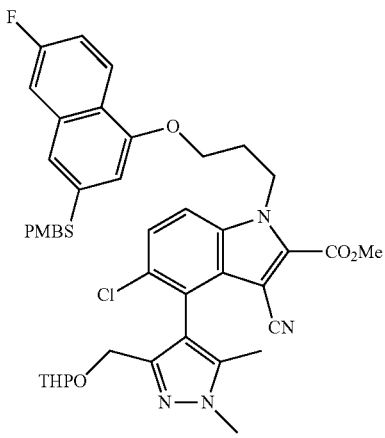

Under Ar, a mixture of methyl 5-chloro-4-(1,5-dimethyl-3-(((tetrahydro-2H-pyran-2-yl)oxy)methyl)-1H-pyrazol-4-yl)-1-(3-((6-fluoro-3-((4-methoxybenzyl)thio)naphthalen-1-yl)oxy)propyl)-3-iodo-1H-indole-2-carboxylate (Intermediate No. 59 of EXAMPLE 103, 400 mg, 0.45 mmol), cyanocopper (199 mg, 2.227 mmol), $Pd_2(dba)_3$ (20.39 mg, 0.022 mmol), dppf (24.69 mg, 0.045 mmol) in dry DMF (5 mL) was stirred at 100° C. for 5 h. After cooling to room temperature, water was added to the reaction mixture and the resulting mixture was extracted with EA twice, the organic layer was combined, washed with brine, dried over $Na_2SO_4$, and concentrated under reduce pressure to afford a yellow oil, which was purified by silica gel column (DCM:MeOH, 20:1) to afford the title compound (100 mg, 28%) as a white solid. MS: 797.5 $(M+H^+)$.

Step B: Methyl 5-chloro-3-cyano-1-(3-((6-fluoro-3-((4-methoxybenzyl)thio)naphthalen-1-yl)oxy)propyl)-4-(3-(hydroxymethyl)-1,5-dimethyl-1H-pyrazol-4-yl)-1H-indole-2-carboxylate (Intermediate No. 61)

Under Ar, to a solution of methyl 5-chloro-3-cyano-4-(1,5-dimethyl-3-(((tetrahydro-2H-pyran-2-yl)oxy)methyl)-1H-pyrazol-4-yl)-1-(3-((6-fluoro-3-((4-methoxybenzyl)thio)naphthalen-1-yl)oxy)propyl)-1H-indole-2-carboxylate (Step A, 100 mg, 0.125 mmol) in a mixed solvent of dry MeOH (5 mL) and DCM (1 mL) was added $TsOH.H_2O$ (11.9 mg, 0.063 mmol), and the reaction mixture was stirred at room temperature for overnight. $NaHCO_3$ (12 mg) was added to quench the reaction and the resulting mixture was concentrated under reduced pressure to give a yellow oil, which was purified by silica gel column (DCM:MeOH, 25:1) to afford the title compound (100 mg, quantitatively) as a white solid. MS: 713.5 $(M+H^+)$.

Example 105

Mcl-1 Activity

The inhibition of Mcl-1, and cell viability in NCI-H929 and OPM-2 cells of representative Compounds of the Disclosure are provided in Table 4. AZD-5991 (chemical name: (Z)-16-chloro-11,21,25,61-tetramethyl-11H,21H,61H-10-oxa-4,8-dithia-1(7,3)-indola-2(4,3),6(3,5)-dipyrazola-9(3,1)-naphthalenacyclotridecaphane-12-carboxylic acid) is a known Mcl-1 inhibitor. See WO 2018/178226.

Inhibition of Mcl-1 by fluorescence polarization (FP) assay.

The relative binding potency of representative Compounds of the Disclosure was determined by a fluorescence polarization (FP) assay (Long et al, *BMC Biotechnology* 13:45 (2013)). The method used a fluorescein labelled peptide (FAM-Bid) which binds to the Mcl-1 protein leading to an increased anisotropy measured in milli-polarization (mP) values using a plate reader. A 21-residue Bid BH3 peptide (residues 79-99) [Swiss-Prot: P55957] was labeled at the N-terminus with 6-carboxyfluorescein succinimidyl ester (FAM) to give FAM-Bid as a tracer in the FP competitive binding assay. Tag-free Mcl-1 protein (residues 171-323) was used in the FP assay (Mady et al, *Scientific Reports* 8: 10210-10210 (2018); Yang et al, *ACS Med. Chem. Lett.* 3:308-312 (2012)). The addition of compounds which binds competitively to the same site as the labelled peptide will result in a greater proportion of unbound peptide in the system indicated by a decreased mP value.

A 10-points serial dilution of each compound was prepared in DMSO and 5 μL solution was transferred into flat bottomed, 96-well back plate (final DMSO concentration 5%). 120 μL of Buffer (PBS, 0.01% BGG (Sigma Cat. #SRE0011), 0.01% Triton X-100), containing the Fluorescein labelled peptide (Final concentration 2 nM) and Mcl-1 protein (final concentration 20 nM) was then added. Assay plates were incubated 30 mins at room temperature with gentle shaking before FP was measured on a Biotek Synergy 1MF reader (Ex. 485 nm, Em. 528 nm, Cut off 510 nm) and mP calculated. The binding of increasing doses of test compounds was expressed as a percentage reduction in mP compared to a window established between 5% DMSO only and 100% inhibition controls (no Mcl-1 protein). 10-points dose response curves were plotted with GraphPad software using Sigmoidal Dose-Response Model and the IC50 values were determined by nonlinear regression fitting of the competition curves.

Cell Viability Assay (NCI-H929 cells)

NCI-H929 cells were obtained from American Type Culture Collection (ATCC). Cells were maintained in the recommended culture medium (RPMI 1640) with 10% FBS and 0.05 mM BME at 37° C. and an atmosphere of 5% $CO_2$.

The effect of Compounds on cell viability was determined using Cell Counting Kit-8 (CCK-8) assay according to the manufacturer's instructions. 95 µL of NCI-H929 cell suspension (20000 cells/well) in culture medium were seeded into 96-well plates and cultured 4 hrs. Each tested compound was serially diluted in in DMSO, then 5 µL of the compound or DMSO was diluted in 95 µL medium once more. At last, 5 µL of the compound dilution was added to the corresponding well of the cell plate. After the addition of the tested compound, the cells were incubated at 37° C. in an atmosphere of 5% $CO_2$ for 24 hrs. At the end, 10 µL of CCK-8 solution was added to each well of the plate and incubated for 1-4 hours. The plates were read at 450 nm on the microplate reader (BioTek Synergy 1MF). The readings were normalized to the vehicle cells, and the $IC_{50}$ was calculated by nonlinear regression analysis using GraphPad Prism 6 software.

Cell Viability Assay (OPM-2 cells)

OPM-2 cells were obtained from Deutsche Sammlung von Mikroorganismen and Zellkulturen GmbH (DSMZ). Cells were maintained in the recommended culture medium with 10% FBS at 37° C. and an atmosphere of 5% $CO_2$.

The effect of representative Compounds of the Disclosure on cell viability was determined using Cell Counting Kit-8 (CCK-8) assay (Shanghai Life iLab Bio Technology) according to the manufacturer's instructions. Each tested compound was serially diluted in culture medium, 100 µL of the compound dilution was added into 96-well plates. 100 µL of an OPM-2 cell suspension (20000 cells/well) in culture medium were seeded into the corresponding well of the plate and the cells were incubated at 37° C. in an atmosphere of 5% $CO_2$ for 24 hours. In the next day, 20 µL of CCK-8 solution was added to each well of the plate and incubated for 4 hours.

The plates were read at 450 nm on the microplate spectrophotometer (SpectraMax plus 384, Molecular devices). The readings were normalized to the vehicle cells, and the $IC_{50}$ was calculated by nonlinear regression analysis using GraphPad Prism 6 software.

TABLE 4

| Cpd No. | Mcl-1 (FP, nM) | OPM-2 (5% FBS, nM) | H929 (5% FBS, nM) |
|---|---|---|---|
| 1 | 7 | 1535 | 165 |
| 2 | 14 | 220 | 53 |
| 3 | 14 | 386 | 391 |
| 4 | 14 | 438 | 49 |
| 5 | 17 | 192 | 33 |
| 6 | 9 | 136 | 39 |
| 7 | >1000 | >10000 | 7443 |
| 8 | 21 | 268 | 70 |
| 9 | 14 | 1254 | 479 |
| 10 | 4 | 4113 | 1852 |
| 11 | 15 | 171 | 68 |
| 12 | 18 | 9862 | 273 |
| 13 | 19 | 649 | 180 |
| 14 | 19 | 52 | 28 |
| 15 | 2 | 52 | 19 |
| 16 | 3200 | 4050 | 2243 |
| 17 | 15 | 94 | 77 |
| 18 | 15 | 189 | 63 |

TABLE 4-continued

| Cpd No. | Mcl-1 (FP, nM) | OPM-2 (5% FBS, nM) | H929 (5% FBS, nM) |
|---|---|---|---|
| 19 | 10 | 449 | 444 |
| 20 | 14 | 613 | 611 |
| 21 | 10 | 223 | 170 |
| 22 | 15 | 73 | 61 |
| 23 | 16 | 1867 | 1066 |
| 24 | 15 | 5422 | 3039 |
| 25 | 21 | 5968 | 4294 |
| 26 | 14 | 992 | 300 |
| 27 | 15 | 258 | 285 |
| 28 | 14 | 66 | 47 |
| 29 | 35 | 1904 | 621 |
| 30 | 17 | 5242 | 1848 |
| 31 | 16 | 1944 | 623 |
| 32 | 36 | 542 | 213 |
| 33 | 5 | 190 | 107 |
| 34 | 2600 | >10000 | 8518 |
| 35 | 15 | 57 | 25 |
| 36 | 27 | 2018 | 696 |
| 37 | 29 | 3156 | 1499 |
| 38 | 7 | 543 | 270 |
| 39 | 9 | 2053 | 948 |
| 40 | 13 | 190 | 159 |
| 41 | 17 | 275 | 198 |
| 42 | 22 | 1509 | 768 |
| 43 | 22 | 1246 | 613 |
| 44 | 23 | 1158 | 780 |
| 45 | 16 | 350 | 253 |
| 46 | 8 | 637 | 300 |
| 47 | 5 | 229 | 170 |
| 48 | 12 | 587 | 243 |
| 49 | 5 | 308 | 204 |
| 50 | 20 | 1636 | 226 |
| 51 | 17 | 5824 | 1542 |
| 52 | 21 | 699 | 87 |
| 53 | 34 | 1706 | 222 |
| 54 | 27 | 3484 | 673 |
| 55 | 24 | 744 | 145 |
| AZD5991 | 7 | 148 | 47 |

Example 106

Microsome Clearance Assay

Representative Compounds of the Disclosure were tested in a microsome clearance assay. Pooled liver microsomes (20 mg/ml) from human, male Wister rat, and male CD-1 mouse were obtained from BD Bioscience (Franklin Lakes, N.J. USA). Incubation reaction mixtures contained a final concentration of 0.1M sodium phosphate buffer (pH 7.4), 0.5 mg/ml microsomal protein, 5 µM of test sample and 1 mM NADPH in a total volume of 400 µl. The incubations were done for 60 minutes and 300 µl of the mixtures was transferred to 150 µl of ice cold methanol to terminate reactions. After vortexes for 3 minutes and centrifuged at 4000 rpm at 4° C. for 10 minutes, the clear supernatant was used directly for analysis. The samples were analyzed by Applied Biosystems API 3200 Q TRAP LC/MS/MS system using electrospray ionization mode. The results are shown in Table 5.

TABLE 5

| Cpd. No. | Mouse Liver Microsome Clint (µL/min/mg protein) | Rat Liver Microsome Clint (µL/min/mg protein) | Human Liver Microsome Clint (µL/min/mg protein) |
|---|---|---|---|
| 1 | 49.0 | 34.4 | 35.2 |
| 2 | 53.0 | 31.2 | 18.2 |
| 4 | 41.2 | 19.8 | 13.8 |

TABLE 5-continued

| Cpd. No. | Mouse Liver Microsome Clint (µL/min/mg protein) | Rat Liver Microsome Clint (µL/min/mg protein) | Human Liver Microsome Clint (µL/min/mg protein) |
| --- | --- | --- | --- |
| 5 | 48.4 | 58.8 | 15.8 |
| 6 | 23.6 | 21.0 | <2.8 |
| 7 | 245 | 111 | 38.0 |
| 8 | 325 | 299 | 86.8 |
| 11 | 145 | 35.4 | 39.6 |
| 12 | 13.8 | 30.6 | 3.60 |
| 14 | 28.6 | 27.2 | 5.0 |
| 15 | 28.0 | 19.6 | <2.8 |
| 16 | 135 | 64.6 | 23.4 |
| 17 | 29.2 | 46.6 | 19.4 |
| 18 | 42.0 | 22.6 | 22.2 |
| 22 | 32.0 | 30.8 | 11.8 |
| 23 | 52.4 | 30.4 | 48.2 |
| 24 | 28.8 | 122 | 21.8 |
| 26 | 41.2 | 14.2 | 12.8 |
| 28 | 116 | 38.4 | 42.8 |
| 29 | 54.6 | 42.0 | 21.4 |
| 31 | 45.2 | 33.0 | 7.40 |
| 32 | 35.0 | 10.8 | 4.40 |
| 33 | 16.0 | 8.6 | <2.8 |
| 34 | 110 | 13.0 | <2.8 |
| 35 | 156 | 42.0 | 53.2 |
| 45 | 21.4 | 12.6 | <2.8 |
| 46 | 43.4 | 21.6 | 8.00 |
| 50 | 65.2 | 22.2 | 10.2 |
| 51 | 30.6 | 15.0 | 7.4 |
| 52 | 53.0 | 29.8 | 28.4 |
| 53 | 59.2 | 30.0 | 18.6 |
| AZD5991 | 20.8 | 16.6 | <2.8 |

Example 107

MV-4-11 Cell Viability Assay

MV-4-11 cells were obtained from American Type Culture Collection (ATCC). Cells were maintained in the recommended culture medium (IMDM) with 10% FBS at 37° C. and an atmosphere of 5% $CO_2$.

The effect of representative Compounds of the Disclosure on cell viability was determined using Cell Counting Kit-8 (CCK-8) assay according to the manufacturer's instructions. 95 µL of MV-4-11 cell suspension (20000 cells/well) in culture medium were seeded into 96-well plates and cultured 4 hrs. Each tested compound was serially diluted in DMSO, then 5 µL of the compound or DMSO was diluted in 95 µL medium once more. At last, 5 µL of the compound dilution was added to the corresponding well of the cell plate. After the addition of the tested compound, the cells were incubated at 37° C. in an atmosphere of 5% $CO_2$ for 24 hrs. At the end, 10 µL of CCK-8 solution was added to each well of the plate and incubated for 1-4 hrs. The plates were read at 450 nm on the microplate reader (BioTek Synergy 1MF). The readings were normalized to the vehicle cells, and the $IC_{50}$ was calculated by nonlinear regression analysis using GraphPad Prism 6 software. The results are presented in Table 6.

TABLE 6

| Cpd. No. | MV-4-11 $IC_{50}$ (5% FBS, nM) |
| --- | --- |
| 5 | 43 |
| 6 | 29 |
| 14 | 28 |
| 15 | 5.4 |
| 18 | 93 |
| 20 | 45 |
| AZD5991 | 29 |

Example 108

In Vivo Efficacy in MV-4-11 Xenograft Model

Figure 2:
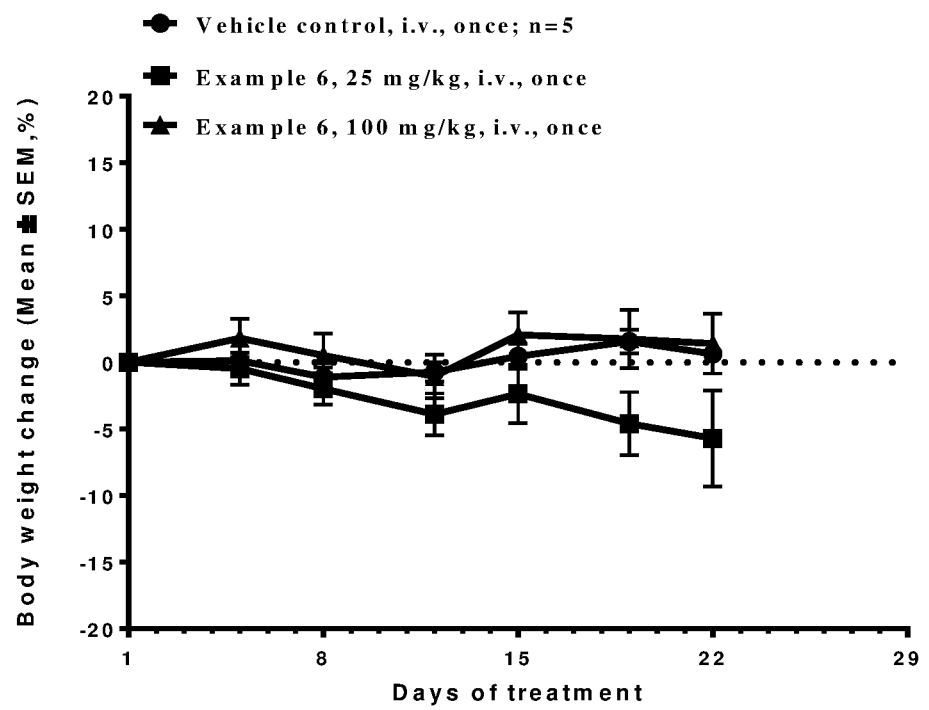
FIG. 2 is a line graph showing body weight change by i.v. administration of Cpd. No. 6 (referred to as Example 6 in the figure) in the subcutaneous MV-4-11 tumor model.
Figure 3:
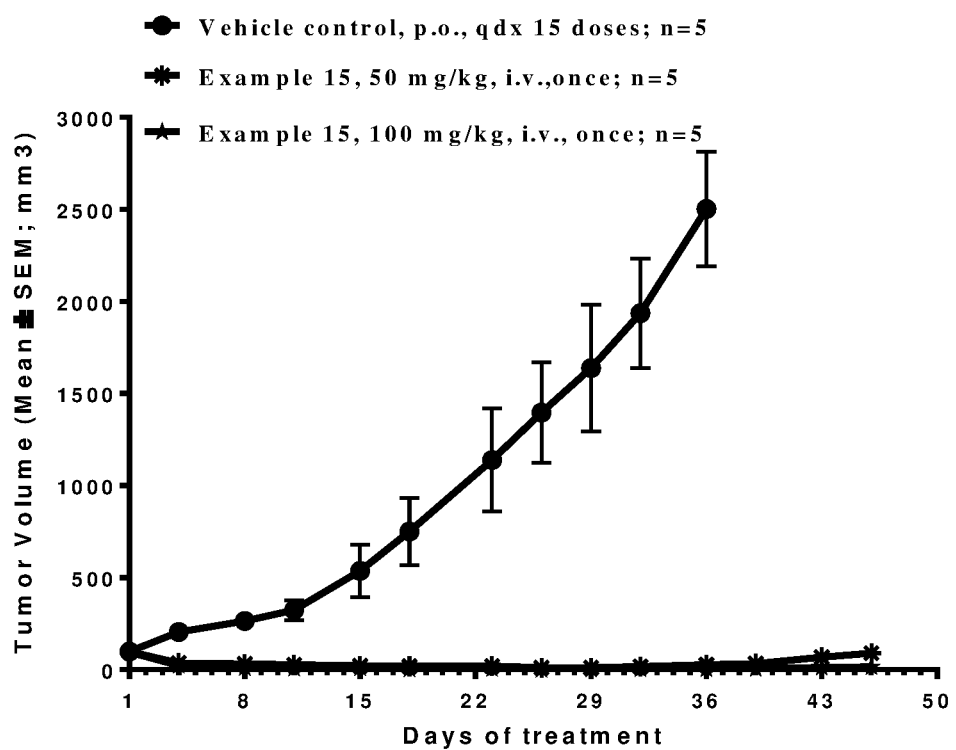
FIG. 3 is a line graph showing the in vivo efficacy by i.v. administration of Cpd. No. 15 (referred to as Example 15 in the figure) in the subcutaneous MV-4-11 tumor model.
Figure 4:
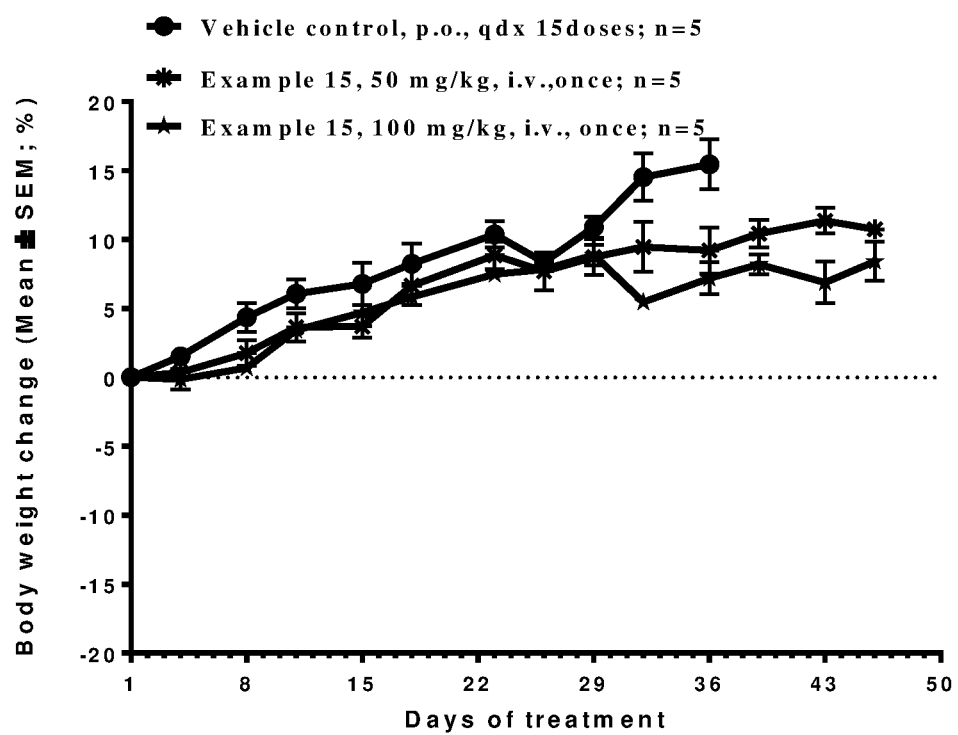
FIG. 4 is a line graph showing body weight change by i.v. administration of Cpd. No. 15 (referred to as Example 15 in the figure) in the subcutaneous MV-4-11 tumor model.
Figure 5:
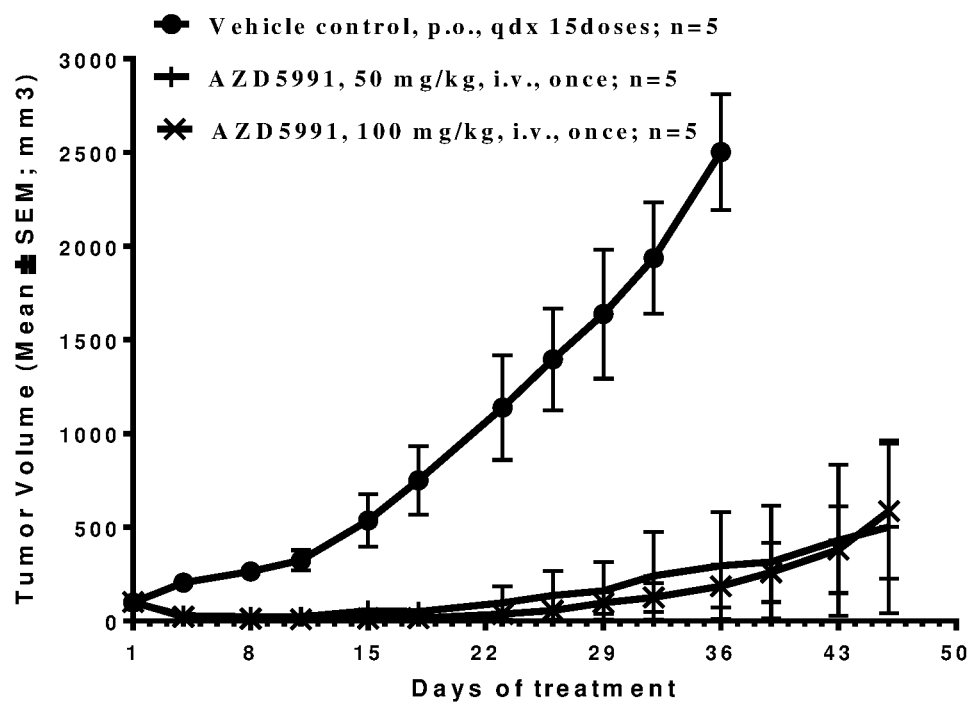
FIG. 5 is a line graph showing the in vivo efficacy by i.v. administration of AZD5991 in the subcutaneous MV-4-11 tumor model.
Figure 6:
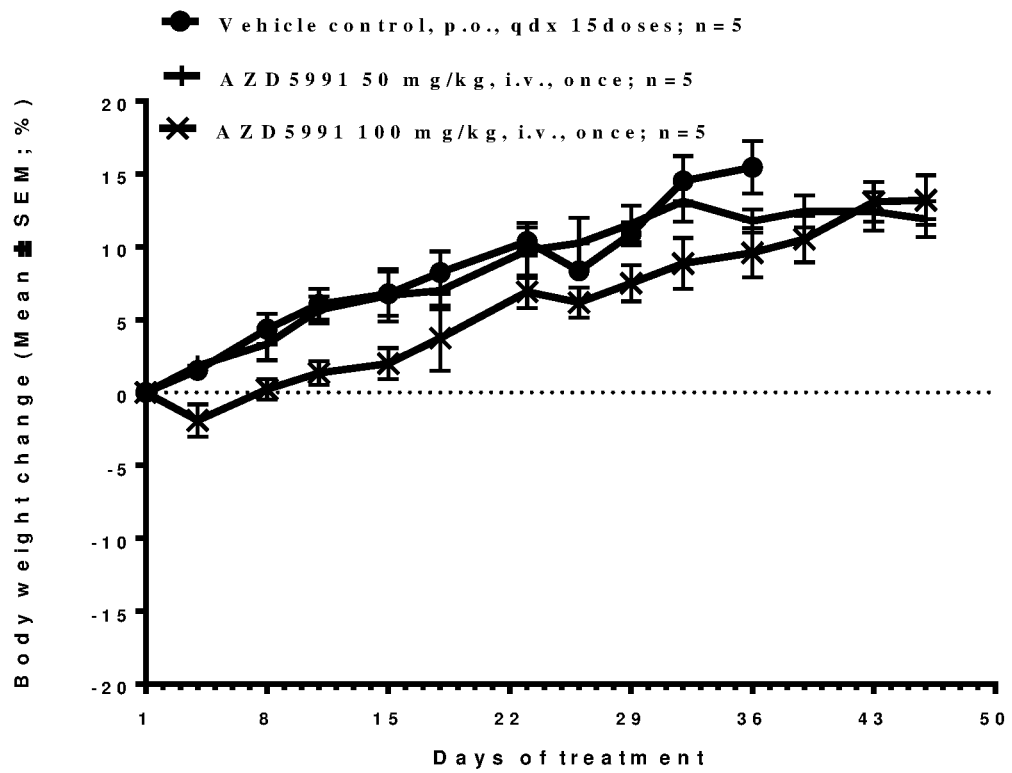
FIG. 6 is a line graph showing body weight change by i.v. administration of AZD5991 in the subcutaneous MV-4-11 tumor model.

Female SCID mice at 4-6 weeks old were purchased from Shanghai Laboratory Animal Center (SLAC), $1 \times 10^7$ MV-4-11 cells per mouse in 0.2 ml of PBS with 30% Matrigel were inoculated subcutaneously to the right flank of mice. Volumes of the tumor were estimated as $V=LW^2$ 12, where L and W stand for tumor length and width. Mice with tumor at 50-150 $mm^3$ were randomized into treatment groups (5 mice per group) and started treatment. Mice were treated with Cpd. No. 6 (referred to in the figures as "Example 6") or Cpd. No. 15 (referred to in the figures as "Example 15") at selected doses by single i.v. administration. Another group of mice were treated with AZD5991 at 50 mg/kg and 100 mg/kg once by i.v. administration, respectively. Vehicle control group was dosed i.v. once with 10% PEG400/5% Chremophor EL/85% PBS (pH 7.2). The individual relative tumor volume (RTV) is calculated as following: $RTV=V_t/V_0$, where $V_t$ is the volume on each day of measurement and $V_0$ is the volume on the initial day of treatment. Therapeutic effect of compound is expressed with relative tumor proliferation rate (T/C). The calculation formula is: T/C=mean RTV of the treated group/mean RTV of the control group. Treatments producing >20% lethality and/or 20% net body weight loss were considered toxic. See FIGS. 1-6.

Example 109

In Vivo Efficacy in H929 Xenograft Model

Figure 7:
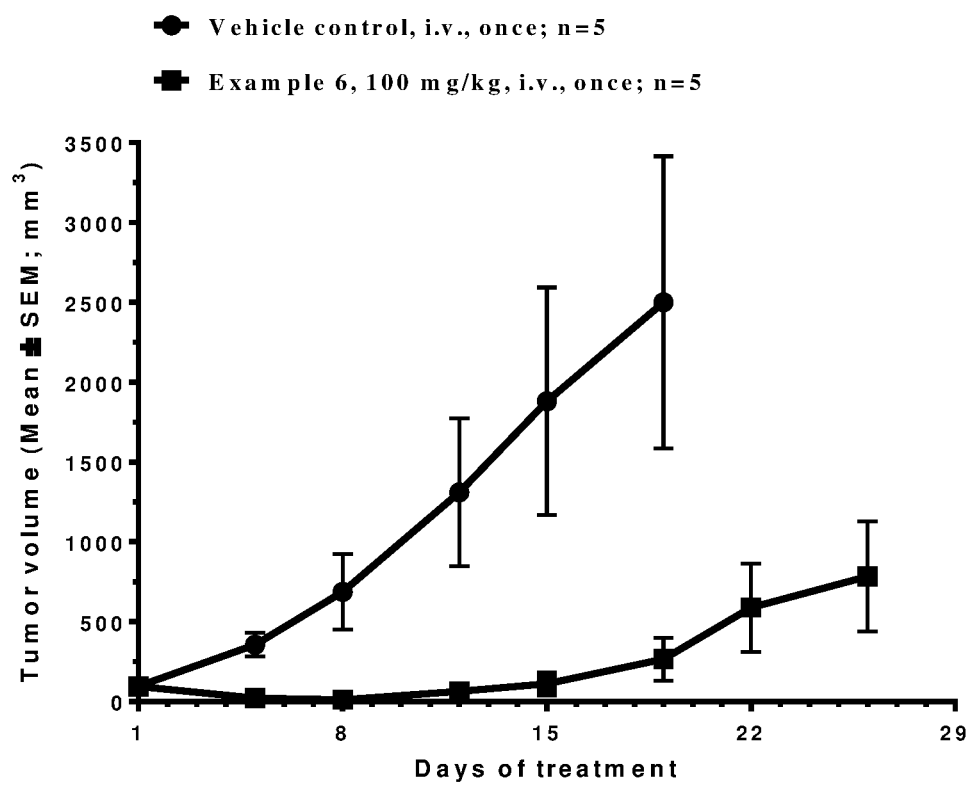
FIG. 7 is a line graph showing the in vivo efficacy by i.v. administration of Cpd. No. 6 (referred to as Example 6 in the figure) in the subcutaneous H929 tumor model.
Figure 8:
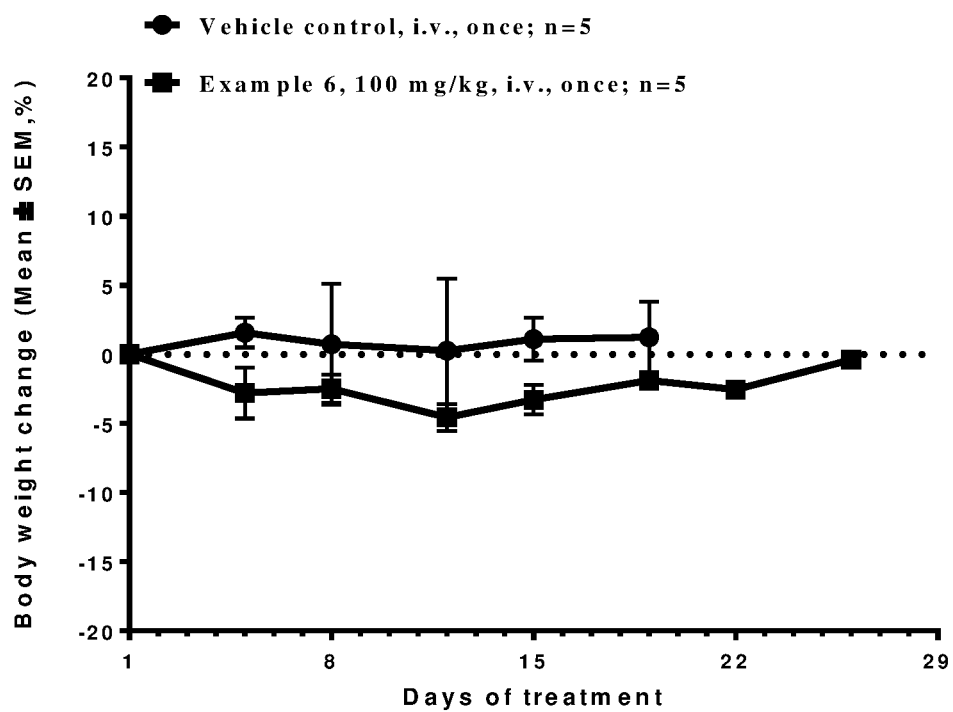
FIG. 8 is a line graph showing body weight change by i.v. administration of Cpd. No. 6 (referred to as Example 6 in the figure) in the subcutaneous H929 tumor model.
Figure 9:
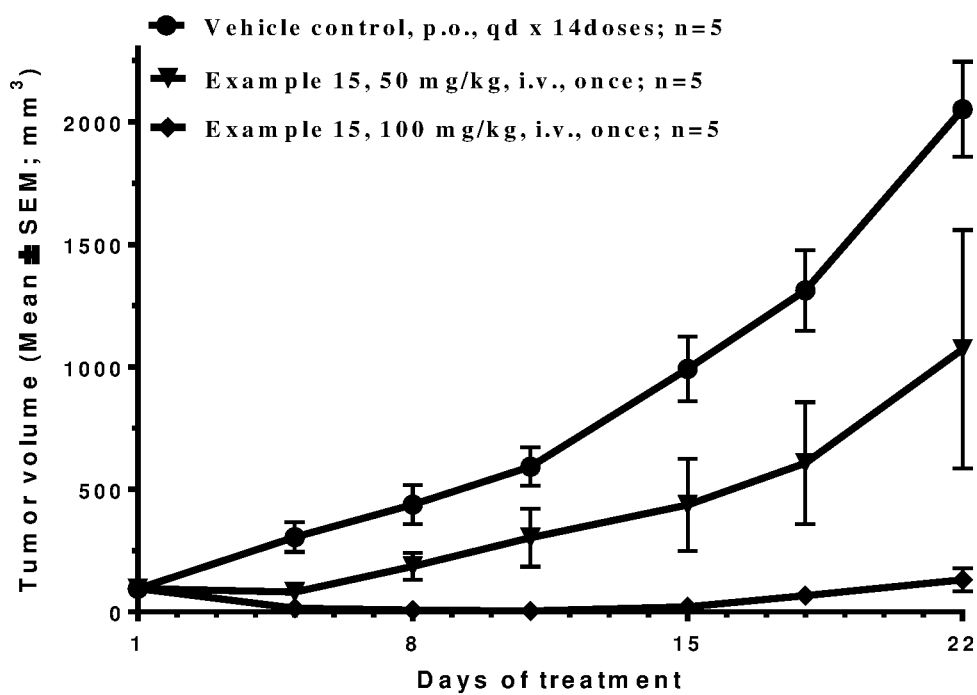
FIG. 9 is a line graph showing the in vivo efficacy by i.v. administration of Cpd. No. 15 (referred to as Example 15 in the figure) in the subcutaneous H929 tumor model.
Figure 10:
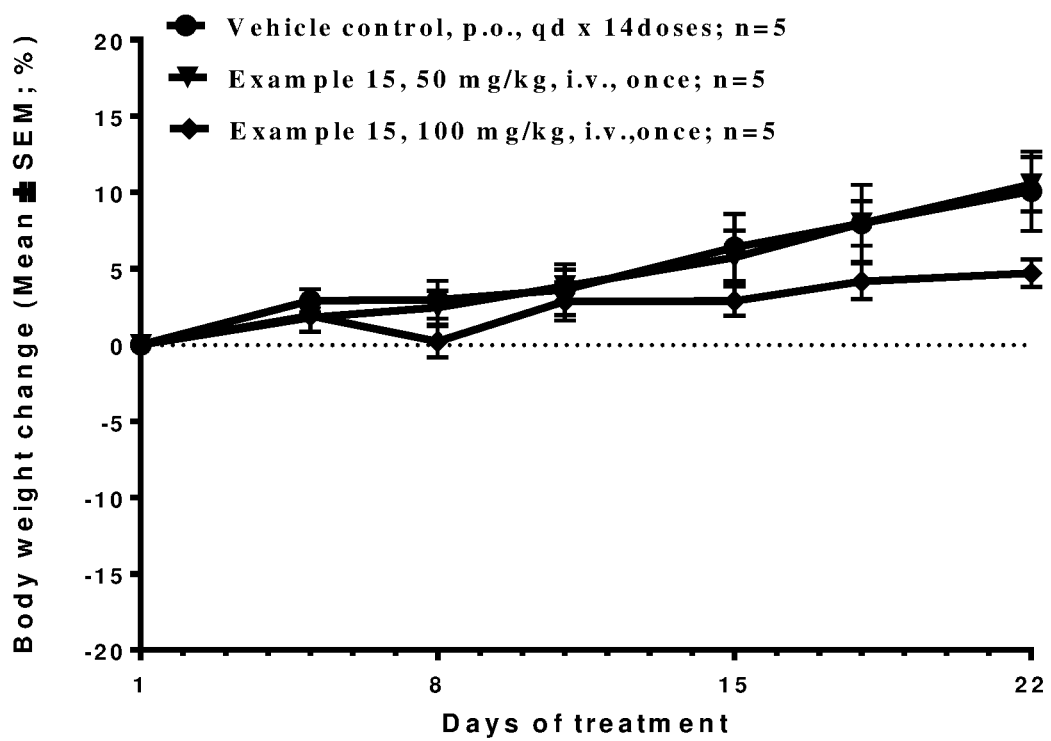
FIG. 10 is a line graph showing body weight change by i.v. administration of Cpd. No. 15 (referred to as Example 15 in the figure) in the subcutaneous H929 tumor model.
Figure 11:
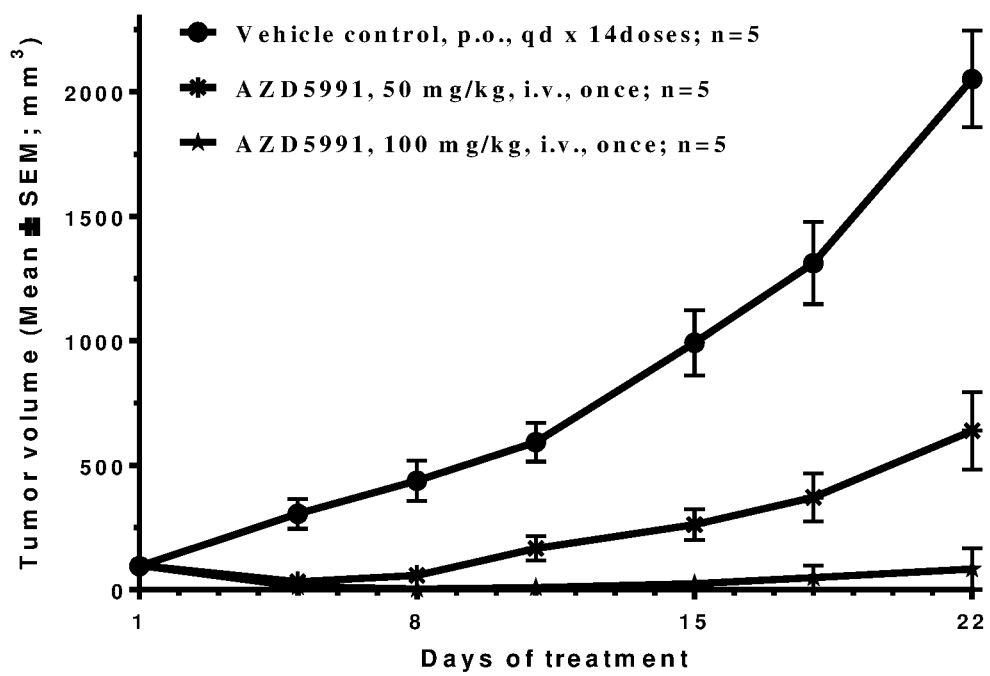
FIG. 11 is a line graph showing the in vivo efficacy by i.v. administration of AZD5991 in the subcutaneous H929 tumor model.
Figure 12:
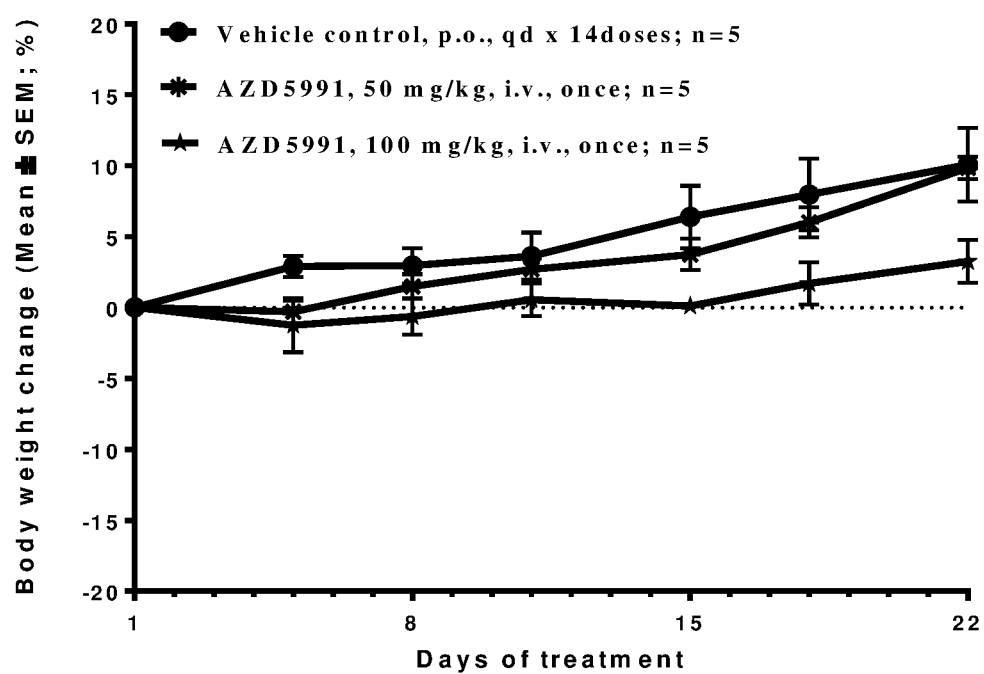
FIG. 12 is a line graph showing body weight change by i.v. administration of AZD5991 in the subcutaneous H929 tumor model.

Female SCID mice at 4-6 weeks old were purchased from Shanghai Laboratory Animal Center (SLAC), $7 \times 10^6$ H929 cells per mouse in 0.2 ml PBS were inoculated subcutaneously to the right flank of the mice. Volumes of the tumor were estimated as $V=LW^2/2$, where L and W stand for tumor length and width. Mice with tumor at 50-150 $mm^3$ were randomized into treatment groups (5 mice per group) and started treatment. Mice were treated with Cpd. No. 6 (referred to in the figures as "Example 6") or Cpd. No. 15 (referred to in the figures as "Example 15") at selected doses once by i.v. administration. The positive control group was treated with AZD5991 at 50 mg/kg and 100 mg/kg once by i.v. administration, respectively. Vehicle control group was dosed i.v. once with 10% PEG400/5 Chremophor EL/85% PBS (pH 7.2). The individual relative tumor volume (RTV) is calculated as following: $RTV=V_t/V_0$, where $V_t$ is the volume on each day of measurement and $V_0$ is the volume on the initial day of treatment. Therapeutic effect of compound is expressed with relative tumor proliferation rate (T/C). The calculation formula is: T/C=mean RTV of the treated group/mean RTV of the control group. Treatments producing >20% lethality and/or 20% net body weight loss were considered toxic. See FIGS. 7-12.

Example 110

Kinetic Solubility Assay

Representative Compounds of the Disclosure were tested in a kinetic solubility assay in PBS buffer. PBS buffer was prepared by dissolving 4.86 g of potassium dihydrogen phosphate and 5.09 g of disodium hydrogen phosphate dodecahydrate in 1 L of ultrapure water (final pH 6.5). 0.5 mg of test sample was dissolved in 1 mL of methanol and the stock solution was transferred into 2 mL EP tube, and evaporated at 50° C. for 3 h. To the tube was added 1 mL of PBS buffer and the mixture was stirred and shaken for 1-2 h. The solution was allowed to stand overnight and then filtered before HPLC analysis. Another 1.5 mg of the sample was dissolved in 3 mL of methanol to prepare a calibration curve with a series of concentration range of 5-500 μM. The solubility of each sample was determined by the measured peak area in HPLC. The results are shown in Table 7.

TABLE 7

| Cpd. No. | Solubility (pH 6.5, μg/mL) |
| --- | --- |
| 2 | <1 |
| 3 | <1 |
| 4 | <1 |
| 5 | 2 |
| 7 | 6 |
| 9 | >400 |
| 11 | <1 |
| 14 | 10 |
| 18 | <1 |
| 26 | <1 |
| 32 | >400 |
| 45 | 94 |
| 52 | 4 |
| AZD5991 | <1 |

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications, and publications cited herein are fully incorporated by reference herein in their entirety.

What is claimed:
1. A compound of Formula I:

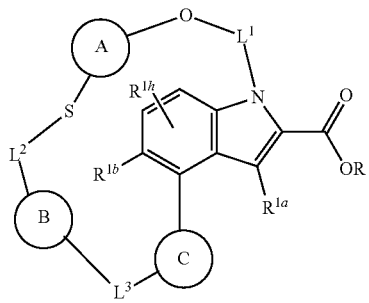

I, wherein:

R is selected from the group consisting of hydrogen and $C_1$-$C_6$ alkyl;

$R^{1a}$ is selected from the group consisting of hydrogen, halo, $C_1$-$C_4$ alkyl, $C_1$-$C_4$ haloalkyl, $C_2$-$C_4$ alkynyl, $C_3$-$C_6$ cycloalkyl, and —$(CH_2)_mN(R^{2a})(R^{2b})$;

$R^{2a}$ is selected from the group consisting of hydrogen and $C_1$-$C_4$ alkyl;

$R^{2b}$ is selected from the group consisting of hydrogen, $C_1$-$C_4$ alkyl, —C(=O)$R^{3a}$, and —S(=O)$_2R^{3b}$; or $R^{2a}$ and $R^{2b}$ taken together with the nitrogen atom to which they are attached form a 3- to 6-membered optionally substituted heterocyclo;

m is 1, 2, or 3;

$R^{3a}$ is selected from the group consisting of $C_1$-$C_4$ alkyl, $C_1$-$C_4$ haloalkyl, $C_3$-$C_6$ cycloalkyl, optionally substituted 4- to 8-membered heterocyclo, optionally substituted $C_6$-$C_{10}$ aryl, and optionally substituted 5- to 10-membered heteroaryl;

$R^{3b}$ is selected from the group consisting of $C_1$-$C_4$ alkyl, $C_1$-$C_4$ haloalkyl, $C_3$-$C_6$ cycloalkyl, optionally substituted 4- to 8-membered heterocyclo, optionally substituted $C_6$-$C_{10}$ aryl, and optionally substituted 5- to 10-membered heteroaryl;

$R^{1b}$ is selected from the group consisting of hydrogen, halo, and $C_1$-$C_4$ alkyl;

$R^{1h}$ is selected from the group consisting of hydrogen, halo, and $C_1$-$C_4$ alkyl;

(A)

is selected from the group consisting of:

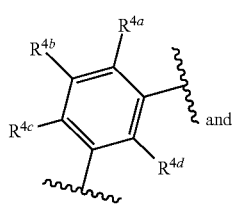

A-1

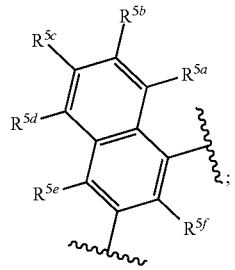

A-2

$R^{4a}$, $R^{4b}$, $R^{4c}$, and $R^{4d}$ are each independently selected from the group consisting of hydrogen, halo, cyano, amino, hydroxyl, $C_1$-$C_4$ alkyl, $C_1$-$C_4$ haloalkyl, and $C_1$-$C_4$ alkoxy;

$R^{5a}$, $R^{5b}$, $R^{5c}$, $R^{5d}$, $R^{5e}$, and $R^{5f}$ are each independently selected from the group consisting of hydrogen, halo, cyano, amino, hydroxyl, $C_1$-$C_4$ alkyl, $C_1$-$C_4$ haloalkyl, and $C_1$-$C_4$ alkoxy;

(B)

is selected from the group consisting of arylene and heteroarylene;

(C)

is selected from the group consisting of:

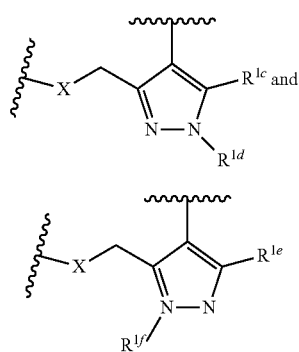

C-1

C-2 wherein —X— is attached to $L^3$;
$R^{1c}$ is selected from the group consisting of hydrogen, $C_1$-$C_4$ alkyl, halo, $C_1$-$C_4$ haloalkyl, and $C_{3\text{-}06}$ cycloalkyl;
$R^{1d}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl; or
$R^{1c}$ and $R^{1d}$ taken together with the atoms to which they are attached form an optionally substituted 4- to 8-membered heterocyclo;
$R^{1e}$ is selected from the group consisting of hydrogen, halo, $C_1$-$C_4$ alkyl, $C_1$-$C_4$ haloalkyl, and $C_3$-$C_6$ cycloalkyl;
$R^{1f}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl;
X is selected from the group consisting of —O—, —S—, —S(=O)—, —S(=O)$_2$—, and —N($R^6$)—;
$R^6$ is selected from the group consisting of hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, —C(=O)$R^{7a}$, —S(=O)$_2R^{8a}$, (hydroxyl)$C_1$-$C_4$ alkyl, (5- to 10-membered heteroaryl)$C_1$-$C_4$ alkyl, ($C_1$-$C_4$ alkoxy)$C_1$-$C_4$ alkyl, (carboxamido)$C_1$-$C_4$ alkyl, —(CH$_2$)$_q$N($R^{13a}$)C(=O)$R^{7b}$, and —(CH$_2$)$_r$N($R^{13b}$)S(=O)$_2R^{8b}$;
$R^{7a}$ is selected from the group consisting of amino, $C_1$-$C_4$ alkyl, $C_1$-$C_4$ alkoxy, optionally substituted $C_3$-$C_6$ cycloalkyl, optionally substituted $C_6$-$C_{10}$ aryl, optionally substituted 5- to 10-membered heteroaryl, and ($C_6$-$C_{10}$ aryl)$C_1$-$C_4$ alkyl;

$R^7b$ is selected from the group consisting of amino, $C_1$-$C_4$ alkyl, $C_1$-$C_4$ alkoxy, optionally substituted $C_3$-$C_6$ cycloalkyl, optionally substituted $C_6$-$C_{10}$ aryl, optionally substituted 5- to 10-membered heteroaryl, and ($C_6$-$C_{10}$ aryl)$C_1$-$C_4$ alkyl;
$R^{8a}$ is selected from the group consisting of amino, $C_1$-$C_4$ alkyl, optionally substituted $C_3$-$C_6$ cycloalkyl, optionally substituted $C_6$-$C_{10}$ aryl, optionally substituted 5- to 10-membered heteroaryl, and ($C_6$-$C_{10}$ aryl)$C_1$-$C_4$ alkyl;
$R^{8b}$ is selected from the group consisting of amino, $C_1$-$C_4$ alkyl, optionally substituted $C_3$-$C_6$ cycloalkyl, optionally substituted $C_6$-$C_{10}$ aryl, optionally substituted 5- to 10-membered heteroaryl, and ($C_6$-$C_{10}$ aryl)$C_1$-$C_4$ alkyl;
$R^{13a}$ is selected from the group consisting of hydrogen and $C_{1\text{-}04}$ alkyl;
$R^{13b}$ is selected from the group consisting of hydrogen and $C_{1\text{-}04}$ alkyl;
q is 1, 2, 3, or 4;
r is 1, 2, 3, or 4;
$L^1$ is —(CR$^{14a}R^{14b}$)$_s$—;
each $R^{14a}$ and $R^{14b}$ are independently selected from the group consisting of hydrogen and $C_1$-$C_4$ alkyl;
s is 2, 3, 4, 5, or 6;
$L^2$ is —(CR$^{14c}R^{14d}$)$_t$—;
each $R^{14c}$ and $R^{14d}$ are independently selected from the group consisting of hydrogen and $C_1$-$C_4$ alkyl;
t is 1, 2, 3, or 4;
$L^3$ is —(CR$^{14e}R^{14f}$)$_v$—;
each $R^{14e}$ and $R^{14f}$ are independently selected from the group consisting of hydrogen and $C_1$-$C_4$ alkyl; and
v is 1, 2, 3, or 4,
wherein the $C_3$-$C_6$ cycloalkyl optionally is substituted with one, two, or three substituents independently selected from the group consisting of from halo, nitro, cyano, hydroxy, amino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, alkenyl, alkynyl, aryl, heteroaryl, heterocyclo, alkoxyalkyl, (amino)alkyl, (carboxamido)alkyl, mercaptoalkyl, and (heterocyclo)alkyl;
wherein aryl is a monocyclic or bicyclic aromatic ring system having an indicated number of carbon atoms, optionally substituted with one to five substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, heterocyclo, alkoxyalkyl, (amino)alkyl, (carboxamido)alkyl, mercaptoalkyl, and (heterocyclo)alkyl;
wherein heteroaryl is a monocyclic or bicyclic aromatic ring systems having 5 to 14 ring atoms, wherein at least one carbon atom of one of the rings is replaced with 1, 2, 3, or 4 heteroatoms independently selected from the group consisting of oxygen, nitrogen and sulfur, optionally substituted with one to four substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, aryl, heteroaryl, heterocyclo, alkoxyalkyl, (amino)alkyl, (carboxamido)alkyl, mercaptoalkyl, and (heterocyclo)alkyl; and wherein heterocyclo is a saturated or partially unsaturated cyclic group containing one, two, or three rings having an indicated number of ring members, wherein at least one carbon atom of one of the rings is replaced with a heteroatom selected from the group consisting of oxygen, sulfur, and/or nitrogen atoms with, optionally substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, alkoxycarbonyl, CF3C(=O)—, arylcarbonyl, alkylsulfonyl, arylsulfonyl, carboxy, carboxyalkyl, alkyl, optionally substituted cycloalkyl, alkenyl, alkynyl, substituted aryl, substituted heteroaryl, substituted heterocyclo, alkoxyalkyl, (amino)alkyl, (carboxamido)alkyl, mercaptoalkyl, and (heterocyclo)alkyl, or a pharmaceutically acceptable salt thereof.

2. The compound of claim 1, wherein $L^3$ and $L^2$, independently, are selected from the group consisting of —CH$_2$— and —CH(CH$_3$)—, or a pharmaceutically acceptable salt thereof.

3. The compound of claim 1, wherein $L^1$ is selected from the group consisting of —CH$_2$CH$_2$—, —CH$_2$CH$_2$CH$_2$—, and —CH$_2$CH—$_2$CH$_2$CH$_2$—, or a pharmaceutically acceptable salt thereof.

4. The compound of claim 1 of Formula II:

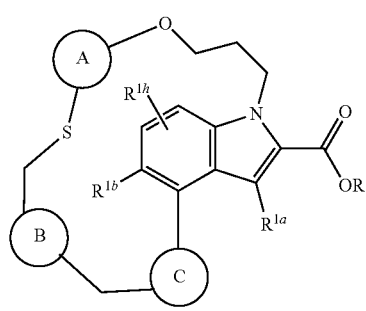

II, or a pharmaceutically acceptable salt thereof.

5. The compound of claim 4 of Formula III:

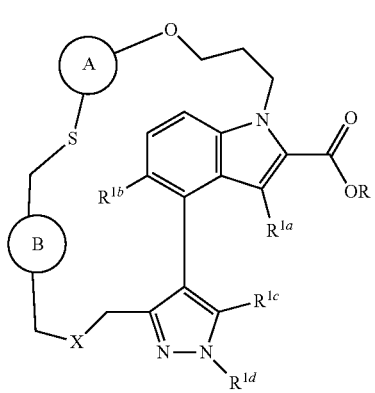

III, or a pharmaceutically acceptable salt thereof.

6. The compound of claim 5 of Formula III-A or III-B:

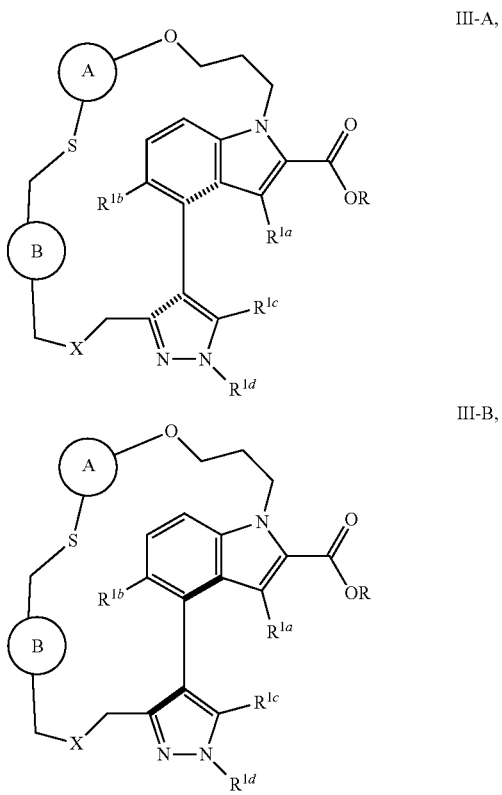

III-A,

III-B, or a pharmaceutically acceptable salt thereof.

7. The compound of claim 1, wherein:
$R^{1c}$ is selected from the group consisting of $C_1$-$C_4$ alkyl and $C_1$-$C_4$ haloalkyl; and
$R^{1d}$ is selected from the group consisting of $C_1$-$C_4$ alkyl and (carboxamido)$C_1$-$C_4$ alkyl,
or a pharmaceutically acceptable salt thereof.

8. The compound of claim 4 of Formula IV:

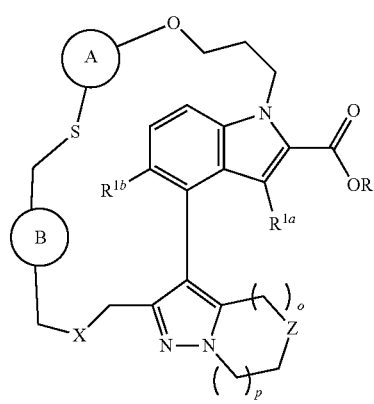

IV, wherein:
o is 0, 1, or 2;
p is 0 or 1;
with the proviso that when p is 0, Z is —CR$^{9a}$R$^{9b}$—;
Z is selected from the group consisting of —CR$^{9a}$R$^{9b}$—, —O—, —S—, S(=O)—, S(=O)$_2$—, and —N(R$^{10}$)—;

$R^{9a}$ and $R^{9b}$ are independently selected from the group consisting of hydrogen and $C_1$-$C_4$ alkyl;

$R^{10}$ is selected from the group consisting of hydrogen, $C_1$-$C_4$ alkyl, —C(=O)$_2$R$^{11}$, and —S(=O)$_2$R$^{12}$;

$R^{11}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl; and $R^{12}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl, or a pharmaceutically acceptable salt thereof.

9. The compound of claim 8 of Formula IV-A or IV-B:

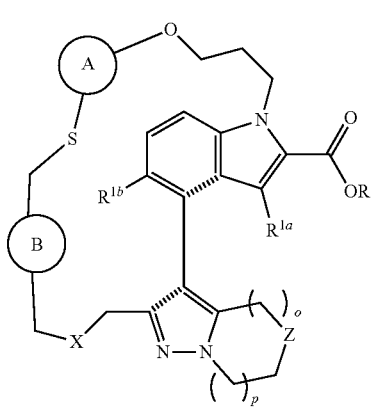

IV-A,

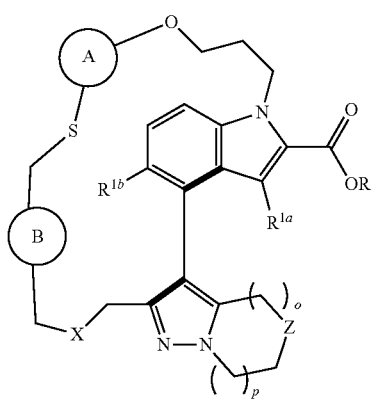

IV-B, or a pharmaceutically acceptable salt thereof.

10. The compound of claim 8, wherein Z is —O—, —CH$_2$—, or —C(CH$_3$)$_2$—, or a pharmaceutically acceptable salt thereof.

11. The compound of claim 4 of Formula V:

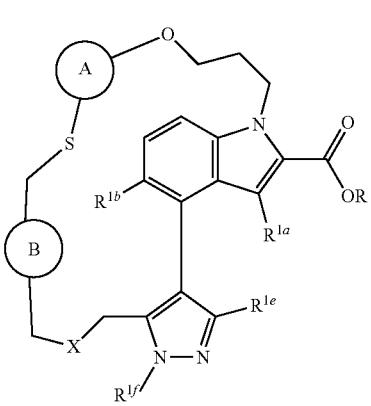

V, or a pharmaceutically acceptable salt thereof.

12. The compound of claim 11 of Formula V-A or V-B:

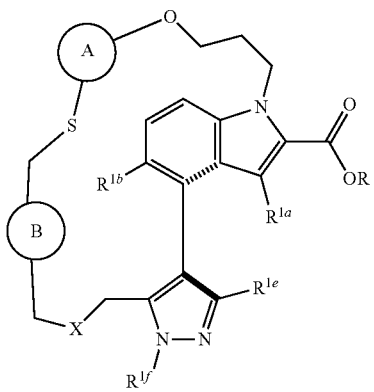

V-A,

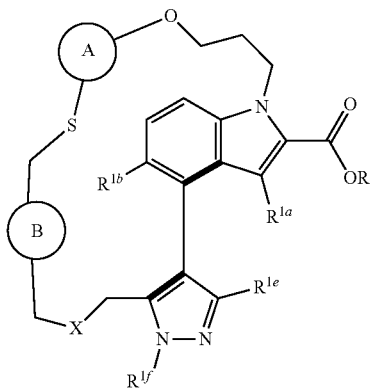

V-B, or a pharmaceutically acceptable salt thereof.

13. The compound of claim 11, wherein:
$R^{1e}$ is selected from the group consisting of $C_1$-$C_4$ alkyl and $C_1$-$C_4$ haloalkyl; and
$R^{1f}$ is selected from the group consisting of $C_1$-$C_4$ alkyl, ($C_1$-$C_4$ alkoxy)$C_1$-$C_4$ alkyl, and (carboxamido)$C_1$-$C_4$ alkyl,
or a pharmaceutically acceptable salt thereof.

14. The compound of claim 1, wherein X is —O—, —S—, —S(=O)$_2$—, or —N(R$^6$)—, or a pharmaceutically acceptable salt thereof.

15. The compound of claim 14, wherein:
R$^6$ is selected from the group consisting of hydrogen, C$_1$-C$_4$ alkyl, optionally substituted C$_6$-C$_{10}$ aryl, (C$_6$-C$_{10}$ aryl)C$_1$-C$_4$ alkyl, —S(=O)$_2$R$^{8a}$, (hydroxyl)C$_1$-C$_4$ alkyl, (5- to 10-membered heteroaryl)C$_1$-C$_4$ alkyl, (C$_1$-C$_4$ alkoxy)C$_1$-C$_4$ alkyl, (carboxamido)C$_1$-C$_4$ alkyl, and —(CH$_2$)$_1$N(H)S(=O)$_2$R$^{8b}$,
R$^{8a}$ is selected from the group consisting of C$_1$-C$_4$ alkyl, optionally substituted C$_3$-C$_6$ cycloalkyl, optionally substituted C$_6$-C$_{10}$ aryl, and (C$_6$-C$_{10}$ aryl)C$_1$-C$_4$ alkyl; and
R$^{8b}$ is C$_1$-C$_4$ alkyl,
or a pharmaceutically acceptable salt thereof.

16. The compound of claim 1, wherein:
R$^{4a}$, R$^{4b}$, and R$^{4c}$ are each independently selected from the group consisting of hydrogen and halo; and
R$^{4d}$ is hydrogen,
or a pharmaceutically acceptable salt thereof.

17. The compound of claim 1, wherein the 1-position of A-2 is attached to the oxygen atom and the 3-position of A-2 is attached to the sulfur atom, or a pharmaceutically acceptable salt thereof.

18. The compound of claim 1, wherein:
R$^{5a}$, R$^{5b}$, R$^{5c}$, R$^{5d}$, and R$^{5e}$ are each independently selected from the group consisting of hydrogen and halo; and
R$^{5f}$ is hydrogen,
or a pharmaceutically acceptable salt thereof.

19. The compound of claim 1, wherein R$^{1a}$ is selected from the group consisting of hydrogen, fluoro, chloro, methyl, ethyl, ethynyl, —CH$_2$N(H)C(=O)CH$_3$, and —CH$_2$N(H)S(=O)$_2$CF$_3$, or a pharmaceutically acceptable salt thereof.

20. The compound of claim 1, wherein Rib is halo or hydrogen, or a pharmaceutically acceptable salt thereof.

21. The compound of claim 1, wherein:

B is selected from the group consisting of:

B-1

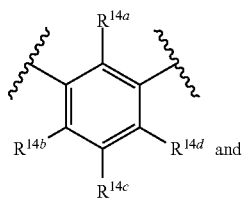

and

B-2

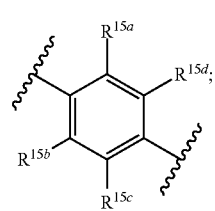

r$^{14a}$, r$^{14b}$, r$^{14c}$, and R$^{14d}$ are independently selected from the group consisting of hydrogen, halo, cyano, C$_1$-C$_4$ alkyl, C$_1$-C$_4$ haloalkyl, C$_1$-C$_4$ alkoxy, and C$_3$-C$_6$ cycloalkyl; and R$^{15a}$, R$^{15b}$, R$^{15c}$, and R$^{15d}$ are independently selected from the group consisting of hydrogen, halo, cyano, C$_1$-C$_4$ alkyl, C$_1$-C$_4$ haloalkyl, C$_1$-C$_4$ alkoxy, and C$_3$-C$_6$ cycloalkyl,
or a pharmaceutically acceptable salt thereof.

22. The compound of claim 1, wherein R$^{14a}$, R$^{14b}$, R$^{14c}$, and R$^{14d}$ are each independently selected from the group consisting of hydrogen, halo, and C$_1$-C$_4$ alkyl, or a pharmaceutically acceptable salt thereof.

23. The compound of claim 1, wherein R$^{15a}$, R$^{15b}$, R$^{15c}$, and R$^{15d}$ are each independently selected from the group consisting of hydrogen, halo, and C$_1$-C$_4$ alkyl, or a pharmaceutically acceptable salt thereof.

24. The compound of claim 1, wherein:

B is selected from the group consisting of:

B-3

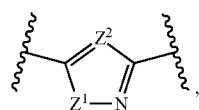

B-4

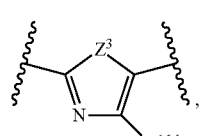

B-5

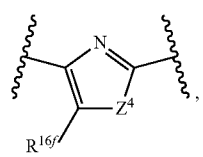

B-6

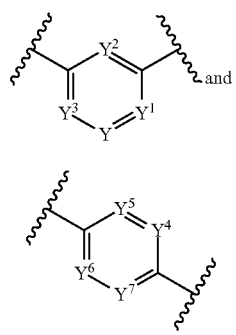

and

B-7

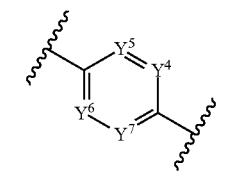

Z$^1$ is selected from the group consisting of —O—, —S—, and —N(R$^{16a}$)—;
R$^{16a}$ is selected from the group consisting of hydrogen, C$_1$-C$_4$ alkyl, and C$_3$-C$_6$ cycloalkyl;
Z$^2$ is selected from the group consisting of —C(R$^{16b}$)= and —N=;
R$^{16b}$ is selected from the group consisting of hydrogen, halo, C$_1$-C$_4$ alkyl, and C$_3$-C$_6$ cycloalkyl;
Z$^3$ is selected from the group consisting of —O—, —S—, and —N(R$^{16c}$)—;
R$^{16c}$ is selected from the group consisting of hydrogen, C$_1$-C$_4$ alkyl, and C$_3$-C$_6$ cycloalkyl;

$R^{16d}$ is selected from the group consisting of hydrogen, halo, $C_1$-$C_4$ alkyl, and $C_3$-$C_6$ cycloalkyl;

$Z^4$ is selected from the group consisting of —O—, —S—, and —N($R^{16e}$)—;

$R^{16e}$ is selected from the group consisting of hydrogen, $C_1$-$C_4$ alkyl, and $C_3$-$C_6$ cycloalkyl;

$R^{16f}$ is selected from the group consisting of hydrogen, halo, $C_1$-$C_4$ alkyl, and $C_3$-$C_6$ cycloalkyl;

Y is selected from the group consisting of —C($R^{17a}$)= and —N=;

$Y^1$ is selected from the group consisting of —C($R^{17b}$)= and —N=;

$Y^2$ is selected from the group consisting of —C($R^{17c}$)= and —N=;

$Y^3$ is selected from the group consisting of —C($R^{17d}$)= and —N=;

with proviso that at least one of Y, $Y^1$, $Y^2$, and $Y^3$ is —N=;

$R^{17a}$, $R^{17b}$, $R^{17c}$, and $R^{17d}$ are independently selected from the group consisting of hydrogen, halo, cyano, $C_1$-$C_4$ alkyl, $C_1$-$C_4$ haloalkyl, and $C_1$-$C_4$ alkoxy;

$Y^4$ is selected from the group consisting of —C($R^{18a}$)= and —N=;

$Y^5$ is selected from the group consisting of —C($R^{18b}$)= and —N=;

Y6 is selected from the group consisting of —C($R^{18c}$)= and —N=;

$Y^7$ is selected from the group consisting of —C($R^{18d}$)= and —N=;

with proviso that at least one of $Y^4$, $Y^5$, $Y^6$, and $Y^7$ is —N=;

$R^{18a}$, $R^{18b}$, $R^{18c}$, and $R^{18d}$ are independently selected from the group consisting of hydrogen, halo, cyano, $C_1$-$C_4$ alkyl, $C_1$-$C_4$ haloalkyl, and $C_1$-$C_4$ alkoxy, or a pharmaceutically acceptable salt thereof.

25. The compound of claim 24, wherein:
$Z^1$ is selected from the group consisting of —O—, —S—, —N(H)—, and —N(CH$_3$)—; and
$Z^2$ is selected from the group consisting of —C(H)=, —C(CH$_3$)=, and —N=,
or a pharmaceutically acceptable salt thereof.

26. The compound of claim 24, wherein:
$Z^3$ is selected from the group consisting of —O—, —S—, —N(H)—, and —N(CH$_3$)—; and
$R^{16d}$ is selected from the group consisting of hydrogen and methyl, or a pharmaceutically acceptable salt thereof.

27. The compound of claim 24, wherein:
$Z^4$ is selected from the group consisting of —O—, —S—, —N(H)—, and —N(CH$_3$)—; and
$R^{16f}$ is selected from the group consisting of hydrogen and methyl,
or a pharmaceutically acceptable salt thereof.

28. The compound of claim 24, wherein:
Y is —N=;
$Y^1$ is selected from the group consisting of —C($R^{17b}$)= and —N=;
$Y^2$ is selected from the group consisting of —C($R^{17c}$)= and —N=;
$Y^3$ is selected from the group consisting of —C($R^{17d}$)= and —N=; and
$R^{17b}$, $R^{17c}$, and $R^{17d}$ are independently selected from the group consisting of hydrogen, halo, and $C_1$-$C_4$ alkyl,
or a pharmaceutically acceptable salt thereof.

29. The compound of claim 1, wherein

Ⓑ is selected from the group consisting of:

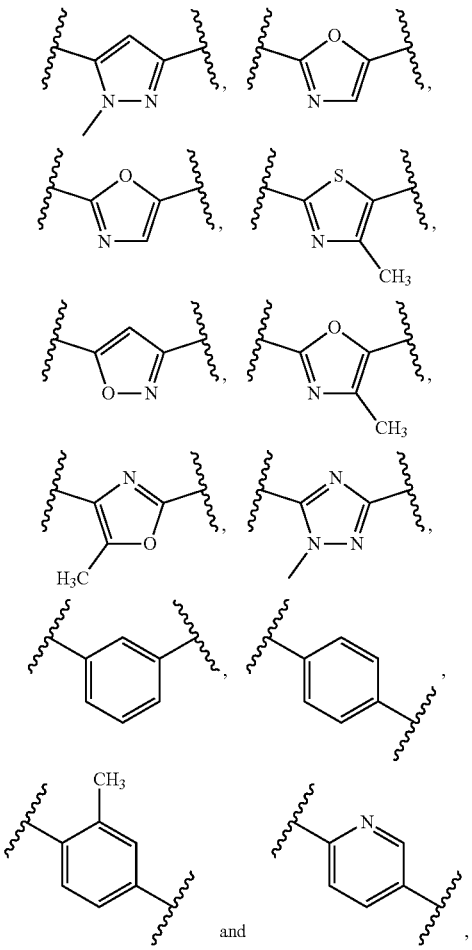

or a pharmaceutically acceptable salt thereof.

30. The compound of claim 29, wherein

Ⓑ is:

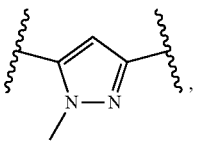 [SMILES: *c1cc(*)n(C)n1]

or a pharmaceutically acceptable salt thereof.

31. A compound selected from the group consisting,
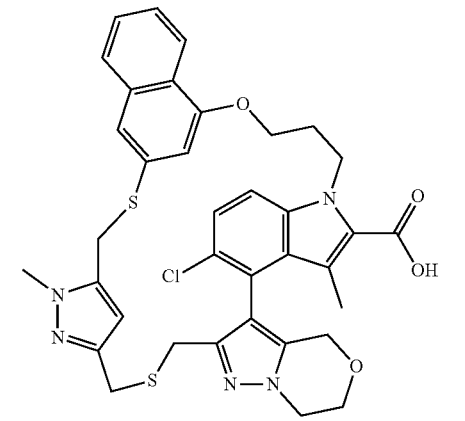
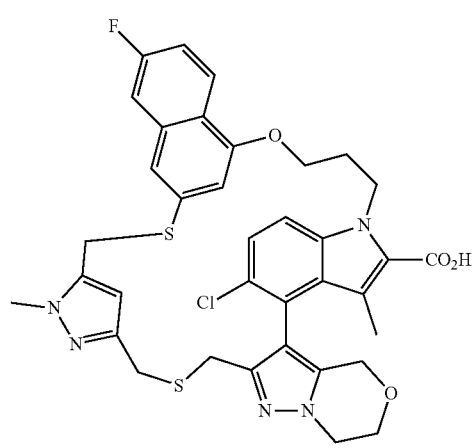
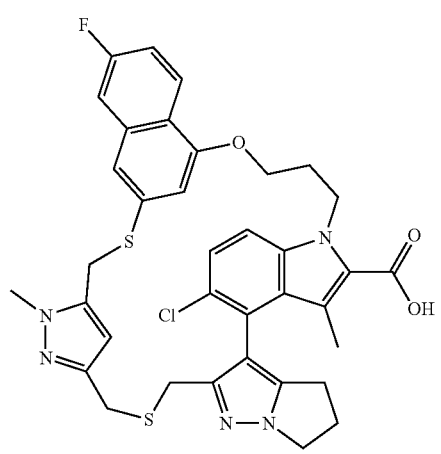
-continued
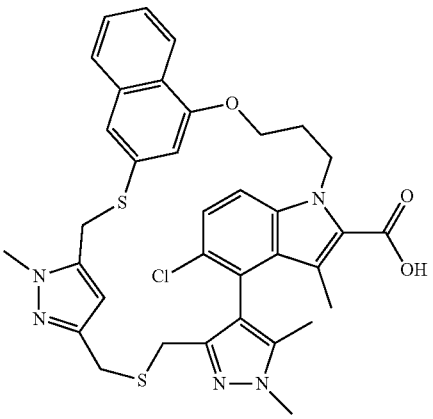
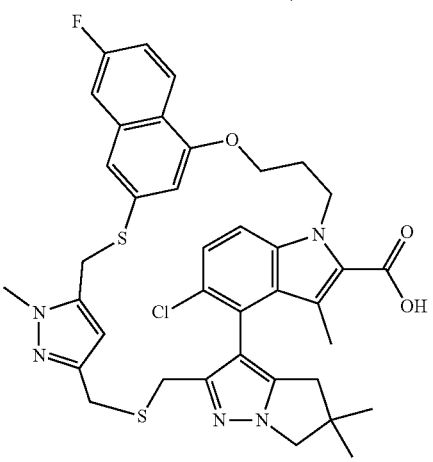
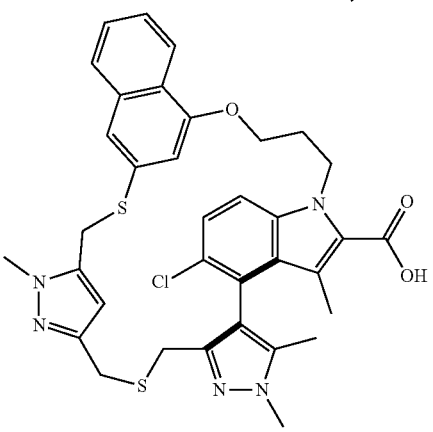
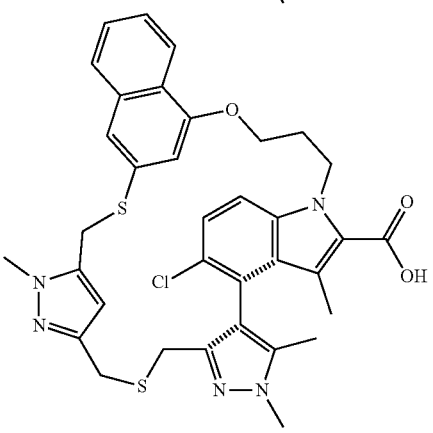

347
-continued
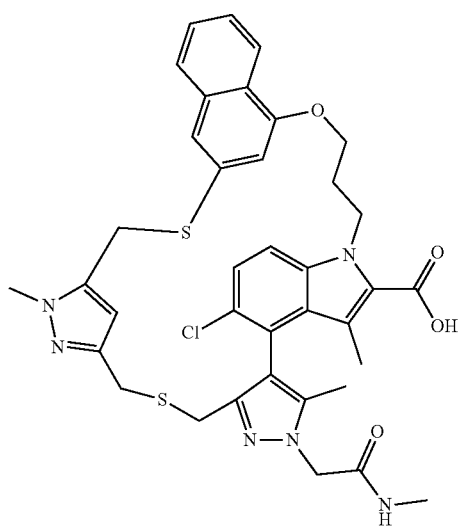
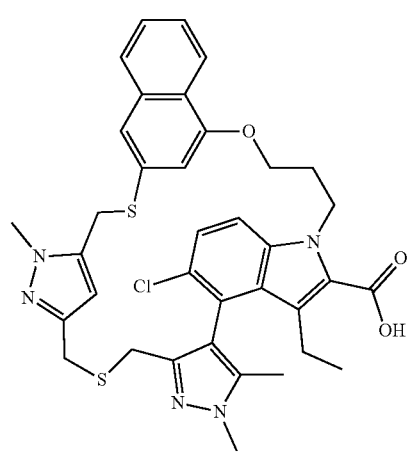
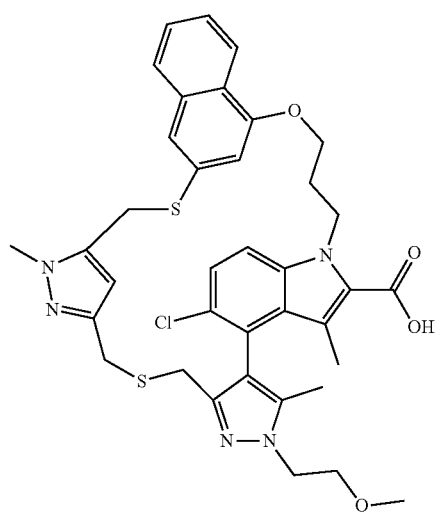
348
-continued
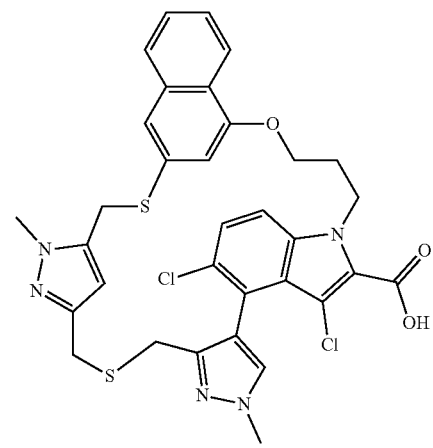 [SMILES: Cn1cc2c(n1)CSCc1cc(n(C)n1)CSc1cc(c3ccccc3c1)OCCCn1c(C(=O)O)c(Cl)c3c-2c(Cl)ccc31]
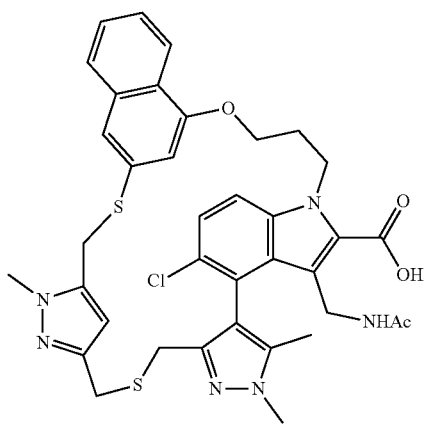
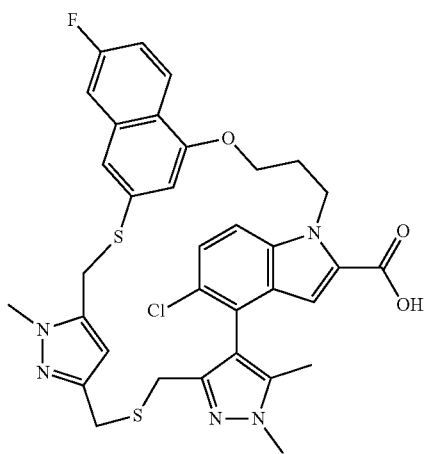

349
-continued
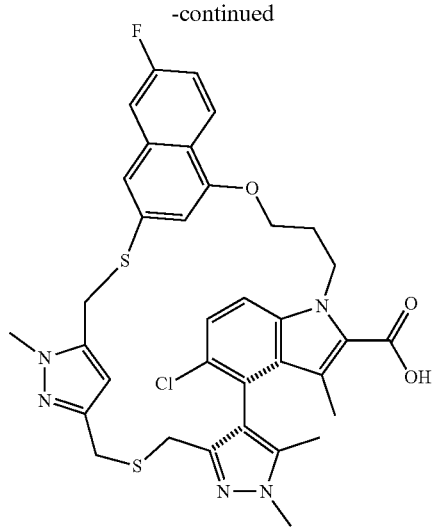
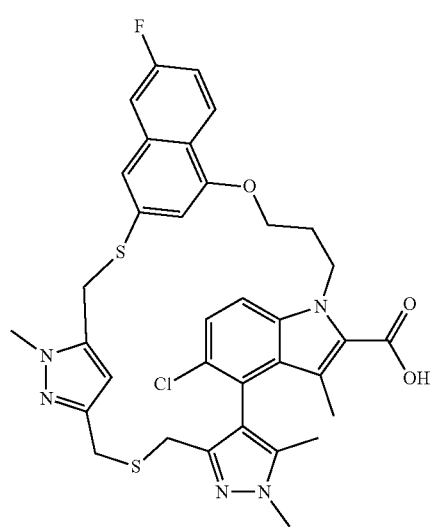
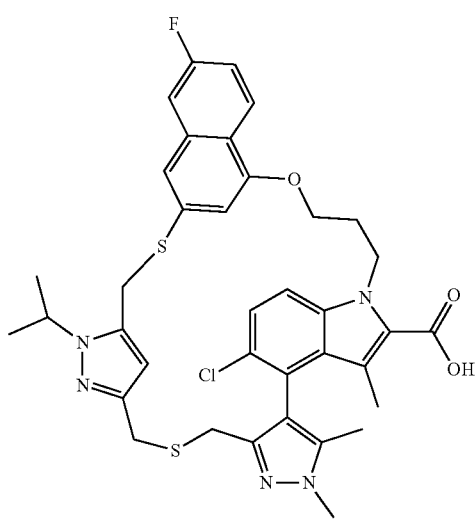
350
-continued
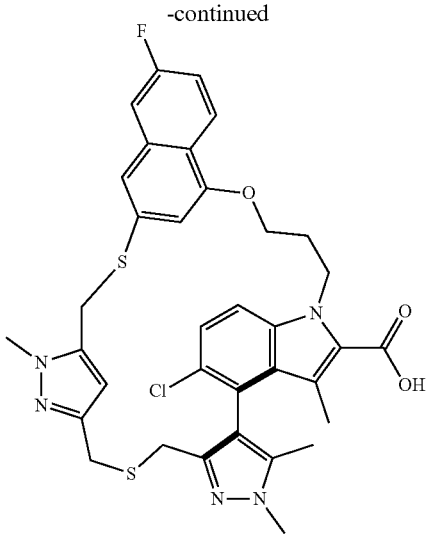
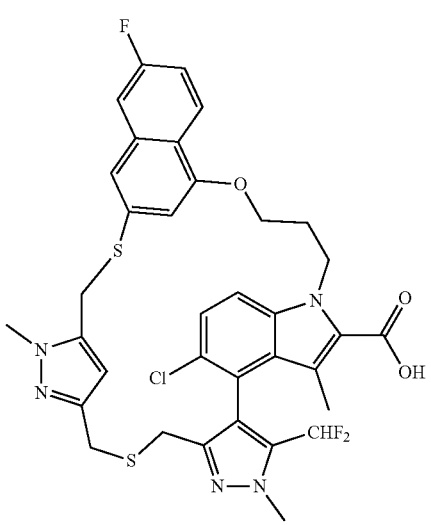
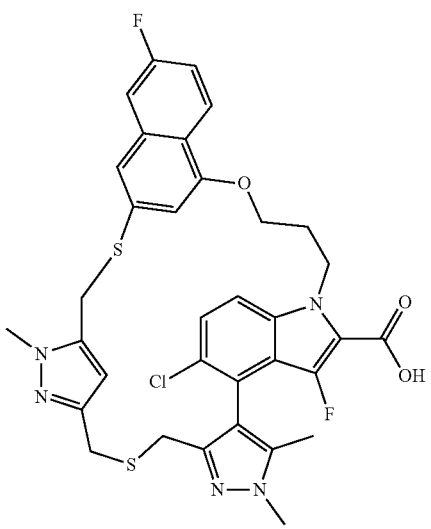

351
-continued
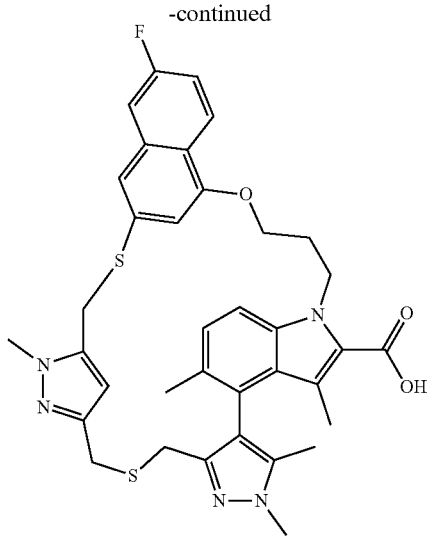
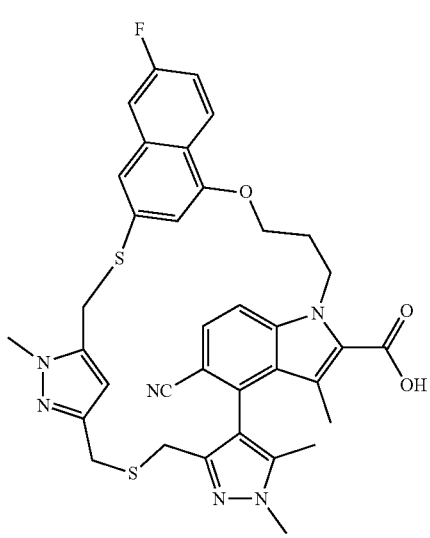
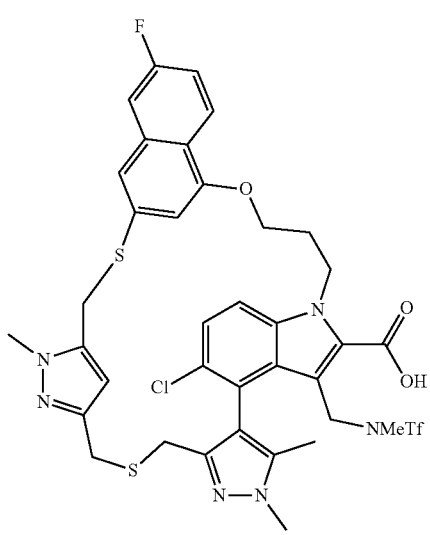
352
-continued
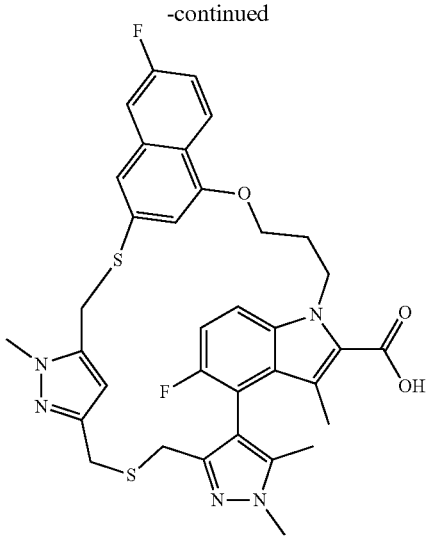
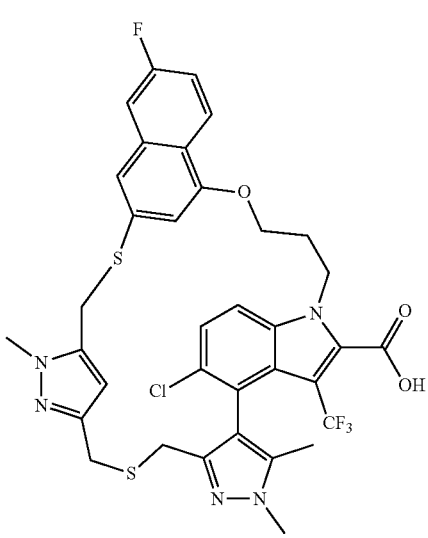
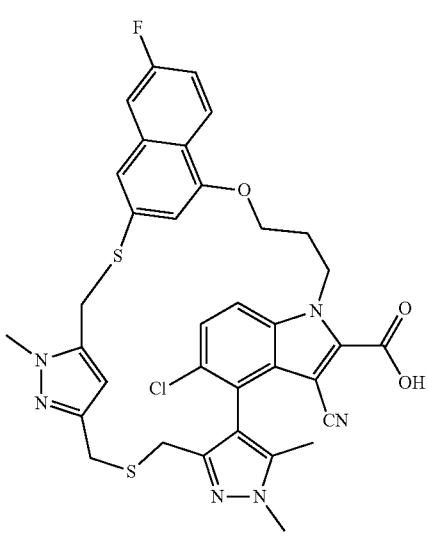

| 353 | 354 |
|---|---|
| -continued | -continued |
| 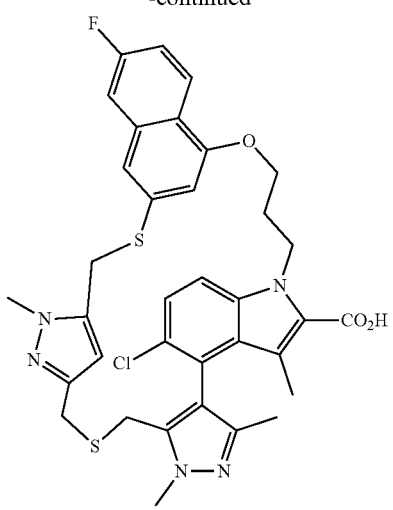 | 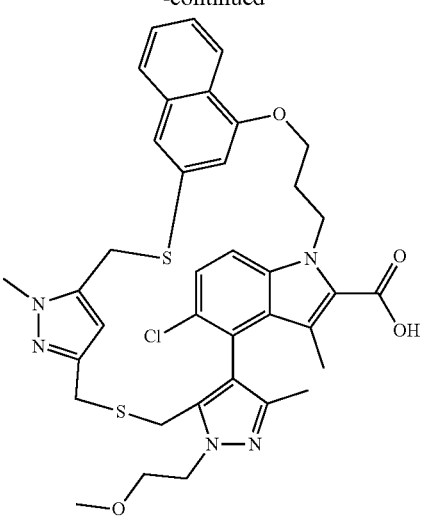 |
| 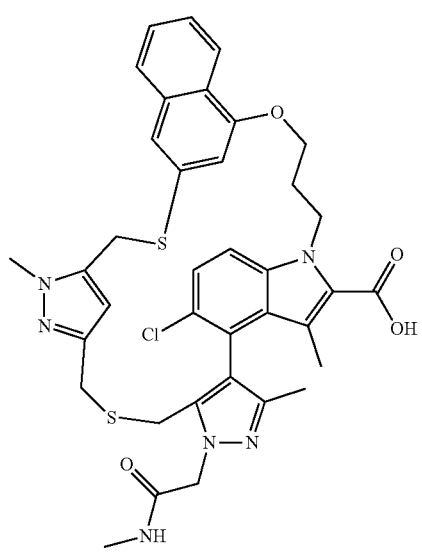 | 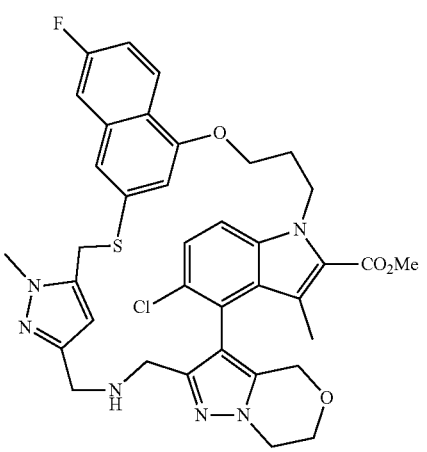 [SMILES: COC(=O)c1c(C)c2c3c(Cl)ccc2n1CCCOc1cc(cc2cc(F)ccc12)SCc1cc(nn1C)CNCc1nn2c(c1-3)COCC2] |
| 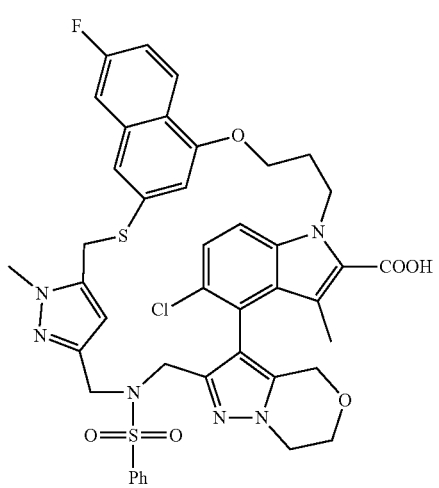 | 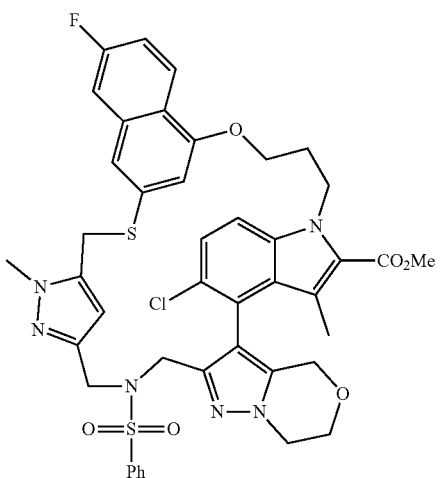 |

355
-continued
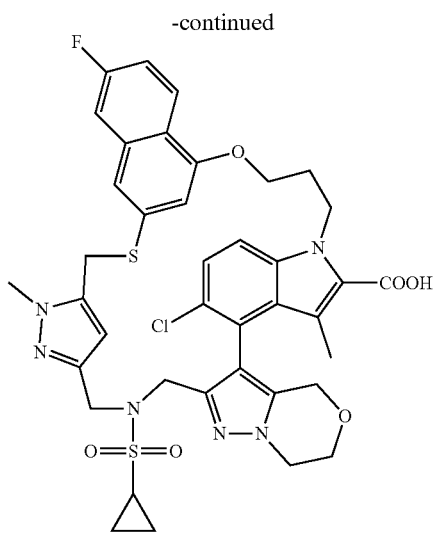
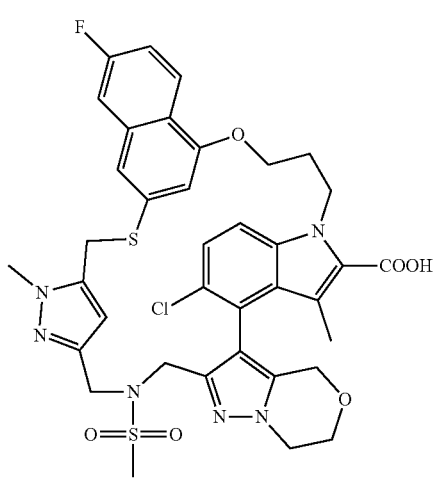
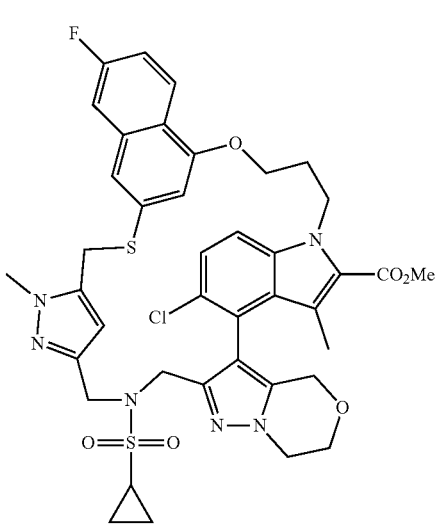
356
-continued
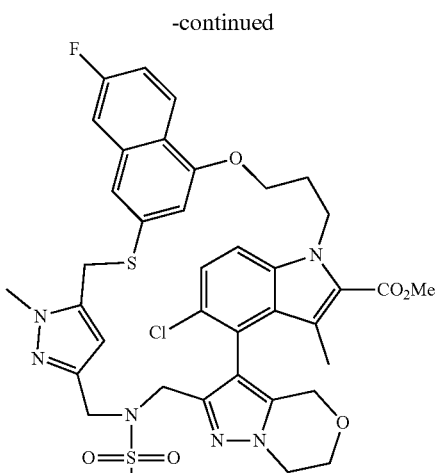
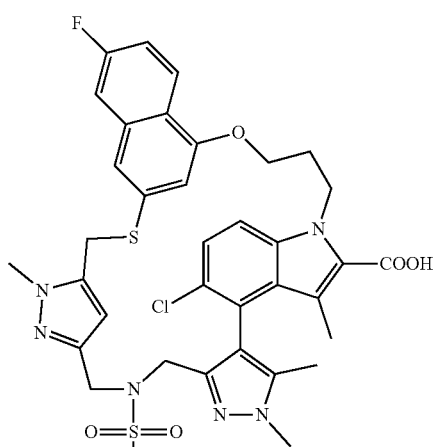
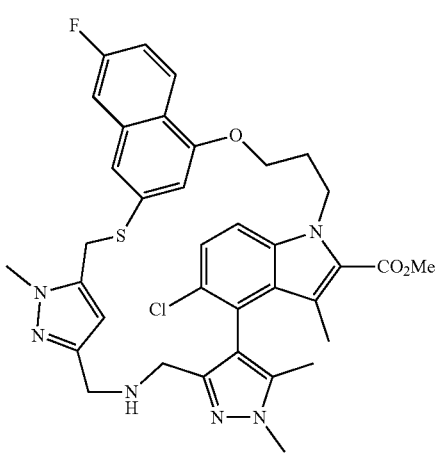

357
-continued
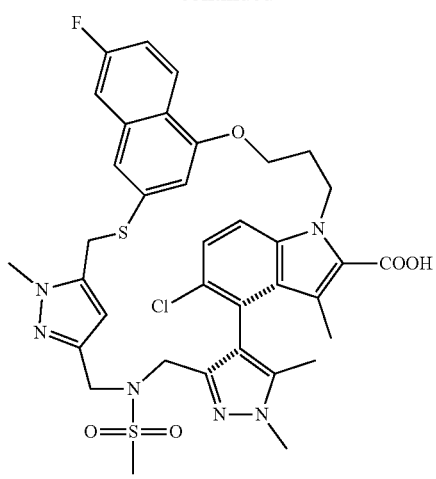
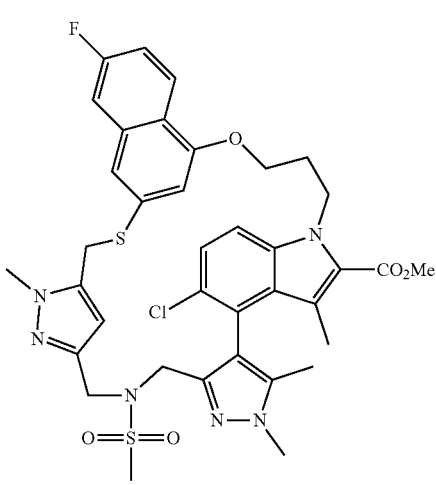
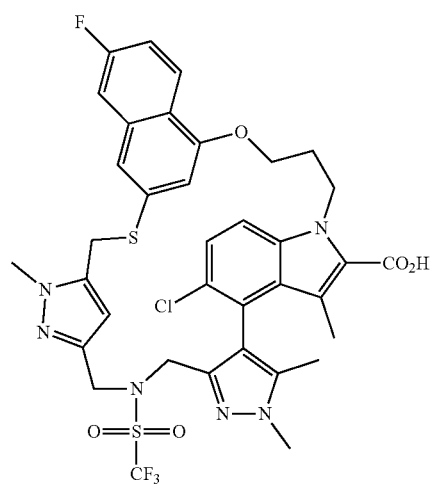
358
-continued
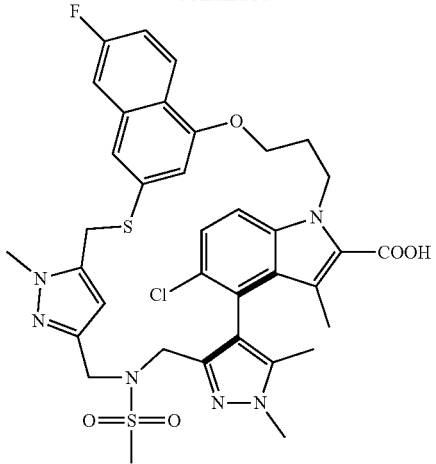
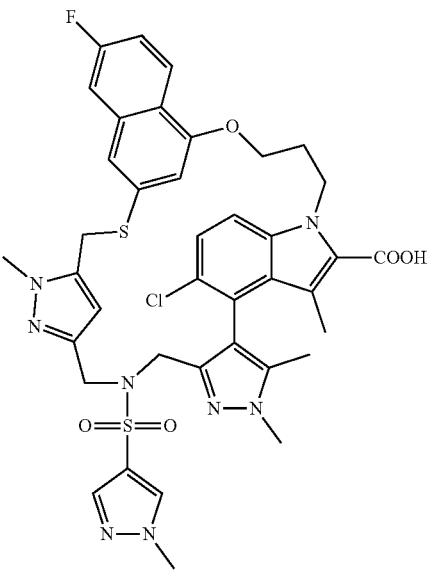
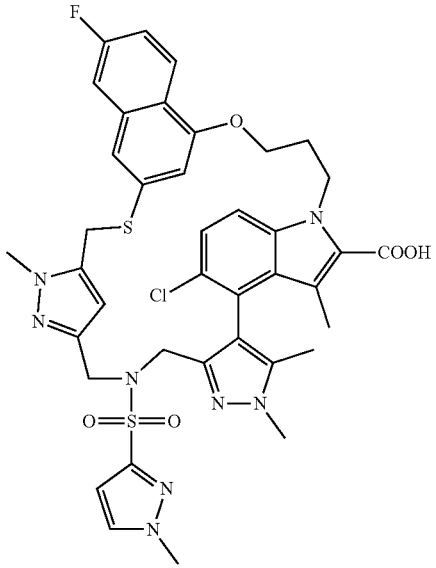

| 359 -continued | 360 -continued |
|---|---|
| 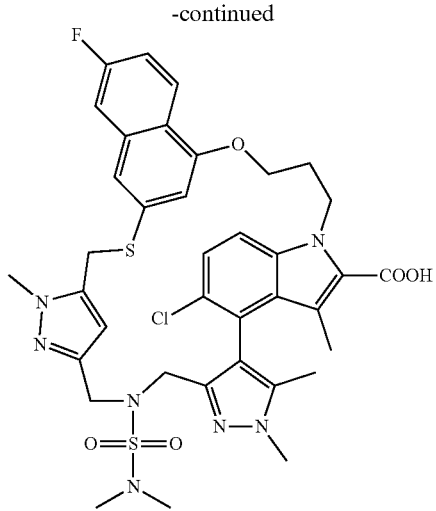 | 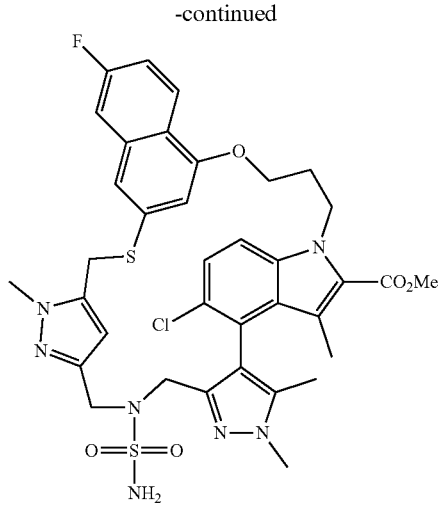 |
| 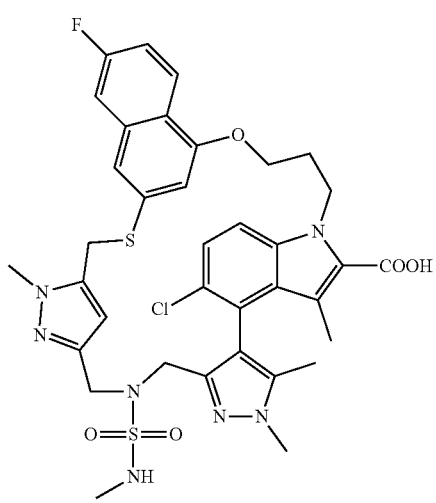 | 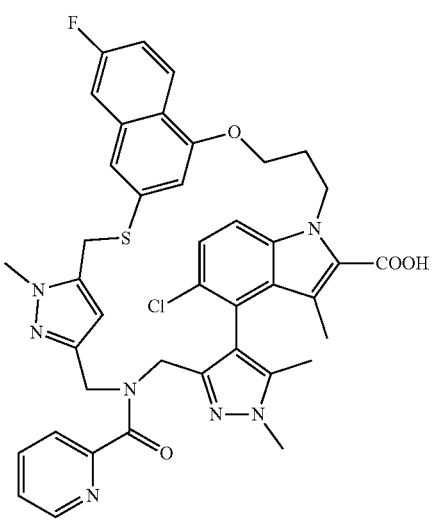 |
| 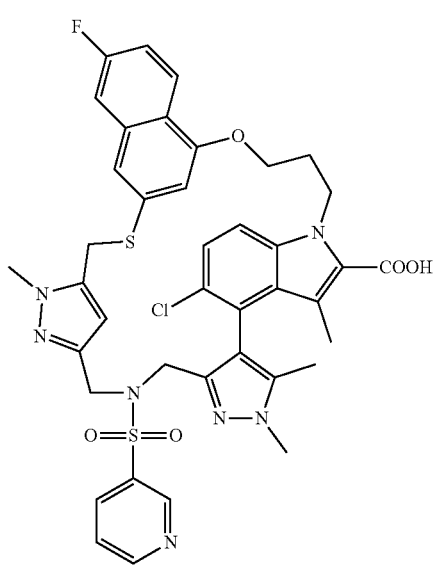 | 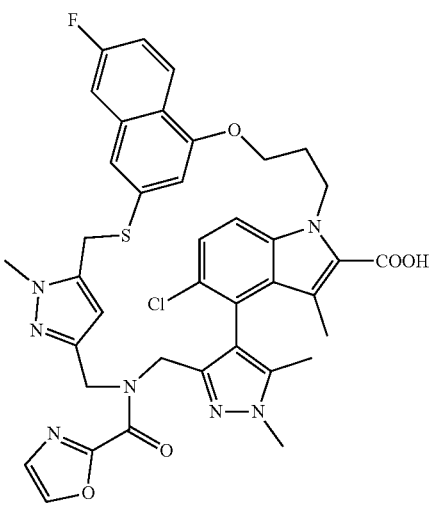 |

361
-continued
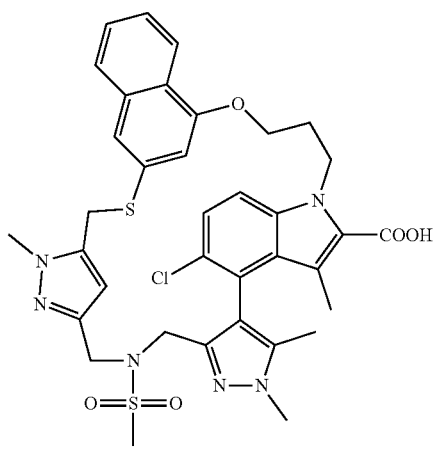
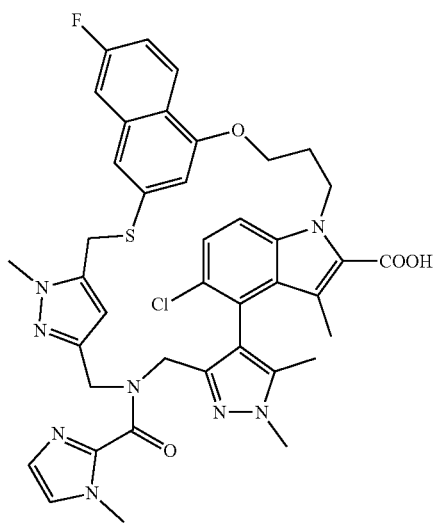
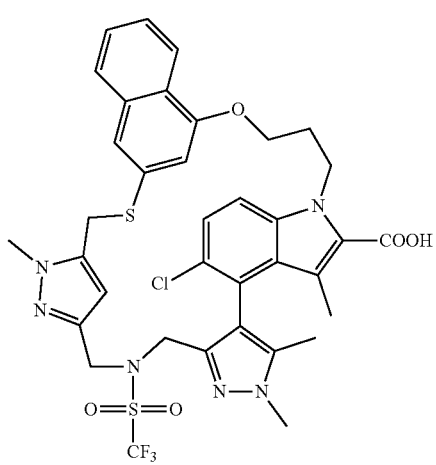
362
-continued
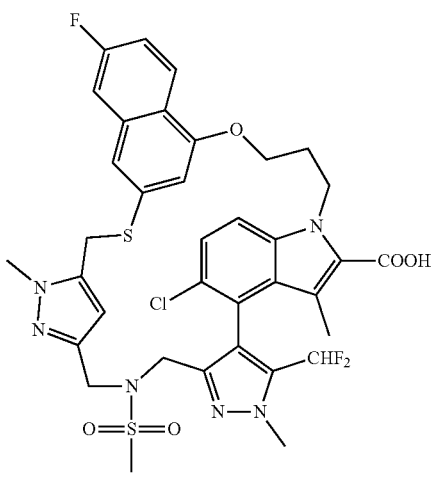
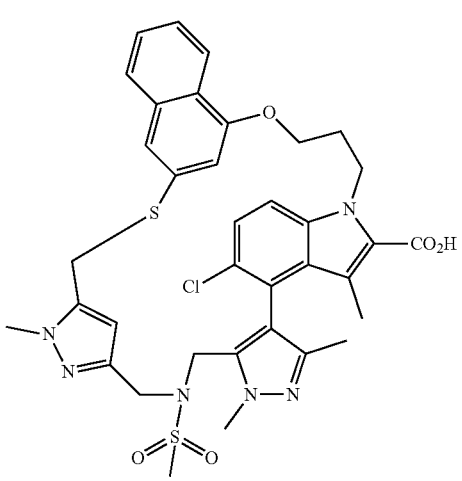
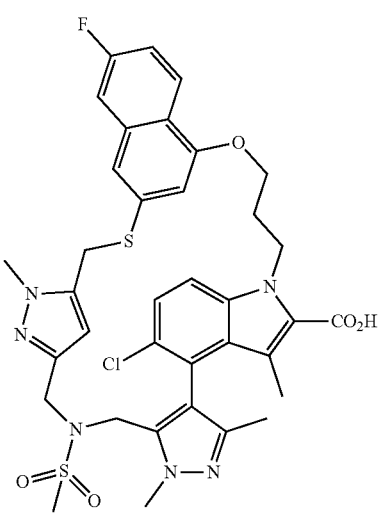

363
-continued
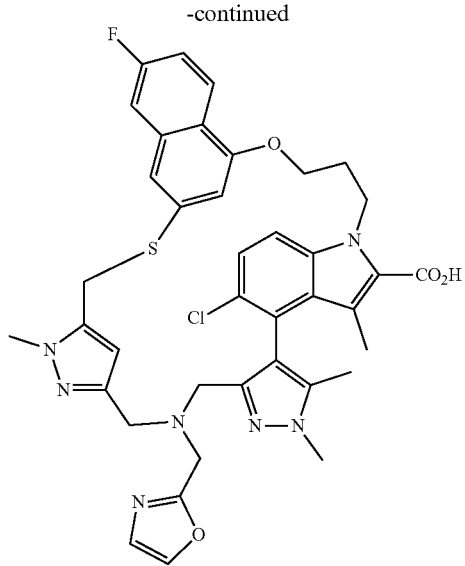
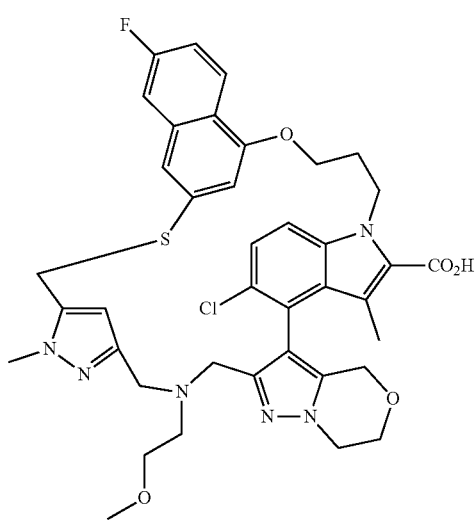
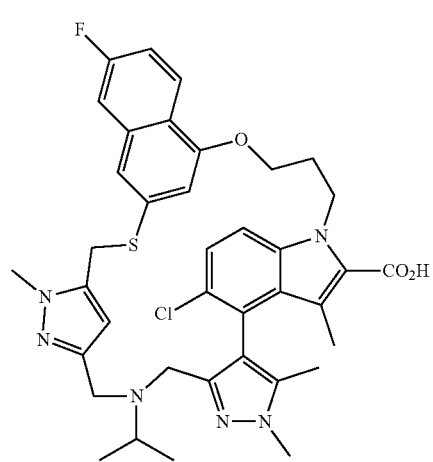
364
-continued
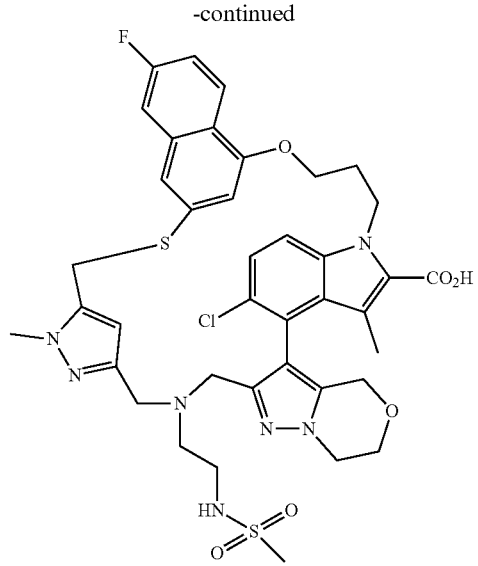
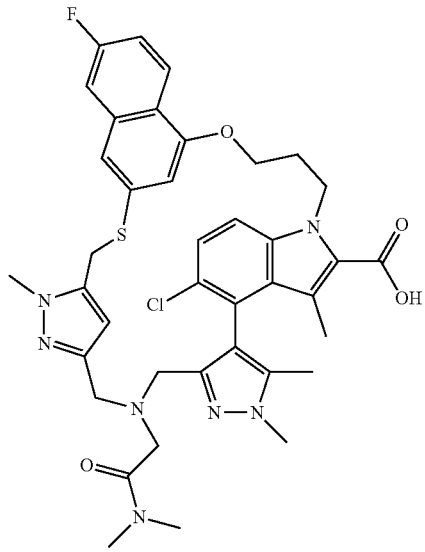
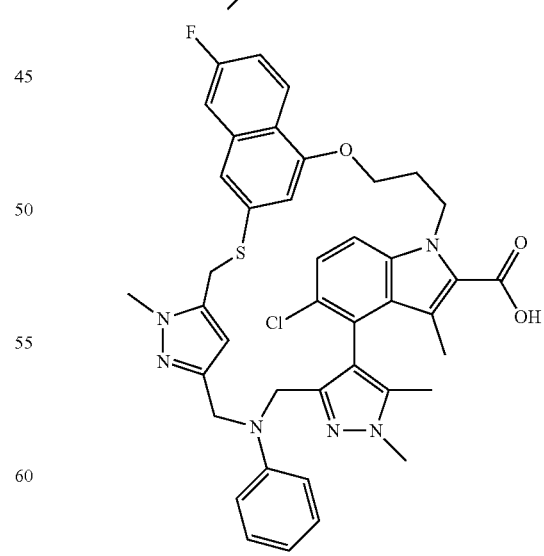
or a pharmaceutically acceptable salt thereof.

32. A pharmaceutical composition comprising the compound of claim 1, or a pharmaceutically acceptable salt thereof, and a pharmaceutically acceptable carrier.

33. A method of treating a subject, the method comprising administering to the subject a therapeutically effective amount of the compound of claim 1, or a pharmaceutically acceptable salt thereof, wherein the subject has B-myelomonocytic leukemia or multiple myeloma.

34. A kit comprising the compound of claim 1, or a pharmaceutically acceptable salt thereof, and instructions for administering the compound, or a pharmaceutically acceptable salt thereof, to a subject having B-myelomonocytic leukemia or multiple myeloma.

35. A compound of Formula XXVI:

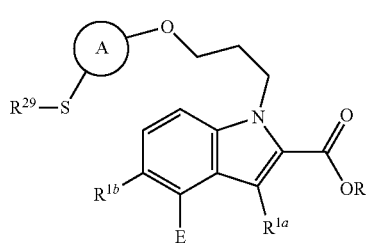

XXVI, wherein:

R is selected from the group consisting of hydrogen and $C_1$-$C_6$ alkyl;

$R^{1a}$ is selected from the group consisting of hydrogen, halo, $C_1$-$C_4$ alkyl, $C_1$-$C_4$ haloalkyl, $C_2$-$C_4$ alkynyl, $C_3$-$C_6$ cycloalkyl, —C(=O)H, and —$(CH_2)_m$N($R^{2a}$)($R^{2b}$);

$R^{2a}$ is selected from the group consisting of hydrogen and $C_1$-$C_4$ alkyl;

$R^{2b}$ is selected from the group consisting of hydrogen, $C_1$-$C_4$ alkyl, —C(=O)$R^{3a}$, and —S(=O)$_2R^{3b}$; or $R^{2a}$ and $R^{2b}$ taken together with the nitrogen atom to which they are attached form a 3- to 6-membered optionally substituted heterocyclo;

m is 1, 2, or 3;

$R^{3a}$ is selected from the group consisting of $C_1$-$C_4$ alkyl, $C_1$-$C_4$ haloalkyl, $C_3$-$C_6$ cycloalkyl, optionally substituted 4- to 8-membered heterocyclo, optionally substituted $C_6$-$C_{10}$ aryl, and optionally substituted 5- to 10-membered heteroaryl;

$R^{3b}$ is selected from the group consisting of $C_1$-$C_4$ alkyl, $C_1$-$C_4$ haloalkyl, $C_3$-$C_6$ cycloalkyl, optionally substituted 4- to 8-membered heterocyclo, optionally substituted $C_6$-$C_{10}$ aryl, and optionally substituted 5- to 10-membered heteroaryl;

$R^{1b}$ is selected from the group consisting of hydrogen, halo, and $C_1$-$C_4$ alkyl;

A is selected from the group consisting of:

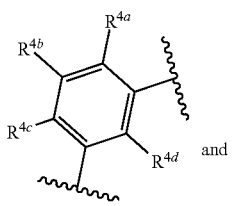

A-1

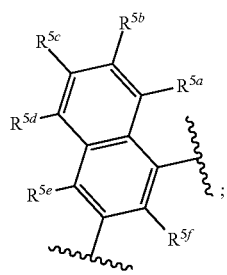

A-2

$R^{4a}$, $R^{4b}$, $R^{4c}$, and $R^{4d}$ are each independently selected from the group consisting of hydrogen, halo, cyano, amino, hydroxyl, $C_1$-$C_4$ alkyl, $C_1$-$C_4$ haloalkyl, and $C_1$-$C_4$ alkoxy;

$R^{5a}$, $R^{5b}$, $R^{5c}$, $R^{5d}$, $R^{5e}$, and $R^{5f}$ are each independently selected from the group consisting of hydrogen, halo, cyano, amino, hydroxyl, $C_1$-$C_4$ alkyl, $C_1$-$C_4$ haloalkyl, and $C_1$-$C_4$ alkoxy; and $R^{29}$ is selected from the group consisting of $R^{19}$ and

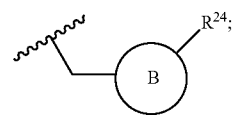

$R^{19}$ is selected from the group consisting of hydrogen and a protecting group;

E is selected from the group consisting of —Br,

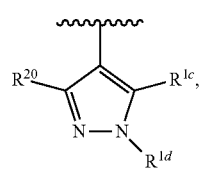

E-1

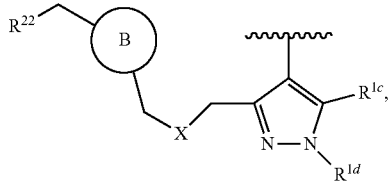

E-2

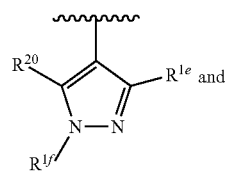

E-3 and

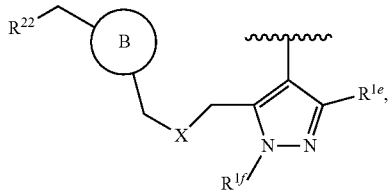

$R^{1c}$ is selected from the group consisting of hydrogen, $C_1$-$C_4$ alkyl, halo, $C_1$-$C_4$ haloalkyl, and $C_3$-$C_6$ cycloalkyl;

$R^{1d}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl; or $R^{1c}$ and $R^{1d}$ taken together with the atoms to which they are attached form an optionally substituted 4- to 8-membered heterocyclo;

$R^{1e}$ is selected from the group consisting of hydrogen, halo, $C_1$-$C_4$ alkyl, $C_1$-$C_4$ haloalkyl, and $C_3$-$C_6$ cycloalkyl;

$R^{1f}$ is selected from the group consisting of hydrogen, $C_1$-$C_4$ alkyl, $C_3$-$C_6$ cydoalkyl, ($C_1$-$C_4$ alkoxy)$C_1$-$C_4$ alkyl, and (carboxamido)$C_1$-$C_4$ alkyl;

$R^{20}$ is selected from the group consisting of —C(=O)H, —CH$_2$-LG, and —CH$_2$X$R^{21}$;

LG is a leaving group;

X is selected from the group consisting of —O—, —S—, and —N(H)—;

$R^{21}$ is selected from the group consisting of hydrogen, $C_1$-$C_4$ alkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, (5- to 10-membered heteroaryl)$C_1$-$C_4$ alkyl, ($C_1$-$C_4$ alkoxy)$C_1$-$C_4$ alkyl, and a protecting group;

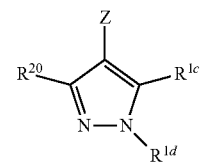

is selected from the group consisting of arylene and heteroarylene;

$R^{22}$ is selected from the group consisting of —O$R^{23}$ and a leaving group;

$R^{23}$ is selected from the group consisting of hydrogen and a protecting group; and $R^{24}$ is selected from the group consisting of —CH$_2$O$R^{25}$ and —C(=O)H; and $R^{25}$ is selected from the group consisting of hydrogen and a protecting group, wherein the $C_3$-$C_6$ cycloalkyl optionally is substituted with one, two, or three substituents independently selected from the group consisting of from halo, nitro, cyano, hydroxy, amino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, alkenyl, alkynyl, aryl, heteroaryl, heterocyclo, alkoxyalkyl, (amino)alkyl, (carboxamido)alkyl, mercaptoalkyl, and (heterocyclo)alkyl;

wherein aryl is a monocyclic or bicyclic aromatic ring system having an indicated number of carbon atoms, optionally substituted with one to five substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, heterocyclo, alkoxyalkyl, (amino)alkyl, (carboxamido)alkyl, mercaptoalkyl, and (heterocyclo)alkyl;

wherein heteroaryl is a monocyclic or bicyclic aromatic ring systems having 5 to 14 ring atoms, wherein at least one carbon atom of one of the rings is replaced with 1, 2, 3, or 4 heteroatoms independently selected from the group consisting of oxygen, nitrogen and sulfur, optionally substituted with one to four substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, aryl, heteroaryl, heterocyclo, alkoxyalkyl, (amino)alkyl, (carboxamido)alkyl, mercaptoalkyl, and (heterocyclo)alkyl; and wherein heterocyclo is a saturated or partially unsaturated cyclic group containing one, two, or three rings having an indicated number of ring members, wherein at least one carbon atom of one of the rings is replaced with a heteroatom selected from the group consisting of oxygen, sulfur, and/or nitrogen atoms with, optionally substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, alkoxycarbonyl, $CF_3C(=O)$—, arylcarbonyl, alkylsulfonyl, arylsulfonyl, carboxy, carboxyalkyl, alkyl, optionally substituted cycloalkyl, alkenyl, alkynyl, substituted aryl, substituted heteroaryl, substituted heterocyclo, alkoxyalkyl, (amino)alkyl, (carboxamido)alkyl, mercaptoalkyl, and (heterocyclo)alkyl, or a pharmaceutically acceptable salt thereof.

36. A process for preparing a compound of claim 35 of Formula XXVI, wherein E is E-1; $R^{29}$ is $R^{19}$; and $R^{19}$ is a protecting group, the process comprising reacting a compound of Formula XXVI, wherein E is —Br; $R^{29}$ is $R^{19}$; and $R^{19}$ is a protecting group, with a compound of Formula XX:

wherein:

XX,

Z is –BR$^{26a}$R$^{26b}$;

$R^{26a}$ and $R^{26b}$ are selected from the group consisting of hydroxy and alkoxy; or $R^{26a}$ and $R^{26b}$ taken together form a linkage —O(CR$^{27a}$R$^{27b}$)$_u$O—;

$R^{27a}$ and $R^{27b}$ are each independently selected from the group consisting of hydrogen and $C_{1-4}$ alkyl;

u is 2, 3, or 4;

$R^{1c}$ is selected from the group consisting of hydrogen, $C_1$-$C_4$ alkyl, halo, $C_1$-$C_4$ haloalkyl, and $C_3$-$C_6$ cycloalkyl;

$R^{1d}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl; or $R^{1c}$ and $R^{1d}$ taken together with the atoms to which they are attached form an optionally substituted 4- to 8-membered heterocyclo;

$R^{20}$ is —CH$_2$XR$^{21}$;

X is selected from the group consisting of —O—, —S—, and —N(H)—; and $R^{21}$ is a protecting group, in presence of a palladium catalyst in a solvent.

37. A process for preparing a compound of claim 35 of Formula XXVI, wherein E is E-3; $R^{29}$ is $R^{19}$; and $R^{19}$ is a protecting group, the process comprising reacting a compound of Formula XXVI, wherein E is —Br; $R^{29}$ is $R^{19}$; and $R^{19}$ is a protecting group, with a compound of Formula XXIV:

wherein:

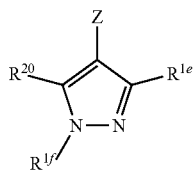

XXIV

Z is —BR$^{26a}$R$^{26b}$;

$R^{26a}$ and $R^{26b}$ are selected from the group consisting of hydroxy and alkoxy; or $R^{26a}$ and $R^{26b}$ taken together form a linkage —O(CR$^{27a}$R$^{27b}$)$_u$O—;

$R^{27a}$ and $R^{27b}$ are each independently selected from the group consisting of hydrogen and $C_{1-4}$ alkyl;

u is 2, 3, or 4;

$R^{1e}$ is selected from the group consisting of hydrogen, halo, $C_{1-04}$ alkyl, $C_1$-$C_4$ haloalkyl, and $C_3$-$C_6$ cycloalkyl;

$R^{1f}$ is selected from the group consisting of hydrogen, $C_1$-$C_4$ alkyl, $C_3$-$C_6$ cycloalkyl, ($C_1$-$C_4$ alkoxy)$C_1$-$C_4$ alkyl, and (carboxamido)$C_1$-$C_4$ alkyl;

$R^{20}$ is —CH$_2$XR$^{21}$;

X is selected from the group consisting of —O—, —S—, and —N(H)—; and $R^{21}$ is a protecting group, in presence of a palladium catalyst in a solvent.

38. A process for preparing a compound of claim 35 of Formula XXVI, wherein E is E-2; $R^{29}$ is $R^{19}$; and $R^{19}$ is a protecting group, the process comprising reacting a compound of Formula XXVI, wherein E is E-1, $R^{29}$ is $R^{19}$; $R^{19}$ is a protecting group, and $R^{20}$ is —CH$_2$-LG, with a compound of Formula XXI:

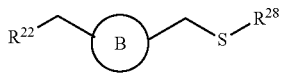

XXI, wherein;

is selected from the group consisting of arylene and heteroarylene;

$R^{22}$ is —OR$^{23}$;

$R^{23}$ is a protecting group;

$R^{28a}$ is —C(=O) R$^{28a}$, and $R^{28a}$ is $C_1$-$C_6$ alkyl, in a solvent in the presence of a base.

39. A process for preparing a compound of claim 35 of Formula XXVI, wherein E is E-4; $R^{29}$ is $R^{19}$; and $R^{19}$ is a protecting group, the process comprising reacting a compound of Formula XXVI, wherein E is E-3, $R^{29}$ is $R^{19}$; $R^{19}$ is a protecting group, and $R^{20}$ is —CH$_2$-LG, with a compound of Formula XXI:

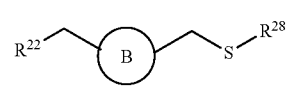

XXI, wherein;

is selected from the group consisting of arylene and heteroarylene;

$R^{22}$ is —OR$^{23}$;

$R^{23}$ is a protecting group;

$R^{28}$ is —C(=O)R$^{28a}$; and $R^{28a}$ is $C_1$-$C_6$ alkyl, in a solvent in the presence of a base.

40. A process for preparing a compound of claim 35 of Formula XXVI, wherein $R^{29}$ is

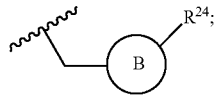

E is E-3; $R^{20}$ is —CH$_2$XR$^{21}$; X is —O—; $R^{21}$ is a protecting group; $R^{24}$ is —CH$_2$OR$^{25}$; and $R^{25}$ is a protecting group, the process comprising reacting a compound of Formula XXVI, wherein E is E-3; $R^{20}$ is —CH$_2$XR$^{21}$; X is —O—; $R^{21}$ is a protecting group; $R^{29}$ is $R^{19}$; and $R^{19}$ is hydrogen, with a compound of Formula XXV:

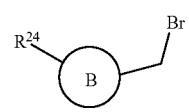

XXV, wherein;

is selected from the group consisting of arylene and heteroarylene;

$R^{24}$ is —$CH_2OR^{25}$; and $R^{25}$ is a protecting group, in a solvent and, optionally, in the presence of a base.

41. A process for preparing a compound of claim 35 of Formula XXVI, wherein $R^{29}$ is

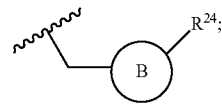

E is E-1; $R^{20}$ is —$CH_2XR^{21}$; X is —O—; $R^{21}$ is a protecting group; $R^{24}$ is —$CH_2OR^{25}$; and $R^{25}$ is a protecting group, the process comprising reacting a compound of Formula XXVI, wherein E is E-1; $R^{20}$ is —$CH_2XR^{21}$; X is —O—; $R^{21}$ is a protecting group; $R^{29}$ is $R^{19}$; and $R^{19}$ is hydrogen, with a compound of Formula XXV:

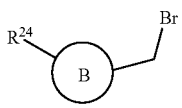

wherein;

is selected from the group consisting of arylene and heteroarylene;

$R^{24}$ is —$CH_2OR^{25}$; and $R^{25}$ is a protecting group, in a solvent and, optionally, in the presence of a base.

* * * * *

UNITED STATES PATENT AND TRADEMARK OFFICE
CERTIFICATE OF CORRECTION

PATENT NO. : 11,691,989 B2  
APPLICATION NO. : 17/047423  
DATED : July 4, 2023  
INVENTOR(S) : Hao Chen et al.

It is certified that error appears in the above-identified patent and that said Letters Patent is hereby corrected as shown below:

On the Title Page

At item (57), Line 3, "$R^{1h}$," should be -- $R^{1h}$, $L^1$, --.

At item (57), Line 3, "in the re)" should be -- in the --.

In the Claims

At Column 334, Line 7, "—(CH$_2$),N(R$^{2a}$)(R$^{2b}$);" should be -- —(CH$_2$)$_m$N(R$^{2a}$)(R$^{2b}$); --.

At Column 335, Lines 27-34, " 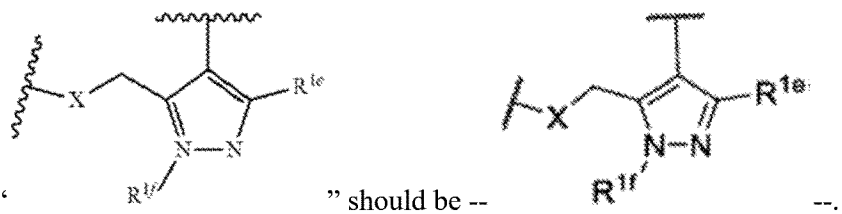 " should be -- --.

At Column 335, Line 38, "$C_{3\text{-}06}$" should be -- $C_3$-$C_6$ --.

At Column 335, Line 46, "$R^{1c}$" should be -- $R^{1e}$ --.

At Column 335, Line 61, "—(CH$_2$)$_1$N" should be -- —(CH$_2$)$_r$N --.

At Column 336, Line 16, "$C_{1\text{-}04}$" should be -- $C_1$-$C_4$ --.

At Column 336, Line 18, "$C_{1\text{-}04}$" should be -- $C_1$-$C_4$ --.

At Column 337, Line 15, "CF3C(=O)—," should be -- CF$_3$C(=O)—, --.

At Column 339, Line 4, "—S(=O)$_2$R$^{12}$;" should be -- —S(=O)$_2$R$^{12}$; --.

Signed and Sealed this  
Twenty-sixth Day of December, 2023

Katherine Kelly Vidal  
*Director of the United States Patent and Trademark Office*

CERTIFICATE OF CORRECTION (continued)
U.S. Pat. No. 11,691,989 B2

At Column 341, Line 7, "—(CH$_2$)$_1$N" should be -- —(CH$_2$)$_r$N --.

At Column 341, Line 34, "Rib" should be -- R$^{1b}$ --.

At Column 341, Line 64, "r$^{14a}$, r$^{14b}$, r$^{14c}$, and R$^{14d}$are" should be -- R$^{14a}$, R$^{14b}$, R$^{14c}$, and R$^{14d}$ are --.

At Column 343, Line 27, "Y6" should be -- Y$^6$ --.

At Column 343, Line 65, "R$^{17b}$," should be -- R$^{17b}$, --.

At Column 344, Lines 11-16, " 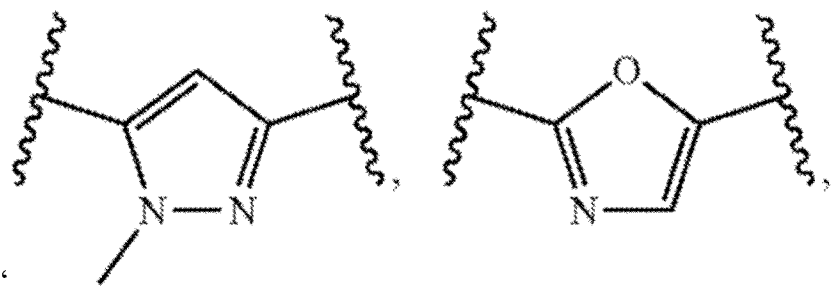 " should be -- 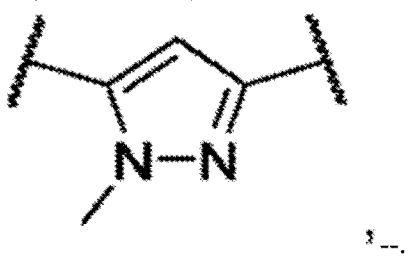 --.

At Column 348, Lines 1-18, " 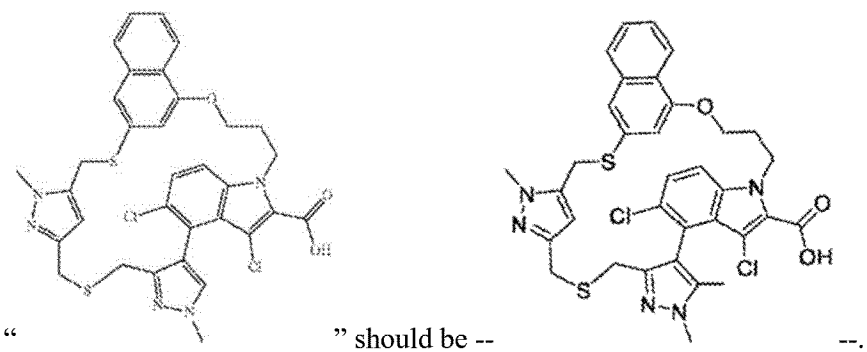 --.

At Column 367, Line 24, "cydoalkyl," should be -- cycloalkyl, --.

At Column 368, Line 65, "—O(CR$^{27a}$R$^{27b}$)$_u$o—;" should be -- —O(CR$^{27a}$R$^{27b}$)$_u$O—; --.

At Column 368, Line 67, "C$_{1-4}$" should be -- C$_1$-C$_4$ --.

At Column 369, Line 41, "C$_{1-4}$" should be -- C$_1$-C$_4$ --.

At Column 369, Line 43, "R$^1$e" should be -- R$^{1e}$ --.

CERTIFICATE OF CORRECTION (continued)
U.S. Pat. No. 11,691,989 B2

At Column 369, Line 44, "$C_{1\text{-}04}$" should be -- $C_1$-$C_4$ --.

At Column 370, Line 1, "wherein;" should be -- wherein: --.

At Column 370, Line 11, "—C(=O)$R^{28a}$," should be -- —C(=O)$R^{28a}$; --.

At Column 370, Line 26, "wherein;" should be -- wherein: --.

At Column 370, Line 48, "$R^{20}$" should be -- $R^{20}$ --.

At Column 370, Line 48, "$_R{}^{21}$" should be -- $R^{21}$ --.

At Column 370, Line 62, "wherein;" should be -- wherein: --.

At Column 371, Line 15, "$_R{}^{21}$" should be -- $R^{21}$ --.

At Column 372, Line 8, "wherein;" should be -- wherein: --.